United States Patent
Fournier et al.

(10) Patent No.: US 10,246,422 B2
(45) Date of Patent: Apr. 2, 2019

(54) HETEROCYCLIC COMPOUNDS AND USE THEREOF IN MEDICINE AND IN COSMETICS

(71) Applicant: GALDERMA RESEARCH & DEVELOPMENT, Biot (FR)

(72) Inventors: Jean-Francois Fournier, Juan les Pins (FR); Laurence Clary, La Colle sur Loup (FR); Etienne Thoreau, Saint Vallier de Thiey (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 15/537,038

(22) PCT Filed: Dec. 22, 2015

(86) PCT No.: PCT/FR2015/053709
§ 371 (c)(1),
(2) Date: Jun. 16, 2017

(87) PCT Pub. No.: WO2016/102882
PCT Pub. Date: Jun. 30, 2016

(65) Prior Publication Data
US 2018/0050992 A1 Feb. 22, 2018

(30) Foreign Application Priority Data

Dec. 23, 2014 (FR) ..................................... 14 63212

(51) Int. Cl.
| | | |
|---|---|---|
| *C07D 239/10* | (2006.01) |
| *C07D 401/14* | (2006.01) |
| *C07D 413/14* | (2006.01) |
| *C07D 401/06* | (2006.01) |
| *C07D 403/06* | (2006.01) |
| *C07D 407/14* | (2006.01) |
| *C07D 409/14* | (2006.01) |
| *C07D 471/04* | (2006.01) |
| *C07D 498/20* | (2006.01) |
| *C07D 211/36* | (2006.01) |
| *C07D 239/80* | (2006.01) |
| *C07D 245/06* | (2006.01) |
| *C07D 403/14* | (2006.01) |
| *A61K 31/499* | (2006.01) |
| *A61P 25/06* | (2006.01) |
| *A61P 17/06* | (2006.01) |

(52) U.S. Cl.
CPC .......... *C07D 239/10* (2013.01); *C07D 211/36* (2013.01); *C07D 239/80* (2013.01); *C07D 245/06* (2013.01); *C07D 401/06* (2013.01); *C07D 401/14* (2013.01); *C07D 403/06* (2013.01); *C07D 403/14* (2013.01); *C07D 407/14* (2013.01); *C07D 409/14* (2013.01); *C07D 413/14* (2013.01); *C07D 471/04* (2013.01); *C07D 498/20* (2013.01)

(58) Field of Classification Search
CPC .. C07D 239/10; C07D 245/06; C07D 401/14; C07D 403/14; C07D 239/80; C07D 211/36; C07D 407/14; C07D 498/20; C07D 409/14; C07D 401/06; C07D 471/04; C07D 403/06; C07D 413/14
See application file for complete search history.

(56) References Cited

FOREIGN PATENT DOCUMENTS

| | | |
|---|---|---|
| WO | WO2004083187 A1 | 9/2004 |
| WO | WO2006029153 A2 | 3/2006 |
| WO | WO2008112159 A2 | 9/2008 |
| WO | WO2008130512 A1 | 10/2008 |
| WO | WO2010139717 A1 | 12/2010 |

OTHER PUBLICATIONS

International Search Report and Written Opinion for International Application No. PCT/FR2015/053709 dated Feb. 3, 2016, 11 pages.

*Primary Examiner* — John M Mauro
(74) *Attorney, Agent, or Firm* — Sunit Talapatra; Foley & Lardner LLP

(57) ABSTRACT

The invention relates to novel heterocyclic compounds of general formula (I), as well as their pharmaceutically acceptable salts, and their enantiomers. The invention also relates to the use thereof as a medicinal product, preferably in the prevention and/or treatment of inflammatory diseases with a neurogenic component or use thereof as a cosmetic. The compounds of the present invention act as antagonists of the CGRP-R receptor.

18 Claims, 4 Drawing Sheets

HETEROCYCLIC COMPOUNDS AND USE THEREOF IN MEDICINE AND IN COSMETICS

The invention relates to novel heterocyclic compounds of general formula (I):

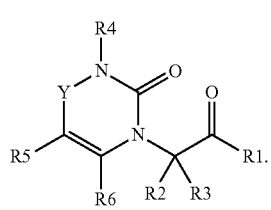

It also relates to their use as a medicinal product, notably in the prevention and/or treatment of inflammatory diseases with a neurogenic component, or as a cosmetic. The compounds of the present invention act as antagonists of the CGRP-R receptor.

The calcitonin gene-related peptide (CGRP) is a neuropeptide of 37 amino acids comprising a C-terminal amide group and a cyclic structure formed with an N-terminal Cys-Cys disulphide bridge (Poyner et al., "The mammalian calcitonin gene-related peptides, adrenomedullin, amylin, and calcitonin receptors", 2002). CGRP is widely expressed in the central and peripheral nervous system and is involved in a certain number of biological functions (Edvinsson et al., "CGRP antagonism and migraine", 2010). There is more and more proof that CGRP plays an important role as a neuromodulator (Ho et al., "CGRP and its receptors provide new insights into migraine pathophysiology", 2010), but it is especially known as a powerful vasodilator (Brain et al., "Calcitonin gene-related peptide is a potent vasodilator", 1985).

CGRP signals mainly via a receptor (CGRP-R) that is a heterodimer formed by the association of a receptor coupled to a protein G (RCPG) of class B (calcitonin receptor (CLR or calcitonin-like receptor)) with a transmembrane protein modifying the activity of the receptors (RAMP1 or receptor activity-modifying protein 1) (McLatchie et al., "RAMPs regulate the transport and ligand specificity of the calcitonin receptor-like receptor", 1998).

The role of CGRP and the activity of the CGRP receptor have been the subject of numerous studies.

As a guide, we may more particularly mention studies that have suggested that migraine crisis is associated with release of CGRP by the meningeal nociceptors of the trigeminal ganglion and that CGRP may therefore play an active role in migraine (Edvinsson et al., "Functional role of perivascular peptides in the control of cerebral circulation", 1985; Goadsby et al., "Vasoactive peptide release in the extracerebral circulation of humans during migraine headache", 1990; Lassen et al., "CGRP may play a causative role in migraine", 2002).

The increasing volume of proof linking CGRP to migraine has led to interest in the development of agents capable of blocking the effects of this neuropeptide. Efforts have notably focused on the development of small molecules that are direct CGRP receptor antagonists (the "gepants") and non-vasoconstrictive for treating migraine.

These molecules are described in the literature for use by the oral route and thus display metabolic stability at the hepatic level (olcegepant, telcagepant and MK-3207).

However, their development has come up against problems of hepatic toxicity.

Moreover, besides its role in migraine, release of CGRP by the trigeminal nerve innervating the face might be involved in the neurogenic inflammation responsible notably for permanent erythema in type 1 rosacea. This hypothesis is supported by common characteristics between rosacea and migraine, which comprises a neurogenic component with vasoactive phenomena, activation of the trigeminal nervous system and release of neuro-inflammatory peptides (CGRP, substance P, etc.). CGRP is thought to exert its vasodilator action mainly by acting on the smooth muscle cells and endothelial cells of the subcutaneous vessels.

Rosacea is a common chronic and progressive inflammatory dermatosis connected with vascular relaxation. It mainly affects the central region of the face and is characterized by a reddening of the face or hot flushes, facial erythema, papules, pustules, telangiectasia and sometimes ocular lesions called ocular rosacea.

Moreover, these primary characteristics are associated with a secondary neurogenic component, i.e. cutaneous hyperreactivity of the skin of the face and neck, characterized by the appearance of redness and subjective sensations of the itching or pruritus type, sensations of burning or heating, sensations of tingling, formication, discomfort, twinges, etc.

Thus, rosacea is treated conventionally orally or topically with active substances such as antiseborrhoeic and anti-infective agents, for example benzoyl peroxide, retinoic acid, metronidazole or the cyclins.

However, these treatments, which act on the infection and the hyperseborrhoea, do not provide effective treatment and/or prevention of all of the symptoms associated with rosacea, in particular treatment of the neurogenic component of this disorder, and notably hyperreactivity of the skin and redness.

Thus, more particularly patent EP0734729 is known, which discloses the use of a CGRP antagonist for treating redness of the skin of neurogenic origin, and notably rosacea and/or erythema pudicitiae.

However, the only antagonist described is CGRP 8-37, an anti-CGRP peptide. It should decrease the vasodilatation induced by capsaicin and/or cause inhibition of CGRP release by the sensitive nerve fibres and/or cause inhibition of contraction of the smooth muscle of the vas deferens induced by CGRP.

Bearing the foregoing in mind, there is therefore a need for active substances that are effective in the treatment of inflammatory diseases with a neurogenic component such as rosacea, which are usable for long periods, with side-effects that are as limited as possible.

One problem that the present invention aims to solve is to propose a treatment for reducing or completely eliminating this inflammation, using a non-peptide antagonist of the CGRP receptor in order to target the neurogenic inflammation, resulting in an effect that persists after the treatment stops, while limiting the side-effects for the patient, in particular the risks of hepatic toxicity.

The applicant has thus identified novel heterocyclic compounds that are CGRP receptor antagonists, selective for the human receptor, which have very good potential as regards biological activity. Unexpectedly, these novel compounds display metabolic instability at the hepatic level, which should limit the risk of hepatotoxicity encountered with many CGRP antagonists known from the prior art, for example olcegepant, telcagepant and MK-3207.

The invention relates to a heterocyclic compound selected from the compounds of general formula (I):

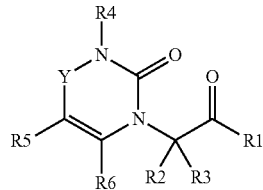

(I)

in which R1, R2, R3, R4, R5, R6 and Y are as defined in the detailed description below, as well as the pharmaceutically acceptable salts of the compounds of general formula (I) and the enantiomers of the compounds of general formula (I).

The invention also relates to a pharmaceutical composition comprising at least one compound of general formula (I) and a pharmaceutically acceptable vehicle, preferably suitable for administration by the topical route.

It also relates to the cosmetic use of a compound of general formula (I).

The invention also relates to a compound of general formula (I) to be used as a medicinal product.

It relates in particular to a compound of general formula (I) for use in the prevention and/or treatment of inflammatory diseases with a neurogenic component.

The invention further relates to the use of a compound of general formula (I) for preparing a medicinal product intended for preventing and/or treating inflammatory diseases with a neurogenic component.

The invention further relates to a method for preventing and/or treating inflammatory diseases with a neurogenic component, comprising the administration of at least one compound of general formula (I).

The invention and the advantages it provides will be better understood on reading the description and the following non-limiting embodiments, written with reference to the appended figures, in which.

Figure 1:
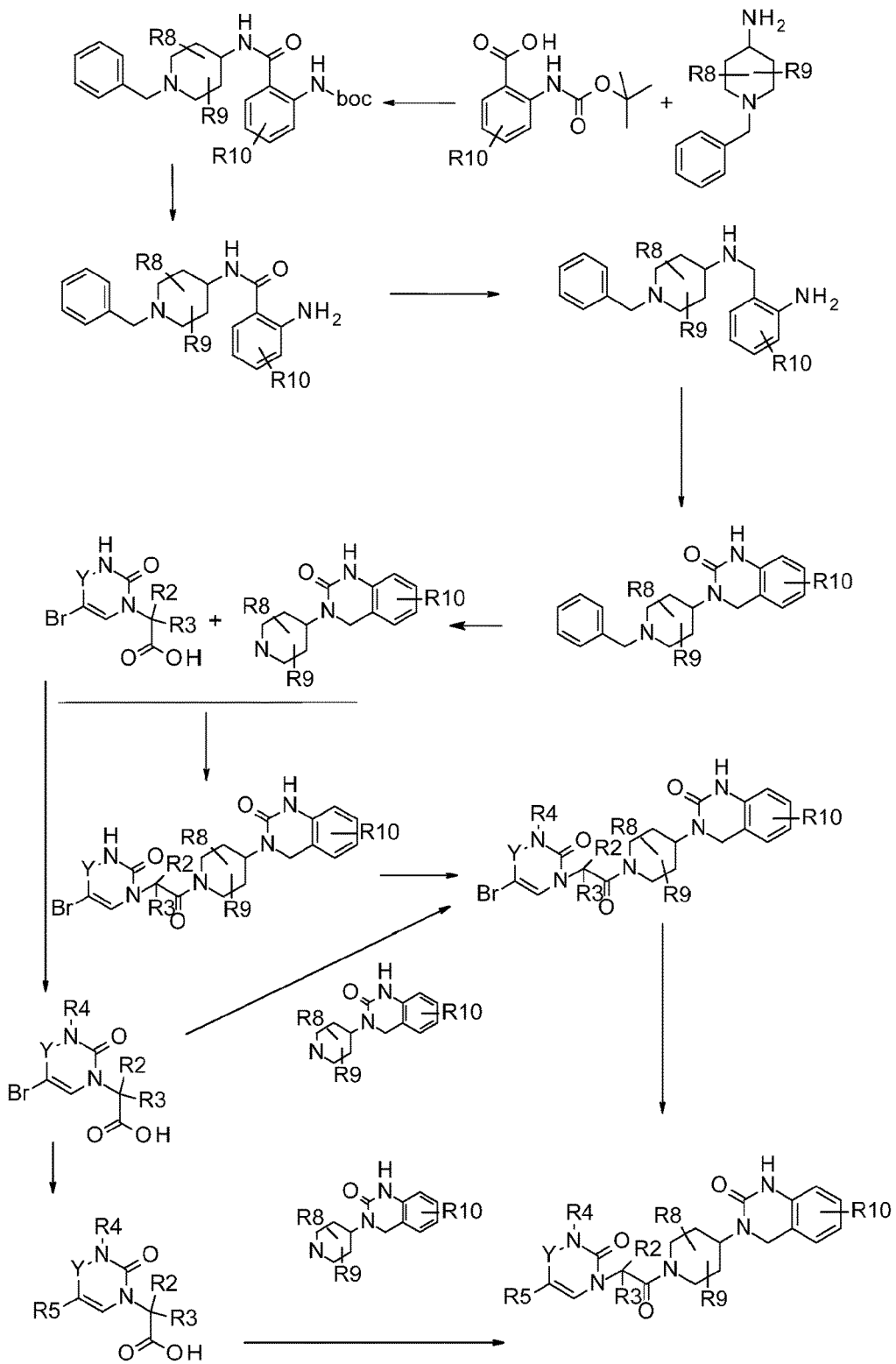
FIG. 1 shows a general route of synthesis in conventional conditions, of compounds according to the invention according to reaction scheme No. 1.
Figure 2:
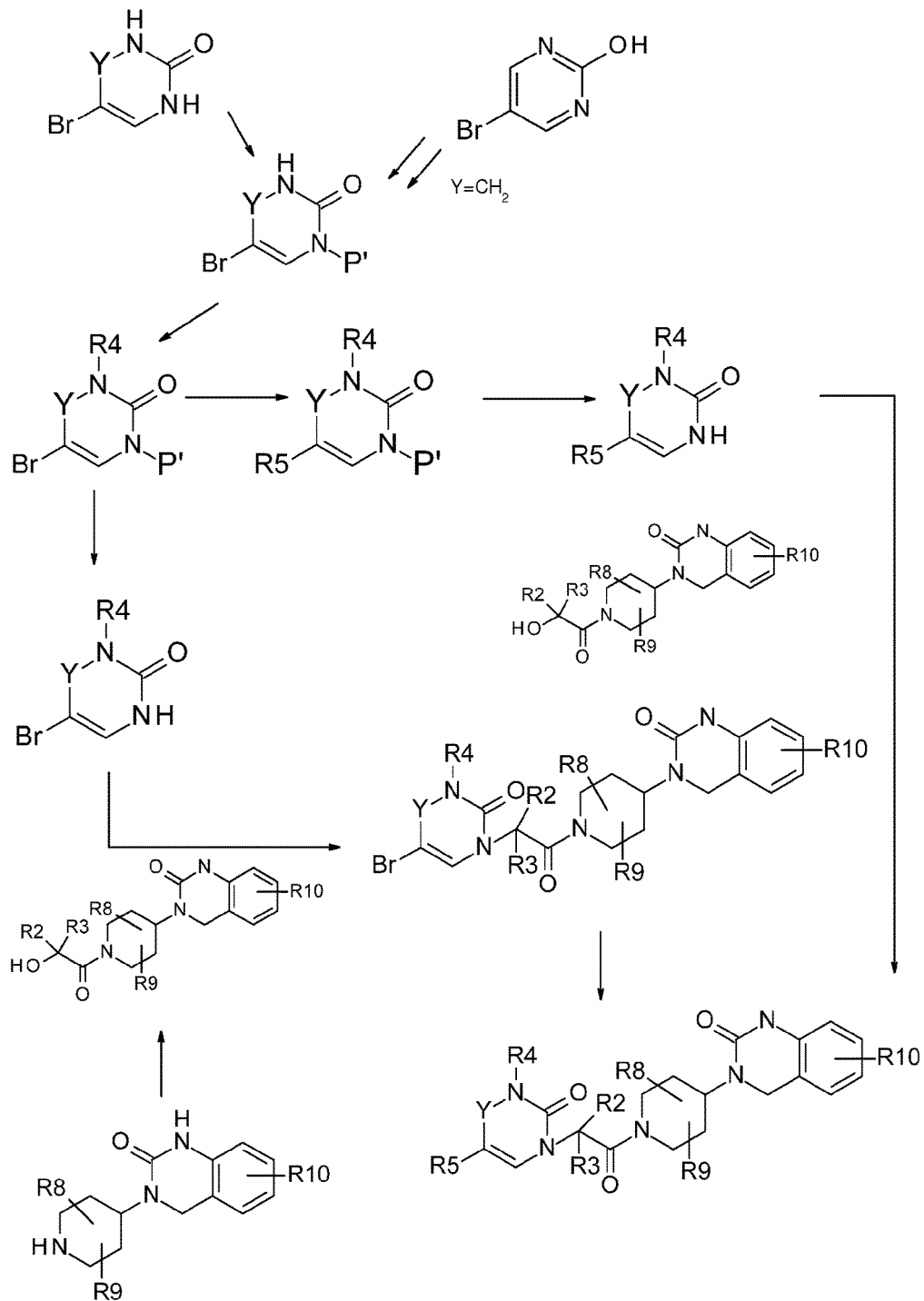
FIG. 2 shows a general route of synthesis in conventional conditions, of compounds according to the invention according to reaction scheme No. 2, in which P' denotes a protecting group of the benzyl, 4-methoxybenzyl, benzhydryl, —COOtBu or other type.
Figure 3:
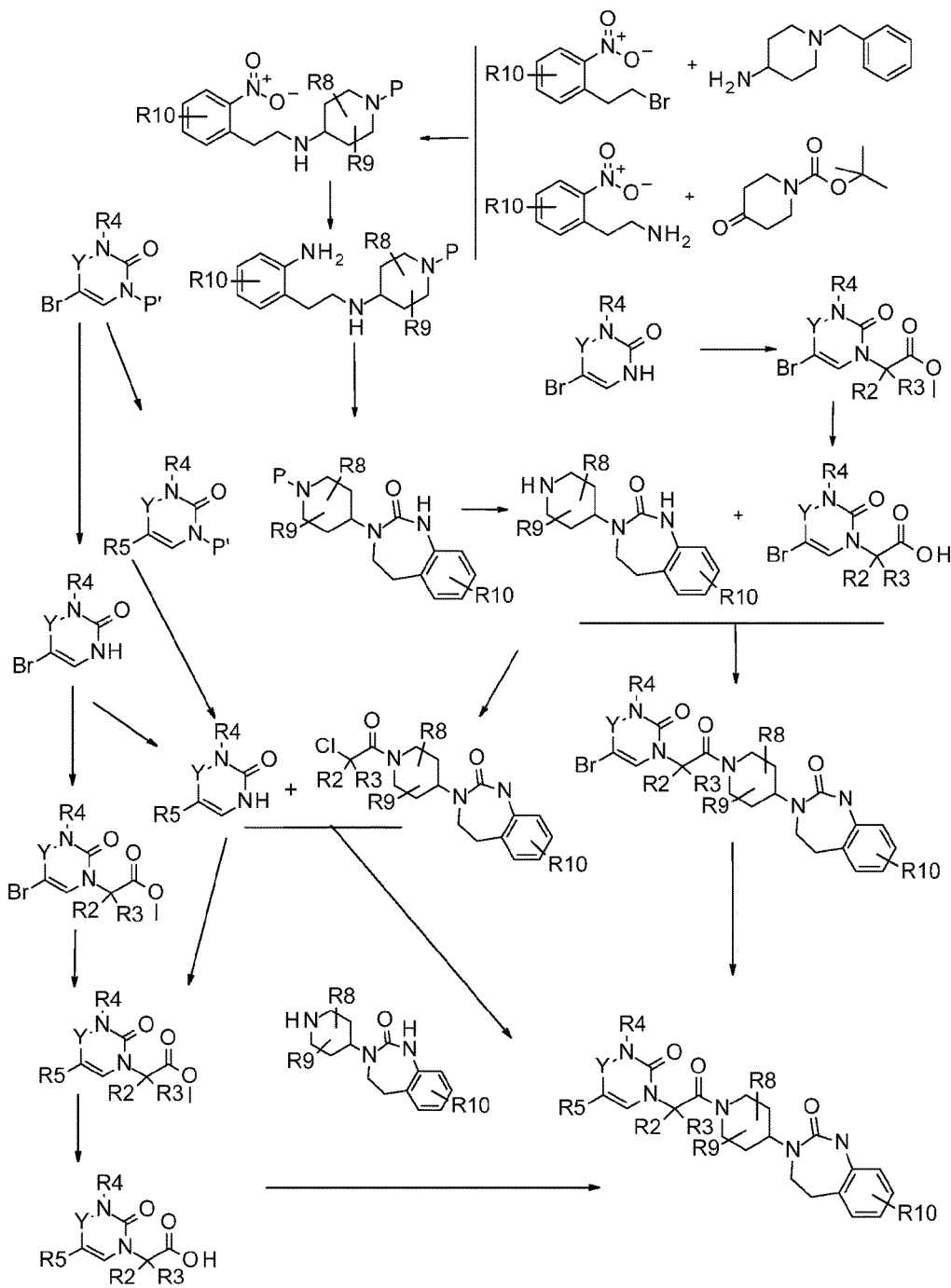
Figure 4:
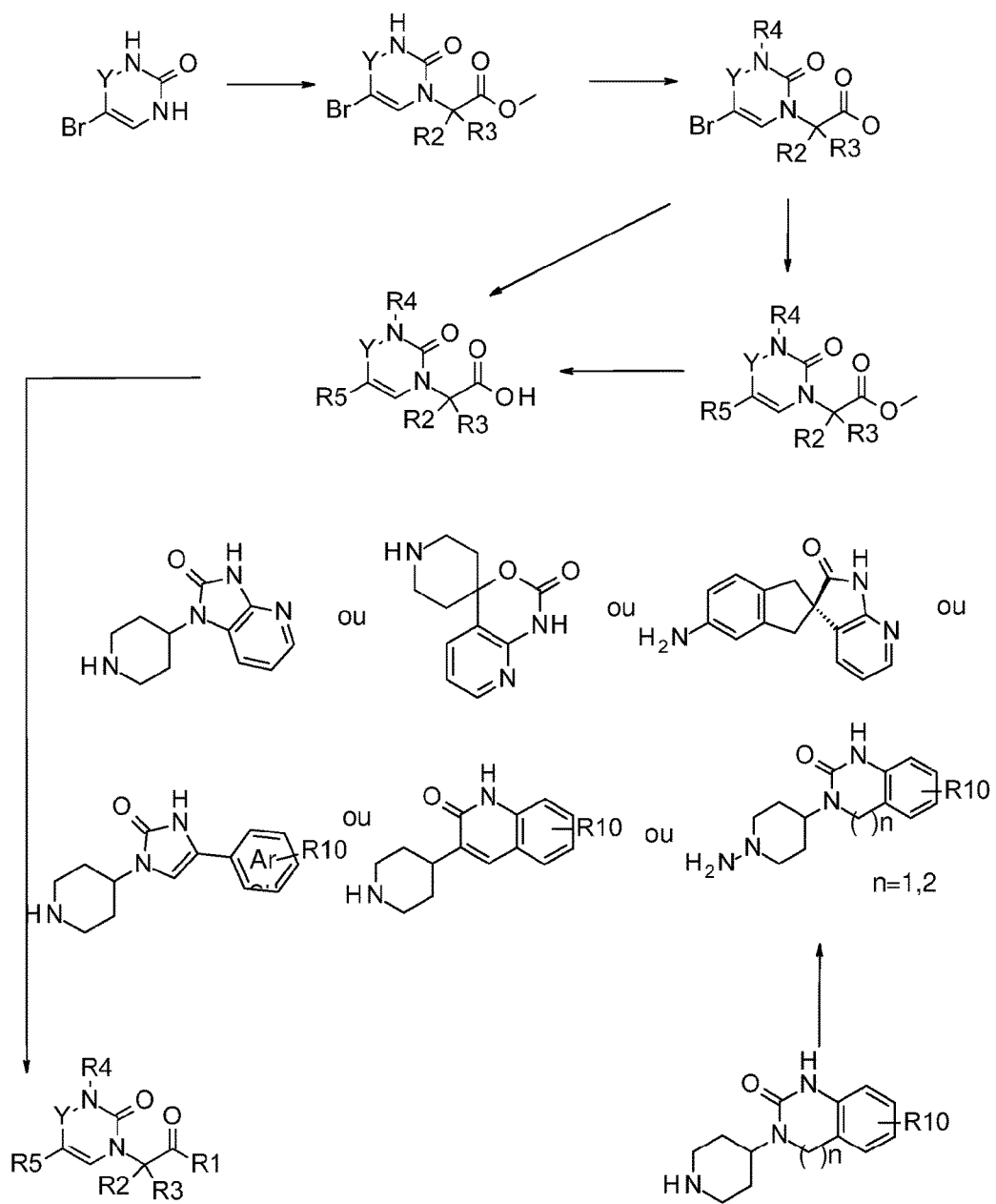

FIG. 3 shows a general route of synthesis in conventional conditions, of compounds according to the invention according to reaction scheme No. 3, in which P' denotes a protecting group of the benzyl, 4-methoxybenzyl, benzhydryl, —COOtBu or other type; and FIG. 4 shows a general route of synthesis in conventional conditions, of compounds according to the invention according to reaction scheme No. 4.

Throughout the present description, unless specified otherwise, it is to be understood that when ranges of concentrations are given, they include the upper and lower limits of said range.

The compounds according to the invention are novel heterocyclic compounds that are CGRP receptor antagonists, selected from the compounds of general formula (I):

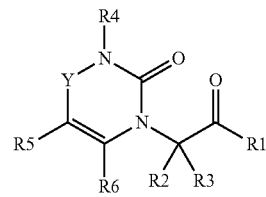

(I)

in which

Y is selected from —CH$_2$, —C(O), —C(CH$_3$)$_2$, or a spirocyclopropyl;

R1 is selected from the following groups (1-1) to (1-12):

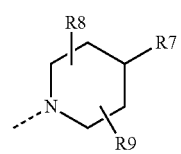

(1-1)

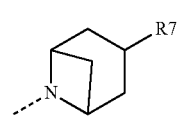

(1-2)

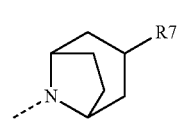

(1-3)

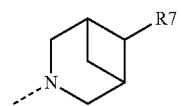

(1-4)

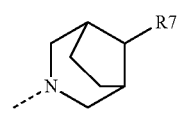

(1-5)

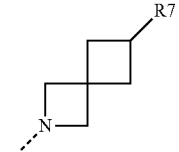

(1-6)

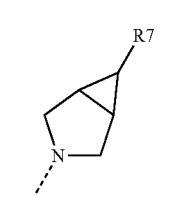

(1-7)

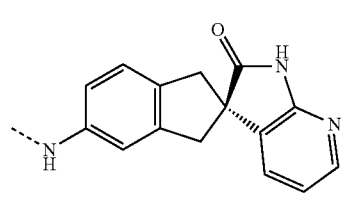

(1-8)

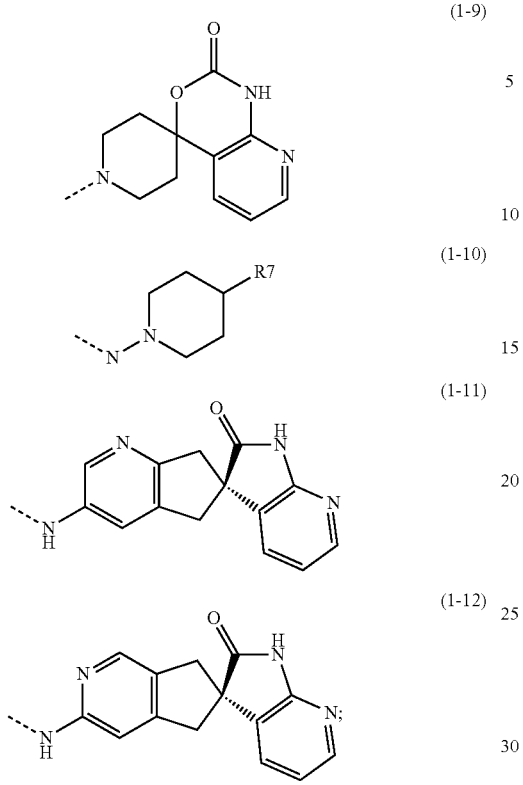
R2, R3, R6, which may be identical or different, are selected from a hydrogen atom, F or —CH$_3$;
R4 is selected from a hydrogen atom, an alkyl, an alkene, an alkyne, a cycloalkyl, a cycloalkene, an aralkyl, a heteroaralkyl, or the following groups (4-1) to (4-55):
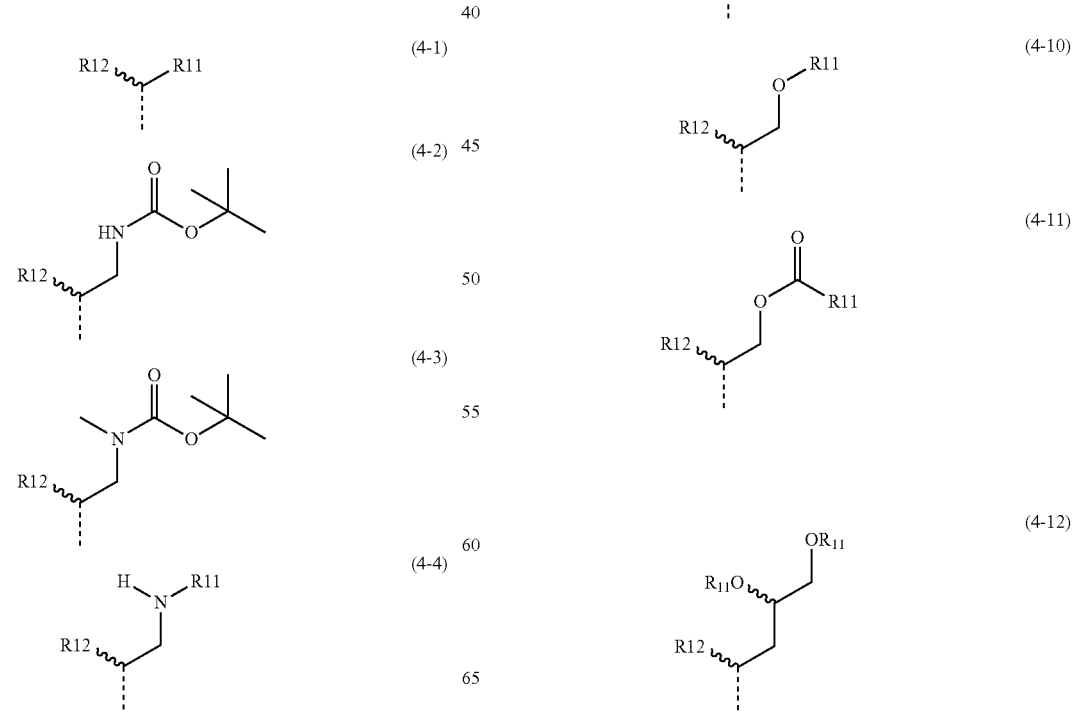

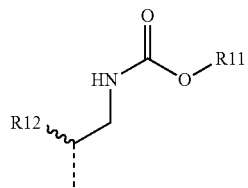 (4-13)
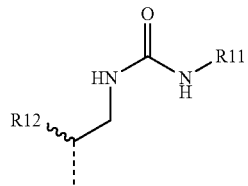 (4-14)
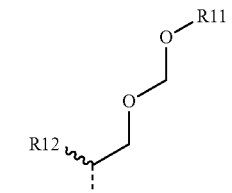 (4-15)
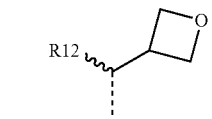 (4-16)
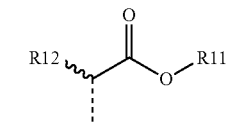 (4-17)
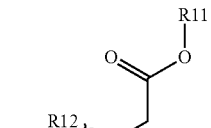 (4-18)
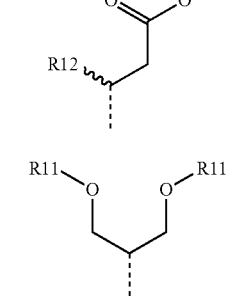 (4-19)
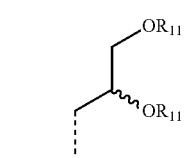 (4-20)
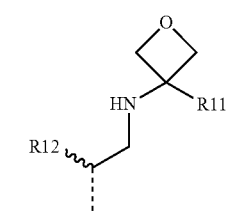 (4-21)
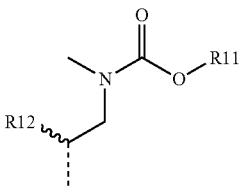 (4-22)
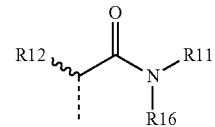 (4-23)
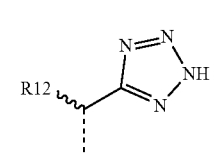 (4-24)
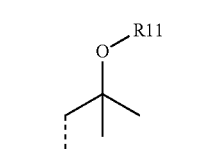 (4-25)
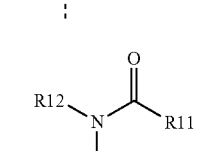 (4-26)
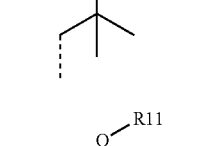 (4-27)
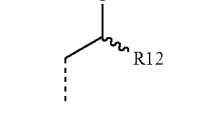 (4-28)
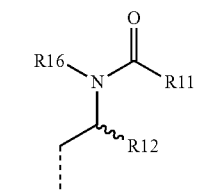 (4-29)
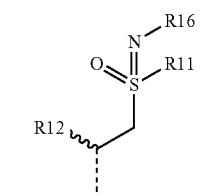 (4-30)
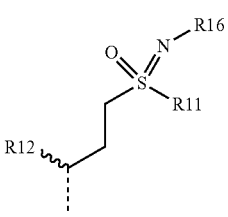

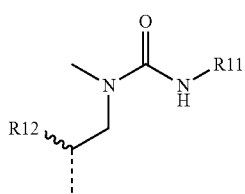
(4-31)
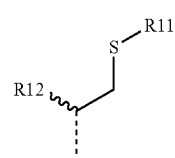
(4-32)
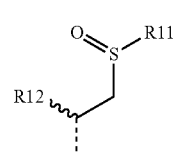
(4-33)
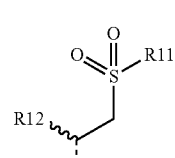
(4-34)
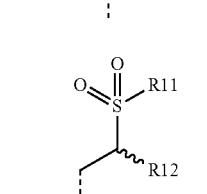
(4-35)
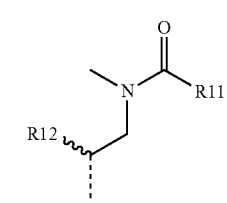
(4-36)
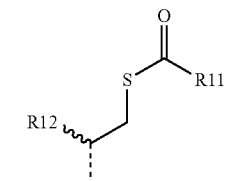
(4-37)
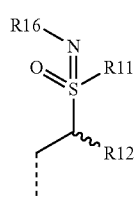
(4-38)
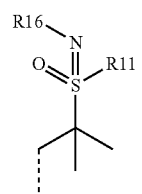
(4-39)
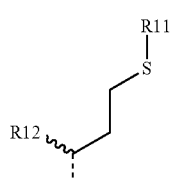
(4-40)
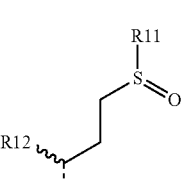
(4-41)
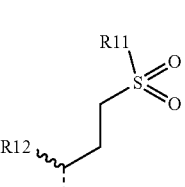
(4-42)
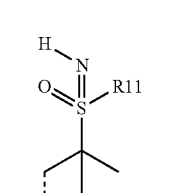
(4-43)
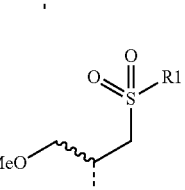
(4-44)
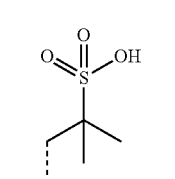
(4-45)
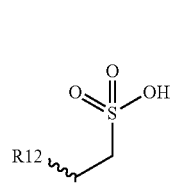
(4-46)

-continued (4-47) 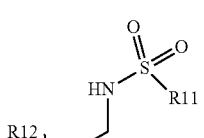

(4-48) 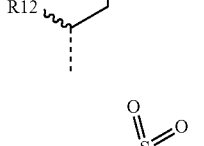

(4-49) 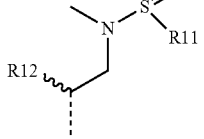

(4-50) 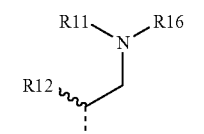

(4-51) 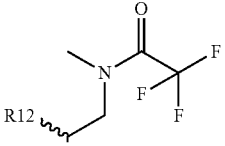

(4-52) 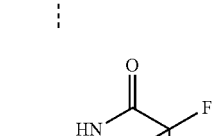

(4-53) 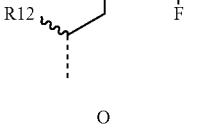

(4-54) 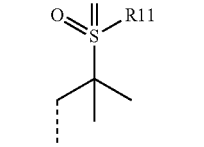

(4-55) 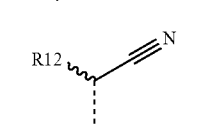

R5 is selected from a halogen, an alkyl, a cycloalkyl optionally substituted with R13, R14 and/or R15, an alkene, a cycloalkene, an alkyne, an ether or the following groups (5-1) to (5-5):

(5-1) 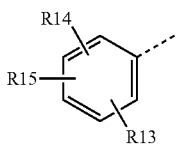

(5-2) 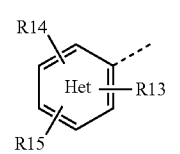

(5-3) 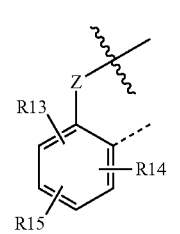

(5-4) 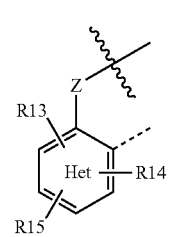

(5-5) 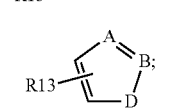

with Het representing 1 to 3 nitrogen atoms among the 6 atoms of the aromatic ring, and these nitrogen atoms may, independently of one another, be substituted with an oxygen atom to form an N-oxide group;

R7 is selected from the following groups (7-1) to (7-28):

(7-1) 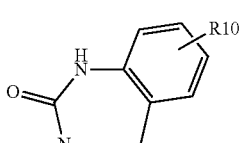

(7-2) 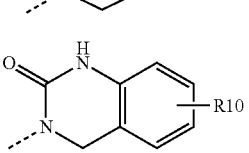

(7-3) 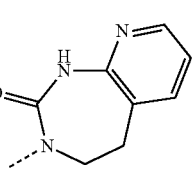

-continued
(7-4) 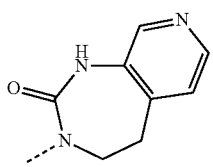
(7-5) 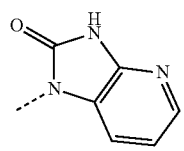
(7-6) 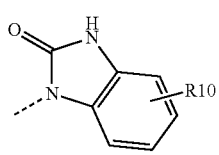
(7-7) 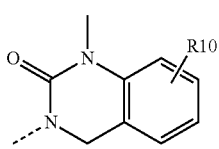
(7-8) 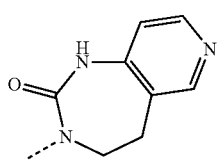
(7-9) 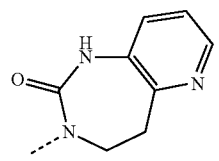
(7-10) 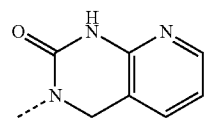
(7-11) 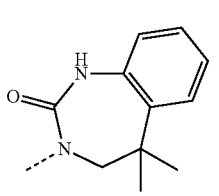
(7-12) 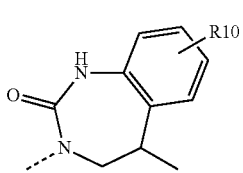
-continued
(7-13) 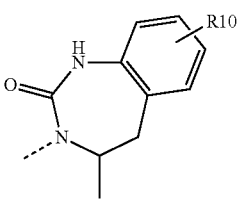
(7-14) 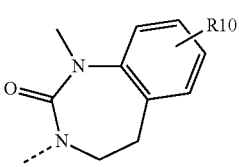
(7-15) 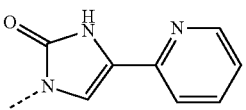
(7-16) 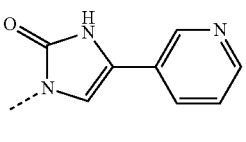
(7-17) 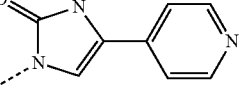
(7-18) 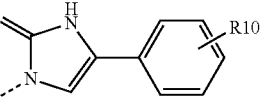
(7-19) 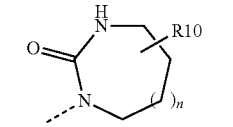
(7-20) 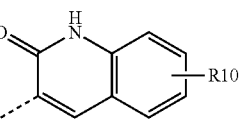
(7-21) 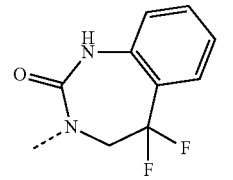
(7-22) 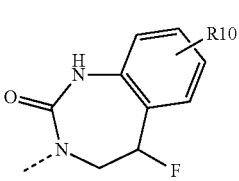

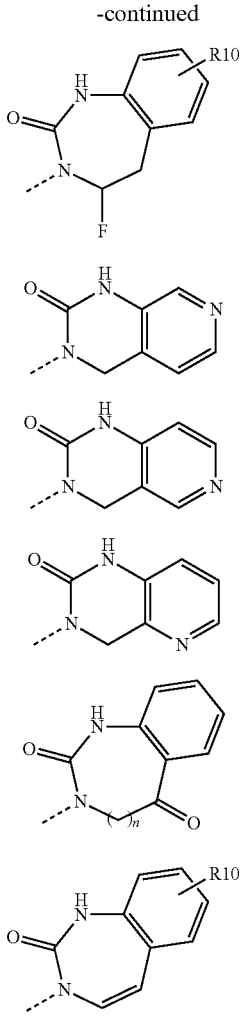

with n = 0 or 1;

R8, R9, which may be identical or different, are selected from a hydrogen atom, F or —CH₃;
R10 is selected from a hydrogen atom, —OR11, —SR11, —NR11R12, —S(O)R11, —SO₂R11, —OC(O)R11, —CO₂R11, a halogen, —NO₂, —CN, —C(O)NR11R12, —CF₃ or —OCF₃;
R11, R12, which may be identical or different, are selected from a hydrogen atom, a C1-C6 alkyl, CF₃ or an ether;
R13, R14, R15, which may be identical or different, are selected from a hydrogen atom, a C1-C6 alkyl, a cycloalkyl, —OR16, —NR16R17, a halogen, —OCF₃, —CF₃, —CN, —CO₂R16, —CONR16R17, —NO₂, —OCH₂OR16, —SR16, —S(O)R16, —SO₂R16 or an ether;
A, B, D, which may be identical or different, are selected from a C, N, O or S atom;
R16 and R17, which may be identical or different, are selected from a hydrogen atom, a C1-C6 alkyl or —C(O)R18;
Z is selected from —CH₂, O or —NR18; and
R18 is selected from a hydrogen atom, a C1-C3 alkyl, as well as their pharmaceutically acceptable salts, and their enantiomers.

"Pharmaceutically acceptable salt" denotes the salts of a compound of interest that possess the desired biological activity. The pharmaceutically acceptable salts comprise salts of acid or basic groups present in the compounds specified. The pharmaceutically acceptable acid addition salts comprise, but are not limited to, hydrochloride, hydrobromide, hydriodide, nitrate, sulphate, bisulphate, phosphate, acid phosphate, isonicotinate, acetate, lactate, salicylate, citrate, tartrate, pantothenate, bitartrate, ascorbate, succinate, maleate, gentisinate, fumarate, gluconate, glucuronate, saccharate, formate, benzoate, glutamate, methanesulphonate, ethanesulphonate, benzenesulphonate, p-toluenesulphonate and pamoate (i.e. 1,1'-methylene-bis(2-hydroxy-3-naphthoate)) salts. Suitable basic salts comprise, but are not limited to, salts of aluminium, calcium, lithium, magnesium, potassium, sodium, zinc, and diethanolamine. A list of pharmaceutically acceptable salts is notably published in the review by Berge et al. (*J. Pharm. Sci.* 1977, 66(1), 1-19).

The term enantiomer denotes the R or S configurations of the compounds of general formula (I) according to the invention.

Unless stated otherwise, the definitions given below apply by default to all of the radicals used for defining the structure of the compounds of general formula (I).

When a characteristic of the substituent differs from that indicated in the definitions given below, this difference is explicitly indicated.

As examples, an alkyl comprising only 3 to 7 carbon atoms would be defined by C3-C7 alkyl; an alkene comprising only 3 to 7 carbon atoms and which is only linear would be defined by linear C3-C7 alkene, all other characteristics moreover being the same as those defined by default for each radical given below.

According to the present invention:
An alkyl denotes, in particular, a saturated, linear or branched hydrocarbon chain, comprising from 1 to 8 carbon atoms, optionally substituted with one or more fluorine atoms.

An alkene denotes, in particular, an unsaturated, linear or branched hydrocarbon chain, comprising from 2 to 8 carbon atoms and comprising one or two double bonds, optionally substituted with one or more fluorine atoms.

An alkyne denotes, in particular, an unsaturated, linear or branched hydrocarbon chain, comprising from 2 to 8 carbon atoms and comprising one or two triple bonds, optionally substituted with one or more fluorine atoms.

A cycloalkyl denotes, in particular, a saturated, cyclic hydrocarbon chain comprising from 3 to 7 carbon atoms, optionally substituted with one or more fluorine atoms.

A cycloalkene denotes, in particular, an unsaturated, cyclic hydrocarbon chain comprising from 4 to 7 carbon atoms and comprising one or two double bonds, optionally substituted with one or more fluorine atoms.

An aryl denotes, in particular, a hydrocarbon-containing aromatic ring or two fused hydrocarbon-containing aromatic rings. The preferred aryl radicals are selected from the phenyl and naphthyl radicals, optionally substituted with one or more groups of atoms selected from an alkyl, an alkoxy, an aryl, a halogen, a hydroxyl, a cyano, a trifluoromethyl, a sulphide, a pentafluorosulphide, a sulphoxide, a sulphone, a carboxylic acid, an ester and a nitro.

An aralkyl denotes, in particular, an alkyl substituted with an aryl.

A heteroaryl denotes, in particular, an aromatic heterocyclic radical, i.e. a cyclic or polycyclic, aromatic hydrocarbon chain, comprising one or more heteroatoms selected from O, S and N, optionally substituted with one or more groups of atoms selected for example from an alkyl, an alkoxy, an aryl, a substituted aryl, a halogen, a hydroxy, a cyano, a trifluoromethyl, a sulphide, a pentafluorosulphide, a sulphoxide, a sulphone, a carboxylic acid, an ester and a nitro.

A heteroaralkyl denotes, in particular, an alkyl substituted with a heteroaryl.

A heterocycle denotes, in particular, a cyclic or bicyclic, saturated or unsaturated hydrocarbon chain, comprising one or more heteroatoms selected from O, S and N, optionally substituted with one or more groups selected from an alkyl, an alkoxy, a halogen, a hydroxyl, a cyano, a trifluoromethyl, a sulphide, a pentafluorosulphide, a sulphoxide, a sulphone, a carboxylic acid, an ester and a nitro.

A halogen denotes a fluorine, chlorine or bromine atom.

An alkoxy denotes an oxygen atom substituted with an alkyl radical.

An ether denotes, in particular, a saturated, linear or branched hydrocarbon chain, comprising from 1 to 8 carbon atoms, and in which 1 to 3 carbon atoms are replaced respectively by 1 to 3 oxygen atoms, two oxygen atoms always being separated by at least one carbon atom, said chain optionally being substituted with one or more fluorine atoms.

The compounds according to the invention are preferably selected from the compounds of general formula (I) in which:

Y is selected from —CH$_2$ or —C(O);

R1 is selected from the following groups:

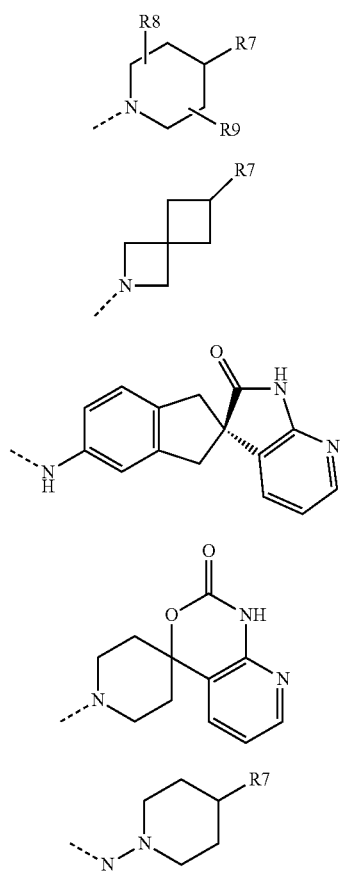

R2, R3, R6, which may be identical or different, are selected from a hydrogen atom, F or —CH$_3$;

R4 is selected from a C1-C4 alkyl, an aralkyl, a heteroaralkyl, or the following groups:

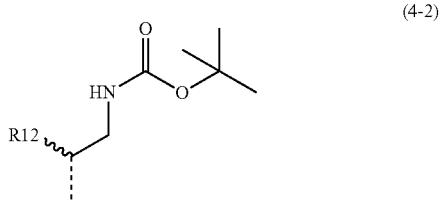

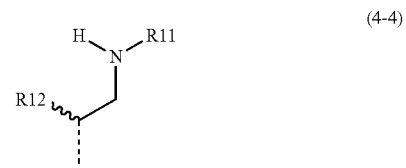

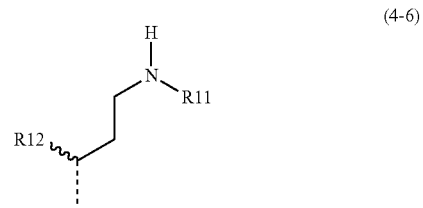

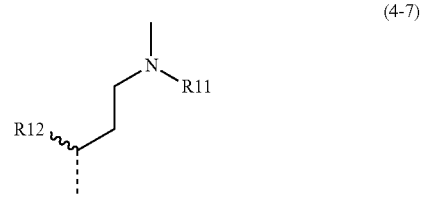

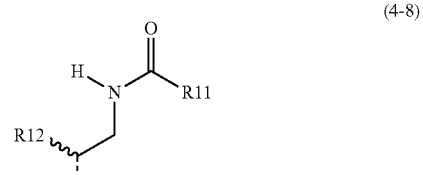

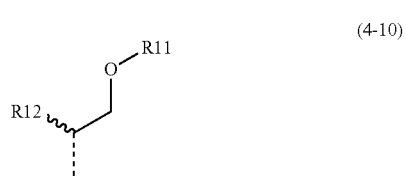

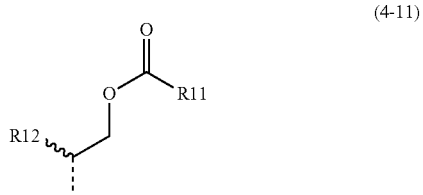

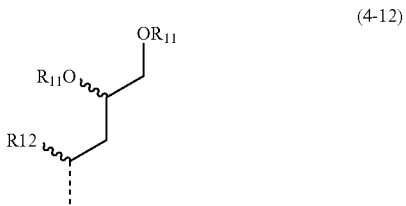

(4-13) 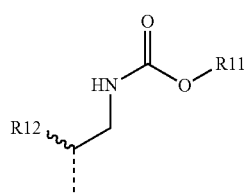
(4-15) 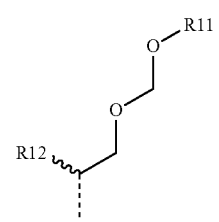
(4-16) 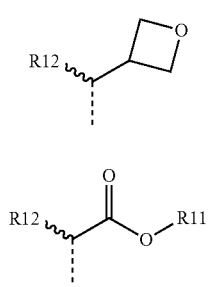
(4-17) 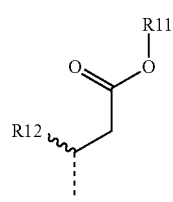
(4-18) 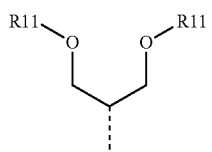
(4-19) 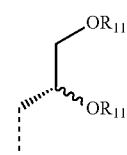
(4-20) 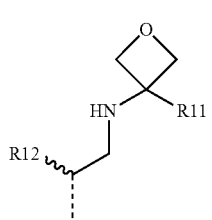
(4-21) 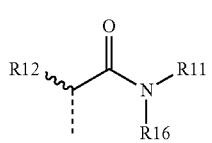
(4-23) 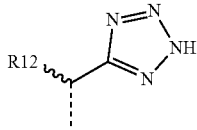
(4-24) 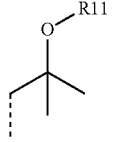
(4-25) 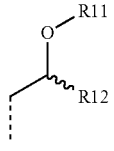
(4-27) 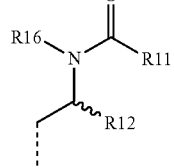
(4-28) 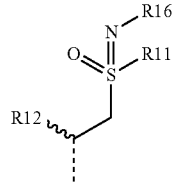
(4-29) 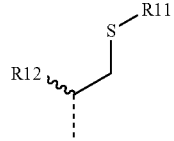
(4-32) 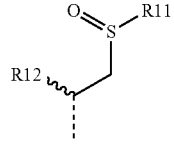
(4-33) 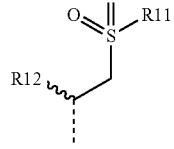
(4-34) 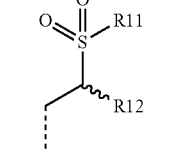
(4-35) 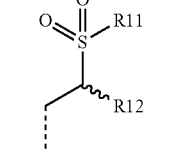

-continued
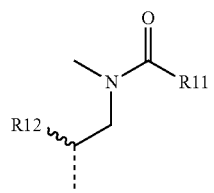 (4-36)
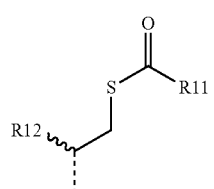 (4-37)
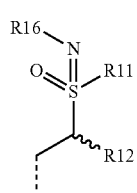 (4-38)
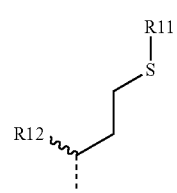 (4-40)
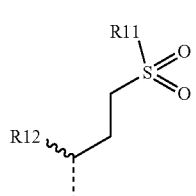 (4-42)
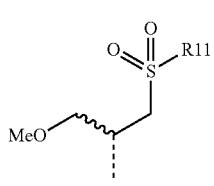 (4-44)
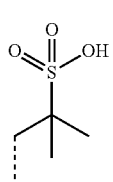 (4-45)
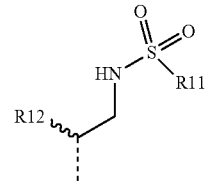 (4-47)
-continued
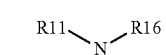 (4-49)
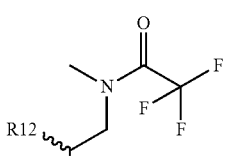 (4-50)
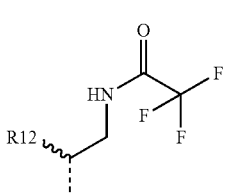 (4-51)
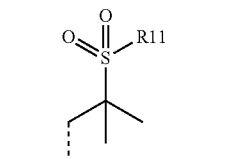 (4-52)
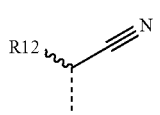 (4-53)
R5 is selected from Br, —CH₃, a cyclohexene or the following groups:
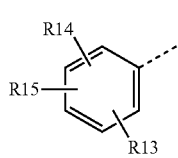 (5-1)
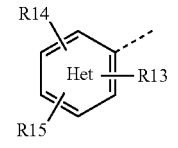 (5-2)
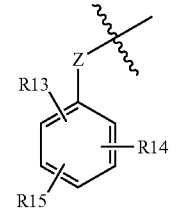 (5-3)
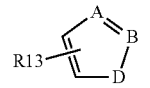 (5-5)

with Het representing 1 to 2 N atoms among the 6 atoms of the aromatic ring, and these nitrogen atoms may, independently of one another, be substituted with an oxygen atom to form an N-oxide group;

R7 is selected from the following groups:

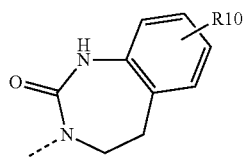
(7-1)

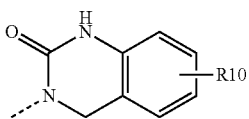
(7-2)

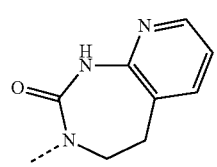
(7-3)

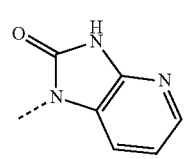
(7-5)

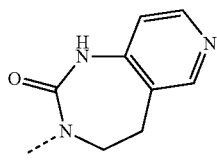
(7-8)

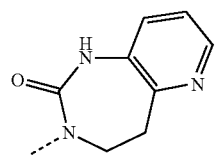
(7-9)

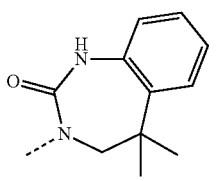
(7-11)

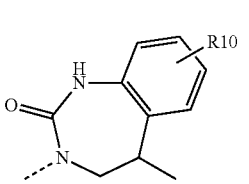
(7-12)

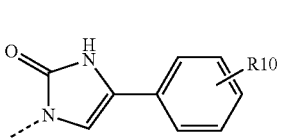
(7-18)

-continued

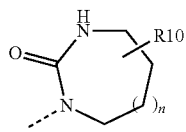
(7-19)

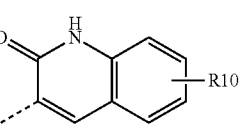
(7-20)

(7-21)

(7-22)

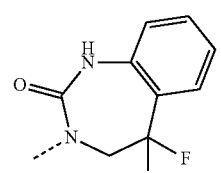

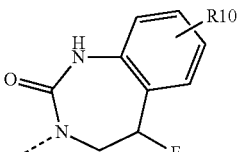
(7-23)

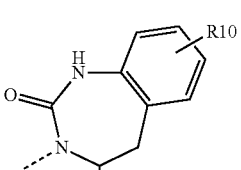

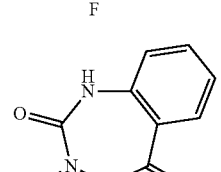
(7-27)

with n = 1;

R8, R9, which may be identical or different, are selected from a hydrogen atom, F or —CH$_3$;

R10 is selected from a hydrogen atom, —OR11, —SR11, —S(O)R11, —SO$_2$R11, —CO$_2$H or a halogen selected from Br or F;

R11, R12, which may be identical or different, are selected from a hydrogen atom, a C1-C3 alkyl or CF$_3$;

R13, R14, R15, which may be identical or different, are selected from a hydrogen atom, —CH$_3$, —OR16, a halogen, —OCF$_3$, —CN, —CO$_2$R16, —SR16, —S(O) R16, or —SO$_2$R16;

A, B, D, which may be identical or different, are selected from a C, N or S atom;

R16 is selected from a hydrogen atom or an alkyl; and

Z is selected from —CH$_2$ or O.

For this purpose, the compounds of general formula (I) according to the invention are more preferably selected from the following compounds:

Compound 1: 5-(3,4-difluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione;

Compound 2: 5-(2-fluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione;

Compound 3: 5-(2,4-difluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione;

Compound 4: 5-(3-fluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione;

Compound 5: 3-methyl-1-{2-oxo-2-[4-(2-oxo-1,4-dihydro-2H-quinazolin-3-yl)-piperidin-1-yl]-ethyl}-5-(1H-pyrazol-3-yl)-1H-pyrimidine-2,4-dione;

Compound 6: 5-(3-methoxyphenyl)-3-methyl-1-{2-oxo-2-[4-(2-oxo-1,4-dihydro-2H-quinazolin-3-yl)-piperidin-1-yl]-ethyl}-1H-pyrimidine-2,4-dione;

Compound 7: 5-(3-hydroxyphenyl)-3-methyl-1-{2-oxo-2-[4-(2-oxo-1,4-dihydro-2H-quinazolin-3-yl)-piperidin-1-yl]-ethyl}-1H-pyrimidine-2,4-dione;

Compound 8: 5-(3,4-difluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione;

Compound 9: 5-cyclohex-1-enyl-3-methyl-1-{2-oxo-2-[4-(2-oxo-1,4-dihydro-2H-quinazolin-3-yl)-piperidin-1-yl]-ethyl}-1H-pyrimidine-2,4-dione;

Compound 10: 3-methyl-1-{2-oxo-2-[4-(2-oxo-1,4-dihydro-2H-quinazolin-3-yl)-piperidin-1-yl]-ethyl}-5-phenyl-1H-pyrimidine-2,4-dione;

Compound 11: 5-bromo-1-{2-oxo-2-[4-(2-oxo-1,4-dihydro-2H-quinazolin-3-yl)-piperidin-1-yl]-ethyl}-3-(2,2,2-trifluoroethyl)-1H-pyrimidine-2,4-dione;

Compound 12: 5-(2,3-difluorophenyl)-3-ethyl-1-{2-oxo-2-[4-(2-oxo-1,4-dihydro-2H-quinazolin-3-yl)-piperidin-1-yl]-ethyl}-1H-pyrimidine-2,4-dione;

Compound 13: 5-(2-chloro-3-fluorophenyl)-3-isopropyl-1-{2-oxo-2-[4-(2-oxo-1,4-dihydro-2H-quinazolin-3-yl)-piperidin-1-yl]-ethyl}-1H-pyrimidine-2,4-dione;

Compound 14: 5-(2-chloro-3-fluorophenyl)-3-((S)-2-methoxy-1-methylethyl)-1-{2-oxo-2-[4-(2-oxo-1,4-dihydro-2H-quinazolin-3-yl)-piperidin-1-yl]-ethyl}-1H-pyrimidine-2,4-dione;

Compound 15: 5-(2,3-difluorophenyl)-3-methyl-1-[1-methyl-2-oxo-2-[4-(2-oxo-1,4-dihydroquinazolin-3-yl)-1-piperidyl]ethyl]pyrimidine-2,4-dione;

Compound 16: 5-(2,3-difluorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 17: 5-(2,3-dichlorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 18: 5-(2-chlorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 19: 3-methyl-1-{2-oxo-2-[4-(2-oxo-1,2,4,5-tetrahydro-benzo[d][1,3]diazepin-3-yl)-piperidin-1-yl]-ethyl}-5-(2-trifluoromethoxyphenyl)-1H-pyrimidine-2,4-dione;

Compound 20: 3-methyl-1-{2-oxo-2-[4-(2-oxo-1,2,4,5-tetrahydro-benzo[d][1,3]diazepin-3-yl)-piperidin-1-yl]-ethyl}-5-thiophen-3-yl-1H-pyrimidine-2,4-dione;

Compound 21: 5-(2-methoxyphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 22: 5-(3-chlorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 23: 5-(3-chloro-2-methylphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 24: 5-(3-chloro-2-methoxyphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 25: 5-(2-methoxy-3-methylphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 26: 5-(3-chloro-2-hydroxyphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 27: 5-(2,3-dimethoxyphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 28: 5-(3-fluoro-2-methylphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 29: 5-(3-chloro-2-fluorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 30: 5-(2,3-dimethylphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 31: 5-(2-chloro-3-fluorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 32: 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 33: 5-(3-fluoro-2-methoxyphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 34: 5-(2,6-difluorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 35: 5-(3,5-dichlorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 36: 4-(3-methyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-benzonitrile;

Compound 37: 3-(3-methyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-benzonitrile;

Compound 38: 2-(3-methyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-benzonitrile;

Compound 39: 3-methyl-5-(3-methyl-pyridin-4-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 40: 3-methyl-5-(2-methyl-pyridin-3-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 41: 3-methyl-5-(4-methyl-pyridin-3-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 42: 3-methyl-5-(6-methyl-pyridin-2-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 43: 3-methyl-5-(6-methyl-1-oxy-pyridin-2-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 44: 3-methyl-5-(1-methyl-1H-pyrazol-4-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 45: 5-(5-chloro-pyridin-3-yl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 46: 5-benzyl-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 47: 5-(3,4-dichlorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 48: 5-(5-chloro-2-methylphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 49: 5-(4,5-dimethyl-pyridin-3-yl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 50: 3-methyl-1-{2-oxo-2-[4-(2-oxo-1,2,4,5-tetrahydro-benzo[d][1,3]diazepin-3-yl)-piperidin-1-yl]-ethyl}-5-phenoxy-1H-pyrimidine-2,4-dione;

Compound 51: 5-(2,3-dimethylphenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 52: 5-(3-chloro-2-methylphenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 53: 5-(2,3-dichlorophenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 54: 5-(2-chloro-3-fluorophenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 55: 5-(3-chloro-2-methoxyphenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 56: 5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-3-propyl-1H-pyrimidine-2,4-dione;

Compound 57: 5-(2-chloro-3-fluorophenyl)-1-{2-oxo-2-[4-(2-oxo-1,2,4,5-tetrahydro-benzo[d][1,3]diazepin-3-yl)-piperidin-1-yl]-ethyl}-3-propyl-1H-pyrimidine-2,4-dione;

Compound 58: 1-{2-oxo-2-[4-(2-oxo-1,2,4,5-tetrahydro-benzo[d][1,3]diazepin-3-yl)-piperidin-1-yl]-ethyl}-3-propyl-5-pyridazin-3-yl-1H-pyrimidine-2,4-dione;

Compound 59: 5-(3-chloro-2-methylphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 60: 5-(3-chloro-2-methoxyphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 61: 5-(3-fluoro-2-methylphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 62: 5-(2,3-difluorophenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 63: 5-(2-chloro-3-fluorophenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 64: 3-isopropyl-5-(2-methoxy-3-methylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 65: 5-(3-chloro-4-methoxyphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 66: 5-(2-fluorobenzyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 67: 5-(3,4-dichlorophenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 68: 5-(2,3-dimethylphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 69: 5-(2-chloro-3-methoxyphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 70: 5-(5-chloro-2-methoxyphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 71: 5-(2,3-difluorobenzyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 72: (5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-acetonitrile;

Compound 73: 3-(5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-propanoic acid;

Compound 74: methyl 3-(3-isopropyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-benzoic acetate;

Compound 75: 3-(3-isopropyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-benzoic acid;

Compound 76: 5-(2-chloro-3-methylsulphanyl-phenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 77: 5-(2-chloro-3-methanesulphinyl-phenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 78: 5-(2-chloro-3-methanesulphonyl-phenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 79: methyl 2-(3-isopropyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-benzoic acetate;

Compound 80: 2-(3-isopropyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-benzoic acid;

Compound 81: 5-(3,4-difluorobenzyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 82: 5-(3,5-difluorobenzyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 83: 5-(2,3-dichlorophenyl)-3-isobutyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 84: 5-(2-chloro-3-fluorophenyl)-3-isobutyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 85: 5-(2,3-dimethylphenyl)-3-isobutyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 86: 5-(3-fluoro-2-methylphenyl)-3-isobutyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 87: [2-(5-(2,3-dimethylphenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-carbamic acid tert-butyl ester;

Compound 88: 3-(2-aminoethyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 89: 3-(2-aminoethyl)-5-(2,3-dichlorophenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 90: 5-(2,3-dichlorophenyl)-3-(2-methylaminoethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 91: 3-((R)-2,3-dihydroxypropyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 92: 3-(3,4-dihydroxybutyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 93: 5-(2,3-dimethylphenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 94: 5-(3,5-dichlorophenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 95: 5-(3-chloro-2-methoxyphenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 96: 5-(2-chloro-3-fluorophenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 97: 5-(2-chloro-3-methoxyphenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 98: 5-(2,3-dimethylphenyl)-3-(2-hydroxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 99: 3-(2-dimethylaminoethyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 100: 5-(2,3-dimethylphenyl)-3-(2-methoxymethoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 101: N-[2-(5-(2,3-dimethylphenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]acetamide;

Compound 102: 5-(2,3-dimethylphenyl)-3-(2-methylaminoethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 103: methyl (5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-acetate;

Compound 104: (5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-acetic acid;

Compound 105: 5-(2-chloro-3-fluorophenyl)-3-oxetan-3-yl-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 106: 5-(2-chloro-3-fluorophenyl)-3-((S)-2-methoxy-1-methylethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 107: methyl (5-bromo-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-acetate;

Compound 108: 5-(2-chloro-3-methoxyphenyl)-3-((S)-2-methoxy-1-methylethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 109: 5-(2,3-difluorophenyl)-3-((S)-2-methoxy-1-methylethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 110: 5-(2-chloro-3-fluorophenyl)-3-((R)-2-methoxy-1-methylethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 111: methyl 2-(5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-propionate;

Compound 112: 5-(2-chloro-3-fluorophenyl)-3-(2-methylsulphanyl-ethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 113: 5-(2,3-difluorophenyl)-3-(2-methylsulphanyl-ethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione;

Compound 114: methyl 3-(5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-propionate;

Compound 115: N—[(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide;

Compound 116: N—[(S)-2-(5-(2-chloro-3-fluorophenyl)-3-{2-[4-(7-methoxy-5-methyl-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide;

Compound 117: N-[2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-ethyl]acetamide;

Compound 118: N-[2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-ethyl]-N-methyl-acetamide;

Compound 119: 3-((S)-2-amino-1-methylethyl)-5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 120: N—[(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-methanesulphonamide;

Compound 121: 5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-3-[(S)-1-methyl-2-(3-methyl-oxetan-3-ylamino)-ethyl]-1H-pyrimidine-2,4-dione;

Compound 122: 5-(2-chloro-3-fluorophenyl)-3-((S)-2-hydroxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 123: (S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl acetate;

Compound 124: 5-(2-chloro-3-methoxyphenyl)-3-((S)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 126: 5-(2,3-difluorophenyl)-3-((S)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 127: 5-(2,3-dichlorophenyl)-3-((R)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 128: 5-(2,3-difluorophenyl)-3-((R)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 129: 5-(2,3-dimethoxyphenyl)-3-((S)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 130: 5-(2-chloro-3-methoxyphenyl)-3-((R)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 131: 5-(2-chloro-3-fluorophenyl)-3-((R)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 132: 5-(2,3-dichlorophenyl)-3-((S)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 133: 5-(2,3-dimethoxyphenyl)-3-((R)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 134: 5-(3-bromo-2-fluorophenyl)-3-((R)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 135: 5-(2-chloro-3-fluorophenyl)-3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 136: 5-(2,3-difluorophenyl)-3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 137: 5-(2,3-dichlorophenyl)-3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 138: 5-(2,3-dimethylphenyl)-3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 139: 5-(2,3-dimethoxyphenyl)-3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 140: 5-(2-chloro-3-methoxyphenyl)-3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 141: 3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-5-methyl-1H-pyrimidine-2,4-dione;

Compound 142: 5-(2-chloro-3-fluorophenyl)-3-((S)-2-methanesulphonyl-1-methylethyl)-1-{2-[4-(7-methoxy- 2-oxo-1,2,4,5-tetrahydro-benzo[d][1,3]diazepin-3-yl)-piperidin-1-yl]-2-oxo-ethyl}-1H-pyrimidine-2,4-dione;

Compound 143: 5-(2-chloro-3-fluorophenyl)-3-((R)-2-methanesulphonyl-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 144: 5-(2,3-dichlorophenyl)-3-((S)-2-methanesulphonyl-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 145: 5-(2,3-dichlorophenyl)-3-((R)-2-methanesulphonyl-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 146: 5-(2-chloro-3-fluorophenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 147: 5-(2,3-dimethoxyphenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 148: 5-(2-chloro-3-methoxyphenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 149: 5-(2-fluoro-3-methoxyphenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 150: 3-isopropyl-1-{2-[4-(7-methoxy-2-oxo-1,2,4,5-tetrahydro-benzo[d][1,3]diazepin-3-yl)-piperidin-1-yl]-2-oxo-ethyl}-5-(2-trifluoromethoxyphenyl)-1H-pyrimidine-2,4-dione;

Compound 151: 3-isopropyl-1-{2-[4-(7-methoxy-2-oxo-1,2,4,5-tetrahydro-benzo[d][1,3]diazepin-3-yl)-piperidin-1-yl]-2-oxo-ethyl}-5-(3-trifluoromethoxyphenyl)-1H-pyrimidine-2,4-dione;

Compound 152: 3-isopropyl-1-{2-[4-(7-methoxy-2-oxo-1,2,4,5-tetrahydro-benzo[d][1,3]diazepin-3-yl)-piperidin-1-yl]-2-oxo-ethyl}-5-(3-methoxy-2-trifluoromethoxyphenyl)-1H-pyrimidine-2,4-dione;

Compound 153: 5-(2,3-difluorophenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 154: 5-(2-chloro-3-ethoxyphenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 155: 5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-3-(2-methylsulphanyl-ethyl)-1H-pyrimidine-2,4-dione;

Compound 156: 5-(2-chloro-3-fluorophenyl)-3-(3-methanesulphonyl-propyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 157: 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-[2-(methylsulphonimidoyl)ethyl]pyrimidine-2,4-dione;

Compound 158: N—[(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-propionamide;

Compound 159: 5-(2-chloro-3-fluorophenyl)-1-{2-[4-(7-fluoro-2-oxo-1,2,4,5-tetrahydro-benzo[d][1,3]diazepin-3-yl)-piperidin-1-yl]-2-oxo-ethyl}-3-((S)-2-methoxy-1-methylethyl)-1H-pyrimidine-2,4-dione;

Compound 160: 5-(2-chloro-3-fluorophenyl)-1-{2-[4-(7-fluoro-2-oxo-1,2,4,5-tetrahydro-benzo[d][1,3]diazepin-3-yl)-piperidin-1-yl]-2-oxo-ethyl}-3-(2-methanesulphonyl-ethyl)-1H-pyrimidine-2,4-dione;

Compound 161: N—[(S)-2-(5-(2-chloro-3-fluorophenyl)-3-{2-[4-(7-fluoro-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide;

Compound 162: N—[(S)-2-(5-(2,3-dichlorophenyl)-3-{2-[4-(7-fluoro-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide;

Compound 163: 5-(2-chloro-3-fluorophenyl)-1-{2-[4-(9-fluoro-2-oxo-1,2,4,5-tetrahydro-benzo[d][1,3]diazepin-3-yl)-piperidin-1-yl]-2-oxo-ethyl}-3-isopropyl-1H-pyrimidine-2,4-dione;

Compound 164: 5-(2,3-difluorophenyl)-3-methyl-1-[2-oxo-2-[4-(2-oxo-3H-imidazo[4,5-b]pyridin-1-yl)-1-piperidyl]ethyl]pyrimidine-2,4-dione;

Compound 165: 5-(2-chloro-3-fluorophenyl)-3-((S)-2-methoxy-1-methylethyl)-2,4-dioxo-3,4-dihydro-2H-pyrimidin-1-yl]-1-[(2R)-2'-oxospiro[1,3-dihydroindene-2,3'-1H-pyrrolo[2,3-b]pyridin]-5-yl]acetamide;

Compound 166: 5-(2-chloro-3-fluorophenyl)-3-isopropyl-pyrimidine-2,4-dione-1-[(2R)-2'-oxospiro[1,3-dihydroindene-2,3'-1H-pyrrolo[2,3-b]pyridin]-5-yl]acetamide;

Compound 167: 5-(2,3-difluorophenyl)-3-[(1S)-2-methoxy-1-methylethyl]-pyrimidine-2,4-dione-1-[(2R)-2'-oxospiro[1,3-dihydroindene-2,3'-1H-pyrrolo[2,3-b]pyridin]-5-yl]acetamide;

Compound 168: 2-[5-(2-chloro-3-fluorophenyl)-2,4-dioxo-1H-pyrimidin-3-yl]acetic acid-1-[(2R)-2'-oxospiro[1,3-dihydroindene-2,3'-1H-pyrrolo[2,3-b]pyridin]-5-yl]acetamide;

Compound 169: 5-(2-chloro-3-methoxyphenyl)-3-(2-methylsulphonylethyl)-pyrimidine-2,4-dione-1-[(2R)-2'-oxospiro[1,3-dihydroindene-2,3'-1H-pyrrolo[2,3-b]pyridin]-5-yl]acetamide;

Compound 170: 5-(2,3-dichlorophenyl)-3-(2-methylsulphonylethyl)-pyrimidine-2,4-dione-1-[(2R)-2'-oxospiro[1,3-dihydroindene-2,3'-1H-pyrrolo[2,3-b]pyridin]-5-yl]acetamide;

Compound 171: 5-(2,3-dimethoxyphenyl)-3-[(1R)-2-methoxy-1-methylethyl]-pyrimidine-2,4-dione-1-[(2R)-2'-oxospiro[1,3-dihydroindene-2,3'-1H-pyrrolo[2,3-b]pyridin]-5-yl]acetamide;

Compound 172: 5-(2-chloro-3-fluorophenyl)-3-(2-methylsulphonylethyl)-pyrimidine-2,4-dione-1-[(2R)-2'-oxospiro[1,3-dihydroindene-2,3'-1H-pyrrolo[2,3-b]pyridin]-5-yl]acetamide;

Compound 173: 5-(2-chloro-3-fluorophenyl)-3-(3-methylsulphonylpropyl)-pyrimidine-2,4-dione-1-[(2R)-2'-oxospiro[1,3-dihydroindene-2,3'-1H-pyrrolo[2,3-b]pyridin]-5-yl]acetamide;

Compound 174: 5-(2,3-dichlorophenyl)-3-methyl-pyrimidine-2,4-dione-1-[(2R)-2'-oxospiro[1,3-dihydroindene-2,3'-1H-pyrrolo[2,3-b]pyridin]-5-yl]acetamide;

Compound 175: 5-(2-chloro-3-fluorophenyl)-3-[(1S)-1-methyl-2-methylsulphonyl-ethyl]-pyrimidine-2,4-dione-1-[(2R)-2'-oxospiro[1,3-dihydroindene-2,3'-1H-pyrrolo[2,3-b]pyridin]-5-yl]acetamide;

Compound 176: 5-(2-chloro-3-methoxyphenyl)-3-[2-methoxy-1-(methoxymethyl)ethyl]-pyrimidine-2,4-dione-1-[(2R)-2'-oxospiro[1,3-dihydroindene-2,3'-1H-pyr-rolo[2,3-b]pyridin]-5-yl]acetamide;
Compound 177: 5-(2,3-dichlorophenyl)-3-[(1R)-2-methoxy-1-methylethyl]-pyrimidine-2,4-dione-1-[(2R)-2'-oxospiro[1,3-dihydroindene-2,3'-1H-pyrrolo[2,3-b]pyridin]-5-yl]acetamide;
Compound 178: 5-(2,3-dichlorophenyl)-3-[(1S)-2-methoxy-1-methylethyl]-pyrimidine-2,4-dione-1-[(2R)-2'-oxospiro[1,3-dihydroindene-2,3'-1H-pyrrolo[2,3-b]pyridin]-5-yl]acetamide;
Compound 179: 5-(2-chloro-3-fluorophenyl)-3-[2-methoxy-1-(methoxymethyl)ethyl]-pyrimidine-2,4-dione-1-[(2R)-2'-oxospiro[1,3-dihydroindene-2,3'-1H-pyrrolo[2,3-b]pyridin]-5-yl]acetamide;
Compound 180: N-[2-[5-(2-chloro-3-fluorophenyl)-2,4-dioxo-pyrimidin-3-yl]ethyl]acetamide-1-[(2R)-2'-oxospiro[1,3-dihydroindene-2,3'-1H-pyrrolo[2,3-b]pyridin]-5-yl]acetamide;
Compound 181: 5-(2-chloro-3-fluorophenyl)-3-[(1R)-2-methoxy-1-methylethyl]-pyrimidine-2,4-dione-1-[(2R)-2'-oxospiro[1,3-dihydroindene-2,3'-1H-pyrrolo[2,3-b]pyridin]-5-yl]acetamide;
Compound 182: 5-(2,3-dichlorophenyl)-3-[2-methoxy-1-(methoxymethyl)ethyl]-pyrimidine-2,4-dione-1-[(2R)-2'-oxospiro[1,3-dihydroindene-2,3'-1H-pyrrolo[2,3-b]pyridin]-5-yl]acetamide;
Compound 183: 5-(2-chloro-3-fluorophenyl)-3-[(1R)-2-methoxy-1-methylethyl]-pyrimidine-2,4-dione-1-[(2R)-2'-oxospiro[1,3-dihydroindene-2,3'-1H-pyrrolo[2,3-b]pyridin]-5-yl]acetamide;
Compound 184: 5-(2-chloro-3-fluorophenyl)-3-(2-methanesulphonyl-ethyl)-1-{2-[4-(7-methanesulphonyl-2-oxo-1,2,4,5-tetrahydro-benzo[d][1,3]diazepin-3-yl)-piperidin-1-yl]-2-oxo-ethyl}-1H-pyrimidine-2,4-dione;
Compound 185: 5-(2-chloro-3-fluorophenyl)-3-isopropyl-1-{2-[4-(7-methanesulphonyl-2-oxo-1,2,4,5-tetrahydro-benzo[d][1,3]diazepin-3-yl)-piperidin-1-yl]-2-oxo-ethyl}-1H-pyrimidine-2,4-dione;
Compound 186: 5-(2-chloro-3-fluorophenyl)-3-(2-methanesulphonyl-ethyl)-1-{2-[4-(7-methylsulphanyl-2-oxo-1,2,4,5-tetrahydro-benzo[d][1,3]diazepin-3-yl)-piperidin-1-yl]-2-oxo-ethyl}-1H-pyrimidine-2,4-dione;
Compound 187: 5-(2-chloro-3-fluorophenyl)-3-((R)-2-methoxy-1-methylethyl)-1-{2-[4-(7-methylsulphanyl-2-oxo-1,2,4,5-tetrahydro-benzo[d][1,3]diazepin-3-yl)-piperidin-1-yl]-2-oxo-ethyl}-1H-pyrimidine-2,4-dione;
Compound 188: 5-(2-chloro-3-fluorophenyl)-3-(2-methoxyethyl)-1-{2-[4-(7-methylsulphanyl-2-oxo-1,2,4,5-tetrahydro-benzo[d][1,3]diazepin-3-yl)-piperidin-1-yl]-2-oxo-ethyl}-1H-pyrimidine-2,4-dione;
Compound 189: 5-(2-chloro-3-fluorophenyl)-3-isopropyl-1-{2-[4-(7-methylsulphanyl-2-oxo-1,2,4,5-tetrahydro-benzo[d][1,3]diazepin-3-yl)-piperidin-1-yl]-2-oxo-ethyl}-1H-pyrimidine-2,4-dione;
Compound 190: 3-(1-{2-[5-(2,3-difluorophenyl)-3-methyl-2-oxo-3,4-dihydro-2H-pyrimidin-1-yl]-acetyl}-piperidin-4-yl)-1,3,4,5-tetrahydro-benzo[d][1,3]diazepin-2-one;
Compound 191: 3-(1-{2-[5-(2,3-dichlorophenyl)-3-methyl-2-oxo-3,4-dihydro-2H-pyrimidin-1-yl]-acetyl}-piperidin-4-yl)-1,3,4,5-tetrahydro-benzo[d][1,3]diazepin-2-one;
Compound 192: 3-(1-{2-[5-(2-chloro-3-fluorophenyl)-3-(2-methoxyethyl)-2-oxo-3,4-dihydro-2H-pyrimidin-1-yl]-acetyl}-piperidin-4-yl)-1,3,4,5-tetrahydro-benzo[d][1,3]diazepin-2-one;
Compound 193: 3-(1-{2-[5-(2-chloro-3-methoxyphenyl)-3-isopropyl-2-oxo-3,4-dihydro-2H-pyrimidin-1-yl]-acetyl}-piperidin-4-yl)-1,3,4,5-tetrahydro-benzo[d][1,3]diazepin-2-one;
Compound 194: 3-(1-{2-[5-(2,3-dichlorophenyl)-2-oxo-3-(2,2,2-trifluoroethyl)-3,4-dihydro-2H-pyrimidin-1-yl]-acetyl}-piperidin-4-yl)-1,3,4,5-tetrahydro-benzo[d][1,3]diazepin-2-one;
Compound 195: 1'-[2-[5-(2,3-dichlorophenyl)-3-methyl-2-oxo-4H-pyrimidin-1-yl]acetyl]spiro[1H-pyrido[2,3-d][1,3]oxazine-4,4'-piperidin]-2-one;
Compound 196: 5-(2,3-dichlorophenyl)-3-methyl-1-{2-oxo-2-[4-(2-oxo-4-phenyl-2,3-dihydro-imidazol-1-yl)-piperidin-1-yl]-ethyl}-3,4-dihydro-1H-pyrimidin-2-one;
Compound 197: 3-(1-{2-[5-(2-chloro-3-fluorophenyl)-3-methyl-2-oxo-3,4-dihydro-2H-pyrimidin-1-yl]-acetyl}-piperidin-4-yl)-1,3,4,5-tetrahydro-benzo[d][1,3]diazepin-2-one;
Compound 198: 3-(1-{2-[5-(2-chloro-3-fluorophenyl)-3-ethyl-2-oxo-3,4-dihydro-2H-pyrimidin-1-yl]-acetyl}-piperidin-4-yl)-1,3,4,5-tetrahydro-benzo[d][1,3]diazepin-2-one;
Compound 199: 3-(1-{2-[5-(2,3-dichlorophenyl)-3-ethyl-2-oxo-3,4-dihydro-2H-pyrimidin-1-yl]-acetyl}-piperidin-4-yl)-1,3,4,5-tetrahydro-benzo[d][1,3]diazepin-2-one;
Compound 200: 3-(1-{2-[5-(2-chloro-3-fluorophenyl)-3-isopropyl-2-oxo-3,4-dihydro-2H-pyrimidin-1-yl]-acetyl}-piperidin-4-yl)-1,3,4,5-tetrahydro-benzo[d][1,3]diazepin-2-one;
Compound 201: 3-(1-{2-[5-(2,3-dichlorophenyl)-3-isopropyl-2-oxo-3,4-dihydro-2H-pyrimidin-1-yl]-acetyl}-piperidin-4-yl)-1,3,4,5-tetrahydro-benzo[d][1,3]diazepin-2-one;
Compound 202: N-[2-(5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]acetamide;
Compound 203: N—[(R)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide;
Compound 204: N—[(R)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-2,2,2-trifluoro-acetamide;
Compound 205: N—[(S)-2-(5-(2,3-dichlorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide;
Compound 206: N—[(S)-2-(5-(2-chloro-3-methoxyphenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide;
Compound 207: N-[2-(5-(2,3-dichlorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-ethyl]acetamide;
Compound 208: 5-(2,3-dichlorophenyl)-3-methyl-1-[2-oxo-2-[4-(2-oxo-5-phenyl-1H-imidazol-3-yl)-1-piperidyl]ethyl]pyrimidine-2,4-dione;
Compound 209: 2-[5-(2,3-dichlorophenyl)-3-methyl-2,4-dioxo-pyrimidin-1-yl]-N-[4-(2-oxo-4,5-dihydro-1H-1,3-benzodiazepin-3-yl)-1-piperidyl]acetamide;
Compound 210: 5-(2,3-dichlorophenyl)-3-isopropyl-1-[2-oxo-2-[4-(2-oxo-4,5-dihydro-1H-1,3-benzodiazepin-3-yl)-1-piperidyl]ethyl]pyrimidine-2,4-dione;

Compound 211: 5-(2,3-dichlorophenyl)-3-methyl-1-[2-oxo-2-(2-oxospiro[1H-pyrido[2,3-d][1,3]oxazine-4,4'-piperidin]-1'-yl)ethyl]pyrimidine-2,4-dione;

Compound 212: 2-[3-ethyl-2,4-dioxo-1-[2-oxo-2-[4-(2-oxo-4,5-dihydro-1H-1,3-benzodiazepin-3-yl)-1-piperidyl]ethyl]pyrimidin-5-yl]benzonitrile;

Compound 213: 5-(2,3-dichlorophenyl)-3-methyl-1-[2-oxo-2-[4-(2-oxo-4,5-dihydro-1H-pyrido[2,3-d][1,3]diazepin-3-yl)-1-piperidyl]ethyl]pyrimidine-2,4-dione;

Compound 214: 5-(2,3-dimethylphenyl)-3-methyl-1-[2-oxo-2-[4-(2-oxo-5-phenyl-1H-imidazol-3-yl)-1-piperidyl]ethyl]pyrimidine-2,4-dione;

Compound 215: 5-(2,3-dichlorophenyl)-3-methyl-1-[2-oxo-2-[4-(2-oxo-1H-quinolin-3-yl)-1-piperidyl]ethyl]pyrimidine-2,4-dione;

Compound 216: 5-(2,3-dimethylphenyl)-3-isopropyl-1-[2-oxo-2-[4-(2-oxo-4,5-dihydro-1H-pyrido[4,3-d][1,3]diazepin-3-yl)-1-piperidyl]ethyl]pyrimidine-2,4-dione;

Compound 217: 5-(2,3-dimethylphenyl)-3-isopropyl-1-[2-oxo-2-[4-(2-oxo-4,5-dihydro-1H-pyrido[3,2-d][1,3]diazepin-3-yl)-1-piperidyl]ethyl]pyrimidine-2,4-dione;

Compound 218: 5-(2,3-dimethylphenyl)-3-isopropyl-1-[2-oxo-2-[4-(2-oxo-4,5-dihydro-1H-pyrido[2,3-d][1,3]diazepin-3-yl)-1-piperidyl]ethyl]pyrimidine-2,4-dione;

Compound 219: 5-(2,3-dimethylphenyl)-3-methyl-1-[2-[4-(1-methyl-2-oxo-4,5-dihydro-1,3-benzodiazepin-3-yl)-1-piperidyl]-2-oxo-ethyl]pyrimidine-2,4-dione;

Compound 220: 5-(3,4-dichlorophenyl)-3-methyl-1-[2-oxo-2-[4-(2-oxo-4,5-dihydro-1H-1,3-benzodiazepin-3-yl)-1-piperidyl]ethyl]pyrimidine-2,4-dione;

Compound 221: 1-[2-[4-(7-bromo-2-oxo-4,5-dihydro-1H-1,3-benzodiazepin-3-yl)-1-piperidyl]-2-oxo-ethyl]-5-(2-chloro-3-fluorophenyl)-3-isopropyl-pyrimidine-2,4-dione;

Compound 222: 5-(2-chloro-3-fluorophenyl)-3-isopropyl-1-[2-[4-methyl-4-(2-oxo-4,5-dihydro-1H-1,3-benzodiazepin-3-yl)-1-piperidyl]-2-oxo-ethyl]pyrimidine-2,4-dione;

Compound 223: 5-(2-chloro-3-fluorophenyl)-3-isopropyl-1-[2-[(2S)-2-methyl-4-(2-oxo-4,5-dihydro-1H-1,3-benzodiazepin-3-yl)-1-piperidyl]-2-oxo-ethyl]pyrimidine-2,4-dione;

Compound 224: 2-[5-(2-chloro-3-fluorophenyl)-2,6-dioxo-3-[2-oxo-2-[4-(2-oxo-4,5-dihydro-1H-1,3-benzodiazepin-3-yl)-1-piperidyl]ethyl]pyrimidin-1-yl]propanoic acid;

Compound 225: 5-(2-chloro-3-fluorophenyl)-3-isopropyl-1-[2-[4-(7-methylsulphinyl-2-oxo-4,5-dihydro-1H-1,3-benzodiazepin-3-yl)-1-piperidyl]-2-oxo-ethyl]pyrimidine-2,4-dione;

Compound 226: 2-[5-(2-chloro-3-fluorophenyl)-2,6-dioxo-3-[2-oxo-2-[4-(2-oxo-4,5-dihydro-1H-1,3-benzodiazepin-3-yl)-1-piperidyl]ethyl]pyrimidin-1-yl]acetamide;

Compound 227: 5-(2-chloro-3-fluorophenyl)-3-(2-methylsulphinylethyl)-1-[2-oxo-2-[4-(2-oxo-4,5-dihydro-1H-1,3-benzodiazepin-3-yl)-1-piperidyl]ethyl]pyrimidine-2,4-dione;

Compound 228: 5-(2-chloro-3-fluorophenyl)-3-(2-methylsulphonylethyl)-1-[2-oxo-2-[4-(2-oxo-4,5-dihydro-1H-1,3-benzodiazepin-3-yl)-1-piperidyl]ethyl]pyrimidine-2,4-dione;

Compound 229: 5-(2-chloro-3-fluorophenyl)-3-((S)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione;

Compound 230: 5-(2-chloro-3-fluorophenyl)-3-isopropyl-1-[2-[4-(7-methoxy-5,5-dimethyl-2-oxo-1,4-dihydro-1,3-benzodiazepin-3-yl)-1-piperidyl]-2-oxo-ethyl]pyrimidine-2,4-dione;

Compound 231: 5-(2,3-difluorophenyl)-3-[methoxy-1-(methoxymethyl)ethyl]-1-[2-[4-(7-methoxy-2-oxo-4,5-dihydro-1H-1,3-benzodiazepin-3-yl)-1-piperidyl]-2-oxo-ethyl]pyrimidine-2,4-dione;

Compound 232: 5-(2-chloro-3-fluorophenyl)-3-[2-methoxy-1-(methoxymethyl)ethyl]-1-[2-[4-(7-methoxy-2-oxo-4,5-dihydro-1H-1,3-benzodiazepin-3-yl)-1-piperidyl]-2-oxo-ethyl]pyrimidine-2,4-dione;

Compound 233: 5-(2-chloro-3-fluorophenyl)-3-[(1S)-2-methoxy-1-methylethyl]-1-[2-[4-(7-methylsulphanyl-2-oxo-4,5-dihydro-1H-1,3-benzodiazepin-3-yl)-1-piperidyl]-2-oxo-ethyl]pyrimidine-2,4-dione;

Compound 234: 5-(2-chloro-3-fluorophenyl)-3-(2-hydroxy-2-methylpropyl)-1-[2-oxo-2-[4-(2-oxo-4,5-dihydro-1H-1,3-benzodiazepin-3-yl)-1-piperidyl]ethyl]pyrimidine-2,4-dione;

Compound 235: 5-(2-chloro-3-fluorophenyl)-1-[2-oxo-2-[4-(2-oxo-4,5-dihydro-1H-1,3-benzodiazepin-3-yl)-1-piperidyl]ethyl]-3-(2H-tetrazol-5-ylmethyl)pyrimidine-2,4-dione;

Compound 236: 5-(2,3-difluorophenyl)-3-(2-methylsulphonylethyl)-1-[2-oxo-2-[4-(2-oxo-4,5-dihydro-1H-1,3-benzodiazepin-3-yl)-1-piperidyl]ethyl]pyrimidine-2,4-dione;

Compound 237: 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-[(1S)-1-methylpropyl]pyrimidine-2,4-dione;

Compound 238: 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-[(1R)-1-methylpropyl]pyrimidine-2,4-dione;

Compound 239: 5-(2-chloro-3-fluorophenyl)-3-[1-(methoxymethyl)propyl]-1-[2-[4-(7-methoxy-2-oxo-4,5-dihydro-1H-1,3-benzodiazepin-3-yl)-1-piperidyl]-2-oxo-ethyl]pyrimidine-2,4-dione;

Compound 240: 5-(2-chloro-3-fluorophenyl)-3-(2-methoxy-2-methylpropyl)-1-[2-[4-(7-methoxy-2-oxo-4,5-dihydro-1H-1,3-benzodiazepin-3-yl)-1-piperidyl]-2-oxo-ethyl]pyrimidine-2,4-dione;

Compound 241: 5-(2-chloro-3-methoxyphenyl)-3-[2-methoxy-1-(methoxymethyl)ethyl]-1-[2-[4-(7-methoxy-2-oxo-4,5-dihydro-1H-1,3-benzodiazepin-3-yl)-1-piperidyl]-2-oxo-ethyl]pyrimidine-2,4-dione;

Compound 242: 5-(2,3-dichlorophenyl)-3-(2-methylsulphonylethyl)-1-[2-oxo-2-[4-(2-oxo-4,5-dihydro-1H-1,3-benzodiazepin-3-yl)-1-piperidyl]ethyl]pyrimidine-2,4-dione;

Compound 243: 5-(2-chloro-3-methoxyphenyl)-3-(2-methylsulphonylethyl)-1-[2-oxo-2-[4-(2-oxo-4,5-dihydro-1H-1,3-benzodiazepin-3-yl)-1-piperidyl]ethyl]pyrimidine-2,4-dione;

Compound 244: 5-(2-chloro-3-fluorophenyl)-3-[(1S)-1-methyl-2-methylsulphonyl-ethyl]-1-[2-oxo-2-[4-(2-oxo-4,5-dihydro-1H-1,3-benzodiazepin-3-yl)-1-piperidyl]ethyl]pyrimidine-2,4-dione;

Compound 245: 5-(2,3-dichlorophenyl)-3-[2-methoxy-1-(methoxymethyl)ethyl]-1-[2-[4-(7-methoxy-2-oxo-4,5-dihydro-1H-1,3-benzodiazepin-3-yl)-1-piperidyl]-2-oxo-ethyl]pyrimidine-2,4-dione;

Compound 246: 3-[5-(2-chloro-3-fluorophenyl)-3-[2-[4-(7-methoxy-2-oxo-4,5-dihydro-1H-1,3-benzodiazepin-3-yl)-1-piperidyl]-2-oxo-ethyl]-2,6-dioxo-pyrimidin-1-yl]propanoic acid;

Compound 247: 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-[2-(1,3,4-oxadiazol-2-yl)ethyl]pyrimidine-2,4-dione;

Compound 248: 2-[5-(2-chloro-3-fluorophenyl)-3-[2-[4-(7-methoxy-2-oxo-4,5-dihydro-1H-1,3-benzodiazepin-3-yl)-1-piperidyl]-2-oxo-ethyl]-2,6-dioxo-pyrimidin-1-yl]acetic acid;

Compound 249: 5-(2-chloro-3-fluorophenyl)-3-[(1R)-1-methyl-2-methylsulphonyl-ethyl]-1-[2-oxo-2-[4-(2-oxo-4,5-dihydro-1H-1,3-benzodiazepin-3-yl)-1-piperidyl]ethyl]pyrimidine-2,4-dione;

Compound 250: 5-(2-chloro-3-fluorophenyl)-3-(2-methylsulphonylethyl)-1-[2-oxo-2-[2-(2-oxo-4,5-dihydro-1H-1,3-benzodiazepin-3-yl)-6-azaspiro[3.3]heptan-6-yl]ethyl]pyrimidine-2,4-dione;

Compound 251: 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-[2-(1,2,4-triazol-4-yl)ethyl]pyrimidine-2,4-dione;

Compound 252: 5-(2-chloro-3-fluorophenyl)-1-[2-[4-(7-fluoro-2-oxo-4,5-dihydro-1H-1,3-benzodiazepin-3-yl)-1-piperidyl]-2-oxo-ethyl]-3-[(1R)-1-methyl-2-methylsulphonyl-ethyl]pyrimidine-2,4-dione;

Compound 253: 3-[1-[2-[5-(2-chloro-3-fluorophenyl)-3-(2-methylsulphonylethyl)-2,4-dioxo-pyrimidin-1-yl]acetyl]-4-piperidyl]-2-oxo-4,5-dihydro-1H-1,3-benzodiazepine-7-carboxylic acid;

Compound 254: S-[2-[5-(2-chloro-3-fluorophenyl)-3-[2-[4-(7-methoxy-2-oxo-4,5-dihydro-1H-1,3-benzodiazepin-3-yl)-1-piperidyl]-2-oxo-ethyl]-2,6-dioxo-pyrimidin-1-yl]ethyl]ethanethioate;

Compound 255: N-[(2S)-2-[5-(2,3-dichlorophenyl)-2,6-dioxo-3-[2-oxo-2-[4-(2-oxo-4,5-dihydro-1H-1,3-benzodiazepin-3-yl)-1-piperidyl]ethyl]pyrimidin-1-yl]propyl]acetamide;

Compound 256: N-[(2S)-2-[5-(2-chloro-3-fluorophenyl)-2,6-dioxo-3-[2-oxo-2-[4-(2-oxo-4,5-dihydro-1H-1,3-benzodiazepin-3-yl)-1-piperidyl]ethyl]pyrimidin-1-yl]propyl]acetamide;

Compound 257: 2-[5-(2-chloro-3-fluorophenyl)-3-[2-[4-(7-methoxy-2-oxo-4,5-dihydro-1H-1,3-benzodiazepin-3-yl)-1-piperidyl]-2-oxo-ethyl]-2,6-dioxo-pyrimidin-1-yl]ethanesulphonic acid;

Compound 258: 5-(2-chloro-3-fluorophenyl)-3-[(1S)-1-(methoxymethyl)-2-methylsulphonyl-ethyl]-1-[2-[4-(7-methoxy-2-oxo-4,5-dihydro-1H-1,3-benzodiazepin-3-yl)-1-piperidyl]-2-oxo-ethyl]pyrimidine-2,4-dione;

Compound 259: 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-(2-methyl-2-methylsulphonyl-propyl)pyrimidine-2,4-dione;

Compound 260: N-[(2S)-2-[5-(2-chloro-3-methoxyphenyl)-3-[2-[4-(7-methoxy-2-oxo-4,5-dihydro-1H-1,3-benzodiazepin-3-yl)-1-piperidyl]-2-oxo-ethyl]-2,6-dioxo-pyrimidin-1-yl]propyl]propanamide;

Compound 261: N-[(2S)-2-[5-(2,3-dichlorophenyl)-3-[2-[4-(7-methoxy-2-oxo-4,5-dihydro-1H-1,3-benzodiazepin-3-yl)-1-piperidyl]-2-oxo-ethyl]-2,6-dioxo-pyrimidin-1-yl]propyl]propanamide;

Compound 262: N-[(2S)-2-[5-(2-chloro-3-fluorophenyl)-3-[2-[4-(7-methoxy-2-oxo-4,5-dihydro-1H-1,3-benzodiazepin-3-yl)-1-piperidyl]-2-oxo-ethyl]-4-methyl-2,6-dioxo-pyrimidin-1-yl]propyl]acetamide;

Compound 263: N-[(2S)-2-[5-(2-chloro-3-fluorophenyl)-3-[2-[4-(7-methoxy-2-oxo-4,5-dihydro-1H-1,3-benzodiazepin-3-yl)-1-piperidyl]-2-oxo-ethyl]-2,6-dioxo-pyrimidin-1-yl]propyl]-2-methyl-propanamide;

Compound 264: N-[(2S)-2-[5-(2-chloro-3-methoxyphenyl)-3-[2-[4-(7-methoxy-2-oxo-4,5-dihydro-1H-1,3-benzodiazepin-3-yl)-1-piperidyl]-2-oxo-ethyl]-2,6-dioxo-pyrimidin-1-yl]propyl]-2-methyl-propanamide;

Compound 265: 3-[1-[2-[5-(2-chloro-3-fluorophenyl)-3-(2-methoxyethyl)-4,4-dimethyl-2-oxo-pyrimidin-1-yl]acetyl]-4-piperidyl]-8-methoxy-4,5-dihydro-1H-1,3-benzodiazepin-2-one;

Compound 266: 3-[1-[2-[4-(2-chloro-3-fluorophenyl)-8-[(1S)-2-methoxy-1-methylethyl]-7-oxo-6,8-diazaspiro[2.5]oct-4-en-6-yl]acetyl]-4-piperidyl]-8-methoxy-4,5-dihydro-1H-1,3-benzodiazepin-2-one;

Compound 267: N-[(2S)-2-[5-(2-chloro-3-methoxyphenyl)-3-[2-[4-(8-methoxy-2-oxo-4,5-dihydro-1H-1,3-benzodiazepin-3-yl)-1-piperidyl]-2-oxo-ethyl]-6,6-dimethyl-2-oxo-pyrimidin-1-yl]propyl]acetamide;

Compound 268: N-[(2S)-2-[4-(2-chloro-3-methoxyphenyl)-6-[2-[4-(8-methoxy-2-oxo-4,5-dihydro-1H-1,3-benzodiazepin-3-yl)-1-piperidyl]-2-oxo-ethyl]-7-oxo-6,8-diazaspiro[2.5]oct-4-en-8-yl]propyl]acetamide;

Compound 269: N-[(2S)-2-[5-(2-chloro-3-fluorophenyl)-3-[2-[4-(5,5-difluoro-7-methoxy-2-oxo-1,4-dihydro-1,3-benzodiazepin-3-yl)-1-piperidyl]-2-oxo-ethyl]-2,6-dioxo-pyrimidin-1-yl]propyl]acetamide;

Compound 270: N-[(2S)-2-[5-(2-chloro-3-fluorophenyl)-3-[2-[4-(5-fluoro-7-methoxy-2-oxo-4,5-dihydro-1H-1,3-benzodiazepin-3-yl)-1-piperidyl]-2-oxo-ethyl]-2,6-dioxo-pyrimidin-1-yl]propyl]acetamide;

Compound 271: N-[(2S)-2-[5-(2-chloro-3-fluorophenyl)-3-[2-[4-(4-fluoro-7-methoxy-2-oxo-4,5-dihydro-1H-1,3-benzodiazepin-3-yl)-1-piperidyl]-2-oxo-ethyl]-2,6-dioxo-pyrimidin-1-yl]propyl]acetamide;

Compound 272: N-[(2S)-2-[5-(2-chloro-3-fluorophenyl)-3-[2-[2,6-dimethyl-4-(2-oxo-4,5-dihydro-1H-1,3-benzodiazepin-3-yl)-1-piperidyl]-2-oxo-ethyl]-2,6-dioxo-pyrimidin-1-yl]propyl]acetamide;

Compound 273: N-[(2S)-2-[5-(2-chloro-3-fluorophenyl)-3-[2-[3,5-dimethyl-4-(2-oxo-4,5-dihydro-1H-1,3-benzodiazepin-3-yl)-1-piperidyl]-2-oxo-ethyl]-2,6-dioxo-pyrimidin-1-yl]propyl]acetamide;

Compound 274: N—[(S)-2-(5-(2-chloro-3-fluorophenyl)-3-{1-fluoro-2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide;

Compound 275: N—[(S)-2-(5-(2-chloro-3-fluorophenyl)-4-fluoro-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide;

Compound 276: N—[(S)-2-(5-(2-chloro-3-fluorophenyl)-3-{2-[3-fluoro-4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide;

Compound 277: N—[(S)-2-(5-(2-chloro-3-methoxyphenyl)-3-{2-[4-(7-methoxy-2,5-dioxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide.

The compounds according to the invention are even more preferably selected from the compounds of general formula (I) in which:
Y is selected from —CH₂ or —C(O);
R1 is selected from the following groups:
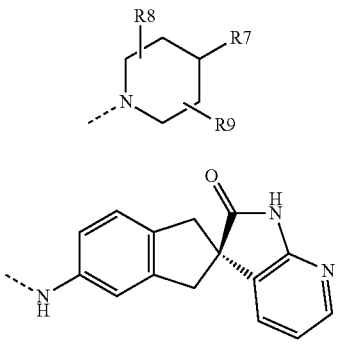
(1-1)
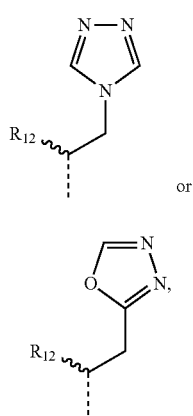
(1-8)
R2, R3, R6 are a hydrogen atom;
R4 is selected from a C1-C4 alkyl, a heteroaralkyl of formula
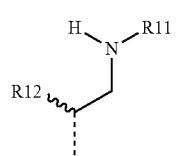
(4-56)
or
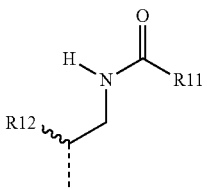
(4-57),
or the following groups:
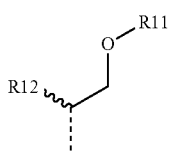
(4-4)
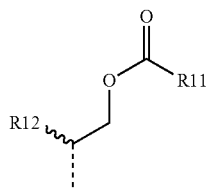
(4-8)
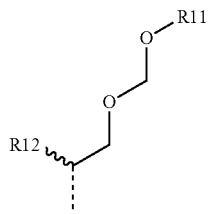
(4-10)
(4-11)
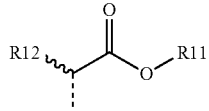
(4-15)
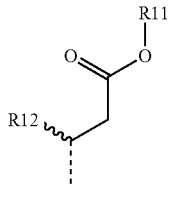
(4-16)
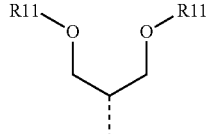
(4-17)
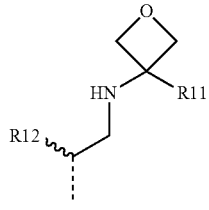
(4-18)
(4-19)
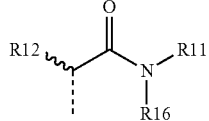
(4-21)
(4-23)

-continued
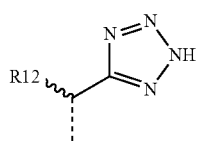 (4-24)
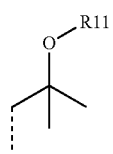 (4-25)
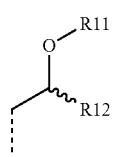 (4-27)
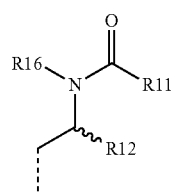 (4-28)
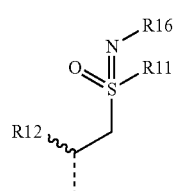 (4-29)
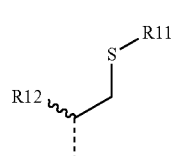 (4-32)
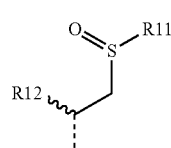 (4-33)
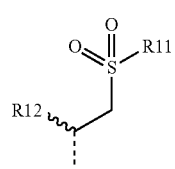 (4-34)
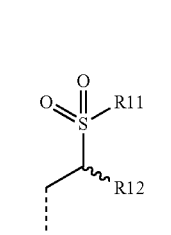 (4-35)
-continued
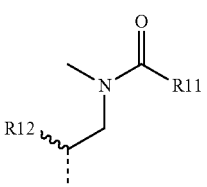 (4-36)
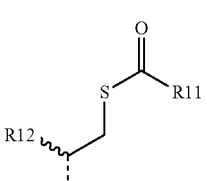 (4-37)
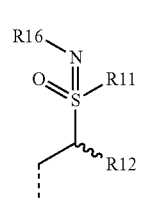 (4-38)
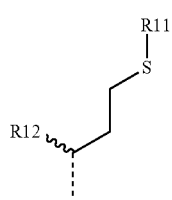 (4-40)
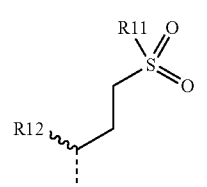 (4-42)
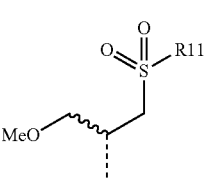 (4-44)
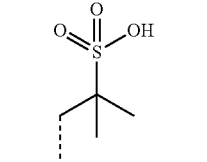 (4-45)
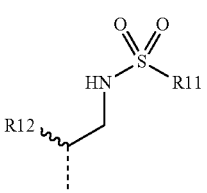 (4-47)

(4-49)

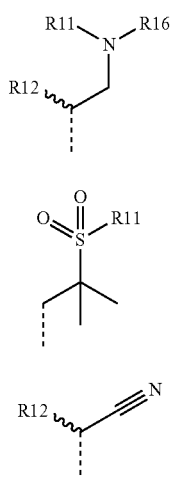

R5 is

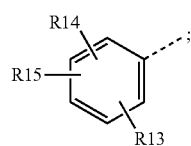

R7 is selected from the following groups:

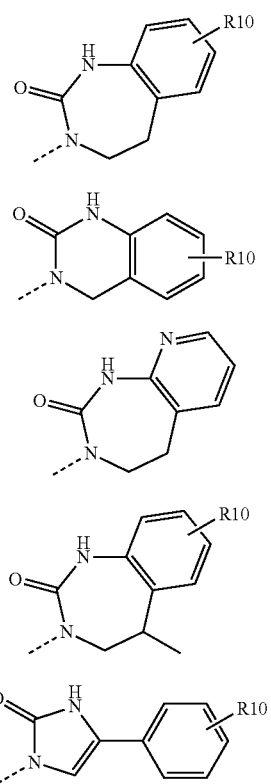

(4-49)
(4-52)
(4-53)
(5-1)
(7-1)
(7-2)
(7-3)
(7-12)
(7-18)

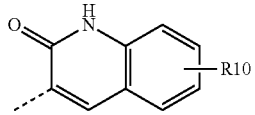

(7-20)

R8, R9 are a hydrogen atom;
R10 is selected from a hydrogen atom, —OR11, —SR11, —S(O)R11, —SO₂R11, —CO₂H or a halogen selected from Br or F;
R11, R12, which may be identical or different, are selected from a hydrogen atom or a C1-C2 alkyl;
R13, R14, R15, which may be identical or different, are selected from a hydrogen atom, —CH₃, —OR16, a halogen, or —OCF₃; and
R16 is selected from a hydrogen atom or an alkyl.

For this purpose, the compounds according to the invention are even more preferably selected from the compounds listed in Table I below and for which the antagonist activity to the CGRP receptor, defined by the apparent Kd or Kdapp, is less than 10 nM (indicated as class A in Table I).

Among the compounds according to the invention, when Y is —C(O), the compounds according to the invention are advantageously uracil derivatives.

According to a particularly preferred embodiment of the invention, the compounds are selected from the compounds of general formula (I) in which:
Y is —C(O);
R1 is selected from the following groups:

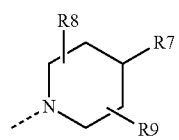

(1-1)

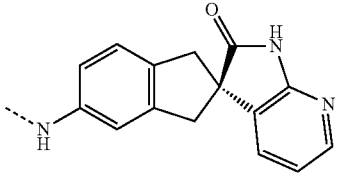

(1-8)

R2, R3, R6 are a hydrogen atom;
R4 is selected from the following groups:

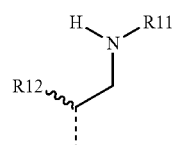

(4-4)

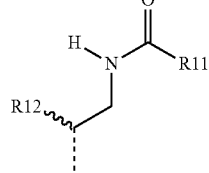

(4-8)

-continued

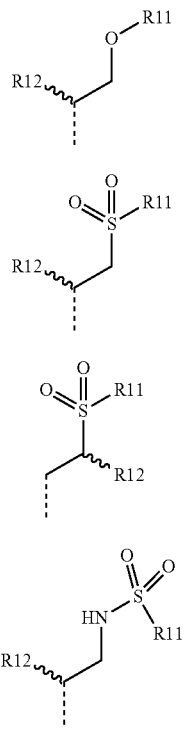

(4-10)

(4-34)

(4-35)

(4-47)

R5 is

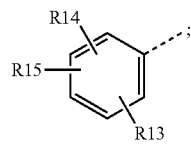

(5-1)

R7 is

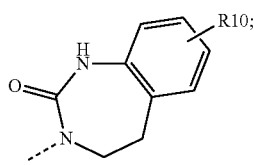

(7-1)

R8, R9 are a hydrogen atom;
R10 is selected from a hydrogen atom, —OR11, —SR11 or Br;
R11, R12, which may be identical or different, are selected from a hydrogen atom or a C1-C2 alkyl;
R13, R14, R15, which may be identical or different, are selected from a hydrogen atom, —OR16, or a halogen selected from F and Cl; and
R16 is a C1-C3 alkyl.

According to an even more particularly preferred embodiment of the invention, the compounds are selected from the compounds of general formula (I) in which:

Y is —C(O);
R1 is

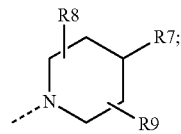

(1-1)

R2, R3, R6 are a hydrogen atom;
R4 is

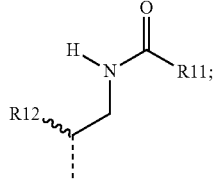

(4-8)

R5 is

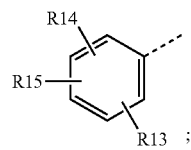

(5-1)

R7 is

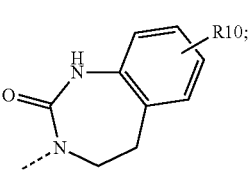

(7-1)

R8, R9 are a hydrogen atom;
R10 is —OR11;
R11, R12, which may be identical or different, are selected from —CH₃ or —CH₂CH₃;
R13, R14, R15, which may be identical or different, are selected from a hydrogen atom, —OR16, or a halogen selected from F and Cl; and
R16 is a C1-C3 alkyl.

Various examples of preparation of the compounds according to the invention will be described, for purposes of illustration and without being limiting in any way.

The compounds corresponding to the present invention may be obtained, non-exhaustively, using conventional conditions in organic synthesis according to the general reaction routes described in reaction schemes No. 1, 2, 3 and 4 in FIGS. 1, 2, 3 and 4, respectively. The experimental conditions relating to each synthesis scheme are disclosed in the examples given below, which in each case refer to the scheme followed for their preparation. Thus, a person skilled in the art will be able to assess whether the conditions described in these schemes are suitable for introducing the desired functional groups and optionally he will adapt the synthesis route by using suitable protecting groups that are stable in the reaction conditions. Certain intermediates, allowing introduction of certain groups R1 envisaged in our compounds, are obtained beforehand following the methods of preparation already described in the literature or described in the examples hereunder.

More particularly, the examples given below describe non-exhaustively the procedures followed for obtaining the compounds according to synthesis schemes No. 1, 2, 3 or 4. Each compound is mainly characterized by its $^1$H NMR spectrum recorded on a Bruker 400 MHz nuclear magnetic resonance spectrometer.

EXAMPLE 1: 5-(3,4-DIFLUOROPHENYL)-3-METHYL-1-{2-OXO-2-[4-(2-OXO-1,4-DIHYDRO-2H-QUINAZOLIN-3-YL)-PIPERIDIN-1-YL]-ETHYL}-1H-PYRIMIDINE-2,4-DIONE (REACTION SCHEME 1, COMPOUND 1)

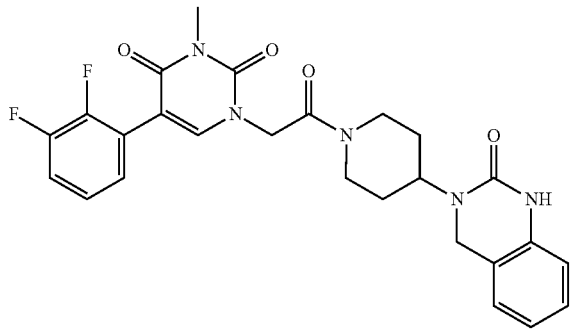 [SMILES: Cn1c(=O)c(-c2cccc(F)c2F)cn(CC(=O)N2CCC(N3Cc4ccccc4NC3=O)CC2)c1=O]

1.1: [2-(1-benzyl-piperidin-4-ylcarbamoyl)-phenyl]-tert-butyl carbamate 8.9 g (46.3 mmol) of 1-ethyl-3-(3-dimethylaminopropyl)carbodiimide hydrochloride is added to a solution of 10 g (42.1 mmol) of 2-tert-butoxycarbonylaminobenzoic acid, 10.3 ml (50.6 mmol) of 1-benzyl-piperidin-4-ylamine, 6.3 g (46.3 mmol) of l-hydroxybenzotriazole and 17.6 ml (126.3 mmol) of triethylamine, in 120 ml of dimethylformamide. The reaction mixture is then stirred before adding [ . . . ]. The reaction mixture is heated at 70° C. for 5 hours and then hydrolysed with an aqueous solution of sodium hydrogen carbonate and diluted with ethyl acetate. The product is extracted with ethyl acetate. The organic phase is washed twice with a saturated aqueous solution of sodium hydrogen carbonate and then with a saturated aqueous solution of sodium chloride and with water, dried over magnesium sulphate and filtered. The solvents are concentrated under vacuum. 17 g (100%) of [2-(1-benzyl-piperidin-4-ylcarbamoyl)-phenyl]-tert-butyl carbamate is obtained in the form of a beige solid.

1.2: 2-amino-N-(1-benzyl-piperidin-4-yl)-benzamide 30 mL (415 mmol) of trifluoroacetic acid is added dropwise to a solution of 17 g (41.5 mmol) of 2-(1-benzyl-piperidin-4-ylcarbamoyl)-phenyl]-tert-butyl carbamate in 170 ml of dichloromethane previously cooled to 0° C. The reaction mixture is stirred from 0° C. to room temperature for 20 hours. After concentration under vacuum, the residue is hydrolysed with an aqueous solution of sodium hydrogen carbonate and then diluted with ethyl acetate. The product is extracted twice with ethyl acetate. The organic phase is washed once with water and then once with a saturated aqueous solution of sodium chloride, dried over magnesium sulphate, filtered and concentrated under vacuum. 14 g (100%) of 2-amino-N-(1-benzyl-piperidin-4-yl)-benzamide is obtained in the form of a beige solid.

1.3: (2-aminobenzyl)-(1-benzyl-piperidin-4-yl)-amine 12 g (38.8 mmol) of 2-amino-N-(1-benzyl-piperidin-4-yl)-benzamide diluted in 72 ml of dioxane is added very slowly to a solution of 5.2 g (135.7 mmol) of lithium aluminium hydride in 260 ml of dioxane, previously heated under reflux. The reaction mixture (grey suspension) is then stirred and heated under reflux for 3 hours. The mixture is cooled to 0° C. and then hydrolysed slowly with 5.2 ml of 15M aqueous soda and 15.5 ml of water. The reaction mixture is then diluted with 240 ml of diethyl ether and stirred at room temperature for 55 minutes. After filtration of the salts, the filtrate is concentrated under vacuum to give 10.7 g (93%) of (2-aminobenzyl)-(1-benzyl-piperidin-4-yl)-amine in the form of a clear oil.

1.4: 3-(1-benzyl-piperidin-4-yl)-3,4-dihydro-1H-quinazolin-2-one 0.9 g (5.7 mmol) of carbonyl diimidazole is added to a solution of 1.6 g (5.2 mmol) of (2-aminobenzyl)-(1-benzyl-piperidin-4-yl)-amine in 25 ml of tetrahydrofuran. The reaction mixture is stirred at room temperature for 5 hours. The solvent is removed under vacuum and then the reaction mixture is hydrolysed and diluted with ethyl acetate. After extraction with ethyl acetate, the organic phases are washed twice with water and then with a saturated aqueous solution of sodium chloride, dried over magnesium sulphate, filtered and concentrated under vacuum. The crude solid obtained is triturated in 15 ml of diethyl ether, then filtered and dried under vacuum to give 1.2 g (72%) of 3-(1-benzyl-piperidin-4-yl)-3,4-dihydro-1H-quinazolin-2-one in the form of a white solid.

1.5: 3-piperidin-4-yl-3,4-dihydro-1H-quinazolin-2-one 120 mg of palladium on charcoal (10 wt %) is added to a solution of 1.2 g (3.7 mmol) of 3-(1-benzyl-piperidin-4-yl)-3,4-dihydro-1H-quinazolin-2-one in 30 ml of methanol, previously degassed with nitrogen. The mixture is then placed under a dihydrogen atmosphere for 48 hours and then filtered on Celite. The filtrate is concentrated under vacuum to give 0.9 g (100%) of 3-piperidin-4-yl-3,4-dihydro-1H-quinazolin-2-one in the form of a white solid.

1.6: 5-bromo-1-{2-oxo-2-[4-(2-oxo-1,4-dihydro-2H-quinazolin-3-yl)-piperidin-1-yl]-ethyl}-1H-pyrimidine-2,4-dione 326 mg (2.4 mmol) of 1-hydroxybenzotriazole and 462 mg (2.4 mmol) of 1-ethyl-3-(3-dimethylaminopropyl)carbodiimide hydrochloride are added to a solution of 500 mg (2 mmol) of (5-bromo-2,4-dioxo-3,4-dihydro-2H-pyrimidin-1-yl)-acetic acid in 12 ml of dimethylformamide. After stirring at room temperature for 10 minutes, 560 mg (2.4 mmol) of 3-piperidin-4-yl-3,4-dihydro-1H-quinazolin-2-one is added.

The reaction mixture is then stirred at room temperature for 18 hours and then hydrolysed with an aqueous solution of sodium hydrogen carbonate and diluted with 20 ml of ethyl acetate. The product is extracted with ethyl acetate and then with n-butanol. The organic phases are combined, washed once with saturated aqueous solution of sodium hydrogen carbonate and once with a saturated aqueous solution of sodium chloride, dried over magnesium sulphate, filtered and concentrated under vacuum. The crude residue is taken up in heptane/ethyl acetate mixture, then filtered and dried under nitrogen. 900 mg (97%) of 5-bromo-1-{2-oxo-2-[4-(2-oxo-1,4-dihydro-2H-quinazolin-3-yl)-piperidin-1-yl]-ethyl}-1H-pyrimidine-2,4-dione is obtained in the form of an off-white solid.

1.7: 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione 143 mg (1 mmol) of potassium carbonate and 0.1 ml (1.3 mmol) of methyl iodide are added to a solution of 400 mg (0.9 mmol) of 5-bromo-1-{2-oxo-2-[4-(2-oxo-1,4-dihydro-2H-quinazolin-3-yl)-piperidin-1-yl]-ethyl}-1H-pyrimidine-2,4-dione in 12 ml of dimethylformamide. The reaction mixture is stirred at room temperature for 3 hours, then hydrolysed and diluted with ethyl acetate. The product is extracted with ethyl acetate. The organic phases are washed once with water, then with a saturated aqueous solution of sodium chloride, dried over magnesium sulphate, filtered and concentrated under vacuum. The crude residue is purified by preparative thin-layer chromatography, eluted with a dichloromethane/methanol 90/10 mixture. 160 mg (39%) of 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione is obtained in the form of a pale yellow solid.

1.8: 5-(3,4-difluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione (Compound 1)

19 mg (0.01 mmol) of tetrakis(triphenylphosphine)palladium(0) and 265 mg (1.7 mmol) of 2,3-difluorophenylboronic acid are added to a solution of 160 mg (0.3 mmol) of 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione and 0.5 ml (1 mmol) of 2M aqueous solution of potassium carbonate in 12 ml of dimethylformamide and 2 ml of water, previously degassed with nitrogen. The reaction mixture is heated at 90° C. for 2 hours. The reaction mixture is treated by adding water and then the product is extracted three times with ethyl acetate. The organic phase is washed with water and then with a saturated solution of sodium chloride, dried over magnesium sulphate, filtered and concentrated under vacuum. The crude residue obtained is purified by silica gel chromatography eluted with a dichloromethane/methanol 95/5 mixture. 60 mg (36%) of 5-(3,4-difluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione is obtained in the form of a white solid with a melting point of 170° C.

$^1$H NMR (δ, DMSO): 1.56-1.75 (m, 3H), 1.76-1.91 (m, 1H), 2.70 (t, J=12.8 Hz, 1H), 3.17 (t, J=12.8 Hz, 1H), 3.26 (s, 3H), 3.98 (d, J=13.5 Hz, 1H), 4.30 (d, J=3.9 Hz, 2H), 4.35-4.51 (m, 2H), 4.81 (s, 2H), 6.77 (d, J=8.0 Hz, 1H), 6.86 (t, J=7.5 Hz, 1H), 7.07-7.17 (m, 2H), 7.18-7.32 (m, 2H), 7.40-7.53 (m, 1H), 7.94 (s, 1H), 9.27 (s, 1H).

EXAMPLE 2: 5-(2-FLUOROPHENYL)-3-METHYL-1-{2-OXO-2-[4-(2-OXO-1,4-DIHYDRO-2H-QUINAZOLIN-3-YL)-PIPERIDIN-1-YL]-ETHYL}-1H-PYRIMIDINE-2,4-DIONE (REACTION SCHEME 2, COMPOUND 2)

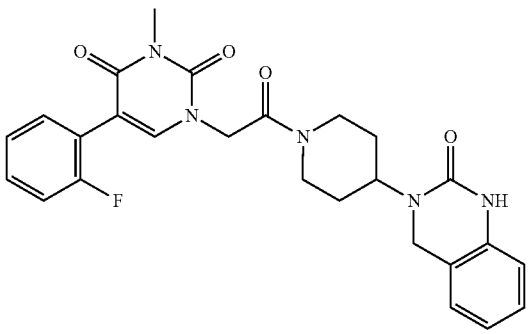 [SMILES: Cn1c(=O)c(-c2ccccc2F)cn(CC(=O)N2CCC(N3Cc4ccccc4NC3=O)CC2)c1=O]

2.1: 1-benzhydryl-5-bromo-1H-pyrimidine-2,4-dione 6.4 mL (26.2 mmol) of N,O-bis(trimethylsilyl)acetamide is added to a solution of 2 g (10.5 mmol) of 5-bromo-1H-pyrimidine-2,4-dione in 40 ml of acetonitrile. The reaction mixture is stirred until a clear solution is obtained, then 3.9 g (15.8 mmol) of benzhydryl bromide and 267 mg (1.1 mmol) of iodine are added. The reaction mixture is heated under reflux for 5 hours and then left at room temperature for 18 hours. The solvents are concentrated under vacuum and then the residue is taken up in 50 ml of ethyl acetate and 50 ml of water. The organic phase is washed once with water and then with a saturated aqueous solution of sodium chloride, dried over magnesium sulphate, filtered and concentrated under vacuum. The crude product is chromatographed on silica gel eluted with a heptane/ethyl acetate mixture, 70/30 and then 50/50. 2.5 g (67%) of 1-benzhydryl-5-bromo-1H-pyrimidine-2,4-dione is obtained in the form of a yellow solid.

2.2: 1-benzhydryl-5-bromo-3-methyl-1H-pyrimidine-2,4-dione 290 mg (2.1 mmol) of potassium carbonate and 0.1 ml (2.1 mmol) of methyl iodide are added to a solution of 500 mg (1.4 mmol) of 1-benzhydryl-5-bromo-1H-pyrimidine-2,4-dione in 10 ml of dimethylformamide. The reaction mixture is stirred at room temperature for 2 hours, then hydrolysed and diluted with ethyl acetate. The product is extracted with ethyl acetate and the organic phase is washed once with water, once with a saturated aqueous solution of sodium chloride, and then dried over magnesium sulphate, filtered and concentrated under vacuum. 490 mg (94%) of 1-benzhydryl-5-bromo-3-methyl-1H-pyrimidine-2,4-dione is obtained in the form of a yellow solid.

2.3: 5-bromo-3-methyl-1H-pyrimidine-2,4-dione 490 mg (1.3 mmol) of 1-benzhydryl-5-bromo-3-methyl-1H-pyrimidine-2,4-dione is added to a solution cooled to 0° C. containing 2 ml of methanesulphonic acid and 4.9 ml of trifluoroacetic acid. The reaction mixture is stirred at 0° C. and then at room temperature for 43 hours. It is poured slowly onto 50 g of ice, and then 150 ml of a saturated aqueous solution of sodium hydrogen carbonate is added. The product is extracted three times with ethyl acetate. The organic phases are washed once with water, then with a saturated aqueous solution of sodium chloride and concentrated under vacuum. The crude residue is chromatographed on silica gel eluted with a dichloromethane/methanol 97/3 mixture. 195 mg (72%) of 5-bromo-3-methyl-1H-pyrimidine-2,4-dione is obtained in the form of a pale yellow solid.

2.4: 3-[1-(2-hydroxyacetyl)-piperidin-4-yl]-3,4-dihydro-1H-quinazolin-2-one 212 mg (1.6 mmol) of 1-hydroxybenzotriazole and 307 mg (1.6 mmol) of 1-ethyl-3-(3-dimethylaminopropyl)carbodiimide hydrochloride are added to a solution of 100 mg (1.3 mmol) of hydroxyacetic acid in 10 ml of dimethylformamide. The reaction mixture is stirred for 5 minutes at room temperature and 304 mg (1.6 mmol) of 3-piperidin-4-yl-3,4-dihydro-1H-quinazolin-2-one (prepared as described in example 1.5) is added. After stirring for two hours at room temperature, the reaction mixture is hydrolysed with a saturated aqueous solution of sodium hydrogen carbonate and diluted with ethyl acetate. The product is extracted twice with ethyl acetate and once with n-butanol. The organic phases are combined, washed once with water and once with a saturated aqueous solution of sodium chloride. They are dried over magnesium sulphate, filtered and concentrated under vacuum. The crude residue is chromatographed on silica gel eluted with a dichloromethane/methanol 97/3 mixture. 140 mg (35%) of 3-[1-(2-hydroxyacetyl)-piperidin-4-yl]-3,4-dihydro-1H-quinazolin-2-one is obtained in the form of a white solid.

2.5: 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione 0.2 ml (1.2 mmol) of diisopropyl azodicarboxylate is added to a solution of 100 mg (0.5 mmol) of 5-bromo-3-methyl-1H-pyrimidine-2,4-dione, 140 mg (0.5 mmol) of 3-[1-(2-hydroxyacetyl)-piperidin-4-yl]-3,4-dihydro-1H-quinazolin-2-one and 321 mg (1.2 mmol) of triphenylphosphine in 10 ml of tetrahydrofuran. The reaction mixture is stirred at room temperature for 18 hours. 15 ml of diethyl ether is added; the suspension is stirred for 10 minutes and then filtered. The solid obtained is rinsed once with diethyl ether and then dried in the stove under vacuum for 3 hours. 160 mg (74%) of 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione is obtained in the form of a white solid.

2.6: 5-(2-fluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione (Compound 2)

Similarly to example 1.8, starting from 62 mg (0.4 mmol) of 2-fluorophenylboronic acid and 140 mg (0.3 mmol) of 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione, 70 mg (50%) of 5-(2-fluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione is obtained in the form of a white solid.

$^1$H NMR (δ, DMSO): 1.57-1.70 (m, 3H), 1.83 (q, J=12.4 Hz, 1H), 2.70 (t, J=12.6 Hz, 1H), 3.16 (t, J=12.6 Hz, 1H), 3.25 (s, 3H), 3.97 (d, J=13.7 Hz, 1H), 4.30 (d, J=4.1 Hz, 2H), 4.37-4.51 (m, 2H), 4.80 (s, 2H), 6.77 (dd, J=7.9, 1.2 Hz, 1H), 6.86 (t, J=7.5 Hz, 1H), 7.06-7.16 (m, 2H), 7.20-7.32 (m, 2H), 7.36-7.48 (m, 2H), 7.86 (s, 1H), 9.26 (s, 1H).

EXAMPLE 3: 5-(2,4-DIFLUOROPHENYL)-3-METHYL-1-{2-OXO-2-[4-(2-OXO-1,4-DIHYDRO-2H-QUINAZOLIN-3-YL)-PIPERIDIN-1-YL]-ETHYL}-1H-PYRIMIDINE-2,4-DIONE (REACTION SCHEME 1, COMPOUND 3)

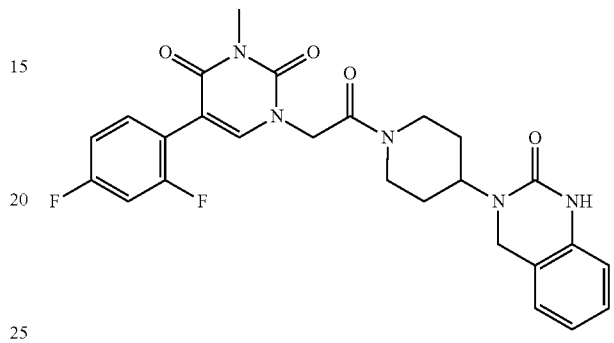

Similarly to example 1.8, starting from 249 mg (1.6 mmol) of 2,4-difluorophenylboronic acid and 150 mg (0.3 mmol) of 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione (prepared as described in example 2.5), 80 mg (51%) of 5-(2,4-difluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione is obtained in the form of a white solid with a melting point of 170° C.

$^1$H NMR (δ, DMSO): 1.54-1.72 (m, 3H), 1.83 (q, J=13.7 Hz, 1H), 2.69 (t, J=12.1 Hz, 1H), 3.16 (t, J=12.6 Hz, 1H), 3.25 (s, 3H), 3.97 (d, J=13.5 Hz, 1H), 4.29 (d, J=4.0 Hz, 2H), 4.42 (m, 2H), 4.79 (s, 2H), 6.77 (d, J=7.8 Hz, 1H), 6.86 (t, J=7.5 Hz, 1H), 7.04-7.23 (m, 3H), 7.33 (t, J=9.8 Hz, 1H), 7.43 (q, J=8.6 Hz, 1H), 7.85 (s, 1H), 9.26 (s, 1H).

EXAMPLE 4: 5-(3-FLUOROPHENYL)-3-METHYL-1-{2-OXO-2-[4-(2-OXO-1,4-DIHYDRO-2H-QUINAZOLIN-3-YL)-PIPERIDIN-1-YL]-ETHYL}-1H-PYRIMIDINE-2,4-DIONE (REACTION SCHEME 1, COMPOUND 4)

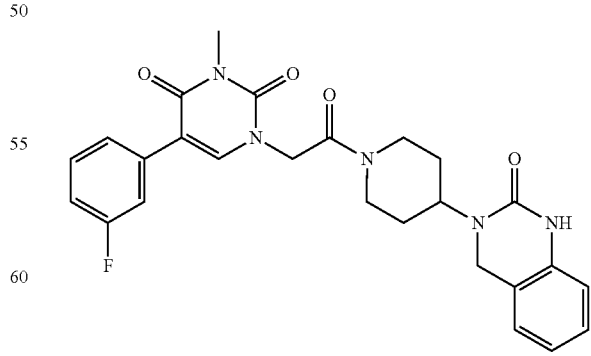

Similarly to example 1.8, starting from 66 mg (0.5 mmol) of 3-fluorophenylboronic acid and 150 mg (0.3 mmol) of 5-bromo-3-methyl-1-{2-oxo-2-[4-(2-oxo-1,4-dihydro-2H- quinazolin-3-yl)-piperidin-1-yl]-ethyl}-1H-pyrimidine-2,4-dione (prepared as described in example 2.5), 30 mg (20%) of 5-(3-fluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione is obtained in the form of a white solid with a melting point of 240° C.

$^1$H NMR (δ, DMSO): 1.54-1.73 (m, 3H), 1.77-1.92 (m, 1H), 2.70 (t, J=12.0 Hz, 1H), 3.19 (t, J=13.0 Hz, 1H), 3.27 (s, 3H), 3.99 (d, J=13.5 Hz, 1H), 4.31 (d, J=4.0 Hz, 2H), 4.37-4.52 (m, 2H), 4.82 (d, J=3.7 Hz, 2H), 6.77 (d, J=7.9 Hz, 1H), 6.87 (t, J=7.5 Hz, 1H), 7.05-7.23 (m, 3H), 7.39-7.51 (m, 3H), 8.07 (s, 1H), 9.27 (s, 1H).

EXAMPLE 5: 3-METHYL-1-{2-OXO-2-[4-(2-OXO-1,4-DIHYDRO-2H-QUINAZOLIN-3-YL)-PIPERIDIN-1-YL]-ETHYL}-5-(1H-PYRAZOL-3-YL)-1H-PYRIMIDINE-2,4-DIONE (REACTION SCHEME 1, COMPOUND 5)

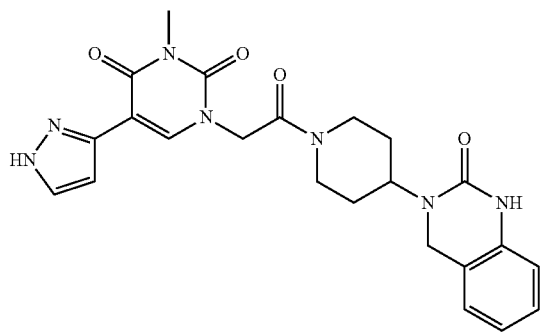 [SMILES: Cn1c(=O)c(-c2cc[nH]n2)cn(CC(=O)N2CCC(N3Cc4ccccc4NC3=O)CC2)c1=O]

Similarly to example 1.8, starting from 70 mg (0.6 mmol) of 1H-pyrazol-3-ylboronic acid, 150 mg (0.3 mmol) of 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione (prepared as described in example 2.5), 131 mg (1.2 mmol) of sodium carbonate and 13 mg (0.02 mmol) of dichloromethane complex of 1,1'-bis(diphenylphosphino)ferrocene-dichloropalladium(II); 10 mg (7%) of 3-methyl-1-{2-oxo-2-[4-(2-oxo-1,4-dihydro-2H-quinazolin-3-yl)-piperidin-1-yl]-ethyl}-5-(1H-pyrazol-3-yl)-1H-pyrimidine-2,4-dione is obtained in the form of a white solid.

HPLC analysis (Kinetex C18 column, 150×3 mm, 2.6 µm, eluent: water/acetonitrile with 0.1% formic acid, 30 min run): tr=12.64 min.

EXAMPLE 6: 5-(3-METHOXYPHENYL)-3-METHYL-1-{2-OXO-2-[4-(2-OXO-1,4-DIHYDRO-2H-QUINAZOLIN-3-YL)-PIPERIDIN-1-YL]-ETHYL}-1H-PYRIMIDINE-2,4-DIONE (REACTION SCHEME 1, COMPOUND 6)

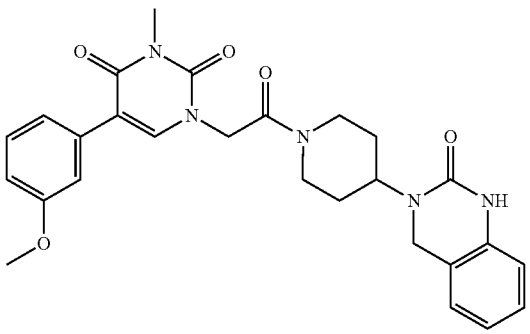 [SMILES: COc1cccc(-c2cn(CC(=O)N3CCC(N4Cc5ccccc5NC4=O)CC3)c(=O)n(C)c2=O)c1]

Similarly to example 1.8, starting from 71 mg (0.5 mmol) of 3-methoxyphenylboronic acid and 150 mg (0.3 mmol) of 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione (prepared as described in example 2.5), 120 mg (77%) of 5-(3-methoxyphenyl)-3-methyl-1-{2-oxo-2-[4-(2-oxo-1,4-dihydro-2H-quinazolin-3-yl)-piperidin-1-yl]-ethyl}-1H-pyrimidine-2,4-dione is obtained in the form of a white solid with a melting point of 251° C.

$^1$H NMR (δ, DMSO): 1.55-1.74 (m, 3H), 1.84 (q, J=12.3 Hz, 1H), 2.62-2.76 (m, 1H), 3.19 (t, J=13.0 Hz, 1H), 3.26 (s, 3H), 3.78 (s, 3H), 3.93-4.03 (m, 1H), 4.31 (d, J=3.9 Hz, 2H), 4.42-4.46 (m, 2H), 4.81 (d, J=3.8 Hz, 2H), 6.77 (d, J=7.8 Hz, 1H), 6.82-6.94 (m, 2H), 7.06-7.20 (m, 4H), 7.32 (t, J=8.0 Hz, 1H), 7.96 (s, 1H), 9.27 (s, 1H).

EXAMPLE 7: 5-(3-HYDROXYPHENYL)-3-METHYL-1-{2-OXO-2-[4-(2-OXO-1,4-DIHYDRO-2H-QUINAZOLIN-3-YL)-PIPERIDIN-1-YL]-ETHYL}-1H-PYRIMIDINE-2,4-DIONE (REACTION SCHEME 1, COMPOUND 7)

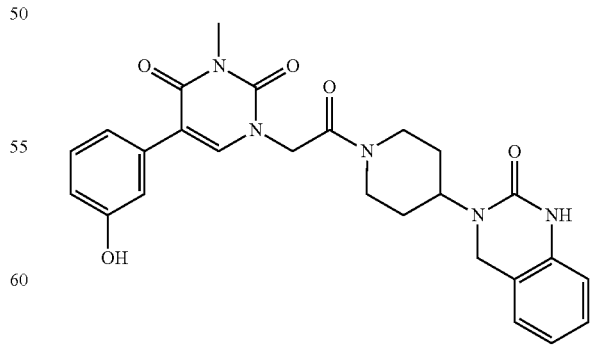

Similarly to example 1.8, starting from 217 mg (1.6 mmol) of 3-hydroxyphenylboronic acid and 150 mg (0.3 mmol) of 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione (prepared as described in example 2.5), 30 mg (20%) of 5-(3-hydroxyphenyl)-3-methyl-1-{2-oxo-2-[4-(2-oxo-1,4-dihydro-2H-quinazolin-3-yl)-piperidin-1-yl]-ethyl}-1H-pyrimidine-2,4-dione is obtained in the form of a grey solid.

¹H NMR (δ, DMSO): 1.56-1.72 (m, 3H), 1.77-1.89 (m, 1H), 2.64-2.75 (m, 1H), 3.12-3.23 (m, 1H), 3.26 (s, 3H), 3.98 (d, J=13.2 Hz, 1H), 4.31 (d, J=4.0 Hz, 2H), 4.38-4.49 (m, 2H), 4.81 (s, 2H), 6.69-6.80 (m, 2H), 6.87 (t, J=7.4 Hz, 1H), 6.94 (d, J=7.7 Hz, 1H), 7.02 (d, J=2.0 Hz, 1H), 7.08-7.24 (m, 3H), 7.88 (s, 1H), 9.26 (s, 1H), 9.44 (s, 1H).

EXAMPLE 8: 5-(3,4-DIFLUOROPHENYL)-3-METHYL-1-{2-OXO-2-[4-(2-OXO-1,4-DIHYDRO-2H-QUINAZOLIN-3-YL)-PIPERIDIN-1-YL]-ETHYL}-1H-PYRIMIDINE-2,4-DIONE (REACTION SCHEME 1, COMPOUND 8)

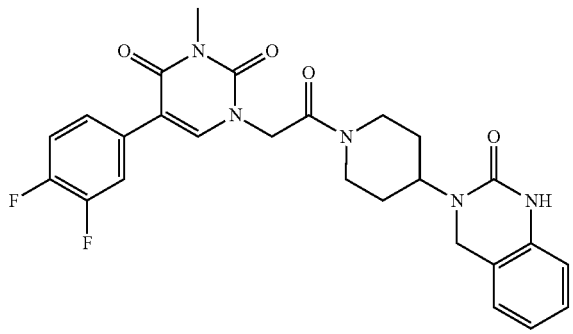 [SMILES: Cn1c(=O)c(-c2ccc(F)c(F)c2)cn(CC(=O)N2CCC(N3Cc4ccccc4NC3=O)CC2)c1=O]

Similarly to example 1.8, starting from 245 mg (1.6 mmol) of 3,4-difluorophenylboronic acid and 150 mg (0.3 mmol) of 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione (prepared as described in example 2.5). After crystallization in a heptane/ethyl acetate 70/30 mixture, filtration and drying under vacuum for 24 hours, 40 mg (25%) of 5-(3,4-difluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione is obtained in the form of a beige solid with a melting point of 153° C.

¹H NMR (δ, DMSO): 1.55-1.74 (m, 3H), 1.77-1.90 (m, 1H), 2.64-2.77 (m, 1H), 3.19 (t, J=13.0 Hz, 1H), 3.27 (s, 3H), 3.99 (d, J=13.1 Hz, 1H), 4.31 (d, J=3.9 Hz, 2H), 4.36-4.52 (m, 2H), 4.81 (d, J=4.5 Hz, 2H), 6.77 (d, J=7.8 Hz, 1H), 6.87 (t, J=7.5 Hz, 1H), 7.11 (d, J=8.0 Hz, 2H), 7.40-7.56 (m, 2H), 7.60-7.74 (m, 1H), 8.06 (s, 1H), 9.27 (s, 1H).

EXAMPLE 9: 5-CYCLOHEX-1-ENYL-3-METHYL-1-{2-OXO-2-[4-(2-OXO-1,4-DIHYDRO-2H-QUINAZOLIN-3-YL)-PIPERIDIN-1-YL]-ETHYL}-1H-PYRIMIDINE-2,4-DIONE (REACTION SCHEME 2, COMPOUND 9)

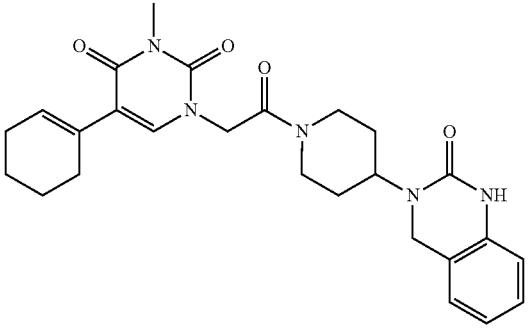 [SMILES: Cn1c(=O)c(C2=CCCCC2)cn(CC(=O)N2CCC(N3Cc4ccccc4NC3=O)CC2)c1=O]

50 mg (0.1 mmol) of 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione (prepared as described in example 2.5), 33.9 µl (0.16 mmol) of pinacol 1-cyclohexenyl-boronate, 30.1 µl (0.2 mmol) of a 5.2M solution of sodium methoxide and 3.7 mg (0.01 mmol) of bis(triphenylphosphine palladium(II) chloride are dissolved in 3 ml of methanol and heated at 70° C. in a sealed tube by microwaves for 5 minutes. The reaction mixture is hydrolysed and then diluted with ethyl acetate. The organic phases are combined, washed once with water and once with a saturated aqueous solution of sodium chloride, then dried over magnesium sulphate, filtered and concentrated under vacuum. The crude product is chromatographed on silica gel eluted with a dichloromethane/methanol 99/1 mixture and then taken up in a heptane/ethyl acetate 80/20 mixture and filtered. The solid obtained is dried under vacuum for 72 hours to give 35 mg (65%) of 5-cyclohex-1-enyl-3-methyl-1-{2-oxo-2-[4-(2-oxo-1,4-dihydro-2H-quinazolin-3-yl)-piperidin-1-yl]-ethyl}-1H-pyrimidine-2,4-dione in the form of a beige solid.

¹H NMR (δ, DMSO): 1.56-1.68 (m, 7H), 1.75-1.90 (m, 1H), 2.10-2.18 (m, 2H), 2.20-2.30 (m, 2H), 2.49-2.51 (m, 1H), 3.15-3.17 (m, 1H), 3.18 (s, 3H), 3.90-4.00 (m, 1H), 4.30 (d, J=4.4 Hz, 2H), 4.35-4.48 (m, 2H), 4.74 (s, 2H), 6.17 (m, 1H), 6.77 (d, J=7.7 Hz, 1H), 6.87 (m, 1H), 7.11 (d, J=7.5 Hz, 2H), 7.53 (s, 1H), 9.26 (s, 1H).

EXAMPLE 10: 3-METHYL-1-{2-OXO-2-[4-(2-OXO-1,4-DIHYDRO-2H-QUINAZOLIN-3-YL)-PIPERIDIN-1-YL]-ETHYL}-5-PHENYL-1H-PYRIMIDINE-2,4-DIONE (REACTION SCHEME 1, COMPOUND 10)

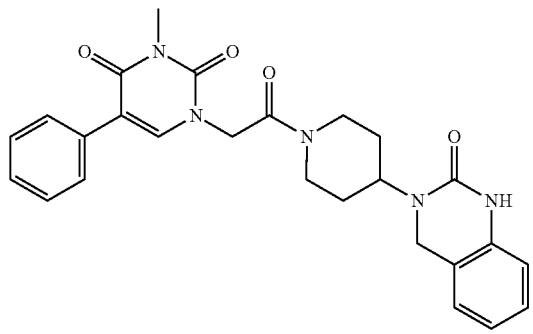 [SMILES: Cn1c(=O)c(-c2ccccc2)cn(CC(=O)N2CCC(N3Cc4ccccc4NC3=O)CC2)c1=O]

Similarly to example 1.8, starting from 61 mg (0.5 mmol) of phenylboronic acid and 160 mg (0.3 mmol) of 5-bromo-3-methyl-1-{2-oxo-2-[4-(2-oxo-1,4-dihydro-2H-quinazolin-3-yl)-piperidin-1-yl]-ethyl}-1H-pyrimidine-2,4-dione (prepared as described in example 2.5), 110 mg (70%) of 3-methyl-1-{2-oxo-2-[4-(2-oxo-1,4-dihydro-2H-quinazolin-3-yl)-piperidin-1-yl]-ethyl}-5-phenyl-1H-pyrimidine-2,4-dione is obtained in the form of a white solid with a melting point of 220° C.

$^1$H NMR (δ, DMSO): 1.57-1.73 (m, 3H), 1.77-1.90 (m, 1H), 2.70 (t, J=12.7 Hz, 1H), 3.18 (t, J=12.5 Hz, 1H), 3.27 (s, 3H), 3.99 (d, J=13.5 Hz, 1H), 4.31 (d, J=3.8 Hz, 2H), 4.37-4.49 (m, 2H), 4.82 (d, J=2.5 Hz, 2H), 6.78 (d, J=8 Hz, 1H), 6.87 (t, J=7.4 Hz, 1H), 7.08-7.14 (m, 2H), 7.29-7.36 (m, 1H), 7.38-7.45 (m, 2H), 7.51-7.58 (m, 2H), 7.93 (s, 1H), 9.27 (s, 1H).

EXAMPLE 11: 5-(2,3-FLUOROPHENYL)-1-{2-OXO-2-[4-(2-OXO-1,4-DIHYDRO-2H-QUINAZOLIN-3-YL)-PIPERIDIN-1-YL]-ETHYL}-3-(2,2,2-TRIFLUOROETHYL)-1H-PYRIMIDINE-2,4-DIONE (REACTION SCHEME 1, COMPOUND 11)

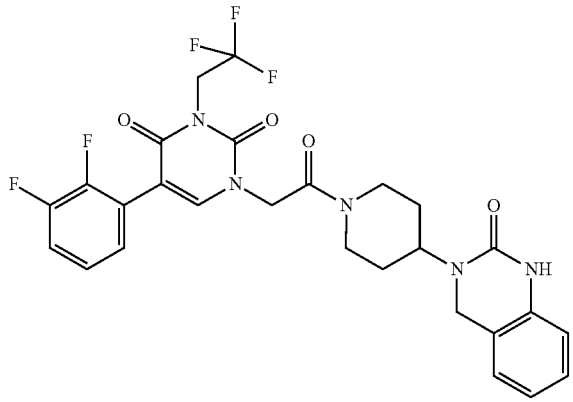 [SMILES: O=C(Cn1cc(-c2cccc(F)c2F)c(=O)n(CC(F)(F)F)c1=O)N1CCC(N2Cc3ccccc3NC2=O)CC1]

11.1: 5-bromo-1-{2-oxo-2-[4-(2-oxo-1,4-dihydro-2H-quinazolin-3-yl)-piperidin-1-yl]-ethyl}-3-(2,2,2-trifluoroethyl)-1H-pyrimidine-2,4-dione Similarly to example 1.7, starting from 230 mg (0.5 mmol) of 5-bromo-1-{2-oxo-2-[4-(2-oxo-1,4-dihydro-2H-quinazolin-3-yl)-piperidin-1-yl]-ethyl}-1H-pyrimidine-2,4-dione (prepared as described in example 1.6) and 0.1 ml (0.8 mmol) of 1,1,1-trifluoro-2-iodoethane, 140 mg (51%) of 5-bromo-1-{2-oxo-2-[4-(2-oxo-1,4-dihydro-2H-quinazolin-3-yl)-piperidin-1-yl]-ethyl}-3-(2,2,2-trifluoroethyl)-1H-pyrimidine-2,4-dione is obtained in the form of a white solid.

11.2: 5-(2,3-fluorophenyl)-1-{2-oxo-2-[4-(2-oxo-1,4-dihydro-2H-quinazolin-3-yl)-piperidin-1-yl]-ethyl}-3-(2,2,2-trifluoroethyl)-1H-pyrimidine-2,4-dione (Compound 11)

Similarly to example 1.8, starting from 203 mg (1.3 mmol) of 2,3-difluorophenylboronic acid and 140 mg (0.3 mmol) of 5-bromo-1-{2-oxo-2-[4-(2-oxo-1,4-dihydro-2H-quinazolin-3-yl)-piperidin-1-yl]-ethyl}-3-(2,2,2-trifluoroethyl)-1H-pyrimidine-2,4-dione, 75 mg (50%) of 5-(2,3-fluorophenyl)-1-{2-oxo-2-[4-(2-oxo-1,4-dihydro-2H-quinazolin-3-yl)-piperidin-1-yl]-ethyl}-3-(2,2,2-trifluoroethyl)-1H-pyrimidine-2,4-dione is obtained in the form of an off-white solid.

$^1$H NMR (δ, DMSO): 1.55-1.75 (m, 3H), 1.76-1.92 (m, 1H), 2.71 (t, J=12.8 Hz, 1H), 3.17 (t, J=12.8 Hz, 1H), 3.97 (d, J=13.4 Hz, 1H), 4.30 (d, J=3.5 Hz, 2H), 4.37-4.52 (m, 2H), 4.74 (q, J=9.1 Hz, 2H), 4.85 (d, J=2.8 Hz, 2H), 6.77 (d, J=7.8 Hz, 1H), 6.86 (t, J=7.2 Hz, 1H), 7.07-7.17 (m, 2H), 7.20-7.34 (m, 2H), 7.43-7.55 (m, 1H), 8.04 (s, 1H), 9.26 (s, 1H).

EXAMPLE 12: 5-(2,3-DIFLUOROPHENYL)-3-ETHYL-1-{2-OXO-2-[4-(2-OXO-1,4-DIHYDRO-2H-QUINAZOLIN-3-YL)-PIPERIDIN-1-YL]-ETHYL}-1H-PYRIMIDINE-2,4-DIONE (REACTION SCHEME 1, COMPOUND 12)

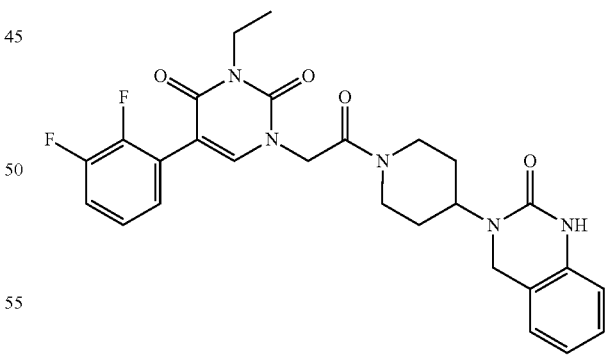

12.1: 5-bromo-3-ethyl-1-{2-oxo-2-[4-(2-oxo-1,4-dihydro-2H-quinazolin-3-yl)-piperidin-1-yl]-ethyl}-1H-pyrimidine-2,4-dione Similarly to example 1.7, starting from 240 mg (0.5 mmol) of 5-bromo-1-{2-oxo-2-[4-(2-oxo-1,4-dihydro-2H-quinazolin-3-yl)-piperidin-1-yl]-ethyl}-1H-pyrimidine-2,4-dione (prepared as described in example 1.6) and 86 μL (1.1 mmol) of iodoethane, 150 mg (59%) of 5-bromo-3-ethyl-1-{2-oxo-2-[4-(2-oxo-1,4-dihydro-2H-quinazolin-3-yl)-piperidin-1-yl]-ethyl}-1H-pyrimidine-2,4-dione is obtained in the form of a white solid.

12.2: 5-(2,3-difluorophenyl)-3-ethyl-1-{2-oxo-2-[4-(2-oxo-1,4-dihydro-2H-quinazolin-3-yl)-piperidin-1-yl]-ethyl}-1H-pyrimidine-2,4-dione (Compound 12)

Similarly to example 1.8, starting from 241 mg (1.5 mmol) of 2,3-difluorophenylboronic acid and 150 mg (0.3 mmol) of 5-bromo-3-ethyl-1-{2-oxo-2-[4-(2-oxo-1,4-dihydro-2H-quinazolin-3-yl)-piperidin-1-yl]-ethyl}-1H-pyrimidine-2,4-dione, 75 mg (48%) of 5-(2,3-difluorophenyl)-3-ethyl-1-{2-oxo-2-[4-(2-oxo-1,4-dihydro-2H-quinazolin-3-yl)-piperidin-1-yl]-ethyl}-1H-pyrimidine-2,4-dione is obtained in the form of an off-white solid.

$^1$H NMR (δ, DMSO): 1.14 (t, J=7.0 Hz, 3H), 1.54-1.75 (m, 3H), 1.75-1.93 (m, 1H), 2.70 (t, J=12.8, 3.2 Hz, 1H), 3.17 (t, J=12.9 Hz, 1H), 3.82-4.02 (m, 3H), 4.30 (d, J=4.1 Hz, 2H), 4.37-4.53 (m, 2H), 4.80 (s, 2H), 6.77 (d, J=7.8 Hz, 1H), 6.86 (t, J=7.4 Hz, 1H), 7.05-7.19 (m, 2H), 7.18-7.35 (m, 2H), 7.39-7.51 (m, 1H), 7.92 (s, 1H), 9.27 (s, 1H).

EXAMPLE 13: 5-(2-CHLORO-3-FLUOROPHENYL)-3-ISOPROPYL-1-{2-OXO-2-[4-(2-OXO-1,4-DIHYDRO-2H-QUINAZOLIN-3-YL)-PIPERIDIN-1-YL]-ETHYL}-1H-PYRIMIDINE-2,4-DIONE (REACTION SCHEME NO. 1, COMPOUND 13)

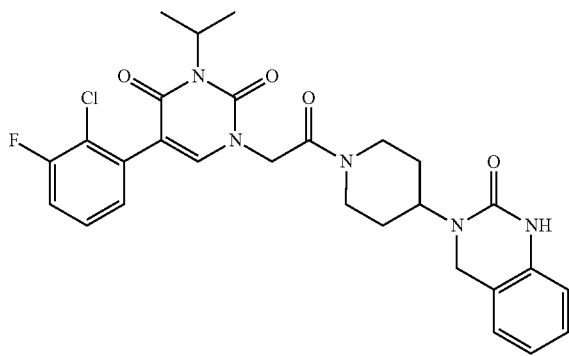 [SMILES: CC(C)n1c(=O)c(-c2cccc(F)c2Cl)cn(CC(=O)N2CCC(N3Cc4ccccc4NC3=O)CC2)c1=O]

13.1: 2-(5-bromo-2,4-dioxo-3,4-dihydro-2H-pyrimidin-1-yl)-methyl acetate 12 ml (128 mmol) of methyl bromoacetate is added to a solution of 25 g (128 mmol) of 5-bromouracil and 17.7 g (128 mmol) of potassium carbonate in 441 ml of dimethylformamide. The reaction mixture is stirred at room temperature for 3 hours. It is hydrolysed and diluted with ethyl acetate. The aqueous phase is neutralized with a 5% aqueous solution of citric acid and then the product is extracted once with ethyl acetate and three times with n-butanol. The organic phases are combined, washed twice with water and then with a saturated aqueous solution of sodium chloride and concentrated under vacuum. The crude product obtained is taken up in 150 mL of ethyl acetate and heated at 80° C. for 10 minutes. After it is brought back to room temperature, the suspension is filtered and the solid obtained is rinsed with diethyl ether and then dried in the stove under vacuum for 20 h. 17 g (50%) of (5-bromo-2,4-dioxo-3,4-dihydro-2H-pyrimidin-1-yl)-methyl acetate is obtained in the form of a white solid.

13.2: (5-bromo-3-isopropyl-2,4-dioxo-3,4-dihydro-2H-pyrimidin-1-yl)-methyl acetate 1 g (30 mmol) of sodium hydride is added in portions to a solution cooled to 0° C. of 6.5 g (24.7 mmol) of (5-bromo-2,4-dioxo-3,4-dihydro-2H-pyrimidin-1-yl)-methyl acetate in 130 ml of dimethylformamide. The reaction mixture is stirred for 5 minutes and then 3.5 ml (37 mmol) of 2-bromopropane is added. After stirring for 30 minutes at room temperature and then 4 hours at 50° C., 2.8 ml (30 mmol) of 2-bromopropane is added and the reaction mixture is heated at 50° C. for a further 2 hours and for 20 hours at room temperature. The reaction mixture is hydrolysed and then diluted with ethyl acetate. The organic phase is washed once with water and once with a saturated aqueous solution of sodium chloride, dried over magnesium sulphate, filtered and concentrated under vacuum. The crude residue is chromatographed on silica gel eluted with a heptane/ethyl acetate 50/50 mixture. 3.5 g (46%) of 2-(5-bromo-3-isopropyl-2,4-dioxo-3,4-dihydro-2H-pyrimidin-1-yl)-methyl acetate is obtained in the form of an off-white solid.

13.3: [5-(2-chloro-3-fluorophenyl)-3-isopropyl-2,4-dioxo-3,4-dihydro-2H-pyrimidin-1-yl]-acetic acid 80 mg (0.1 mmol) of dichloromethane complex of 1,1'-bis(diphenylphosphino) ferrocene-dichloropalladium(II) is added to a solution, previously degassed with nitrogen for 5 minutes, containing 600 mg (2 mmol) of 2-(5-bromo-3-isopropyl-2,4-dioxo-3,4-dihydro-2H-pyrimidin-1-yl)-methyl acetate, 625 mg (5.9 mmol) of sodium carbonate and 411 mg (2.4 mmol) of 2-chloro-3-fluorophenyl boronic acid, in 60 ml of 1,4-dioxane and 6 ml of water. The reaction mixture is heated at 100° C. for 30 minutes and then 343 mg (2 mmol) of 2-chloro-3-fluorophenyl boronic acid is added. The mixture is heated at 100° C. for one more hour. 3 ml (3 mmol) of a 1M aqueous solution of lithium hydroxide and 3 ml of water are added. The reaction mixture is brought back to room temperature and stirred for 1 hour. It is hydrolysed and then diluted with ethyl acetate. The aqueous phase is adjusted to acid pH with 1N aqueous solution of hydrochloric acid. The product is extracted with ethyl acetate. The organic phase is washed once with water and once with a saturated aqueous solution of sodium chloride, then dried over magnesium sulphate, filtered and concentrated under vacuum. The product is taken up in diethyl ether and concentrated under vacuum. 680 mg (100%) of [5-(2-chloro-3-fluorophenyl)-3-isopropyl-2,4-dioxo-3,4-dihydro-2H-pyrimidin-1-yl]-acetic acid is obtained in the form of a beige solid.

13.4: 5-(2-chloro-3-fluorophenyl)-3-isopropyl-1-{2-oxo-2-[4-(2-oxo-1,4-dihydro-2H-quinazolin-3-yl)-piperidin-1-yl]-ethyl}-1H-pyrimidine-2,4-dione (Compound 13)

112 mg (0.5 mmol) of 3-piperidin-4-yl-3,4-dihydro-1H-quinazolin-2-one (prepared as described in example 1.5) and 0.1 ml (0.5 mmol) of triethylamine are added to a solution, previously stirred for 5 minutes, containing 150 mg (0.4 mmol) of [5-(2-chloro-3-fluorophenyl)-3-isopropyl-2,4-dioxo-3,4-dihydro-2H-pyrimidin-1-yl]-acetic acid, 70 mg (0.5 mmol) of 1-hydroxybenzotriazole and 101.3 mg (0.5 mmol)

of 1-ethyl-3-(3-dimethylaminopropyl)carbodiimide hydrochloride in 6 ml of dimethylformamide. The reaction mixture is stirred at room temperature for 14 hours. The reaction mixture is hydrolysed with a saturated aqueous solution of sodium hydrogen carbonate and then diluted with ethyl acetate. The organic phase is washed once with a saturated aqueous solution of sodium hydrogen carbonate, once with water and once with a saturated aqueous solution of sodium chloride, dried over magnesium sulphate and then filtered and concentrated under vacuum. The crude residue is purified by silica gel chromatography eluted with a dichloromethane/methanol 95/5 mixture, then recrystallized from ethyl acetate. 39 mg (16%) of 5-(2-chloro-3-fluorophenyl)-3-isopropyl-1-{2-oxo-2-[4-(2-oxo-1,4-dihydro-2H-quinazolin-3-yl)-piperidin-1-yl]-ethyl}-1H-pyrimidine-2,4-dione is obtained in the form of an off-white solid.

$^1$H NMR (δ, DMSO): 1.41 (d, J=6.9 Hz, 6H); 1.64-1.68 (m, 3H); 1.82-1.85 (m, 1H); 2.67-2.73 (m, 1H); 3.17 (t, J=13.1 Hz, 1H); 3.96 (d, J=13.6 Hz, 1H); 4.30 (d, J=3.3 Hz, 2H); 4.39-4.48 (m, 2H); 4.76 (s, 2H); 5.07-5.14 (m, 1H); 6.77-6.79 (m, 1H); 6.84-6.88 (m, 1H); 7.09-7.15 (m, 2H); 7.21-7.23 (m, 1H); 7.43-7.46 (m, 2H); 7.79 (s, 1H); 9.24 (s, 1H).

EXAMPLE 14: 5-(2-CHLORO-3-FLUOROPHE-NYL)-3-((S)-2-METHOXY-1-METHYLETHYL)-1-{2-OXO-2-[4-(2-OXO-1,4-DIHYDRO-2H-QUI-NAZOLIN-3-YL)-PIPERIDIN-1-YL]-ETHYL}-1H-PYRIMIDINE-2,4-DIONE (REACTION SCHEME NO. 1, COMPOUND 14)

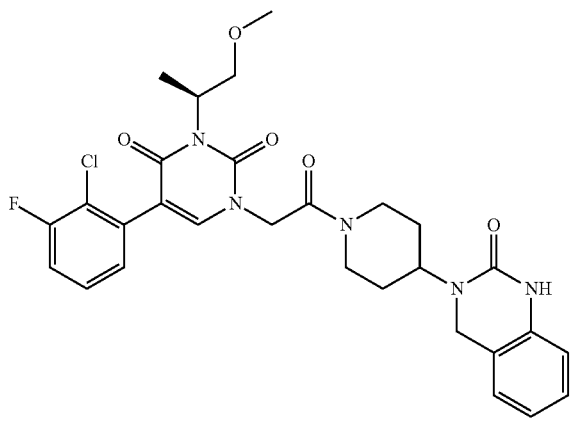 [SMILES: COC[C@H](C)n1c(=O)c(-c2cccc(F)c2Cl)cn(CC(=O)N2CCC(N3Cc4ccccc4NC3=O)CC2)c1=O]

14.1: [5-bromo-3-((S)-2-methoxy-1-methylethyl)-2,4-dioxo-3,4-dihydro-2H-pyrimidin-1-yl]-methyl acetate Similarly to example 2.5, starting from 1 g (3.8 mmol) of (5-bromo-2,4-dioxo-3,4-dihydro-2H-pyrimidin-1-yl)-methyl acetate of 0.4 ml (4 mmol) of (R)-1-methoxypropan-2-ol and after purification by silica gel chromatography eluted with a heptane/ethyl acetate 60/40 mixture, 1.2 g (78%) of [5-bromo-3-((S)-2-methoxy-1-methylethyl)-2,4-dioxo-3,4-dihydro-2H-pyrimidin-1-yl]-methyl acetate is obtained in the form of a colourless oil.

14.2: [5-(2-chloro-fluorophenyl)-3-((S)-2-methoxy-1-methylethyl)-2,4-dioxo-3,4-dihydro-2H-pyrimidin-1-yl]-acetic acid Similarly to example 1.8, starting from 250 mg (1.4 mmol) of 2-chloro-3-fluorophenylboronic acid and 400 mg (1.2 mmol) of [5-bromo-3-((S)-2-methoxy-1-methylethyl)-2,4-dioxo-3,4-dihydro-2H-pyrimidin-1-yl]-methyl acetate, 345 mg (78%) of [5-(2-chloro-3-fluorophenyl)-3-((S)-2-methoxy-1-methylethyl)-2,4-dioxo-3,4-dihydro-2H-pyrimidin-1-yl]-acetic acid is obtained in the form of brown oil.

14.3: 5-(2-chloro-3-fluorophenyl)-3-((S)-2-methoxy-1-methylethyl)-1-{2-oxo-2-[4-(2-oxo-1,4-dihydro-2H-quinazolin-3-yl)-piperidin-1-yl]-ethyl}-1H-pyrimidine-2,4-dione (Compound 14)

Similarly to example 13.4, starting from 345 mg (0.9 mmol) of [5-(2-chloro-3-fluorophenyl)-3-((S)-2-methoxy-1-methylethyl)-2,4-dioxo-3,4-dihydro-2H-pyrimidin-1-yl]-acetic acid, 170 mg (30%) of 5-(2-chloro-3-fluorophenyl)-3-((S)-2-methoxy-1-methylethyl)-1-{2-oxo-2-[4-(2-oxo-1,4-dihydro-2H-quinazolin-3-yl)-piperidin-1-yl]-ethyl}-1H-pyrimidine-2,4-dione is obtained in the form of a white solid.

$^1$H NMR (δ, DMSO): 1.34 (d, J=7.0 Hz, 3H); 1.66 (m, 3H); 1.82-1.85 (m, 1H); 2.68-2.74 (m, 1H); 3.17 (t, J=13.0 Hz, 1H); 3.24 (s, 3H); 3.53-3.57 (m, 1H); 3.90-3.98 (m, 2H); 4.29-4.30 (m, 2H); 4.42-4.48 (m, 2H); 4.76 (s, 2H); 5.14-5.16 (m, 1H); 6.77-6.79 (m, 1H); 6.84-6.88 (m, 1H); 7.09-7.15 (m, 2H); 7.21-7.23 (m, 1H); 7.44-7.47 (m, 2H); 7.81 (s, 1H); 9.24 (s, 1H).

EXAMPLE 15: 5-(2,3-DIFLUOROPHENYL)-3-METHYL-1-[1-METHYL-2-OXO-2-[4-(2-OXO-1,4-DIHYDROQUINAZOLIN-3-YL)-1-PIPERIDYL]ETHYL]PYRIMIDINE-2,4-DIONE (REACTION SCHEME NO. 2, COMPOUND 15)

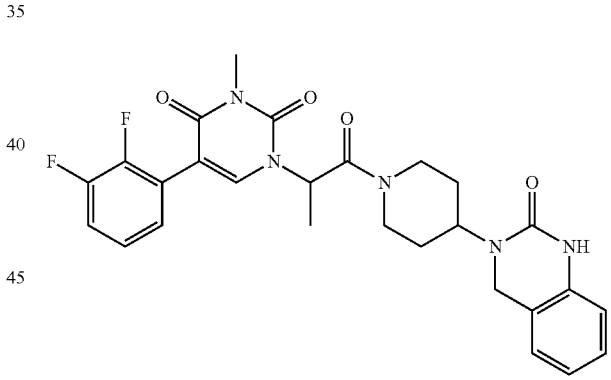

15.1: 1-benzhydryl-5-(2,3-difluorophenyl)-3-methyl-1H-pyrimidine-2,4-dione

Similarly to example 1.8, starting from 4.3 g (27 mmol) of 2,3-difluorophenylboronic acid and 2 g (5.4 mmol) of 1-benzhydryl-5-bromo-3-methyl-1H-pyrimidine-2,4-dione (prepared as described in example 2.2), 1.6 g (73%) of 1-benzhydryl-5-(2,3-difluorophenyl)-3-methyl-1H-pyrimidine-2,4-dione is obtained in the form of a white solid.

15.2: 5-(2,3-difluorophenyl)-3-methyl-1H-pyrimidine-2,4-dione

Similarly to example 2.3, starting from 1.6 g (4 mmol) of 1-benzhydryl-5-(2,3-difluorophenyl)-3-methyl-1H-pyrimidine-2,4-dione, 900 mg (96%) of 5-(2,3-difluorophenyl)-3-methyl-1H-pyrimidine-2,4-dione is obtained in the form of a cream-coloured solid.

15.3: 3-[1-(2-bromo-propionyl)-piperidin-4-yl]-3,4-dihydro-1H-quinazolin-2-one Similarly to example 2.4, starting from 0.2 ml (2.7 mmol) of 2-bromopropionic acid and 300 mg (1.2 mmol) of 3-piperidin-4-yl-3,4-dihydro-1H-quinazolin-2-one (prepared as described in example 1.5), 400 mg (94%) of 3-[1-(2-bromo-propionyl)-piperidin-4-yl]-3,4-dihydro-1H-quinazolin-2-one is obtained in the form of an off-white solid.

15.4: 5-(2,3-difluorophenyl)-3-methyl-1-[1-methyl-2-oxo-2-[4-(2-oxo-1,4-dihydroquinazolin-3-yl)-1-piperidyl]ethyl]pyrimidine-2,4-dione (Compound 15)

Similarly to example 2.2, starting from 50 mg (0.2 mmol) of 5-(2,3-difluorophenyl)-3-methyl-1H-pyrimidine-2,4-dione and 72 mg (0.2 mmol) of 3-[1-(2-bromo-propionyl)-piperidin-4-yl]-3,4-dihydro-1H-quinazolin-2-one and after purification of the crude residue by silica gel chromatography eluted with a dichloromethane/methanol 98/2 mixture, 20 mg (18%) of 5-(2,3-difluorophenyl)-3-methyl-1-[1-methyl-2-oxo-2-[4-(2-oxo-1,4-dihydroquinazolin-3-yl)-1-piperidyl]ethyl]pyrimidine-2,4-dione is obtained in the form of a white solid.

$^1$H NMR (δ, DMSO): 1.43-1.73 (m, 7H), 2.62-2.78 (m, 1H), 3.25 (s, 1H), 3.29 (s, 3H); 4.06-4.21 (m, 1H), 4.22-4.36 (m, 2H), 4.36-4.51 (m, 2H), 5.64-5.76 (m, 1H), 6.77 (d, J=7.8 Hz, 1H), 6.86 (t, J=7.6 Hz, 1H), 7.02-7.17 (m, 2H), 7.20-7.32 (m, 2H), 7.38-7.51 (m, 1H), 7.92 (s, 1H), 9.26 (s, 1H).

EXAMPLE 16: 5-(2,3-DIFLUOROPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 16)

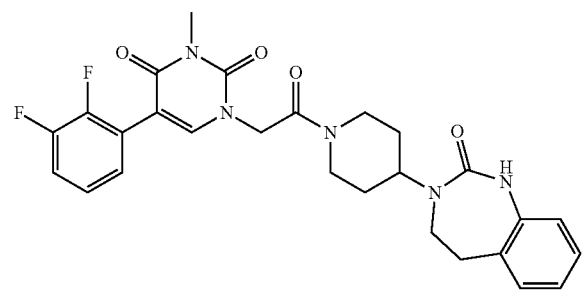 [SMILES: Cn1c(=O)c(-c2cccc(F)c2F)cn(CC(=O)N2CCC(N3CCc4ccccc4NC3=O)CC2)c1=O]

16.1: (1-benzyl-piperidin-4-yl)-[2-(2-nitrophenyl)-ethyl]-amine 8 ml (40 mmol) of 1-benzyl-piperidin-4-ylamine is added to 4 g (17.4 mmol) of 1-(2-bromoethyl)-2-nitrobenzene and the mixture is heated at 100° C. for 18 hours. After cooling, diethyl ether is added, the mixture is filtered and the filtrate is concentrated. The crude residue is purified by silica gel chromatography eluted with an ethyl acetate/heptane mixture, 60/40 and then dichloromethane/methanol/ammonia, 95/3/2. 4.9 g (82%) of (1-benzyl-piperidin-4-yl)-[2-(2-nitrophenyl)-ethyl]-amine is obtained in the form of an orange-coloured oil.

16.2: [2-(2-aminophenyl)-ethyl]-(1-benzyl-piperidin-4-yl)-amine

Similarly to example 1.5, starting from 4.8 g (14 mmol) of (1-benzyl-piperidin-4-yl)-[2-(2-nitrophenyl)-ethyl]-amine, 140 mg of platinum oxide (10 mol %) and after purification of the residue by silica gel chromatography eluted with a dichloromethane/methanol/ammonia mixture 90/8/2, 4.6 g (100%) of [2-(2-aminophenyl)-ethyl]-(1-benzyl-piperidin-4-yl)-amine is obtained in the form of a brown oil.

16.3: 3-(1-benzyl-piperidin-4-yl)-1,3,4,5-tetrahydro-benzo[d][1,3]diazepin-2-one Similarly to example 1.4, starting from 1 g (6.5 mmol) of [2-(2-aminophenyl)-ethyl]-(1-benzyl-piperidin-4-yl)-amine, 3.9 g (78%) of 3-(1-benzyl-piperidin-4-yl)-1,3,4,5-tetrahydro-benzo[d][1,3]diazepin-2-one is obtained in the form of a white powder.

16.4: 3-piperidin-4-yl-1,3,4,5-tetrahydro-benzo[d][1,3]diazepin-2-one

Similarly to example 1.5, starting from 3.7 g (11 mmol) of 3-(1-benzyl-piperidin-4-yl)-1,3,4,5-tetrahydro-benzo[d][1,3]diazepin-2-one, placing the reaction mixture under 5 bar of dihydrogen, 2.6 g (96%) of 3-piperidin-4-yl-1,3,4,5-tetrahydro-benzo[d][1,3]diazepin-2-one is obtained in the form of a white powder.

16.5: 1-benzhydryl-5-(2,3-difluorophenyl)-3-methyl-1H-pyrimidine-2,4-dione

Similarly to example 1.8, starting from 2 g (5.4 mmol) of 1-benzhydryl-5-bromo-3-methyl-1H-pyrimidine-2,4-dione (prepared as described in example 2.2) and 4.3 g (27 mmol) of 2,3-difluorophenylboronic acid, and after purification by silica gel chromatography eluted with a heptane/ethyl acetate 80/20 mixture, 1.6 g (73%) of 1-benzhydryl-5-(2,3-difluorophenyl)-3-methyl-1H-pyrimidine-2,4-dione is obtained in the form of a white solid.

16.6: 5-(2,3-difluorophenyl)-3-methyl-1H-pyrimidine-2,4-dione

Similarly to example 2.3, starting from 1.6 g (4 mmol) of 1-benzhydryl-5-(2,3-difluorophenyl)-3-methyl-1H-pyrimidine-2,4-dione and after triturating the crude residue in diethyl ether, filtration and drying under nitrogen; 900 mg (96%) of 5-(2,3-difluorophenyl)-3-methyl-1H-pyrimidine-2,4-dione is obtained in the form of a beige solid.

16.7: [5-(2,3-difluorophenyl)-3-methyl-2,4-dioxo-3,4-dihydro-2H-pyrimidin-1-yl]-methyl acetate Similarly to example 13.1, starting from 450 mg (1.9 mmol) of 5-(2,3-difluorophenyl)-3-methyl-1H-pyrimidine-2,4-dione and 0.2 ml (2.1 mmol) of methyl chloroacetate, 475 mg (81%) of [5-(2,3-difluorophenyl)-3-methyl-2,4-dioxo-3,4-dihydro-2H-pyrimidin-1-yl]-methyl acetate is obtained in the form of a white solid.

16.8: [5-(2,3-difluorophenyl)-3-methyl-2,4-dioxo-3,4-dihydro-2H-pyrimidin-1-yl]-acetic acid 2.3 ml (2.3 mmol) of a 1N aqueous solution of lithium hydroxide is added to a solution of 475 mg (1.5 mmol) of [5-(2,3-difluorophenyl)-3-methyl-2,4-dioxo-3,4-dihydro-2H-pyrimidin-1-yl]-methyl acetate in 15 ml of tetrahydrofuran and 3 mL of water. The reaction mixture is stirred at room temperature for 2 hours, and then adjusted to pH6 by adding 4 ml of 1N aqueous solution of acetic acid. The product is extracted with ethyl acetate. The organic phase is washed with water and then with a saturated aqueous solution of sodium chloride, dried over magnesium sulphate, filtered and concentrated under vacuum. 400 mg (88%) of [5-(2,3-difluorophenyl)-3-methyl-2,4-dioxo-3,4-dihydro-2H-pyrimidin-1-yl]-acetic acid is obtained in the form of a white solid.

16.9: 5-(2,3-difluorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 16)

Similarly to example 1.6, starting from 100 mg (0.3 mmol) of [5-(2,3-difluorophenyl)-3-methyl-2,4-dioxo-3,4-dihydro-2H-pyrimidin-1-yl]-acetic acid and 100 mg (0.4 mmol) of 3-piperidin-4-yl-1,3,4,5-tetrahydro-benzo[d][1,3]diazepin-2-one (prepared as described in example 16.4) and after crystallization in a heptane/ethyl acetate mixture, 70/30; 120 mg (67%) of 5-(2,3-difluorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 160° C.

$^1$H NMR (δ, DMSO): 1.46-1.62 (m, 1H), 1.62-1.82 (m, 3H), 2.67 (t, J=16 Hz, 1H), 2.89 (t, J=4.9 Hz, 2H), 3.15 (t, J=16 Hz, 1H), 3.25 (s, 3H), 3.33-3.41 (m, 2H), 3.95 (d, J=13.5 Hz, 1H), 4.27-4.37 (m, 1H), 4.41 (d, J=8 Hz, 1H), 4.79 (s, 2H), 6.73-6.85 (m, 1H), 6.96-7.10 (m, 3H), 7.16-7.34 (m, 2H), 7.38-7.55 (m, 1H), 7.93 (s, 1H), 8.54 (s, 1H).

EXAMPLE 17: 5-(2,3-DICHLOROPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 17)

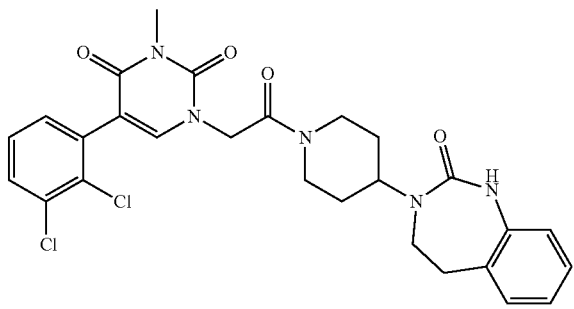

17.1: (5-bromo-3-methyl-2,4-dioxo-3,4-dihydro-2H-pyrimidin-1-yl)-methyl acetate Similarly to example 13.1, starting from 1.5 g (7.1 mmol) of 5-bromo-3-methyl-1H-pyrimidine-2,4-dione (prepared as described in example 2.3) and 0.7 ml (7.8 mmol) of methyl chloroacetate, 1.6 g (79%) of (5-bromo-3-methyl-2,4-dioxo-3,4-dihydro-2H-pyrimidin-1-yl)-methyl acetate is obtained in the form of a white solid.

17.2: (5-bromo-3-methyl-2,4-dioxo-3,4-dihydro-2H-pyrimidin-1-yl)-acetic acid Similarly to example 16.8, starting from 1.6 g (5.6 mmol) of (5-bromo-3-methyl-2,4-dioxo-3,4-dihydro-2H-pyrimidin-1-yl)-methyl acetate, 1.1 g (76%) of (5-bromo-3-methyl-2,4-dioxo-3,4-dihydro-2H-pyrimidin-1-yl)-acetic acid is obtained in the form of a white solid.

17.3: 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione Similarly to example 1.6, starting from 960 mg (3.7 mmol) of (5-bromo-3-methyl-2,4-dioxo-3,4-dihydro-2H-pyrimidin-1-yl)-acetic acid and 895 mg (3.7 mmol) of 3-piperidin-4-yl-1,3,4,5-tetrahydro-benzo[d][1,3]diazepin-2-one (prepared as described in example 16.4), 1.7 g (95%) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid.

17.4: 5-(2,3-dichlorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 17)

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione and 58 mg (0.3 mmol) of 2,3-dichlorophenylboronic acid, and after purification by silica gel chromatography eluted with a dichloromethane/methanol 99/1 mixture, 40 mg (35%) of 5-(2,3-dichlorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 170° C.

$^1$H NMR (δ, DMSO): 1.39-1.53 (m, 1H), 1.55-1.72 (m, 3H), 2.61 (t, J=12.4 Hz, 1H), 2.77-2.88 (m, 2H), 3.08 (t, J=12.7 Hz, 1H), 3.18 (s, 3H), 3.27-3.34 (m, 2H), 3.87 (d, J=13.6 Hz, 1H), 4.24-4.34 (m, 1H), 4.35 (d, J=12.9 Hz, 1H), 4.70 (d, J=3.4 Hz, 2H), 6.66-6.80 (m, 1H), 6.89-7.04 (m, 3H), 7.26 (dd, J=7.7, 1.6 Hz, 1H), 7.36 (t, J=7.8 Hz, 1H), 7.62 (dd, J=8.1, 1.6 Hz, 1H), 7.76 (s, 1H), 8.48 (s, 1H).

EXAMPLE 18: 5-(2-CHLOROPHENYL)-3-METHYL-1-{2-OXO-2-[4-(2-OXO-1,2,4,5-TETRAHYDROBENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 18)

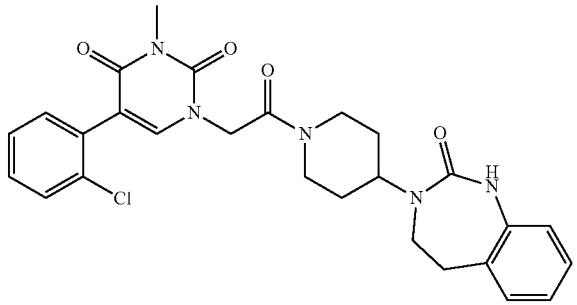 [SMILES: Cn1c(=O)c(-c2ccccc2Cl)cn(CC(=O)N2CCC(N3CCc4ccccc4NC3=O)CC2)c1=O]

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 48 mg (0.3 mmol) of 2-chlorophenylboronic acid, 40 mg (38%) of 5-(2-chlorophenyl)-3-methyl-1-{2-oxo-2-[4-(2-oxo-1,2,4,5 tetrahydrobenzo[d][1,3]diazepin-3-yl)-piperidin-1-yl]-ethyl}-1H-pyrimidine-2,4-dione is obtained in the form of a beige solid with a melting point of 175° C.

$^1$H NMR (δ, DMSO): 1.40-1.55 (m, 1H), 1.58-1.70 (m, 3H), 2.55-2.68 (m, 1H), 2.82 (t, J=4.7 Hz, 2H), 3.05-3.12 (m, 1H), 3.18 (s, 3H), 3.30 (t, J=4.4 Hz, 2H), 3.88 (m, 1H), 4.20-4.30 (m, 1H), 4.38 (m, 1H), 4.70 (d, J=4.2 Hz, 2H), 6.72-6.75 (m, 1H), 6.95-6.98 (m, 3H), 7.26-7.28 (m, 1H), 7.31-7.36 (m, 2H), 7.46-7.48 (m, 1H), 7.71 (s, 1H), 8.47 (s, 1H).

EXAMPLE 19: 3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-5-(2-TRIFLUOROMETHOXYPHENYL)-1H-PYRIMIDINE-2,4-DIONE (REACTION SCHEME NO. 3, COMPOUND 19)

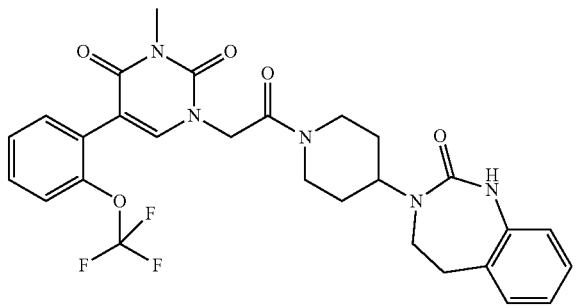 [SMILES: Cn1c(=O)c(-c2ccccc2OC(F)(F)F)cn(CC(=O)N2CCC(N3CCc4ccccc4NC3=O)CC2)c1=O]

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 63 mg (0.3 mmol) of 2-(trifluoromethoxy)benzene boronic acid, 40 mg (34%) of 3-methyl-1-{2-oxo-2-[4-(2-oxo-1,2,4,5-tetrahydro-benzo[d][1,3]diazepin-3-yl)-piperidin-1-yl]-ethyl}-5-(2-trifluoromethoxyphenyl)-1H-pyrimidine-2,4-dione is obtained in the form of a pink solid with a melting point of 235° C.

$^1$H NMR (δ, DMSO): 1.40-1.55 (m, 1H), 1.58-1.72 (m, 3H), 2.55-2.68 (m, 1H), 2.82 (t, J=4.5 Hz, 2H), 3.05-3.15 (m, 1H), 3.18 (s, 3H), 3.30 (t, J=4.5 Hz, 2H), 3.90 (m, 1H), 4.20-4.30 (m, 1H), 4.35 (m, 1H), 4.71 (s, 2H), 6.71-6.75 (m, 1H), 6.95-6.98 (m, 3H), 7.33-7.40 (m, 3H), 7.44-7.48 (m, 1H), 7.74 (s, 1H), 8.47 (s, 1H).

EXAMPLE 20: 3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-5-THIOPHEN-3-YL-1H-PYRIMIDINE-2,4-DIONE (REACTION SCHEME NO. 3, COMPOUND 20)

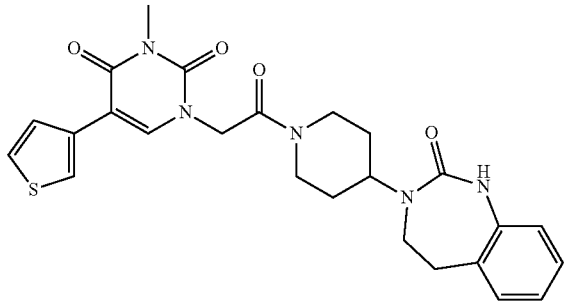 [SMILES: Cn1c(=O)c(-c2ccsc2)cn(CC(=O)N2CCC(N3CCc4ccccc4NC3=O)CC2)c1=O]

Similarly to example 9, starting from 150 mg (0.3 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 59 mg (0.5 mmol) of thiophene-3-boronic acid, 70 mg (46%) of 3-methyl-1-{2-oxo-2-[4-(2-oxo-1,2,4,5-tetrahydro-benzo[d][1,3]diazepin-3-yl)-piperidin-1-yl]-ethyl}-5-thiophen-3-yl-1H-pyrimidine-2,4-dione is obtained in the form of a pink solid with a melting point of 283° C.

$^1$H NMR (δ, DMSO): 1.40-1.55 (m, 1H), 1.58-1.70 (m, 3H), 2.60-2.68 (m, 1H), 2.83 (t, J=4.5 Hz, 2H), 3.05-3.15 (m, 1H), 3.20 (s, 3H), 3.32 (t, J=4.6 Hz, 2H), 3.85-3.95 (m, 1H), 4.20-4.30 (m, 1H), 4.35-4.40 (m, 1H), 4.72 (d, J=4.3 Hz, 2H), 6.72-6.76 (m, 1H), 6.95-6.98 (m, 3H), 7.37 (dd, J=1.2-5 Hz, 1H), 7.52 (dd, J=3.0-5.1 Hz, 1H), 7.91 (dd, J=1.2-3 Hz, 1H), 8.10 (s, 1H), 8.48 (s, 1H).

EXAMPLE 21: 5-(2-METHOXYPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 21)

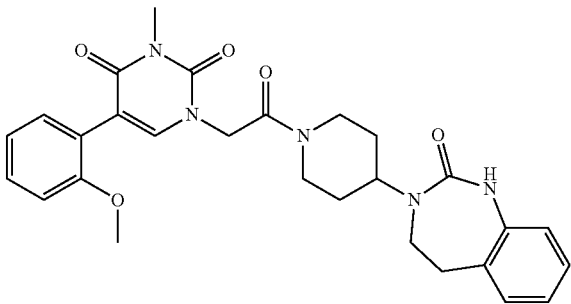

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 47 mg (0.3 mmol) of 2-methoxyphenyl boronic acid, 25 mg (24%) of 5-(2-methoxyphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 250° C.

$^1$H NMR (δ, DMSO): 1.40-1.55 (m, 1H), 1.56-1.72 (m, 3H), 2.55-2.65 (m, 1H), 2.82 (t, J=4.6 Hz, 2H), 3.05-3.14 (m, 1H), 3.15 (s, 3H), 3.29 (t, J=4.9 Hz, 2H), 3.67 (s, 3H), 3.88 (m, 1H), 4.20-4.30 (m, 1H), 4.35 (m, 1H), 4.68 (d, J=5.8 Hz, 2H), 6.70-6.78 (m, 1H), 6.90 (m, 1H), 6.95-7.00 (m, 4H), 7.10 (dd, J=1.72-7.4 Hz, 1H), 7.30 (m, 1H), 7.57 (s, 1H), 8.47 (s, 1H).

EXAMPLE 22: 5-(3-CHLOROPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 22)

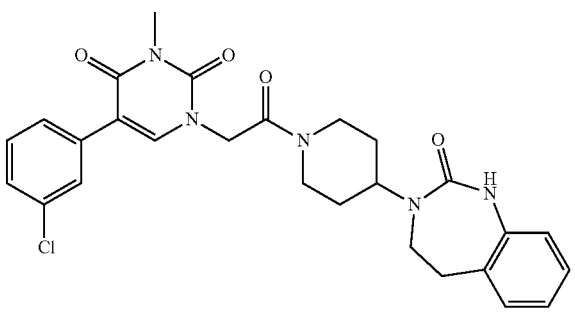 [SMILES: Cn1c(=O)c(-c2cccc(Cl)c2)cn(CC(=O)N2CCC(N3CCc4ccccc4NC3=O)CC2)c1=O]

Similarly to example 1.8, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 48 mg (0.3 mmol) of 3-chlorophenylboronic acid, 55 mg (52%) of 5-(3-chlorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 220° C.

$^1$H NMR (δ, DMSO): 1.50-1.60 (m, 1H), 1.62-1.70 (m, 3H), 2.69 (m, 1H), 2.90 (t, J=4.8 Hz, 2H), 3.26 (m, 1H), 3.33 (s, 3H), 3.38 (t, J=4.6 Hz, 2H), 3.95 (m, 1H), 4.30-4.40 (m, 1H), 4.45 (m, 1H), 4.81 (s, 2H), 6.79-6.82 (m, 1H), 7.03-7.05 (m, 3H), 7.38-7.41 (m, 1H), 7.45 (t, J=7.9 Hz, 1H), 7.55-7.65 (m, 1H), 7.65 (d, J=1.8 Hz, 1H), 8.05 (s, 1H), 8.55 (s, 1H).

EXAMPLE 23: 5-(3-CHLORO-2-METHYLPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 23)

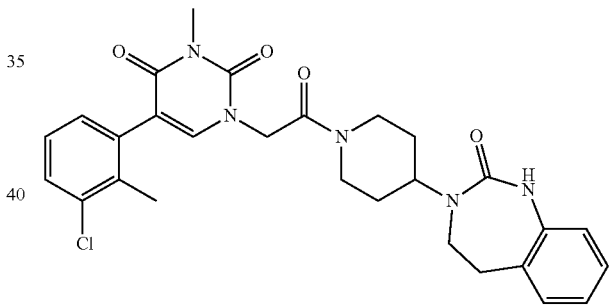

Similarly to example 9, starting from 150 mg (0.3 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 78 mg (0.5 mmol) of 3-chloro-2-methylphenylboronic acid, 75 mg (46%) of 5-(3-chloro-2-methylphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a grey solid with a melting point of 190° C.

$^1$H NMR (δ, DMSO): 1.45-1.60 (m, 1H), 1.62-1.80 (m, 3H), 2.20 (s, 3H), 2.70 (m, 1H), 2.89 (t, J=4.5 Hz, 2H), 3.15 (m, 1H), 3.25 (s, 3H), 3.37 (t, J=4.8 Hz, 2H), 3.95 (m, 1H), 4.35 (m, 1H), 4.45 (m, 1H), 4.76 (d, J=2.6 Hz, 2H), 6.78-6.85 (m, 1H), 7.02-7.05 (m, 3H), 7.13 (d, J=6.8 Hz, 1H), 7.26 (t, J=7.8 Hz, 1H), 7.47 (d, J=7.2 Hz, 1H), 7.72 (s, 1H), 8.54 (s, 1H).

EXAMPLE 24: 5-(3-CHLORO-2-METHOXYPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 24)

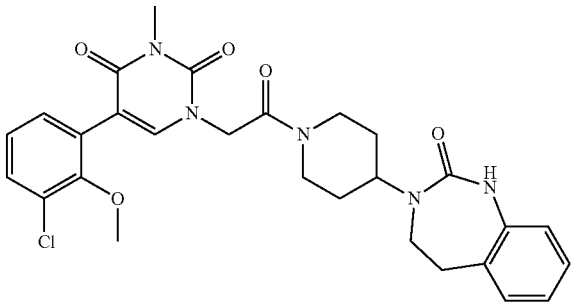

Similarly to example 9, starting from 150 mg (0.3 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 86 mg (0.5 mmol) of 3-chloro-2-methoxyphenyl boronic acid, 60 mg (36%) of 5-(3-chloro-2-methoxyphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 260° C.

$^1$H NMR (δ, DMSO): 1.50-1.60 (m, 1H), 1.62-1.80 (m, 3H), 2.68 (m, 1H), 2.89 (t, J=4.4 Hz, 2H), 3.15 (m, 1H), 3.26 (s, 3H), 3.37 (t, J=4.5 Hz, 2H), 3.65 (s, 3H), 3.95 (m, 1H), 4.30 (m, 1H), 4.45 (m, 1H), 4.78 (d, J=2.44 Hz, 2H), 6.78-6.85 (m, 1H), 7.02-7.05 (m, 3H), 7.18 (t, J=7.8 Hz, 1H), 7.27 (dd, J=1.7-7.7 Hz, 1H), 7.49 (dd, J=1.7-8.0 Hz, 1H), 7.80 (s, 1H), 8.54 (s, 1H).

EXAMPLE 25: 5-(2-METHOXY-3-METHYLPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 25)

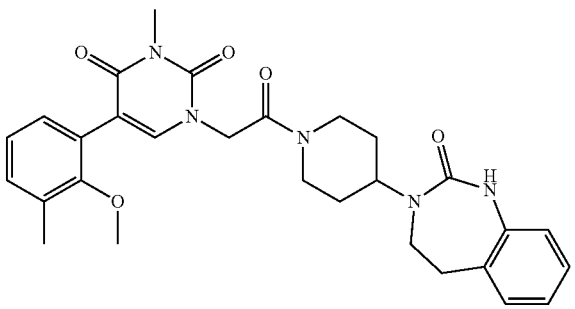 [SMILES: COc1c(C)cccc1-c1cn(CC(=O)N2CCC(N3CCc4ccccc4NC3=O)CC2)c(=O)n(C)c1=O]

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 51 mg (0.3 mmol) of 2-methoxy-3-methyl phenylboronic acid, 20 mg (17%) of 5-(2-methoxy-3-methylphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 148° C.

$^1$H NMR (δ, DMSO): 1.48-1.60 (m, 1H), 1.62-1.80 (m, 3H), 2.26 (s, 3H), 2.70 (m, 1H), 2.90 (m, 2H), 3.15 (m, 1H), 3.25 (s, 3H), 3.40 (m, 2H), 3.53 (s, 3H), 3.95 (m, 1H), 4.35 (m, 1H), 4.45 (m, 1H), 4.77 (d, J=3.92 Hz, 2H), 6.85 (m, 1H), 7.00-7.08 (m, 4H), 7.10 (m, 1H), 7.20 (m, 1H), 7.72 (s, 1H), 8.54 (s, 1H).

EXAMPLE 26: 5-(3-CHLORO-2-HYDROXYPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 26)

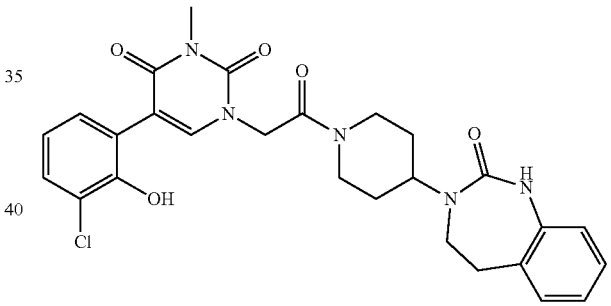

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 53 mg (0.3 mmol) of 3-chloro-2-hydroxy phenyl boronic acid, 45 mg (41%) of 5-(3-chloro-2-hydroxyphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a grey solid with a melting point of 270° C.

$^1$H NMR (δ, DMSO): 1.45-1.58 (m, 1H), 1.65-1.76 (m, 3H), 2.68 (t, J=12.4 Hz, 1H), 2.90 (d, J=3.4 Hz, 2H), 3.12-3.18 (m, 1H), 3.24 (s, 3H), 3.36 (d, J=4.0 Hz, 2H), 3.96 (d, J=12.6 Hz, 1H), 4.30-4.35 (m, 1H), 4.42 (d, J=12.2 Hz, 1H), 4.71-4.83 (m, 2H), 6.52-6.78 (m, 1H), 6.86 (t, J=7.8 Hz, 1H), 7.02-7.09 (m, 4H), 7.37 (dd, J=1.2-7.9 Hz, 1H), 7.76 (s, 1H), 8.54 (s, 1H), 9.34 (s, 1H).

EXAMPLE 27: 5-(2,3-DIMETHOXYPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 27)

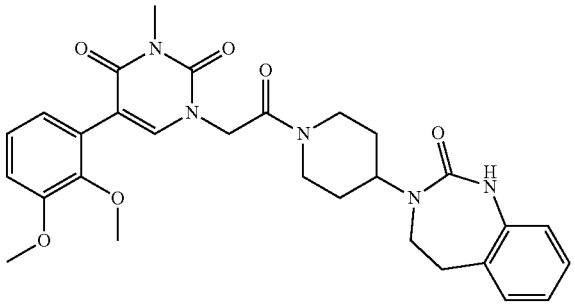 [SMILES: COc1cccc(-c2cn(CC(=O)N3CCC(N4CCc5ccccc5NC4=O)CC3)c(=O)n(C)c2=O)c1OC]

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 56 mg (0.3 mmol) of 2,3-dimethoxyphenyl boronic acid, 54 mg (60%) of 5-(2,3-dimethoxyphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a grey solid with a melting point of 236° C.

$^1$H NMR (δ, DMSO): 1.51-1.55 (m, 1H), 1.64-1.76 (m, 3H), 2.64-2.70 (m, 1H), 2.89 (t, J=3.5 Hz, 2H), 3.14-3.19 (m, 1H), 3.24 (s, 3H), 3.37 (t, J=4.1 Hz, 2H), 3.66 (s, 3H), 3.83 (s, 3H), 3.94 (d, J=12.9 Hz, 1H), 4.30-4.35 (m, 1H), 4.42 (d, J=12.8 Hz, 1H), 4.76 (d, J=3.2 Hz, 2H), 6.78-6.82 (m, 2H), 7.02-7.08 (m, 5H), 7.64 (s, 1H), 8.54 (s, 1H).

EXAMPLE 28: 5-(3-FLUORO-2-METHYLPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 28)

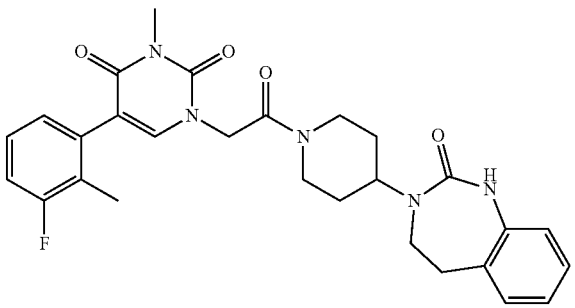 [SMILES: Cc1c(F)cccc1-c1cn(CC(=O)N2CCC(N3CCc4ccccc4NC3=O)CC2)c(=O)n(C)c1=O]

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 47 mg (0.3 mmol) of 3-fluoro-2-methylphenyl boronic acid, 50 mg (47%) of 5-(3-fluoro-2-methylphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a grey solid with a melting point of 160° C.

$^1$H NMR (δ, DMSO): 1.50-1.60 (m, 1H), 1.55-1.74 (m, 3H), 2.08 (d, J=2 Hz, 3H), 2.55-2.70 (m, 1H), 2.89 (t, J=4.5 Hz, 2H), 3.10-3.20 (m, 1H), 3.25 (s, 3H), 3.37 (d, J=4.4 Hz, 2H), 3.95 (d, J=13.7 Hz, 1H), 4.30-4.40 (m, 1H), 4.42 (d, J=12.5 Hz, 1H), 4.77 (d, J=2 Hz, 2H), 6.78-6.82 (m, 1H), 7.00-7.05 (m, 4H), 7.18 (t, J=8.8 Hz, 1H), 7.24-7.27 (m, 1H), 7.71 (s, 1H), 8.54 (s, 1H).

EXAMPLE 29: 5-(3-CHLORO-2-FLUOROPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 29)

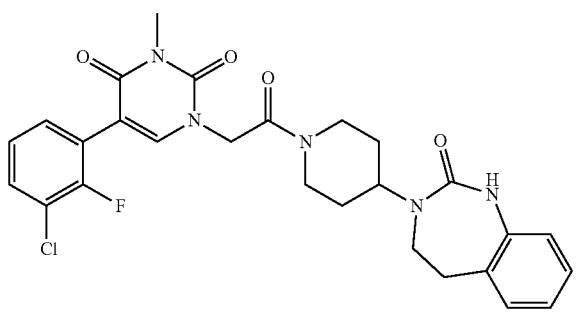

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 53 mg (0.3 mmol) of 3-chloro-2-fluorophenyl boronic acid, 65 mg (57%) of 5-(3-chloro-2-fluorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a grey solid with a melting point of 206° C.

$^1$H NMR (δ, DMSO): 1.50-1.60 (m, 1H), 1.65-1.80 (m, 3H), 2.69 (t, J=12 Hz, 1H), 2.90 (m, 2H), 3.16 (t, J=10 Hz, 1H), 3.26 (s, 3H), 3.37 (m, 2H), 3.95 (d, J=12.6 Hz, 1H), 4.30-4.40 (m, 1H), 4.42 (d, J=11.7 Hz, 1H), 4.80 (s, 2H), 6.81 (d, J=3.7 Hz, 1H), 7.03-7.04 (m, 3H), 7.29 (t, J=7.8 Hz, 1H), 7.37 (t, J=6.5 Hz, 1H), 7.61 (t, J=7.2 Hz, 1H), 7.93 (s, 1H), 8.54 (s, 1H).

EXAMPLE 30: 5-(2,3-DIMETHYLPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 30)

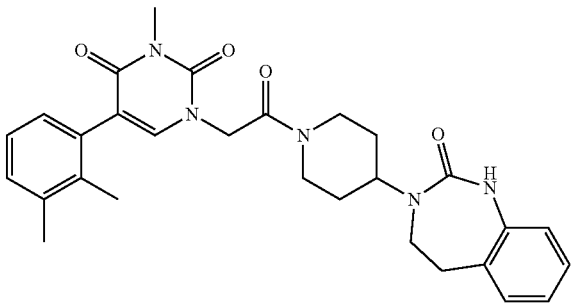 [SMILES: Cc1cccc(-c2cn(CC(=O)N3CCC(N4CCc5ccccc5NC4=O)CC3)c(=O)n(C)c2=O)c1C]

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 46 mg (0.3 mmol) of 2,3-dimethylphenyl boronic acid, 50 mg (48%) of 5-(2,3-dimethylphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of an off-white solid with a melting point of 253° C.

$^1$H NMR (δ, DMSO): 1.50-1.60 (m, 1H), 1.55-1.80 (m, 3H), 2.06 (s, 3H), 2.28 (s, 3H), 2.68 (t, J=12 Hz, 1H), 2.90 (t, J=4 Hz, 2H), 3.15 (t, J=12 Hz, 1H), 3.25 (s, 3H), 3.39 (t, J=4 Hz, 2H), 3.95 (d, J=12 Hz, 1H), 4.30-4.40 (m, 1H), 4.44 (d, J=12 Hz, 1H), 4.77 (d, J=4 Hz, 2H), 6.79-6.83 (m, 1H), 6.96 (d, J=8 Hz, 1H), 7.02-7.05 (m, 3H), 7.11 (t, J=8 Hz, 1H), 7.18 (d, J=8 Hz, 1H), 7.60 (s, 1H), 8.52 (s, 1H).

EXAMPLE 31: 5-(2-CHLORO-3-FLUOROPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 31)

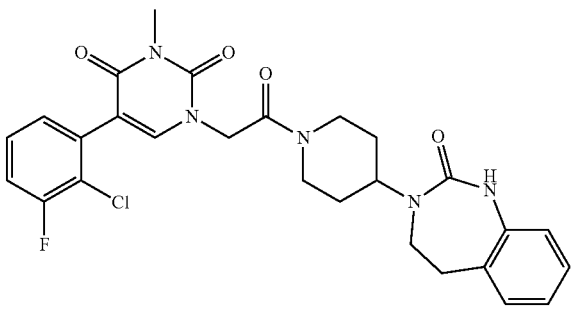 [SMILES: Cn1c(=O)c(-c2cccc(F)c2Cl)cn(CC(=O)N2CCC(N3CCc4ccccc4NC3=O)CC2)c1=O]

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 53 mg (0.3 mmol) of 2-chloro-3-fluorophenyl-phenylboronic acid, 75 mg (68%) of 5-(2-chloro-3-fluorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a grey solid with a melting point of 162° C.

$^1$H NMR (δ, DMSO): 1.50-1.60 (m, 1H), 1.65-1.75 (m, 3H), 2.68 (t, J=12 Hz, 1H), 2.89 (t, J=4.4 Hz, 2H), 3.15 (t, J=12 Hz, 1H), 3.25 (s, 3H), 3.37 (t, J=4.3 Hz, 2H), 3.94 (d, J=12 Hz, 1H), 4.31-4.34 (m, 1H), 4.42 (d, J=12 Hz, 1H), 4.78 (d, J=1.96 Hz, 2H), 6.78-6.82 (m, 1H), 7.02-7.05 (m, 3H), 7.20-7.22 (m, 1H), 7.43-7.47 (m, 2H), 7.84 (s, 1H), 8.54 (s, 1H).

EXAMPLE 32: 5-BROMO-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 32)

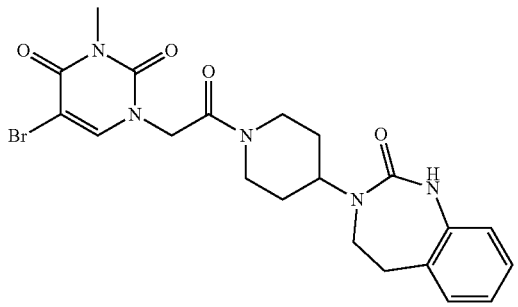 [SMILES: Cn1c(=O)c(Br)cn(CC(=O)N2CCC(N3CCc4ccccc4NC3=O)CC2)c1=O]

Similarly to example 1.6, starting from 930 mg (3.5 mmol) of (5-bromo-3-methyl-2,4-dioxo-3,4-dihydro-2H-pyrimidin-1-yl)-acetic acid (prepared as described in example 17.2) and 1 g (4.2 mmol) of 3-piperidin-4-yl-1,3,4,5-tetrahydro-benzo[d][1,3]diazepin-2-one (prepared as described in example 16.4), 1.4 g (80%) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid.

$^1$H NMR (δ, DMSO): 1.50-1.60 (m, 1H), 1.65-1.80 (m, 3H), 2.70 (t, J=12 Hz, 1H), 2.90 (t, J=4 Hz, 2H), 3.15 (t, J=12 Hz, 1H), 3.23 (s, 3H), 3.40 (t, J=4 Hz, 2H), 4.95 (d, J=12 Hz, 1H), 4.30-4.38 (m, 1H), 4.40 (d, J=12 Hz, 1H), 4.73 (s, 2H), 6.80-6.85 (m, 1H), 7.04 (m, 3H), 8.20 (s, 1H), 8.54 (s, 1H).

EXAMPLE 33: 5-(3-FLUORO-2-METHOXYPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 33)

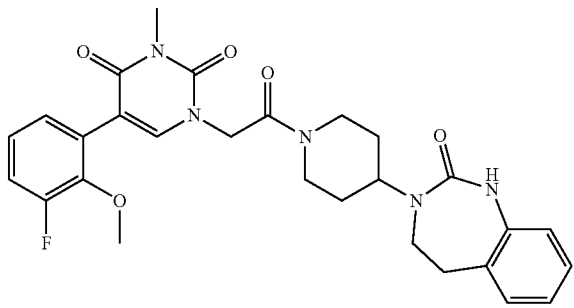

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 52 mg (0.3 mmol) of 3-fluoro-2-methoxyphenyl boronic acid, 75 mg (68%) of 5-(3-fluoro-2-methoxyphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a grey solid with a melting point of 152° C.

$^1$H NMR (δ, DMSO): 1.50-1.60 (m, 1H), 1.55-1.80 (m, 3H), 2.68 (d, J=12 Hz, 1H), 2.89 (t, J=4 Hz, 2H), 3.15 (d, J=12 Hz, 1H), 3.25 (s, 3H), 3.37 (t, J=4 Hz, 2H), 3.78 (d, J=1.4 Hz, 3H), 3.94 (d, J=12 Hz, 1H), 4.30-4.40 (m, 1H), 4.42 (d, J=12 Hz, 1H), 4.77 (d, J=2.3 Hz, 2H), 6.78-6.82 (m, 1H), 7.02-7.07 (m, 4H), 7.11-7.16 (m, 1H), 7.26-7.31 (m, 1H), 7.73 (s, 1H), 8.54 (s, 1H).

EXAMPLE 34: 5-(2,6-DIFLUOROPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 34)

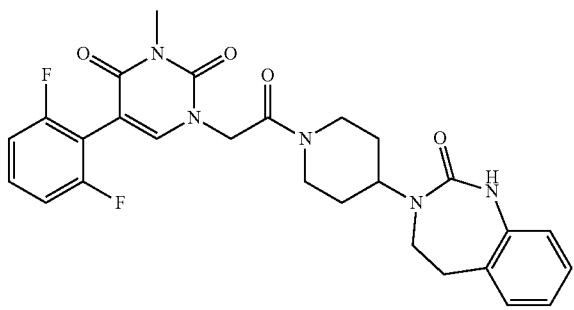 [SMILES: Cn1c(=O)c(-c2c(F)cccc2F)cn(CC(=O)N2CCC(N3CCc4ccccc4NC3=O)CC2)c1=O]

2.3 mg (0.01 mmol) of palladium(II) acetate, 7.2 mg (0.02 mmol) of 2-dicyclohexylphosphine biphenyl and 164.3 mg (1 mmol) of 2,6-difluorophenylboronic acid are added to a solution of 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3) and 0.5 ml (1 mmol) of 2M aqueous solution of tribasic potassium phosphate in 5 ml of dimethylformamide, previously degassed with nitrogen. The reaction mixture is heated at 90° C. for 2 hours. The reaction mixture is treated by adding water and then the product is extracted three times with ethyl acetate. The organic phase is washed with water and then with a saturated solution of sodium chloride, dried over magnesium sulphate, filtered and concentrated under vacuum. The crude residue obtained is purified by silica gel chromatography eluted with a dichloromethane/methanol mixture 96/4. 8 mg (6%) of 5-(2,6-difluorophenyl)-3-methyl-1-{2-oxo-2-[4-(2-oxo-1,4-dihydro-2H-quinazolin-3-yl)-piperidin-1-yl]-ethyl}-1H-pyrimidine-2,4-dione is obtained in the form of a white solid.

$^1$H NMR (δ, DMSO): 1.55-1.65 (m, 1H), 1.70-1.85 (m, 3H), 2.74 (t, J=12 Hz, 1H), 2.95 (m, 2H), 3.24 (t, J=12 Hz, 1H), 3.31 (s, 3H), 3.45 (m, 2H), 3.99 (d, J=12 Hz, 1H), 4.30-4.40 (m, 1H), 4.47 (d, J=12 Hz, 1H), 4.84 (s, 2H), 6.84-6.88 (m, 1H), 7.08-7.10 (m, 3H), 7.25 (t, J=8.6 Hz, 2H), 7.54-7.58 (m, 1H), 7.96 (s, 1H), 8.59 (s, 1H).

EXAMPLE 35: 5-(3,5-DICHLOROPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 35)

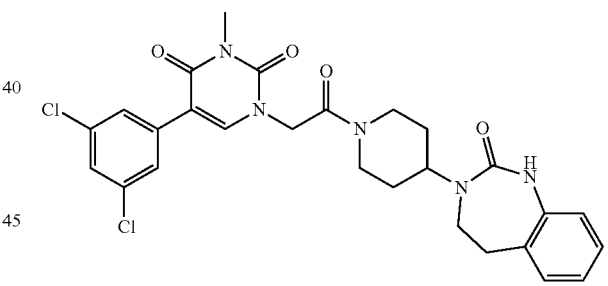

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 78 mg (0.4 mmol) of 3,5-dichlorophenyl boronic acid, and after crystallization in a heptane/ethyl acetate mixture 70/30, 50 mg (44%) of 5-(3,5-dichlorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 170° C.

$^1$H NMR (δ, DMSO): 1.40-1.55 (m, 1H), 1.58-1.70 (m, 3H), 2.55 (m, 1H), 2.83 (t, J=4.4 Hz, 2H), 3.10 (m, 1H), 3.20 (s, 3H), 3.31 (t, J=4.7 Hz, 2H), 3.90 (m, 1H), 4.30 (m, 1H), 4.35 (m, 1H), 4.74 (s, 2H), 6.71-6.76 (m, 1H), 6.96-6.98 (m, 3H), 7.49-7.63 (m, 3H), 8.11 (s, 1H), 8.47 (s, 1H).

EXAMPLE 36: 4-(3-METHYL-2,4-DIOXO-1-{2-OXO-2-[4-(2-OXO-1,2,4,5-TETRAHYDRO-BENZO[D][1,3]DIAZEPIN-3-YL)-PIPERIDIN-1-YL]-ETHYL}-1,2,3,4-TETRAHYDRO-PYRIMIDIN-5-YL)-BENZONITRILE (REACTION SCHEME NO. 3, COMPOUND 36)

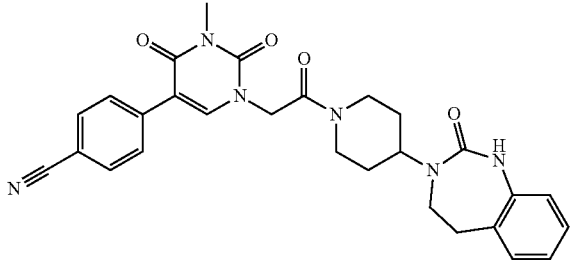 [SMILES: Cn1c(=O)c(-c2ccc(C#N)cc2)cn(CC(=O)N2CCC(N3CCc4ccccc4NC3=O)CC2)c1=O]

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 45 mg (0.3 mmol) of 4-(cyanophenyl)-boronic acid, 13 mg (11%) of 4-(3-methyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-benzonitrile is obtained in the form of a white solid.

$^1$H NMR (δ, DMSO): 1.50-1.60 (m, 1H), 1.62-1.80 (m, 3H), 2.7 (m, 1H), 2.90 (t, 2H), 3.15 (m, 1H), 3.27 (s, 3H), 3.40 (t, 2H), 3.95 (d, 1H), 4.30-4.40 (m, 1H), 4.42 (d, 1H), 4.83 (s, 2H), 6.80 (m, 1H), 7.00-7.05 (m, 3H), 7.80 (d, J=8.6 Hz, 2H), 7.88 (d, J=8.5 Hz, 2H), 8.15 (s, 1H), 8.54 (s, 1H).

EXAMPLE 37: 3-(3-METHYL-2,4-DIOXO-1-{2-OXO-2-[4-(2-OXO-1,2,4,5-TETRAHYDRO-BENZO[D][1,3]DIAZEPIN-3-YL)-PIPERIDIN-1-YL]-ETHYL}-1,2,3,4-TETRAHYDRO-PYRIMIDIN-5-YL)-BENZONITRILE (REACTION SCHEME NO. 3, COMPOUND 37)

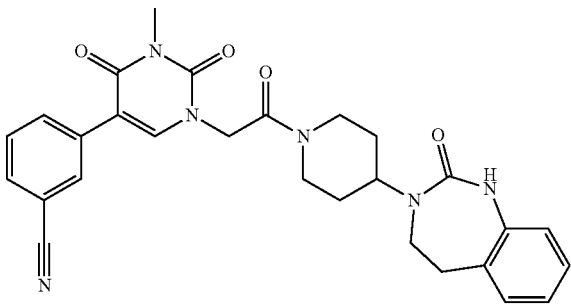 [SMILES: Cn1c(=O)c(-c2cccc(C#N)c2)cn(CC(=O)N2CCC(N3CCc4ccccc4NC3=O)CC2)c1=O]

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 45 mg (0.3 mmol) of 3-(cyanophenyl)-boronic acid, 50 mg (46%) of 3-(3-methyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-benzonitrile is obtained in the form of a white solid with a melting point of 258° C.

$^1$H NMR (δ, DMSO): 1.50-1.60 (m, 1H), 1.62-1.80 (m, 3H), 2.7 (m, 1H), 2.90 (t, 2H), 3.15 (m, 1H), 3.27 (s, 3H), 3.40 (t, 2H), 3.95 (d, 1H), 4.30-4.40 (m, 1H), 4.42 (d, 1H), 4.83 (s, 2H), 6.80 (m, 1H), 7.00-7.05 (m, 3H), 7.64 (t, J=8.0 Hz, 1H), 7.79 (d, J=7.6 Hz, 1H), 7.95 (d, J=8.0 Hz, 1H), 8.01 (s, 1H), 8.13 (s, 1H), 8.54 (s, 1H).

EXAMPLE 38: 2-(3-METHYL-2,4-DIOXO-1-{2-OXO-2-[4-(2-OXO-1,2,4,5-TETRAHYDRO-BENZO[D][1,3]DIAZEPIN-3-YL)-PIPERIDIN-1-YL]-ETHYL}-1,2,3,4-TETRAHYDRO-PYRIMIDIN-5-YL)-BENZONITRILE (REACTION SCHEME NO. 3, COMPOUND 38)

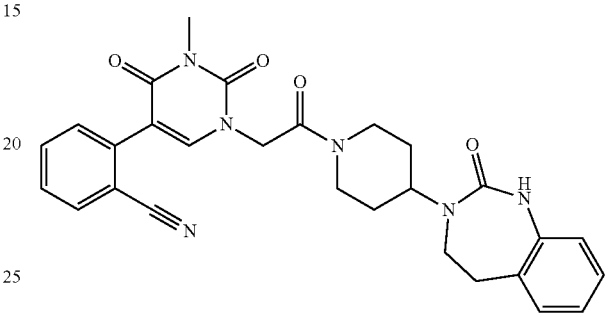

Similarly to example 9, starting from 100 mg (0.2 mmol) of 5-bromo-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 17.3), and 45 mg (0.3 mmol) of 2-(cyanophenyl)-boronic acid, 60 mg (57%) of 2-(3-methyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-benzonitrile is obtained in the form of a beige solid with a melting point of 196° C.

$^1$H NMR (δ, DMSO): 1.50-1.60 (m, 1H), 1.62-1.80 (m, 3H), 2.70 (t, J=12 Hz, 1H), 2.89 (t, J=4.6 Hz, 2H), 3.15 (t, J=12 Hz, 1H), 3.27 (s, 3H), 3.37 (t, J=4.6 Hz, 2H), 3.95 (d, J=12 Hz, 1H), 4.30-4.40 (m, 1H), 4.42 (d, J=12 Hz, 1H), 4.81 (s, 2H), 7.02-7.05 (m, 1H), 7.02-7.08 (m, J=0.6-7.8 Hz, 3H), 7.50 (dd, J=06-7.8 Hz, 1H), 7.59 (dd, J=1.2-7.6 Hz, 1H), 7.76 (dd, J=1.4-7.7 Hz, 1H), 7.92 (dd, J=0.9-7.7 Hz, 1H), 7.98 (s, 1H), 8.53 (s, 1H).

EXAMPLE 39: 3-METHYL-5-(3-METHYL-PYRIDIN-4-YL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 39)

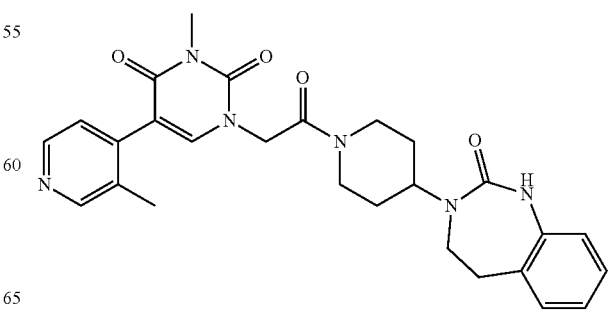

39.1: 3-[1-(2-chloroacetyl)-piperidin-4-yl]-1,3,4,5-tetrahydro-benzo[d][1,3]diazepin-2-one Similarly to example 2.4, starting from 300 mg (1.2 mmol) of 3-piperidin-4-yl-1,3,4,5-tetrahydro-benzo[d][1,3]diazepin-2-one (prepared as described in example 16.4) and 254 mg (2.7 mmol) of chloroacetic acid, 350 mg (89%) of 3-[1-(2-chloroacetyl)-piperidin-4-yl]-1,3,4,5-tetrahydro-benzo[d][1,3]diazepin-2-one is obtained in the form of a white solid.

39.2: 1-benzhydryl-3-methyl-5-(3-methyl-pyridin-4-yl)-1H-pyrimidine-2,4-dione Similarly to example 1.8, starting from 280 mg (0.8 mmol) of 1-benzhydryl-5-bromo-3-methyl-1H-pyrimidine-2,4-dione (prepared as described in example 2.2), and 207 mg (1.5 mmol) of 3-methylpyridine-4-boronic acid, 250 mg (86%) of 1-benzhydryl-3-methyl-5-(3-methyl-pyridin-4-yl)-1H-pyrimidine-2,4-dione is obtained in the form of a colourless oil.

39.3: 3-methyl-5-(3-methyl-pyridin-4-yl)-1H-pyrimidine-2,4-dione

Similarly to example 2.3, starting from 250 mg (0.7 mmol) of 1-benzhydryl-3-methyl-5-(3-methyl-pyridin-4-yl)-1H-pyrimidine-2,4-dione, 50 mg (35%) of 3-methyl-5-(3-methyl-pyridin-4-yl)-1H-pyrimidine-2,4-dione is obtained in the form of a white solid.

39.4: 3-methyl-5-(3-methyl-pyridin-4-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 39)

Similarly to example 13.1, starting from 82 mg (0.3 mmol) of 3-[1-(2-chloroacetyl)-piperidin-4-yl]-1,3,4,5-tetrahydro-benzo[d][1,3]diazepin-2-one (prepared as described in example 39.1), and 50 mg (0.2 mmol) of 3-methyl-5-(3-methyl-pyridin-4-yl)-1H-pyrimidine-2,4-dione, and after purification by silica gel chromatography eluted with a dichloromethane/methanol 97/3 mixture, 60 mg (52%) of 3-methyl-5-(3-methyl-pyridin-4-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 178° C.

¹H NMR (δ, DMSO): 1.40-1.55 (m, 1H), 1.58-1.70 (m, 3H), 2.13 (s, 3H), 2.61 (t, J=12 Hz, 1H), 2.82 (t, J=4.5 Hz, 2H), 3.08 (t, J=12 Hz, 1H), 3.18 (s, 3H), 3.30 (t, J=4.6 Hz, 2H), 3.87 (d, J=13 Hz, 1H), 4.20-4.30 (m, 1H), 4.35 (d, J=13 Hz, 1H), 4.71 (s, 2H), 6.71-6.75 (m, 1H), 6.95-6.98 (m, 3H), 7.10 (d, J=4.9 Hz, 1H), 7.72 (s, 1H), 8.34 (d, J=4.8 Hz, 1H), 8.41 (s, 1H), 8.45 (s, 1H).

EXAMPLE 40: 3-METHYL-5-(2-METHYL-PYRIDIN-3-YL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2, 4-DIONE (REACTION SCHEME NO. 3, COMPOUND 40)

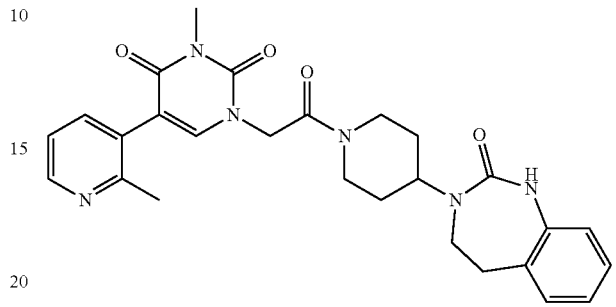

40.1: 1-benzhydryl-3-methyl-5-(2-methyl-pyridin-3-yl)-1H-pyrimidine-2,4-dione Similarly to example 1.8, starting from 280 mg (0.8 mmol) of 1-benzhydryl-5-bromo-3-methyl-1H-pyrimidine-2,4-dione (prepared as described in example 2.2), and 207 mg (1.5 mmol) of 2-methylpyridine-3-boronic acid, 40 mg (14%) of 1-benzhydryl-3-methyl-5-(2-methyl-pyridin-3-yl)-1H-pyrimidine-2,4-dione is obtained in the form of a colourless oil.

40.2: 3-methyl-5-(2-methyl-pyridin-3-yl)-1H-pyrimidine-2,4-dione

Similarly to example 2.3, starting from 40 mg (0.1 mmol) of 1-benzhydryl-3-methyl-5-(2-methyl-pyridin-3-yl)-1H-pyrimidine-2,4-dione, 23 mg (100%) of 3-methyl-5-(2-methyl-pyridin-3-yl)-1H-pyrimidine-2,4-dione is obtained in the form of a yellow solid.

40.3: 3-methyl-5-(2-methyl-pyridin-3-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 40)

Similarly to example 13.1, starting from 37 mg (0.1 mmol) of 3-[1-(2-chloroacetyl)-piperidin-4-yl]-1,3,4,5-tetrahydro-benzo[d][1,3]diazepin-2-one (prepared as described in example 39.1), and 23 mg (0.1 mmol) of 3-methyl-5-(2-methyl-pyridin-3-yl)-1H-pyrimidine-2,4-dione, 15 mg (28%) of 3-methyl-5-(2-methyl-pyridin-3-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 163° C.

¹H NMR (δ, DMSO): 1.48-1.60 (m, 1H), 1.62-1.80 (m, 3H), 2.38 (s, 3H), 2.70 (t, J=12 Hz, 1H), 2.89 (t, J=4.5 Hz, 2H), 3.15 (t, J=12 Hz, 1H), 3.25 (s, 3H), 3.37 (t, J=4.5 Hz, 2H), 3.95 (d, J=12 Hz, 1H), 4.28-4.38 (m, 1H), 4.42 (d, J=12 Hz, 1H), 4.77 (s, 2H), 6.78-6.83 (m, 1H), 7.02-7.04 (m, 3H), 7.27 (m, 1H), 7.53 (dd, J=1.7-7.7 Hz, 1H), 7.75 (s, 1H), 8.45 (q, J=1.7 Hz, 1H), 5.84 (s, 1H).

EXAMPLE 41: 3-METHYL-5-(4-METHYL-PYRIDIN-3-YL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 41)

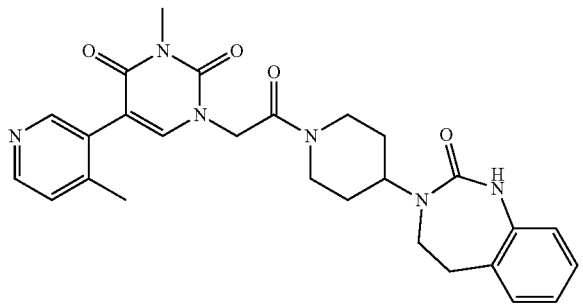 [SMILES: Cc1ccncc1-c1cn(CC(=O)N2CCC(N3CCc4ccccc4NC3=O)CC2)c(=O)n(C)c1=O]

41.1: 1-benzhydryl-3-methyl-5-(4-methyl-pyridin-3-yl)-1H-pyrimidine-2,4-dione Similarly to example 1.8, starting from 280 mg (0.8 mmol) of 1-benzhydryl-5-bromo-3-methyl-1H-pyrimidine-2,4-dione (prepared as described in example 2.2), and 207 mg (1.5 mmol) of 4-methylpyridine-3-boronic acid, 270 mg (93%) of 1-benzhydryl-3-methyl-5-(4-methyl-pyridin-3-yl)-1H-pyrimidine-2,4-dione is obtained in the form of an orange-coloured oil.

41.2: 3-methyl-5-(4-methyl-pyridin-3-yl)-1H-pyrimidine-2,4-dione

Similarly to example 2.3, starting from 270 mg (0.7 mmol) of 1-benzhydryl-3-methyl-5-(4-methyl-pyridin-3-yl)-1H-pyrimidine-2,4-dione, 153 mg (100%) of 3-methyl-5-(4-methyl-pyridin-3-yl)-1H-pyrimidine-2,4-dione is obtained in the form of a yellow solid.

41.3: 3-methyl-5-(4-methyl-pyridin-3-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 41)

Similarly to example 13.1, starting from 140 mg (0.4 mmol) of 3-[1-(2-chloroacetyl)-piperidin-4-yl]-1,3,4,5-tetrahydro-benzo[d][1,3]diazepin-2-one (prepared as described in example 39.1), and 86 mg (0.4 mmol) of 3-methyl-5-(4-methyl-pyridin-3-yl)-1H-pyrimidine-2,4-dione, 20 mg (10%) of 3-methyl-5-(4-methyl-pyridin-3-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 170° C.

$^1$H NMR (δ, DMSO): 1.48-1.60 (m, 1H), 1.62-1.80 (m, 3H), 2.21 (s, 3H), 2.7 (t, J=12 Hz, 1H), 2.88 (t, J=4.3 Hz, 2H), 3.15 (t, J=12 Hz, 1H), 3.25 (s, 3H), 3.36 (t, J=4.4 Hz, 2H), 3.95 (d, J=12 Hz, 1H), 4.28-4.38 (m, 1H), 4.45 (d, J=12 Hz, 1H), 4.78 (s, 2H), 6.78-6.82 (m, 1H), 7.01-7.04 (m, 3H), 7.31 (d, J=5 Hz, 1H), 7.79 (s, 1H), 8.28 (s, 1H), 8.43 (d, J=5 Hz, 1H), 8.54 (s, 1H).

EXAMPLE 42: 3-METHYL-5-(6-METHYL-PYRIDIN-2-YL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 42)

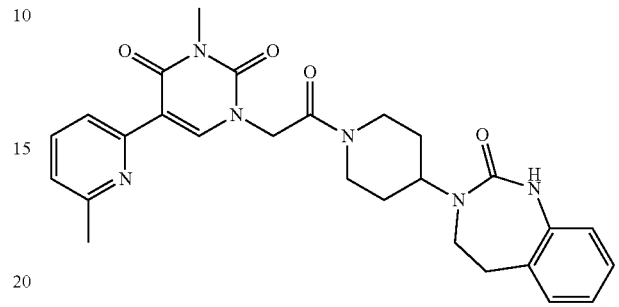

42.1: 1-benzhydryl-3-methyl-5-(6-methyl-1-oxy-pyridin-2-yl)-1H-pyrimidine-2,4-dione 15 mg (0.1 mmol) of palladium(II) acetate and 20 mg (0.1 mmol) of tri-tert-butylphosphonium tetrafluoroborate are added to a solution of 500 mg (1.4 mmol) of 1-benzhydryl-5-bromo-3-methyl-1H-pyrimidine-2,4-dione (prepared as described in example 2.2), 294 mg (2.7 mmol) of 2-picoline-N-oxide, and 279 mg (2 mmol) of potassium carbonate in 10 ml of toluene, previously degassed with nitrogen for 10 minutes. The reaction mixture is heated at 110° C. in a sealed tube for 40 hours. It is filtered on Celite and the filtrate is concentrated under vacuum. The crude residue is chromatographed on silica gel eluted with a dichloromethane/acetone mixture 70/30. 220 mg (41%) of 1-benzhydryl-3-methyl-5-(6-methyl-1-oxy-pyridin-2-yl)-1H-pyrimidine-2,4-dione is obtained in the form of an off-white solid.

42.2: 1-benzhydryl-3-methyl-5-(6-methyl-pyridin-2-yl)-1H-pyrimidine-2,4-dione 87 mg (2 mmol) of iron is added to a solution of 125 mg (0.3 mmol) of 1-benzhydryl-3-methyl-5-(6-methyl-1-oxy-pyridin-2-yl)-1H-pyrimidine-2,4-dione in 9.4 ml of acetic acid. The reaction mixture is heated at 70° C. in a sealed tube for 4 hours. It is filtered on Celite and then the filtrate is hydrolysed with a saturated aqueous solution of sodium hydrogen carbonate. The product is extracted with ethyl acetate. The organic phase is washed with a saturated aqueous solution of sodium hydrogen carbonate, then with water and with a saturated aqueous solution of sodium chloride, dried over magnesium sulphate, filtered and concentrated under vacuum. 120 mg (100%) of 1-benzhydryl-3-methyl-5-(6-methyl-pyridin-2-yl)-1H-pyrimidine-2,4-dione is obtained in the form of a beige solid.

42.3: 3-methyl-5-(6-methyl-pyridin-2-yl)-1H-pyrimidine-2,4-dione

Similarly to example 2.3, starting from 135 mg (0.4 mmol) of 1-benzhydryl-3-methyl-5-(6-methyl-pyridin-2-yl)-1H-pyrimidine-2,4-dione, 76 mg (100%) of 3-methyl-5-(6-methyl-pyridin-2-yl)-1H-pyrimidine-2,4-dione is obtained in the form of a yellow solid.

42.4: 3-methyl-5-(6-methyl-pyridin-2-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 42)

Similarly to example 13.1, starting from 136 mg (0.4 mmol) of 3-[1-(2-chloroacetyl)-piperidin-4-yl]-1,3,4,5-tetrahydro-benzo[d][1,3]diazepin-2-one (prepared as described in example 39.1), and 66 mg (0.4 mmol) of 3-methyl-5-(6-methyl-pyridin-2-yl)-1H-pyrimidine-2,4-dione, 105 mg (59%) of 3-methyl-5-(6-methyl-pyridin-2-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 248° C.

$^1$H NMR (δ, DMSO): 1.65-1.71 (m, 4H); 2.50 (s, 3H); 2.69 (t, J=12.3 Hz, 1H); 2.88-2.93 (m, 2H); 3.18 (t, J=13.1 Hz, 1H); 3.28 (s, 3H); 3.38-3.41 (m, 2H); 3.95 (d, J=13.6 Hz, 1H); 4.29-4.36 (m, 1H); 4.43 (d, J=13.0 Hz, 1H); 4.94 (s, 2H); 6.80-6.82 (m, 1H); 7.03-7.05 (m, 3H); 7.16 (d, J=7.6 Hz, 1H); 7.71 (t, J=7.8 Hz, 1H); 8.08 (d, J=8.0 Hz, 1H); 8.45 (s, 1H); 8.54 (s, 1H).

EXAMPLE 43: 3-METHYL-5-(6-METHYL-1-OXY-PYRIDIN-2-YL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 43)

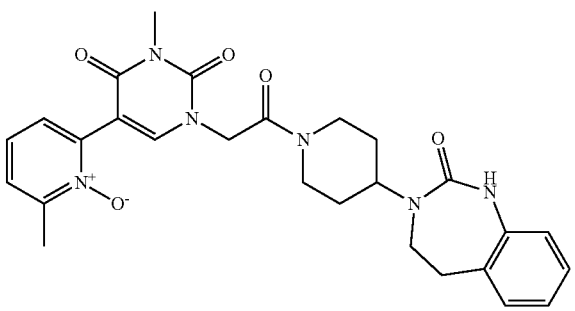 [SMILES: Cc1cccc(-c2cn(CC(=O)N3CCC(N4CCc5ccccc5NC4=O)CC3)c(=O)n(C)c2=O)[n+]1[O-]]

43.1: 3-methyl-5-(6-methyl-1-oxy-pyridin-2-yl)-1H-pyrimidine-2,4-dione

Similarly to example 2.3, starting from 63 mg (0.2 mmol) of 1-benzhydryl-3-methyl-5-(6-methyl-1-oxy-pyridin-2-yl)-1H-pyrimidine-2,4-dione (prepared as described in example 42.1), 37 mg (100%) of 3-methyl-5-(6-methyl-1-oxy-pyridin-2-yl)-1H-pyrimidine-2,4-dione is obtained in the form of a white solid.

43.2: 3-methyl-5-(6-methyl-1-oxy-pyridin-2-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 43)

Similarly to example 13.1, starting from 61 mg (0.2 mmol) of 3-[1-(2-chloroacetyl)-piperidin-4-yl]-1,3,4,5-tetrahydro-benzo[d][1,3]diazepin-2-one (prepared as described in example 39.1), and 37 mg (0.2 mmol) of 3-methyl-5-(6-methyl-pyridin-2-yl)-1H-pyrimidine-2,4-dione, 15 mg (18%) of 3-methyl-5-(6-methyl-1-oxy-pyridin-2-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid.

$^1$H NMR (δ, DMSO): 1.62-1.69 (m, 4H); 2.38 (s, 3H); 2.68 (m, 1H); 2.88-2.90 (m, 2H); 3.15 (m, 1H); 3.24 (s, 3H); 3.36-3.38 (m, 2H); 3.94 (d, J=13.7 Hz, 1H); 4.32 (m, 1H); 4.42 (d, J=13.0 Hz, 1H); 4.81 (s, 2H); 6.80-6.82 (m, 1H); 7.03-7.05 (m, 3H); 7.27 (t, J=7.8 Hz, 1H); 7.47-7.50 (m, 2H); 8.29 (s, 1H); 8.54 (s, 1H).

EXAMPLE 44: 3-METHYL-5-(1-METHYL-1H-PYRAZOL-4-YL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 44)

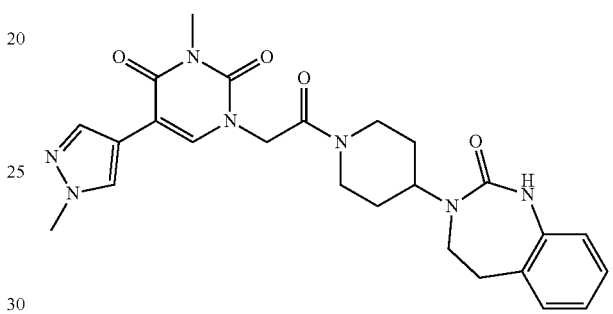

44.1: [3-methyl-5-(1-methyl-1H-pyrazol-4-yl)-2,4-dioxo-3,4-dihydro-2H-pyrimidin-1-yl]-methyl acetate 44.2 mg (50 μmol) of dichloromethane complex of 1,1'-bis(diphenylphosphino) ferrocene-dichloropalladium(II) is added to a solution containing 300 mg (1.1 mmol) of (5-bromo-3-methyl-2,4-dioxo-3,4-dihydro-2H-pyrimidin-1-yl)-methyl acetate (prepared as described in example 17.1), 338 mg (1.6 mmol) of 1-methyl-4-(4,4,5,5-tetramethyl-[1,3,2]dioxaborolan-2-yl)-1H-pyrazole and 344 mg (3.3 mmol) of sodium carbonate in 30 ml of 1,4-dioxane and 3 ml of water, previously degassed with nitrogen for 5 minutes. The reaction mixture is then heated at 100° C. for 1 hour. It is hydrolysed and then diluted with ethyl acetate. The product is extracted with ethyl acetate, the organic phases are combined, washed once with water and once with a saturated aqueous solution of sodium chloride, then dried over magnesium sulphate, filtered and concentrated under vacuum. The crude residue is chromatographed on silica gel eluted with a dichloromethane/methanol 97/3 mixture. 60 mg (20%) of [3-methyl-5-(1-methyl-1H-pyrazol-4-yl)-2,4-dioxo-3,4-dihydro-2H-pyrimidin-1-yl]-methyl acetate is obtained in the form of a beige solid.

44.2: [3-methyl-5-(1-methyl-1H-pyrazol-4-yl)-2,4-dioxo-3,4-dihydro-2H-pyrimidin-1-yl]-acetic acid Similarly to example 16.8, starting from 60 mg (0.2 mmol) of [3-methyl-5-(1-methyl-1H-pyrazol-4-yl)-2,4-dioxo-3,4-dihydro-2H-pyrimidin-1-yl]-methyl acetate, 57 mg (100%) of [3-methyl-5-(1-methyl-1H-pyrazol-4-yl)-2,4-dioxo-3,4-dihydro-2H-pyrimidin-1-yl]-acetic acid is obtained in the form of a beige solid.

44.3: 3-methyl-5-(1-methyl-1H-pyrazol-4-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 44)

Similarly to example 1.6, starting from 67 mg (0.2 mmol) of [3-methyl-5-(1-methyl-1H-pyrazol-4-yl)-2,4-dioxo-3,4-dihydro-2H-pyrimidin-1-yl]-acetic acid and 58 mg (0.2 mmol) of 3-piperidin-4-yl-1,3,4,5-tetrahydro-benzo[d][1,3]diazepin-2-one (prepared as described in example 16.4), and after recrystallization from ethanol, 45 mg (42%) of 3-methyl-5-(1-methyl-1H-pyrazol-4-yl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 290° C.

$^1$H NMR (δ, DMSO): 1.61-1.70 (m, 4H); 2.69 (t, J=12.8 Hz, 1H); 2.91 (m, 2H); 3.10-3.26 (m, 2H); 3.25 (s, 3H); 3.36-3.41 (m, 2H); 3.86 (s, 3H); 3.98 (d, J=13.6 Hz, 1H); 4.28-4.38 (m, 1H); 4.43 (d, J=13.0 Hz, 1H); 4.75 (d, J=6.0 Hz, 2H); 6.80-6.82 (m, 1H); 7.04-7.05 (m, 3H); 7.74 (s, 1H); 8.03 (s, 1H); 8.10 (s, 1H); 8.55 (s, 1H).

EXAMPLE 45: 5-(5-CHLORO-PYRIDIN-3-YL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 45)

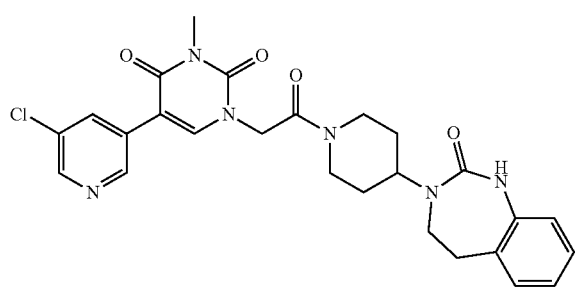 [SMILES: Cn1c(=O)c(-c2cncc(Cl)c2)cn(CC(=O)N2CCC(N3CCc4ccccc4NC3=O)CC2)c1=O]

45.1: 1-benzhydryl-5-(5-chloro-pyridin-3-yl)-3-methyl-1H-pyrimidine-2,4-dione Similarly to example 44.1, starting from 191 mg (1.2 mmol) of 5-chloropyridine-3-boronic acid and 300 mg (0.8 mmol) of 1-benzhydryl-5-bromo-3-methyl-1H-pyrimidine-2,4-dione (prepared as described in example 2.2), 340 mg (96%) of 1-benzhydryl-5-(5-chloro-pyridin-3-yl)-3-methyl-1H-pyrimidine-2,4-dione is obtained in the form of a white solid.

45.2: 5-(5-chloro-pyridin-3-yl)-3-methyl-1H-pyrimidine-2,4-dione

Similarly to example 2.3, starting from 326 mg (0.8 mmol) of 1-benzhydryl-5-(5-chloro-pyridin-3-yl)-3-methyl-1H-pyrimidine-2,4-dione, 190 mg (99%) of 5-(5-chloro-pyridin-3-yl)-3-methyl-1H-pyrimidine-2,4-dione is obtained in the form of a white solid.

45.3: 5-(5-chloro-pyridin-3-yl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 45)

Similarly to example 13.1, starting from 190 mg (0.8 mmol) of 5-(5-chloro-pyridin-3-yl)-3-methyl-1H-pyrimidine-2,4-dione and 283 mg (0.9 mmol) of 3-[1-(2-chloro-acetyl)-piperidin-4-yl]-1,3,4,5-tetrahydro-benzo[d][1,3]diazepin-2-one (prepared as described in example 39.1), after heating at 80° C. for 1.5 h and purification by silica gel chromatography eluted with a dichloromethane/methanol mixture 95/5, 180 mg (43%) of 5-(5-chloro-pyridin-3-yl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 250° C.

$^1$H NMR (δ, DMSO): 1.56-1.65 (m, 4H); 2.69 (t, J=12.2 Hz, 1H); 2.87-2.92 (m, 2H); 3.16-3.21 (m, 1H); 3.27 (s, 3H); 3.36-3.39 (m, 2H); 3.97 (d, J=13.6 Hz, 1H); 4.27-4.40 (m, 1H); 4.42 (d, J=13.1 Hz, 1H); 4.81 (s, 2H); 6.80-6.81 (m, 1H); 7.02-7.05 (m, 3H); 8.14 (t, J=2.1 Hz, 1H); 8.22 (s, 1H); 8.55 (s, 1H); 8.58 (d, J=2.4 Hz, 1H); 8.75 (d, J=1.9 Hz, 1H).

EXAMPLE 46: 5-BENZYL-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (COMPOUND 46)

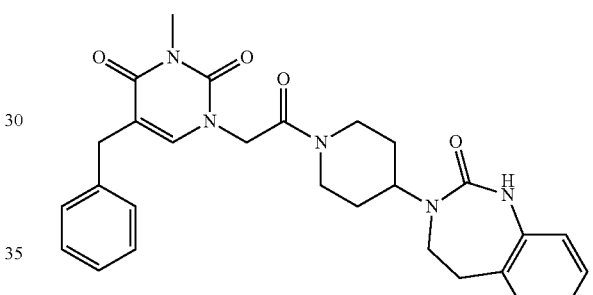

46.1: 5-benzyl-1H-pyrimidine-2,4-dione 20 ml of benzene is added to a solution of 2 g (14 mmol) of 5-hydroxymethyl-1H-pyrimidine-2,4-dione in 40 ml of trifluoroacetic acid. The mixture is heated at 130° C. for 20 minutes in sealed tubes. After cooling, the solvents are evaporated and the residue is taken up in dichloromethane. The product precipitates; it is filtered and dried under vacuum. 2.4 g (84%) of 5-benzyl-1H-pyrimidine-2,4-dione is obtained in the form of a white solid.

46.2: (5-benzyl-2,4-dioxo-3,4-dihydro-2H-pyrimidin-1-yl)-methyl acetate

Similarly to example 13.1, starting from 200 mg (1 mmol) of 5-benzyl-1H-pyrimidine-2,4-dione, 105 mg (39%) of (5-benzyl-2,4-dioxo-3,4-dihydro-2H-pyrimidin-1-yl)-methyl acetate is obtained in the form of a white solid.

46.3: (5-benzyl-3-methyl-2,4-dioxo-3,4-dihydro-2H-pyrimidin-1-yl)-acetic acid 75.6 mg (0.6 mmol) of potassium carbonate and 27 μl (0.4 mmol) of iodomethane are added to a solution of (5-benzyl-2,4-dioxo-3,4-dihydro-2H-pyrimidin-1-yl)-methyl acetate in 5 ml of dimethylformamide. The reaction mixture is heated at 50° C. for 1.5 h. 0.6 ml (0.6 mmol) of a 1M aqueous solution of lithium hydroxide is added with 1 ml of water and 2.5 ml of tetrahydrofuran. After stirring for 20 hours at room temperature, the mixture is hydrolysed with 1N aqueous solution of hydrochloric acid and then diluted with ethyl acetate. The product is extracted with ethyl acetate. The organic phases are combined, washed twice with water and once with a saturated aqueous solution of sodium chloride, then dried over magnesium sulphate, filtered and concentrated under vacuum. 100 mg (100%) of (5-benzyl-3-methyl-2,4-dioxo-3,4-dihydro-2H-pyrimidin-1-yl)-acetic acid is obtained in the form of a colourless oil.

46.4: 5-benzyl-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 46)

Similarly to example 1.6, starting from 100 mg (0.4 mmol) of (5-benzyl-3-methyl-2,4-dioxo-3,4-dihydro-2H-pyrimidin-1-yl)-acetic acid and 107 mg (0.4 mmol) of 3-piperidin-4-yl-1,3,4,5-tetrahydro-benzo[d][1,3]diazepin-2-one (prepared as described in example 16.4), 150 mg (79%) of 5-benzyl-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 266° C.

$^1$H NMR (δ, DMSO): 1.56-1.68 (m, 4H); 2.67 (t, J=12.6 Hz, 1H); 2.87-2.92 (m, 2H); 3.11-3.14 (m, 1H); 3.18 (m, 3H); 3.36-3.39 (m, 2H); 3.59 (s, 2H); 3.93 (d, J=13.6 Hz, 1H); 4.32 (m, 1H); 4.42 (d, J=13.0 Hz, 1H); 4.71 (d, J=2.6 Hz, 2H); 6.80-6.81 (m, 1H); 7.04-7.05 (m, 3H); 7.24-7.26 (m, 5H); 7.53 (s, 1H); 8.54 (s, 1H).

EXAMPLE 47: 5-(3,4-DICHLOROPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 47)

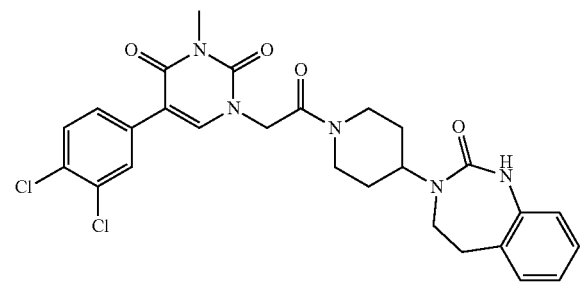 [SMILES: Cn1c(=O)c(-c2ccc(Cl)c(Cl)c2)cn(CC(=O)N2CCC(N3CCc4ccccc4NC3=O)CC2)c1=O]

47.1: [5-(3,4-dichlorophenyl)-3-methyl-2,4-dioxo-3,4-dihydro-2H-pyrimidin-1-yl]-acetic acid Similarly to example 44.1, starting from 450 mg (1.6 mmol) of (5-bromo-3-methyl-2,4-dioxo-3,4-dihydro-2H-pyrimidin-1-yl)-methyl acetate (prepared as described in example 17.1) and 620 mg (3.3 mmol) of 3,4-dichlorophenylboronic acid, and after adding 5 ml of a 1N aqueous soda solution and heating at 100° C. for 1 hour, 520 mg (97%) of [5-(3,4-dichlorophenyl)-3-methyl-2,4-dioxo-3,4-dihydro-2H-pyrimidin-1-yl]-acetic acid is obtained in the form of a beige solid.

47.2: 5-(3,4-dichlorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 47)

Similarly to example 1.6, starting from 400 mg (1.2 mmol) of [5-(3,4-dichlorophenyl)-3-methyl-2,4-dioxo-3,4-dihydro-2H-pyrimidin-1-yl]-acetic acid and 358 mg (1.5 mmol) of 3-piperidin-4-yl-1,3,4,5-tetrahydro-benzo[d][1,3]diazepin-2-one (prepared as described in example 16.4), 320 mg (47%) of 5-(3,4-dichlorophenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid.

$^1$H NMR (δ, DMSO): 1.52-1.61 (m, 4H). 2.63 (t, J=10.6 Hz, 1H); 2.84 (m, 2H); 3.10 (m, 1H); 3.19 (s, 3H); 3.30-3.33 (m, 2H); 3.90 (d, J=13.6 Hz, 1H); 4.26 (m, 1H); 4.35 (d, J=12.5 Hz, 1H); 4.74 (s, 2H); 6.73-6.74 (m, 1H); 6.96-6.97 (m, 3H); 7.55 (dd, J=8.5, 2.1 Hz, 1H); 7.62 (d, J=8.5 Hz, 1H); 7.81 (d, J=2.1 Hz, 1H); 8.05 (s, 1H); 8.47 (s, 1H).

EXAMPLE 48: 5-(5-CHLORO-2-METHYLPHENYL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 48)

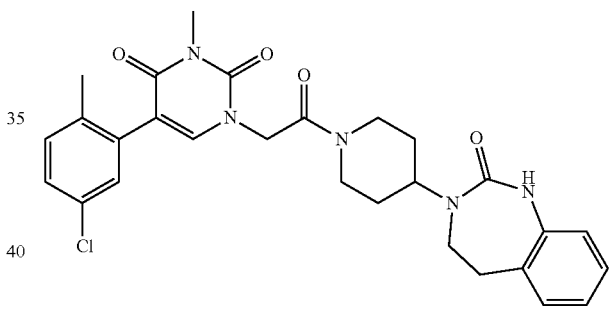

48.1: [5-(5-chloro-2-methylphenyl)-3-methyl-2,4-dioxo-3,4-dihydro-2H-pyrimidin-1-yl]-acetic acid Similarly to example 47.1, starting from 400 mg (1.4 mmol) of (5-bromo-3-methyl-2,4-dioxo-3,4-dihydro-2H-pyrimidin-1-yl)-methyl acetate (prepared as described in example 17.1) and 492 mg (2.9 mmol) of (5-chloro-2-methylphenyl)boronic acid, and after adding 5 ml of a 1N aqueous soda solution and heating at 100° C. for 1 hour, 440 mg (99%) of [5-(5-chloro-2-methylphenyl)-3-methyl-2,4-dioxo-3,4-dihydro-2H-pyrimidin-1-yl]-acetic acid is obtained in the form of a beige solid.

48.2: 5-(5-chloro-2-methylphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 48)

Similarly to example 1.6, starting from 445 mg (1.4 mmol) of [5-(5-chloro-2-methylphenyl)-3-methyl-2,4-dioxo-3,4-dihydro-2H-pyrimidin-1-yl]-acetic acid and 424 mg (1.7 mmol) of 3-piperidin-4-yl-1,3,4,5-tetrahydro-benzo[d][1,3]diazepin-2-one (prepared as described in example 16.4), 162 mg (19%) of 5-(5-chloro-2-methylphenyl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid.

¹H NMR (δ, DMSO): 1.57-1.66 (m, 4H); 2.16 (s, 3H); 2.68 (t, J=12.6 Hz, 1H); 2.89 (d, J=6.7 Hz, 2H); 3.15 (t, J=12.3 Hz, 1H); 3.24 (s, 3H); 3.35-3.38 (m, 2H); 3.94 (d, J=13.7 Hz, 1H); 4.26-4.39 (m, 1H); 4.42 (d, J=12.9 Hz, 1H); 4.76 (d, J=2.6 Hz, 2H); 6.79-6.80 (m, 1H); 7.03-7.05 (m, 3H); 7.19 (d, J=2.3 Hz, 1H); 7.29 (d, J=8.3 Hz, 1H); 7.34 (dd, J=8.2, 2.3 Hz, 1H); 7.73 (s, 1H); 8.52 (s, 1H).

EXAMPLE 49: 5-(4,5-DIMETHYL-PYRIDIN-3-YL)-3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 49)

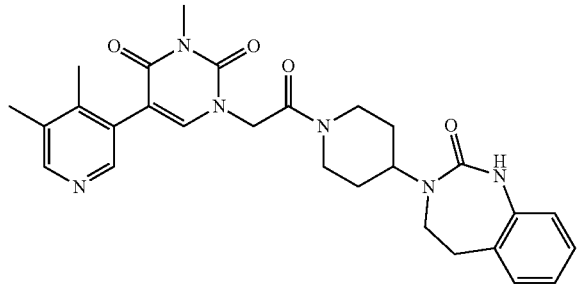 [SMILES: Cc1cncc(-c2cn(CC(=O)N3CCC(N4CCc5ccccc5NC4=O)CC3)c(=O)n(C)c2=O)c1C]

49.1: 1-benzhydryl-5-(4,5-dimethyl-pyridin-3-yl)-3-methyl-1H-pyrimidine-2,4-dione Similarly to example 44.1, starting from 244 mg (1.6 mmol) of 4,5-dimethyl-pyridine boronic acid and 400 mg (1.1 mmol) of 1-benzhydryl-5-bromo-3-methyl-1H-pyrimidine-2,4-dione (prepared as described in example 2.2), 290 mg (68%) of 1-benzhydryl-5-(4,5-dimethyl-pyridin-3-yl)-3-methyl-1H-pyrimidine-2,4-dione is obtained in the form of a clear yellow oil.

49.2: 5-(4,5-dimethyl-pyridin-3-yl)-3-methyl-1H-pyrimidine-2,4-dione

Similarly to example 2.3, starting from 290 mg (0.7 mmol) of 1-benzhydryl-5-(4,5-dimethyl-pyridin-3-yl)-3-methyl-H-pyrimidine-2,4-dione, 120 mg (71%) of 5-(4,5-dimethyl-pyridin-3-yl)-3-methyl-1H-pyrimidine-2,4-dione is obtained in the form of a white solid.

49.3: 5-(4,5-dimethyl-pyridin-3-yl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 49)

Similarly to example 13.1, starting from 120 mg (0.5 mmol) of 5-(4,5-dimethyl-pyridin-3-yl)-3-methyl-1H-pyrimidine-2,4-dione and 184 mg (0.6 mmol) of 3-[1-(2-chloroacetyl)-piperidin-4-yl]-1,3,4,5-tetrahydro-benzo[d][1,3]diazepin-2-one (prepared as described in example 39.1), after heating at 50° C. for 18 hours and purification by crystallization in ethanol, 120 mg (45%) of 5-(4,5-dimethyl-pyridin-3-yl)-3-methyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 225° C.

¹H NMR (δ, DMSO): 1.58-1.70 (m, 4H); 2.10 (s, 3H); 2.28 (s, 3H); 2.69 (t, J=12.5 Hz, 1H); 2.87-2.92 (m, 2H); 3.16 (t, J=12.2 Hz, 1H); 3.26 (s, 3H); 3.36-3.39 (m, 2H); 3.96 (d, J=13.6 Hz, 1H); 4.33 (m, 1H); 4.43 (d, J=13.0 Hz, 1H); 4.78 (s, 2H); 6.80-6.81 (m, 1H); 7.03-7.04 (m, 3H); 7.75 (s, 1H); 8.12 (s, 1H); 8.33 (s, 1H); 8.54 (s, 1H).

EXAMPLE 50: 3-METHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-5-PHENOXY-1H-PYRIMIDINE-2,4-DIONE (REACTION SCHEME NO. 3, COMPOUND 50)

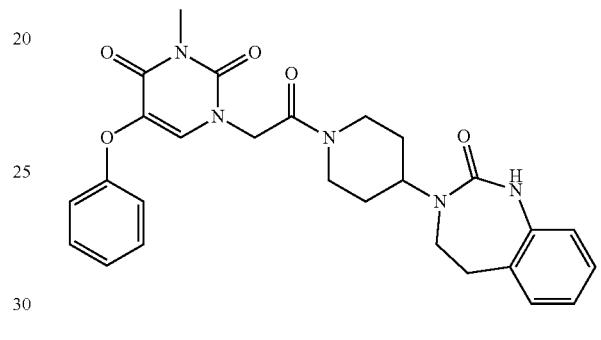

50.1: 1-benzhydryl-3-methyl-5-phenoxy-1H-pyrimidine-2,4-dione 254 mg (2.7 mmol) of phenol, 67 mg (0.7 mmol) of copper chloride, 25 mg (0.1 mmol) of 2,2,6,6-tetramethyl-3,5-heptanedione and 878 mg (2.7 mmol) of caesium carbonate are added to a solution of 500 mg (1.4 mmol) of 1-benzhydryl-5-bromo-3-methyl-1H-pyrimidine-2,4-dione in 2.5 ml of 1-methyl-2-pyrrolidinone, previously degassed with nitrogen. The reaction mixture is heated at 120° C. for 22 hours and then diluted in 6 ml of ethyl acetate and filtered on Celite. The solvents are evaporated, the residue is washed once with 1N aqueous solution of hydrochloric acid and then with 1N aqueous solution of sodium hydroxide and with water. The organic phase is dried over magnesium sulphate, filtered and concentrated under vacuum. The crude residue is chromatographed on silica gel eluted with a heptane/ethyl acetate 80/20 mixture. 105 mg (20%) of 1-benzhydryl-3-methyl-5-phenoxy-1H-pyrimidine-2,4-dione is obtained in the form of a yellow solid.

50.2: 3-methyl-5-phenoxy-1H-pyrimidine-2,4-dione

Similarly to example 2.3, starting from 145 mg (0.4 mmol) of 1-benzhydryl-3-methyl-5-phenoxy-1H-pyrimidine-2,4-dione, 85 mg (100%) of 3-methyl-5-phenoxy-1H-pyrimidine-2,4-dione is obtained in the form of a yellow oil.

50.3: 3-methyl-1-{2-oxo-2-[4-(2-oxo-1,2,4,5-tetrahydro-benzo[d][1,3]diazepin-3-yl)-piperidin-1-yl]-ethyl}-5-phenoxy-1H-pyrimidine-2,4-dione (Compound 50)

Similarly to example 13.1, starting from 85 mg (0.4 mmol) of 3-methyl-5-phenoxy-1H-pyrimidine-2,4-dione, 125 mg (0.4 mmol) of 3-[1-(2-chloroacetyl)-piperidin-4-yl]-1,3,4,5-tetrahydro-benzo[d][1,3]diazepin-2-one (prepared as described in example 39.1), and after heating at 50° C. for 18 hours, 65 mg (32%) of 3-methyl-1-{2-oxo-2-[4-(2-oxo-1,2,4,5-tetrahydro-benzo[d][1,3]diazepin-3-yl)-piperidin-1-yl]-ethyl}-5-phenoxy-1H-pyrimidine-2,4-dione is obtained in the form of a pale yellow solid with a melting point of 163° C.

$^1$H NMR (δ, DMSO): 1.55-1.68 (m, 4H); 2.69 (t, J=12.5 Hz, 1H); 2.90 (m, 2H); 3.15 (m, 1H); 3.21 (s, 3H); 3.38 (m, 2H); 3.94 (d, J=13.6 Hz, 1H); 4.33 (m, 1H); 4.44 (d, J=13.0 Hz, 1H); 4.74 (s, 2H); 6.80-6.83 (m, 1H); 7.01-7.03 (m, 6H); 7.33 (t, J=7.8 Hz, 2H); 7.92 (s, 1H); 8.54 (s, 1H).

EXAMPLE 51: 5-(2,3-DIMETHYLPHENYL)-3-ETHYL-1-{2-OXO-2-[4-(2-OXO-1,2,4,5-TETRA-HYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 51)

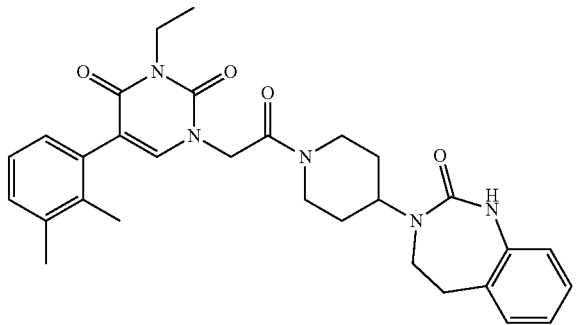 [SMILES: CCn1c(=O)c(-c2cccc(C)c2C)cn(CC(=O)N2CCC(N3CCc4ccccc4NC3=O)CC2)c1=O]

51.1: (5-bromo-3-ethyl-2,4-dioxo-3,4-dihydro-2H-pyrimidin-1-yl)-methyl acetate 2.4 g (17 mmol) of potassium carbonate and 1.4 ml (17 mmol) of iodoethane are added to a solution of 3 g (11 mmol) of (5-bromo-2,4-dioxo-3,4-dihydro-2H-pyrimidin-1-yl)-methyl acetate (prepared as described in example 13.1) in 60 ml of dimethylformamide. The reaction mixture is heated at 50° C. for 2 hours and then hydrolysed and extracted with ethyl acetate. The organic phase is washed once with water and once with a saturated aqueous solution of sodium chloride, then dried over magnesium sulphate, filtered and concentrated under vacuum. The crude residue is taken up in diethyl ether, then filtered and dried under nitrogen. 1.7 g (50%) of (5-bromo-3-ethyl-2,4-dioxo-3,4-dihydro-2H-pyrimidin-1-yl)-methyl acetate is obtained in the form of a cream-coloured solid.

51.2: [5-(2,3-dimethylphenyl)-3-ethyl-2,4-dioxo-3,4-dihydro-2H-pyrimidin-1-yl]-methyl acetate Similarly to example 44.1, starting from 350 mg (1.2 mmol) of (5-bromo-3-ethyl-2,4-dioxo-3,4-dihydro-2H-pyrimidin-1-yl)-methyl acetate and 289 mg (1.9 mmol) of 2,3-dimethylphenylboronic acid, and after purification by silica gel chromatography eluted with a heptane/ethyl acetate mixture 70/30, 255 mg (67%) of [5-(2,3-dimethylphenyl)-3-ethyl-2,4-dioxo-3,4-dihydro-2H-pyrimidin-1-yl]-methyl acetate is obtained in the form of a white solid.

51.3: [5-(2,3-dimethylphenyl)-3-ethyl-2,4-dioxo-3,4-dihydro-2H-pyrimidin-1-yl]-acetic acid Similarly to example 16.8, starting from 255 mg (0.8 mmol) of [5-(2,3-dimethylphenyl)-3-ethyl-2,4-dioxo-3,4-dihydro-2H-pyrimidin-1-yl]-methyl acetate, 220 mg (90%) of [5-(2,3-dimethylphenyl)-3-ethyl-2,4-dioxo-3,4-dihydro-2H-pyrimidin-1-yl]-acetic acid is obtained in the form of a white solid.

51.4: 5-(2,3-dimethylphenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 51)

Similarly to example 1.6, starting from 220 mg (0.7 mmol) of [5-(2,3-dimethylphenyl)-3-ethyl-2,4-dioxo-3,4-dihydro-2H-pyrimidin-1-yl]-acetic acid, 196 mg (0.8 mmol) of 3-piperidin-4-yl-1,3,4,5-tetrahydro-benzo[d][1,3]diazepin-2-one (prepared as described in example 16.4) and 0.1 ml (0.9 mmol) of triethylamine and after purification by silica gel chromatography eluted with a dichloromethane/methanol 97/3 mixture followed by crystallization in a heptane/ethyl acetate mixture 70/30, 280 mg (72%) of 5-(2,3-dimethylphenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 170° C.

$^1$H NMR (δ, DMSO): 1.13 (t, J=7 Hz, 3H), 1.48-1.60 (m, 1H), 1.62-1.80 (m, 3H), 2.05 (t, 3H), 2.30 (t, 3H), 2.68 (t, J=11.7 Hz, 1H), 2.89 (t, J=4.6 Hz, 2H), 3.15 (t, J=11.7 Hz, 1H), 3.37 (t, J=4.6 Hz, 2H), 3.88-3.95 (m, 3H), 4.28-4.36 (m, 1H), 4.43 (d, J=12.7 Hz, 1H), 4.75 (d, J=6.4 Hz, 2H), 6.77-6.83 (m, 1H), 6.96 (d, J=7 Hz, 1H), 7.02-7.06 (m, 3H), 7.10 (t, J=7.5 Hz, 1H), 7.17 (d, J=7.3 Hz, 1H), 7.58 (s, 1H), 8.52 (s, 1H).

EXAMPLE 52: 5-(3-CHLORO-2-METHYLPHENYL)-3-ETHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 52)

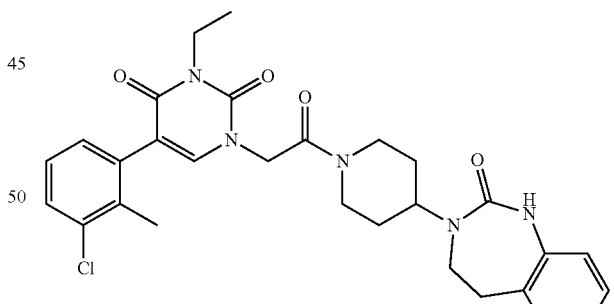

52.1: [5-(3-chloro-2-methylphenyl)-3-ethyl-2,4-dioxo-3,4-dihydro-2H-pyrimidin-1-yl]-acetic acid Similarly to example 13.3, starting from 350 mg (1.2 mmol) of (5-bromo-3-ethyl-2,4-dioxo-3,4-dihydro-2H-pyrimidin-1-yl)-methyl acetate (prepared as described in example 51.1), and 328 mg (1.9 mmol) of 3-chloro-2-methylphenyl boronic acid, 330 mg (85%) of [5-(3-chloro-2-methylphenyl)-3-ethyl-2,4-dioxo-3,4-dihydro-2H-pyrimidin-1-yl]-acetic acid is obtained in the form of a beige solid.

52.2: 5-(3-chloro-2-methylphenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 52)

Similarly to example 51.4, starting from 330 mg (1 mmol) of [5-(3-chloro-2-methylphenyl)-3-ethyl-2,4-dioxo-3,4-dihydro-2H-pyrimidin-1-yl]-acetic acid and 276 mg (1.1 mmol) of 3-piperidin-4-yl-1,3,4,5-tetrahydro-benzo[d][1,3]diazepin-2-one (prepared as described in example 16.4), 290 mg (51%) of 5-(3-chloro-2-methylphenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 247° C.

$^1$H NMR (δ, DMSO): 1.13 (t, J=7 Hz, 3H), 1.50-1.62 (m, 1H), 1.52-1.80 (m, 3H), 2.19 (s, 3H), 2.68 (t, J=12.2 Hz, 1H), 2.89 (t, J=4.1 Hz, 2H), 3.15 (t, J=12.2 Hz, 1H), 3.37 (t, J=4.1 Hz, 2H), 3.88-3.96 (m, 3H), 4.29-4.35 (m, 1H), 4.43 (d, J=12.7 Hz, 1H), 4.76 (d, J=4.2 Hz, 2H), 6.78-6.83 (m, 1H), 7.02-7.05 (m, 3H), 7.14 (d, J=6.8 Hz, 1H), 7.26 (t, J=7.8 Hz, 1H), 7.46 (d, J=7.2 Hz, 1H), 7.70 (s, 1H), 8.52 (s, 1H).

EXAMPLE 53: 5-(2,3-DICHLOROPHENYL)-3-ETHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 53)

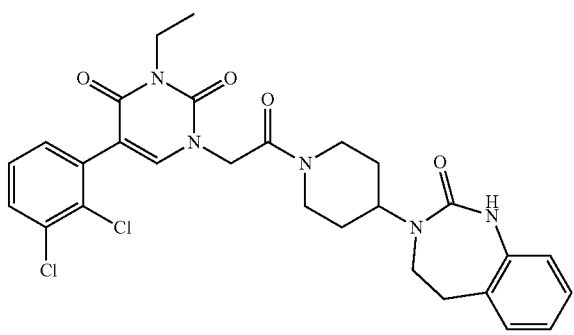

53.1: [5-(2,3-dichlorophenyl)-3-ethyl-2,4-dioxo-3,4-dihydro-2H-pyrimidin-1-yl]-acetic acid Similarly to example 13.3, starting from 350 mg (1.2 mmol) of (5-bromo-3-ethyl-2,4-dioxo-3,4-dihydro-2H-pyrimidin-1-yl)-methyl acetate (prepared as described in example 51.1), and 367 mg (1.9 mmol) of 2,3-dichlorophenylboronic acid, 120 mg (29%) of [5-(2,3-dichlorophenyl)-3-ethyl-2,4-dioxo-3,4-dihydro-2H-pyrimidin-1-yl]-acetic acid is obtained in the form of a beige solid.

53.2: 5-(2,3-dichlorophenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 53)

Similarly to example 51.4, starting from 120 mg (0.4 mmol) of [5-(2,3-dichlorophenyl)-3-ethyl-2,4-dioxo-3,4-dihydro-2H-pyrimidin-1-yl]-acetic acid and 94 mg (0.4 mmol) of 3-piperidin-4-yl-1,3,4,5-tetrahydro-benzo[d][1,3]diazepin-2-one (prepared as described in example 16.4), 130 mg (63%) of 5-(2,3-dichlorophenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 170° C.

$^1$H NMR (δ, DMSO): 1.13 (t, J=6.9 Hz, 3H), 1.48-1.60 (m, 1H), 1.62-1.80 (m, 3H), 2.68 (t, J=11 Hz, 1H), 2.88 (t, J=4.4 Hz, 2H), 3.15 (t, J=11 Hz, 1H), 3.37 (t, J=4.0 Hz, 2H), 3.89-3.91 (m, 2H), 3.95 (d, J=13 Hz, 1H), 4.28-4.38 (m, 1H), 4.45 (d, J=13 Hz, 1H), 4.76 (d, J=5.2 Hz, 2H), 6.75-6.83 (m, 1H), 7.02-7.04 (m, 3H), 7.33 (dd, J=1.6-7.6 Hz, 1H), 7.42 (t, J=7.8 Hz, 1H), 7.68 (dd, J=1.6-8.1 Hz, 1H), 7.80 (s, 1H), 8.54 (s, 1H).

EXAMPLE 54: 5-(2-CHLORO-3-FLUOROPHENYL)-3-ETHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 54)

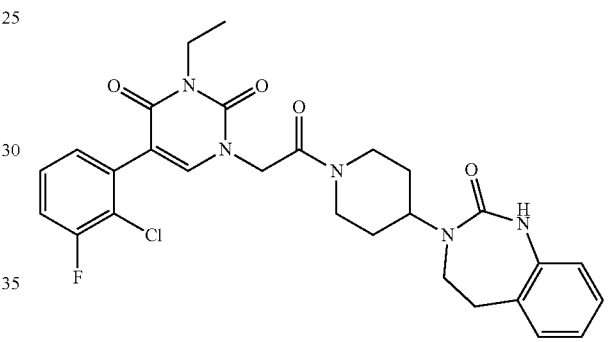

54.1: [5-(2-chloro-3-fluorophenyl)-3-ethyl-2,4-dioxo-3,4-dihydro-2H-pyrimidin-1-yl]-acetic acid Similarly to example 13.3, starting from 300 mg (1 mmol) of (5-bromo-3-ethyl-2,4-dioxo-3,4-dihydro-2H-pyrimidin-1-yl)-methyl acetate (prepared as described in example 51.1), and 270 mg (1.6 mmol) of 2-chloro-3-fluorophenyl boronic acid, 255 mg (76%) of [5-(2-chloro-3-fluorophenyl)-3-ethyl-2,4-dioxo-3,4-dihydro-2H-pyrimidin-1-yl]-acetic acid is obtained in the form of a brown solid.

54.2: 5-(2-chloro-3-fluorophenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 54)

Similarly to example 51.4, starting from 255 mg (0.8 mmol) of [5-(2-chloro-3-fluorophenyl)-3-ethyl-2,4-dioxo-3,4-dihydro-2H-pyrimidin-1-yl]-acetic acid and 211 mg (0.9 mmol) of 3-piperidin-4-yl-1,3,4,5-tetrahydro-benzo[d][1,3]diazepin-2-one (prepared as described in example 16.4), 190 mg (44%) of 5-(2-chloro-3-fluorophenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 248° C.

$^1$H NMR (δ, DMSO): 1.13 (t, J=6.9 Hz, 3H), 1.45-1.60 (m, 1H), 1.62-1.80 (m, 3H), 2.68 (t, J=12.1 Hz, 1H), 2.89 (t, J=4.2 Hz, 2H), 3.15 (t, J=10.3 Hz, 1H), 3.37 (t, J=4.2 Hz,

2H), 3.88-3.95 (m, 3H), 4.3-4.35 (m, 1H), 4.43 (d, J=12.6 Hz, 1H), 4.77 (d, J=4.4 Hz, 2H), 6.78-6.82 (m, 1H), 7.02-7.05 (m, 3H), 7.21-7.23 (m, 1H), 7.43-7.48 (m, 2H), 7.82 (s, 1H), 8.54 (s, 1H).

EXAMPLE 55: 5-(3-CHLORO-2-METHOXYPHE-NYL)-3-ETHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 55)

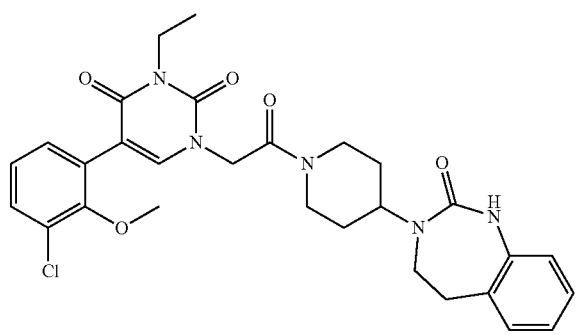 [SMILES: CCn1c(=O)c(-c2cccc(Cl)c2OC)cn(CC(=O)N2CCC(N3CCc4ccccc4NC3=O)CC2)c1=O]

55.1: [5-(3-chloro-2-methoxyphenyl)-3-ethyl-2,4-dioxo-3,4-dihydro-2H-pyrimidin-1-yl]-acetic acid Similarly to example 13.3, starting from 400 mg (1.4 mmol) of (5-bromo-3-ethyl-2,4-dioxo-3,4-dihydro-2H-pyrimidin-1-yl)-methyl acetate (prepared as described in example 51.1), and 410 mg (2.2 mmol) of 3-chloro-2-methoxyphenyl boronic acid, 307 mg (65%) of [5-(3-chloro-2-methoxyphenyl)-3-ethyl-2,4-dioxo-3,4-dihydro-2H-pyrimidin-1-yl]-acetic acid is obtained in the form of a white solid.

55.2: 5-(3-chloro-2-methoxyphenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 55)

Similarly to example 51.4, starting from 300 mg (0.9 mmol) of [5-(3-chloro-2-methoxyphenyl)-3-ethyl-2,4-dioxo-3,4-dihydro-2H-pyrimidin-1-yl]-acetic acid and 239 mg (1 mmol) of 3-piperidin-4-yl-1,3,4,5-tetrahydro-benzo[d][1,3]diazepin-2-one (prepared as described in example 16.4), 395 mg (78%) of 5-(3-chloro-2-methoxyphenyl)-3-ethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 219° C.

$^1$H NMR (δ, DMSO): 1.14 (t, J=7.0 Hz, 3H); 1.45-1.80 (m, 4H); 2.68 (t, J=12.5 Hz, 1H); 2.86-2.91 (m, 2H); 3.15 (t, J=12.5 Hz, 1H); 3.34-3.39 (m, 2H); 3.67 (s, 3H); 3.90-3.93 (m, 3H); 4.28-4.35 (m, 1H); 4.43 (d, J=13.0 Hz, 1H); 4.77-4.79 (m, 2H); 6.79-6.80 (m, 1H); 7.03-7.05 (m, 3H); 7.18 (t, J=7.8 Hz, 1H); 7.27 (dd, J=7.7, 1.7 Hz, 1H); 7.49 (dd, J=8.0, 1.7 Hz, 1H); 7.77 (s, 1H); 8.54 (s, 1H).

EXAMPLE 56: 5-(2,3-DIMETHYLPHENYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-3-PROPYL-1H-PYRIMIDINE-2,4-DIONE (REACTION SCHEME NO. 3, COMPOUND 56)

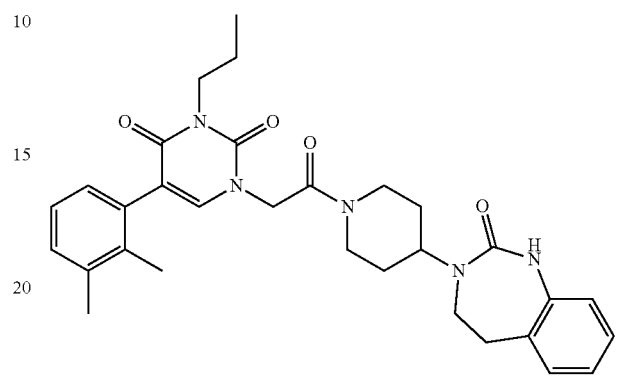

56.1: (5-bromo-2,4-dioxo-3-propyl-3,4-dihydro-2H-pyrimidin-1-yl)-methyl acetate

Similarly to example 51.1, starting from 4 g (20 mmol) of (5-bromo-2,4-dioxo-3,4-dihydro-2H-pyrimidin-1-yl)-methyl acetate (prepared as described in example 13.1) and 2.1 ml (20 mmol) of 1-bromopropane, 2.9 g (61%) of (5-bromo-2,4-dioxo-3-propyl-3,4-dihydro-2H-pyrimidin-1-yl)-methyl acetate is obtained in the form of a white solid.

56.2: [5-(2,3-dimethylphenyl)-2,4-dioxo-3-propyl-3,4-dihydro-2H-pyrimidin-1-yl]-methyl acetate Similarly to example 44.1, starting from 300 mg (1 mmol) of (5-bromo-2,4-dioxo-3-propyl-3,4-dihydro-2H-pyrimidin-1-yl)-methyl acetate and 221 mg (1.5 mmol) of 2,3-dimethylphenyl boronic acid, 260 mg (80%) of [5-(2,3-dimethylphenyl)-2,4-dioxo-3-propyl-3,4-dihydro-2H-pyrimidin-1-yl]-methyl acetate is obtained in the form of a white solid.

56.3: [5-(2,3-dimethylphenyl)-2,4-dioxo-3-propyl-3,4-dihydro-2H-pyrimidin-1-yl]-acetic acid Similarly to example 16.8, starting from 260 mg (0.8 mmol) of [5-(2,3-dimethylphenyl)-2,4-dioxo-3-propyl-3,4-dihydro-2H-pyrimidin-1-yl]-methyl acetate, 230 mg (92%) of [5-(2,3-dimethylphenyl)-2,4-dioxo-3-propyl-3,4-dihydro-2H-pyrimidin-1-yl]-acetic acid is obtained in the form of a white solid.

56.4: 5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-3-propyl-1H-pyrimidine-2,4-dione (Compound 56)

Similarly to example 51.4, starting from 230 mg (0.7 mmol) of [5-(2,3-dimethylphenyl)-2,4-dioxo-3-propyl-3,4-dihydro-2H-pyrimidin-1-yl]-acetic acid and 196 mg (0.8 mmol) of 3-piperidin-4-yl-1,3,4,5-tetrahydro-benzo[d][1,3]diazepin-2-one (prepared as described in example 16.4), 250 mg (63%) of 5-(2,3-dimethylphenyl)-1-{2-oxo-2-[4-(2-oxo-1,2,4,5-tetrahydro-benzo[d][1,3]diazepin-3-yl)-piperidin-1- yl]-ethyl}-3-propyl-1H-pyrimidine-2,4-dione is obtained in the form of a white solid with a melting point of 194° C.

$^1$H NMR (δ, DMSO): 0.86 (t, J=3.7 Hz, 3H), 1.52-1.60 (m, 3H), 1.62-1.80 (m, 3H), 2.04 (s, 3H), 2.27 (s, 3H), 2.67 (t, J=11 Hz, 1H), 2.89 (t, J=4.4 Hz, 2H), 3.14 (t, J=11 Hz, 1H), 3.37 (t, J=4.4 Hz, 2H), 3.83 (t, J=7 Hz, 2H), 3.93 (d, J=13.7 Hz, 1H), 4.28-4.38 (m, 1H), 4.43 (d, J=12.6 Hz, 1H), 4.75 (d, J=6.2 Hz, 2H), 6.78-6.82 (m, 1H), 6.96 (d, J=7.2 Hz, 1H), 7.01-7.05 (m, 3H), 7.10 (t, J=7.5 Hz, 1H), 7.17 (d, J=7.3 Hz, 1H), 7.59 (s, 1H), 8.54 (s, 1H).

EXAMPLE 57: 5-(2-CHLORO-3-FLUOROPHE-NYL)-1-{2-OXO-2-[4-(2-OXO-1,2,4,5-TETRA-HYDRO-BENZO[D][1,3]DIAZEPIN-3-YL)-PIP-ERIDIN-1-YL]-ETHYL}-3-PROPYL-1H-PYRIMIDINE-2,4-DIONE (REACTION SCHEME NO. 3, COMPOUND 57)

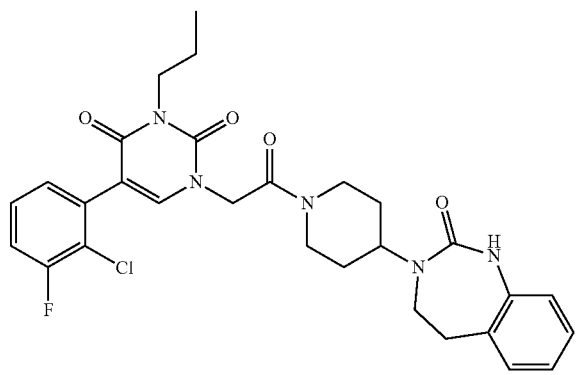 [SMILES: CCCn1c(=O)c(-c2cccc(F)c2Cl)cn(CC(=O)N2CCC(N3CCc4ccccc4NC3=O)CC2)c1=O]

57.1: [5-(2-chloro-3-fluorophenyl)-2,4-dioxo-3-pro-pyl-3,4-dihydro-2H-pyrimidin-1-yl]-acetic acid Similarly to example 13.3, starting from 300 mg (1 mmol) of (5-bromo-2,4-dioxo-3-propyl-3,4-dihydro-2H-pyrimidin-1-yl)-methyl acetate (prepared as described in example 56.1) and 257 mg (1.5 mmol) of 2-chloro-3-fluorophenyl boronic acid, 200 mg (60%) of [5-(2-chloro-3-fluorophenyl)-2,4-dioxo-3-propyl-3,4-dihydro-2H-pyrimidin-1-yl]-acetic acid is obtained in the form of a beige solid.

57.2: 5-(2-chloro-3-fluorophenyl)-1-{2-oxo-2-[4-(2-oxo-1,2,4,5-tetrahydro-benzo[d][1,3]diazepin-3-yl)-piperidin-1-yl]-ethyl}-3-propyl-1H-pyrimidine-2,4-dione (Compound 57)

Similarly to example 51.4, starting from 200 mg (0.6 mmol) of [5-(2-chloro-3-fluorophenyl)-2,4-dioxo-3-propyl-3,4-dihydro-2H-pyrimidin-1-yl]-acetic acid and 158 mg (0.7 mmol) of 3-piperidin-4-yl-1,3,4,5-tetrahydro-benzo[d][1,3]diazepin-2-one (prepared as described in example 16.4), and after recrystallization from ethanol, 240 mg (71%) of 5-(2-chloro-3-fluorophenyl)-1-{2-oxo-2-[4-(2-oxo-1,2,4,5-tetra-hydro-benzo[d][1,3]diazepin-3-yl)-piperidin-1-yl]-ethyl}-3-propyl-1H-pyrimidine-2,4-dione is obtained in the form of a white solid with a melting point of 242° C.

$^1$H NMR (δ, DMSO): 0.88 (t, J=7.4 Hz, 3H); 1.54-1.85 (m, 6H); 2.68 (t, J=12.6 Hz, 1H); 2.89 (m, 2H); 3.15 (t, J=12.6 Hz, 1H); 3.35-3.38 (m, 2H); 3.84 (t, J=7.3 Hz, 2H); 3.94 (d, J=13.6 Hz, 1H); 4.28-4.36 (m, 1H); 4.42 (d, J=13.6 Hz, 1H); 4.77 (d, J=3.5 Hz, 2H); 6.79-6.81 (m, 1H); 7.02-7.05 (m, 3H); 7.21 (dd, J=6.6, 2.5 Hz, 1H); 7.43-7.47 (m, 2H); 7.82 (s, 1H); 8.54 (s, 1H).

EXAMPLE 58: 1-{2-OXO-2-[4-(2-OXO-1,2,4,5-TETRAHYDRO-BENZO[D][1,3]DIAZEPIN-3-YL)-PIPERIDIN-1-YL]-ETHYL}-3-PROPYL-5-PYRIDAZIN-3-YL-1H-PYRIMIDINE-2,4-DIONE (REACTION SCHEME NO. 3, COMPOUND 58)

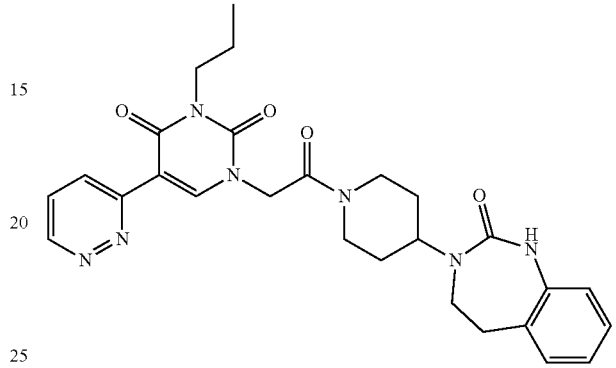

58.1: 1-benzhydryl-5-bromo-3-propyl-1H-pyrimi-dine-2,4-dione

Similarly to example 2.2, starting from 3 g (8.4 mmol) of 1-benzhydryl-5-bromo-1H-pyrimidine-2,4-dione (prepared as described in example 2.1) and 1.2 ml (12.6 mmol) of 1-bromopropane, 2.5 g (73%) of 1-benzhydryl-5-bromo-3-propyl-1H-pyrimidine-2,4-dione is obtained in the form of a beige solid.

58.2: 1-benzhydryl-5-(2-oxy-pyridazin-3-yl)-3-pro-pyl-1H-pyrimidine-2,4-dione

Similarly to example 42.1, starting from 500 mg (1.3 mmol) of 1-benzhydryl-5-bromo-3-propyl-1H-pyrimidine-2,4-dione and 241 mg (2.5 mmol) of N-oxide-pyridazine, in 5 ml of dioxane, 250 mg (48%) of 1-benzhydryl-5-(2-oxy-pyridazin-3-yl)-3-propyl-1H-pyrimidine-2,4-dione is obtained in the form of a beige solid.

58.3: 1-benzhydryl-3-propyl-5-pyridazin-3-yl-1H-pyrimidine-2,4-dione

Similarly to example 42.2, starting from 250 mg (0.6 mmol) of 1-benzhydryl-5-(2-oxy-pyridazin-3-yl)-3-propyl-1H-pyrimidine-2,4-dione, 120 mg (50%) of 1-benzhydryl-3-propyl-5-pyridazin-3-yl-1H-pyrimidine-2,4-dione is obtained in the form of a beige solid.

58.4: 3-propyl-5-pyridazin-3-yl-1H-pyrimidine-2,4-dione

Similarly to example 42.3, starting from 120 mg (0.3 mmol) of 1-benzhydryl-3-propyl-5-pyridazin-3-yl-1H-pyrimidine-2,4-dione, 70 mg (100%) of 3-propyl-5-pyridazin-3-yl-1H-pyrimidine-2,4-dione is obtained in the form of a yellow solid.

58.5: 1-{2-oxo-2-[4-(2-oxo-1,2,4,5-tetrahydro-benzo[d][1,3]diazepin-3-yl)-piperidin-1-yl]-ethyl}-3-propyl-5-pyridazin-3-yl-1H-pyrimidine-2,4-dione (Compound 58)

Similarly to example 13.1, starting from 70 mg (0.3 mmol) of 3-propyl-5-pyridazin-3-yl-1H-pyrimidine-2,4-dione and 107 mg (0.3 mmol) of 3-[1-(2-chloroacetyl)-piperidin-4-yl]-1,3,4,5-tetrahydro-benzo[d][1,3]diazepin-2-one (prepared as described in example 39.1), and after purification by silica gel flash chromatography eluted with a dichloromethane/methanol mixture 95/5 and recrystallization from ethanol, 60 mg (38%) of 1-{2-oxo-2-[4-(2-oxo-1,2,4,5-tetrahydro-benzo[d][1,3]diazepin-3-yl)-piperidin-1-yl]-ethyl}-3-propyl-5-pyridazin-3-yl-1H-pyrimidine-2,4-dione is obtained in the form of a white solid with a melting point of 210° C.

$^1$H NMR (δ, DMSO): 0.89 (t, J=7.4 Hz, 3H); 1.50-1.90 (m, 6H); 2.70 (t, J=11.7 Hz, 1H); 2.91 (m, 2H); 3.17 (t, J=12.8 Hz, 1H); 3.38-3.41 (m, 2H); 3.89-3.92 (m, 3H); 4.30-4.37 (m, 1H); 4.43 (d, J=13.0 Hz, 1H); 4.96 (d, J=4.5 Hz, 2H); 6.80-6.82 (m, 1H); 7.03-7.05 (m, 3H); 7.73 (dd, J=8.7, 4.9 Hz, 1H); 8.37 (dd, J=8.7, 1.6 Hz, 1H); 8.55 (s, 1H); 8.75 (s, 1H); 9.16 (dd, J=4.9, 1.6 Hz, 1H).

EXAMPLE 59: 5-(3-CHLORO-2-METHYLPHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 59)

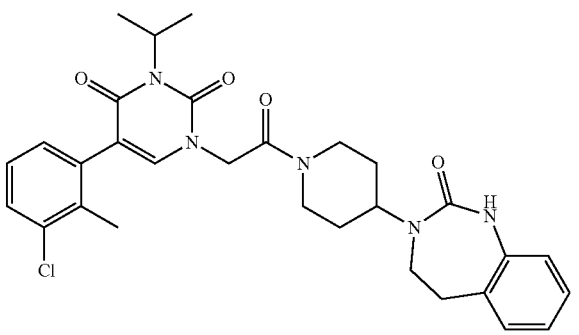 [SMILES: Cc1c(Cl)cccc1-c1cn(CC(=O)N2CCC(N3CCc4ccccc4NC3=O)CC2)c(=O)n(C(C)C)c1=O]

59.1: (5-bromo-3-isopropyl-2,4-dioxo-3,4-dihydro-2H-pyrimidin-1-yl)-methyl acetate Similarly to example 51.1, starting from 5 g (19 mmol) of (5-bromo-2,4-dioxo-3,4-dihydro-2H-pyrimidin-1-yl)-methyl acetate (prepared as described in example 13.1) and 2.7 ml (29 mmol) of 2-bromopropane, 3.4 g (59%) of (5-bromo-3-isopropyl-2,4-dioxo-3,4-dihydro-2H-pyrimidin-1-yl)-methyl acetate is obtained in the form of a white solid.

59.2: [5-(3-chloro-2-methylphenyl)-3-isopropyl-2,4-dioxo-3,4-dihydro-2H-pyrimidin-1-yl]-methyl acetate Similarly to example 44.1, starting from 300 mg (1 mmol) of (5-bromo-3-isopropyl-2,4-dioxo-3,4-dihydro-2H-pyrimidin-1-yl)-methyl acetate and 275 mg (1.5 mmol) of 3-chloro-2-methylphenyl boronic acid, 190 mg (55%) of [5-(3-chloro-2-methylphenyl)-3-isopropyl-2,4-dioxo-3,4-dihydro-2H-pyrimidin-1-yl]-methyl acetate is obtained in the form of a white solid.

59.3: [5-(3-chloro-2-methylphenyl)-3-isopropyl-2,4-dioxo-3,4-dihydro-2H-pyrimidin-1-yl]-acetic acid Similarly to example 16.8, starting from 190 mg (0.5 mmol) of [5-(3-chloro-2-methylphenyl)-3-isopropyl-2,4-dioxo-3,4-dihydro-2H-pyrimidin-1-yl]-methyl acetate, 180 mg (99%) of [5-(3-chloro-2-methylphenyl)-3-isopropyl-2,4-dioxo-3,4-dihydro-2H-pyrimidin-1-yl]-acetic acid is obtained in the form of a white solid.

59.4: 5-(3-chloro-2-methylphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 59)

Similarly to example 51.4, starting from 180 mg (0.5 mmol) of [5-(3-chloro-2-methylphenyl)-3-isopropyl-2,4-dioxo-3,4-dihydro-2H-pyrimidin-1-yl]-acetic acid and 144 mg (0.6 mmol) of 3-piperidin-4-yl-1,3,4,5-tetrahydro-benzo[d][1,3]diazepin-2-one (prepared as described in example 16.4), 250 mg (83%) of 5-(3-chloro-2-methylphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 166° C.

$^1$H NMR (δ, DMSO): 1.41 (d, J=6.9 Hz, 6H), 1.51-1.59 (m, 1H), 1.68-1.79 (m, 3H), 2.19 (s, 3H), 2.68 (t, J=12.9 Hz, 1H), 2.89 (t, J=4.3 Hz, 2H), 3.15 (t, J=12 Hz, 1H), 3.38 (t, J=4.4 Hz, 2H), 3.93 (d, J=13 Hz, 1H), 4.29-4.36 (m, 1H), 4.43 (d, J=13 Hz, 1H), 4.73 (dd, J=16.3-20.2 Hz, 2H), 5.08-5.15 (m, 1H), 7.78-6.84 (m, 1H), 7.02-7.06 (m, 3H), 7.13 (dd, J=1-7.7 Hz, 1H), 7.25 (t, J=7.7 Hz, 1H), 7.45 (d, J=7.2 Hz, 1H), 7.65 (s, 1H), 8.50 (s, 1H).

EXAMPLE 60: 5-(3-CHLORO-2-METHOXYPHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 60)

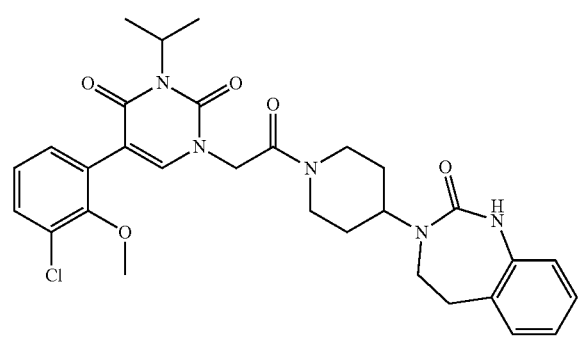 [SMILES: COc1c(Cl)cccc1-c1cn(CC(=O)N2CCC(N3CCc4ccccc4NC3=O)CC2)c(=O)n(C(C)C)c1=O]

60.1: [5-(3-chloro-2-methoxyphenyl)-3-isopropyl-2,4-dioxo-3,4-dihydro-2H-pyrimidin-1-yl]-methyl acetate Similarly to example 44.1, starting from 300 mg (1 mmol) of (5-bromo-3-isopropyl-2,4-dioxo-3,4-dihydro-2H-pyrimidin-1-yl)-methyl acetate (prepared as described in example 59.1) and 293 mg (1.6 mmol) of 3-chloro-2-methoxyphenyl boronic acid, 325 mg (90%) of [5-(3-chloro-2-methoxyphenyl)-3-isopropyl-2,4-dioxo-3,4-dihydro-2H-pyrimidin-1-yl]-methyl acetate is obtained in the form of a white solid.

60.2: [5-(3-chloro-2-methoxyphenyl)-3-isopropyl-2,4-dioxo-3,4-dihydro-2H-pyrimidin-1-yl]-acetic acid Similarly to example 16.8, starting from 325 mg (0.9 mmol) of [5-(3-chloro-2-methoxyphenyl)-3-isopropyl-2,4-dioxo-3,4-dihydro-2H-pyrimidin-1-yl]-methyl acetate, 300 mg (96%) of [5-(3-chloro-2-methoxyphenyl)-3-isopropyl-2,4-dioxo-3,4-dihydro-2H-pyrimidin-1-yl]-acetic acid is obtained in the form of a white solid.

60.3: 5-(3-chloro-2-methoxyphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 60)

Similarly to example 51.4, starting from 180 mg (0.5 mmol) of [5-(3-chloro-2-methoxyphenyl)-3-isopropyl-2,4-dioxo-3,4-dihydro-2H-pyrimidin-1-yl]-acetic acid and 230 mg (0.9 mmol) of 3-piperidin-4-yl-1,3,4,5-tetrahydro-benzo[d][1,3]diazepin-2-one (prepared as described in example 16.4), 400 mg (81%) of 5-(3-chloro-2-methoxyphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 155° C.

$^1$H NMR (δ, DMSO): 1.40 (d, J=7 Hz, 6H), 1.53-1.60 (m, 1H), 1.65-1.78 (m, 3H), 2.67 (t, J=12 Hz, 1H), 2.89 (t, J=4.7 Hz, 2H), 3.15 (t, J=12 Hz, 1H), 3.37 (t, J=4.6 Hz, 2H), 3.68 (s, 3H), 3.94 (d, J=12.7 Hz, 1H), 4.29-4.35 (m, 1H), 4.43 (d, J=12.6 Hz, 1H), 4.73 (dd, J=16.2-19.6 Hz, 2H), 5.09-5.16 (m, 1H), 6.79-6.83 (m, 1H), 7.02-7.06 (m, 3H), 7.17 (t, J=7.9 Hz, 1H), 7.25 (dd, J=1.6-7.6 Hz, 1H), 7.48 (dd, J=1.6-8 Hz, 1H), 7.71 (s, 1H), 8.50 (s, 1H).

EXAMPLE 61: 5-(3-FLUORO-2-METHYLPHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 61)

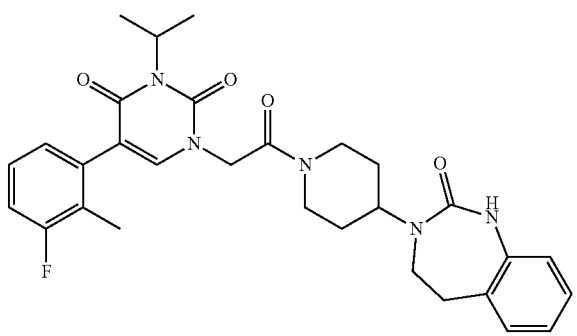

61.1: [5-(3-fluoro-2-methylphenyl)-3-isopropyl-2,4-dioxo-3,4-dihydro-2H-pyrimidin-1-yl]-acetic acid Similarly to example 44.1, starting from 200 mg (0.7 mmol) of (5-bromo-3-isopropyl-2,4-dioxo-3,4-dihydro-2H-pyrimidin-1-yl)-methyl acetate (prepared as described in example 59.1) and 161 mg (1.1 mmol) of 3-fluoro-2-methylphenyl boronic acid, and after purification by silica gel flash chromatography eluted with a dichloromethane/methanol mixture 94/6 with 0.1% of acetic acid; 175 mg (83%) of [5-(3-fluoro-2-methylphenyl)-3-isopropyl-2,4-dioxo-3,4-dihydro-2H-pyrimidin-1-yl]-acetic acid is obtained in the form of a beige solid.

61.2: 5-(3-fluoro-2-methylphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 61)

Similarly to example 51.4, starting from 180 mg (0.5 mmol) of [5-(3-fluoro-2-methylphenyl)-3-isopropyl-2,4-dioxo-3,4-dihydro-2H-pyrimidin-1-yl]-acetic acid and 134 mg (0.6 mmol) of 3-piperidin-4-yl-1,3,4,5-tetrahydro-benzo[d][1,3]diazepin-2-one (prepared as described in example 16.4), 240 mg (79%) of 5-(3-fluoro-2-methylphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 244° C.

$^1$H NMR (δ, DMSO): 1.40 (d, J=6.8 Hz, 6H), 1.52-1.57 (m, 1H), 1.64-1.73 (m, 3H), 2.06 (d, J=2.1 Hz, 3H), 2.68 (d, J=11 Hz, 1H), 2.88 (t, J=4.4 Hz, 2H), 3.14 (d, J=11 Hz, 1H), 3.37 (t, J=4.4 Hz, 2H), 3.93 (d, J=13 Hz, 1H), 4.31-4.33 (m, 1H), 4.43 (d, J=13 Hz, 1H), 4.73 (d, J=6.6 Hz, 2H), 5.11 (q, J=6.9 Hz, 1H), 6.78-6.82 (m, 1H), 7.00-7.05 (m, 4H), 7.15-7.19 (m, 1H), 7.23-7.28 (m, 1H), 7.66 (s, 1H), 8.54 (s, 1H).

EXAMPLE 62: 5-(2,3-DIFLUOROPHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 62)

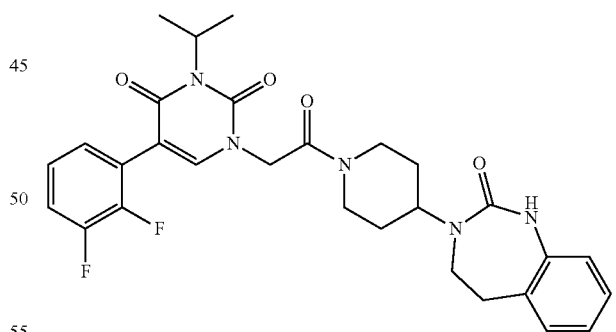

62.1: [5-(2,3-difluorophenyl)-3-isopropyl-2,4-dioxo-3,4-dihydro-2H-pyrimidin-1-yl]-methyl acetate Similarly to example 44.1, starting from 200 mg (0.7 mmol) of (5-bromo-3-isopropyl-2,4-dioxo-3,4-dihydro-2H-pyrimidin-1-yl)-methyl acetate (prepared as described in example 59.1) and 422 mg (2.6 mmol) of 2,3-difluorophenyl boronic acid, 110 mg (50%) of [5-(2,3-difluorophenyl)-3-isopropyl-2,4-dioxo-3,4-dihydro-2H-pyrimidin-1-yl]-methyl acetate is obtained in the form of a colourless oil.

62.2: [5-(2,3-difluorophenyl)-3-isopropyl-2,4-dioxo-3,4-dihydro-2H-pyrimidin-1-yl]-acetic acid Similarly to example 16.8, starting from 135 mg (0.4 mmol) of [5-(2,3-difluorophenyl)-3-isopropyl-2,4-dioxo-3,4-dihydro-2H-pyrimidin-1-yl]-methyl acetate, 130 mg (100%) of [5-(2,3-difluorophenyl)-3-isopropyl-2,4-dioxo-3,4-dihydro-2H-pyrimidin-1-yl]-acetic acid is obtained in the form of a colourless oil.

62.3: 5-(2,3-difluorophenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 62)

Similarly to example 51.4, starting from 130 mg (0.4 mmol) of [5-(2,3-difluorophenyl)-3-isopropyl-2,4-dioxo-3,4-dihydro-2H-pyrimidin-1-yl]-acetic acid and 98 mg (0.4 mmol) of 3-piperidin-4-yl-1,3,4,5-tetrahydro-benzo[d][1,3]diazepin-2-one (prepared as described in example 16.4), 160 mg (72%) of 5-(2,3-difluorophenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 242° C.
$^1$H NMR (δ, DMSO): 1.40 (d, J=6.9 Hz, 6H), 1.45-1.60 (m, 1H), 1.62-1.80 (m, 3H), 2.68 (t, J=12 Hz, 1H), 2.89 (t, J=4.5 Hz, 2H), 3.15 (t, J=12 Hz, 1H), 3.38 (t, J=4.4 Hz, 2H), 3.95 (d, J=12 Hz, 1H), 4.30-4.40 (m, 1H), 4.45 (d, J=12 Hz, 1H), 4.75 (d, J=2 Hz, 2H), 5.11 (q, J=6.9 Hz, 1H), 6.78-6.82 (m, 1H), 7.02-7.04 (m, 3H), 7.19-7.26 (m, 2H), 7.44 (dd, J=1.9-10.2 Hz, 1H), 7.86 (s, 1H), 8.55 (s, 1H).

EXAMPLE 63: 5-(2-CHLORO-3-FLUOROPHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 63)

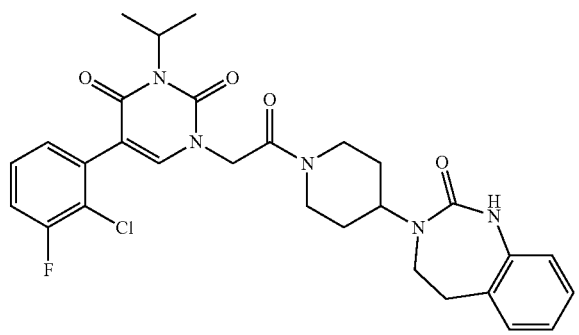 [SMILES: CC(C)n1c(=O)c(-c2cccc(F)c2Cl)cn(CC(=O)N2CCC(N3CCc4ccccc4NC3=O)CC2)c1=O]

63.1: [5-(2-chloro-3-fluorophenyl)-3-isopropyl-2,4-dioxo-3,4-dihydro-2H-pyrimidin-1-yl]-methyl acetate Similarly to example 44.1, starting from 200 mg (0.7 mmol) of (5-bromo-3-isopropyl-2,4-dioxo-3,4-dihydro-2H-pyrimidin-1-yl)-methyl acetate (prepared as described in example 59.1) and 183 mg (1.1 mmol) of 2-chloro-3-fluorophenyl boronic acid, 130 mg (56%) of [5-(2-chloro-3-fluorophenyl)-3-isopropyl-2,4-dioxo-3,4-dihydro-2H-pyrimidin-1-yl]-methyl acetate is obtained in the form of a beige solid.

63.2: [5-(2-chloro-3-fluorophenyl)-3-isopropyl-2,4-dioxo-3,4-dihydro-2H-pyrimidin-1-yl]-acetic acid Similarly to example 16.8, starting from 165 mg (0.5 mmol) of [5-(2-chloro-3-fluorophenyl)-3-isopropyl-2,4-dioxo-3,4-dihydro-2H-pyrimidin-1-yl]-methyl acetate, 160 mg (100%) of [5-(2-chloro-3-fluorophenyl)-3-isopropyl-2,4-dioxo-3,4-dihydro-2H-pyrimidin-1-yl]-acetic acid is obtained in the form of a brown oil.

63.3: 5-(2-chloro-3-fluorophenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 63)

Similarly to example 51.4, starting from 160 mg (0.5 mmol) of [5-(2-chloro-3-fluorophenyl)-3-isopropyl-2,4-dioxo-3,4-dihydro-2H-pyrimidin-1-yl]-acetic acid and 115 mg (0.5 mmol) of 3-piperidin-4-yl-1,3,4,5-tetrahydro-benzo[d][1,3]diazepin-2-one (prepared as described in example 16.4), 170 mg (63%) of 5-(2-chloro-3-fluorophenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 254° C.
$^1$H NMR (δ, DMSO): 1.40 (d, J=6.8 Hz, 6H), 1.48-1.60 (m, 1H), 1.62-1.80 (m, 3H), 2.68 (t, J=12 Hz, 1H), 2.89 (t, J=4.5 Hz, 2H), 3.14 (t, J=12 Hz, 1H), 3.37 (t, J=4.5 Hz, 2H), 3.93 (d, J=13.9 Hz, 1H), 4.28-4.38 (m, 1H), 4.43 (d, J=13.9 Hz, 1H), 4.74 (d, J=6.2 Hz, 2H), 5.10 (q, J=6.9 Hz, 1H), 6.78-6.82 (m, 1H), 7.02-7.04 (m, 3H), 7.20-7.22 (m, 1H), 7.41-7.47 (m, 2H), 7.77 (s, 1H), 8.54 (s, 1H).

EXAMPLE 64: 3-ISOPROPYL-5-(2-METHOXY-3-METHYLPHENYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (COMPOUND 64)

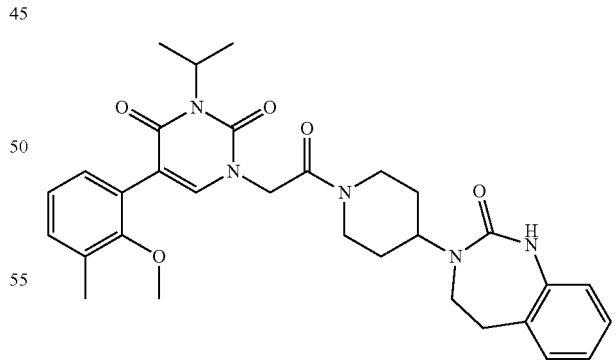

64.1: [3-isopropyl-5-(2-methoxy-3-methylphenyl)-2,4-dioxo-3,4-dihydro-2H-pyrimidin-1-yl]-acetic acid Similarly to example 13.3, starting from 500 mg (1.6 mmol) of (5-bromo-3-isopropyl-2,4-dioxo-3,4-dihydro-2H-pyrimidin-1-yl)-methyl acetate (prepared as described in example 59.1) and 408 mg (2.5 mmol) of 2-methoxy-3- methylphenyl boronic acid, 495 mg (91%) of [3-isopropyl-5-(2-methoxy-3-methylphenyl)-2,4-dioxo-3,4-dihydro-2H-pyrimidin-1-yl]-acetic acid is obtained in the form of a beige solid.

64.2: 3-isopropyl-5-(2-methoxy-3-methylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 64)

Similarly to example 51.4, starting from 495 mg (1.5 mmol) of [3-isopropyl-5-(2-methoxy-3-methylphenyl)-2,4-dioxo-3,4-dihydro-2H-pyrimidin-1-yl]-acetic acid and 384 mg (1.6 mmol) of 3-piperidin-4-yl-1,3,4,5-tetrahydro-benzo[d][1,3]diazepin-2-one (prepared as described in example 16.4), and after recrystallization from n-butanol, 285 mg (34%) of 3-isopropyl-5-(2-methoxy-3-methylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 260° C.

$^1$H NMR (δ, DMSO): 1.34 (d, J=6.9 Hz, 6H); 1.52-1.59 (m, 4H); 2.19 (s, 3H); 2.60 (t, J=12.6 Hz, 1H); 2.79-2.84 (m, 2H); 3.07 (t, J=12.7 Hz, 1H); 3.29-3.32 (m, 2H); 3.47 (s, 3H); 3.86 (d, J=13.5 Hz, 1H); 4.24-4.28 (m, 1H); 4.36 (d, J=12.9 Hz, 1H); 4.66 (d, J=7.7 Hz, 2H); 5.05-5.07 (m, 1H); 6.72-6.74 (m, 1H); 6.94-7.02 (m, 5H); 7.12 (d, J=7.3 Hz, 1H); 7.56 (s, 1H); 8.47 (s, 1H).

EXAMPLE 65: 5-(3-CHLORO-4-METHOXYPHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 65)

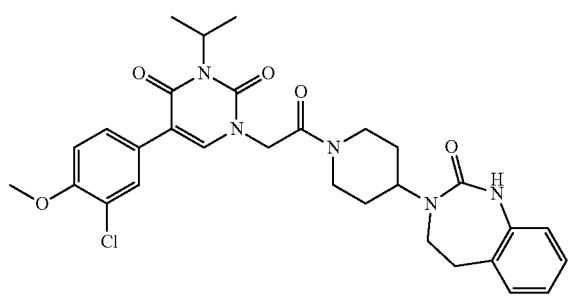 [SMILES: COc1ccc(-c2cn(CC(=O)N3CCC(N4CCc5ccccc5NC4=O)CC3)c(=O)n(C(C)C)c2=O)cc1Cl]

65.1: [5-(3-chloro-4-methoxyphenyl)-3-isopropyl-2,4-dioxo-3,4-dihydro-2H-pyrimidin-1-yl]-acetic acid Similarly to example 13.3, starting from 300 mg (1 mmol) of (5-bromo-3-isopropyl-2,4-dioxo-3,4-dihydro-2H-pyrimidin-1-yl)-methyl acetate (prepared as described in example 59.1) and 367 mg (2 mmol) of 3-chloro-4-methoxyphenyl boronic acid, 160 mg (46%) of [5-(3-chloro-4-methoxyphenyl)-3-isopropyl-2,4-dioxo-3,4-dihydro-2H-pyrimidin-1-yl]-acetic acid is obtained in the form of a yellow solid.

65.2: 5-(3-chloro-4-methoxyphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 65)

Similarly to example 51.4, starting from 150 mg (0.4 mmol) of [5-(3-chloro-4-methoxyphenyl)-3-isopropyl-2,4-dioxo-3,4-dihydro-2H-pyrimidin-1-yl]-acetic acid and 125 mg (0.5 mmol) of 3-piperidin-4-yl-1,3,4,5-tetrahydro-benzo[d][1,3]diazepin-2-one (prepared as described in example 16.4), 138 mg (55%) of 5-(3-chloro-4-methoxyphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 250° C.

$^1$H NMR (δ, DMSO): 1.41 (d, J=6.9 Hz, 6H); 1.57 (d, J=13.0 Hz, 1H); 1.63-1.76 (m, 3H); 2.69 (t, J=12.5 Hz, 1H); 2.91 (s, 2H); 3.16 (t, J=12.1 Hz, 1H); 3.40 (d, J=6.6 Hz, 2H); 3.89 (s, 3H); 3.96 (d, J=13.5 Hz, 1H); 4.33 (m, 1H); 4.44 (d, J=12.9 Hz, 1H); 4.76 (s, 2H); 5.14-5.16 (m, 1H); 6.80-6.82 (m, 1H); 7.04-7.06 (m, 3H); 7.19 (d, J=8.7 Hz, 1H); 7.51 (dd, J=8.6, 2.3 Hz, 1H); 7.62 (d, J=2.2 Hz, 1H); 7.89 (s, 1H); 8.54 (s, 1H).

EXAMPLE 66: 5-(2-FLUOROBENZYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 66)

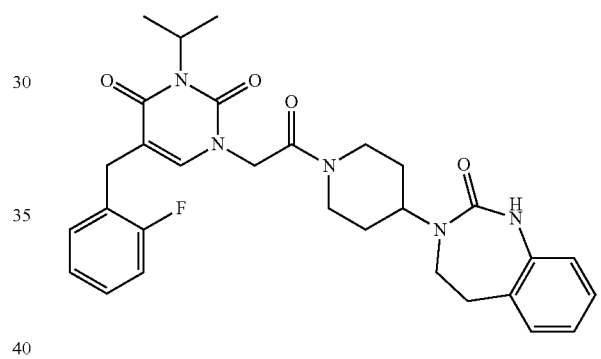

66.1: [5-(2-fluorobenzyl)-3-isopropyl-2,4-dioxo-3,4-dihydro-2H-pyrimidin-1-yl]-acetic acid Similarly to example 44.1, starting from 100 mg (0.3 mmol) of (5-bromo-3-isopropyl-2,4-dioxo-3,4-dihydro-2H-pyrimidin-1-yl)-methyl acetate (prepared as described in example 59.1) and 186 mg (0.8 mmol) of ester of 2-fluorobenzyl pinacol boronic acid, 35 mg (33%) of [5-(2-fluorobenzyl)-3-isopropyl-2,4-dioxo-3,4-dihydro-2H-pyrimidin-1-yl]-acetic acid is obtained in the form of a beige solid.

66.2: 5-(2-fluorobenzyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 66)

Similarly to example 51.4, starting from 35 mg (0.1 mmol) of [5-(2-fluorobenzyl)-3-isopropyl-2,4-dioxo-3,4-dihydro-2H-pyrimidin-1-yl]-acetic acid and 32 mg (0.1 mmol) of 3-piperidin-4-yl-1,3,4,5-tetrahydro-benzo[d][1,3]diazepin-2-one (prepared as described in example 16.4), 20 mg (29%) of 5-(2-fluorobenzyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid.

¹H NMR (δ, DMSO): 1.35 (d, J=6.9 Hz, 6H); 1.54-1.69 (m, 4H); 2.60-2.73 (m, 1H); 2.90 (m, 2H); 3.13 (t, J=12.6 Hz, 1H); 3.33 (m, 2H); 3.59 (m, 2H); 3.91 (d, J=13.8 Hz, 1H); 4.31 (m, 1H); 4.42 (d, J=12.9 Hz, 1H); 4.68 (s, 2H); 5.05-5.08 (m, 1H); 6.80-6.83 (m, 1H); 7.02-7.05 (m, 3H); 7.15-7.17 (m, 2H); 7.29 (m, 2H); 7.36 (s, 1H); 8.53 (s, 1H).

EXAMPLE 67: 5-(3,4-DICHLOROPHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 67)

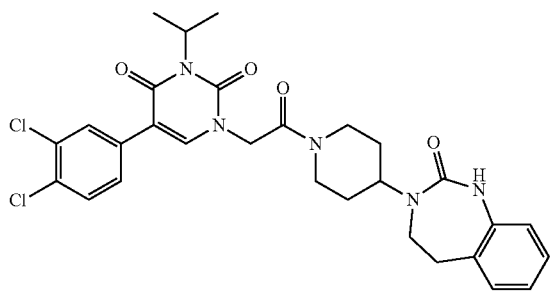 [SMILES: CC(C)n1c(=O)c(-c2ccc(Cl)c(Cl)c2)cn(CC(=O)N2CCC(N3CCc4ccccc4NC3=O)CC2)c1=O]

67.1: [5-(3,4-dichlorophenyl)-3-isopropyl-2,4-dioxo-3,4-dihydro-2H-pyrimidin-1-yl]-acetic acid Similarly to example 13.3, starting from 650 mg (2 mmol) of (5-bromo-3-isopropyl-2,4-dioxo-3,4-dihydro-2H-pyrimidin-1-yl)-methyl acetate (prepared as described in example 59.1), and 691 mg (3.6 mmol) of 3,4-dichloro-phenyl boronic acid, 700 mg (92%) of [5-(3,4-dichlorophenyl)-3-isopropyl-2,4-dioxo-3,4-dihydro-2H-pyrimidin-1-yl]-acetic acid is obtained in the form of a beige solid.

67.2: 5-(3,4-dichlorophenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 67)

Similarly to example 51.4, starting from 760 mg (2 mmol) of [5-(3,4-dichlorophenyl)-3-isopropyl-2,4-dioxo-3,4-dihydro-2H-pyrimidin-1-yl]-acetic acid and 627 mg (2.6 mmol) of 3-piperidin-4-yl-1,3,4,5-tetrahydro-benzo[d][1,3]diazepin-2-one (prepared as described in example 16.4), and after crystallization in isopropanol, 1 g (88%) of 5-(3,4-dichlorophenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 237° C.

¹H NMR (δ, DMSO): 1.42 (d, J=6.9 Hz, 6H); 1.71-1.60 (m, 4H); 2.69 (t, J=12.5 Hz, 1H); 2.89-2.92 (m, 2H); 3.24-3.11 (m, 1H); 3.96 (d, J=13.6 Hz, 2H); 4.27-4.38 (m, 1H); 4.29-4.45 (m, J=12.9 Hz, 1H); 4.78 (s, 2H); 5.14-5.15 (m, 1H); 6.80-6.81 (m, 1H); 7.04-7.05 (m, 3H); 7.59 (dd, J=8.5, 2.1 Hz, 1H); 7.68 (d, J=8.5 Hz, 1H); 7.85 (d, J=2.1 Hz, 1H); 8.54 (s, 1H); 8.05 (s, 1H).

EXAMPLE 68: 5-(2,3-DIMETHYLPHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 68)

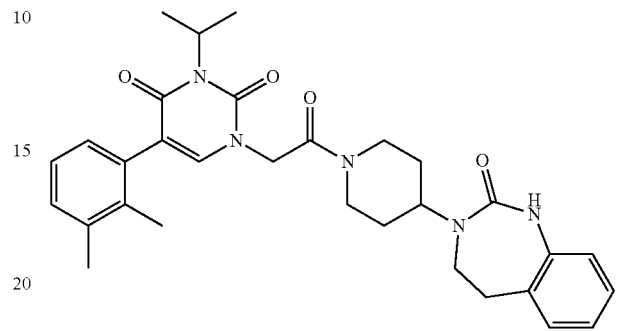

68.1: [5-(2,3-dimethylphenyl)-3-isopropyl-2,4-dioxo-3,4-dihydro-2H-pyrimidin-1-yl]-methyl acetate Similarly to example 44.1, starting from 300 mg (1 mmol) of (5-bromo-3-isopropyl-2,4-dioxo-3,4-dihydro-2H-pyrimidin-1-yl)-methyl acetate (prepared as described in example 59.1) and 236 mg (1.6 mmol) of 2,3-dimethylphenyl boronic acid, 200 mg (62%) of [5-(2,3-dimethylphenyl)-3-isopropyl-2,4-dioxo-3,4-dihydro-2H-pyrimidin-1-yl]-methyl acetate is obtained in the form of a colourless oil.

68.2: [5-(2,3-dimethylphenyl)-3-isopropyl-2,4-dioxo-3,4-dihydro-2H-pyrimidin-1-yl]-acetic acid Similarly to example 16.8, starting from 200 mg (0.6 mmol) of [5-(2,3-dimethylphenyl)-3-isopropyl-2,4-dioxo-3,4-dihydro-2H-pyrimidin-1-yl]-methyl acetate, 190 mg (99%) of [5-(2,3-dimethylphenyl)-3-isopropyl-2,4-dioxo-3,4-dihydro-2H-pyrimidin-1-yl]-acetic acid is obtained in the form of a white solid.

68.3: 5-(2,3-dimethylphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 68)

Similarly to example 51.4, starting from 190 mg (0.6 mmol) of [5-(2,3-dimethylphenyl)-3-isopropyl-2,4-dioxo-3,4-dihydro-2H-pyrimidin-1-yl]-acetic acid and 162 mg (0.7 mmol) of 3-piperidin-4-yl-1,3,4,5-tetrahydro-benzo[d][1,3]diazepin-2-one (prepared as described in example 16.4), 200 mg (61%) of 5-(2,3-dimethylphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 269° C.

¹H NMR (δ, DMSO): 1.40 (d, J=6.8 Hz, 6H), 1.52-1.56 (m, 1H), 1.64-1.76 (m, 3H), 2.04 (s, 3H), 2.27 (s, 3H), 2.67 (t, J=12.5 Hz, 1H), 2.88 (t, J=4.4 Hz, 2H), 3.14 (t, J=12.5 Hz, 1H), 3.37 (t, J=4.6 Hz, 2H), 3.93 (d, J=13.3 Hz, 1H), 4.31-4.33 (m, 1H), 4.43 (d, J=13.3 Hz, 1H), 4.71 (d, J=8.5 Hz, 2H), 5.09-5.13 (m, 1H), 6.78-6.82 (m, 1H), 6.95 (d, J=7.1 Hz, 1H), 7.01-7.05 (m, 3H), 7.09 (t, J=7.5 Hz, 1H), 7.16 (d, J=7.4 Hz, 1H), 7.54 (s, 1H), 8.53 (s, 1H).

EXAMPLE 69: 5-(2-CHLORO-3-METHOXYPHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 69)

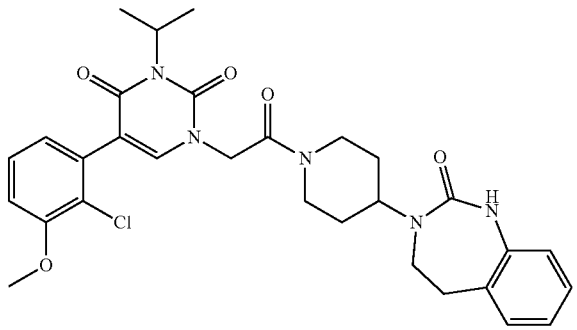 [SMILES: COc1cccc(-c2cn(CC(=O)N3CCC(N4CCc5ccccc5NC4=O)CC3)c(=O)n(C(C)C)c2=O)c1Cl]

69.1: [5-(2-chloro-3-methoxyphenyl)-3-isopropyl-2,4-dioxo-3,4-dihydro-2H-pyrimidin-1-yl]-acetic acid Similarly to example 13.3, starting from 300 mg (1 mmol) of (5-bromo-3-isopropyl-2,4-dioxo-3,4-dihydro-2H-pyrimidin-1-yl)-methyl acetate (prepared as described in example 59.1) and 275 mg (1.5 mmol) of 2-chloro-3-methoxyphenyl boronic acid, 115 mg (33) of [5-(2-chloro-3-methoxyphenyl)-3-isopropyl-2,4-dioxo-3,4-dihydro-2H-pyrimidin-1-yl]-acetic acid is obtained in the form of a brown oil.

69.2: 5-(2-chloro-3-methoxyphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 69)

Similarly to example 51.4, starting from 105 mg (0.3 mmol) of [5-(2-chloro-3-methoxyphenyl)-3-isopropyl-2,4-dioxo-3,4-dihydro-2H-pyrimidin-1-yl]-acetic acid and 88 mg (0.4 mmol) of 3-piperidin-4-yl-1,3,4,5-tetrahydro-benzo[d][1,3]diazepin-2-one (prepared as described in example 16.4), 85 mg (48%) of 5-(2-chloro-3-methoxyphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid.

$^1$H NMR (δ, DMSO): 1.40 (d, J=6.9 Hz, 6H); 1.53-1.56 (m, 1H); 1.65-1.70 (m, 3H); 2.60-2.75 (m, 1H); 2.90 (m, 2H); 3.10-3.20 (m, 1H); 3.38 (m, 2H); 3.89 (s, 3H); 3.90 (m, 1H); 4.20-4.40 (m, 1H); 4.40-4.50 (in, 1H); 4.73 (d, J=6.0 Hz, 2H); 5.10 (t, J=6.9 Hz, 1H); 6.80-6.82 (m, 1H); 6.91 (dd, J=7.6, 1.4 Hz, 1H); 7.04-7.06 (m, 3H); 7.17-7.18 (m, 1H); 7.34 (t, J=8.0 Hz, 1H); 7.67 (s, 1H); 8.53 (s, 1H).

EXAMPLE 70: 5-(5-CHLORO-2-METHOXYPHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 70)

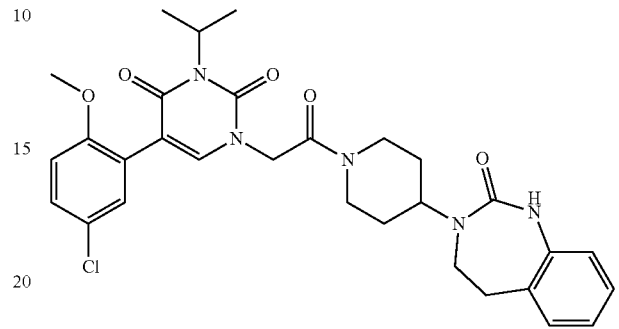

70.1: [5-(5-chloro-2-methoxyphenyl)-3-isopropyl-2,4-dioxo-3,4-dihydro-2H-pyrimidin-1-yl]-methyl acetate Similarly to example 44.1, starting from 500 mg (1.6 mmol) of (5-bromo-3-isopropyl-2,4-dioxo-3,4-dihydro-2H-pyrimidin-1-yl)-methyl acetate (prepared as described in example 59.1) and 458 mg (2.5 mmol) of 5-chloro-2-methoxyphenyl boronic acid, 275 mg (46%) of [5-(5-chloro-2-methoxyphenyl)-3-isopropyl-2,4-dioxo-3,4-dihydro-2H-pyrimidin-1-yl]-methyl acetate is obtained in the form of a brown oil.

70.2: [5-(5-chloro-2-methoxyphenyl)-3-isopropyl-2,4-dioxo-3,4-dihydro-2H-pyrimidin-1-yl]-acetic acid Similarly to example 16.8, starting from 270 mg (0.7 mmol) of [5-(5-chloro-2-methoxyphenyl)-3-isopropyl-2,4-dioxo-3,4-dihydro-2H-pyrimidin-1-yl]-methyl acetate, 241 mg (93%) of [5-(5-chloro-2-methoxyphenyl)-3-isopropyl-2,4-dioxo-3,4-dihydro-2H-pyrimidin-1-yl]-acetic acid is obtained in the form of a white solid.

70.3: 5-(5-chloro-2-methoxyphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 70)

Similarly to example 51.4, starting from 230 mg (0.7 mmol) of [5-(5-chloro-2-methoxyphenyl)-3-isopropyl-2,4-dioxo-3,4-dihydro-2H-pyrimidin-1-yl]-acetic acid and 192 mg (0.8 mmol) of 3-piperidin-4-yl-1,3,4,5-tetrahydro-benzo[d][1,3]diazepin-2-one (prepared as described in example 16.4), 308 mg (81%) of 5-(2-chloro-3-methoxyphenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid.

$^1$H NMR (δ, DMSO): 1.40 (d, J=6.9 Hz, 6H); 1.59-1.71 (m, 4H); 2.66 (d, J=12.7 Hz, 1H); 2.90 (s, 2H); 3.13 (d, J=12.8 Hz, 1H); 3.38 (t, J=4.7 Hz, 2H); 3.75 (s, 3H); 3.94 (d, J=13.3 Hz, 1H); 4.33 (t, J=9.9 Hz, 1H); 4.43 (d, J=13.0 Hz, 1H); 4.72 (d, J=5.1 Hz, 2H); 5.09-5.10 (m, 1H); 6.80-6.81

(m, 1H); 7.05-7.06 (m, 4H); 7.25 (d, J=2.7 Hz, 1H); 7.39 (dd, J=8.8, 2.7 Hz, 1H); 7.68 (s, 1H); 8.53 (s, 1H).

EXAMPLE 71: 5-(2,3-DIFLUOROBENZYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 71)

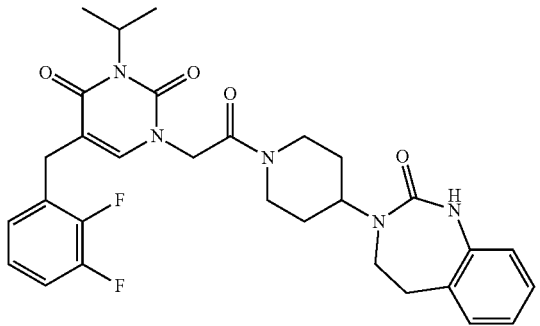 [SMILES: CC(C)n1c(=O)c(Cc2cccc(F)c2F)cn(CC(=O)N2CCC(N3CCc4ccccc4NC3=O)CC2)c1=O]

71.1: 2-(2,3-difluorobenzyl)-4,4,5,5-tetramethyl-[1,3,2]dioxaborolane

Similarly to example 1.8, starting from 2 ml (16 mmol) of 2,3-difluorobenzyl bromide and 4.8 g (19 mmol) of bis pinacol borane, 2.5 g (62%) of 2-(2,3-difluorobenzyl)-4,4,5,5-tetramethyl-[1,3,2]dioxaborolane is obtained in the form of a colourless oil.

71.2: [5-(2,3-difluorobenzyl)-3-isopropyl-2,4-dioxo-3,4-dihydro-2H-pyrimidin-1-yl]-acetic acid Similarly to example 44.1, starting from 300 mg (1 mmol) of (5-bromo-3-isopropyl-2,4-dioxo-3,4-dihydro-2H-pyrimidin-1-yl)-methyl acetate (prepared as described in example 59.1) and 1 g (4 mmol) of 2-(2,3-difluorobenzyl)-4,4,5,5-tetramethyl-[1,3,2]dioxaborolane, 270 mg (32%) of [5-(2,3-difluorobenzyl)-3-isopropyl-2,4-dioxo-3,4-dihydro-2H-pyrimidin-1-yl]-acetic acid is obtained in the form of a brown oil.

71.3: 5-(2,3-difluorobenzyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 71)

Similarly to example 51.4, starting from 270 mg (0.8 mmol) of [5-(2,3-difluorobenzyl)-3-isopropyl-2,4-dioxo-3,4-dihydro-2H-pyrimidin-1-yl]-acetic acid and 235 mg (1 mmol) of 3-piperidin-4-yl-1,3,4,5-tetrahydro-benzo[d][1,3]diazepin-2-one (prepared as described in example 16.4), 60 mg (13%) of 5-(2,3-difluorobenzyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 230° C.
$^1$H NMR (δ, DMSO): 1.35 (d, J=6.9 Hz, 6H); 1.50-1.80 (m, 4H); 2.67 (t, J=12.5 Hz, 1H); 2.90 (m, 2H); 3.13 (t, J=10.5 Hz, 1H); 3.39 (m, 2H); 3.63 (s, 2H); 3.92 (d, J=13.6 Hz, 1H); 4.31 (m, 1H); 4.42 (d, J=12.9 Hz, 1H); 4.68 (d, J=2.9 Hz, 2H); 5.05-5.06 (m, 1H); 6.80-6.82 (m, 1H); 7.03-7.05 (m, 3H); 7.12-7.14 (m, 2H); 7.28-7.31 (m, 1H); 7.42 (s, 1H); 8.54 (s, 1H).

Similarly to example 70, using the appropriate reagents, commercially available or previously prepared, the following compounds are obtained:

Compound 72: (5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-acetonitrile

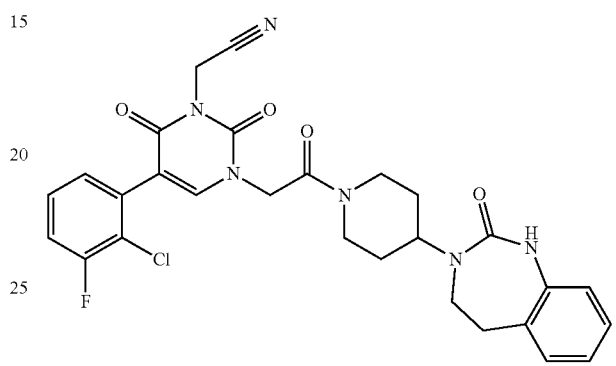

$^1$H NMR (400 MHz, DMSO): δ (ppm) 1.56 (d, J=13.8 Hz, 1H); 1.65-1.77 (m, 3H); 2.70 (t, J=12.5 Hz, 1H); 2.90 (t, J=4.9 Hz, 2H); 3.17 (t, J=12.6 Hz, 1H); 3.38 (s, 2H); 3.93-3.96 (m, 1H); 4.33 (t, J=11.4 Hz, 1H); 4.43 (d, J=12.9 Hz, 1H); 4.85 (s, 2H); 4.94 (s, 2H); 6.79-6.83 (m, 1H); 7.04 (t, J=4.5 Hz, 3H); 7.24-7.29 (m, 4H); 7.44-7.49 (m, 2H); 7.98 (s, 1H); 8.53 (s, 1H).

Compound 73: 3-(5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-propanoic acid

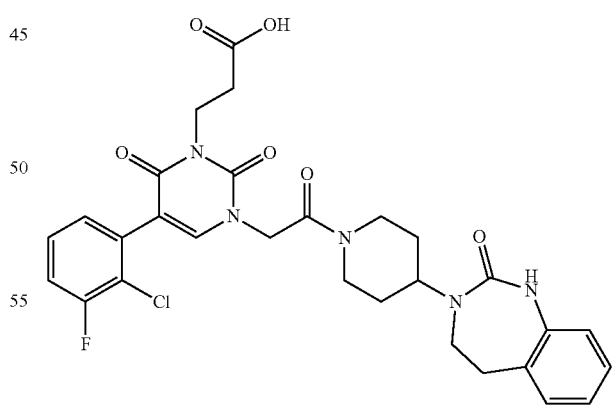

$^1$H NMR (400 MHz, DMSO): δ (ppm) 1.55 (d, J=12.9 Hz, 1H); 1.72 (t, J=21.2 Hz, 3H); 2.50 (m, 2H); 2.69 (t, J=12.4 Hz, 1H); 2.90 (m, 2H); 3.16 (m, 1H); 3.38 (m, 2H); 3.95 (d, J=13.6 Hz, 1H); 4.09 (t, J=7.7 Hz, 2H); 4.33 (s, 1H); 4.43 (d, J=12.8 Hz, 1H); 4.78 (s, 2H); 6.81 (dt, J=7.8, 4.2 Hz, 1H); 7.04 (t, J=4.0 Hz, 3H); 7.22 (dd, J=6.3, 2.8 Hz, 1H); 7.43-7.46 (m, 2H); 7.84 (s, 1H); 8.53 (s, 1H).

EXAMPLE 74: 3-(3-ISOPROPYL-2,4-DIOXO-1-{2-OXO-2-[4-(2-OXO-1,2,4,5-TETRAHYDRO-BENZO[D][1,3]DIAZEPIN-3-YL)-PIPERIDIN-1-YL]-ETHYL}-1,2,3,4-TETRAHYDRO-PYRIMIDIN-5-YL)-METHYL BENZOIC ACETATE (REACTION SCHEME NO. 3, COMPOUND 74)

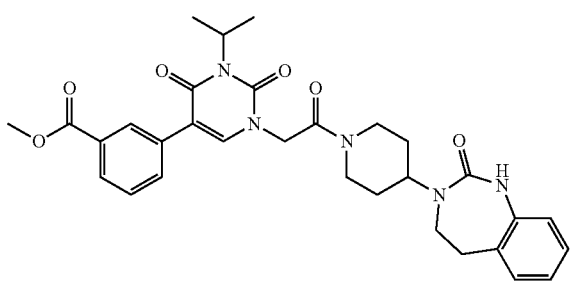 [SMILES: COC(=O)c1cccc(-c2cn(CC(=O)N3CCC(N4CCc5ccccc5NC4=O)CC3)c(=O)n(C(C)C)c2=O)c1]

74.1: (5-bromo-3-isopropyl-2,4-dioxo-3,4-dihydro-2H-pyrimidin-1-yl)-acetic acid Similarly to example 16.8, starting from 1.9 g (10 mmol) of (5-bromo-3-isopropyl-2,4-dioxo-3,4-dihydro-2H-pyrimidin-1-yl)-methyl acetate (prepared as described in example 59.1), 1.8 g (100%) of (5-bromo-3-isopropyl-2,4-dioxo-3,4-dihydro-2H-pyrimidin-1-yl)-acetic acid is obtained in the form of a white solid.

74.2: 5-bromo-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione Similarly to example 1.6, starting from 1 g (3 mmol) of (5-bromo-3-isopropyl-2,4-dioxo-3,4-dihydro-2H-pyrimidin-1-yl)-acetic acid and 1 g (4 mmol) of 3-piperidin-4-yl-1,3,4,5-tetrahydro-benzo[d][1,3]diazepin-2-one (prepared as described in example 16.4), 1.8 g (100%) of 5-bromo-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid.

74.3: 3-(3-isopropyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-methyl benzoic acetate (Compound 74)

Similarly to example 44.1, starting from 300 mg (0.6 mmol) of 5-bromo-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione and 146 mg (0.8 mmol) of 3-methoxycarbonyl phenyl boronic acid, 51 mg (15%) of 3-(3-isopropyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-methyl benzoic acetate is obtained in the form of a white solid.

$^1$H NMR (δ, DMSO): 1.43 (d, J=6.9 Hz, 6H); 1.55-1.61 (m, 1H); 1.62-1.82 (m, 3H); 2.68 (m, 1H); 2.91 (m, 2H); 3.17 (t, J=12 Hz, 1H); 3.41 (m, 1H); 3.89 (s, 3H); 4.03 (d, J=8 Hz; 1H); 4.34 (m, 1H); 4.45 (d, J=12 Hz, 1H); 4.80 (s, 2H); 5.15-5.18 (m, 1H); 6.81-6.83 (m, 1H); 7.04-7.06 (m, 3H); 7.52 (t, J=7.8 Hz, 1H); 7.78 (d, J=7.5 Hz, 1H); 7.89 (d, J=7.7 Hz, 1H); 7.95 (s, 1H); 8.12 (s, 1H); 8.53 (s, 1H).

EXAMPLE 75: 3-(3-ISOPROPYL-2,4-DIOXO-1-{2-OXO-2-[4-(2-OXO-1,2,4,5-TETRAHYDRO-BENZO[D][1,3]DIAZEPIN-3-YL)-PIPERIDIN-1-YL]-ETHYL}-1,2,3,4-TETRAHYDRO-PYRIMIDIN-5-YL)-BENZOIC ACID (REACTION SCHEME NO. 3, COMPOUND 75)

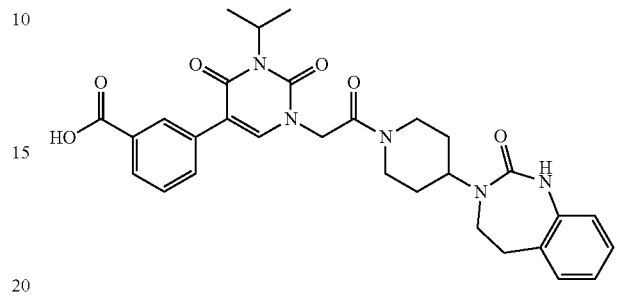

Similarly to example 44.1, starting from 300 mg (0.6 mmol) of 5-bromo-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione and 146 mg (0.8 mmol) of 3-methoxycarbonyl phenyl boronic acid, and after purification by preparative high-performance liquid chromatography (Xbridge C18 column, isocratic, 41% acetonitrile in water), 92 mg (28%) of 3-(3-isopropyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-benzoic acid is obtained in the form of a white solid.

$^1$H NMR (δ, DMSO): 1.43 (d, J=6.9 Hz, 6H); 1.55-1.61 (m, 1H); 1.62-1.82 (m, 3H); 2.68 (m, 1H); 2.91 (m, 2H); 3.17 (t, J=12 Hz, 1H); 3.41 (m, 1H); 3.96 (d, J=12 Hz; 1H); 4.03 (s, 1H); 4.34 (m, 1H); 4.45 (d, J=12 Hz, 1H); 4.80 (s, 2H); 5.15-5.18 (m, 1H); 6.81-6.83 (m, 1H); 7.04-7.06 (m, 3H); 7.52 (t, J=7.8 Hz, 1H); 7.78 (d, J=7.5 Hz, 1H); 7.89 (d, J=7.7 Hz, 1H); 7.95 (s, 1H); 8.12 (s, 1H); 8.53 (s, 1H).

EXAMPLE 76: 5-(2-CHLORO-3-METHYLSULPHANYL-PHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 76)

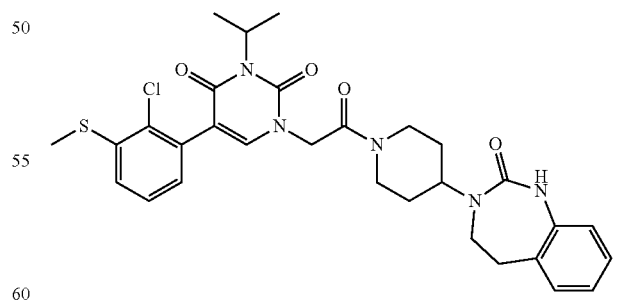

76.1: 1-bromo-2-chloro-3-methylsulphanyl-benzene 1.6 ml (4 mmol) of a 2.5M solution of n-butyllithium in hexane is added to a solution cooled to −78° C. of 1 g (3.7 mmol) of 1,3-dibromo-2-chlorobenzene in 20 ml of diethyl ether. The mixture is stirred at −78° C. for 30 minutes, then 0.4 ml (4 mmol) of dimethyl disulphide is added dropwise. The reaction mixture is stirred for 15 minutes at −78° C. and then 30 minutes at room temperature. It is slowly hydrolysed and then extracted with ethyl acetate. The organic phase is washed once with water and once with a saturated aqueous solution of sodium chloride, then dried over magnesium sulphate, filtered and concentrated under vacuum. The crude residue is chromatographed on silica gel eluted with pure heptane. 0.4 g (43%) of 1-bromo-2-chloro-3-methylsulphanyl-benzene is obtained in the form of a colourless oil.

76.2: [5-(2-chloro-3-methylsulphanyl-phenyl)-3-isopropyl-2,4-dioxo-3,4-dihydro-2H-pyrimidin-1-yl]-methyl acetate 65 mg (0.1 mmol) of dichloromethane complex of 1,1'-bis(diphenylphosphino) ferrocene-dichloropalladium(II) is added to a solution previously degassed with nitrogen of 380 mg (1.6 mmol) of 1-bromo-2-chloro-3-methylsulphanyl-benzene, 447 mg (1.8 mmol) of bis pinacol borane and 471 mg (4.8 mmol) of potassium acetate, in 15 ml of dimethylformamide. The reaction mixture is heated at 90° C. for 2 hours. After cooling, 565 mg (5.3 mmol) of sodium carbonate, 488 mg (1.6 mmol) of (5-bromo-3-isopropyl-2,4-dioxo-3,4-dihydro-2H-pyrimidin-1-yl)-methyl acetate (prepared as described in example 59.1), 65 mg (0.1 mmol) of dichloromethane complex of 1,1'-bis(diphenylphosphino)ferrocene-dichloropalladium(II) and 1.5 ml of water are added. After 4 hours of heating at 90° C., the reaction mixture is hydrolysed and then diluted with ethyl acetate. The product is extracted with ethyl acetate. The organic phases are combined, washed with water and then with a saturated aqueous solution of sodium chloride, dried over magnesium sulphate, filtered and concentrated under vacuum. The crude residue is chromatographed on silica gel eluted with a heptane/ethyl acetate mixture 70/30. 80 mg (13%) of [5-(2-chloro-3-methylsulphanyl-phenyl)-3-isopropyl-2,4-dioxo-3,4-dihydro-2H-pyrimidin-1-yl]-methyl acetate is obtained in the form of a colourless oil.

76.3: [5-(2-chloro-3-methylsulphanyl-phenyl)-3-isopropyl-2,4-dioxo-3,4-dihydro-2H-pyrimidin-1-yl]-acetic acid Similarly to example 16.8, starting from 80 mg (0.2 mmol) of [5-(2-chloro-3-methylsulphanyl-phenyl)-3-isopropyl-2,4-dioxo-3,4-dihydro-2H-pyrimidin-1-yl]-methyl acetate, 70 mg (91%) of [5-(2-chloro-3-methylsulphanyl-phenyl)-3-isopropyl-2,4-dioxo-3,4-dihydro-2H-pyrimidin-1-yl]-acetic acid is obtained in the form of a yellow solid.

76.4: 5-(2-chloro-3-methylsulphanyl-phenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 76)

64 mg (0.3 mmol) of 3-piperidin-4-yl-1,3,4,5-tetrahydro-benzo[d][1,3]diazepin-2-one (prepared as described in example 16.4) and 40 µl (0.3 mmol) of triethylamine are added to a solution of 80 mg (0.2 mmol) of [5-(2-chloro-3-methylsulphanyl-phenyl)-3-isopropyl-2,4-dioxo-3,4-dihydro-2H-pyrimidin-1-yl]-acetic acid, 29 mg (0.3 mmol) of 1-oxy-pyridin-2-ol and 50 mg (0.3 mmol) of 1-ethyl-3-(3-dimethylaminopropyl)carbodiimide chloride, in 3.2 ml of dimethylformamide. The reaction mixture is stirred at room temperature for 18 hours. It is hydrolysed with a saturated aqueous solution of sodium hydrogen carbonate and then diluted with ethyl acetate. The product is extracted with ethyl acetate. The organic phases are combined, washed with a saturated aqueous solution of sodium hydrogen carbonate, with water and then with a saturated aqueous solution of sodium chloride, dried over magnesium sulphate, filtered and concentrated under vacuum. The crude residue is chromatographed on silica gel eluted with a dichloromethane/methanol 97/3 mixture. The product is crystallized in ethyl acetate. 70 mg (54%) of 5-(2-chloro-3-methylsulphanyl-phenyl)-3-isopropyl-1-{2-oxo-2-[4-(2-oxo-1,2,4,5-tetrahydrobenzo[d][1,3]diazepin-3-yl)-piperidin-1-yl]-ethyl}-1H-pyrimidine-2,4-dione is obtained in the form of a white solid with a melting point of 261° C.

$^1$H NMR (δ, DMSO): 1.40 (d, J=6.9 Hz, 6H); 1.50-1.80 (m, 4H); 2.55 (s, 3H); 2.68 (t, J=12.4 Hz, 1H); 2.90 (m, 2H); 3.15 (t, J=12.3 Hz, 1H); 3.38 (m, 2H); 3.94 (d, J=13.5 Hz, 1H); 4.33 (m, 1H); 4.44 (d, J=12.8 Hz, 1H); 4.73 (d, J=5.4 Hz, 2H); 5.08-5.11 (m, 1H); 6.79-6.83 (m, 1H); 7.02-7.05 (m, 3H); 7.11 (dd, J=7.5, 1.6 Hz, 1H); 7.31-7.33 (m, 1H); 7.40 (t, J=7.7 Hz, 1H); 7.70 (s, 1H); 8.53 (s, 1H).

EXAMPLE 77: 5-(2-CHLORO-3-METHANESULPHINYL-PHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 77)

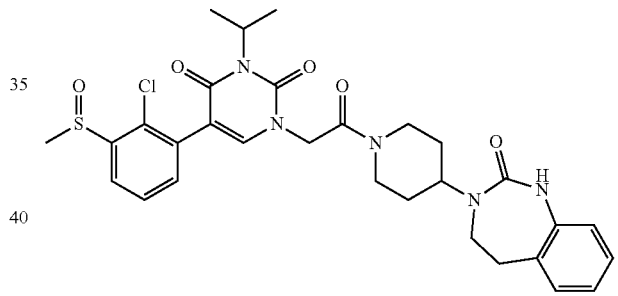

7.5 mg (0.03 mmol) of 3-chloroperoxybenzoic acid in 0.2 ml of dichloromethane is added to a solution of 20 mg (0.03 mmol) of 5-(2-chloro-3-methylsulphanyl-phenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 76.4) in 0.2 ml of dichloromethane. The reaction mixture is stirred at room temperature for 30 minutes. It is diluted with dichloromethane. The organic phase is washed once with a saturated aqueous solution of sodium hydrogen carbonate, once with a 10% aqueous solution of sodium thiosulphate, dried over magnesium sulphate, filtered and concentrated under vacuum. The crude residue is chromatographed on silica gel eluted with a dichloromethane/methanol 97/3 mixture. 12 mg (58%) of 5-(2-chloro-3-methanesulphinyl-phenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid.

$^1$H NMR (δ, DMSO): 1.41 (d, J=6.9 Hz, 6H); 1.53-1.76 (m, 4H); 2.66-2.72 (m, 1H); 2.83 (s, 3H); 2.90 (m, 2H); 3.15 (t, J=11.9 Hz, 1H); 3.38 (m, 2H); 3.94 (d, J=13.6 Hz, 1H); 4.33 (m, 1H); 4.43 (d, J=12.9 Hz, 1H); 4.75 (m, 2H); 5.07-5.14 (m, 1H); 6.79-6.83 (m, 1H); 7.02-7.05 (m, 3H);

7.56 (dd, J=7.5, 1.7 Hz, 1H); 7.71 (t, J=7.7 Hz, 1H); 7.80 (s, 1H); 7.87 (dd, J=7.8, 1.6 Hz, 1H); 8.53 (s, 1H).

EXAMPLE 78: 5-(2-CHLORO-3-METHANESULPHONYL-PHENYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 78)

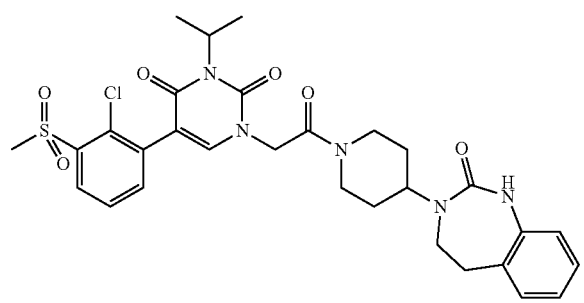 [SMILES: CC(C)n1c(=O)c(-c2cccc(S(C)(=O)=O)c2Cl)cn(CC(=O)N2CCC(N3CCc4ccccc4NC3=O)CC2)c1=O]

A solution containing 2 mg (2 µmol) of ammonium molybdate tetrahydrate in 76 µl (0.7 mmol) of hydrogen peroxide is added to 22 mg (40 µmol) of 5-(2-chloro-3-methylsulphanyl-phenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 76.4), in 0.9 ml of ethanol. The reaction mixture is stirred at room temperature for 2 hours, it is hydrolysed with a saturated aqueous solution of sodium hydrogen carbonate and then extracted with ethyl acetate. The organic phase is washed twice with 10% aqueous solution of sodium thiosulphate, once with water, dried over magnesium sulphate, filtered and concentrated under vacuum. The product precipitates in diethyl ether and then the solvent is removed under nitrogen and the white solid obtained is dried under vacuum. 18 mg (76%) of 5-(2-chloro-3-methanesulphonyl-phenyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid.

$^1$H NMR (δ, DMSO): 1.42 (d, J=6.9 Hz, 6H); 1.51-1.74 (m, 4H); 2.69 (t, J=12.4 Hz, 1H); 2.89-2.91 (m, 2H); 3.15 (t, J=12.3 Hz, 1H); 3.37-3.39 (m, 2H); 3.42 (s, 3H); 3.94 (d, J=13.6 Hz, 1H); 4.30-4.35 (m, 1H); 4.44 (d, J=12.9 Hz, 1H); 4.71-4.81 (m, 2H); 5.08-5.15 (m, 1H); 6.79-6.83 (m, 1H); 7.02-7.05 (m, 3H); 7.65-7.74 (m, 2H); 7.81 (s, 1H); 8.11 (dd, J=7.7, 1.9 Hz, 1H); 8.53 (s, 1H).

EXAMPLE 79: 2-(3-ISOPROPYL-2,4-DIOXO-1-{2-OXO-2-[4-(2-OXO-1,2,4,5-TETRAHYDRO-BENZO[D][1,3]DIAZEPIN-3-YL)-PIPERIDIN-1-YL]-ETHYL}-1,2,3,4-TETRAHYDRO-PYRIMIDIN-5-YL)-METHYL BENZOIC ACETATE (REACTION SCHEME NO. 3, COMPOUND 79)

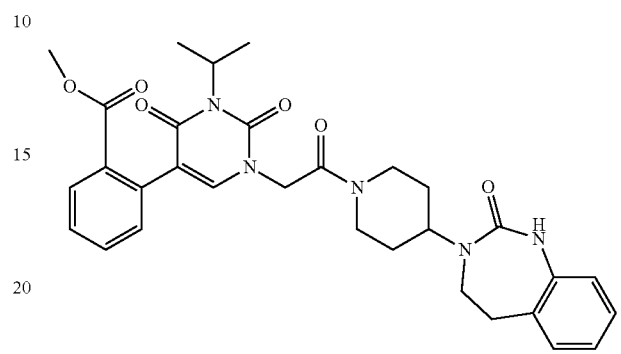

Similarly to example 44.1, starting from 400 mg (0.8 mmol) of 5-bromo-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (prepared as described in example 74.2) and 278 mg (1.5 mmol) of 2-methoxycarbonyl phenyl boronic acid and after purification by preparative high-performance liquid chromatography (Xbridge C18 column, isocratic, 46% acetonitrile in water), 150 mg (33%) of 2-(3-isopropyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-methyl benzoic acetate is obtained in the form of a white solid.

$^1$H NMR (δ, DMSO): 1.39 (d, J=6.9 Hz, 6H); 1.62-1.51 (m, 1H); 1.80-1.63 (m, 3H); 2.70 (t, J=12.1 Hz, 1H); 2.90 (m, 2H); 3.16 (t, J=12.6 Hz, 1H); 3.39 (m, 2H); 3.68 (s, 3H); 3.96 (d, J=13.5 Hz, 1H); 4.34 (m, 1H); 4.46 (d, J=12.9 Hz, 1H); 4.77 (s, 2H); 5.11-5.04 (m, 1H); 6.83-6.79 (m, 1H); 7.05 (t, J=3.6 Hz, 3H); 7.32-7.30 (m, 1H); 7.49 (td, J=7.6, 1.3 Hz, 1H); 7.63 (td, J=7.6, 1.5 Hz, 1H); 7.74 (s, 1H); 7.80 (dd, J=7.7, 1.4 Hz, 1H); 8.54 (s, 1H).

EXAMPLE 80: 2-(3-ISOPROPYL-2,4-DIOXO-1-{2-OXO-2-[4-(2-OXO-1,2,4,5-TETRAHYDRO-BENZO[D][1,3]DIAZEPIN-3-YL)-PIPERIDIN-1-YL]-ETHYL}-1,2,3,4-TETRAHYDRO-PYRIMIDIN-5-YL)-BENZOIC ACID (REACTION SCHEME NO. 3, COMPOUND 80)

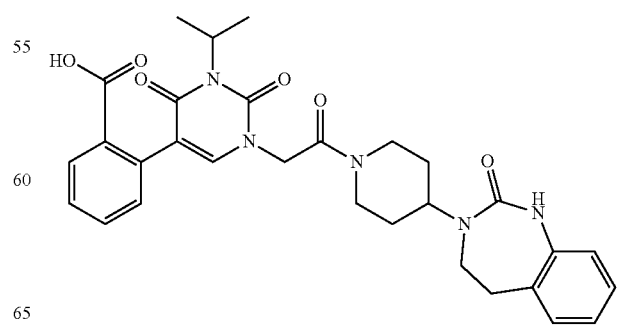

371 mg (1.2 mmol) of barium hydroxide octahydrate is added to a solution of 45 mg (78 µmol) of 2-(3-isopropyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-methyl benzoic acetate in 2 ml of methanol. The mixture is stirred at room temperature for 25 hours. Water is added to the mixture. The aqueous phase is adjusted to pH 5 with 1N aqueous solution of hydrochloric acid, then after extraction with ethyl acetate, the organic phase is dried over anhydrous sodium sulphate and then filtered and concentrated to dryness. The crude residue is purified by preparative high-performance liquid chromatography (Xbridge C18 column, isocratic, 37% acetonitrile in water). 12 mg (27%) of 2-(3-isopropyl-2,4-dioxo-1-{2-oxo-2-[4-(2-oxo-1,2,4,5-tetrahydro-benzo[d][1,3]diazepin-3-yl)-piperidin-1-yl]-ethyl}-1,2,3,4-tetrahydro-pyrimidin-5-yl)-benzoic acid is obtained in the form of a white solid.

$^1$H NMR (δ, DMSO): 0.67 (d, J=6.9 Hz, 6H), 0.86-1.20 (m, 4H), 1.96 (t, J=13.0 Hz, 1H), 2.14-2.23 (m, 2H), 2.41-2.44 (m, 1H), 2.63-2.79 (m, 3H), 3.25 (d, J=13.7 Hz, 1H), 3.54-3.69 (m, 1H), 3.79-3.96 (m, 2H), 4.32-4.45 (m, 1H), 6.00-6.16 (m, 2H), 6.26 (d, J=7.7 Hz, 2H), 6.53 (d, J=7.5 Hz, 1H), 6.59-6.70 (m, 2H), 6.74 (t, J=7.4 Hz, 1H), 7.12 (d, J=7.8 Hz, 1H).

EXAMPLE 81: 5-(3,4-DIFLUOROBENZYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (COMPOUND 81)

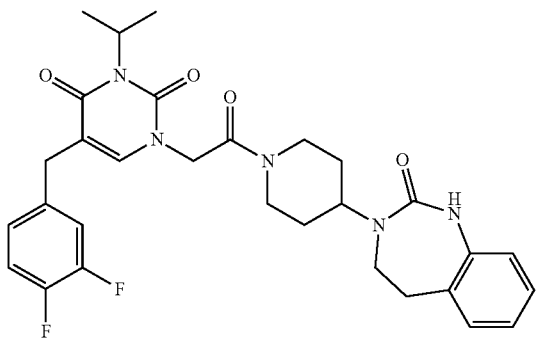 [SMILES: CC(C)n1c(=O)c(Cc2ccc(F)c(F)c2)cn(CC(=O)N2CCC(N3CCc4ccccc4NC3=O)CC2)c1=O]

81.1: 5-(tert-butyl-dimethyl-silanyloxymethyl)-1H-pyrimidine-2,4-dione 2.6 g (20 mmol) of tert-butyl-dimethyl-chlorosilane is added to a solution of 2 g (10 mmol) of 5-hydroxymethyl-1H-pyrimidine-2,4-dione and 2.4 g (40 mmol) of imidazole in 20 ml of dimethylformamide. The reaction mixture is heated at 60° C. for 1.5 h. It is hydrolysed and then diluted with ethyl acetate. The organic phase is washed with water and then dried over magnesium sulphate, filtered and concentrated under vacuum. The white paste obtained is taken up in 10 ml of methanol and 100 ml of diethyl ether. The suspension is filtered to give 2.8 g (78%) of 5-(tert-butyl-dimethyl-silanyloxymethyl)-1H-pyrimidine-2,4-dione in the form of a white solid.

81.2: [5-(tert-butyl-dimethyl-silanyloxymethyl)-2,4-dioxo-3,4-dihydro-2H-pyrimidin-1-yl]-methyl acetate Similarly to example 13.1, starting from 2.8 g (11 mmol) of 5-(tert-butyl-dimethyl-silanyloxymethyl)-1H-pyrimidine-2,4-dione and 1 ml (11 mmol) of methyl bromoacetate, 3.5 g (96%) of [5-(tert-butyl-dimethyl-silanyloxymethyl)-2,4-dioxo-3,4-dihydro-2H-pyrimidin-1-yl]-methyl acetate is obtained in the form of a white solid.

81.3: [5-(tert-butyl-dimethyl-silanyloxymethyl)-3-isopropyl-2,4-dioxo-3,4-dihydro-2H-pyrimidin-1-yl]-methyl acetate Similarly to example 1.7, starting from 3.5 g (11 mmol) of [5-(tert-butyl-dimethyl-silanyloxymethyl)-2,4-dioxo-3,4-dihydro-2H-pyrimidin-1-yl]-methyl acetate and 2 ml (21 mmol) of 2-bromopropane, and after purification by silica gel flash chromatography eluted with a heptane/ethyl acetate 80/20 mixture, 2.7 g (68%) of [5-(tert-butyl-dimethyl-silanyloxymethyl)-3-isopropyl-2,4-dioxo-3,4-dihydro-2H-pyrimidin-1-yl]-methyl acetate is obtained in the form of a colourless oil.

81.4: (5-hydroxymethyl-3-isopropyl-2,4-dioxo-3,4-dihydro-2H-pyrimidin-1-yl)-methyl acetate 6.1 ml (6 mmol) of a 1M solution of tetrabutylammonium fluoride is added to a solution of 1.5 g (4 mmol) of [5-(tert-butyl-dimethyl-silanyloxymethyl)-3-isopropyl-2,4-dioxo-3,4-dihydro-2H-pyrimidin-1-yl]-methyl acetate in 15 ml of tetrahydrofuran, cooled to 0° C. The reaction mixture is stirred at room temperature for 45 minutes. The reaction mixture is hydrolysed with a saturated aqueous solution of ammonium chloride and then diluted with ethyl acetate. The organic phase is washed with water and then with a saturated aqueous solution of sodium chloride, dried over magnesium sulphate, filtered and concentrated under vacuum. The crude residue is chromatographed on silica gel eluted with a dichloromethane/methanol 98/2 mixture. 0.75 g (72%) of (5-hydroxymethyl-3-isopropyl-2,4-dioxo-3,4-dihydro-2H-pyrimidin-1-yl)-methyl acetate is obtained in the form of a colourless oil.

81.5: (5-bromomethyl-3-isopropyl-2,4-dioxo-3,4-dihydro-2H-pyrimidin-1-yl)-methyl acetate 0.2 ml (2.5 mmol) of a solution of phosphorus tribromide in 4 ml of dichloromethane is added to a solution of 0.6 g (2.3 mmol) of (5-hydroxymethyl-3-isopropyl-2,4-dioxo-3,4-dihydro-2H-pyrimidin-1-yl)-methyl acetate in 12 ml of dichloromethane, cooled to 0° C. The mixture is stirred at 0° C. for 30 minutes. After returning to room temperature, the mixture is hydrolysed with water and then with a saturated aqueous solution of sodium hydrogen carbonate. The product is extracted with dichloromethane. The organic phase is washed once with water and then dried over magnesium sulphate, filtered and concentrated under vacuum. The crude residue is purified by silica gel chromatography eluted with a dichloromethane/methanol 99/1 mixture. 0.41 g (29%) of (5-bromomethyl-3-isopropyl-2,4-dioxo-3,4-dihydro-2H-pyrimidin-1-yl)-methyl acetate is obtained in the form of a white solid.

81.6: [5-(3,4-difluorobenzyl)-3-isopropyl-2,4-dioxo-3,4-dihydro-2H-pyrimidin-1-yl]-acetic acid Similarly to example 34, starting from 210 mg (0.7 mmol) of (5-bromomethyl-3-isopropyl-2,4-dioxo-3,4-dihydro-2H-pyrimidin-1-yl)-methyl acetate and 156 mg (1 mmol) of 3,4-difluorophenylboronic acid, 45 mg (20%) of [5-(3,4- difluorobenzyl)-3-isopropyl-2,4-dioxo-3,4-dihydro-2H-pyrimidin-1-yl]-acetic acid is obtained in the form of a yellow oil.

81.7: 5-(3,4-difluorobenzyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 81)

Similarly to example 13.4, starting from 45 mg (0.1 mmol) of [5-(3,4-difluorobenzyl)-3-isopropyl-2,4-dioxo-3,4-dihydro-2H-pyrimidin-1-yl]-acetic acid and 39 mg (0.2 mmol) of 3-piperidin-4-yl-1,3,4,5-tetrahydro-benzo[d][1,3]diazepin-2-one (prepared as described in example 16.4), and after purification by silica gel chromatography eluted with a dichloromethane/methanol 97/3 mixture, 35 mg (46%) of 5-(3,4-difluorobenzyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 224° C.

$^1$H NMR (δ, DMSO): 1.35 (d, J=6.9 Hz, 6H); 1.56-1.68 (m, 4H); 2.67 (t, J=12.6 Hz, 1H); 2.90 (m, 2H); 3.09-3.15 (m, 1H); 3.36-3.41 (m, 2H); 3.56 (s, 2H); 3.92 (d, J=13.5 Hz, 1H); 4.31 (m, 1H); 4.43 (d, J=13.0 Hz, 1H); 4.67 (d, J=3.5 Hz, 2H); 5.05-5.06 (m, 1H); 6.80-6.81 (m, 1H); 7.04-7.05 (m, 4H); 7.32-7.33 (m, 2H); 7.44 (s, 1H); 8.54 (s, 1H).

EXAMPLE 82: 5-(3,5-DIFLUOROBENZYL)-3-ISOPROPYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 82)

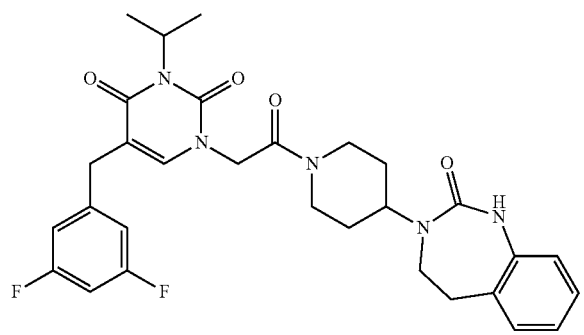 [SMILES: CC(C)n1c(=O)c(Cc2cc(F)cc(F)c2)cn(CC(=O)N2CCC(N3CCc4ccccc4NC3=O)CC2)c1=O]

82.1: [5-(3,5-difluorobenzyl)-3-isopropyl-2,4-dioxo-3,4-dihydro-2H-pyrimidin-1-yl]-acetic acid Similarly to example 34, starting from 200 mg (0.6 mmol) of (5-bromomethyl-3-isopropyl-2,4-dioxo-3,4-dihydro-2H-pyrimidin-1-yl)-methyl acetate (prepared as described in example 81.5) and 158 mg (1 mmol) of 3,5-difluorophenylboronic acid, and after adding 0.9 ml (0.9 mmol) of a 1M aqueous solution of lithium hydroxide, 60 mg (28%) of [5-(3,5-difluorobenzyl)-3-isopropyl-2,4-dioxo-3,4-dihydro-2H-pyrimidin-1-yl]-acetic acid is obtained in the form of a white solid.

82.2: 5-(3,5-difluorobenzyl)-3-isopropyl-1-{2-oxo-2-[4-(2-oxo-1,2,4,5-tetrahydrobenzo[d][1,3]diazepin-3-yl)-piperidin-1-yl]-ethyl}-1H-pyrimidine-2,4-dione (Compound 82)

Similarly to example 13.4, starting from 60 mg (0.2 mmol) of [5-(3,5-difluorobenzyl)-3-isopropyl-2,4-dioxo-3,4-dihydro-2H-pyrimidin-1-yl]-acetic acid and 52 mg (0.2 mmol) of 3-piperidin-4-yl-1,3,4,5-tetrahydro-benzo[d][1,3]diazepin-2-one (prepared as described in example 16.4), and after purification by silica gel chromatography eluted with a dichloromethane/methanol 97/3 mixture and precipitation of the product in diethyl ether, filtration and drying, 55 mg (54%) of 5-(3,5-difluorobenzyl)-3-isopropyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 238° C.

$^1$H NMR (δ, DMSO): 1.35 (d, J=6.9 Hz, 6H); 1.50-1.80 (m, 4H); 2.68 (m, 1H); 2.90 (m, 2H); 3.14 (m, 1H); 3.39 (m, 2H); 3.59 (s, 2H); 3.93 (d, J=13.6 Hz, 1H); 4.32 (m, 1H); 4.43 (d, J=12.9 Hz, 1H); 4.68 (d, J=3.4 Hz, 2H); 5.05-5.06 (m, 1H); 6.80-6.81 (m, 1H); 6.96-6.99 (m, 2H); 7.04-7.06 (m, 4H); 7.49 (s, 1H); 8.54 (s, 1H).

EXAMPLE 83: 5-(2,3-DICHLOROPHENYL)-3-ISOBUTYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 83)

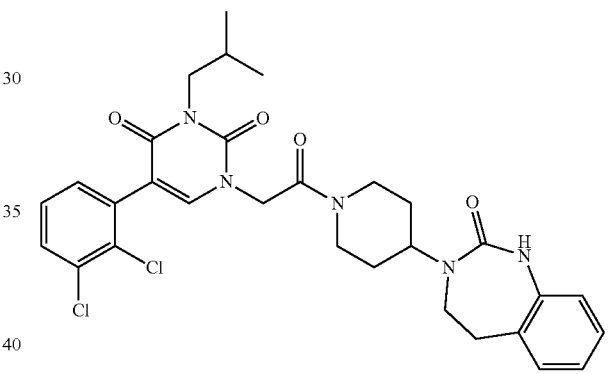

83.1: (5-bromo-3-isobutyl-2,4-dioxo-3,4-dihydro-2H-pyrimidin-1-yl)-methyl acetate Similarly to example 1.7, starting from 2 g (8 mmol) of (5-bromo-2,4-dioxo-3,4-dihydro-2H-pyrimidin-1-yl)-methyl acetate (prepared as described in example 13.1), and 1.2 ml (11 mmol) of 1-bromo-2-methyl propane, and after heating the mixture at 50° C. for 4 hours, 1.8 g (74%) of (5-bromo-3-isobutyl-2,4-dioxo-3,4-dihydro-2H-pyrimidin-1-yl)-methyl acetate is obtained in the form of a white solid.

83.2: [5-(2,3-dichlorophenyl)-3-isobutyl-2,4-dioxo-3,4-dihydro-2H-pyrimidin-1-yl]-methyl acetate Similarly to example 44.1, starting from 400 mg (1.3 mmol) of (5-bromo-3-isobutyl-2,4-dioxo-3,4-dihydro-2H-pyrimidin-1-yl)-methyl acetate and 717 mg (3.8 mmol) of 2,3-dichlorophenylboronic acid and after purification by silica gel chromatography eluted with a heptane/ethyl acetate 80/20 mixture, 260 mg (54%) of [5-(2,3-dichlorophenyl)-3-isobutyl-2,4-dioxo-3,4-dihydro-2H-pyrimidin-1-yl]-methyl acetate is obtained in the form of a pale yellow solid.

83.3: [5-(2,3-dichlorophenyl)-3-isobutyl-2,4-dioxo-3,4-dihydro-2H-pyrimidin-1-yl]-acetic acid Similarly to example 16.8, starting from 260 mg (0.7 mmol) of [5-(2,3-dichlorophenyl)-3-isobutyl-2,4-dioxo-3,4-dihydro-2H-pyrimidin-1-yl]-methyl acetate, 250 mg (100%) of [5-(2,3-dichlorophenyl)-3-isobutyl-2,4-dioxo-3,4-dihydro-2H-pyrimidin-1-yl]-acetic acid is obtained in the form of a beige solid.

83.4: 5-(2,3-dichlorophenyl)-3-isobutyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 83)

Similarly to example 13.4, starting from 250 mg (0.7 mmol) of [5-(2,3-dichlorophenyl)-3-isopropyl-2,4-dioxo-3,4-dihydro-2H-pyrimidin-1-yl]-acetic acid and 192 mg (0.7 mmol) of 3-piperidin-4-yl-1,3,4,5-tetrahydro-benzo[d][1,3]diazepin-2-one (prepared as described in example 16.4), and after crystallization in ethyl acetate, 290 mg (71%) of 5-(2,3-dichlorophenyl)-3-isobutyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 248° C.
$^1$H NMR (δ, DMSO): 0.86 (d, J=6.7 Hz, 6H), 1.48-1.60 (m, 1H), 1.62-1.80 (m, 3H), 2.03 (m, 1H), 2.67 (t, J=12 Hz, 1H), 2.89 (t, J=4.5 Hz, 2H), 3.14 (t, J=12 Hz, 1H), 3.36 (t, J=4.5 Hz, 2H), 3.71 (d, J=7.3 Hz, 2H), 3.92 (d, J=13 Hz, 1H), 4.28-4.38 (m, 1H), 4.42 (d, J=13 Hz, 1H), 4.76 (d, J=2.2 Hz, 2H), 6.75-6.82 (m, 1H), 7.01-7.04 (m, 3H), 7.32 (dd, J=1.5-7.6 Hz, 1H), 7.42 (t, J=7.8 Hz, 1H), 7.68 (dd, J=1.48 Hz, 1H), 7.81 (s, 1H), 8.53 (s, 1H).

EXAMPLE 84: 5-(2-CHLORO-3-FLUOROPHENYL)-3-ISOBUTYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 84)

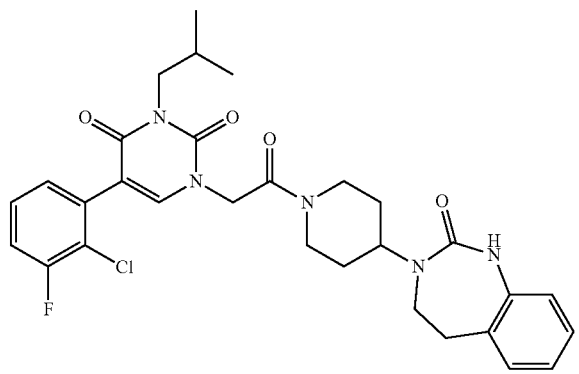 [SMILES: CC(C)Cn1c(=O)c(-c2cccc(F)c2Cl)cn(CC(=O)N2CCC(N3CCc4ccccc4NC3=O)CC2)c1=O]

84.1: [5-(2-chloro-3-fluorophenyl)-3-isobutyl-2,4-dioxo-3,4-dihydro-2H-pyrimidin-1-yl]-acetic acid Similarly to example 13.3, starting from 300 mg (0.9 mmol) of (5-bromo-3-isobutyl-2,4-dioxo-3,4-dihydro-2H-pyrimidin-1-yl)-methyl acetate (prepared as described in example 83.1) and 246 mg (1.4 mmol) of 2-chloro-3-fluorophenylboronic acid, 215 mg (64%) of [5-(2-chloro-3-fluorophenyl)-3-isobutyl-2,4-dioxo-3,4-dihydro-2H-pyrimidin-1-yl]-acetic acid is obtained in the form of a yellow oil.

84.2: 5-(2-chloro-3-fluorophenyl)-3-isobutyl-1-{2-oxo-2-[4-(2-oxo-1,2,4,5-tetrahydrobenzo[d][1,3]diazepin-3-yl)-piperidin-1-yl]-ethyl}-1H-pyrimidine-2,4-dione (Compound 84)

Similarly to example 13.4, starting from 215 mg (0.6 mmol) of [5-(2-chloro-3-fluorophenyl)-3-isopropyl-2,4-dioxo-3,4-dihydro-2H-pyrimidin-1-yl]-acetic acid and 164 mg (0.7 mmol) of 3-piperidin-4-yl-1,3,4,5-tetrahydro-benzo[d][1,3]diazepin-2-one (prepared as described in example 16.4), and after recrystallization from acetone, 140 mg (38%) of 5-(2-chloro-3-fluorophenyl)-3-isobutyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 248° C.
$^1$H NMR (δ, DMSO): 0.87 (d, J=6.7 Hz, 6H), 1.48-1.60 (m, 1H), 1.62-1.80 (m, 3H), 2.04 (m, 1H), 2.68 (t, J=11 Hz, 1H), 2.89 (t, J=4.3 Hz, 2H), 3.15 (t, J=11 Hz, 1H), 3.37 (t, J=4.3 Hz, 2H), 3.72 (d, J=7.3 Hz, 2H), 3.94 (d, J=13.4 Hz, 1H), 4.32 (m, 1H), 4.42 (d, J=13.1 Hz, 1H), 4.77 (d, J=2.2 Hz, 2H), 6.78-6.82 (m, 1H), 7.02-7.05 (m, 3H), 7.20-7.22 (m, 1H), 7.43-7.47 (m, 2H), 7.83 (s, 1H), 8.54 (s, 1H).

EXAMPLE 85: 5-(2,3-DIMETHYLPHENYL)-3-ISOBUTYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 85)

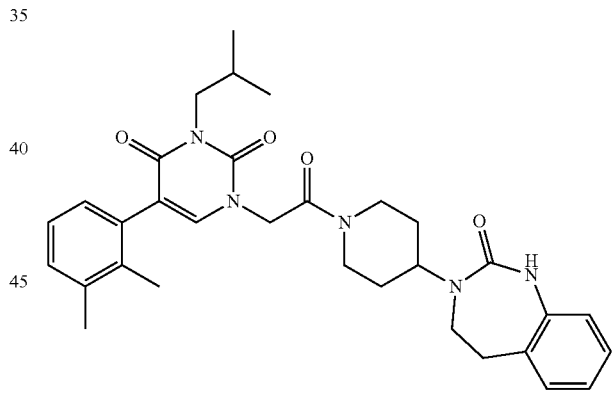

85.1: [5-(2,3-dimethylphenyl)-3-isobutyl-2,4-dioxo-3,4-dihydro-2H-pyrimidin-1-yl]-methyl acetate Similarly to example 44.1, starting from 300 mg (0.9 mmol) of (5-bromo-3-isobutyl-2,4-dioxo-3,4-dihydro-2H-pyrimidin-1-yl)-methyl acetate (prepared as described in example 83.1) and 211 mg (1.4 mmol) of 2,3-dimethylphenylboronic acid, 255 mg (79%) of [5-(2,3-dimethylphenyl)-3-isobutyl-2,4-dioxo-3,4-dihydro-2H-pyrimidin-1-yl]-methyl acetate is obtained in the form of a yellow oil.

85.2: [5-(2,3-dimethylphenyl)-3-isobutyl-2,4-dioxo-3,4-dihydro-2H-pyrimidin-1-yl]-acetic acid Similarly to example 16.8, starting from 255 mg (0.7 mmol) of [5-(2,3-dimethylphenyl)-3-isobutyl-2,4-dioxo-3, 4-dihydro-2H-pyrimidin-1-yl]-methyl acetate, 230 mg (94%) of [5-(2,3-dimethylphenyl)-3-isobutyl-2,4-dioxo-3,4-dihydro-2H-pyrimidin-1-yl]-acetic acid is obtained in the form of a white solid.

85.3: 5-(2,3-dimethylphenyl)-3-isobutyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 85)

Similarly to example 13.4, starting from 230 mg (0.7 mmol) of [5-(2,3-dimethylphenyl)-3-isopropyl-2,4-dioxo-3,4-dihydro-2H-pyrimidin-1-yl]-acetic acid and 188 mg (0.8 mmol) of 3-piperidin-4-yl-1,3,4,5-tetrahydro-benzo[d][1,3]diazepin-2-one (prepared as described in example 16.4), and after recrystallization from an acetone/heptane 50/50 mixture, 170 mg (43%) of [5-(2,3-dimethylphenyl)-3-isobutyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 270° C.

$^1$H NMR (δ, DMSO): 0.86 (d, J=6.7 Hz, 6H), 1.48-1.60 (m, 1H), 1.62-1.80 (m, 3H), 2.03 (s, 3H), 2.06 (m, 1H), 2.27 (s, 3H), 2.67 (t, J=11 Hz, 1H), 2.89 (t, J=4.5 Hz, 2H), 3.15 (t, J=11 Hz, 1H), 3.37 (t, J=4.4 Hz, 2H), 3.72 (d, J=7.2 Hz, 2H), 3.95 (d, J=13 Hz, 1H), 4.28-4.38 (m, 1H), 3.95 (d, J=13 Hz, 1H), 4.75 (d, J=5.2 Hz, 2H), 6.80-6.82 (m, 1H), 6.96 (d, J=7.1 Hz, 1H), 7.02 (s, 1H), 7.04 (d, J=3.7 Hz, 2H), 7.10 (t, J=7.5 Hz, 1H), 7.17 (d, J=7.4 Hz, 1H), 7.60 (s, 1H), 8.54 (s, 1H).

EXAMPLE 86: 5-(3-FLUORO-2-METHYLPHENYL)-3-ISOBUTYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 86)

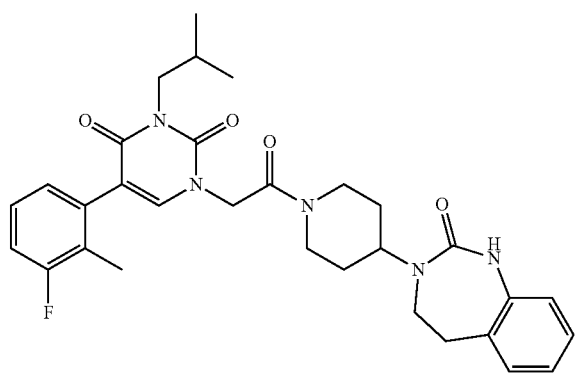 [SMILES: Cc1cccc(-c2cn(CC(=O)N3CCC(N4CCc5ccccc5NC4=O)CC3)c(=O)n(CC(C)C)c2=O)c1C]

86.1: [5-(3-fluoro-2-methylphenyl)-3-isobutyl-2,4-dioxo-3,4-dihydro-2H-pyrimidin-1-yl]-methyl acetate Similarly to example 44.1, starting from 500 mg (1.6 mmol) of (5-bromo-3-isobutyl-2,4-dioxo-3,4-dihydro-2H-pyrimidin-1-yl)-methyl acetate (prepared as described in example 83.1) and 386 mg (2.5 mmol) of 3-fluoro-2-methylphenylboronic acid, and after purification by silica gel chromatography eluted with a heptane/ethyl acetate 80/20 mixture, 620 mg (100%) of [5-(3-fluoro-2-methylphenyl)-3-isobutyl-2,4-dioxo-3,4-dihydro-2H-pyrimidin-1-yl]-methyl acetate is obtained in the form of a yellow oil.

86.2: [5-(3-fluoro-2-methylphenyl)-3-isobutyl-2,4-dioxo-3,4-dihydro-2H-pyrimidin-1-yl]-acetic acid Similarly to example 16.8, starting from 545 mg (1.6 mmol) of [5-(3-fluoro-2-methylphenyl)-3-isobutyl-2,4-dioxo-3,4-dihydro-2H-pyrimidin-1-yl]-methyl acetate, 440 mg (84%) of [5-(3-fluoro-2-methylphenyl)-3-isobutyl-2,4-dioxo-3,4-dihydro-2H-pyrimidin-1-yl]-acetic acid is obtained in the form of a beige solid.

86.3: 5-(3-fluoro-2-methylphenyl)-3-isobutyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 86)

Similarly to example 13.4, starting from 440 mg (1.3 mmol) of [5-(3-fluoro-2-methylphenyl)-3-isopropyl-2,4-dioxo-3,4-dihydro-2H-pyrimidin-1-yl]-acetic acid and 355 mg (1.5 mmol) of 3-piperidin-4-yl-1,3,4,5-tetrahydro-benzo[d][1,3]diazepin-2-one (prepared as described in example 16.4), and after recrystallization from ethanol, 530 mg (71%) of [5-(3-fluoro-2-methylphenyl)-3-isobutyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 251° C.

$^1$H NMR (δ, DMSO): 0.87 (d, J=6.7 Hz, 6H); 1.52-1.73 (m, 4H); 2.01-2.07 (m, 4H); 2.68 (t, J=12.6 Hz, 1H); 2.86-2.91 (m, 2H); 3.15 (t, J=12.4 Hz, 1H); 3.34-3.39 (m, 2H); 3.73 (d, J=7.3 Hz, 2H); 3.94 (d, J=13.7 Hz, 1H); 4.28-4.35 (m, 1H); 4.43 (d, J=12.9 Hz, 1H); 4.77 (d, J=3.2 Hz, 2H); 6.79-6.80 (m, 1H); 7.00-7.05 (m, 4H); 7.16-7.27 (m, 2H); 7.72 (s, 1H); 8.54 (s, 1H).

EXAMPLE 87: [2-(5-(2,3-DIMETHYLPHENYL)-2,6-DIOXO-3-{2-OXO-2-[4-(2-OXO-1,2,4,5-TETRAHYDRO-BENZO[D][1,3]DIAZEPIN-3-YL)-PIPERIDIN-1-YL]-ETHYL}-3,6-DIHYDRO-2H-PYRIMIDIN-1-YL)-ETHYL]-CARBAMIC ACID TERT-BUTYL ESTER (REACTION SCHEME NO. 3, COMPOUND 87)

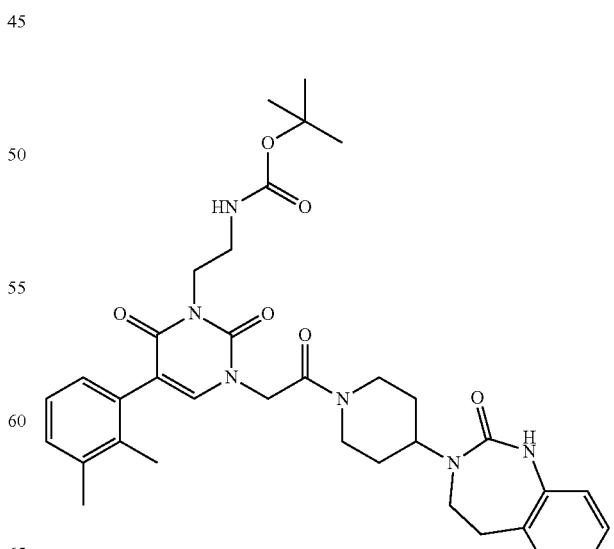

87.1: [5-bromo-3-(2-tert-butoxycarbonylamino-ethyl)-2,4-dioxo-3,4-dihydro-2H-pyrimidin-1-yl]-methyl acetate Similarly to example 1.7, starting from 0.5 g (2 mmol) of (5-bromo-2,4-dioxo-3,4-dihydro-2H-pyrimidin-1-yl)-methyl acetate (prepared as described in example 13.1), and 511 mg (2 mmol) of tert-butyl-N-(2-bromoethyl)carbamate, and after heating the mixture at 50° C. for 3 hours, 0.63 mg (82%) of [5-bromo-3-(2-tert-butoxycarbonylaminoethyl)-2,4-dioxo-3,4-dihydro-2H-pyrimidin-1-yl]-methyl acetate is obtained in the form of a colourless oil.

87.2: [3-(2-tert-butoxycarbonylaminoethyl)-5-(2,3-dimethylphenyl)-2,4-dioxo-3,4-dihydro-2H-pyrimidin-1-yl]-acetic acid Similarly to example 44.1, starting from 632 mg (1.6 mmol) of [5-bromo-3-(2-tert-butoxycarbonylaminoethyl)-2,4-dioxo-3,4-dihydro-2H-pyrimidin-1-yl]-methyl acetate and 350 mg (2.3 mmol) of 2,3-dimethylphenylboronic acid, 380 mg (59%) of [3-(2-tert-butoxycarbonylaminoethyl)-5-(2,3-dimethylphenyl)-2,4-dioxo-3,4-dihydro-2H-pyrimidin-1-yl]-acetic acid is obtained in the form of a beige solid.

87.3: [2-(5-(2,3-dimethylphenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-tert-butyl carbamate (compound 87)

Similarly to example 13.4, starting from 380 mg (0.9 mmol) of [3-(2-tert-butoxycarbonylaminoethyl)-5-(2,3-dimethylphenyl)-2,4-dioxo-3,4-dihydro-2H-pyrimidin-1-yl]-acetic acid and 246 mg (1 mmol) of 3-piperidin-4-yl-1,3,4,5-tetrahydro-benzo[d][1,3]diazepin-2-one (prepared as described in example 16.4), and after crystallization in a heptane/ethyl acetate mixture 70/30, 325 mg (55%) of [2-(5-(2,3-dimethylphenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-tert-butyl carbamate is obtained in the form of a beige solid with a melting point of 169° C.

¹H NMR (δ, DMSO): 1.36 (s, 9H); 1.55-1.67 (m, 4H); 2.07 (s, 3H); 2.27 (s, 3H); 2.68 (t, J=12.5 Hz, 1H); 2.89 (m, 2H); 3.11-3.19 (m, 3H); 3.35-3.40 (m, 2H); 3.94 (m, 3H); 4.30 (m, 1H); 4.43 (d, J=12.9 Hz, 1H); 4.74 (s, 2H); 6.80-6.83 (m, 2H); 6.95 (d, J=7.5 Hz, 1H); 7.02-7.04 (m, 3H); 7.10 (t, J=7.5 Hz, 1H); 7.17 (d, J=7.6 Hz, 1H); 7.57 (s, 1H); 8.53 (s, 1H).

EXAMPLE 88: 3-(2-AMINOETHYL)-5-(2,3-DIMETHYLPHENYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 88)

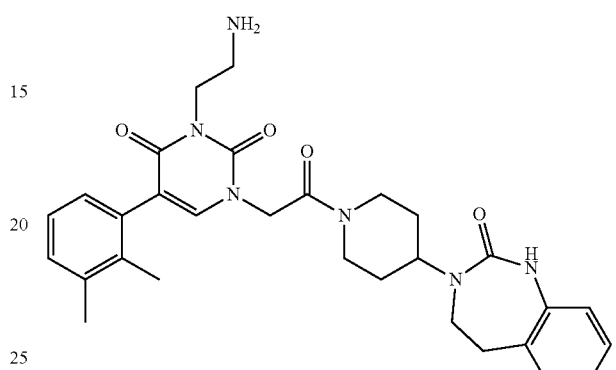

2 ml (5 mmol) of a 2.5M solution of hydrochloric acid in ethanol is added to 100 mg (0.2 mmol) of [2-(5-(2,3-dimethylphenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-tert-butyl carbamate (prepared as described in example 87.3). The reaction mixture is stirred for 3 hours at room temperature and then concentrated under vacuum. The mixture is hydrolysed with a saturated aqueous solution of sodium hydrogen carbonate and then diluted with ethyl acetate. The organic phase is washed with a saturated aqueous solution of sodium hydrogen carbonate, then with water and with a saturated aqueous solution of sodium chloride; dried over magnesium sulphate, filtered and concentrated under vacuum. The white solid obtained is taken up in diethyl ether, then filtered and dried under vacuum. 80 mg (93%) of 3-(2-aminoethyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 230° C.

¹H NMR (δ, DMSO): 1.55-1.80 (m, 6H); 2.05 (s, 3H); 2.27 (s, 3H); 2.64-2.71 (m, 3H); 2.89 (m, 2H); 3.14 (t, J=12.5 Hz, 1H); 3.37 (m, 2H); 3.87 (t, J=7.0 Hz, 2H); 3.94 (d, J=13.5 Hz, 1H); 4.32 (m, 1H); 4.43 (d, J=13.0 Hz, 1H); 4.75 (d, J=6.1 Hz, 2H); 6.79-6.81 (m, 1H); 6.95-7.04 (m, 4H); 7.08-7.18 (m, 2H); 7.58 (s, 1H); 8.54 (s, 1H).

EXAMPLE 89: 3-(2-AMINOETHYL)-5-(2,3-DI-CHLOROPHENYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 89)

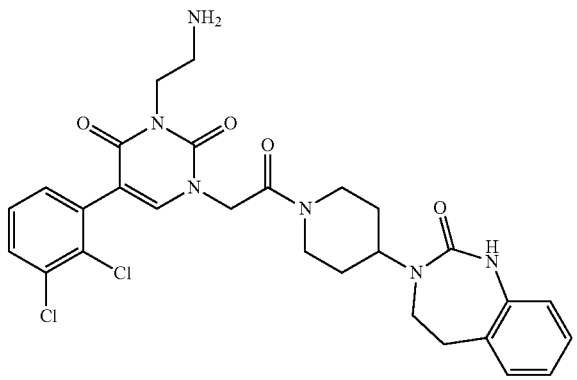 [SMILES: NCCn1c(=O)c(-c2cccc(Cl)c2Cl)cn(CC(=O)N2CCC(N3CCc4ccccc4NC3=O)CC2)c1=O]

89.1: [3-(2-tert-butoxycarbonylaminoethyl)-5-(2,3-dichlorophenyl)-2,4-dioxo-3,4-dihydro-2H-pyrimidin-1-yl]-acetic acid Similarly to example 44.1, starting from 700 mg (1.7 mmol) of [5-bromo-3-(2-tert-butoxycarbonylaminoethyl)-2,4-dioxo-3,4-dihydro-2H-pyrimidin-1-yl]-methyl acetate (prepared as described in example 87.1) and 526 mg (2.8 mmol) of 2,3-dichlorophenylboronic acid, 210 mg (27%) of [3-(2-tert-butoxycarbonylaminoethyl)-5-(2,3-dichlorophenyl)-2,4-dioxo-3,4-dihydro-2H-pyrimidin-1-yl]-acetic acid is obtained in the form of an orange-coloured oil.

89.2: [2-(5-(2,3-dichlorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-tert-butyl carbamate Similarly to example 13.4, starting from 210 mg (0.5 mmol) of [3-(2-tert-butoxycarbonylaminoethyl)-5-(2,3-dichlorophenyl)-2,4-dioxo-3,4-dihydro-2H-pyrimidin-1-yl]-acetic acid and 112 mg (0.5 mmol) of 3-piperidin-4-yl-1,3,4,5-tetrahydro-benzo[d][1,3]diazepin-2-one (prepared as described in example 16.4), 190 mg (60%) of [2-(5-(2,3-dichlorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-tert-butyl-carbamate is obtained in the form of a white solid.

89.3: 3-(2-aminoethyl)-5-(2,3-dichlorophenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 89)

Similarly to example 88, starting from 190 mg (0.3 mmol) of [2-(5-(2,3-dichlorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-tert-butyl-carbamate, 145 mg (88%) of 3-(2-aminoethyl)-5-(2,3-dichlorophenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 250° C.

$^1$H NMR (δ, DMSO): 1.48-1.85 (m, 4H); 2.65-2.73 (m, 3H); 2.89 (m, 2H); 3.11-3.16 (m, 1H); 3.35-3.50 (m, 2H); 3.89-3.93 (m, 3H); 4.32 (m, 1H); 4.42 (d, J=12.7 Hz, 1H); 4.79 (s, 2H); 6.79-6.81 (m, 1H); 7.02-7.04 (m, 3H); 7.34 (dd, J=7.6, 1.6 Hz, 1H); 7.43 (t, J=7.9 Hz, 1H); 7.69 (dd, J=8.0, 1.6 Hz, 1H); 7.85 (s, 1H); 8.55 (s, 1H).

EXAMPLE 90: 5-(2,3-DICHLOROPHENYL)-3-(2-METHYLAMINOETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 90)

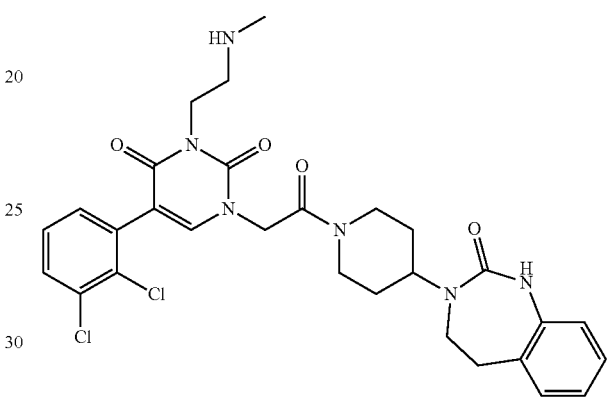

90.1: [3-(2-tert-butoxycarbonylaminoethyl)-5-(2,3-dichlorophenyl)-2,4-dioxo-3,4-dihydro-2H-pyrimidin-1-yl]-methyl acetate Similarly to example 44.1, starting from 700 mg (1.7 mmol) of [5-bromo-3-(2-tert-butoxycarbonylaminoethyl)-2,4-dioxo-3,4-dihydro-2H-pyrimidin-1-yl]-methyl acetate (prepared as described in example 87.1) and 526 mg (2.8 mmol) of 2,3-dichlorophenylboronic acid, 130 mg (16%) of [3-(2-tert-butoxycarbonylaminoethyl)-5-(2,3-dichlorophenyl)-2,4-dioxo-3,4-dihydro-2H-pyrimidin-1-yl]-methyl acetate is obtained in the form of a beige solid.

90.2: [3-[2-(tert-butoxycarbonyl-methylamino)-ethyl]-5-(2,3-dichlorophenyl)-2,4-dioxo-3,4-dihydro-2H-pyrimidin-1-yl]-acetic acid Similarly to example 13.2, starting from 130 mg (0.3 mmol) of [3-(2-tert-butoxycarbonylaminoethyl)-5-(2,3-dichlorophenyl)-2,4-dioxo-3,4-dihydro-2H-pyrimidin-1-yl]-methyl acetate and 26 μl (0.4 mmol) of iodomethane, 100 mg (77%) of [3-[2-(tert-butoxycarbonyl-methylamino)-ethyl]-5-(2,3-dichlorophenyl)-2,4-dioxo-3,4-dihydro-2H-pyrimidin-1-yl]-acetic acid is obtained in the form of a pale yellow solid.

90.3: [2-(5-(2,3-dichlorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-methyl-tert-butyl carbamate Similarly to example 13.4, starting from 100 mg (0.2 mmol) of [3-[2-(tert-butoxycarbonyl-methylamino)-ethyl]-

5-(2,3-dichlorophenyl)-2,4-dioxo-3,4-dihydro-2H-pyrimidin-1-yl]-acetic acid and 52 mg (0.2 mmol) of 3-piperidin-4-yl-1,3,4,5-tetrahydro-benzo[d][1,3]diazepin-2-one (prepared as described in example 16.4), 95 mg (64%) of [2-(5-(2,3-dichlorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-methyl-tert-butyl carbamate is obtained in the form of a white solid.

90.4: 5-(2,3-dichlorophenyl)-3-(2-methylaminoethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 90)

Similarly to example 88, starting from 95 mg (0.1 mmol) [2-(5-(2,3-dichlorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-methyl-tert-butyl carbamate, and after recrystallization from ethanol, 55 mg (66%) of 5-(2,3-dichlorophenyl)-3-(2-methylaminoethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 225° C.

$^1$H NMR (δ, DMSO): 1.45-1.69 (m, 4H); 2.29 (s, 3H); 2.65-2.71 (m, 3H); 2.90 (m, 2H); 3.14-3.20 (m, 1H); 3.38 (m, 2H); 3.95 (t, J=7.0 Hz, 2H); 4.33 (m, 1H); 4.43 (d, J=12.9 Hz, 1H); 4.77 (d, J=2.9 Hz, 2H); 6.80-6.81 (m, 1H); 7.03-7.05 (m, 3H); 7.34 (dd, J=7.7, 1.6 Hz, 1H); 7.43 (t, J=7.9 Hz, 1H); 7.69 (dd, J=8.0, 1.6 Hz, 1H); 7.81 (s, 1H); 8.53 (s, 1H).

EXAMPLE 91: 3-((R)-2,3-DIHYDROXYPROPYL)-5-(2,3-DIMETHYLPHENYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 91)

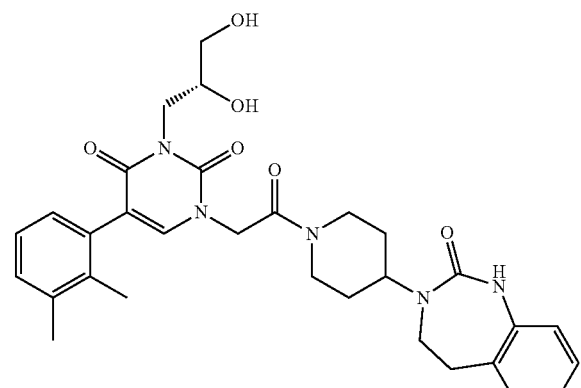

91.1: [5-bromo-3-((R)-2,2-dimethyl-[1,3]dioxolan-4-ylmethyl)-2,4-dioxo-3,4-dihydro-2H-pyrimidin-1-yl]-acetic acid 0.8 g (5.7 mmol) of potassium carbonate and 0.6 ml (4.6 mmol) of (S)-(−)-4-(chloromethyl)-2,2-dimethyl-1,3-dioxolane are added to a solution of 1 g (3.8 mmol) of (5-bromo-2,4-dioxo-3,4-dihydro-2H-pyrimidin-1-yl)-methyl acetate (prepared as described in example 13.1), in 25 ml of dimethylformamide. The reaction mixture is heated at 70° C. for 2.5 h. 1.5 g (4 mmol) of tetrabutylammonium iodide is added, as well as 0.5 ml (4 mmol) of (S)-(−)-4-(chloromethyl)-2,2-dimethyl-1,3-dioxolane. After heating for 20 hours at 130° C., the reaction mixture is hydrolysed and then diluted with ethyl acetate. The aqueous phase is adjusted to pH=5 with 1N aqueous solution of hydrochloric acid. The product is extracted with ethyl acetate. The organic phase is washed with water and with a saturated aqueous solution of sodium chloride, then dried over magnesium sulphate, filtered and concentrated under vacuum. The crude residue is chromatographed on silica gel eluted with a dichloromethane/methanol 97/3 mixture. 115 mg (8%) of [5-bromo-3-((R)-2,2-dimethyl-[1,3]dioxolan-4-ylmethyl)-2,4-dioxo-3,4-dihydro-2H-pyrimidin-1-yl]-acetic acid is obtained in the form of an orange-coloured oil.

91.2: 5-bromo-3-((R)-2,3-dihydroxypropyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione Similarly to example 13.4, starting from 115 mg (0.3 mmol) of [5-bromo-3-((R)-2,2-dimethyl-[1,3]dioxolan-4-ylmethyl)-2,4-dioxo-3,4-dihydro-2H-pyrimidin-1-yl]-acetic acid and 82 mg (0.3 mmol) of 3-piperidin-4-yl-1,3,4,5-tetrahydro-benzo[d][1,3]diazepin-2-one (prepared as described in example 16.4), 16 mg (9%) of 5-bromo-3-((R)-2,3-dihydroxypropyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid.

91.3: 3-((R)-2,3-dihydroxypropyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (compound 91)

Similarly to example 44.1, starting from 16 mg (30 μmol) of 5-bromo-3-((R)-2,3-dihydroxypropyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione and 7 mg (40 μmol) of 2,3-dimethylphenylboronic acid, 4 mg (20%) of 3-((R)-2,3-dihydroxypropyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a light yellow solid.

HPLC analysis (Kinetex C18 column, 150×2.1 mm, 1.7 μm, eluent: water/acetonitrile with 0.1% formic acid, 30 min run): tr=9.37 min.

EXAMPLE 92: 3-(3,4-DIHYDROXYBUTYL)-5-(2,3-DIMETHYLPHENYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 92)

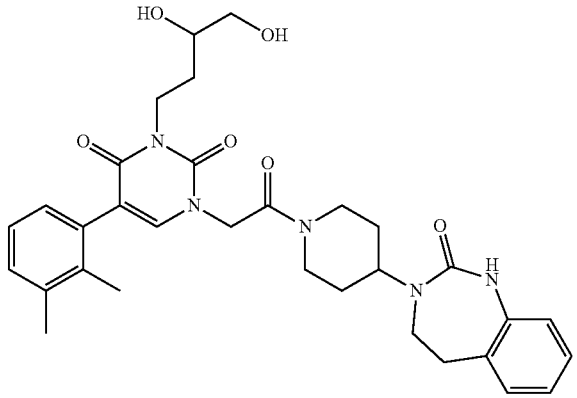 [SMILES: Cc1cccc(-c2cn(CC(=O)N3CCC(N4CCc5ccccc5NC4=O)CC3)c(=O)n(CCC(O)CO)c2=O)c1C]

92.1: [5-bromo-3-((S)-2-oxiranyl-ethyl)-2,4-dioxo-3,4-dihydro-2H-pyrimidin-1-yl]-methyl acetate Similarly to example 83.1, starting from 1 g (3.8 mmol) of (5-bromo-2,4-dioxo-3,4-dihydro-2H-pyrimidin-1-yl)-methyl acetate (prepared as described in example 13.1) and 0.6 g (3.8 mmol) of (S)-2-(2-bromoethyl)-oxirane, 0.8 g (66%) of [5-bromo-3-((S)-2-oxiranyl-ethyl)-2,4-dioxo-3,4-dihydro-2H-pyrimidin-1-yl]-methyl acetate is obtained in the form of a white solid.

92.2: [3-(3,4-dihydroxybutyl)-5-(2,3-dimethylphenyl)-2,4-dioxo-3,4-dihydro-2H-pyrimidin-1-yl]-acetic acid Similarly to example 13.3, starting from 400 mg (1.2 mmol) of [5-bromo-3-((S)-2-oxiranyl-ethyl)-2,4-dioxo-3,4-dihydro-2H-pyrimidin-1-yl]-methyl acetate and 270 mg (1.8 mmol) of 2,3-dimethylphenylboronic acid, 280 mg (64%) of [3-(3,4-dihydroxybutyl)-5-(2,3-dimethylphenyl)-2,4-dioxo-3,4-dihydro-2H-pyrimidin-1-yl]-acetic acid is obtained in the form of a pink solid.

92.3: 3-(3,4-dihydroxybutyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 92)

Similarly to example 13.4, starting from 280 mg (0.8 mmol) of [3-(3,4-dihydroxybutyl)-5-(2,3-dimethylphenyl)-2,4-dioxo-3,4-dihydro-2H-pyrimidin-1-yl]-acetic acid and 227 mg (0.9 mmol) of 3-piperidin-4-yl-1,3,4,5-tetrahydro-benzo[d][1,3]diazepin-2-one (prepared as described in example 16.4), 75 mg (16%) of 3-(3,4-dihydroxybutyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a pink solid with a melting point of 175° C.

$^1$H NMR (δ, DMSO): 1.49-1.80 (m, 6H); 2.04 (s, 3H); 2.27 (s, 3H); 2.68 (t, J=12.4 Hz, 1H); 2.89 (m, 2H); 3.14 (t, J=12.4 Hz, 1H); 3.22-3.24 (m, 1H); 3.30-3.32 (m, 1H); 3.35-3.39 (m, 2H); 3.45-3.48 (m, 1H); 3.83-3.88 (m, 1H); 3.94 (d, J=13.7 Hz, 1H); 4.05-4.08 (m, 1H); 4.28-4.36 (m, 1H); 4.43 (d, J=12.9 Hz, 1H); 4.53-4.54 (m, 2H); 4.75 (d, J=3.5 Hz, 2H); 6.79-6.80 (m, 1H); 6.96 (d, J=7.5 Hz, 1H); 7.03-7.05 (m, 3H); 7.10 (t, J=7.5 Hz, 1H); 7.17 (d, J=7.5 Hz, 1H); 7.59 (s, 1H); 8.55 (s, 1H).

EXAMPLE 93: 5-(2,3-DIMETHYLPHENYL)-3-(2-METHOXYETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 93)

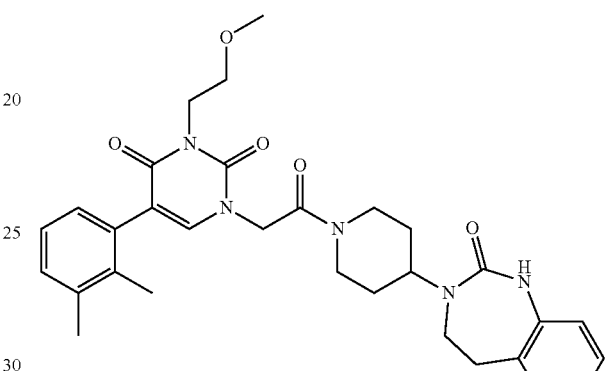

93.1: [5-bromo-3-(2-methoxyethyl)-2,4-dioxo-3,4-dihydro-2H-pyrimidin-1-yl]-methyl acetate Similarly to example 83.1, starting from 1 g (3.8 mmol) of (5-bromo-2,4-dioxo-3,4-dihydro-2H-pyrimidin-1-yl)-methyl acetate (prepared as described in example 13.1), and 0.8 g (5.7 mmol) of 2-bromoethyl methyl ether, 0.8 g (62%) of [5-bromo-3-(2-methoxyethyl)-2,4-dioxo-3,4-dihydro-2H-pyrimidin-1-yl]-methyl acetate is obtained in the form of a white solid.

93.2: [5-(2,3-dimethylphenyl)-3-(2-methoxyethyl)-2,4-dioxo-3,4-dihydro-2H-pyrimidin-1-yl]-acetic acid Similarly to example 13.3, starting from 400 mg (1.3 mmol) of [5-bromo-3-(2-methoxyethyl)-2,4-dioxo-3,4-dihydro-2H-pyrimidin-1-yl]-methyl acetate and 280 mg (1.9 mmol) of 2,3-dimethylphenylboronic acid, 410 mg (99%) of [5-(2,3-dimethylphenyl)-3-(2-methoxyethyl)-2,4-dioxo-3,4-dihydro-2H-pyrimidin-1-yl]-acetic acid is obtained in the form of an orange-coloured oil.

93.3: 5-(2,3-dimethylphenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 93)

Similarly to example 13.4, starting from 410 mg (1.2 mmol) of [5-(2,3-dimethylphenyl)-3-(2-methoxyethyl)-2,4-dioxo-3,4-dihydro-2H-pyrimidin-1-yl]-acetic acid and 363 mg (1.5 mmol) of 3-piperidin-4-yl-1,3,4,5-tetrahydro-benzo[d][1,3]diazepin-2-one (prepared as described in example 16.4), and after recrystallization from ethanol, 400 mg (57%) of 5-(2,3-dimethylphenyl)-3-(2-methoxyethyl)-1-{2- oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 227° C.

¹H NMR (δ, DMSO): 1.50-1.80 (m, 4H); 2.05 (s, 3H); 2.28 (s, 3H); 2.68 (t, J=12.6 Hz, 1H); 2.86-2.91 (m, 2H); 3.15 (t, J=12.5 Hz, 1H); 3.26 (s, 3H); 3.36-3.39 (m, 2H); 3.52 (t, J=6.1 Hz, 2H); 3.94 (d, J=13.6 Hz, 1H); 4.07 (t, J=6.1 Hz, 2H); 4.33 (m, 1H); 4.43 (d, J=12.9 Hz, 1H); 4.76 (d, J=4.9 Hz, 2H); 6.80-6.81 (m, 1H); 6.97 (d, J=7.5 Hz, 1H); 7.04-7.06 (m, 3H); 7.11 (t, J=7.5 Hz, 1H); 7.18 (d, J=7.5 Hz, 1H); 7.60 (s, 1H); 8.53 (s, 1H).

EXAMPLE 94: 5-(3,5-DICHLOROPHENYL)-3-(2-METHOXYETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 94)

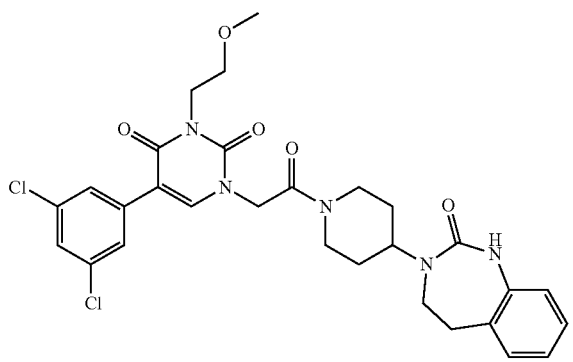 [SMILES: COCCn1c(=O)c(-c2cc(Cl)cc(Cl)c2)cn(CC(=O)N2CCC(N3CCc4ccccc4NC3=O)CC2)c1=O]

94.1: [5-(3,5-dichlorophenyl)-3-(2-methoxyethyl)-2,4-dioxo-3,4-dihydro-2H-pyrimidin-1-yl]-acetic acid Similarly to example 13.3, starting from 430 mg (1.3 mmol) of [5-bromo-3-(2-methoxyethyl)-2,4-dioxo-3,4-dihydro-2H-pyrimidin-1-yl]-methyl acetate (prepared as described in example 93.1) and 383 mg (2 mmol) of 3,5-dichlorophenylboronic acid, 580 mg (100%) of [5-(3,5-dichlorophenyl)-3-(2-methoxyethyl)-2,4-dioxo-3,4-dihydro-2H-pyrimidin-1-yl]-acetic acid is obtained in the form of a beige solid.

94.2: 5-(3,5-dichlorophenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 94)

Similarly to example 13.4, starting from 500 mg (1.3 mmol) of [5-(3,5-dichlorophenyl)-3-(2-methoxyethyl)-2,4-dioxo-3,4-dihydro-2H-pyrimidin-1-yl]-acetic acid and 394 mg (1.6 mmol) of 3-piperidin-4-yl-1,3,4,5-tetrahydro-benzo[d][1,3]diazepin-2-one (prepared as described in example 16.4), and after recrystallization from ethanol, 350 mg (43%) of 5-(3,5-dichlorophenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 148° C.

¹H NMR (δ, DMSO): 1.56-1.65 (m, 4H); 2.67-2.71 (m, 1H); 2.87-2.92 (m, 2H); 3.13-3.20 (m, 1H); 3.25 (s, 3H); 3.36-3.39 (m, 2H); 3.52 (t, J=6.0 Hz, 2H); 3.95 (d, J=12.9 Hz, 1H); 4.08 (t, J=6.1 Hz, 2H); 4.28-4.40 (m, 1H); 4.42 (d, J=12.9 Hz, 1H); 4.81 (s, 2H); 6.79-6.80 (m, 1H); 7.03-7.05 (m, 3H); 7.57 (s, 1H); 7.69 (d, J=1.9 Hz, 2H); 8.17 (s, 1H); 8.55 (s, 1H).

EXAMPLE 95: 5-(3-CHLORO-2-METHOXYPHENYL)-3-(2-METHOXYETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 95)

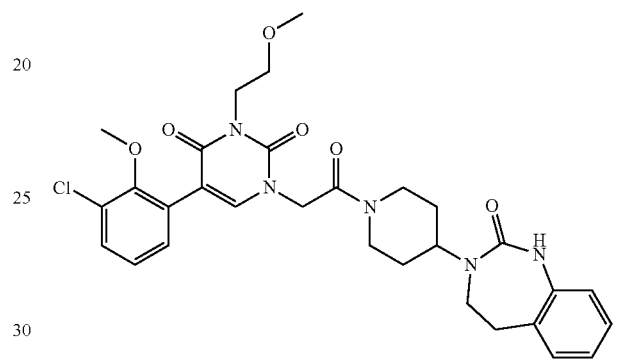

95.1: [5-(3-chloro-2-methoxyphenyl)-3-(2-methoxyethyl)-2,4-dioxo-3,4-dihydro-2H-pyrimidin-1-yl]-acetic acid Similarly to example 13.3, starting from 300 mg (0.9 mmol) of [5-bromo-3-(2-methoxyethyl)-2,4-dioxo-3,4-dihydro-2H-pyrimidin-1-yl]-methyl acetate (prepared as described in example 93.1) and 261 mg (1.4 mmol) of 3-chloro-2-methoxyphenylboronic acid, 340 mg (98%) of [5-(3-chloro-2-methoxyphenyl)-3-(2-methoxyethyl)-2,4-dioxo-3,4-dihydro-2H-pyrimidin-1-yl]-acetic acid is obtained in the form of a brown oil.

95.2: 5-(3-chloro-2-methoxyphenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 95)

Similarly to example 13.4, starting from 340 mg (0.9 mmol) of [5-(3-chloro-2-methoxyphenyl)-3-(2-methoxyethyl)-2,4-dioxo-3,4-dihydro-2H-pyrimidin-1-yl]-acetic acid and 271 mg (1.1 mmol) of 3-piperidin-4-yl-1,3,4,5-tetrahydro-benzo[d][1,3]diazepin-2-one (prepared as described in example 16.4), and after recrystallization from ethanol, 360 mg (63%) of 5-(3-chloro-2-methoxyphenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 206° C.

¹H NMR (δ, DMSO): 1.61-1.69 (m, 4H); 2.68 (t, J=12.6 Hz, 1H); 2.90 (m, 2H); 3.15 (t, J=12.6 Hz, 1H); 3.26 (s, 3H); 3.36-3.39 (m, 2H); 3.53 (t, J=6.1 Hz, 2H); 3.67 (s, 3H); 3.95 (d, J=13.6 Hz, 1H); 4.08 (t, J=6.1 Hz, 2H); 4.29-4.36 (m, 1H); 4.43 (d, J=12.9 Hz, 1H); 4.79 (s, 2H); 6.80-6.81 (m,

1H); 7.03-7.05 (m, 3H); 7.19 (t, J=7.8 Hz, 1H); 7.27 (dd, J=7.7, 1.7 Hz, 1H); 7.50 (dd, J=7.9, 1.7 Hz, 1H); 7.78 (s, 1H); 8.53 (s, 1H).

EXAMPLE 96: 5-(2-CHLORO-3-FLUOROPHENYL)-3-(2-METHOXYETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 96)

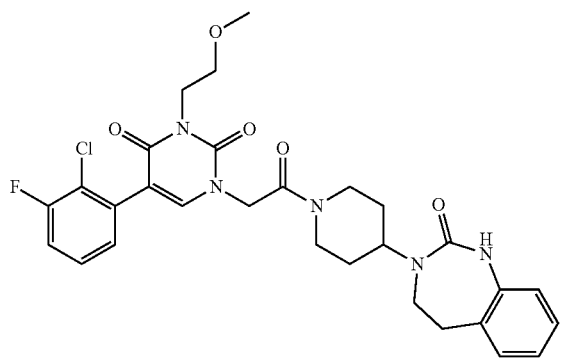 [SMILES: COCCn1c(=O)c(-c2cccc(F)c2Cl)cn(CC(=O)N2CCC(N3CCc4ccccc4NC3=O)CC2)c1=O]

96.1: [5-(2-chloro-3-fluorophenyl)-3-(2-methoxyethyl)-2,4-dioxo-3,4-dihydro-2H-pyrimidin-1-yl]-acetic acid Similarly to example 13.3, starting from 300 mg (0.9 mmol) of [5-bromo-3-(2-methoxyethyl)-2,4-dioxo-3,4-dihydro-2H-pyrimidin-1-yl]-methyl acetate (prepared as described in example 93.1) and 244 mg (1.4 mmol) of 2-chloro-3-fluorophenylboronic acid, 300 mg (90%) of [5-(2-chloro-3-fluorophenyl)-3-(2-methoxyethyl)-2,4-dioxo-3,4-dihydro-2H-pyrimidin-1-yl]-acetic acid is obtained in the form of a brown oil.

96.2: 5-(2-chloro-3-fluorophenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 96)

Similarly to example 13.4, starting from 300 mg (0.8 mmol) of [5-(2-chloro-3-fluorophenyl)-3-(2-methoxyethyl)-2,4-dioxo-3,4-dihydro-2H-pyrimidin-1-yl]-acetic acid and 248 mg (1 mmol) of 3-piperidin-4-yl-1,3,4,5-tetrahydro-benzo[d][1,3]diazepin-2-one (prepared as described in example 16.4), and after recrystallization from n-butanol/ethanol mixture, 140 mg (27%) of 5-(2-chloro-3-fluorophenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 232° C.

$^1$H NMR (δ, DMSO): 1.59-1.71 (m, 4H); 2.69 (t, J=12.6 Hz, 1H); 2.90 (m, 2H); 3.15 (t, J=12.3 Hz, 1H); 3.26 (s, 3H); 3.36-3.39 (m, 2H); 3.53 (t, J=6.0 Hz, 2H); 3.95 (d, J=13.6 Hz, 1H); 4.07 (t, J=6.1 Hz, 2H); 4.26-4.37 (m, 1H); 4.43 (d, J=13.0 Hz, 1H); 4.78 (d, J=2.7 Hz, 1H); 6.80-6.81 (m, 1H); 7.03-7.05 (m, 3H); 7.21-7.22 (m, 1H); 7.45-7.46 (m, 2H); 7.84 (s, 1H); 8.54 (s, 1H).

EXAMPLE 97: 5-(2-CHLORO-3-METHOXYPHENYL)-3-(2-METHOXYETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 97)

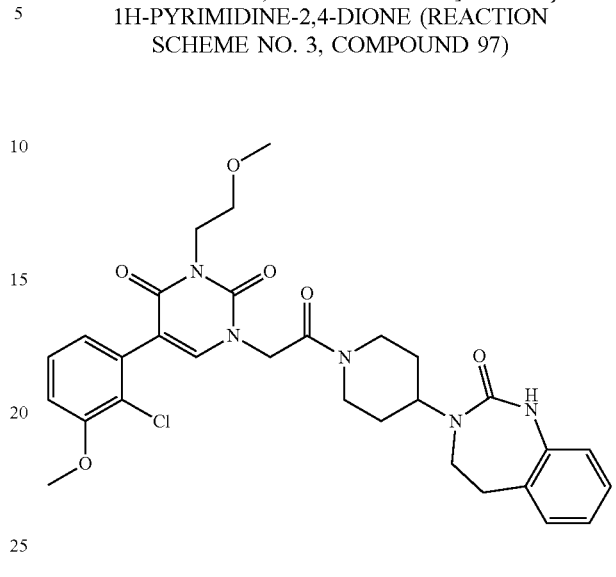

97.1: [5-(2-chloro-3-methoxyphenyl)-3-(2-methoxyethyl)-2,4-dioxo-3,4-dihydro-2H-pyrimidin-1-yl]-acetic acid Similarly to example 13.3, starting from 200 mg (0.6 mmol) of [5-bromo-3-(2-methoxyethyl)-2,4-dioxo-3,4-dihydro-2H-pyrimidin-1-yl]-methyl acetate (prepared as described in example 93.1) and 232 mg (1.3 mmol) of 2-chloro-3-methoxyphenylboronic acid, 158 mg (69%) of [5-(2-chloro-3-methoxyphenyl)-3-(2-methoxyethyl)-2,4-dioxo-3,4-dihydro-2H-pyrimidin-1-yl]-acetic acid is obtained in the form of a yellow oil.

97.2: 5-(2-chloro-3-methoxyphenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 97)

Similarly to example 13.4, starting from 150 mg (0.4 mmol) of [5-(2-chloro-3-methoxyphenyl)-3-(2-methoxyethyl)-2,4-dioxo-3,4-dihydro-2H-pyrimidin-1-yl]-acetic acid and 120 mg (0.5 mmol) of 3-piperidin-4-yl-1,3,4,5-tetrahydro-benzo[d][1,3]diazepin-2-one (prepared as described in example 16.4), 180 mg (72%) of 5-(2-chloro-3-methoxyphenyl)-3-(2-methoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid.

$^1$H NMR (δ, DMSO): 1.55 (m, 1H); 1.71 (m, 3H); 2.68-2.70 (m, 1H); 2.90 (m, 2H); 3.13-3.17 (m, 1H); 3.26 (s, 3H); 3.38 (m, 2H); 3.51 (t, J=6.1 Hz, 2H); 3.89 (s, 3H); 3.94 (d, J=14.0 Hz, 1H); 4.06 (t, J=6.1 Hz, 2H); 4.31-4.33 (m, 1H); 4.43 (d, J=12.8 Hz, 1H); 4.76-4.78 (m, 2H); 6.80-6.81 (m, 1H); 6.92 (dd, J=7.6, 1.4 Hz, 1H); 7.04-7.06 (m, 3H); 7.19 (dd, J=8.4, 1.4 Hz, 1H); 7.35 (t, J=8.0 Hz, 1H); 7.73 (s, 1H); 8.54 (s, 1H).

EXAMPLE 98: 5-(2,3-DIMETHYLPHENYL)-3-(2-HYDROXYETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 98)

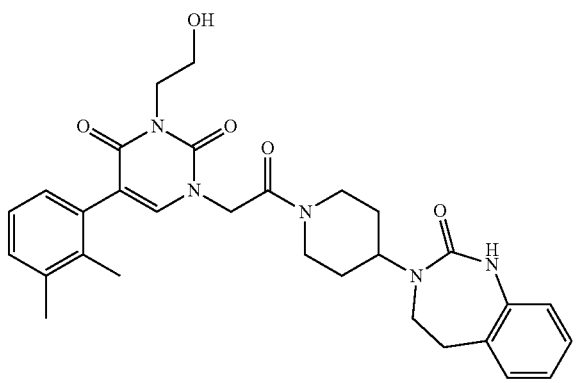 [SMILES: Cc1cccc(-c2cn(CC(=O)N3CCC(N4CCc5ccccc5NC4=O)CC3)c(=O)n(CCO)c2=O)c1C]

98.1: [3-(2-benzyloxy-ethyl)-5-bromo-2,4-dioxo-3,4-dihydro-2H-pyrimidin-1-yl]-methyl acetate Similarly to example 83.1, starting from 1 g (3.8 mmol) of (5-bromo-2,4-dioxo-3,4-dihydro-2H-pyrimidin-1-yl)-methyl acetate (prepared as described in example 13.1), and 0.7 ml (4.2 mmol) of benzyl-2-bromoethyl ether, 0.9 g (60%) of [3-(2-benzyloxy-ethyl)-5-bromo-2,4-dioxo-3,4-dihydro-2H-pyrimidin-1-yl]-methyl acetate is obtained in the form of a beige solid.

98.2: [3-(2-benzyloxy-ethyl)-5-(2,3-dimethylphenyl)-2,4-dioxo-3,4-dihydro-2H-pyrimidin-1-yl]-acetic acid Similarly to example 13.3, starting from 400 mg (1 mmol) of [3-(2-benzyloxy-ethyl)-5-bromo-2,4-dioxo-3,4-dihydro-2H-pyrimidin-1-yl]-methyl acetate and 242 mg (1.6 mmol) of 2,3-dimethylphenylboronic acid, 410 mg (100%) of [3-(2-benzyloxy-ethyl)-5-(2,3-dimethylphenyl)-2,4-dioxo-3,4-dihydro-2H-pyrimidin-1-yl]-acetic acid is obtained in the form of an orange-coloured oil.

98.3: 3-(2-benzyloxy-ethyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione Similarly to example 13.4, starting from 410 mg (1 mmol) of [3-(2-benzyloxy-ethyl)-5-(2,3-dimethylphenyl)-2,4-dioxo-3,4-dihydro-2H-pyrimidin-1-yl]-acetic acid and 296 mg (1.2 mmol) of 3-piperidin-4-yl-1,3,4,5-tetrahydro-benzo[d][1,3]diazepin-2-one (prepared as described in example 16.4), 320 mg (50%) of 3-(2-benzyloxy-ethyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a pale pink solid.

98.4: 5-(2,3-dimethylphenyl)-3-(2-hydroxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 98)

Similarly to example 1.5, starting from 320 mg (0.5 mmol) of 3-(2-benzyloxy-ethyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione and 256 mg (0.1 mmol) of 10% palladium on charcoal, placing the reaction mixture under 3 bar of dihydrogen for 24 hours, 180 mg (66%) of 5-(2,3-dimethylphenyl)-3-(2-hydroxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 237° C.

$^1$H NMR (δ, DMSO): 1.58-1.70 (m, 4H); 2.05 (s, 3H); 2.28 (s, 3H); 2.68 (t, J=12.5 Hz, 1H); 2.89 (m, 2H); 3.15 (t, J=12.3 Hz, 1H); 3.36-3.39 (m, 2H); 3.53 (q, J=6.4 Hz, 2H); 3.94-3.97 (m, 3H); 4.33-4.34 (m, 1H); 4.43 (d, J=12.9 Hz, 1H); 4.70-4.85 (m, 3H); 6.80-6.81 (m, 1H); 6.97 (d, J=7.5 Hz, 1H); 7.04-7.06 (m, 3H); 7.11 (t, J=7.5 Hz, 1H); 7.18 (d, J=7.5 Hz, 1H); 7.59 (s, 1H); 8.53 (s, 1H).

EXAMPLE 99: 3-(2-DIMETHYLAMINOETHYL)-5-(2,3-DIMETHYLPHENYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 99)

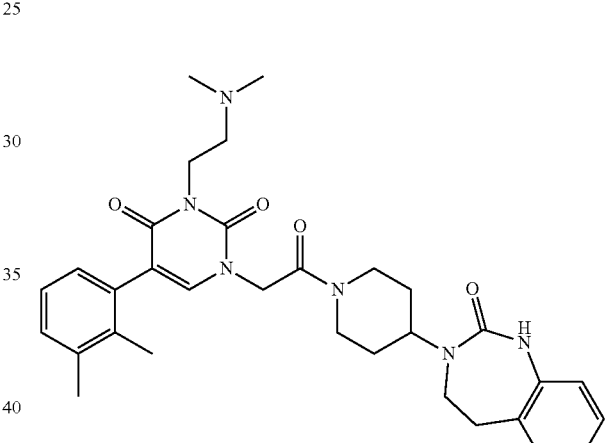

99.1: [5-bromo-3-(2-dimethylaminoethyl)-2,4-dioxo-3,4-dihydro-2H-pyrimidin-1-yl]-methyl acetate Similarly to example 83.1, starting from 1 g (3.8 mmol) of (5-bromo-2,4-dioxo-3,4-dihydro-2H-pyrimidin-1-yl)-methyl acetate (prepared as described in example 13.1), 0.7 g (4.6 mmol) of 2-dimethylaminoethyl chloride hydrochloride and 0.6 ml (4.6 mmol) of triethylamine, 0.7 g (55%) of [5-bromo-3-(2-dimethylaminoethyl)-2,4-dioxo-3,4-dihydro-2H-pyrimidin-1-yl]-methyl acetate is obtained in the form of a white solid.

99.2: 3-(2-dimethylaminoethyl)-5-(2,3-dimethylphenyl)-2,4-dioxo-3,4-dihydro-2H-pyrimidin-1-yl]-acetic acid Similarly to example 13.3, starting from 400 mg (1.2 mmol) of [5-bromo-3-(2-dimethylaminoethyl)-2,4-dioxo-3,4-dihydro-2H-pyrimidin-1-yl]-methyl acetate and 269 mg (1.8 mmol) of 2,3-dimethylphenylboronic acid, 60 mg (15%) of 3-(2-dimethylaminoethyl)-5-(2,3-dimethylphenyl)-2,4-dioxo-3,4-dihydro-2H-pyrimidin-1-yl]-acetic acid is obtained in the form of a white solid.

99.3: 3-(2-dimethylaminoethyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 99)

Similarly to example 13.4, starting from 60 mg (0.2 mmol) of 3-(2-dimethylaminoethyl)-5-(2,3-dimethylphenyl)-2,4-dioxo-3,4-dihydro-2H-pyrimidin-1-yl]-acetic acid and 51 mg (0.2 mmol) of 3-piperidin-4-yl-1,3,4,5-tetrahydro-benzo[d][1,3]diazepin-2-one (prepared as described in example 16.4), 50 mg (50%) of 3-(2-dimethylaminoethyl)-5-(2,3-dimethylphenyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 170° C.

$^1$H NMR (δ, DMSO): 1.55-1.68 (m, 4H); 2.05 (s, 3H); 2.23 (s, 6H); 2.28 (s, 3H); 2.49-2.51 (m, 2H); 2.68 (m, 1H); 2.89 (m, 2H); 3.15 (t, J=9.7 Hz, 1H); 3.38 (m, 2H); 3.96-4.00 (m, 3H); 4.33 (m, 1H); 4.43 (d, J=12.9 Hz, 1H); 4.76 (d, J=4.2 Hz, 2H); 6.81 (m, 1H); 6.97 (d, J=7.5 Hz, 1H); 7.04-7.06 (m, 3H); 7.11 (t, J=7.5 Hz, 1H); 7.18 (d, J=7.5 Hz, 1H); 7.60 (s, 1H); 8.53 (s, 1H).

EXAMPLE 100: 5-(2,3-DIMETHYLPHENYL)-3-(2-METHOXYMETHOXYETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 100)

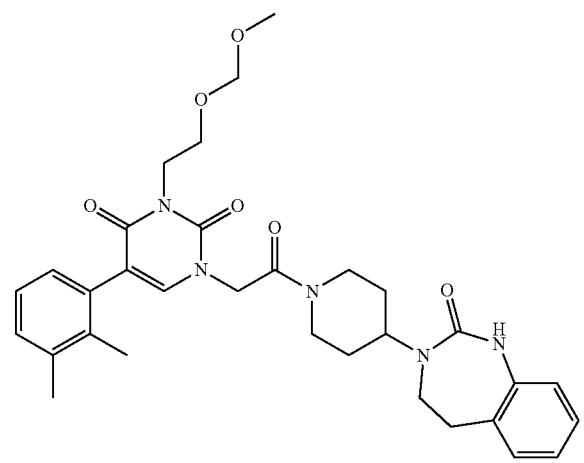 [SMILES: COCOCCn1c(=O)c(-c2cccc(C)c2C)cn(CC(=O)N2CCC(N3CCc4ccccc4NC3=O)CC2)c1=O]

100.1: [5-bromo-3-(2-methoxymethoxyethyl)-2,4-dioxo-3,4-dihydro-2H-pyrimidin-1-yl]-methyl acetate Similarly to example 83.1, starting from 1 g (3.8 mmol) of (5-bromo-2,4-dioxo-3,4-dihydro-2H-pyrimidin-1-yl)-methyl acetate (prepared as described in example 13.1), and 0.5 ml (4.6 mmol) of 1-bromo-2-methoxymethoxyethane, 0.6 g (43%) of [5-bromo-3-(2-methoxymethoxyethyl)-2,4-dioxo-3,4-dihydro-2H-pyrimidin-1-yl]-methyl acetate is obtained in the form of a white solid.

100.2: [5-(2,3-dimethylphenyl)-3-(2-methoxymethoxyethyl)-2,4-dioxo-3,4-dihydro-2H-pyrimidin-1-yl]-acetic acid Similarly to example 13.3, starting from 300 mg (0.9 mmol) of [5-bromo-3-(2-methoxymethoxyethyl)-2,4-dioxo-3,4-dihydro-2H-pyrimidin-1-yl]-methyl acetate and 205 mg (1.4 mmol) of 2,3-dimethylphenylboronic acid, 250 mg (81%) of [5-(2,3-dimethylphenyl)-3-(2-methoxymethoxyethyl)-2,4-dioxo-3,4-dihydro-2H-pyrimidin-1-yl]-acetic acid is obtained in the form of a brown oil.

100.3: 5-(2,3-dimethylphenyl)-3-(2-methoxymethoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 100)

Similarly to example 13.4, starting from 250 mg (0.7 mmol) of [5-(2,3-dimethylphenyl)-3-(2-methoxymethoxyethyl)-2,4-dioxo-3,4-dihydro-2H-pyrimidin-1-yl]-acetic acid and 203 mg (0.8 mmol) of 3-piperidin-4-yl-1,3,4,5-tetrahydro-benzo[d][1,3]diazepin-2-one (prepared as described in example 16.4), and after recrystallization from a heptane/acetone 50/50 mixture; 200 mg (49%) of 5-(2,3-dimethylphenyl)-3-(2-methoxymethoxyethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 160° C.

$^1$H NMR (δ, DMSO): 1.50-1.80 (m, 4H); 2.05 (s, 3H); 2.28 (s, 3H); 2.68 (m, 1H); 2.89 (m, 2H); 3.16 (m, 1H); 3.23 (s, 3H); 3.38 (m, 2H); 3.65 (t, J=6.1 Hz, 2H); 4.95 (d, J=12.9 Hz, 1H); 4.10 (t, J=6.2 Hz, 2H); 4.33 (m, 1H); 4.43 (d, J=12.9 Hz, 1H); 4.54 (s, 2H); 4.76 (d, J=3.8 Hz, 2H); 6.80-6.81 (m, 1H); 6.96 (d, J=7.5 Hz, 1H); 7.03-7.05 (m, 3H); 7.11 (t, J=7.5 Hz, 1H); 7.18 (d, J=7.5 Hz, 1H); 7.61 (s, 1H); 8.53 (s, 1H).

EXAMPLE 101: N-[2-(5-(2,3-DIMETHYLPHENYL)-2,6-DIOXO-3-{2-OXO-2-[4-(2-OXO-1,2,4,5-TETRAHYDRO-BENZO[D][1,3]DIAZEPIN-3-YL)-PIPERIDIN-1-YL]-ETHYL}-3,6-DIHYDRO-2H-PYRIMIDIN-1-YL)-ETHYL]ACETAMIDE (REACTION SCHEME NO. 3, COMPOUND 101)

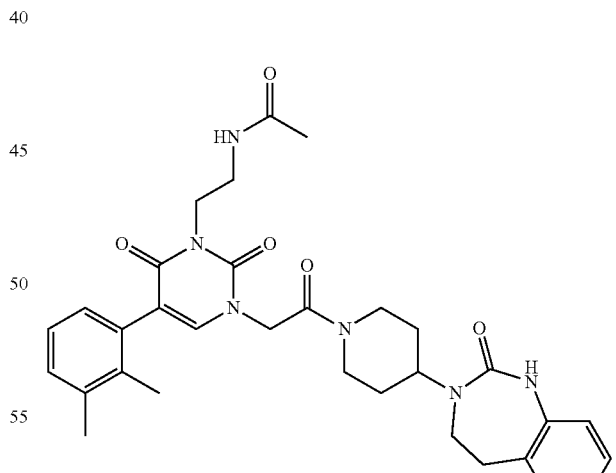

101.1: [3-(2-acetylaminoethyl)-5-bromo-2,4-dioxo-3,4-dihydro-2H-pyrimidin-1-yl]-methyl acetate Similarly to example 83.1, starting from 1 g (3.8 mmol) of (5-bromo-2,4-dioxo-3,4-dihydro-2H-pyrimidin-1-yl)-methyl acetate (prepared as described in example 13.1), and 0.4 ml (3.8 mmol) of N-(2-chloro-ethyl)-acetamide, 170 mg (13%) of [3-(2-acetylaminoethyl)-5-bromo-2,4-dioxo-3,4-dihydro-2H-pyrimidin-1-yl]-methyl acetate is obtained in the form of a pale yellow solid.

101.2: [3-(2-acetylaminoethyl)-5-(2,3-dimethylphenyl)-2,4-dioxo-3,4-dihydro-2H-pyrimidin-1-yl]-acetic acid Similarly to example 44.1, starting from 170 mg (0.5 mmol) of [3-(2-acetylaminoethyl)-5-bromo-2,4-dioxo-3,4-dihydro-2H-pyrimidin-1-yl]-methyl acetate and 117 mg (0.8 mmol) of 2,3-dimethylphenylboronic acid, 35 mg (20%) of [3-(2-acetylaminoethyl)-5-(2,3-dimethylphenyl)-2,4-dioxo-3,4-dihydro-2H-pyrimidin-1-yl]-acetic acid is obtained in the form of a pink solid.

101.3: N-[2-(5-(2,3-dimethylphenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]acetamide (compound 101)

Similarly to example 13.4, starting from 35 mg (0.1 mmol) of [3-(2-acetylaminoethyl)-5-(2,3-dimethylphenyl)-2,4-dioxo-3,4-dihydro-2H-pyrimidin-1-yl]-acetic acid and 29 mg (0.1 mmol) of 3-piperidin-4-yl-1,3,4,5-tetrahydro-benzo[d][1,3]diazepin-2-one (prepared as described in example 16.4), and after crystallization in ethyl acetate, 8 mg (14%) of N-[2-(5-(2,3-dimethylphenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]acetamide is obtained in the form of a white solid with a melting point of 267° C.

$^1$H NMR (δ, DMSO): 1.56-1.68 (m, 4H), 1.76 (s, 3H), 2.07 (s, 3H), 2.28 (s, 3H), 2.68-2.72 (m, 1H), 2.90 (m, 2H), 3.14 (t, 1H), 3.25-3.28 (m, 2H), 3.36-3.38 (m, 2H), 3.95 (m, 3H), 4.32 (m, 1H), 4.44 (m, 1H), 4.76 (s, 2H), 6.81 (m, 1H), 6.96 (d, J=7.5 Hz, 1H), 7.05 (m, 3H), 7.11 (t, J=7.5 Hz, 1H), 7.18 (d, J=7.5 Hz, 1H), 7.58 (s, 1H), 7.92 (t, J=5.9 Hz, 1H), 8.52 (s, 1H).

EXAMPLE 102: 5-(2,3-DIMETHYLPHENYL)-3-(2-METHYLAMINOETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 102)

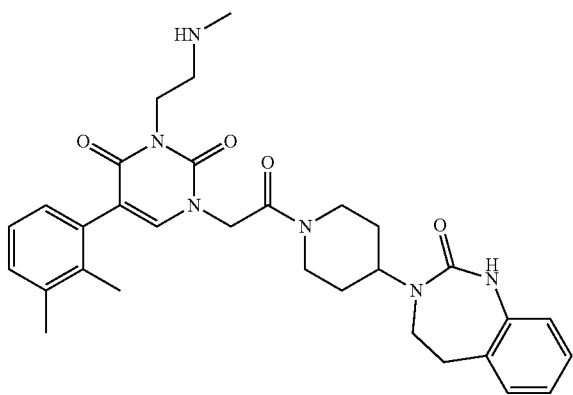 [SMILES: CNCCn1c(=O)c(-c2cccc(C)c2C)cn(CC(=O)N2CCC(N3CCc4ccccc4NC3=O)CC2)c1=O]

102.1: [3-(2-tert-butoxycarbonylaminoethyl)-5-(2,3-dimethylphenyl)-2,4-dioxo-3,4-dihydro-2H-pyrimidin-1-yl]-acetic acid Similarly to example 44.1, starting from 500 mg (1.2 mmol) of [5-bromo-3-(2-tert-butoxycarbonylaminoethyl)-2,4-dioxo-3,4-dihydro-2H-pyrimidin-1-yl]-methyl acetate (prepared as described in example 87.1), and 295 mg (2 mmol) of 2,3-dimethylphenylboronic acid, 460 mg (90%) of [3-(2-tert-butoxycarbonylaminoethyl)-5-(2,3-dimethylphenyl)-2,4-dioxo-3,4-dihydro-2H-pyrimidin-1-yl]-acetic acid is obtained in the form of a beige solid.

102.2: [3-[2-(tert-butoxycarbonyl-methylamino)-ethyl]-5-(2,3-dimethylphenyl)-2,4-dioxo-3,4-dihydro-2H-pyrimidin-1-yl]-acetic acid Similarly to example 90.2, starting from 100 mg (0.2 mmol) of [3-(2-tert-butoxycarbonylaminoethyl)-5-(2,3-dimethylphenyl)-2,4-dioxo-3,4-dihydro-2H-pyrimidin-1-yl]-acetic acid and 93 µl (1.5 mmol) of iodomethane, and after stirring for 4 hours in 5 ml of tetrahydrofuran, 85 mg (82%) of [3-[2-(tert-butoxycarbonyl-methylamino)-ethyl]-5-(2,3-dimethylphenyl)-2,4-dioxo-3,4-dihydro-2H-pyrimidin-1-yl]-acetic acid is obtained in the form of a colourless oil.

102.3: [2-(5-(2,3-dimethylphenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-methyl-tert-butyl carbamate Similarly to example 13.4, starting from 85 mg (0.2 mmol) of [3-[2-(tert-butoxycarbonyl-methylamino)-ethyl]-5-(2,3-dimethylphenyl)-2,4-dioxo-3,4-dihydro-2H-pyrimidin-1-yl]-acetic acid and 58 mg (0.2 mmol) of 3-piperidin-4-yl-1,3,4,5-tetrahydro-benzo[d][1,3]diazepin-2-one (prepared as described in example 16.4), 110 mg (85%) of [2-(5-(2,3-dimethylphenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-methyl-tert-butyl carbamate is obtained in the form of a white solid.

102.4: 5-(2,3-dimethylphenyl)-3-(2-methylaminoethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 102)

Similarly to example 88, starting from 110 mg (0.2 mmol) of [2-(5-(2,3-dimethylphenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]-methyl-tert-butyl carbamate, and after recrystallization from an acetone/heptane 50/50 mixture, 50 mg (48%) of 5-(2,3-dimethylphenyl)-3-(2-methylaminoethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a beige solid with a melting point of 203° C.

$^1$H NMR (δ, DMSO): 1.53-1.67 (m, 4H); 2.04 (s, 3H); 2.26-2.27 (m, 6H); 2.63-2.66 (m, 3H); 2.88 (m, 2H); 3.14 (t, J=12.4 Hz, 1H); 3.36 (m, 2H); 3.92-3.96 (m, 3H); 4.32 (m, 1H); 4.42 (d, J=12.9 Hz, 1H); 4.74 (d, J=6.4 Hz, 2H); 6.80 (m, 1H); 6.96 (d, J=7.7 Hz, 1H); 7.03-7.05 (m, 3H); 7.10 (t, J=7.5 Hz, 1H); 7.17 (d, J=7.6 Hz, 1H); 7.58 (s, 1H); 8.54 (s, 1H).

EXAMPLE 103: (5-(2-CHLORO-3-FLUOROPHENYL)-2,6-DIOXO-3-{2-OXO-2-[4-(2-OXO-1,2,4,5-TETRAHYDRO-BENZO[D][1,3]DIAZEPIN-3-YL)-PIPERIDIN-1-YL]-ETHYL}-3,6-DIHYDRO-2H-PYRIMIDIN-1-YL)-METHYL ACETATE (REACTION SCHEME NO. 3, COMPOUND 103)

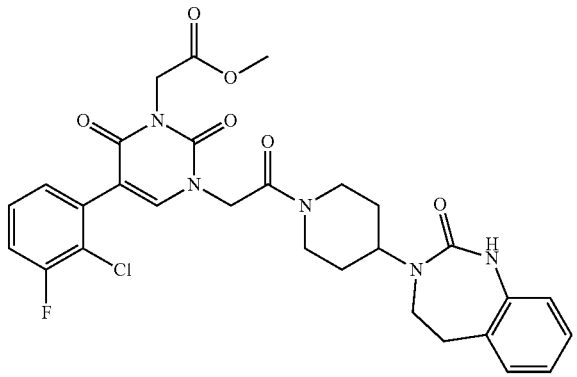 [SMILES: COC(=O)Cn1c(=O)c(-c2cccc(F)c2Cl)cn(CC(=O)N2CCC(N3CCc4ccccc4NC3=O)CC2)c1=O]

103.1: (3-benzhydryl-5-bromo-2,6-dioxo-3,6-dihydro-2H-pyrimidin-1-yl)-methyl acetate Similarly to example 2.2, starting from 1 g (2.8 mmol) of 1-benzhydryl-5-bromo-1H-pyrimidine-2,4-dione (prepared as described in example 2.1) and 346 µl (3.6 mmol) of methyl bromoacetate, 960 mg (80%) of (3-benzhydryl-5-bromo-2,6-dioxo-3,6-dihydro-2H-pyrimidin-1-yl)-methyl acetate is obtained in the form of a white paste.

103.2: [3-benzhydryl-5-(2-chloro-3-fluorophenyl)-2,6-dioxo-3,6-dihydro-2H-pyrimidin-1-yl]-methyl acetate Similarly to example 44.1, starting from 500 mg (1.2 mmol) of (3-benzhydryl-5-bromo-2,6-dioxo-3,6-dihydro-2H-pyrimidin-1-yl)-methyl acetate and 305 mg (1.8 mmol) of 2-chloro-3-fluorophenylboronic acid, and after purification by silica gel chromatography eluted with a heptane/ethyl acetate 80/20 mixture, 208 mg (37%) of [3-benzhydryl-5-(2-chloro-3-fluorophenyl)-2,6-dioxo-3,6-dihydro-2H-pyrimidin-1-yl]-methyl acetate is obtained in the form of a beige solid.

103.3: [5-(2-chloro-3-fluorophenyl)-2,6-dioxo-3,6-dihydro-2H-pyrimidin-1-yl]-methyl acetate Similarly to example 2.3, starting from 200 mg (0.4 mmol) of [3-benzhydryl-5-(2-chloro-3-fluorophenyl)-2,6-dioxo-3,6-dihydro-2H-pyrimidin-1-yl]-methyl acetate and after stirring for 10 days at room temperature, 75 mg (57%) of [5-(2-chloro-3-fluorophenyl)-2,6-dioxo-3,6-dihydro-2H-pyrimidin-1-yl]-methyl acetate is obtained in the form of a brown oil.

103.4: (5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-methyl acetate (Compound 103)

Similarly to example 39.4, starting from 74 mg (0.2 mmol) of 3-[1-(2-chloroacetyl)-piperidin-4-yl]-1,3,4,5-tetrahydro-benzo[d][1,3]diazepin-2-one (prepared as described in example 39.1) and 65 mg (0.2 mmol) of [5-(2-chloro-3-fluorophenyl)-2,6-dioxo-3,6-dihydro-2H-pyrimidin-1-yl]-methyl acetate, 72 mg (57%) of (5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-methyl acetate is obtained in the form of a white solid.

$^1$H NMR (δ, DMSO): 1.51-1.59 (m, 1H); 1.65-1.75 (m, J=22.0 Hz, 3H); 2.69 (t, J=12.6 Hz, 1H); 2.88-2.90 (m, 2H); 3.15 (t, J=12.0 Hz, 1H); 3.36-3.38 (m, 2H); 3.69 (s, 3H); 3.95 (d, J=13.5 Hz, 1H); 4.30-4.33 (m, 1H); 4.43 (d, J=12.9 Hz, 1H); 4.66 (s, 2H); 4.82 (s, 2H); 6.81 (dt, J=7.7, 4.2 Hz, 1H); 7.06-7.04 (m, 3H); 7.24 (dd, J=6.5, 2.7 Hz, 1H); 7.48-7.46 (m, 2H); 7.93 (s, 1H); 8.53 (s, 1H).

EXAMPLE 104: (5-(2-CHLORO-3-FLUOROPHENYL)-2,6-DIOXO-3-{2-OXO-2-[4-(2-OXO-1,2,4,5-TETRAHYDRO-BENZO[D][1,3]DIAZEPIN-3-YL)-PIPERIDIN-1-YL]-ETHYL}-3,6-DIHYDRO-2H-PYRIMIDIN-1-YL)-ACETIC ACID (REACTION SCHEME NO. 3, COMPOUND 104)

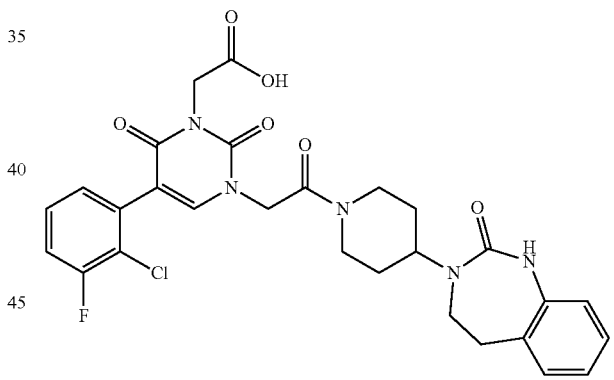

Similarly to example 16.8, starting from 50 mg (80 µmol) of (5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-methyl acetate, and after purification by silica gel chromatography eluted with a dichloromethane/methanol 98/2 mixture, 10 mg (20%) of (5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-acetic acid is obtained in the form of a white solid.

$^1$H NMR (δ, DMSO): 1.51-1.59 (m, 1H); 1.65-1.75 (m, J=22.0 Hz, 3H); 2.69 (t, J=12.6 Hz, 1H); 2.88-2.90 (m, 2H); 3.15 (t, J=12.0 Hz, 1H); 3.36-3.38 (m, 2H); 3.95 (d, J=13.5 Hz, 1H); 4.30-4.33 (m, 1H); 4.43 (d, J=12.9 Hz, 1H); 4.66 (s, 2H); 4.82 (s, 2H); 6.81 (dt, J=7.7, 4.2 Hz, 1H); 7.06-7.04 (m, 3H); 7.24 (dd, J=6.5, 2.7 Hz, 1H); 7.48-7.46 (m, 2H); 7.93 (s, 1H); 8.53 (s, 1H).

EXAMPLE 105: 5-(2-CHLORO-3-FLUOROPHE-NYL)-3-OXETAN-3-YLMETHYL-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 105)

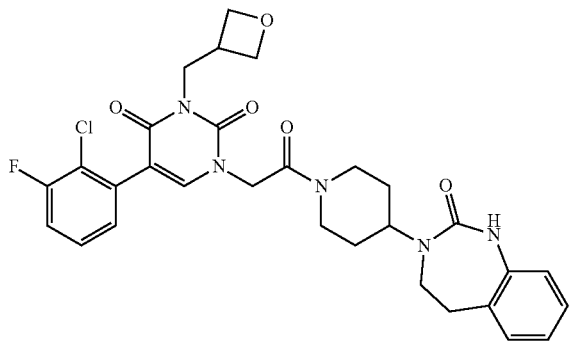 [SMILES: O=C(Cn1cc(-c2cccc(F)c2Cl)c(=O)n(CC2COC2)c1=O)N1CCC(N2CCc3ccccc3NC2=O)CC1]

105.1: (5-bromo-3-oxetan-3-ylmethyl-2,4-dioxo-3,4-dihydro-2H-pyrimidin-1-yl)-methyl acetate Similarly to example 13.2, starting from 500 mg (1.9 mmol) of (5-bromo-2,4-dioxo-3,4-dihydro-2H-pyrimidin-1-yl)-methyl acetate (prepared as described in example 13.1), and 0.15 ml (2.9 mmol) of 3-bromomethyl-oxetane, 310 mg (49%) of (5-bromo-3-oxetan-3-ylmethyl-2,4-dioxo-3,4-dihydro-2H-pyrimidin-1-yl)-methyl acetate is obtained in the form of a white solid.

105.2: [5-(2-chloro-3-fluorophenyl)-3-oxetan-3-ylmethyl-2,4-dioxo-3,4-dihydro-2H-pyrimidin-1-yl]-acetic acid Similarly to example 44.1, starting from 310 mg (0.9 mmol) of (5-bromo-3-oxetan-3-ylmethyl-2,4-dioxo-3,4-dihydro-2H-pyrimidin-1-yl)-methyl acetate and 243 mg (1.4 mmol) of 2-chloro-3-fluorophenylboronic acid, 80 mg (23%) of [5-(2-chloro-3-fluorophenyl)-3-oxetan-3-ylmethyl-2,4-dioxo-3,4-dihydro-2H-pyrimidin-1-yl]-acetic acid is obtained in the form of a brown oil.

105.3: 5-(2-chloro-3-fluorophenyl)-3-oxetan-3-ylmethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (compound 105)

Similarly to example 13.4, starting from 80 mg (0.2 mmol) of [5-(2-chloro-3-fluorophenyl)-3-oxetan-3-ylmethyl-2,4-dioxo-3,4-dihydro-2H-pyrimidin-1-yl]-acetic acid and 59 mg (0.2 mmol) of 3-piperidin-4-yl-1,3,4,5-tetrahydro-benzo[d][1,3]diazepin-2-one (prepared as described in example 16.4), 30 mg (22%) of 5-(2-chloro-3-fluorophenyl)-3-oxetan-3-ylmethyl-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 244° C.

$^1$H NMR (δ, DMSO): 1.53-1.56 (m, 1H); 1.66-1.72 (m, 3H); 2.69 (t, J=12.3 Hz, 1H); 2.90 (m, 2H); 3.15 (t, J=12.2 Hz, 1H); 3.25-3.30 (m, 1H); 3.37-3.39 (m, 2H); 3.92-3.95 (m, 1H); 4.19 (d, J=6.7 Hz, 2H); 4.33 (m, 1H); 4.40-4.43 (m, 3H); 4.60 (dd, J=7.9, 6.0 Hz, 2H); 4.78 (s, 2H); 6.79-6.83 (m, 1H); 7.02-7.05 (m, 3H); 7.21-7.23 (m, 1H); 7.44-7.48 (m, 2H); 7.85 (s, 1H); 8.53 (s, 1H).

EXAMPLE 106: 5-(2-CHLORO-3-FLUOROPHE-NYL)-3-((S)-2-METHOXY-1-METHYLETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 106)

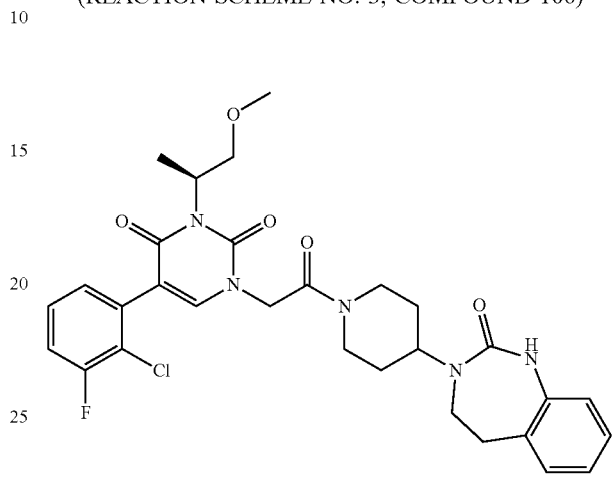

106.1: [5-bromo-3-((S)-2-methoxy-1-methylethyl)-2,4-dioxo-3,4-dihydro-2H-pyrimidin-1-yl]-methyl acetate Similarly to example 2.5, starting from 1 g (3.8 mmol) of (5-bromo-2,4-dioxo-3,4-dihydro-2H-pyrimidin-1-yl)-methyl acetate (prepared as described in example 13.1), 0.8 ml (7.8 mmol) of (R)-1-methoxy-propan-2-ol and 1.2 ml (7.6 mmol) of diethyl azodicarboxylate added at 0° C., and after purification by silica gel chromatography eluted with a heptane/ethyl acetate 60/40 mixture, 1.2 g (78%) of [5-bromo-3-((S)-2-methoxy-1-methylethyl)-2,4-dioxo-3,4-dihydro-2H-pyrimidin-1-yl]-methyl acetate is obtained in the form of a colourless oil.

106.2: [5-(2-chloro-3-fluorophenyl)-3-((S)-2-methoxy-1-methylethyl)-2,4-dioxo-3,4-dihydro-2H-pyrimidin-1-yl]-methyl acetate Similarly to example 44.1, starting from 300 mg (0.9 mmol) of [5-bromo-3-((S)-2-methoxy-1-methylethyl)-2,4-dioxo-3,4-dihydro-2H-pyrimidin-1-yl]-methyl acetate, 234 mg (1.3 mmol) of 2-chloro-3-fluorophenylboronic acid, and 1.3 ml (2.7 mmol) of a 2M aqueous solution of potassium carbonate, in 8 ml of toluene, 130 mg (38%) of [5-(2-chloro-3-fluorophenyl)-3-((S)-2-methoxy-1-methylethyl)-2,4-dioxo-3,4-dihydro-2H-pyrimidin-1-yl]-methyl acetate is obtained in the form of a colourless oil.

106.3: [5-(2-chloro-3-fluorophenyl)-3-((S)-2-methoxy-1-methylethyl)-2,4-dioxo-3,4-dihydro-2H-pyrimidin-1-yl]-acetic acid Similarly to example 16.8, starting from 130 mg (0.3 mmol) [5-(2-chloro-3-fluorophenyl)-3-((S)-2-methoxy-1-methylethyl)-2,4-dioxo-3,4-dihydro-2H-pyrimidin-1-yl]-methyl acetate, 125 mg (100%) of [5-(2-chloro-3-fluorophenyl)-3-((S)-2-methoxy-1-methylethyl)-2,4-dioxo-3,4-dihydro-2H-pyrimidin-1-yl]-acetic acid is obtained in the form of a colourless oil.

106.4: 5-(2-chloro-3-fluorophenyl)-3-((S)-2-methoxy-1-methylethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 106)

Similarly to example 13.4, starting from 125 mg (0.3 mmol) of [5-(2-chloro-3-fluorophenyl)-3-((S)-2-methoxy-1-methylethyl)-2,4-dioxo-3,4-dihydro-2H-pyrimidin-1-yl]-acetic acid and 99 mg (0.4 mmol) of 3-piperidin-4-yl-1,3,4,5-tetrahydro-benzo[d][1,3]diazepin-2-one (prepared as described in example 16.4), and after crystallization in ethyl acetate, 150 mg (73%) of 5-(2-chloro-3-fluorophenyl)-3-((S)-2-methoxy-1-methylethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 228° C.

$^1$H NMR (δ, DMSO): 1.34 (d, J=7.0 Hz, 3H); 1.50-1.80 (m, 4H); 2.68 (t, J=12.5 Hz, 1H); 2.90 (m, 2H); 3.15 (m, 1H); 3.33 (s, 3H); 3.38 (m, 2H); 3.54 (dd, J=9.9, 5.9 Hz, 1H); 3.90-3.95 (m, 2H); 4.33 (m, 1H); 4.43 (d, J=12.9 Hz, 1H); 4.75 (m, 2H); 5.15 (m, 1H); 6.80-6.81 (m, 1H); 7.04-7.06 (m, 3H); 7.20-7.21 (m, 1H); 7.44-7.45 (m, 2H); 7.80 (s, 1H); 8.53 (s, 1H).

EXAMPLE 107: (5-BROMO-2,6-DIOXO-3-{2-OXO-2-[4-(2-OXO-1,2,4,5-TETRAHYDRO-BENZO[D][1,3]DIAZEPIN-3-YL)-PIPERIDIN-1-YL]-ETHYL}-3,6-DIHYDRO-2H-PYRIMIDIN-1-YL)-METHYL ACETATE (REACTION SCHEME NO. 3, COMPOUND 107)

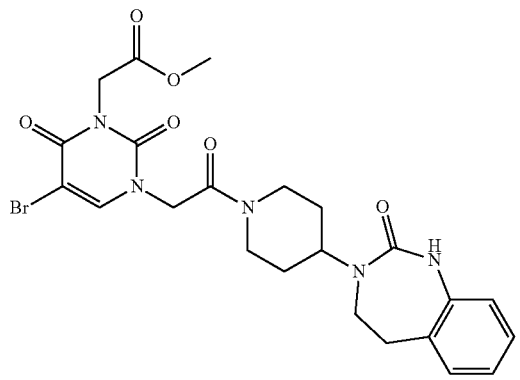 [SMILES: COC(=O)Cn1c(=O)c(Br)cn(CC(=O)N2CCC(N3CCc4ccccc4NC3=O)CC2)c1=O]

107.1: (5-bromo-2,6-dioxo-3,6-dihydro-2H-pyrimidin-1-yl)-methyl acetate

Similarly to example 2.3, starting from 400 mg (0.9 mmol) of (3-benzhydryl-5-bromo-2,6-dioxo-3,6-dihydro-2H-pyrimidin-1-yl)-methyl acetate (prepared as described in example 103.1), 172 mg (70%) of (5-bromo-2,6-dioxo-3,6-dihydro-2H-pyrimidin-1-yl)-methyl acetate is obtained in the form of a white solid.

107.2: (5-bromo-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-methyl acetate (Compound 107)

Similarly to example 83.1, starting from 160 mg (0.6 mmol) of (5-bromo-2,6-dioxo-3,6-dihydro-2H-pyrimidin-1-yl)-methyl acetate and 215 mg (0.7 mmol) of 3-[1-(2-chloroacetyl)-piperidin-4-yl]-1,3,4,5-tetrahydro-benzo[d][1,3]diazepin-2-one (prepared as described in example 39.1), 300 mg (89%) of (5-bromo-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-methyl acetate is obtained in the form of a white solid.

$^1$H NMR (δ, DMSO): 1.54 (m, 1H); 1.71 (m, 3H); 2.69 (m, 1H); 2.91 (s, 2H); 3.15 (m, 1H); 3.39 (s, 2H); 3.69 (s, 3H); 3.90 (m, 1H); 4.33 (m, 1H); 4.42 (m, 1H); 4.64 (s, 2H); 4.78 (s, 2H); 6.82 (s, 1H); 7.06-7.04 (m, 3H); 8.29 (s, 1H); 8.53 (s, 1H).

EXAMPLE 108: 5-(2-CHLORO-3-METHOXYPHENYL)-3-((S)-2-METHOXY-1-METHYLETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 108)

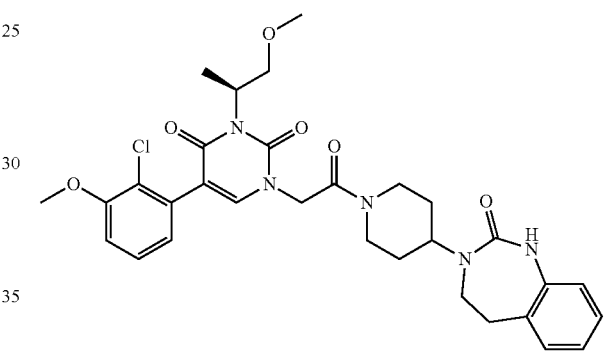

108.1: [5-(2-chloro-3-methoxyphenyl)-3-((S)-2-methoxy-1-methylethyl)-2,4-dioxo-3,4-dihydro-2H-pyrimidin-1-yl]-acetic acid Similarly to example 13.3, starting from 800 mg (2.4 mmol) of [5-bromo-3-((S)-2-methoxy-1-methylethyl)-2,4-dioxo-3,4-dihydro-2H-pyrimidin-1-yl]-methyl acetate (prepared as described in example 106.1) and 534 mg (2.9 mmol) of 2-chloro-3-methoxyphenylboronic acid, 912 mg (100%) of [5-(2-chloro-3-methoxyphenyl)-3-((S)-2-methoxy-1-methylethyl)-2,4-dioxo-3,4-dihydro-2H-pyrimidin-1-yl]-acetic acid is obtained in the form of a brown oil.

108.2: 5-(2-chloro-3-methoxyphenyl)-3-((S)-2-methoxy-1-methylethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 108)

Similarly to example 13.4, starting from 450 mg (1.2 mmol) of [5-(2-chloro-3-methoxyphenyl)-3-((S)-2-methoxy-1-methylethyl)-2,4-dioxo-3,4-dihydro-2H-pyrimidin-1-yl]-acetic acid and 346 mg (1.4 mmol) of 3-piperidin-4-yl-1,3,4,5-tetrahydro-benzo[d][1,3]diazepin-2-one (prepared as described in example 16.4), and after crystallization in ethyl acetate, 250 mg (35%) of 5-(2-chloro-3-methoxyphenyl)-3-((S)-2-methoxy-1-methylethyl)-1-{2-oxo-2-[4-(2-oxo-1,2,4,5-tetrahydro-benzo[d][1,3]diazepin- 3-yl)-piperidin-1-yl]-ethyl}-1H-pyrimidine-2,4-dione is obtained in the form of a white solid with a melting point of 274° C.

$^1$H NMR (δ, DMSO): 1.33 (d, J=6.9 Hz, 3H); 1.53-1.56 (m, 1H); 1.65-1.70 (m, 3H); 2.68 (t, J=12.4 Hz, 1H); 2.88-2.90 (m, 2H); 3.14 (t, J=12.5 Hz, 1H); 3.23 (s, 3H); 3.37-3.39 (m, 2H); 3.54 (dd, J=9.9, 5.9 Hz, 1H); 3.89 (s, 3H); 3.91-3.95 (m, 2H); 4.26-4.36 (m, 1H); 4.42-4.45 (m, 1H); 4.73-4.77 (m, 2H); 5.09-5.19 (m, 1H); 6.79-6.83 (m, 1H); 6.91 (dd, J=7.6, 1.4 Hz, 1H); 7.02-7.05 (m, 3H); 7.18 (dd, J=8.4, 1.4 Hz, 1H); 7.33-7.37 (m, 1H); 7.69 (s, 1H); 8.53 (s, 1H).

EXAMPLE 109: 5-(2,3-DIFLUOROPHENYL)-3-((S)-2-METHOXY-1-METHYLETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 109)

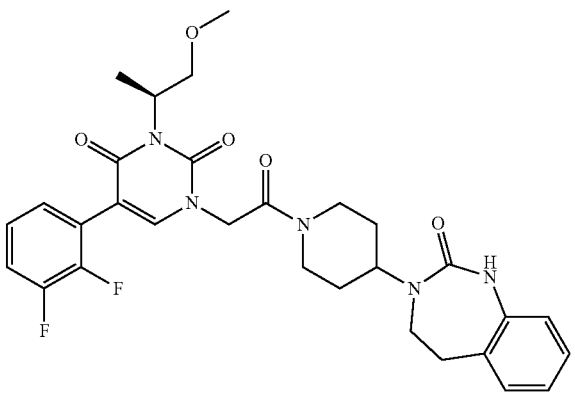 [SMILES: COC[C@H](C)n1c(=O)c(-c2cccc(F)c2F)cn(CC(=O)N2CCC(N3CCc4ccccc4NC3=O)CC2)c1=O]

109.1: [5-(2,3-difluorophenyl)-3-((S)-2-methoxy-1-methylethyl)-2,4-dioxo-3,4-dihydro-2H-pyrimidin-1-yl]-methyl acetate Similarly to example 44.1, starting from 1.4 g (4.2 mmol) of [5-bromo-3-((S)-2-methoxy-1-methylethyl)-2,4-dioxo-3,4-dihydro-2H-pyrimidin-1-yl]-methyl acetate (prepared as described in example 106.1) and 2.7 g (16.7 mmol) of 2,3-difluorophenylboronic acid, and after purification by silica gel chromatography eluted with a heptane/ethyl acetate 60/40 mixture, 0.9 g (60%) of [5-(2,3-difluorophenyl)-3-((S)-2-methoxy-1-methylethyl)-2,4-dioxo-3,4-dihydro-2H-pyrimidin-1-yl]-methyl acetate is obtained in the form of a colourless oil.

109.2: [5-(2,3-difluorophenyl)-3-((S)-2-methoxy-1-methylethyl)-2,4-dioxo-3,4-dihydro-2H-pyrimidin-1-yl]-acetic acid Similarly to example 16.8, starting from 920 mg (2.5 mmol) of [5-(2,3-difluorophenyl)-3-((S)-2-methoxy-1-methylethyl)-2,4-dioxo-3,4-dihydro-2H-pyrimidin-1-yl]-methyl acetate, 840 mg (95%) of [5-(2,3-difluorophenyl)-3-((S)-2-methoxy-1-methylethyl)-2,4-dioxo-3,4-dihydro-2H-pyrimidin-1-yl]-acetic acid is obtained in the form of a white solid.

109.3: 5-(2,3-difluorophenyl)-3-((S)-2-methoxy-1-methylethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 109)

Similarly to example 76.4, starting from 150 mg (0.4 mmol) of [5-(2,3-difluorophenyl)-3-((S)-2-methoxy-1-methylethyl)-2,4-dioxo-3,4-dihydro-2H-pyrimidin-1-yl]-acetic acid and 125 mg (0.5 mmol) of 3-piperidin-4-yl-1,3,4,5-tetrahydro-benzo[d][1,3]diazepin-2-one (prepared as described in example 16.4), 150 mg (59%) of 5-(2,3-difluorophenyl)-3-((S)-2-methoxy-1-methylethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 234° C.

$^1$H NMR (δ, DMSO): 1.34 (d, J=7.0 Hz, 3H); 1.53-1.80 (m, 4H); 2.69 (t, J=12.4 Hz, 1H); 2.90 (m, 2H); 3.15 (t, J=12.3 Hz, 1H); 3.23 (s, 3H); 3.38-3.40 (m, 2H); 3.54 (dd, J=9.9, 5.9 Hz, 1H); 3.90-3.95 (m, 2H); 4.28-4.38 (m, 1H); 4.43 (d, J=12.9 Hz, 1H); 4.77 (s, 2H); 5.15-5.17 (m, 1H); 6.79-6.83 (m, 1H); 7.02-7.05 (m, 3H); 7.19-7.29 (m, 2H); 7.42-7.49 (m, 1H); 7.89 (s, 1H); 8.53 (s, 1H).

EXAMPLE 110: 5-(2-CHLORO-3-FLUOROPHENYL)-3-((R)-2-METHOXY-1-METHYLETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 110)

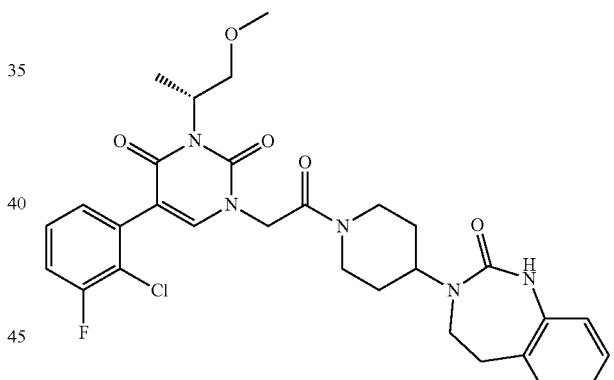

110.1: [5-bromo-3-((R)-2-methoxy-1-methylethyl)-2,4-dioxo-3,4-dihydro-2H-pyrimidin-1-yl]-methyl acetate Similarly to example 106.1, starting from 1 g (3.8 mmol) of (5-bromo-2,4-dioxo-3,4-dihydro-2H-pyrimidin-1-yl)-methyl acetate (prepared as described in example 13.1), and 0.4 ml (4.2 mmol) of (S)-1-methoxy-propan-2-ol, 0.8 g (63%) of [5-bromo-3-((R)-2-methoxy-1-methylethyl)-2,4-dioxo-3,4-dihydro-2H-pyrimidin-1-yl]-methyl acetate is obtained in the form of a colourless oil.

110.2: [5-(2-chloro-3-fluorophenyl)-3-((R)-2-methoxy-1-methylethyl)-2,4-dioxo-3,4-dihydro-2H-pyrimidin-1-yl]-acetic acid Similarly to example 13.3, starting from 300 mg (0.9 mmol) of [5-bromo-3-((R)-2-methoxy-1-methylethyl)-2,4- dioxo-3,4-dihydro-2H-pyrimidin-1-yl]-methyl acetate and 156 mg (0.9 mmol) of 2-chloro-3-fluorophenylboronic acid, 180 mg (54%) of [5-(2-chloro-3-fluorophenyl)-3-((R)-2-methoxy-1-methylethyl)-2,4-dioxo-3,4-dihydro-2H-pyrimidin-1-yl]-acetic acid is obtained in the form of a brown oil.

110.3: 5-(2-chloro-3-fluorophenyl)-3-((R)-2-methoxy-1-methylethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (Compound 110)

Similarly to example 13.4, starting from 180 mg (0.5 mmol) of [5-(2-chloro-3-fluorophenyl)-3-((R)-2-methoxy-1-methylethyl)-2,4-dioxo-3,4-dihydro-2H-pyrimidin-1-yl]-acetic acid and 143 mg (0.6 mmol) of 3-piperidin-4-yl-1,3,4,5-tetrahydro-benzo[d][1,3]diazepin-2-one (prepared as described in example 16.4), and after crystallization in ethyl acetate, 105 mg (36%) of 5-(2-chloro-3-fluorophenyl)-3-((R)-2-methoxy-1-methylethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 225° C.

$^1$H NMR (δ, DMSO): 1.34 (d, J=7.0 Hz, 3H); 1.50-1.80 (m, 4H); 2.68 (t, J=12.5 Hz, 1H); 2.90 (m, 2H); 3.15 (m, 1H); 3.33 (s, 3H); 3.38 (m, 2H); 3.54 (dd, J=9.9, 5.9 Hz, 1H); 3.90-3.95 (m, 2H); 4.33 (m, 1H); 4.43 (d, J=12.9 Hz, 1H); 4.75 (m, 2H); 5.15 (m, 1H); 6.80-6.81 (m, 1H); 7.04-7.06 (m, 3H); 7.20-7.21 (m, 1H); 7.44-7.45 (m, 2H); 7.80 (s, 1H); 8.53 (s, 1H).

EXAMPLE 111: 2-(5-(2-CHLORO-3-FLUOROPHENYL)-2,6-DIOXO-3-{2-OXO-2-[4-(2-OXO-1,2,4,5-TETRAHYDRO-BENZO[D][1,3]DIAZEPIN-3-YL)-PIPERIDIN-1-YL]-ETHYL}-3,6-DIHYDRO-2H-PYRIMIDIN-1-YL)-METHYL PROPIONATE (REACTION SCHEME NO. 3, COMPOUND 111)

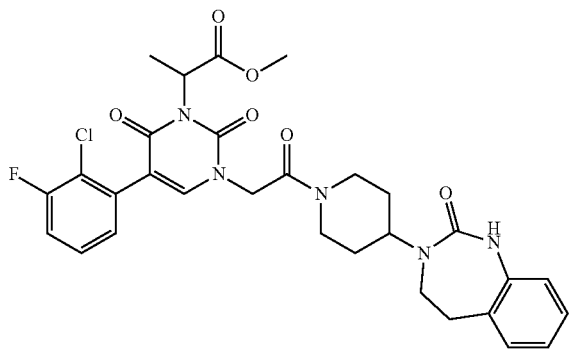 [SMILES: COC(=O)C(C)n1c(=O)c(-c2cccc(F)c2Cl)cn(CC(=O)N2CCC(N3CCc4ccccc4NC3=O)CC2)c1=O]

111.1: (3-benzhydryl-5-bromo-2,6-dioxo-3,6-dihydro-2H-pyrimidin-1-yl)-methyl acetate Similarly to example 2.2, starting from 10 g (30 mmol) of 1-benzhydryl-5-bromo-1H-pyrimidine-2,4-dione (prepared as in example 2.1) and 3.5 ml (40 mmol) of methyl bromoacetate, 11.1 g (92%) of (3-benzhydryl-5-bromo-2,6-dioxo-3,6-dihydro-2H-pyrimidin-1-yl)-methyl acetate is obtained in the form of a white solid.

111.2: 2-(3-benzhydryl-5-bromo-2,6-dioxo-3,6-dihydro-2H-pyrimidin-1-yl)-methyl propionate 3.7 g (20 mmol) of potassium bis(trimethylsilyl)amide and 1.7 ml (20 mmol) of iodomethane are added to a solution containing 1 g (2 mmol) of (3-benzhydryl-5-bromo-2,6-dioxo-3,6-dihydro-2H-pyrimidin-1-yl)-methyl acetate in 20 ml of tetrahydrofuran previously cooled to −78° C. The mixture is stirred at −78° C. for 2 hours and then poured into a saturated solution of ammonium chloride and extracted with dichloromethane. The organic phase is dried over anhydrous sodium sulphate, then filtered and concentrated to dryness. 640 mg (62%) 2-(3-benzhydryl-5-bromo-2,6-dioxo-3,6-dihydro-2H-pyrimidin-1-yl)-methyl propionate is obtained in the form of a yellow solid.

111.3: 2-[3-benzhydryl-5-(2-chloro-3-fluorophenyl)-2,6-dioxo-3,6-dihydro-2H-pyrimidin-1-yl]-methyl propionate Similarly to example 44.1, starting from 450 mg (1 mmol) of 2-(3-benzhydryl-5-bromo-2,6-dioxo-3,6-dihydro-2H-pyrimidin-1-yl)-methyl propionate and 354 mg (2 mmol) of 2-chloro-3-fluorophenylboronic acid, and after purification by silica gel chromatography eluted with a mixture of ethyl acetate in heptane, following a polarity gradient (from 5% to 30% of ethyl acetate in heptane), 150 mg (30%) of 2-[3-benzhydryl-5-(2-chloro-3-fluorophenyl)-2,6-dioxo-3,6-dihydro-2H-pyrimidin-1-yl]-methyl propionate is obtained in the form of a yellow solid.

111.4: 2-[5-(2-chloro-3-fluorophenyl)-2,6-dioxo-3,6-dihydro-2H-pyrimidin-1-yl]-methyl propionate Similarly to example 2.3, starting from 150 mg (0.3 mmol) of 2-[3-benzhydryl-5-(2-chloro-3-fluorophenyl)-2,6-dioxo-3,6-dihydro-2H-pyrimidin-1-yl]-methyl propionate, 125 mg (126%) of 2-[5-(2-chloro-3-fluorophenyl)-2,6-dioxo-3,6-dihydro-2H-pyrimidin-1-yl]-methyl propionate is obtained in the form of a brown oil.

111.5: 3-[1-(2-chloroacetyl)-piperidin-4-yl]-1,3,4,5-tetrahydro-benzo[d][1,3]diazepin-2-one Similarly to example 2.4, starting from 5 g (20 mmol) of 3-piperidin-4-yl-1,3,4,5-tetrahydro-benzo[d][1,3]diazepin-2-one (prepared as in example 16.4) and 4.2 g (44.8 mmol) of chloroacetic acid, 7 g (107%) of 3-[1-(2-chloroacetyl)-piperidin-4-yl]-1,3,4,5-tetrahydro-benzo[d][1,3]diazepin-2-one is obtained in the form of a white solid.

111.6: 2-(5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-methyl propionate (Compound 111)

A solution containing 125 mg (0.4 mmol) of 2-[5-(2-chloro-3-fluorophenyl)-2,6-dioxo-3,6-dihydro-2H-pyrimidin-1-yl]-methyl propionate in 2.5 ml of N,N-dimethylformamide is added to 148 mg (0.5 mmol) of 3-[1-(2-chloroacetyl)-piperidin-4-yl]-1,3,4,5-tetrahydro-benzo[d][1,3]diazepin-2-one, 63 mg (0.5 mmol) of potassium carbonate and 13 mg (0.1 mmol) of potassium iodide. The mixture is stirred for 45 minutes at 50° C. It is hydrolysed and then extracted with ethyl acetate. The organic phase is washed with water and then dried over anhydrous sodium sulphate, filtered and concentrated to dryness. The yellow oil obtained is purified by preparative HPLC. After evaporation, 95 mg (40%) of 2-(5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-methyl propionate is obtained in the form of a white solid.

$^1$H NMR (400 MHz, MeOD-d4) δ: 1.59 (d, J=6.9 Hz, 3H), 1.68-2.02 (m, 4H), 2.79 (m, 1H), 2.95-3.08 (m, 2H), 3.19-3.31 (m, 1H), 3.48-3.62 (m, 2H), 3.72 (s, 3H), 4.05 (m, 1H), 4.36-4.51 (m, 1H), 4.56-4.69 (m, 1H), 4.71-5.03 (m, 2H), 5.55 (q, J=6.9 Hz, 1H), 6.86-6.97 (m, 2H), 7.09 (m, 2H), 7.24 (m, 1H), 7.30 (m, 1H), 7.39 (m, 1H), 7.71 (s, 1H); NH not observed in methanol.

EXAMPLE 112: 5-(2-CHLORO-3-FLUOROPHE-NYL)-3-(2-METHYLSULPHANYL-ETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 112)

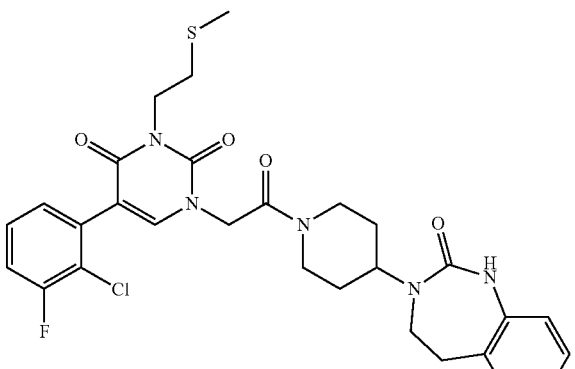

112.1: [5-bromo-3-(2-methylsulphanyl-ethyl)-2,4-dioxo-3,4-dihydro-2H-pyrimidin-1-yl]-methyl acetate Similarly to example 1.7, starting from 0.5 g (1.9 mmol) of 5-bromo-2,4-dioxo-3,4-dihydro-2H-pyrimidin-1-yl)-methyl acetate (prepared as in example 13.1) and 420 mg (3.8 mmol) of 2-chloroethyl methyl sulphide, and after heating the mixture at 50° C. for 5 hours, 520 mg (81%) of [5-bromo-3-(2-methylsulphanyl-ethyl)-2,4-dioxo-3,4-dihydro-2H-pyrimidin-1-yl]-methyl acetate is obtained in the form of a white solid.

112.2: [5-(2-chloro-3-fluorophenyl)-3-(2-methylsulphanyl-ethyl)-2,4-dioxo-3,4-dihydro-2H-pyrimidin-1-yl]-acetic acid Similarly to example 13.3, starting from 520 mg (1.5 mmol) of [5-bromo-3-(2-methylsulphanyl-ethyl)-2,4-dioxo-3,4-dihydro-2H-pyrimidin-1-yl]-methyl acetate and 296 mg (1.7 mmol) of 2-chloro-3-fluorophenylboronic acid, 490 mg (85%) of [5-(2-chloro-3-fluorophenyl)-3-(2-methylsulpha-nyl-ethyl)-2,4-dioxo-3,4-dihydro-2H-pyrimidin-1-yl]-acetic acid is obtained in the form of a beige solid.

112.3: 5-(2-chloro-3-fluorophenyl)-3-(2-methylsul-phanyl-ethyl)-1-{2-oxo-2-[4-(2-oxo-1,2,4,5-tetra-hydro-benzo[d][1,3]diazepin-3-yl)-piperidin-1-yl]-ethyl}-1H-pyrimidine-2,4-dione (Compound 112)

Similarly to example 13.4, starting from 490 mg (1.3 mmol) of [5-(2-chloro-3-fluorophenyl)-3-(2-methylsulpha-nyl-ethyl)-2,4-dioxo-3,4-dihydro-2H-pyrimidin-1-yl]-acetic acid and 387 mg (1.6 mmol) of 3-piperidin-4-yl-1,3,4,5-tetrahydro-benzo[d][1,3]diazepin-2-one (prepared as described in example 16.4), and after recrystallization from n-butanol, 470 mg (58%) of 5-(2-chloro-3-fluorophenyl)-3-(2-methylsulphanyl-ethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 207° C.

$^1$H NMR (δ, DMSO): 1.50-1.80 (m, 4H), 2.12 (s, 3H), 2.69 (t, 3H, J=7.19 Hz), 2.90 (m, 2H), 3.16 (m, 1H), 3.38 (m, 2H), 3.95 (d, 1H, J=13.66 Hz), 4.08 (t, 2H, J=7.21 Hz), 4.33 (m, 1H), 4.43 (d, 1H, J=12.91 Hz), 4.79 (s, 2H), 6.79-6.83 (m, 1H), 7.02-7.05 (m, 3H), 7.21-7.23 (m, 1H), 7.44-7.48 (m, 2H), 7.85 (s, 1H), 8.52 (s, 1H).

EXAMPLE 113: 5-(2,3-DIFLUOROPHENYL)-3-(2-METHYLSULPHANYL-ETHYL)-1-{2-OXO-2-[4-(2-OXO-1,2,4,5-TETRAHYDRO-BENZO[D][1,3]DIAZEPIN-3-YL)-PIPERIDIN-1-YL]-ETHYL}-1H-PYRIMIDINE-2,4-DIONE (REACTION SCHEME NO. 3, COMPOUND 113)

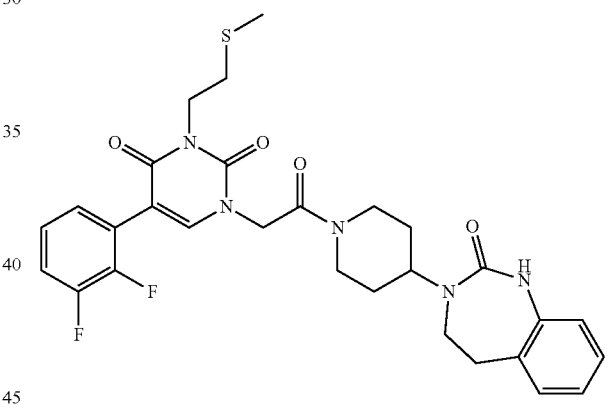

113.1: (5-bromo-2,4-dioxo-3,4-dihydro-2H-pyrimi-din-1-yl)-methyl acetate 23 ml (0.2 mmol) of 1,8-diazabicyclo[5,4,0]undec-7-ene is added to a solution containing 30 g (0.2 mmol) of 5-bromouracil in 294 ml of acetonitrile. The mixture goes into solution and then relapses after 5 min. It is then cooled to −5° C. with an ice/acetone bath and then 16 ml (0.2 mmol) of methyl bromoacetate is added. The medium is stirred for 45 minutes at room temperature, treated by pouring in 150 ml of water, then filtered. The white precipitate is rinsed with a little methyl tert-butyl ether and dried under vacuum at 40° C. 25.5 g (63%) of (5-bromo-2,4-dioxo-3,4-dihydro-2H-pyrimidin-1-yl)-methyl acetate is obtained in the form of a white solid.

113.2: [5-bromo-3-(2-methylsulphanyl-ethyl)-2,4-dioxo-3,4-dihydro-2H-pyrimidin-1-yl]-methyl acetate Similarly to example 1.7, starting from 1.2 g (4.6 mmol) of (5-bromo-2,4-dioxo-3,4-dihydro-2H-pyrimidin-1-yl)- methyl acetate and 1.4 ml (13.7 mmol) of 2-chloroethyl methyl sulphide, and after heating the mixture at 50° C. overnight, 850 mg (55%) of [5-bromo-3-(2-methylsulphanyl-ethyl)-2,4-dioxo-3,4-dihydro-2H-pyrimidin-1-yl]-methyl acetate is obtained in the form of a colourless oil, which crystallizes.

113.3: [5-(2,3-difluorophenyl)-3-(2-methylsulphanyl-ethyl)-2,4-dioxo-3,4-dihydro-2H-pyrimidin-1-yl]-methyl acetate Similarly to example 44.1, starting from 550 mg (1.6 mmol) of [5-bromo-3-(2-methylsulphanyl-ethyl)-2,4-dioxo-3,4-dihydro-2H-pyrimidin-1-yl]-methyl acetate and 1.1 g (6.5 mmol) of 2,3-difluorophenylboronic acid, 450 mg (75%) of [5-(2,3-difluorophenyl)-3-(2-methylsulphanyl-ethyl)-2,4-dioxo-3,4-dihydro-2H-pyrimidin-1-yl]-methyl acetate is obtained in the form of a white solid.

113.4: [5-(2,3-difluorophenyl)-3-(2-methylsulphanyl-ethyl)-2,4-dioxo-3,4-dihydro-2H-pyrimidin-1-yl]-acetic acid Similarly to example 16.8, starting from 450 mg (1.2 mmol) of [5-(2,3-difluorophenyl)-3-(2-methylsulphanyl-ethyl)-2,4-dioxo-3,4-dihydro-2H-pyrimidin-1-yl]-methyl acetate, 430 mg (99%) of [5-(2,3-difluorophenyl)-3-(2-methylsulphanyl-ethyl)-2,4-dioxo-3,4-dihydro-2H-pyrimidin-1-yl]-acetic acid is obtained in the form of a beige solid.

113.5: 5-(2,3-difluorophenyl)-3-(2-methylsulphanyl-ethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione (compound 113)

Similarly to example 13.4, starting from 200 mg (0.6 mmol) of [5-(2,3-difluorophenyl)-3-(2-methylsulphanyl-ethyl)-2,4-dioxo-3,4-dihydro-2H-pyrimidin-1-yl]-acetic acid and 165 mg (0.7 mmol) of 3-piperidin-4-yl-1,3,4,5-tetrahydro-benzo[d][1,3]diazepin-2-one, and after crystallization in a heptane/ethyl acetate 50/50 mixture, 230 mg (65%) of 5-(2,3-difluorophenyl)-3-(2-methylsulphanyl-ethyl)-1-{2-oxo-2-[4-(2-oxo-1,2,4,5-tetrahydro-benzo[d][1,3]diazepin-3-yl)-piperidin-1-yl]-ethyl}-1H-pyrimidine-2,4-dione is obtained in the form of a white solid with a melting point of 220° C.

$^1$H NMR (400 MHz, DMSO-d6) δ: 1.50-1.63 (m, 1H), 1.69 (m, 3H), 2.12 (s, 3H), 2.69 (m, 3H), 2.82-2.97 (m, 2H), 3.16 (m, 1H), 3.35-3.48 (m, 2H), 3.95 (m, 1H), 4.03-4.15 (m, 2H), 4.28-4.38 (m, 1H), 4.43 (m, 1H), 4.80 (s, 2H), 6.73-6.88 (m, 1H), 6.96-7.10 (m, 3H), 7.17-7.35 (m, 2H), 7.46 (m, 1H), 7.94 (s, 1H), 8.53 (s, 1H).

EXAMPLE 114: 3-(5-(2-CHLORO-3-FLUORO-PHENYL)-2,6-DIOXO-3-{2-OXO-2-[4-(2-OXO-1,2,4,5-TETRAHYDRO-BENZO[D][1,3]DIAZEPIN-3-YL)-PIPERIDIN-1-YL]-ETHYL}-3,6-DIHYDRO-2H-PYRIMIDIN-1-YL)-METHYL PROPIONATE (REACTION SCHEME NO. 3, COMPOUND 114)

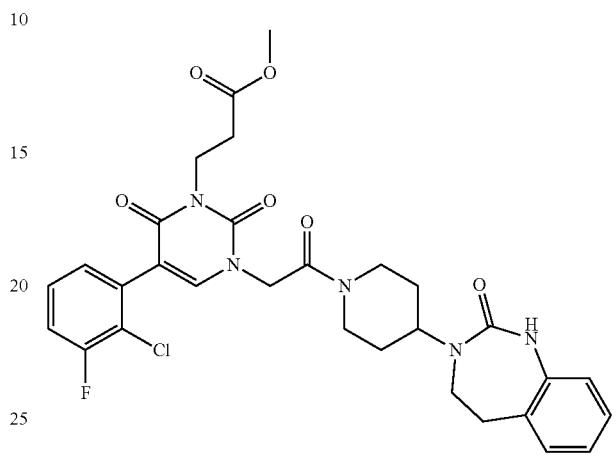

114.1: 3-(3-benzhydryl-5-bromo-2,6-dioxo-3,6-dihydro-2H-pyrimidin-1-yl)-methyl propionate Similarly to example 2.2, starting from 1 g (2.8 mmol) of 1-benzhydryl-5-bromo-1H-pyrimidine-2,4-dione (prepared as in example 2.1) and 608 mg (3.6 mmol) of methyl 3-bromopropionate, 1.1 g (85%) of 3-(3-benzhydryl-5-bromo-2,6-dioxo-3,6-dihydro-2H-pyrimidin-1-yl)-methyl propionate is obtained in the form of a white solid.

114.2: 3-[3-benzhydryl-5-(2-chloro-3-fluorophenyl)-2,6-dioxo-3,6-dihydro-2H-pyrimidin-1-yl]-methyl propionate Similarly to example 44.1, starting from 1.1 g (2.4 mmol) of 3-(3-benzhydryl-5-bromo-2,6-dioxo-3,6-dihydro-2H-pyrimidin-1-yl)-methyl propionate and 620 mg (3.6 mmol) of 2-chloro-3-fluorophenylboronic acid, and after purification by silica gel chromatography eluted with a heptane/ethyl acetate 80/20 mixture, 660 mg (57%) of 3-[3-benzhydryl-5-(2-chloro-3-fluorophenyl)-2,6-dioxo-3,6-dihydro-2H-pyrimidin-1-yl]-methyl propionate is obtained in the form of a yellow solid.

114.3: 3-[5-(2-chloro-3-fluorophenyl)-2,6-dioxo-3,6-dihydro-2H-pyrimidin-1-yl]-methyl propionate Similarly to example 2.3, starting from 500 mg (1.0 mmol) of 3-[3-benzhydryl-5-(2-chloro-3-fluorophenyl)-2,6-dioxo-3,6-dihydro-2H-pyrimidin-1-yl]-methyl propionate, 310 mg (94%) of 3-[5-(2-chloro-3-fluorophenyl)-2,6-dioxo-3,6-dihydro-2H-pyrimidin-1-yl]-methyl propionate is obtained in the form of a yellowish solid.

114.4: 3-[1-(2-chloroacetyl)-piperidin-4-yl]-1,3,4,5-tetrahydro-benzo[d][1,3]diazepin-2-one Similarly to example 2.4, starting from 6 g (24.5 mmol) of 3-piperidin-4-yl-1,3,4,5-tetrahydro-benzo[d][1,3]diazepin-2-one (prepared as in example 16.4) and 5 g (53.8 mmol) of chloroacetic acid, 6.4 g (81%) of 3-[1-(2-chloro-acetyl)-piperidin-4-yl]-1,3,4,5-tetrahydro-benzo[d][1,3]diazepin-2-one is obtained in the form of a white solid.

114.5: 3-(5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-methyl propionate (Compound 114)

Similarly to example 111.6, starting from 150 mg (0.5 mmol) of 3-[5-(2-chloro-3-fluorophenyl)-2,6-dioxo-3,6-dihydro-2H-pyrimidin-1-yl]-methyl propionate and 163 mg (0.5 mmol) of 3-[1-(2-chloroacetyl)-piperidin-4-yl]-1,3,4,5-tetrahydro-benzo[d][1,3]diazepin-2-one, and after crystallization in ethyl acetate and then heptane, 230 mg (80%) of 3-(5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-methyl propionate is obtained in the form of an off-white solid.

$^1$H NMR (δ, DMSO): 1.55 (d, J=13.8 Hz, 1H); 1.69 (d, J=23.0 Hz, 3H); 2.59 (t, J=7.4 Hz, 2H); 2.69 (t, 1H); 2.90 (m, 2H); 3.16 (br s, 1H); 3.38 (m, 2H); 3.60 (s, 3H); 3.95 (d, J=13.5 Hz, 1H); 4.13 (t, J=7.4 Hz, 2H); 4.33 (br s, 1H); 4.43 (d, J=12.9 Hz, 1H); 4.78 (s, 2H); 6.81 (dt, J=7.8, 4.3 Hz, 1H); 7.04 (t, J=3.8 Hz, 3H); 7.21-7.23 (m, 1H); 7.44-7.47 (m, 2H); 7.85 (s, 1H); 8.52 (s, 1H).

Another compound synthesized according to a similar procedure using the appropriate reagents, commercially available or previously prepared:

Compound 202: N-[2-(5-(2-chloro-3-fluorophenyl)-2,6-dioxo-3-{2-oxo-2-[4-(2-oxo-1,2,4,5-tetrahydro-benzo[d][1,3]diazepin-3-yl)-piperidin-1-yl]-ethyl}-3,6-dihydro-2H-pyrimidin-1-yl)-ethyl]acetamide

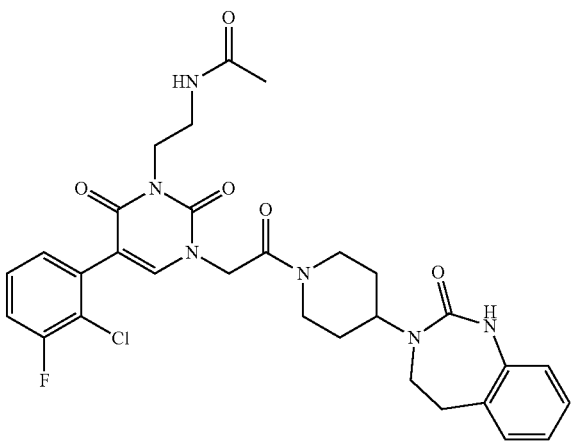

$^1$H NMR (δ, DMSO): 1.47-1.83 (m, 4H), 1.76 (s, 3H), 2.62-2.77 (m, 1H), 2.81-2.97 (m, 2H), 3.07-3.20 (m, 1H), 3.26 (q, J=6.43 Hz, 2H), 3.34-3.44 (m, 2H), 3.84-4.04 (m, 3H), 4.25-4.38 (m, 1H), 4.43 (d, J=13.11 Hz, 1H), 4.78 (s, 2H), 6.68-6.87 (m, 1H), 6.90-7.10 (m, 3H), 7.14-7.31 (m, 1H), 7.34-7.56 (m, 2H), 7.82 (s, 1H), 7.92 (t, J=5.91 Hz, 1H), 8.52 (s, 1H).

EXAMPLE 115: N—[(S)-2-(5-(2-CHLORO-3-FLUOROPHENYL)-3-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-2,6-DIOXO-3,6-DIHYDRO-2H-PYRIMIDIN-1-YL)-PROPYL]ACETAMIDE (REACTION SCHEME 3 OR 4, COMPOUND 115)

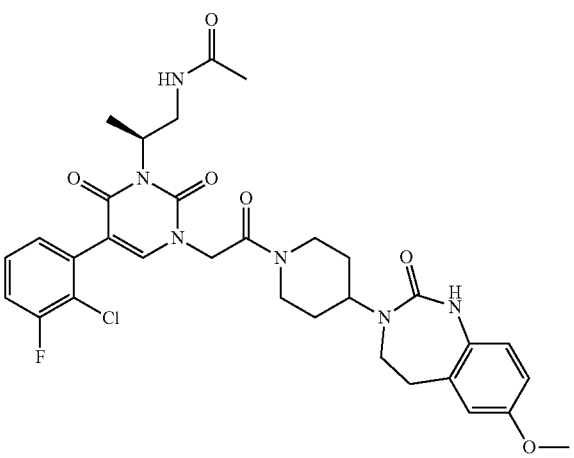 [SMILES: COc1ccc2c(c1)CCN(C1CCN(C(=O)Cn3cc(-c4cccc(F)c4Cl)c(=O)n([C@@H](C)CNC(C)=O)c3=O)CC1)C(=O)N2]

115.1: (5-methoxy-2-nitrophenyl)-acetonitrile

A solution containing 30.5 g (199 mmol) of 4-nitroanisole and 40 g (239 mmol) of (4-chlorophenoxy)-acetonitrile in 305 ml of N,N-dimethylformamide is added at −20° C. under nitrogen to a solution containing 53.6 g (478 mmol) of potassium tert-butylate in 610 ml of N,N-dimethylformamide. The reaction mixture is left to return to 0° C. and is maintained at this temperature. After 1 hour, the reaction mixture is cooled to −50° C. and hydrolysed slowly with 1000 ml of an iced aqueous solution of 6N hydrochloric acid, then 1000 ml of ethyl acetate and 500 ml of water are added. The aqueous phase is extracted with ethyl acetate. The organic phase is washed with a saturated aqueous solution of ammonium chloride and then with water, and then dried over anhydrous sodium sulphate, filtered and concentrated. The residue obtained is taken up in toluene and evaporated. The oil thus obtained is taken up, with stirring, in 250 ml of an ethyl acetate/heptane mixture (50/50) overnight and then the mixture is cooled in an ice bath and filtered. After rinsing with heptane, 26.7 g (68%) of (5-methoxy-2-nitrophenyl)-acetonitrile is obtained in the form of an orange-coloured solid.

115.2: 2-(5-methoxy-2-nitrophenyl)-ethylamine 200 ml (200 mmol) of a complexed solution of borane-tetrahydrofuran is added to a solution containing 26 g (136 mmol) of (5-methoxy-2-nitrophenyl)-acetonitrile in 130 ml of 2-methyltetrahydrofuran at 60° C. After 3 hours, heating is stopped and 35 ml (863 mmol) of methanol is added slowly, as well as 200 ml of 1N aqueous solution of sodium hydroxide. The aqueous phase is then extracted with 250 ml of methyl-tetrahydrofuran. The organic phase is washed with water, dried over anhydrous sodium sulphate, filtered and concentrated partially. 400 ml of tert-butyl ether and 10 ml (175 mmol) of acetic acid are added. The mixture is cooled, left with stirring overnight and then concentrated and coevaporated with toluene. 40.6 g (100%) of 2-(5-methoxy-2-nitrophenyl)-ethylamine acetate is obtained in the form of a brown oil.

115.3: 4-[2-(5-methoxy-2-nitrophenyl)-ethylamino]-piperidine-1-methyl carboxylate 44.5 g (210 mmol) of sodium triacetoxyhydroborate is added to a solution under nitrogen containing 40.6 g (136 mmol) of 2-(5-methoxy-2-nitrophenyl)-ethylamine acetic acid, 35.9 g (180 mmol) of N-(tert-butoxycarbonyl)-4-piperidone in 360 ml of 2-methyltetrahydrofuran. After 2 hours, the reaction mixture is hydrolysed with a 2N aqueous solution of sodium hydroxide. The aqueous phase is extracted with methyltetrahydrofuran. The organic phase is washed with water for adjustment to pH=6, dried over sodium sulphate, filtered and evaporated. 69.2 g (100%) of 4-[2-(5-methoxy-2-nitrophenyl)-ethylamino]-piperidine-1-methyl carboxylate is obtained in the form of a dark oil.

115.4: 4-[2-(2-amino-5-methoxyphenyl)-ethylamino]-piperidine-1-tert-butyl carboxylate 3.7 g (70 mmol) of ammonium chloride and 31.3 g (560 mmol) of iron are added to a solution containing 69.2 g (137 mmol) of 4-[2-(5-methoxy-2-nitrophenyl)-ethylamino]-piperidine-1-methyl carboxylate in 130 ml of 2-methyltetrahydrofuran, 130 ml of methanol and 130 ml of water. The reaction mixture is heated under reflux for 4 hours and then left to return to room temperature. After 16 hours, the reaction mixture is filtered on Celite and the filtrate is concentrated until the methanol has evaporated. Methyltetrahydrofuran is added, as well as a 10% solution of ethylenediaminetetraacetic acid. The organic phase is washed with water and then dried over anhydrous sodium sulphate, filtered and concentrated. 53.2 g (100%) of 4-[2-(2-amino-5-methoxyphenyl)-ethylamino]-piperidine-1-tert-butyl carboxylate is obtained in the form of an orange-coloured oil.

115.5: 4-(7-methoxy-2-oxo-1,2,4,5-tetrahydro-benzo[d][1,3]diazepin-3-yl)-piperidine-1-tert-butyl carboxylate 27.2 g (168 mmol) of N,N'-carbonyldiimidazole is added in portions to a solution containing 53.2 g (137 mmol) of 4-[2-(2-amino-5-methoxyphenyl)-ethylamino]-piperidine-1-tert-butyl carboxylate at 90% in 1000 ml of toluene. After 1 hour, the precipitate formed is filtered and the filtrate is concentrated partially. The residue is washed twice with an aqueous solution of ammonium chloride. The organic phase is dried over anhydrous sodium sulphate, filtered and concentrated. 58 g of an orange-coloured oil is obtained. After purification by silica gel chromatography eluted with a mixture of ethyl acetate in heptane, following a polarity gradient (from 20% to 70% of ethyl acetate in heptane), 35 g of a yellow solid is obtained and is taken up in 200 ml of isopropyl ether under reflux, 100 ml of isopropyl ether, 100 ml of tetrahydrofuran, 80 ml of ethanol and 300 ml of methanol. The mixture is filtered and then concentrated. After purification by silica gel chromatography eluted with a mixture of ethyl acetate in heptane, following a polarity gradient (from 20% to 100% of ethyl acetate in heptane), 21.1 g (34%) of 4-(7-methoxy-2-oxo-1,2,4,5-tetrahydro-benzo[d][1,3]diazepin-3-yl)-piperidine-1-tert-butyl carboxylate is obtained in the form of a beige solid.

115.6: 7-methoxy-3-piperidin-4-yl-1,3,4,5-tetrahydro-benzo[d][1,3]diazepin-2-one 35 ml (380 mmol) of trifluoroacetic acid is added at 0° C. to a solution containing 83% of 4-(7-methoxy-2-oxo-1,2,4,5-tetrahydro-benzo[d][1,3]diazepin-3-yl)-piperidine-1-tert-butyl carboxylate in 300 ml of dichloromethane. After 15 hours, the reaction mixture is concentrated slowly in a rotary evaporator. The residue is coevaporated with toluene, taken up in 250 ml of dichloromethane, and then the mixture is adjusted to pH=10 with 1N aqueous solution of sodium hydroxide. The aqueous phase is extracted with dichloromethane, the organic phase is dried over anhydrous sodium sulphate, filtered and concentrated. 12.7 g (96%) of 7-methoxy-3-piperidin-4-yl-1,3,4,5-tetrahydro-benzo[d][1,3]diazepin-2-one is obtained in the form of a beige solid.

115.7: [5-bromo-3-((S)-2-tert-butoxycarbonylamino-1-methylethyl)-2,4-dioxo-3,4-dihydro-2H-pyrimidin-1-yl]-methyl acetate Similarly to example 2.5, starting from 3.3 g (12.6 mmol) of (5-bromo-2,4-dioxo-3,4-dihydro-2H-pyrimidin-1-yl)-methyl acetate (prepared as in example 13.1) and 2 g (11.4 mmol) of ((R)-2-hydroxypropyl)-tert-butyl carbamate, and after purification by silica gel chromatography eluted with a mixture of ethyl acetate in heptane, following a polarity gradient (from 20% to 50% of ethyl acetate in heptane), 4.1 g (85%) of [5-bromo-3-((S)-2-tert-butoxycarbonylamino-1-methylethyl)-2,4-dioxo-3,4-dihydro-2H-pyrimidin-1-yl]-methyl acetate is obtained in the form of a viscous oil.

115.8: [3-((S)-2-tert-butoxycarbonylamino-1-methylethyl)-5-(2-chloro-3-fluorophenyl)-2,4-dioxo-3,4-dihydro-2H-pyrimidin-1-yl]-methyl acetate Similarly to example 44.1, starting from 1.9 g (11.1 mmol) of 2-chloro-3-fluorophenylboronic acid and 3.1 g (7.4 mmol) of [5-bromo-3-((S)-2-tert-butoxycarbonylamino-1-methylethyl)-2,4-dioxo-3,4-dihydro-2H-pyrimidin-1-yl]-methyl acetate, 2.4 g (68%) of [3-((S)-2-tert-butoxycarbonylamino-1-methylethyl)-5-(2-chloro-3-fluorophenyl)-2,4-dioxo-3,4-dihydro-2H-pyrimidin-1-yl]-methyl acetate is obtained in the form of a meringue.

115.9: [3-((S)-2-tert-butoxycarbonylamino-1-methylethyl)-5-(2-chloro-3-fluorophenyl)-2,4-dioxo-3,4-dihydro-2H-pyrimidin-1-yl]-acetic acid Similarly to example 16.8, starting from 1 g (2.1 mmol) of [3-((S)-2-tert-butoxycarbonylamino-1-methylethyl)-5-(2-chloro-3-fluorophenyl)-2,4-dioxo-3,4-dihydro-2H-pyrimidin-1-yl]-methyl acetate, 983 mg (101%) of [3-((S)-2-tert-butoxycarbonylamino-1-methylethyl)-5-(2-chloro-3-fluorophenyl)-2,4-dioxo-3,4-dihydro-2H-pyrimidin-1-yl]-acetic acid is obtained in the form of a beige solid.

115.10: [(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-tert-butyl carbamate 490 mg (2.6 mmol) of 1-ethyl-3-(3-dimethylaminopropyl)carbodiimide hydrochloride and 284 mg (2.6 mmol) of 1-oxy-pyridin-2-ol are added to a solution containing 971 mg (2.1 mmol) of [3-((S)-2-tert-butoxycarbonylamino-1-methylethyl)-5-(2-chloro-3-fluorophenyl)-2,4-dioxo-3,4-dihydro-2H-pyrimidin-1-yl]-acetic acid in 5 ml of N,N-dimethylformamide. The reaction mixture is stirred for 5 minutes and then 645 mg (2.3 mmol) of 7-methoxy-3-piperidin-4-yl-1,3,4,5-tetrahydro-benzo[d][1,3]diazepin-2-one and 0.4 ml (2.6 mmol) of triethylamine are added. The reaction mixture is stirred at room temperature for 12 hours and then diluted with ethyl acetate and water. The aqueous phase is extracted three times with ethyl acetate, the organic phase is washed with a saturated solution of sodium carbonate and then with 1N aqueous solution of hydrochloric acid. After drying over magnesium sulphate, the solution is filtered and concentrated under vacuum. After purification by silica gel chromatography eluted with a mixture of methanol in dichloromethane, following a polarity gradient (from 0% to 5% of methanol in dichloromethane), 1.2 g (79%) of [(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-tert-butyl carbamate is obtained in the form of a beige solid.

115.11: 3-((S)-2-amino-1-methylethyl)-5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione 0.8 ml (7.8 mmol) of trifluoroacetic acid is added to a solution containing 800 mg (1.1 mmol) of [(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-tert-butyl carbamate in 7 ml of dichloromethane. The mixture is stirred at room temperature for two hours and then two equivalents of trifluoroacetic acid are added. The mixture is concentrated under vacuum and taken up in dichloromethane and treated with 1N aqueous solution of sodium hydroxide. The aqueous phase is extracted three times with dichloromethane; the organic phase is washed with water and then with brine. The organic phase is dried over anhydrous sodium sulphate, filtered and concentrated to dryness. 646 mg (94%) of 3-((S)-2-amino-1-methylethyl)-5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione is obtained in the form of an off-white solid.

115.12: N—[(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl] acetamide (Compound 115)

0.1 ml (0.8 mmol) of triethylamine and 68 mg (0.7 mmol) of acetic anhydride are added at −10° C. to a solution containing 391 mg (0.6 mmol) of 3-((S)-2-amino-1-methylethyl)-5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione in 3.2 ml of tetrahydrofuran. The mixture is hydrolysed after 5 minutes at −10° C. with water and diluted with ethyl acetate. The aqueous phase is extracted three times with ethyl acetate, the organic phase is washed with 1N soda and then with brine. After drying over magnesium sulphate, the solution is filtered and then concentrated. The precipitate is taken up in ethyl acetate and stirred for 24 hours at room temperature. 190 mg (44%) of N—[(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide is obtained in the form of a white solid with a melting point of 200° C.

$^1$H NMR (δ, DMSO): 1.34 (d, J=6.5 Hz, 3H), 1.42-1.75 (m, 4H), 1.77 (s, 3H), 2.60-2.75 (m, 1H), 2.82-2.93 (m, 2H), 3.14 (t, J=12.6 Hz, 1H), 3.32-3.42 (m, 2H), 3.40-3.61 (m, 2H), 3.67 (s, 3H), 3.94 (bt d, J=13.3 Hz, 1H), 4.18-4.38 (m, 1H), 4.43 (d, J=12.7 Hz, 1H), 4.58-4.90 (m, 2H), 4.99 (m, 1H), 6.62 (d, J=2.9 Hz, 1H), 6.66 (dd, J=2.9, 8.8 Hz, 1H), 6.98 (d, J=8.8 Hz, 1H), 7.13-7.31 (m, 1H), 7.35-7.57 (m, 2H), 7.8 (s, 1H), 7.88-8.02 (m, 1H), 8.32 (s, 1H).

The following compounds were synthesized according to a similar procedure using the appropriate reagents, commercially available or previously prepared:

Compound 203: N—[(R)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide

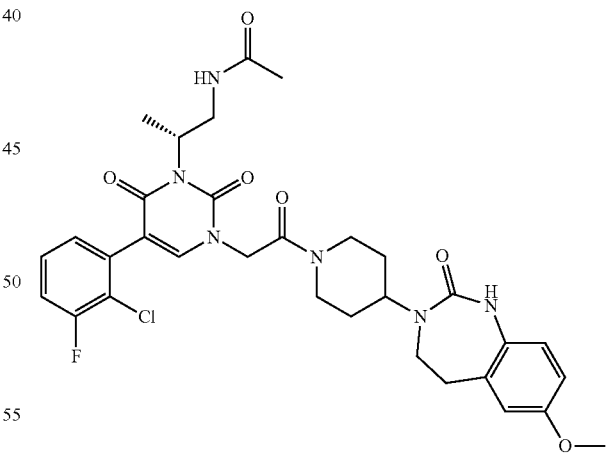

$^1$H NMR (δ, DMSO): 1.34 (dd, J=6.8, 1.4, 3H), 1.45-1.75 (m, 4H), 1.67-1.87 (m, 3H), 2.62-2.78 (m, 1H), 2.81-2.94 (m, 2H), 3.14 (t, J=12.5 Hz, 1H), 3.32-3.43 (m, 2H), 3.39-3.62 (m, 2H), 3.67 (s, 3H), 3.87-3.99 (m, 1H), 4.17-4.35 (m, 1H), 4.44 (d, J=12.6 Hz, 1H), 4.60-4.86 (m, 2H), 4.99 (q, J=7.2 Hz, 1H), 6.44-6.76 (m, 2H), 6.98 (d, J=8.8 Hz, 1H), 7.21 (dd, J=5.7, 3.3 Hz, 1H), 7.39-7.58 (m, 2H), 7.79 (s, 1H), 7.93 (t, J=6.1 Hz, 1H), 8.32 (s, 1H).

Compound 204: N—[(R)-2-(5-(2-chloro-3-fluoro-phenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-2,2,2-trifluoro-acetamide

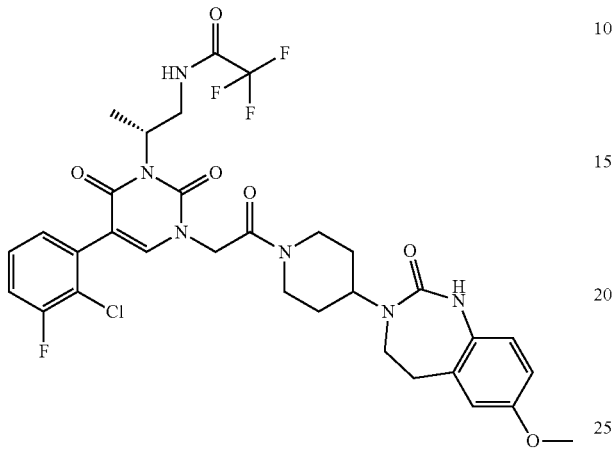

¹H NMR (δ, DMSO): 1.39 (dd, J=7.0 Hz, 2.3, 3H), 1.47-1.83 (m, 4H), 2.63-2.76 (m, 1H), 2.87 (d, J=5.9 Hz, 2H), 3.04-3.26 (m, 1H), 3.36 (d, J=4.7 Hz, 2H), 3.56-3.66 (m, 1H), 3.67 (s, 3H), 3.75 (d, J=8.1 Hz, 1H), 3.96 (d, J=13.6 Hz, 1H), 4.22-4.37 (m, 1H), 4.44 (d, J=12.7 Hz, 1H), 4.68 (d, J=16.5 Hz, 1H), 4.82 (d, J=16.5 Hz, 1H), 4.98-5.33 (m, 1H), 6.45-6.80 (m, 2H), 6.98 (d, J=8.8 Hz, 1H), 7.12-7.26 (m, 1H), 7.37-7.58 (m, 2H), 7.80 (s, 1H), 8.33 (s, 1H), 9.58 (d, J=5.3 Hz, 1H).

Compound 205: N—[(S)-2-(5-(2,3-dichlorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide

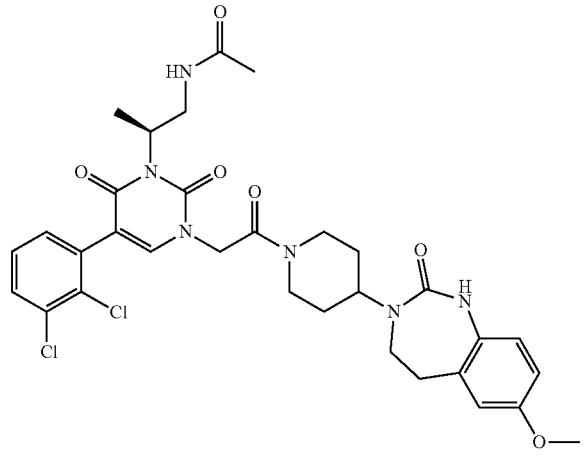

¹H NMR (δ, DMSO): 1.34 (d, J=6.9 Hz, 3H); 1.56-1.71 (m, 4H); 1.77 (s, 3H); 2.68 (t, J=12.3 Hz, 1H); 2.88 (m, 2H); 3.15 (m, 1H); 3.36 (m, 2H); 3.46-3.58 (m, 2H); 3.67 (s, 3H); 3.95 (d, J=13.6 Hz, 1H); 4.28 (m, 1H); 4.44 (d, J=12.8 Hz, 1H); 4.67-4.81 (m, 2H); 4.99 (m, 1H); 6.63-6.68 (m, 2H); 6.98 (d, J=8.8 Hz, 1H); 7.33 (d, J=7.7 Hz, 1H); 7.43 (t, J=7.9 Hz, 1H); 7.68 (dd, J=8.0, 1.6 Hz, 1H); 7.77 (s, 1H); 7.93 (t, J=5.9 Hz, 1H); 8.32 (s, 1H).

Compound 206: N—[(S)-2-(5-(2-chloro-3-methoxy-phenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide

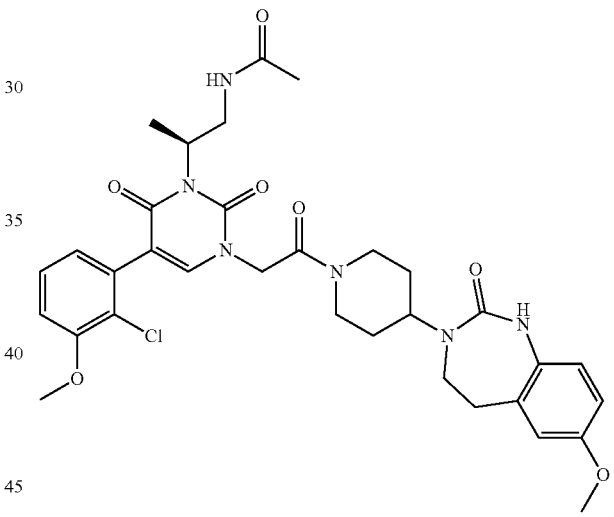

¹H NMR (δ, DMSO): 1.33 (d; J=6.91 Hz; 3H); 1.56 (m; 1H); 1.68 (m; J=20.83 Hz; 3H); 1.77 (s; 3H); 2.68 (t; J=12.42 Hz; 1H); 2.88 (d; J=6.51 Hz; 2H); 3.14 (t; J=12.32 Hz; 1H); 3.36 (d; J=6.38 Hz; 2H); 3.46-3.41 (m; 1H); 3.59-3.54 (m; 1H); 3.67 (s; 3H); 3.89 (s; 3H); 3.94 (d; J=13.73 Hz; 1H); 4.28 (m; 1H); 4.44 (d; J=12.77 Hz; 1H); 4.80-4.66 (m; 2H); 4.99-4.97 (m; 1H); 6.69-6.63 (m; 2H); 6.91 (d; J=7.64 Hz; 1H); 6.98 (d; J=8.79 Hz; 1H); 7.18 (dd; J=8.37; 1.40 Hz; 1H); 7.34 (t; J=7.96 Hz; 1H); 7.68 (s; 1H); 7.92 (t; J=5.78 Hz; 1H); 8.32 (s; 1H).

EXAMPLE 116: N—[(S)-2-(5-(2-CHLORO-3-FLUOROPHENYL)-3-{2-[4-(7-METHOXY-5-METHYL-2-OXO-1,2,4,5-TETRAHYDRO-BENZO[D][1,3]DIAZEPIN-3-YL)-PIPERIDIN-1-YL]-2-OXO-ETHYL}-2,6-DIOXO-3,6-DIHYDRO-2H-PYRIMIDIN-1-YL)-PROPYL]ACETAMIDE (REACTION SCHEME NO. 4, COMPOUND 116)

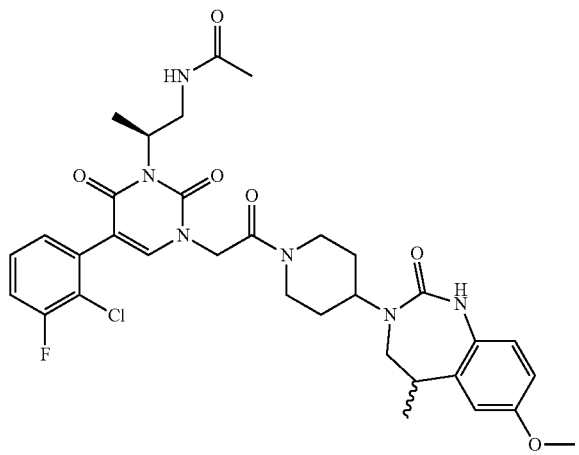 [SMILES: COc1ccc2c(c1)C(C)CN(C1CCN(C(=O)Cn3cc(-c4cccc(F)c4Cl)c(=O)n([C@@H](C)CNC(C)=O)c3=O)CC1)C(=O)N2]

116.1: 2-(5-methoxy-2-nitrophenyl)-propionitrile

A solution containing 1 g (5.2 mmol) of (5-methoxy-2-nitrophenyl)-acetonitrile (prepared as in example 115.1) and 0.6 ml (8.9 mmol) of iodomethane in 5 ml of N,N-dimethylformamide is added at 0° C. to a solution containing 208 mg (5.2 mmol) of sodium hydride in 7 ml (91 mmol) of N,N-dimethylformamide. After 1 hour, the mixture is diluted with ethyl acetate and then with water. The aqueous phase is extracted three times with ethyl acetate, the organic phase is washed with water and then brine. After drying over magnesium sulphate, the solution is filtered and then concentrated under vacuum. After purification by silica gel chromatography, 663 mg (62%) of 2-(5-methoxy-2-nitrophenyl)-propionitrile is obtained in the form of a clear oil.

116.2: 2-(5-methoxy-2-nitrophenyl)-propylamine

Similarly to example 115.2, starting from 663 mg (3.2 mmol) of 2-(5-methoxy-2-nitrophenyl)-propionitrile, 900 mg (104%) of 2-(5-methoxy-2-nitrophenyl)-propylamine is obtained in the form of an oil.

116.3: 4-[2-(5-methoxy-2-nitrophenyl)-propylamino]-piperidine-1-tert-butyl carboxylate Similarly to example 115.3, starting from 677 mg (3.2 mmol) of 2-(5-methoxy-2-nitrophenyl)-propylamine, 1.2 g (95%) of 4-[2-(5-methoxy-2-nitrophenyl)-propylamino]-piperidine-1-tert-butyl carboxylate is obtained in the form of an orange-coloured oil.

116.4: 4-[2-(2-amino-5-methoxyphenyl)-propylamino]-piperidine-1-tert-butyl carboxylate Similarly to example 115.4, starting from 1.2 g (3.2 mmol) of 4-[2-(5-methoxy-2-nitrophenyl)-propylamino]-piperidine-1-tert-butyl carboxylate, 1.2 g (103%) of 4-[2-(2-amino-5-methoxyphenyl)-propylamino]-piperidine-1-tert-butyl carboxylate is obtained in the form of an orange-coloured solid.

116.5: 4-(7-methoxy-5-methyl-2-oxo-1,2,4,5-tetrahydro-benzo[d][1,3]diazepin-3-yl)-piperidine-1-tert-butyl carboxylate Similarly to example 115.5, starting from 1.2 g (3.2 mmol) of 4-[2-(2-amino-5-methoxyphenyl)-propylamino]-piperidine-1-tert-butyl carboxylate, 455 mg (36%) of 4-(7-methoxy-5-methyl-2-oxo-1,2,4,5-tetrahydro-benzo[d][1,3]diazepin-3-yl)-piperidine-1-tert-butyl carboxylate is obtained in the form of a beige solid.

116.6: 7-methoxy-5-methyl-3-piperidin-4-yl-1,3,4,5-tetrahydro-benzo[d][1,3]diazepin-2-one Similarly to example 115.6, starting from 455 mg (1.2 mmol) of 4-(7-methoxy-5-methyl-2-oxo-1,2,4,5-tetrahydro-benzo[d][1,3]diazepin-3-yl)-piperidine-1-tert-butyl carboxylate, 335 mg (99%) of 7-methoxy-5-methyl-3-piperidin-4-yl-1,3,4,5-tetrahydro-benzo[d][1,3]diazepin-2-one is obtained in the form of a beige solid.

116.7: [(S)-2-(5-(2-chloro-3-fluorophenyl)-3-{2-[4-(7-methoxy-5-methyl-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-tert-butyl carbamate Similarly to example 115.10, starting from 549 mg (1.2 mmol) of [3-((S)-2-tert-butoxycarbonylamino-1-methylethyl)-5-(2-chloro-3-fluorophenyl)-2,4-dioxo-3,4-dihydro-2H-pyrimidin-1-yl]-acetic acid (prepared as in example 115.9) and 332 mg (1.2 mmol) of 7-methoxy-5-methyl-3-piperidin-4-yl-1,3,4,5-tetrahydro-benzo[d][1,3]diazepin-2-one, 832 mg (100%) of [(S)-2-(5-(2-chloro-3-fluorophenyl)-3-{2-[4-(7-methoxy-5-methyl-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-tert-butyl carbamate is obtained.

116.8: 3-((S)-2-amino-1-methylethyl)-5-(2-chloro-3-fluorophenyl)-1-{2-[4-(7-methoxy-5-methyl-2-oxo-1,2,4,5-tetrahydro-benzo[d][1,3]diazepin-3-yl)-piperidin-1-yl]-2-oxo-ethyl}-1H-pyrimidine-2,4-dione Similarly to example 115.11, starting from 836 mg (1.2 mmol) of [(S)-2-(5-(2-chloro-3-fluorophenyl)-3-{2-[4-(7-methoxy-5-methyl-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-]-tert-butyl carbamate, and after adding 412 mg (1.2 mmol) of (+)-o,o-dibenzoyl-D-tartaric acid in methanol, heating and purification by silica gel chromatography, 492 mg (68%) of 3-((S)-2-amino-1-methylethyl)-5-(2-chloro-3-fluorophenyl)-1-{2-[4-(7-methoxy-5-methyl-2-oxo-1,2,4,5-tetrahydro-benzo[d][1,3]diazepin-3-yl)-piperidin-1-yl]-2-oxo-ethyl}-1H-pyrimidine-2,4-dione is obtained.

116.9: N—[(S)-2-(5-(2-chloro-3-fluorophenyl)-3-{2-[4-(7-methoxy-5-methyl-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide (Compound 116)

Similarly to example 115.12, starting from 100 mg (0.2 mmol) of 3-((S)-2-amino-1-methylethyl)-5-(2-chloro-3- fluorophenyl)-1-{2-[4-(7-methoxy-5-methyl-2-oxo-1,2,4,5-tetrahydro-benzo[d][1,3]diazepin-3-yl)-piperidin-1-yl]-2-oxo-ethyl}-1H-pyrimidine-2,4-dione, 7 mg (6%) of N—[(S)-2-(5-(2-chloro-3-fluorophenyl)-3-{2-[4-(7-methoxy-5-methyl-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide is obtained in the form of a beige solid.

$^1$H NMR (400 MHz, DMSO-d6) δ: 1.18 (m, 3H), 1.34 (dd, J=7.0, 1.8 Hz, 3H), 1.68 (m, 4H), 1.76 (s, 3H), 2.59-2.73 (m, 1H), 3.04 (m, 1H), 3.13 (m, 1H), 3.30 (m, 2H), 3.51 (m, 2H), 3.68 (s, 3H), 3.95 (m, 1H), 4.25 (m, 1H), 4.44 (m, 1H), 4.57-4.86 (m, 2H), 4.98 (m, 1H), 6.57-6.73 (m, 2H), 6.97 (d, J=8.6 Hz, 1H), 7.21 (m, 1H), 7.36-7.52 (m, 2H), 7.79 (s, 1H), 7.95 (t, J=6.1 Hz, 1H), 8.36 (s, 1H).

EXAMPLE 117: N-[2-(5-(2-CHLORO-3-FLUORO-PHENYL)-3-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-2,6-DIOXO-3,6-DIHYDRO-2H-PYRIMIDIN-1-YL)-ETHYL]ACETAMIDE (REACTION SCHEME NO. 3, COMPOUND 117)

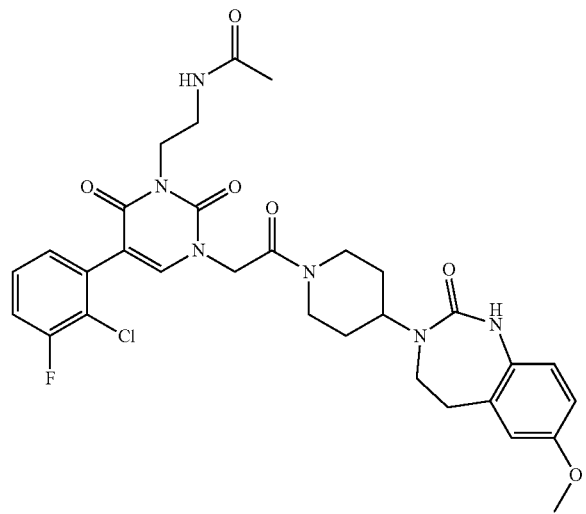 [SMILES: COc1ccc2c(c1)CCN(C1CCN(C(=O)Cn3cc(-c4cccc(F)c4Cl)c(=O)n(CCNC(C)=O)c3=O)CC1)C(=O)N2]

117.1: [5-bromo-3-(2-tert-butoxycarbonylamino-ethyl)-2,4-dioxo-3,4-dihydro-2H-pyrimidin-1-yl]-methyl acetate 2.4 g (17.1 mmol) of potassium carbonate and 3.1 g (13.7 mmol) of N-(2-bromoethyl)tert-butyl carbamate are added to a solution containing 3 g (11.4 mmol) of (5-bromo-2,4-dioxo-3,4-dihydro-2H-pyrimidin-1-yl)-methyl acetate (prepared as in example 13.1) in 60 ml of N,N-dimethylformamide. The reaction mixture is heated at 50° C. for 2 hours and is then hydrolysed and diluted with ethyl acetate. The product is extracted with ethyl acetate, the organic phase is washed twice with water and once with a saturated aqueous solution of sodium chloride, then dried over magnesium sulphate, filtered and concentrated under vacuum. The product is precipitated in 100 ml of diethyl ether and then filtered and dried under vacuum for 2 hours. 3.5 g (76%) of [5-bromo-3-(2-tert-butoxycarbonylaminoethyl)-2,4-dioxo-3,4-dihydro-2H-pyrimidin-1-yl]-methyl acetate is obtained in the form of a white solid.

117.2: [3-(2-tert-butoxycarbonylaminoethyl)-5-(2-chloro-3-fluorophenyl)-2,4-dioxo-3,4-dihydro-2H-pyrimidin-1-yl]-methyl acetate Similarly to example 115.8, starting from 429 mg (2.5 mmol) of 2-chloro-3-fluorophenylboronic acid and 500 mg (1.2 mmol) of [5-bromo-3-(2-tert-butoxycarbonylaminoethyl)-2,4-dioxo-3,4-dihydro-2H-pyrimidin-1-yl]-methyl acetate, and after purification by silica gel chromatography eluted with a mixture of ethyl acetate in heptane, following a polarity gradient (from 40% to 80% of ethyl acetate in heptane), 370 mg (66%) of [3-(2-tert-butoxycarbonylaminoethyl)-5-(2-chloro-3-fluorophenyl)-2,4-dioxo-3,4-dihydro-2H-pyrimidin-1-yl]-methyl acetate is obtained in the form of a beige solid.

117.3: [3-(2-tert-butoxycarbonylaminoethyl)-5-(2-chloro-3-fluorophenyl)-2,4-dioxo-3,4-dihydro-2H-pyrimidin-1-yl]-acetic acid Similarly to example 115.9, starting from 370 mg (0.8 mmol) of [3-(2-tert-butoxycarbonylaminoethyl)-5-(2-chloro-3-fluorophenyl)-2,4-dioxo-3,4-dihydro-2H-pyrimidin-1-yl]-methyl acetate, 353 mg (98%) of [3-(2-tert-butoxycarbonylaminoethyl)-5-(2-chloro-3-fluorophenyl)-2,4-dioxo-3,4-dihydro-2H-pyrimidin-1-yl]-acetic acid is obtained in the form of a yellow solid.

117.4 [2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-ethyl]-tert-butyl carbamate Similarly to example 115.10, starting from 353 mg (0.8 mmol) of [3-(2-tert-butoxycarbonylaminoethyl)-5-(2-chloro-3-fluorophenyl)-2,4-dioxo-3,4-dihydro-2H-pyrimidin-1-yl]-acetic acid and 242 mg (0.9 mmol) of 7-methoxy-3-piperidin-4-yl-1,3,4,5-tetrahydro-benzo[d][1,3]diazepin-2-one (prepared as in example 115.6), 270 mg (48%) of [2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-ethyl]-tert-butyl carbamate is obtained in the form of a colourless paste.

117.5: 3-(2-aminoethyl)-5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione Similarly to example 115.11, starting from 270 mg (13.1 mmol) of [2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-ethyl]-tert-butyl carbamate, 240 mg (104%) of 3-(2-aminoethyl)-5-(2-chloro-3-fluorophenyl)-1-{2-[4-(7-methoxy-2-oxo-1,2,4,5-tetrahydro-benzo[d][1,3]

diazepin-3-yl)-piperidin-1-yl]-2-oxo-ethyl}-1H-pyrimidine-2,4-dione is obtained in the form of a beige solid.

117.6: N-[2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-ethyl]acetamide (Compound 117)

Similarly to example 115.12, starting from 240 mg (0.4 mmol) of 3-(2-aminoethyl)-5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione and 2.5 mg (0.02 mmol) of 4-dimethylaminopyridine, 202 mg (76%) of N-[2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-ethyl]acetamide is obtained in the form of a white solid with a melting point of 266° C.

$^1$H NMR (δ, DMSO): 1.56-1.51 (1H, m), 1.73-1.65 (3H, m), 1.76 (3H, s), 2.68 (1H, t, J=12.29 Hz), 2.88 (2H, m), 3.15 (1H, t, J=11.94 Hz), 3.28-3.23 (2H, m), 3.40-3.30 (2H, m), 3.67 (3H, s), 3.95 (3H, t, J=6.79 Hz), 4.28 (1H, m), 4.43 (1H, d, J=12.86 Hz), 4.78 (2H, s), 6.68-6.62 (2H, m), 6.98 (1H, d, J=8.78 Hz), 7.22-7.20 (1H, m), 7.47-7.44 (2H, m), 7.82 (1H, s), 7.93 (1H, t, J=5.87 Hz), 8.33 (1H, s).

Another compound synthesized according to a similar procedure using the appropriate reagents, or previously prepared:

Compound 207: N-[2-(5-(2,3-dichlorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-ethyl]acetamide

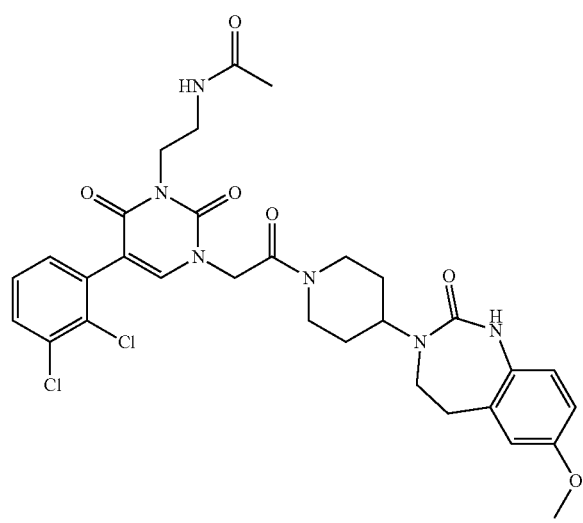 [SMILES: COc1ccc2c(c1)CCN(C1CCN(C(=O)Cn3cc(-c4cccc(Cl)c4Cl)c(=O)n(CCNC(C)=O)c3=O)CC1)C(=O)N2]

Mass=657

EXAMPLE 118: N-[2-(5-(2-CHLORO-3-FLUOROPHENYL)-3-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-2,6-DIOXO-3,6-DIHYDRO-2H-PYRIMIDIN-1-YL)-ETHYL]-N-METHYL-ACETAMIDE (REACTION SCHEME NO. 3, COMPOUND 118)

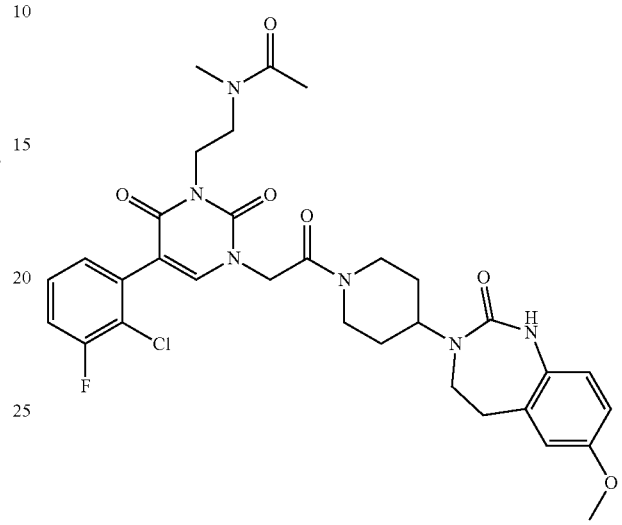

118.1: (2-chloro-ethyl)-methyl-tert-butyl carbamate 1.2 g (5.6 mmol) of di-tert-butyl dicarbonate is added to a solution containing 0.5 g (5.3 mmol) of (2-chloro-ethyl)-methylamine in 10 ml of dichloromethane. The mixture is stirred at room temperature for two hours, water is added and then the product is extracted with dichloromethane. The organic phase is dried over anhydrous sodium sulphate, then filtered and concentrated to dryness. 1 g (97%) of (2-chloro-ethyl)-methyl-tert-butyl carbamate is obtained in the form of a colourless oil.

118.2: [5-bromo-3-[2-(tert-butoxycarbonyl-methyl-amino)-ethyl]-2,4-dioxo-3,4-dihydro-2H-pyrimidin-1-yl]-methyl acetate 0.6 g (4.2 mmol) of potassium carbonate and 0.8 g (4.2 mmol) of (2-chloro-ethyl)-methyl-tert-butyl carbamate are added to a solution containing 1 g (3.8 mmol) of (5-bromo-2,4-dioxo-3,4-dihydro-2H-pyrimidin-1-yl)-methyl acetate (prepared as in example 13.1) in 13 ml of N,N-dimethylformamide. The mixture is heated at 70° C. for three hours, then water is added and the mixture is extracted twice with ethyl acetate. The organic phase is washed with water, dried over magnesium sulphate, filtered and evaporated. After purification by silica gel chromatography, 300 mg (19%) of [5-bromo-3-[2-(tert-butoxycarbonyl-methylamino)-ethyl]-2,4-dioxo-3,4-dihydro-2H-pyrimidin-1-yl]-methyl acetate is obtained in the form of a colourless oil.

118.3: [3-[2-(tert-butoxycarbonyl-methylamino)-ethyl]-5-(2-chloro-3-fluorophenyl)-2,4-dioxo-3,4-dihydro-2H-pyrimidin-1-yl]-methyl acetate Similarly to example 115.8, starting from 300 mg (0.7 mmol) of [5-bromo-3-[2-(tert-butoxycarbonyl-methylamino)-ethyl]-2,4-dioxo-3,4-dihydro-2H-pyrimidin-1-yl]-methyl acetate and 249 mg (1.4 mmol) of 2-chloro-3-fluorophenylboronic acid, and after purification by silica gel chromatography eluted with a mixture of ethyl acetate in heptane, following a polarity gradient (from 40% to 70% of ethyl acetate in heptane), 140 mg (42%) of [3-[2-(tert-butoxycarbonyl-methylamino)-ethyl]-5-(2-chloro-3-fluoro-phenyl)-2,4-dioxo-3,4-dihydro-2H-pyrimidin-1-yl]-methyl acetate is obtained in the form of a beige solid.

118.4: [3-[2-(tert-butoxycarbonyl-methylamino)-ethyl]-5-(2-chloro-3-fluorophenyl)-2,4-dioxo-3,4-dihydro-2H-pyrimidin-1-yl]-acetic acid Similarly to example 115.9, starting from 140 mg (0.3 mmol) of [3-[2-(tert-butoxycarbonyl-methylamino)-ethyl]-5-(2-chloro-3-fluorophenyl)-2,4-dioxo-3,4-dihydro-2H-pyrimidin-1-yl]-methyl acetate, 160 mg (118%) of [3-[2-(tert-butoxycarbonyl-methylamino)-ethyl]-5-(2-chloro-3-fluorophenyl)-2,4-dioxo-3,4-dihydro-2H-pyrimidin-1-yl]-acetic acid is obtained in the form of a colourless oil.

118.5: [2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-di-oxo-3,6-dihydro-2H-pyrimidin-1-yl)-ethyl]-methyl-tert-butyl carbamate Similarly to example 115.10, starting from 160 mg (0.4 mmol) of [3-[2-(tert-butoxycarbonyl-methylamino)-ethyl]-5-(2-chloro-3-fluorophenyl)-2,4-dioxo-3,4-dihydro-2H-pyrimidin-1-yl]-acetic acid and 106 mg (0.4 mmol) of 7-methoxy-3-piperidin-4-yl-1,3,4,5-tetrahydro-benzo[d][1,3]diazepin-2-one (prepared as in example 115.6), 120 mg (48%) of [2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-ethyl]-methyl-tert-butyl carbamate is obtained in the form of a colourless oil.

118.6: 5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-3-(2-methylaminoethyl)-1H-pyrimidine-2,4-dione Similarly to example 115.11, starting from 120 mg (0.2 mmol) of [2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-ethyl]-methyl-tert-butyl carbamate, 120 mg (116%) of 5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-3-(2-methylaminoethyl)-1H-pyrimidine-2,4-dione is obtained in the form of a white solid.

118.7: N-[2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-di-oxo-3,6-dihydro-2H-pyrimidin-1-yl)-ethyl]-N-methyl-acetamide (Compound 118)

0.03 ml (0.2 mmol) of triethylamine and 1 mg (0.01 mmol) of 4-dimethylaminopyridine are added to a solution containing 120 mg (0.2 mmol) of 5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-3-(2-meth-ylaminoethyl)-1H-pyrimidine-2,4-dione in 6 ml of tetrahydrofuran. The mixture is cooled to −10° C., then 0.01 ml (0.2 mmol) of acetyl chloride is added. After stirring for 30 minutes at −10° C., the mixture is poured into a saturated aqueous solution of sodium carbonate, and then extracted twice with ethyl acetate. The organic phase is dried over anhydrous sodium sulphate, then filtered and concentrated to dryness. The solid obtained is purified by silica gel chromatography eluted with a mixture of methanol in dichloromethane, following a polarity gradient (from 0% to 5% of methanol in dichloromethane). After taking up in dichloromethane and heptane, precipitation and concentration to dryness, 58 mg (45%) of N-[2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-ethyl]-N-methyl-acetamide is obtained in the form of a white solid.

$^1$H NMR (400 MHz, DMSO-d6) δ: 1.46-1.61 (m, 1H), 1.61-1.82 (m, 3H), 1.89 (s, 1.5H), 1.95 (s, 1.5H), 2.67 (m, 1H), 2.87 (m, 2H), 2.82 (s, 1.5H), 2.95 (s, 1.5H), 3.14 (m, 1H), 3.33-3.42 (m, 2H), 3.52 (m, 2H), 3.67 (s, 3H), 3.95 (m, 1H), 4.01-4.18 (m, 2H), 4.28 (m, 1H), 4.42 (d, J=12.8 Hz, 1H), 4.78 (d, J=10.3 Hz, 2H), 6.98 (d, J=8.7 Hz, 1H), 7.19 (m, 1H), 7.45 (m, 2H), 7.84 (d, J=28 Hz, 1H), 8.32 (s, 1H).

EXAMPLE 119: 3-((S)-2-AMINO-1-METHYL-ETHYL)-5-(2-CHLORO-3-FLUOROPHENYL)-1-{2-[4-(7-METHOXY-2-OXO-1,2,4,5-TETRA-HYDRO-BENZO[D][1,3]DIAZEPIN-3-YL)-PIPERIDIN-1-YL]-2-OXO-ETHYL}-1H-PYRIMIDINE-2,4-DIONE (REACTION SCHEME NO. 3, COMPOUND 119)

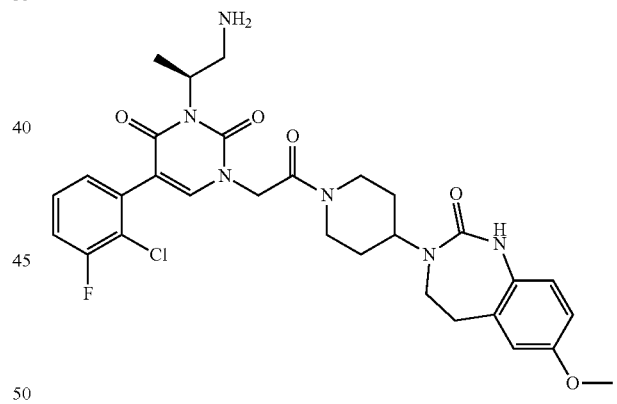

Similarly to example 115.10, starting from 280 mg (0.5 mmol) of [(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-tert-butyl carbamate (prepared as in example 115.10), and after purification by silica gel chromatography, 265 mg (95%) of 3-((S)-2-amino-1-methy-lethyl)-5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione is obtained in the form of an off-white solid with a melting point of 206° C.

$^1$H NMR (δ, DMSO): 1.34 (d, J=6.9 Hz, 3H), 1.38-1.58 (m, 3H), 1.67 (m, 3H), 2.68 (m, 1H), 2.80-2.94 (m, 3H), 3.04 (m, 1H), 3.14 (m, 1H), 3.34-3.43 (m, 2H), 3.67 (s, 3H), 3.93 (d, J=13.5 Hz, 1H), 4.19-4.35 (m, 1H), 4.43 (d, J=13.0 Hz,

1H), 4.74 (m, 2H), 4.82 (m, 1H), 6.62 (d, J=3.0 Hz, 1H), 6.67 (dd, J=8.8, 3.0 Hz, 1H), 6.98 (d, J=8.8 Hz, 1H), 7.22 (m, 1H), 7.36-7.53 (m, 2H), 7.78 (s, 1H), 8.32 (s, 1H).

EXAMPLE 120: N—[(S)-2-(5-(2-CHLORO-3-FLUOROPHENYL)-3-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-2,6-DIOXO-3,6-DIHYDRO-2H-PYRIMIDIN-1-YL)-PROPYL]-METHANESULPHONAMIDE (REACTION SCHEME NO. 3 OR 4, COMPOUND 120)

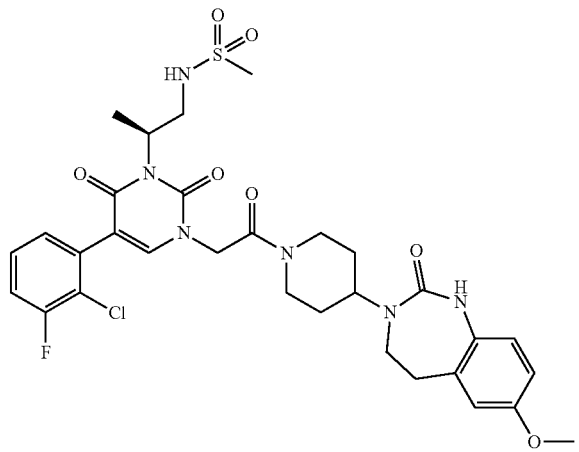 [SMILES: COc1ccc2c(c1)CCN(C1CCN(C(=O)Cn3cc(-c4cccc(F)c4Cl)c(=O)n([C@@H](C)CNS(C)(=O)=O)c3=O)CC1)C(=O)N2]

0.3 ml (3.7 mmol) of methanesulphonyl chloride and 0.5 ml (3.7 mmol) of triethylamine are added at 0° C. to a solution containing 1.5 g (2.5 mmol) of 3-((S)-2-amino-1-methylethyl)-5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione (prepared as in example 119) in 15 ml of dichloromethane. After 30 minutes, dichloromethane is added and the reaction mixture is hydrolysed with 1N aqueous solution of hydrochloric acid. The aqueous phase is extracted again with dichloromethane. The organic phase is dried over anhydrous sodium sulphate, filtered and concentrated. After purification by chromatography, taking up in pentane and filtration, 0.8 g (45%) of N—[(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-methanesulphonamide is obtained in the form of a white solid.

$^1$H NMR (δ, DMSO): 1.36 (dd, J=2.1, 7.0 Hz, 3H), 1.43-1.80 (m, 4H), 2.59-2.72 (m, 1H), 2.86 (br s, 3+2H), 3.13 (t, J=12.4 Hz, 1H), 3.34-3.40 (m, 2H), 3.46-3.63 (m, 2H), 3.66 (s, 3H), 3.94 (d, J=13.5 Hz, 1H), 4.18-4.35 (m, 1H), 4.42 (d, J=12.9 Hz, 1H), 4.66-4.82 (m, 2H), 4.88-5.16 (m, 1H), 6.61 (d, J=3.0 Hz, 1H), 6.66 (dd, J=3.0, 8.7 Hz, 1H), 6.97 (d, J=8.8 Hz, 1H), 7.15-7.30 (m, 1H), 7.38-7.51 (m, 2H), 7.80 (s, 1H), 8.34 (s, 1H).

EXAMPLE 121: 5-(2-CHLORO-3-FLUOROPHENYL)-1-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-3-[(S)-1-METHYL-2-(3-METHYL-OXETAN-3-YLAMINO)-ETHYL]-1H-PYRIMIDINE-2,4-DIONE (REACTION SCHEME NO. 3, COMPOUND 121)

121.1: [5-bromo-3-((S)-2-chloro-1-methylethyl)-2,4-dioxo-3,4-dihydro-2H-pyrimidin-1-yl]-methyl acetate 1.3 g (5.7 mmol) of di-tert-butyl azodicarboxylate is added slowly to a solution previously cooled to 0° C. containing 1 g (3.8 mmol) of (5-bromo-2,4-dioxo-3,4-dihydro-2H-pyrimidin-1-yl)-methyl acetate (prepared as in example 13.1), 0.4 ml (4.6 mmol) of (R)-1-chloro-propan-2-ol and 1.5 g (5.7 mmol) of triphenylphosphine in 20 ml of tetrahydrofuran. After stirring at room temperature for 4 hours, the tetrahydrofuran is removed under vacuum and then the residue is taken up in ethyl acetate. The organic phase is washed once with a saturated aqueous solution of sodium hydrogen carbonate, once with water and then with a saturated aqueous solution of sodium chloride, dried over magnesium sulphate, filtered and concentrated under vacuum. After purification by silica gel chromatography eluted with a mixture of ethyl acetate in heptane, following a polarity gradient (from 2% to 50% of ethyl acetate in heptane), 1.2 g (93%) of [5-bromo-3-((S)-2-chloro-1-methylethyl)-2,4-dioxo-3,4-dihydro-2H-pyrimidin-1-yl]-methyl acetate is obtained in the form of a colourless oil.

121.2: [5-bromo-3-((S)-2-hydroxy-1-methylethyl)-2,4-dioxo-3,4-dihydro-2H-pyrimidin-1-yl]-methyl acetate 1 ml (7.1 mmol) of triethylamine and 3.6 ml of methanol are added to a solution containing 1.2 g (3.5 mmol) of [5-bromo-3-((S)-2-chloro-1-methylethyl)-2,4-dioxo-3,4-dihydro-2H-pyrimidin-1-yl]-methyl acetate in 12 ml of tetrahydrofuran and 2.7 ml (151 mmol) of water. The reaction mixture is heated at 70° C. for 22 hours and then the solvents are concentrated under vacuum. 440 mg (39%) of [5-bromo- 3-((S)-2-hydroxy-1-methylethyl)-2,4-dioxo-3,4-dihydro-2H-pyrimidin-1-yl]-methyl acetate is obtained in the form of a clear oil.

121.3: [5-bromo-3-((S)-1-methyl-2-oxo-ethyl)-2,4-dioxo-3,4-dihydro-2H-pyrimidin-1-yl]-methyl acetate 697 mg (1.6 mmol) of Dess-Martin periodinane is added at room temperature to a solution containing 440 mg (1.4 mmol) of [5-bromo-3-((S)-2-hydroxy-1-methylethyl)-2,4-dioxo-3,4-dihydro-2H-pyrimidin-1-yl]-methyl acetate in 13 ml of dichloromethane. After 20 hours, water and dichloromethane are added. The organic phase is recovered and then concentrated under vacuum. 440 mg of [5-bromo-3-((S)-1-methyl-2-oxo-ethyl)-2,4-dioxo-3,4-dihydro-2H-pyrimidin-1-yl]-methyl acetate is obtained.

121.4: [5-bromo-3-[(S)-1-methyl-2-(3-methyl-oxetan-3-ylamino)-ethyl]-2,4-dioxo-3,4-dihydro-2H-pyrimidin-1-yl]-methyl acetate 440 mg (1.4 mmol) of [5-bromo-3-((S)-1-methyl-2-oxo-ethyl)-2,4-dioxo-3,4-dihydro-2H-pyrimidin-1-yl]-methyl acetate, 0.1 ml (1.4 mmol) of acetic acid and 0.1 ml (1.4 mmol) of 3-methyloxetan-3-amine are diluted in 8.8 ml of dichloromethane. 409 mg (1.9 mmol) of sodium triacetoxyborohydride and 87 mg (1.4 mmol) of sodium cyanoborohydride are then added. Stirring at room temperature is maintained for 20 hours. The mixture is then poured into 1N aqueous solution of sodium hydroxide and then extracted with dichloromethane. The organic phase is dried over anhydrous sodium sulphate, then filtered and concentrated to dryness. 220 mg (41%) of [5-bromo-3-[(S)-1-methyl-2-(3-methyl-oxetan-3-ylamino)-ethyl]-2,4-dioxo-3,4-dihydro-2H-pyrimidin-1-yl}-methyl acetate is obtained in the form of a colourless oil.

121.5: [5-(2-chloro-3-fluorophenyl)-3-[(S)-1-methyl-2-(3-methyl-oxetan-3-ylamino)-ethyl]-2,4-dioxo-3,4-dihydro-2H-pyrimidin-1-yl]-methyl acetate Similarly to example 115.8, starting from a solution containing 220 mg (0.6 mmol) of [5-bromo-3-[(S)-1-methyl-2-(3-methyl-oxetan-3-ylamino)-ethyl]-2,4-dioxo-3,4-dihydro-2H-pyrimidin-1-yl}-methyl acetate in 2.2 ml of toluene and 1.4 ml of potassium carbonate and after purification by silica gel chromatography eluted with a mixture of methanol in dichloromethane, following a polarity gradient (from 0% to 5% of methanol in dichloromethane), 30 mg (12%) of [5-(2-chloro-3-fluorophenyl)-3-[(S)-1-methyl-2-(3-methyl-oxetan-3-ylamino)-ethyl]-2,4-dioxo-3,4-dihydro-2H-pyrimidin-1-yl]-methyl acetate is obtained in the form of a yellow oil.

121.6: [5-(2-chloro-3-fluorophenyl)-3-[(S)-1-methyl-2-(3-methyl-oxetan-3-ylamino)-ethyl]-2,4-dioxo-3,4-dihydro-2H-pyrimidin-1-yl}-acetic acid Similarly to example 115.9, starting from 30 mg (0.1 mmol) of [5-(2-chloro-3-fluorophenyl)-3-[(S)-1-methyl-2-(3-methyl-oxetan-3-ylamino)-ethyl]-2,4-dioxo-3,4-dihydro-2H-pyrimidin-1-yl]-methyl acetate, 29 mg (100%) of [5-(2-chloro-3-fluorophenyl)-3-[(S)-1-methyl-2-(3-methyl-oxetan-3-ylamino)-ethyl]-2,4-dioxo-3,4-dihydro-2H-pyrimidin-1-yl}-acetic acid is obtained in the form of a brown oil.

121.7: 5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-3-[(S)-1-methyl-2-(3-methyl-oxetan-3-ylamino)-ethyl]-1H-pyrimidine-2,4-dione (Compound 121)

10 mg (0.1 mmol) of 1-oxy-pyridin-2-ol and 21 mg (0.1 mmol) of 7-methoxy-3-piperidin-4-yl-1,3,4,5-tetrahydrobenzo[d][1,3]diazepin-2-one (prepared as in example 115.6) are added to a solution containing 30 mg (0.1 mmol) of [5-(2-chloro-3-fluorophenyl)-3-[(S)-1-methyl-2-(3-methyl-oxetan-3-ylamino)-ethyl]-2,4-dioxo-3,4-dihydro-2H-pyrimidin-1-yl]-acetic acid in 0.6 ml of N,N-dimethylformamide. 17.6 mg (0.1 mmol) of 1-ethyl-3-(3-dimethylaminopropyl) carbodiimide hydrochloride is added, and stirring is maintained for 20 hours at room temperature. The mixture is poured into water and then extracted with dichloromethane. The organic phase is washed with a saturated aqueous solution of sodium hydrogen carbonate and then rinsed with water, dried over anhydrous sodium sulphate, then filtered and concentrated to dryness. After purification by silica gel chromatography eluted with a mixture of methanol in dichloromethane, following a polarity gradient (from 0% to 10% of methanol in dichloromethane), 18 mg (37%) of 5-(2-chloro-3-fluorophenyl)-1-[2-[4-(7-methoxy-2-oxo-1,2,4,5-tetrahydro-benzo[d][1,3]diazepin-3-yl)-piperidin-1-yl]-2-oxo-ethyl]-3-[(S)-1-methyl-2-(3-methyl-oxetan-3-ylamino)-ethyl]-1H-pyrimidine-2,4-dione is obtained in the form of a white solid.

$^1$H NMR (δ, DMSO): 1.33 (s; 3H); 1.36-1.39 (m; 4H); 1.53-1.56 (m; 1H); 1.65-1.75 (m; 3H); 2.68 (m; 1H); 2.87-2.92 (m; 3H); 3.02-3.07 (m; 1H); 3.12-3.22 (m; 1H); 3.36 (m; 2H); 3.67 (s; 3H); 3.94 (d; J=13.50 Hz; 1H); 4.16 (t; J=5.37 Hz; 2H); 4.28 (m; 1H); 4.39 (d; J=5.31 Hz; 2H); 4.43 (d; J=12.35 Hz; 1H); 4.74 (m; 2H); 4.89 (m; 1H); 6.62 (d; J=2.75 Hz; 1H); 6.67 (dd; J=8.79; 2.92 Hz; 1H); 6.98 (d; J=8.79 Hz; 1H); 7.20-7.22 (m; 1H); 7.43-7.46 (m; 2H); 7.78 (s; 1H); 8.32 (s; 1H).

EXAMPLE 122: 5-(2-CHLORO-3-FLUOROPHENYL)-3-((S)-2-HYDROXY-1-METHYLETHYL)-1-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-1H-PYRIMIDINE-2,4-DIONE (REACTION SCHEME NO. 3 OR 4, COMPOUND 122)

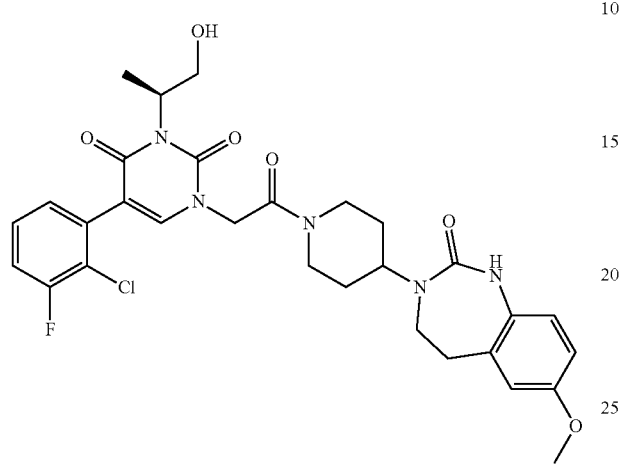

122.1: [5-(2-chloro-3-fluorophenyl)-3-((S)-2-hydroxy-1-methylethyl)-2,4-dioxo-3,4-dihydro-2H-pyrimidin-1-yl]-acetic acid Similarly to example 115.8, starting from 366 mg (2.1 mmol) of 2-chloro-3-fluorophenylboronic acid and 450 mg (1.4 mmol) of [5-bromo-3-((S)-2-hydroxy-1-methylethyl)-2,4-dioxo-3,4-dihydro-2H-pyrimidin-1-yl]-methyl acetate (prepared as in example 121.2), 500 mg (100%) of [5-(2-chloro-3-fluorophenyl)-3-((S)-2-hydroxy-1-methylethyl)-2,4-dioxo-3,4-dihydro-2H-pyrimidin-1-yl]-acetic acid is obtained.

122.2: 5-(2-chloro-3-fluorophenyl)-3-((S)-2-hydroxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione (Compound 122)

Similarly to example 115.10, starting from 110 mg (0.3 mmol) of [5-(2-chloro-3-fluorophenyl)-3-((S)-2-hydroxy-1-methylethyl)-2,4-dioxo-3,4-dihydro-2H-pyrimidin-1-yl]-acetic acid and 93 mg (0.3 mmol) of 7-methoxy-3-piperidin-4-yl-1,3,4,5-tetrahydro-benzo[d][1,3]diazepin-2-one (prepared as in example 115.6), 150 mg (78%) of 5-(2-chloro-3-fluorophenyl)-3-((S)-2-hydroxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione is obtained in the form of a white solid with a melting point of 138° C.

$^1$H NMR (δ, DMSO): 1.32 (dd, J=7.1, 2.1 Hz, 3H), 1.55 (m, 1H), 1.61-1.83 (m, 3H), 2.68 (m, 1H), 2.82-2.92 (m, 2H), 3.14 (m, 1H), 3.34-3.41 (m, 2H), 3.67 (s, 3H), 3.69 (m, 1H), 3.83 (m, 1H), 3.94 (d, J=13.7 Hz, 1H), 4.27 (m, 1H), 4.43 (d, J=13.0 Hz, 1H), 4.74 (m, 2H), 4.79 (t, J=5.7 Hz, 1H), 4.96 (h, J=6.9 Hz, 1H), 6.62 (d, J=3.0 Hz, 1H), 6.67 (dd, J=8.9, 3.0 Hz, 1H), 6.98 (d, J=8.8 Hz, 1H), 7.21 (m, 1H), 7.35-7.52 (m, 2H), 7.78 (s, 1H), 8.32 (s, 1H).

EXAMPLE 123: (S)-2-(5-(2-CHLORO-3-FLUOROPHENYL)-3-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-2,6-DIOXO-3,6-DIHYDRO-2H-PYRIMIDIN-1-YL)-PROPYL ACETATE (REACTION SCHEME NO. 3, COMPOUND 123)

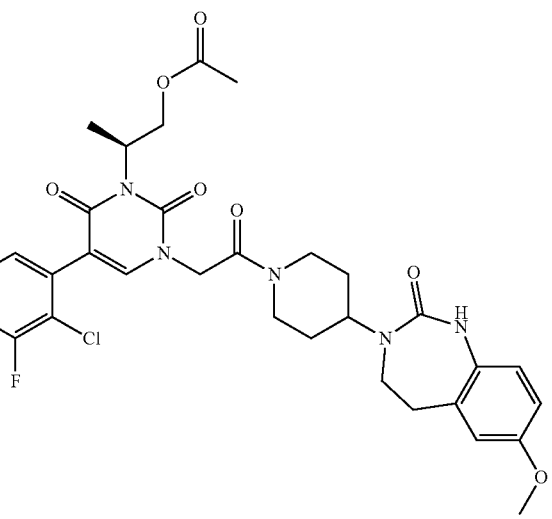

Similarly to example 115.12, starting from 80 mg (0.1 mmol) of 5-(2-chloro-3-fluorophenyl)-3-((S)-2-hydroxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione (prepared as in example 122.2), 62 mg (71%) of (S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl acetate is obtained in the form of a white solid with a melting point of 193° C.

$^1$H NMR (δ, DMSO): 1.39 (d, J=6.9 Hz, 3H), 1.55 (m, 1H), 1.70 (m, 3H), 1.97 (s, 3H), 2.68 (m, 1H), 2.78-2.93 (m, 2H), 3.14 (m, 1H), 3.34-3.43 (m, 2H), 3.67 (s, 3H), 3.93 (d, J=13.7 Hz, 1H), 4.18-4.38 (m, 2H), 4.46 (m, 2H), 4.66-4.85 (m, 2H), 5.18 (q, J=7.2 Hz, 1H), 6.62 (d, J=3.0 Hz, 1H), 6.67 (dd, J=8.7, 2.9 Hz, 1H), 6.98 (d, J=8.8 Hz, 1H), 7.22 (m, 1H), 7.37-7.55 (m, 2H), 7.82 (s, 1H), 8.32 (s, 1H).

EXAMPLE 124: 5-(2-CHLORO-3-METHOXY-PHENYL)-3-((S)-2-METHOXY-1-METHYL-ETHYL)-1-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-1H-PYRIMIDINE-2,4-DIONE (REACTION SCHEME NO. 3, COMPOUND 124)

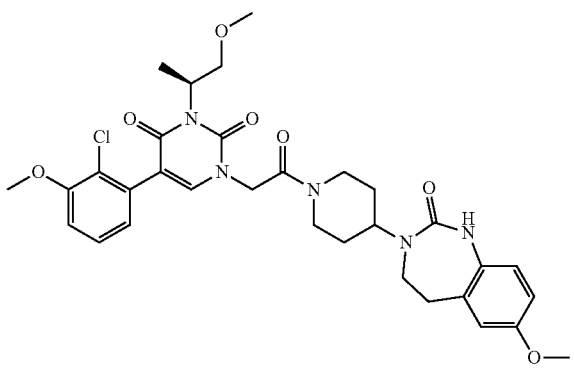

124.1: [5-bromo-3-((S)-2-methoxy-1-methylethyl)-2,4-dioxo-3,4-dihydro-2H-pyrimidin-1-yl]-methyl acetate Similarly to example 2.5, starting from 3 g (11.4 mmol) of (5-bromo-2,4-dioxo-3,4-dihydro-2H-pyrimidin-1-yl)-methyl acetate (prepared as in example 13.1) and 1.2 ml (12.6 mmol) of (R)-1-methoxy-propan-2-ol, and after purification by silica gel chromatography eluted with a mixture of ethyl acetate in heptane, following a polarity gradient (from 30% to 50% of ethyl acetate in heptane), 2.6 g (67%) of [5-bromo-3-((S)-2-methoxy-1-methylethyl)-2,4-dioxo-3,4-dihydro-2H-pyrimidin-1-yl]-methyl acetate is obtained in the form of a colourless oil.

124.2: [5-(2-chloro-3-methoxyphenyl)-3-((S)-2-methoxy-1-methylethyl)-2,4-dioxo-3,4-dihydro-2H-pyrimidin-1-yl]-acetic acid 759 mg (7.2 mmol) of sodium carbonate and 979 mg (5.3 mmol) of 2-chloro-3-methoxyphenylboronic acid are added to a solution containing 800 mg (2.4 mmol) of [5-bromo-3-((S)-2-methoxy-1-methylethyl)-2,4-dioxo-3,4-dihydro-2H-pyrimidin-1-yl]-methyl acetate in 80 ml of 1,4-dioxane and 8 ml of water. The mixture is degassed with nitrogen for 15 minutes, then 194 mg (0.2 mmol) of dichloromethane complex of 1,1'-bis(diphenylphosphino) ferrocene-dichloropalladium(II) is added and the mixture is heated at 100° C. for 2 hours. After cooling, 3.6 ml of lithium hydroxide monohydrate and 16 ml of water are added to the reaction mixture, which is left overnight. Water and ethyl acetate are added to the reaction mixture. The aqueous phase is acidified to pH4 with 1N aqueous solution of hydrochloric acid. This phase is extracted twice with ethyl acetate. The organic phase is washed with water and then with a saturated aqueous solution of sodium chloride and dried over anhydrous sodium sulphate, filtered and concentrated to dryness. 912 mg (100%) of [5-(2-chloro-3-methoxyphenyl)-3-((S)-2-methoxy-1-methylethyl)-2,4-dioxo-3,4-dihydro-2H-pyrimidin-1-yl]-acetic acid is obtained in the form of a brown oil.

124.3: 5-(2-chloro-3-methoxyphenyl)-3-((S)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione (Compound 124)

Similarly to example 115.10, starting from 415 mg (1.1 mmol) of [5-(2-chloro-3-methoxyphenyl)-3-((S)-2-methoxy-1-methylethyl)-2,4-dioxo-3,4-dihydro-2H-pyrimidin-1-yl]-acetic acid and 328 mg (1.2 mmol) of 7-methoxy-3-piperidin-4-yl-1,3,4,5-tetrahydro-benzo[d][1,3]diazepin-2-one (prepared as in example 115.6), 180 mg (26%) of 5-(2-chloro-3-methoxyphenyl)-3-((S)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione is obtained in the form of a white solid with a melting point of 269° C.

$^1$H NMR (δ, DMSO): 1.33 (d, J=6.9 Hz, 3H); 1.55-1.69 (m, 4H); 2.67-2.68 (m, 1H); 2.87 (m, 2H); 3.13 (m, 1H); 3.23 (s, 3H); 3.35-3.37 (m, 2H); 3.52-3.56 (m, 1H); 3.67 (s, 3H); 3.89 (s, 3H), 3.91 (m, 2H); 4.28 (m, 1H); 4.41-4.44 (m, 1H); 4.73 (m, 2H); 5.14 (m, 1H); 6.62 (d, J=2.9 Hz, 1H); 6.67 (dd, J=8.8, 2.9 Hz, 1H); 6.91 (dd, J=7.6, 1.4 Hz, 1H); 6.98 (d, J=8.8 Hz, 1H); 7.18 (dd, J=8.4, 1.4 Hz, 1H); 7.35 (m, 1H); 7.69 (s, 1H); 8.33 (s, 1H).

The following compounds were synthesized according to a similar procedure, starting from appropriate reagents, commercially available or previously prepared:

Compound 125: 5-(2-chloro-3-fluorophenyl)-3-((S)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

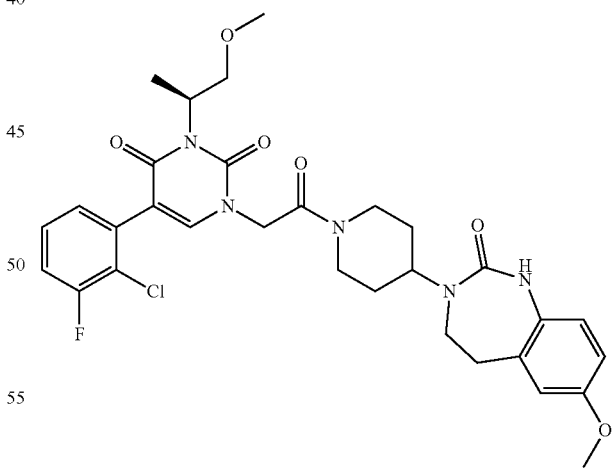

$^1$H NMR (δ, DMSO): 1.34 (d, J=6.9 Hz, 3H); 1.52-1.80 (m, 4H); 2.68 (t, J=12.4 Hz, 1H); 2.88 (m, 2H); 3.14 (t, J=12.4 Hz, 1H); 3.24 (s, 3H); 3.35-3.37 (m, 2H); 3.52-3.56 (m, 1H); 3.67 (s, 3H); 3.92 (m, 2H); 4.28 (m, 1H); 4.43 (d, J=12.8 Hz, 1H); 4.75 (s, 2H); 5.15 (m, 1H); 6.62-6.68 (m, 2H); 6.98 (d, J=8.8 Hz, 1H); 7.20-7.22 (m, 1H); 7.43-7.47 (m, 2H); 7.80 (s, 1H); 8.33 (s, 1H).

Compound 126: 5-(2,3-difluorophenyl)-3-((S)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

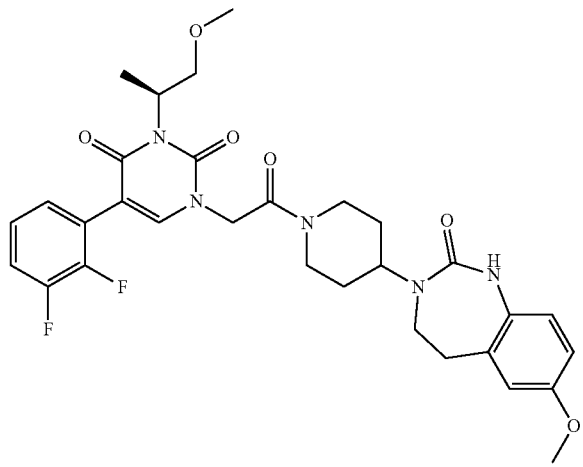 [SMILES: COC[C@H](C)n1c(=O)c(-c2cccc(F)c2F)cn(CC(=O)N2CCC(N3CCc4cc(OC)ccc4NC3=O)CC2)c1=O]

¹H NMR (δ, DMSO): 1.34 (d, J=7.0 Hz, 3H); 1.52-1.70 (m, 4H); 2.68 (t, J=12.5 Hz, 1H); 2.88 (m, 2H); 3.15 (t, J=12.4 Hz, 1H); 3.23 (s, 3H); 3.36-3.38 (m, 2H); 3.54 (dd, J=9.9, 5.9 Hz, 1H); 3.67 (s, 3H); 3.90-3.95 (m, 2H); 4.28 (m, 1H); 4.43 (d, J=12.9 Hz, 1H); 4.77 (s, 2H); 5.16 (m, 1H); 6.63-6.69 (m, 2H); 6.98 (d, J=8.8 Hz, 1H); 7.19-7.29 (m, 2H); 7.42-7.49 (m, 1H); 7.88 (s, 1H); 8.33 (s, 1H).

Compound 127: 5-(2,3-dichlorophenyl)-3-((R)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

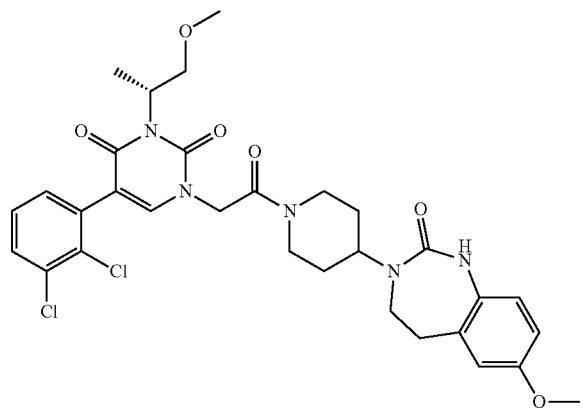 [SMILES: COC[C@@H](C)n1c(=O)c(-c2cccc(Cl)c2Cl)cn(CC(=O)N2CCC(N3CCc4cc(OC)ccc4NC3=O)CC2)c1=O]

¹H NMR (δ, DMSO): 1.33 (d, J=7.0 Hz, 3H); 1.54 (d, J=14.1 Hz, 1H); 1.67 (d, J=21.3 Hz, 3H); 2.68 (t, J=12.4 Hz, 1H); 2.87 (m, 2H); 3.15 (d, J=13.4 Hz, 1H); 3.23 (s, 3H); 3.36 (d, J=6.2 Hz, 2H); 3.54 (dd, J=9.9, 5.9 Hz, 1H); 3.67 (s, 3H); 3.90-3.95 (m, 2H); 4.28 (m, 1H); 4.43 (d, J=12.8 Hz, 1H); 4.74 (d, J=4.4 Hz, 2H); 5.14 (m, 1H); 6.62 (d, J=2.9 Hz, 1H); 6.67 (dd, J=8.8, 2.9 Hz, 1H); 6.98 (d, J=8.8 Hz, 1H); 7.33 (dd, J=7.6, 1.6 Hz, 1H); 7.42 (t, J=7.9 Hz, 1H); 7.69 (dd, J=8.0, 1.6 Hz, 1H); 7.79 (s, 1H); 8.34 (s, 1H).

Compound 128: 5-(2,3-difluorophenyl)-3-((R)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

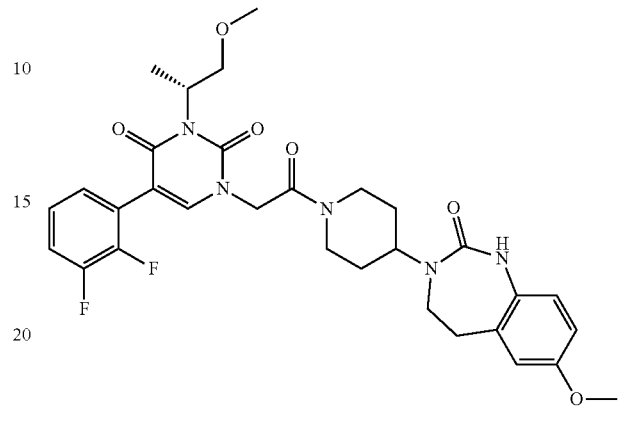

¹H NMR (δ, DMSO): 1.34 (d, J=6.9 Hz, 3H); 1.53-1.56 (m, 1H); 1.65-1.71 (m, 3H); 2.68 (t, J=12.5 Hz, 1H); 2.88 (d, J=6.5 Hz, 2H); 3.14 (t, J=10.2 Hz, 1H); 3.23 (s, 3H); 3.37 (m, 2H); 3.54 (dd, J=9.9, 5.9 Hz, 1H); 3.67 (s, 3H); 3.94 (d, J=11.6 Hz, 2H); 4.28 (m, 1H); 4.43 (d, J=12.8 Hz, 1H); 4.77 (s, 2H); 5.17 (m, 1H); 6.63-6.68 (m, 2H); 6.98 (d, J=8.8 Hz, 1H); 7.19-7.29 (m, 2H); 7.46 (q, J=8.9 Hz, 1H); 7.89 (s, 1H); 8.33 (s, 1H).

Compound 129: 5-(2,3-dimethoxyphenyl)-3-((S)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

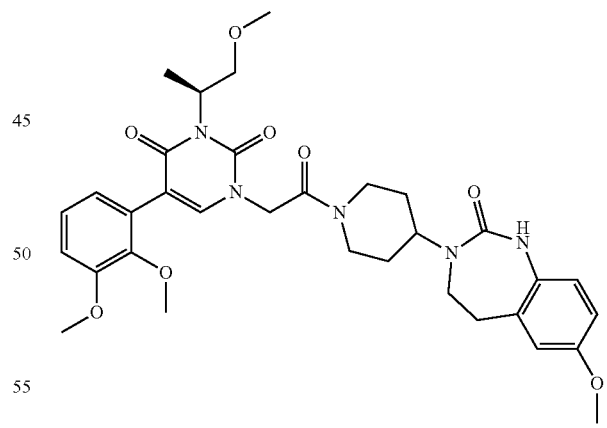

¹H NMR (δ, DMSO): 1.34 (d, J=6.9 Hz, 3H); 1.49-1.58 (m, 1H); 1.62-1.79 (m, 3H); 2.64-2.70 (m, 1H); 2.86-2.88 (m, 2H); 3.13 (t, J=12.5 Hz, 1H); 3.24 (s, 3H); 3.35-3.37 (m, 2H); 3.55 (dd, J=9.9, 5.9 Hz, 1H); 3.68 (d, J=4.4 Hz, 6H); 3.83 (s, 3H); 3.91-3.95 (m, 2H); 4.24-4.32 (m, 1H); 4.43 (d, J=12.8 Hz, 1H); 4.73 (d, J=3.6 Hz, 2H); 5.12-5.17 (m, 1H); 6.62 (d, J=2.9 Hz, 1H); 6.67 (dd, J=8.8, 2.9 Hz, 1H); 6.79 (t, J=4.6 Hz, 1H); 6.98 (d, J=8.8 Hz, 1H); 7.06-7.07 (m, 2H); 7.57 (s, 1H); 8.32 (s, 1H).

Compound 130: 5-(2-chloro-3-methoxyphenyl)-3-((R)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

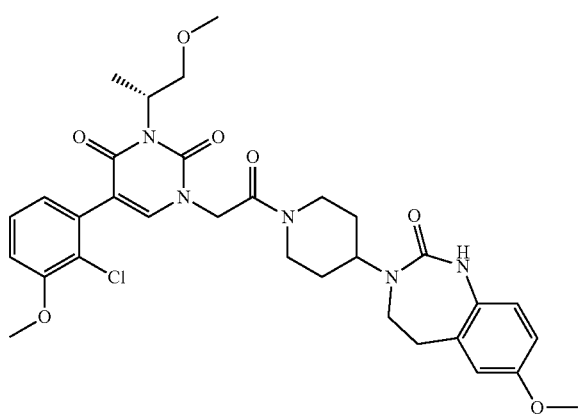 [SMILES: COC[C@@H](C)n1c(=O)c(-c2cccc(OC)c2Cl)cn(CC(=O)N2CCC(N3CCc4cc(OC)ccc4NC3=O)CC2)c1=O]

$^1$H NMR (δ, DMSO): 1.33 (d, J=6.9 Hz, 3H); 1.55 (m, 1H); 1.70 (m, 3H); 2.67 (t, J=11.9 Hz, 1H); 2.88 (d, J=6.9 Hz, 2H); 3.13 (m, 1H); 3.23 (s, 3H); 3.36 (d, J=6.6 Hz, 2H); 3.54 (dd, J=9.9, 5.9 Hz, 1H); 3.67 (s, 3H); 3.89 (s, 3H); 3.93 (m, 2H); 4.28 (m, 1H); 4.43 (d, J=12.8 Hz, 1H); 4.73 (m, 2H); 5.14 (m, 1H); 6.62-6.68 (m, 2H); 6.91 (dd, J=7.6, 1.4 Hz, 1H); 6.98 (d, J=8.8 Hz, 1H); 7.18 (dd, J=8.4, 1.4 Hz, 1H); 7.35 (t, J=8.0 Hz, 1H); 7.69 (s, 1H); 8.33 (s, 1H).

Compound 131: 5-(2-chloro-3-fluorophenyl)-3-((R)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

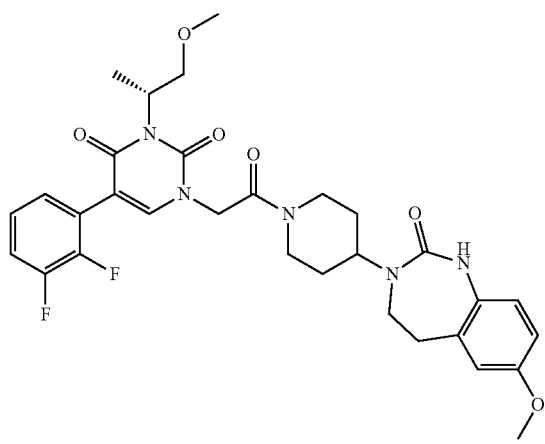 [SMILES: COC[C@@H](C)n1c(=O)c(-c2cccc(F)c2F)cn(CC(=O)N2CCC(N3CCc4cc(OC)ccc4NC3=O)CC2)c1=O]

$^1$H NMR (δ, DMSO): 1.34 (d, J=6.9 Hz, 3H); 1.53-1.56 (m, 1H); 1.65-1.70 (m, 3H); 2.68 (t, J=12.5 Hz, 1H); 2.88 (m, 2H); 3.14 (m, 1H); 3.24 (s, 3H); 3.36 (d, J=6.5 Hz, 2H); 3.54 (dd, J=9.9, 5.9 Hz, 1H); 3.67 (s, 3H); 3.92 (t, J=10.3 Hz, 2H); 4.28 (m, 1H); 4.43 (d, J=12.8 Hz, 1H); 4.75 (s, 2H); 5.15 (m, 1H); 6.62-6.68 (m, 2H); 6.98 (d, J=8.8 Hz, 1H); 7.20-7.22 (m, 1H); 7.44-7.47 (m, 2H); 7.80 (s, 1H); 8.33 (s, 1H).

Compound 132: 5-(2,3-dichlorophenyl)-3-((S)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

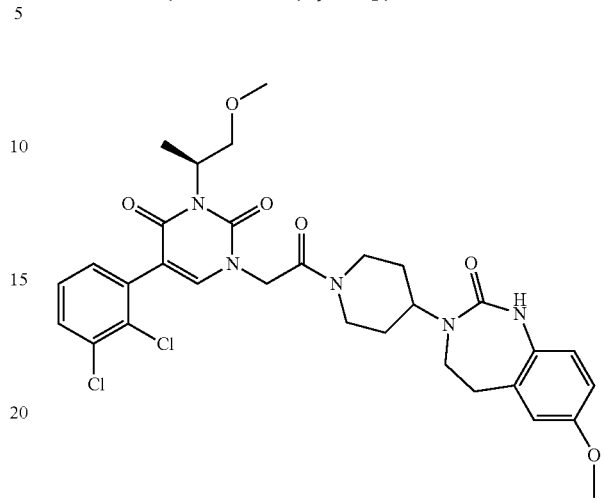

$^1$H NMR (δ, DMSO): 1.32 (d, J=6.9 Hz, 3H); 1.49-1.58 (m, 1H); 1.63-1.74 (m, 3H); 2.64-2.70 (m, 1H); 2.85-2.87 (m, 2H); 3.10-3.16 (m, 1H); 3.22 (s, 3H); 3.34-3.36 (m, 2H); 3.53 (dd, J=9.9, 5.9 Hz, 1H); 3.66 (s, 3H); 3.89-3.95 (m, 2H); 4.22-4.29 (m, 1H); 4.42 (d, J=12.8 Hz, 1H); 4.72-4.73 (m, 2H); 5.08-5.15 (m, 1H); 6.61 (d, J=2.9 Hz, 1H); 6.66 (dd, J=8.8, 2.9 Hz, 1H); 6.97 (d, J=8.8 Hz, 1H); 7.32 (dd, J=7.7, 1.6 Hz, 1H); 7.41 (t, J=7.9 Hz, 1H); 7.68 (dd, J=8.0, 1.6 Hz, 1H); 7.77 (s, 1H); 8.32 (s, 1H).

Compound 133: 5-(2,3-dimethoxyphenyl)-3-((R)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

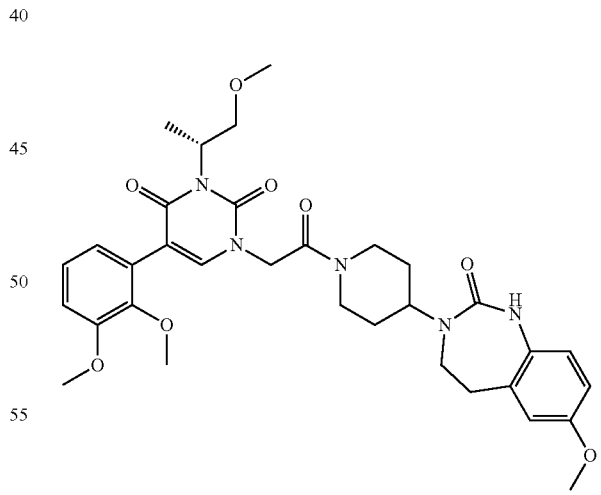

$^1$H NMR (δ, DMSO): 1.34 (d, J=6.9 Hz, 3H); 1.54 (d, J=13.8 Hz, 1H); 1.67 (br d, J=19.0 Hz, 3H); 2.68 (m, 1H); 2.87 (m, 2H); 3.13 (t, J=12.5 Hz, 1H); 3.24 (s, 3H); 3.36 (d, J=6.3 Hz, 2H); 3.55 (dd, J=9.9, 5.9 Hz, 1H); 3.68 (d, J=4.4 Hz, 6H); 3.83 (s, 3H); 3.93 (t, J=9.3 Hz, 2H); 4.28 (m, 1H); 4.43 (d, J=12.8 Hz, 1H); 4.73 (s, 2H); 5.15 (m, 1H); 6.62-6.68 (m, 2H); 6.79 (t, J=4.6 Hz, 1H); 6.98 (d, J=8.8 Hz, 1H); 7.07 (d, J=4.7 Hz, 2H); 7.57 (s, 1H); 8.33 (s, 1H).

Compound 134: 5-(3-bromo-2-fluorophenyl)-3-((R)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

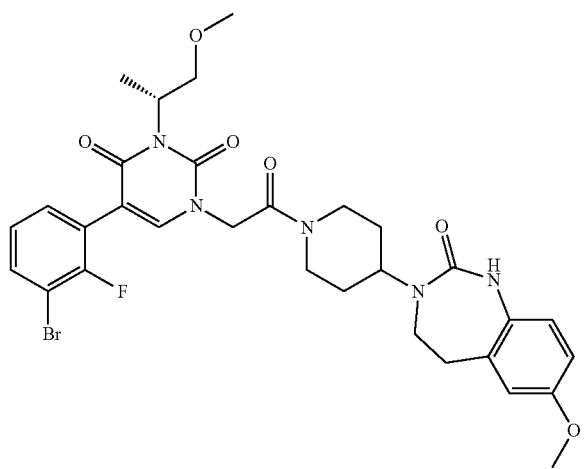 [SMILES: COC[C@@H](C)n1c(=O)c(-c2cccc(Br)c2F)cn(CC(=O)N2CCC(N3CCc4cc(OC)ccc4NC3=O)CC2)c1=O]

¹H NMR (δ, DMSO): 1.21-1.46 (m, 3H), 1.48-1.81 (m, 4H), 2.63-2.74 (m, 1H), 2.83-2.95 (m, 2H), 3.14 (t, J=11.8 Hz, 1H), 3.23 (s, 3H), 3.34-3.47 (m, 2H), 3.54 (dd, J=9.9, 5.9 Hz, 1H), 3.67 (s, 3H), 3.85-3.99 (m, 2H), 4.20-4.34 (m, 1H), 4.43 (d, J=12.9, 1H), 4.76 (s, 2H), 5.07-5.27 (m, 1H), 6.53-6.77 (m, 2H), 6.98 (d, J=8.8 Hz, 1H), 7.22 (td, J=7.8, 0.8 Hz, 1H), 7.40 (ddd, J=8.2, 6.7, 1.7 Hz, 1H), 7.72 (ddd, J=8.2, 6.7, 1.7 Hz, 1H), 7.87 (s, 1H), 8.32 (s, 1H).

EXAMPLE 135: 5-(2-CHLORO-3-FLUOROPHENYL)-3-(2-METHANESULPHONYL-ETHYL)-1-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-1H-PYRIMIDINE-2,4-DIONE (REACTION SCHEME NO. 3, COMPOUND 135)

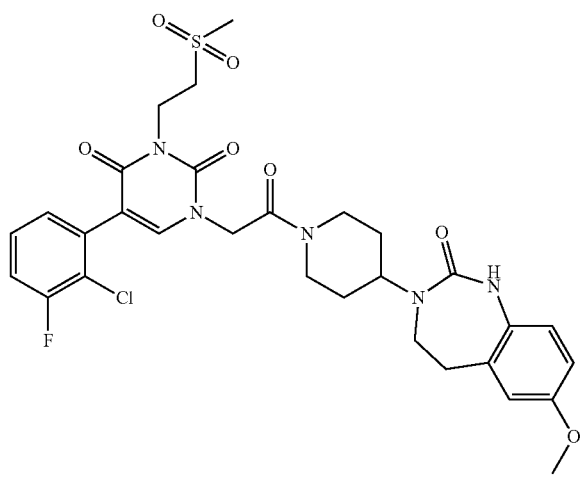 [SMILES: COc1ccc2c(c1)CCN(C1CCN(C(=O)Cn3cc(-c4cccc(F)c4Cl)c(=O)n(CCS(C)(=O)=O)c3=O)CC1)C(=O)N2]

135.1: [5-(2-chloro-3-fluorophenyl)-3-(2-methylsulphanyl-ethyl)-2,4-dioxo-3,4-dihydro-2H-pyrimidin-1-yl]-acetic acid Similarly to example 115.8, starting from 300 mg (0.9 mmol) of [5-bromo-3-(2-methylsulphanyl-ethyl)-2,4-dioxo-3,4-dihydro-2H-pyrimidin-1-yl]-methyl acetate (prepared as in example 112.1) and 171 mg (1.0 mmol) of 2-chloro-3-fluorophenylboronic acid, 320 mg (96%) of [5-(2-chloro-3-fluorophenyl)-3-(2-methylsulphanyl-ethyl)-2,4-dioxo-3,4-dihydro-2H-pyrimidin-1-yl]-acetic acid is obtained in the form of a brown solid.

135.2: 5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-3-(2-methylsulphanyl-ethyl)-1H-pyrimidine-2,4-dione Similarly to example 115.10, starting from 284 mg (1.0 mmol) of 7-methoxy-3-piperidin-4-yl-1,3,4,5-tetrahydro-benzo[d][1,3]diazepin-2-one (prepared as in example 115.6) and 320 mg (0.9 mmol) of [5-(2-chloro-3-fluorophenyl)-3-(2-methylsulphanyl-ethyl)-2,4-dioxo-3,4-dihydro-2H-pyrimidin-1-yl]-acetic acid, and after purification by silica gel chromatography eluted with a dichloromethane/methanol mixture 97/3, 325 mg (60%) of 5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-3-(2-methylsulphanyl-ethyl)-1H-pyrimidine-2,4-dione is obtained in the form of a white solid.

135.3: 5-(2-chloro-3-fluorophenyl)-3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione (Compound 135)

A mixture containing 71 mg (0.06 mmol) of ammonium molybdate tetrahydrate in 311 mg (9.2 mmol) of hydrogen peroxide is added to a solution containing 240 mg (0.4 mmol) of 5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-3-(2-methylsulphanyl-ethyl)-1H-pyrimidine-2,4-dione in 4.8 ml of ethanol. After stirring at room temperature for 46 hours, 5 ml of dichloromethane is added and the reaction mixture is stirred at room temperature for a further 48 hours. It is then hydrolysed with a saturated aqueous solution of sodium hydrogen carbonate and the product is extracted with dichloromethane. The organic phase is washed twice with 10% aqueous solution of sodium thiosulphate and once with water, dried over magnesium sulphate, filtered and concentrated under vacuum. The crude product is chromatographed on silica gel eluted with a dichloromethane/methanol mixture 97/3, the white solid obtained is taken up in 2 ml of ethyl acetate and stirred slowly at room temperature for 16 hours. The suspension obtained is filtered and rinsed once with 2 ml of diethyl ether, then dried under vacuum. 150 mg (59%) of 5-(2-chloro-3-fluorophenyl)-3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione is obtained in the form of a white solid with a melting point of 212° C.

¹H NMR (δ, DMSO): 1.45-1.61 (m, 1H), 1.70 (m, 3H), 2.68 (m, 1H), 2.80-2.93 (m, 2H), 3.08 (s, 3H), 3.14 (m, 1H), 3.36 (m, 2H), 3.41 (t, J=7.3 Hz, 2H), 3.67 (s, 3H), 3.95 (d, J=13.8 Hz, 1H), 4.31 (m, 3H), 4.42 (d, J=12.9 Hz, 1H), 4.80

(m, 2H), 6.62 (d, J=3.0 Hz, 1H), 6.67 (dd, J=8.7, 3.0 Hz, 1H), 6.98 (d, J=8.8 Hz, 1H), 7.15-7.28 (m, 1H), 7.37-7.54 (m, 2H), 7.88 (s, 1H), 8.35 (s, 1H).

The following compounds were synthesized according to a similar procedure, using the appropriate reagents, commercially available or previously prepared:

Compound 136: 5-(2,3-difluorophenyl)-3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

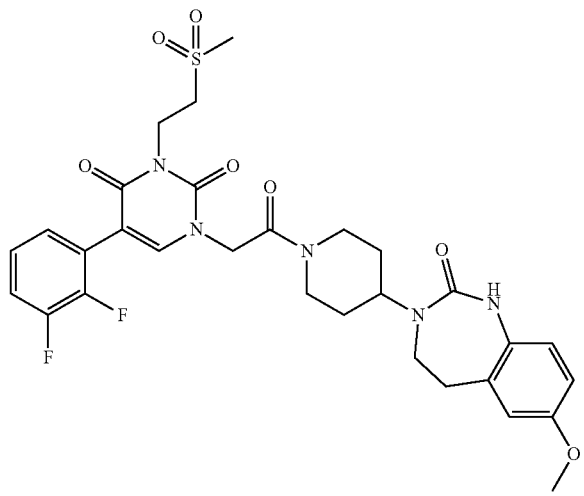 [SMILES: COc1ccc2c(c1)CCN(C1CCN(C(=O)Cn3cc(-c4cccc(F)c4F)c(=O)n(CCS(C)(=O)=O)c3=O)CC1)C(=O)N2]

¹H NMR (δ, DMSO): 1.51-1.70 (m, 4H); 2.68 (t, J=12.4 Hz, 1H); 2.88 (m, 2H); 3.09 (s, 3H); 3.15 (t, J=12.5 Hz, 1H); 3.36-3.44 (m, 4H); 3.67 (s, 3H); 3.96 (d, J=13.5 Hz, 1H); 4.31 (m, 3H); 4.42 (d, J=12.7 Hz, 1H); 4.81 (s, 2H); 6.63-6.69 (m, 2H); 6.98 (d, J=8.8 Hz, 1H); 7.22-7.31 (m, 2H); 7.44-7.51 (m, 1H); 7.97 (s, 1H); 8.35 (s, 1H).

Compound 137: 5-(2,3-dichlorophenyl)-1-[2-[4-(7-methoxy-2-oxo-4,5-dihydro-1H-1,3-benzodiazepin-3-yl)-1-piperidyl]-2-oxo-ethyl]-3-(2-methylsulphonylethyl)pyrimidine-2,4-dione

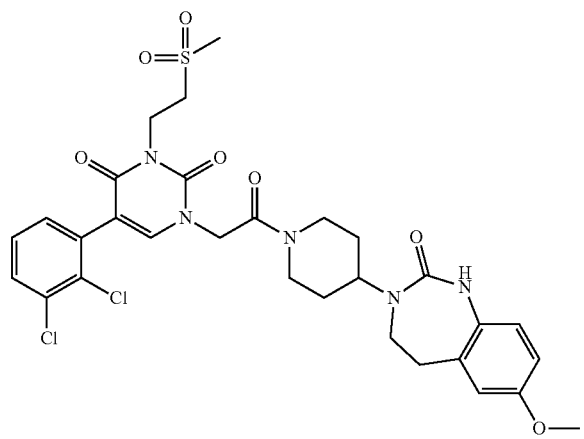 [SMILES: COc1ccc2c(c1)CCN(C1CCN(C(=O)Cn3cc(-c4cccc(Cl)c4Cl)c(=O)n(CCS(C)(=O)=O)c3=O)CC1)C(=O)N2]

¹H NMR (δ, DMSO): 1.52-1.70 (in, 4H); 2.68 (t, J=12.2 Hz, 1H); 2.88 (m, 2H); 3.08 (s, 3H); 3.15 (m, 1H); 3.36 (m, 2H); 3.41 (t, J=7.2 Hz, 2H); 3.67 (s, 3H); 3.95 (d, J=13.4 Hz, 1H); 4.29-4.33 (m, 3H); 4.43 (d, J=12.7 Hz, 1H); 4.79 (s, 2H); 6.62-6.68 (m, 2H); 6.98 (d, J=8.8 Hz, 1H); 7.33 (dd, J=7.7, 1.6 Hz, 1H); 7.44 (t, J=7.9 Hz, 1H); 7.70 (dd, J=8.1, 1.6 Hz, 1H); 7.87 (s, 1H); 8.33 (s, 1H).

Compound 138: 5-(2,3-dimethylphenyl)-3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

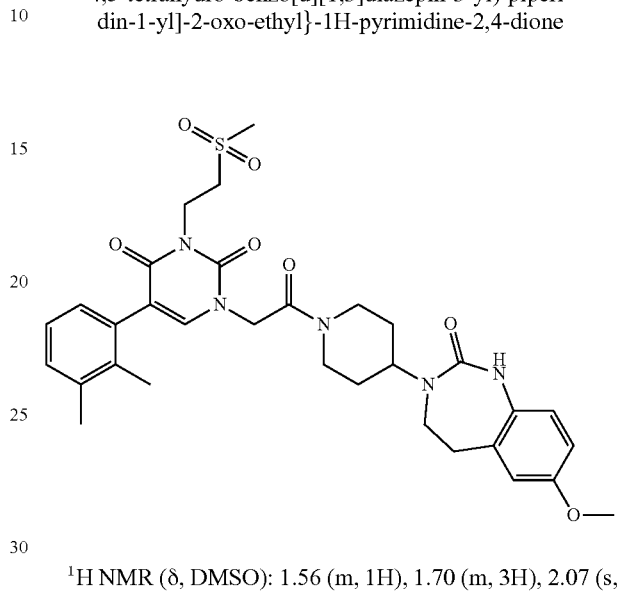

¹H NMR (δ, DMSO): 1.56 (m, 1H), 1.70 (m, 3H), 2.07 (s, 3H), 2.28 (s, 3H), 2.71 (m, 1H), 2.87 (m, 2H), 3.08 (s, 3H), 3.14 (m, 1H), 3.34-3.38 (m, 2H), 3.41 (t, J=7.1 Hz, 2H), 3.67 (s, 3H), 3.95 (d, J=13.7 Hz, 1H), 4.29 (m, 3H), 4.43 (d, J=13.0 Hz, 1H), 4.77 (m, 2H), 6.62 (d, J=2.9 Hz, 1H), 6.67 (dd, J=8.7, 2.9 Hz, 1H), 6.97 (m, 2H), 7.11 (t, J=7.5 Hz, 1H), 7.19 (d, J=7.4 Hz, 1H), 7.63 (s, 1H), 8.32 (s, 1H).

Compound 139: 5-(2,3-dimethoxyphenyl)-3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

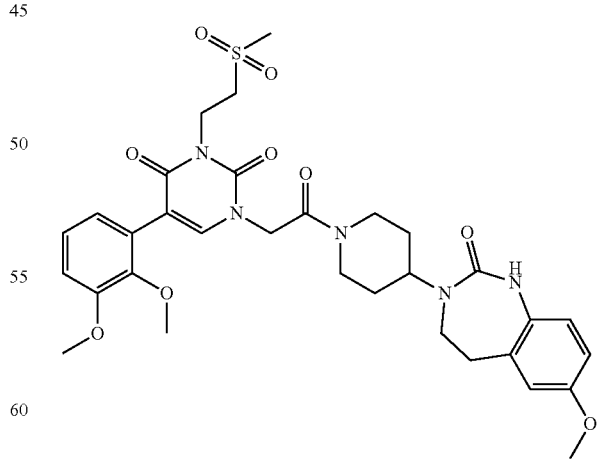

¹H NMR (δ, DMSO): 1.50-1.80 (m, 4H); 2.68 (m, 1H); 2.88 (m, 2H); 3.08 (s, 3H); 3.14 (t, J=13.0 Hz, 1H); 3.36 (m, 2H); 3.41 (t, J=7.2 Hz, 2H); 3.68 (d, J=3.5 Hz, 6H); 3.84 (s, 3H); 3.95 (d, J=13.4 Hz, 1H); 4.29-4.33 (m, 3H); 4.43 (d,

J=12.7 Hz, 1H); 4.78 (s, 2H); 6.62 (d, J=2.9 Hz, 1H); 6.67 (dd, J=8.8, 2.9 Hz, 1H); 6.81 (dd, J=5.3, 3.9 Hz, 1H); 6.98 (d, J=8.8 Hz, 1H); 7.08-7.09 (m, 2H); 7.67 (s, 1H); 8.32 (s, 1H).

Compound 140: 5-(2-chloro-3-methoxyphenyl)-3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

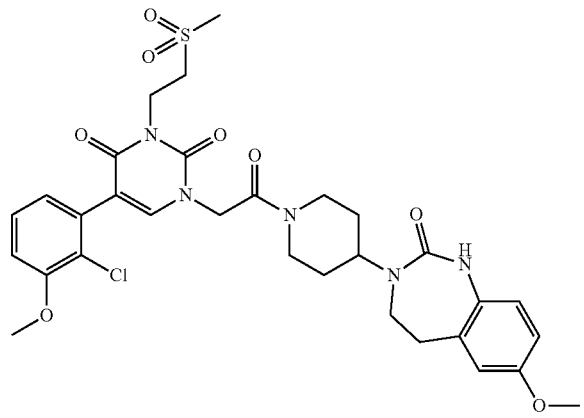 [SMILES: COc1ccc2c(c1)CCN(C1CCN(C(=O)Cn3cc(-c4cccc(OC)c4Cl)c(=O)n(CCS(C)(=O)=O)c3=O)CC1)C(=O)N2]

¹H NMR (δ, DMSO): 1.55 (1H, m), 1.68 (3H, m), 2.68 (1H, t, J=12.29 Hz), 2.88 (2H, m), 3.08 (3H, s), 3.15 (1H, t, J=12 Hz), 3.42-3.33 (4H, m), 3.67 (3H, s), 3.90 (3H, s), 3.95 (1H, d, J=14.37 Hz), 4.30 (3H, t, J=7.38 Hz), 4.43 (1H, d, J=12.88 Hz), 4.78 (2H, s), 6.68-6.62 (2H, m), 6.93-6.91 (1H, m), 6.98 (1H, d, J=8.78 Hz), 7.20 (1H, d, J=8.34 Hz), 7.36 (1H, t, J=7.98 Hz), 7.77 (1H, s), 8.33 (1H, s).

EXAMPLE 141: 3-(2-METHANESULPHONYL-ETHYL)-1-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-5-METHYL-1H-PYRIMIDINE-2,4-DIONE
(REACTION SCHEME NO. 3, COMPOUND 141)

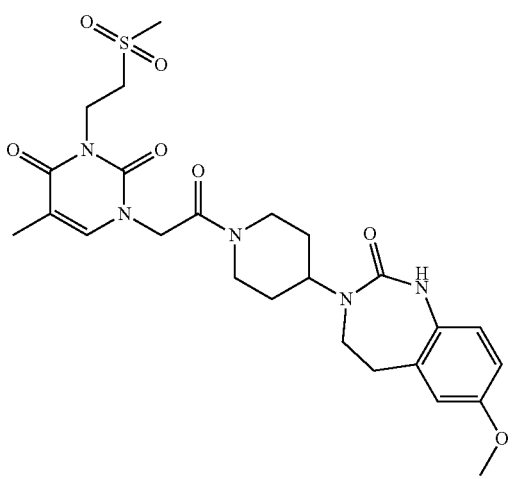 [SMILES: COc1ccc2c(c1)CCN(C1CCN(C(=O)Cn3cc(C)c(=O)n(CCS(C)(=O)=O)c3=O)CC1)C(=O)N2]

141.1: [5-bromo-3-(2-methanesulphonyl-ethyl)-2,4-dioxo-3,4-dihydro-2H-pyrimidin-1-yl]-methyl acetate Similarly to example 135.3, starting from 2.4 g (7.1 mmol) of [5-bromo-3-(2-methylsulphanyl-ethyl)-2,4-dioxo-3,4-dihydro-2H-pyrimidin-1-yl]-methyl acetate (prepared as in example 112.1), 2.2 g (82%) of [5-bromo-3-(2-methanesulphonyl-ethyl)-2,4-dioxo-3,4-dihydro-2H-pyrimidin-1-yl]-methyl acetate is obtained in the form of a white solid.

141.2: [3-(2-methanesulphonyl-ethyl)-5-methyl-2,4-dioxo-3,4-dihydro-2H-pyrimidin-1-yl]-methyl acetate 500 mg (1.4 mmol) of [5-bromo-3-(2-methanesulphonyl-ethyl)-2,4-dioxo-3,4-dihydro-2H-pyrimidin-1-yl]-methyl acetate, 562 mg (4.1 mmol) of potassium carbonate and 0.2 ml (1.4 mmol) of trimethylboroxine are dissolved in 5 ml of dioxane. The mixture is degassed with nitrogen for 5 minutes, then 111 mg (0.1 mmol) of dichloromethane complex of 1,1'-bis(diphenylphosphino)ferrocene-dichloropalladium (II) is added. The reaction mixture is heated at 100° C. for 1 hour. The mixture is poured into water and then extracted twice with ethyl acetate. The organic phase is dried over anhydrous sodium sulphate, then filtered and concentrated to dryness. After purification by silica gel chromatography eluted with a mixture of methanol in dichloromethane, following a polarity gradient (from 0% to 10% of methanol in dichloromethane), 170 mg (41%) of [3-(2-methanesulphonyl-ethyl)-5-methyl-2,4-dioxo-3,4-dihydro-2H-pyrimidin-1-yl]-methyl acetate is obtained in the form of brown oil.

141.3: [3-(2-methanesulphonyl-ethyl)-5-methyl-2,4-dioxo-3,4-dihydro-2H-pyrimidin-1-yl]-acetic acid Similarly to example 115.9, starting from 170 mg (0.6 mmol) of [3-(2-methanesulphonyl-ethyl)-5-methyl-2,4-dioxo-3,4-dihydro-2H-pyrimidin-1-yl]-methyl acetate, 130 mg (80%) of [3-(2-methanesulphonyl-ethyl)-5-methyl-2,4-dioxo-3,4-dihydro-2H-pyrimidin-1-yl]-acetic acid is obtained in the form of a brown oil.

141.4: 3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-5-methyl-1H-pyrimidine-2,4-dione (compound 141)

Similarly to example 115.10, starting from 136 mg (0.5 mmol) of 7-methoxy-3-piperidin-4-yl-1,3,4,5-tetrahydro-benzo[d][1,3]diazepin-2-one (prepared as in example 115.6) and 130 mg (0.5 mmol) of [3-(2-methanesulphonyl-ethyl)-5-methyl-2,4-dioxo-3,4-dihydro-2H-pyrimidin-1-yl]-acetic acid, and after purification by silica gel chromatography eluted with an acetonitrile/water mixture 24/76, 11 mg (4%) of 3-(2-methanesulphonyl-ethyl)-1-{2-[4-(7-methoxy-2-oxo-1,2,4,5-tetrahydro-benzo[d][1,3]diazepin-3-yl)-piperidin-1-yl]-2-oxo-ethyl}-5-methyl-1H-pyrimidine-2,4-dione is obtained in the form of a brown oil.

¹H NMR (δ, chloroform): 1.87 (m, 4H), 1.97 (s, 3H), 2.73 (t, J=12.6 Hz, 1H), 3.00 (m, 2H), 3.06 (s, 3H), 3.27 (t, J=12.8 Hz, 1H), 3.40 (t, J=6.9 Hz, 2H), 3.48 (d, J=8.9 Hz, 2H), 3.78 (s, 3H), 3.93 (d, J=13.4 Hz, 1H), 4.35 (d, J=15.8 Hz, 1H), 4.46 (t, J=7 Hz, 3H), 4.71 (d, J=13.4 Hz, 1H), 4.81 (d, J=15.9 Hz, 1H), 6.63 (t, J=1.5 Hz, 1H), 6.66-6.77 (m, 3H), 7.02 (d, J=1.8 Hz, 1H).

EXAMPLE 142: 5-(2-CHLORO-3-FLUOROPHE-NYL)-3-((S)-2-METHANESULPHONYL-1-METHYLETHYL)-1-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-1H-PYRIMIDINE-2,4-DIONE (REACTION SCHEME NO. 3, COMPOUND 142)

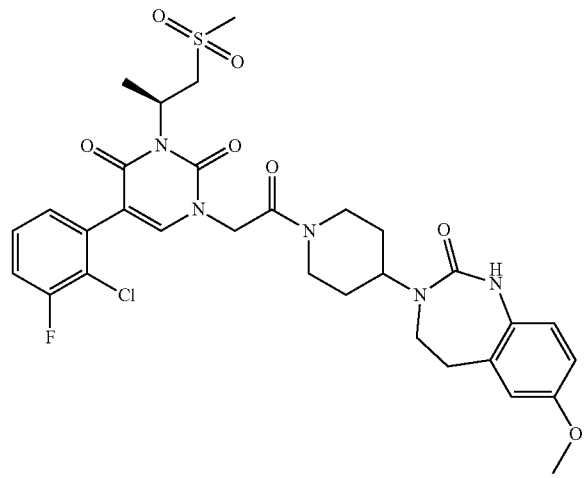 [SMILES: COc1ccc2c(c1)CCN(C1CCN(C(=O)Cn3cc(-c4cccc(F)c4Cl)c(=O)n([C@@H](C)CS(C)(=O)=O)c3=O)CC1)C(=O)N2]

142.1: (R)-1-methylsulphanyl-propan-2-ol 4.8 ml (69 mmol) of (R)-(+)-propylene-1,2 oxide is added dropwise to a solution containing 7.2 g (103.3 mmol) of sodium methanethiolate in 32 ml of acetonitrile. The mixture is agitated in a sealed tube for 4 hours at 80° C. and then diluted with water and with dichloromethane. The aqueous phase is extracted three times with dichloromethane, the organic phase is washed with water and then with brine. After drying over magnesium sulphate, the solution is filtered and then concentrated under vacuum. 3.5 g (48%) of (R)-1-methylsulphanyl-propan-2-ol is obtained in the form of an amber-coloured oil.

142.2: [5-bromo-3-((S)-1-methyl-2-methylsulphanyl-ethyl)-2,4-dioxo-3,4-dihydro-2H-pyrimidin-1-yl]-methyl acetate Similarly to example 121.1, starting from 3.7 g (14.1 mmol) of (5-bromo-2,4-dioxo-3,4-dihydro-2H-pyrimidin-1-yl)-methyl acetate (prepared as in example 13.1) and 1.5 g (14.1 mmol) of (R)-1-methylsulphanyl-propan-2-ol, 1.6 g (32%) of [5-bromo-3-((S)-1-methyl-2-methylsulphanyl-ethyl)-2,4-dioxo-3,4-dihydro-2H-pyrimidin-1-yl]-methyl acetate is obtained in the form of a viscous oil.

142.3: [5-(2-chloro-3-fluorophenyl)-3-((S)-1-methyl-2-methylsulphanyl-ethyl)-2,4-dioxo-3,4-dihydro-2H-pyrimidin-1-yl]-methyl acetate Similarly to example 115.8, starting from 1.6 g (4.6 mmol) of [5-bromo-3-((S)-1-methyl-2-methylsulphanyl-ethyl)-2,4-dioxo-3,4-dihydro-2H-pyrimidin-1-yl]-methyl acetate and 1.6 g (9.1 mmol) of 2-chloro-3-fluorophenylboronic acid, 1.7 g (93%) of [5-(2-chloro-3-fluorophenyl)-3-((S)-1-methyl-2-methylsulphanyl-ethyl)-2,4-dioxo-3,4-dihydro-2H-pyrimidin-1-yl]-methyl acetate is obtained in the form of a brown solid.

142.4: [5-(2-chloro-3-fluorophenyl)-3-((S)-2-methanesulphonyl-1-methylethyl)-2,4-dioxo-3,4-dihydro-2H-pyrimidin-1-yl]-methyl acetate 1.7 g (4.2 mmol) of 5-(2-chloro-3-fluorophenyl)-3-((S)-1-methyl-2-methylsulphanyl-ethyl)-2,4-dioxo-3,4-dihydro-2H-pyrimidin-1-yl]-methyl acetate is added to a mixture containing 262 mg (0.2 mmol) of ammonium molybdate tetrahydrate in 4.3 ml (42.4 mmol) of 30% aqueous solution of hydrogen peroxide at 0° C. After stirring for 2 hours at room temperature, the mixture is hydrolysed with 30 ml of water and then extracted with ethyl acetate. The organic phase is washed with an aqueous solution of sodium sulphate, water and then brine, dried over anhydrous magnesium sulphate and concentrated under vacuum. 1.8 g (96%) of [5-(2-chloro-3-fluorophenyl)-3-((S)-2-methanesulphonyl-1-methylethyl)-2,4-dioxo-3,4-dihydro-2H-pyrimidin-1-yl]-methyl acetate is obtained in the form of a solid.

142.5: 5-(2-chloro-3-fluorophenyl)-3-((S)-2-methanesulphonyl-1-methylethyl)-2,4-dioxo-3,4-dihydro-2H-pyrimidin-1-yl]-acetic acid 1.8 g (4.2 mmol) of [5-(2-chloro-3-fluorophenyl)-3-((R)-2-methanesulphonyl-1-methylethyl)-2,4-dioxo-3,4-dihydro-2H-pyrimidin-1-yl]-methyl acetate is added to 20 ml of tetrahydrofuran and 2.8 ml (5.5 mmol) of 1N aqueous solution of sodium hydroxide. After 2 hours, the mixture is diluted with ethyl acetate and with water, the aqueous phase is adjusted to pH 3 with 1N aqueous solution of hydrochloric acid. This phase is then extracted three times with ethyl acetate, the organic phase is washed with water and then brine. After drying over anhydrous magnesium sulphate, the solution is filtered and then concentrated under vacuum. 1.4 g (80%) of 5-(2-chloro-3-fluorophenyl)-3-((S)-2-methanesulphonyl-1-methylethyl)-2,4-dioxo-3,4-dihydro-2H-pyrimidin-1-yl]-acetic acid is obtained in the form of an oil.

142.6: 5-(2-chloro-3-fluorophenyl)-3-((S)-2-methanesulphonyl-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione (Compound 142)

Similarly to example 115.10, starting from 1.4 g (3.3 mmol) of [5-(2-chloro-3-fluorophenyl)-3-((S)-2-methanesulphonyl-1-methylethyl)-2,4-dioxo-3,4-dihydro-2H-pyrimidin-1-yl]-acetic acid and 1 g (3.7 mmol) of 7-methoxy-3-piperidin-4-yl-1,3,4,5-tetrahydro-benzo[d][1,3]diazepin-2-one (prepared as in example 115.6), 720 mg (31%) of 5-(2-chloro-3-fluorophenyl)-3-((S)-2-methanesulphonyl-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione is obtained in the form of a white solid.

$^1$H NMR (δ, DMSO): 1.23 (d, J=6.9 Hz, 3H), 1.44-1.83 (m, 4H), 2.67 (dd, J=3.5, 1.8 Hz, 1H), 2.87 (d, J=7.6 Hz, 2H), 3.05 (s, 3H), 3.09-3.21 (m, 1H), 3.32-3.40 (m, 2H), 3.52 (br s, 1H), 3.66 (s, 3H), 3.93 (d, J=13.2 Hz, 1H), 4.12-4.35 (m, 3H), 4.42 (d, J=13.1 Hz, 1H), 4.79 (s, 2H), 6.54-6.73 (m, 2H), 6.97 (d, J=8.8 Hz, 1H), 7.15-7.26 (m, 1H), 7.41-7.51 (m, 2H), 7.89 (s, 1H), 8.31 (s, 1H).

The following compounds were synthesized according to a similar procedure, using the appropriate reagents, commercially available or previously prepared:

Compound 143: 5-(2-chloro-3-fluorophenyl)-3-((R)-2-methanesulphonyl-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

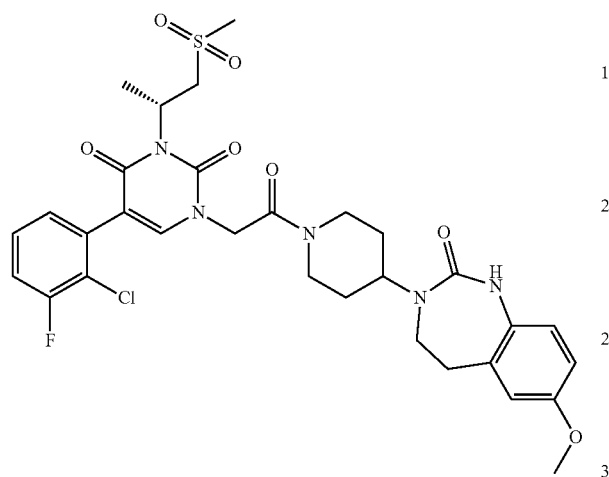

¹H NMR (δ, DMSO): 1.24 (d, J=7.0 Hz, 3H); 1.55 (m, 1H); 1.80-1.60 (m, 3H); 2.68 (t, J=12.5 Hz, 1H); 2.88 (m, 2H); 3.06 (s, 3H); 3.15 (t, J=12.5 Hz, 1H); 3.40-3.32 (m, 2H); 3.53 (m, 1H); 3.67 (s, 3H); 3.94 (d, J=13.5 Hz, 1H); 4.28-4.22 (m, 3H); 4.43 (d, J=12.8 Hz, 1H); 4.80 (s, 2H); 6.68-6.62 (m, 2H); 6.98 (d, J=8.8 Hz, 1H); 7.23 (dd, J=6.3, 2.8 Hz, 1H); 7.48-7.45 (m, 2H); 7.90 (s, 1H); 8.32 (s, 1H).

Compound 144: 5-(2,3-dichlorophenyl)-3-((S)-2-methanesulphonyl-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

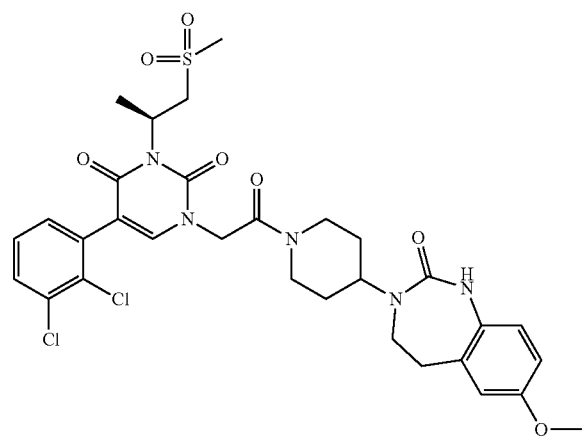 [SMILES: COc1ccc2c(c1)CCN(C1CCN(C(=O)Cn3cc(-c4cccc(Cl)c4Cl)c(=O)n([C@@H](C)CS(C)(=O)=O)c3=O)CC1)C(=O)N2]

¹H NMR (δ, DMSO): 1.24 (d, J=7.02 Hz, 3H), 1.42-1.83 (m, 4H), 2.62-2.77 (m, 1H), 2.83-2.96 (m, 2H), 3.06 (s, 3H), 3.10-3.23 (m, 1H), 3.33-3.39 (m, 2H), 3.52 (dt, J=7.17, 11.03 Hz, 1H), 3.67 (s, 3H), 3.94 (d, J=13.53 Hz, 1H), 4.13-4.38 (m, 3H), 4.43 (d, J=12.91 Hz, 1H), 4.79 (s, 2H), 6.62 (d, J=2.91 Hz, 1H), 6.67 (dd, J=2.97, 8.78 Hz, 1H), 6.98 (d, J=8.78 Hz, 1H), 7.35 (dd, J=1.59, 7.68 Hz, 1H), 7.44 (t, J=7.85 Hz, 1H), 7.71 (dd, J=1.61, 8.03 Hz, 1H), 7.89 (s, 1H), 8.33 (s, 1H).

Compound 145: 5-(2,3-dichlorophenyl)-3-((R)-2-methanesulphonyl-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

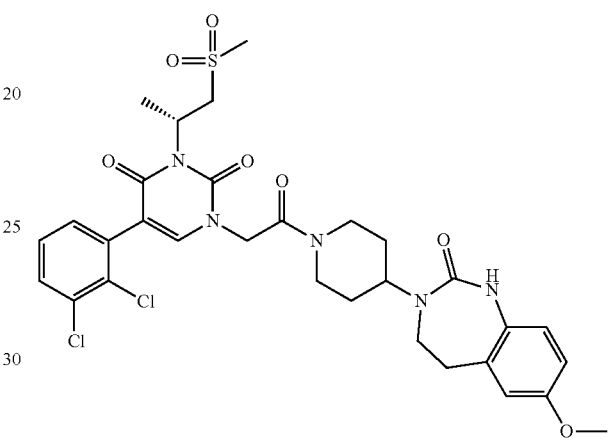

¹H NMR (δ, DMSO): 1.23 (d, J=7.02 Hz, 3H), 1.40-1.81 (m, 4H), 2.61-2.75 (m, 1H), 2.77-2.96 (m, 2H), 3.05 (s, 3H), 3.09-3.28 (m, 1H), 3.32-3.41 (m, 2H), 3.45-3.61 (m, 1H), 3.67 (s, 3H), 3.94 (d, J=13.4 Hz, 1H), 4.12-4.35 (m, 3H), 4.42 (d, J=12.9 Hz, 1H), 4.79 (br s, 2H), 6.42-6.78 (m, 2H), 6.97 (d, J=8.8 Hz, 1H), 7.34 (dd, J=1.6, 7.6 Hz, 1H), 7.44 (t, J=7.9 Hz, 1H), 7.70 (dd, J=1.57, 8.1 Hz, 1H), 7.88 (s, 1H), 8.32 (s, 1H).

EXAMPLE 146: 5-(2-CHLORO-3-FLUOROPHENYL)-3-ISOPROPYL-1-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-1H-PYRIMIDINE-2,4-DIONE (REACTION SCHEME NO. 3, COMPOUND 146)

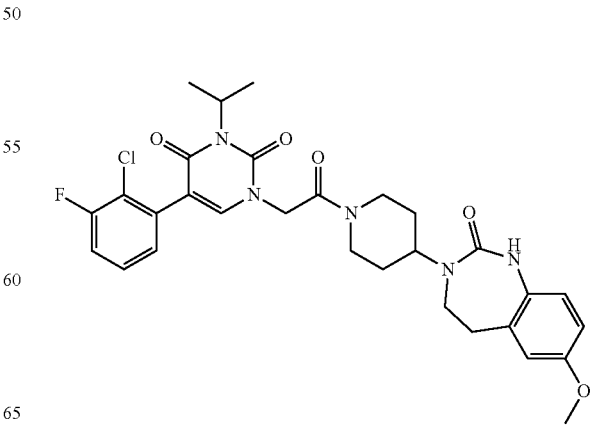

146.1: (5-bromo-3-isopropyl-2,4-dioxo-3,4-dihydro-2H-pyrimidin-1-yl)-methyl acetate 1.2 g (29.7 mmol) of sodium hydride is added in portions to a solution previously cooled to 0° C. of 6.5 g (24.7 mmol) of (5-bromo-2,4-dioxo-3,4-dihydro-2H-pyrimidin-1-yl)-methyl acetate (prepared as in example 13.1) in 130 ml of N,N-dimethylformamide. The reaction mixture is stirred for 5 minutes and then 6.3 ml (66.7 mmol) of 2-bromopropane is added. The reaction mixture is heated at 50° C. for 6 hours and then stirred at room temperature overnight. The mixture is hydrolysed and then diluted with ethyl acetate. The product is extracted with ethyl acetate, the organic phase is washed once with water and once with a saturated aqueous solution of sodium chloride, then dried over magnesium sulphate, filtered and concentrated under vacuum. After purification by silica gel chromatography eluted with a heptane/ethyl acetate 50/50 mixture, 3.5 g (46%) of (5-bromo-3-isopropyl-2,4-dioxo-3,4-dihydro-2H-pyrimidin-1-yl)-methyl acetate is obtained in the form of an off-white solid.

146.2: [5-(2-chloro-3-fluorophenyl)-3-isopropyl-2,4-dioxo-3,4-dihydro-2H-pyrimidin-1-yl]-methyl acetate Similarly to example 115.8, starting from 3.4 g (19.7 mmol) of 2-chloro-3-fluorophenylboronic acid and 3.0 g (9.8 mmol) of 5-bromo-3-isopropyl-2,4-dioxo-3,4-dihydro-2H-pyrimidin-1-yl)-methyl acetate, 1.4 g (34%) of [5-(2-chloro-3-fluorophenyl)-3-isopropyl-2,4-dioxo-3,4-dihydro-2H-pyrimidin-1-yl]-methyl acetate is obtained in the form of a beige solid.

146.3: [5-(2-chloro-3-fluorophenyl)-3-isopropyl-2,4-dioxo-3,4-dihydro-2H-pyrimidin-1-yl]-acetic acid Similarly to example 142.5, starting from 500 mg (1.4 mmol) of [5-(2-chloro-3-fluorophenyl)-3-isopropyl-2,4-dioxo-3,4-dihydro-2H-pyrimidin-1-yl]-methyl acetate, 470 mg (98%) of [5-(2-chloro-3-fluorophenyl)-3-isopropyl-2,4-dioxo-3,4-dihydro-2H-pyrimidin-1-yl]-acetic acid is obtained in the form of an oil.

146.4: 5-(2-chloro-3-fluorophenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione (compound 146)

Similarly to example 115.10, starting from 427 mg (1.6 mmol) of 7-methoxy-3-piperidin-4-yl-1,3,4,5-tetrahydro-benzo[d][1,3]diazepin-2-one (prepared as in example 115.6) and 480 mg (1.4 mmol) of [5-(2-chloro-3-fluorophenyl)-3-isopropyl-2,4-dioxo-3,4-dihydro-2H-pyrimidin-1-yl]-acetic acid, 684 mg (81%) of 5-(2-chloro-3-fluorophenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione is obtained in the form of a white solid with a melting point of 230° C.

$^1$H NMR (δ, DMSO): 1.39 (d, J=6.9 Hz, 6H); 1.51-1.69 (m, 4H); 2.66 (m, 1H); 2.85 (d, J=6.7 Hz, 2H); 3.12 (t, J=11.9 Hz, 1H); 3.36-3.33 (m, 2H); 3.66 (s, 3H); 3.89-3.93 (m, 1H); 4.24-4.30 (m, 1H); 4.41 (d, J=12.8 Hz, 1H); 4.72 (d, J=6.4 Hz, 2H); 5.05-5.12 (m, 1H); 6.60 (d, J=2.9 Hz, 1H); 6.63-6.66 (m, 1H); 6.96 (d, J=8.8 Hz, 1H); 7.20 (d, J=2.6 Hz, 1H); 7.41-7.45 (m, 2H); 7.76 (s, 1H); 8.33 (s, 1H).

The following compounds were synthesized according to a similar procedure, using the appropriate reagents, commercially available or previously prepared:

Compound 147: 5-(2,3-dimethoxyphenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

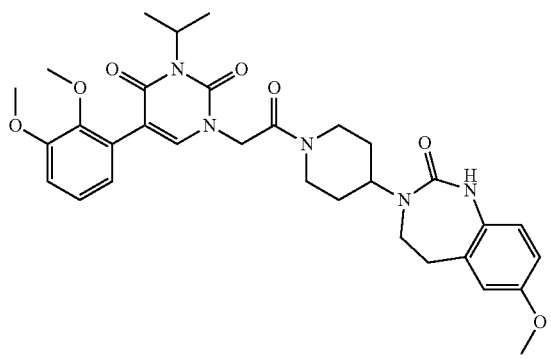

$^1$H NMR (δ, DMSO): 1.39 (6H, d, J=6.9 Hz); 1.56-1.47 (1H, m); 1.74-1.62 (3H, m); 2.65 (1H, br t, J=12.4 Hz); 2.86-2.84 (2H, m); 3.11 (1H, br t, J=12.6 Hz); 3.35-3.32 (2H, m); 3.65 (3H, s); 3.67 (3H, s); 3.81 (3H, s); 3.91 (1H, Br d, J=13.4 Hz); 4.26 (1H, tt, J=11.6, 4.2 Hz); 4.41 (1H, d, J=12.9 Hz); 4.70-4.69 (2H, m); 5.13-5.06 (1H, m); 6.60 (1H, d, J=2.9 Hz); 6.65 (1H, dd, J=8.8, 2.9 Hz); 6.77 (1H, t, J=4.6 Hz); 6.96 (1H, d, J=8.8 Hz); 7.05 (2H, d, J=4.7 Hz); 7.54 (1H, s); 8.30 (1H, s).

Compound 148: 5-(2-chloro-3-methoxyphenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

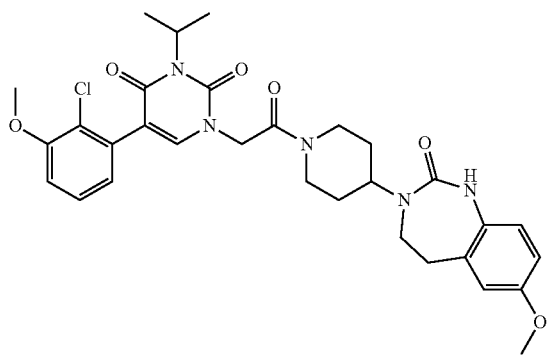

$^1$H NMR (δ, DMSO): 1.38 (6H, d, J=6.89 Hz); 1.55-1.68 (4H, m); 2.69-2.63 (1H, m); 2.85 (2H, s); 3.12 (1H, br t, J=12.3 Hz); 3.35-3.33 (2H, m); 3.65 (3H, s); 3.87 (3H, s); 3.92 (1H, m); 4.30-4.22 (1H, m); 4.41 (1H, d, J=12.9 Hz); 4.76-4.66 (2H, m); 5.11-5.04 (1H, m); 6.66-6.60 (2H, m); 6.89 (1 H, dd, J=7.6, 1.4 Hz); 6.96 (1H, d, J=8.8 Hz); 7.16 (1H, dd, J=8.4, 1.4 Hz); 7.32 (1H, t, J=8.0 Hz); 7.65 (1H, s); 8.30 (1H, s).

Compound 149: 5-(2-fluoro-3-methoxyphenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

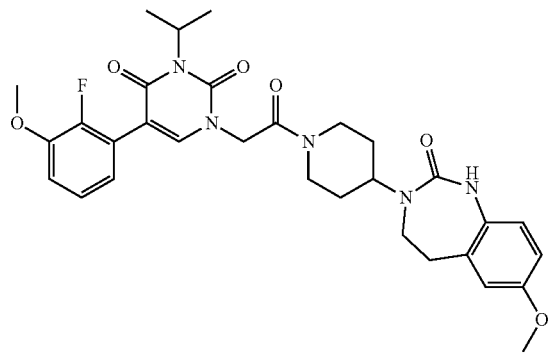 [SMILES: COc1ccc2c(c1)CCN(C1CCN(C(=O)Cn3cc(-c4cccc(F)c4Cl)c(=O)n(C(C)C)c3=O)CC1)C(=O)N2]

¹H NMR (δ, DMSO): 1.38 (6H, d, J=6.89 Hz); 1.57-1.48 (1H, m); 1.69-1.63 (3H, m); 2.65 (1H, br t, J=12.5 Hz); 2.87-2.85 (2H, m); 3.12 (1H, br t, J=12.4 Hz); 3.36-3.34 (2H, m); 3.65 (3H, s); 3.85 (3H, s); 3.91 (1H, Br d, J=13.6 Hz); 4.26 (1H, tt, J=11.5, 4.3 Hz); 4.41 (1H, d, J=12.9 Hz); 4.72 (2H, d, J=3.0 Hz); 5.13-5.06 (1H, m); 6.61 (1H, d, J=2.9 Hz); 6.65 (1H, dd, J=8.8, 3.0 Hz); 6.89-6.84 (1H, m); 6.96 (1H, d, J=8.8 Hz); 7.18-7.11 (2H, m); 7.74 (1H, s); 8.30 (1H, s).

Compound 150: 3-isopropyl-1-{2-[4-(7-methoxy-2-oxo-1,2,4,5-tetrahydro-benzo[d][1,3]diazepin-3-yl)-piperidin-1-yl]-2-oxo-ethyl}-5-(2-trifluoromethoxyphenyl)-1H-pyrimidine-2,4-dione

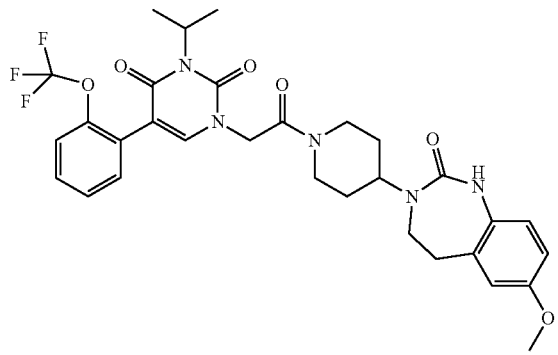 [SMILES: COc1ccc2c(c1)CCN(C1CCN(C(=O)Cn3cc(-c4ccccc4OC(F)(F)F)c(=O)n(C(C)C)c3=O)CC1)C(=O)N2]

¹H NMR (δ, DMSO): 1.38 (d, J=6.9 Hz, 6H); 1.50-1.73 (m, 4H); 2.65 (t, J=12.5 Hz, 1H); 2.86 (br s, 2H); 3.12 (t, J=12.2 Hz, 1H); 3.33-3.35 (m, 2H); 3.65 (s, 3H); 3.92 (d, J=13.6 Hz, 1H); 4.24-4.27 (m, 1H); 4.41 (d, J=12.9 Hz, 1H); 4.72 (d, J=2.6 Hz, 2H); 5.04-5.11 (m, 1H); 6.60-6.66 (m, 2H); 6.96 (d, J=8.8 Hz, 1H); 7.38-7.48 (m, 4H); 7.73 (s, 1H); 8.31 (s, 1H).

Compound 151: 3-isopropyl-1-{2-[4-(7-methoxy-2-oxo-1,2,4,5-tetrahydro-benzo[d][1,3]diazepin-3-yl)-piperidin-1-yl]-2-oxo-ethyl}-5-(3-trifluoromethoxyphenyl)-1H-pyrimidine-2,4-dione

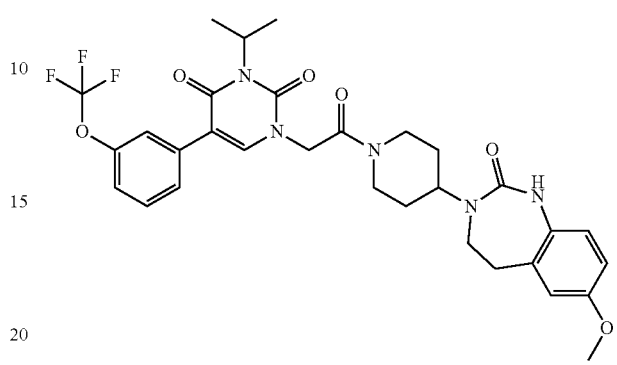

¹H NMR (δ, DMSO): 1.40 (d, J=6.9 Hz, 6H); 1.50-1.68 (m, 4H); 2.63-2.69 (m, 1H); 2.87 (br s, 2H); 3.10-3.17 (m, 1H); 3.35-3.37 (m, 2H); 3.65 (s, 3H); 3.94 (d, J=13.5 Hz, 1H); 4.23-4.31 (m, 1H); 4.41 (d, J=12.9 Hz, 1H); 4.76 (br s, 2H); 5.10-5.17 (m, 1H); 6.61-6.67 (m, 2H); 6.96 (d, J=8.8 Hz, 1H); 7.31 (d, J=8.0 Hz, 1H); 7.51-7.59 (m, 3H); 7.99 (s, 1H); 8.32 (s, 1H).

Compound 152: 3-isopropyl-1-{2-[4-(7-methoxy-2-oxo-1,2,4,5-tetrahydro-benzo[d][1,3]diazepin-3-yl)-piperidin-1-yl]-2-oxo-ethyl}-5-(3-methoxy-2-trifluoromethoxyphenyl)-1H-pyrimidine-2,4-dione

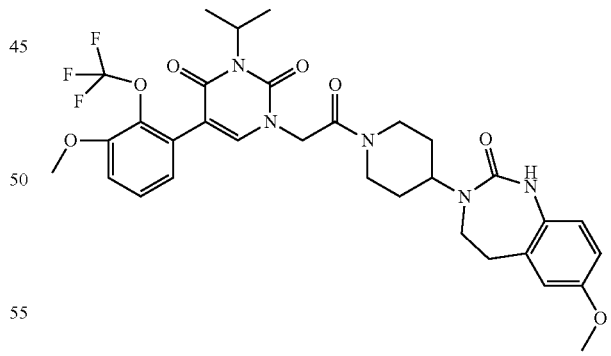

¹H NMR (δ, DMSO): 1.37 (d, J=6.9 Hz, 6H); 1.49-1.72 (m, 4H); 2.62-2.68 (m, 1H); 2.85-2.87 (m, 2H); 3.06-3.14 (m, 1H); 3.33-3.35 (m, 2H); 3.65 (s, 3H); 3.86 (s, 3H); 3.92 (d, J=13.3 Hz, 1H); 4.24 (d, J=11.7 Hz, 1H); 4.41 (d, J=13.0 Hz, 1H); 4.71 (d, J=3.3 Hz, 2H); 5.04-5.11 (m, 1H); 6.60-6.66 (m, 2H); 6.89-6.96 (m, 2H); 7.24 (dd, J=8.4, 1.5 Hz, 1H); 7.37 (t, J=8.0 Hz, 1H); 7.71 (s, 1H); 8.31 (s, 1H).

Compound 153: 5-(2,3-difluorophenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

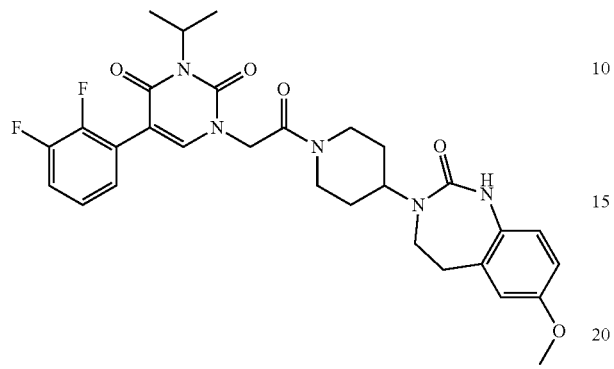

¹H NMR (δ, DMSO): 1.39 (d, J=6.9 Hz, 6H); 1.50-1.73 (m, 4H); 2.66 (t, J=12.4 Hz, 1H); 2.86 (br s, 2H); 3.13 (t, J=12.1 Hz, 1H); 3.34-3.36 (m, 2H); 3.65 (s, 3H); 3.92 (d, J=13.5 Hz, 1H); 4.21-4.27 (m, 1H); 4.41 (d, J=12.9 Hz, 1H); 4.74 (s, 2H); 5.06-5.13 (m, 1H); 6.61-6.67 (m, 2H); 6.96 (d, J=8.8 Hz, 1H); 7.17-7.27 (m, 2H); 7.40-7.48 (m, 1H); 7.85 (s, 1H); 8.31 (s, 1H).

Compound 154: 5-(2-chloro-3-ethoxyphenyl)-3-isopropyl-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

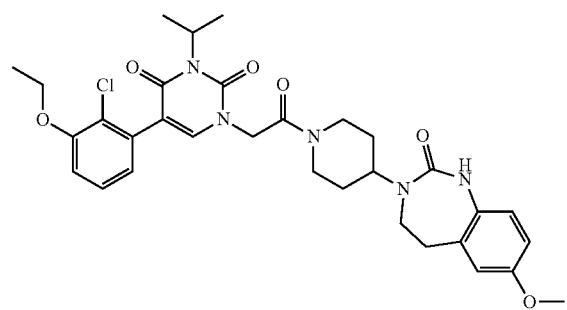 [SMILES: CCOc1cccc(-c2cn(CC(=O)N3CCC(N4CCc5cc(OC)ccc5NC4=O)CC3)c(=O)n(C(C)C)c2=O)c1Cl]

¹H NMR (δ, DMSO): 1.36-1.41 (m, 9H); 1.53-1.68 (m, 4H); 2.67-2.68 (m, 1H); 2.87 (m, 2H); 3.14 (m, 1H); 3.37 (m, 2H); 3.67 (s, 3H); 3.93 (d, J=13.4 Hz, 1H); 4.15 (q, J=7.0 Hz, 2H); 4.28 (m, 1H); 4.43 (d, J=12.7 Hz, 1H); 4.71-4.73 (m, 2H); 5.08-5.11 (m, 1H); 6.62-6.68 (m, 2H); 6.89 (dd, J=7.6, 1.4 Hz, 1H); 6.98 (d, J=8.8 Hz, 1H); 7.16 (dd, J=8.4, 1.4 Hz, 1H); 7.31 (t, J=8.0 Hz, 1H); 7.66 (s, 1H); 8.33 (s, 1H).

EXAMPLE 155: 5-(2-CHLORO-3-FLUOROPHENYL)-1-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-3-(2-METHYLSULPHANYL-ETHYL)-1H-PYRIMIDINE-2,4-DIONE (REACTION SCHEME NO. 3, COMPOUND 155)

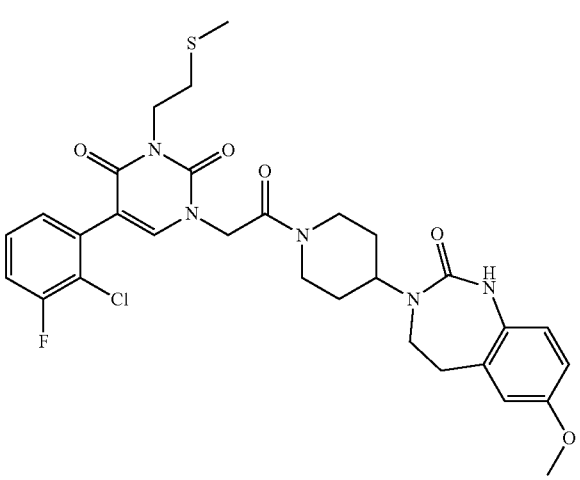 [SMILES: COc1ccc2c(c1)CCN(C1CCN(C(=O)Cn3cc(-c4cccc(F)c4Cl)c(=O)n(CCSC)c3=O)CC1)C(=O)N2]

Similarly to example 115.10, starting from 284 mg (1 mmol) of 7-methoxy-3-piperidin-4-yl-1,3,4,5-tetrahydro-benzo[d][1,3]diazepin-2-one (prepared as in example 115.6) and 320 mg (0.9 mmol) of [5-(2-chloro-3-fluorophenyl)-3-(2-methylsulphanyl-ethyl)-2,4-dioxo-3,4-dihydro-2H-pyrimidin-1-yl]-acetic acid (prepared as in example 125.1), 325 mg (60%) of 5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-3-(2-methylsulphanyl-ethyl)-1H-pyrimidine-2,4-dione is obtained in the form of a white solid with a melting point of 230° C.

¹H NMR (δ, DMSO): 1.50-1.80 (m, 4H); 2.12 (s, 3H); 2.65-2.71 (m, 3H); 2.88 (m, 2H); 3.15 (t, J=12.1 Hz, 1H); 3.35-3.37 (m, 2H); 3.67 (s, 3H); 3.94 (d, J=13.6 Hz, 1H); 4.08 (t, J=7.2 Hz, 2H); 4.22-4.32 (m, 1H); 4.43 (d, J=12.8 Hz, 1H); 4.79 (s, 2H); 6.62 (d, J=2.9 Hz, 1H); 6.67 (dd, J=8.8, 2.9 Hz, 1H); 6.98 (d, J=8.8 Hz, 1H); 7.21-7.23 (m, 1H); 7.40-7.50 (m, 2H); 7.85 (s, 1H); 8.33 (s, 1H).

EXAMPLE 156: 5-(2-CHLORO-3-FLUOROPHENYL)-3-(3-METHANESULPHONYL-PROPYL)-1-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-1H-PYRIMIDINE-2,4-DIONE (REACTION SCHEME NO. 3, COMPOUND 156)

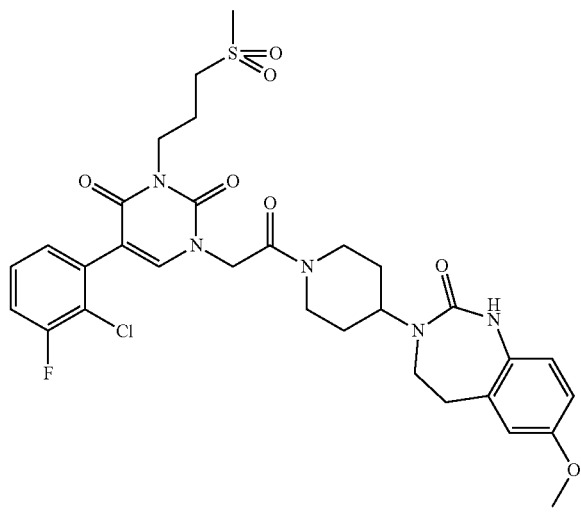 [SMILES: COc1ccc2c(c1)CCN(C1CCN(C(=O)Cn3cc(-c4cccc(F)c4Cl)c(=O)n(CCCS(C)(=O)=O)c3=O)CC1)C(=O)N2]

156.1: [5-bromo-3-(3-methylsulphanyl-propyl)-2,4-dioxo-3,4-dihydro-2H-pyrimidin-1-yl]-methyl acetate Similarly to example 121.1, starting from 3 g (11.4 mmol) of (5-bromo-2,4-dioxo-3,4-dihydro-2H-pyrimidin-1-yl)-methyl acetate (prepared as in example 13.1) and 1.4 ml (13.7 mmol) of 3-methylthiopropanol, 3.5 g (87%) of [5-bromo-3-(3-methylsulphanyl-propyl)-2,4-dioxo-3,4-dihydro-2H-pyrimidin-1-yl]-methyl acetate is obtained in the form of a white solid.

156.2: [5-(2-chloro-3-fluorophenyl)-3-(3-methylsulphanyl-propyl)-2,4-dioxo-3,4-dihydro-2H-pyrimidin-1-yl]-methyl acetate Similarly to example 115.8, starting from 695 mg (4 mmol) of 2-chloro-3-fluorophenylboronic acid and 1 g (2.9 mmol) of [5-bromo-3-(3-methylsulphanyl-propyl)-2,4-dioxo-3,4-dihydro-2H-pyrimidin-1-yl]-methyl acetate, 750 mg (66%) of [5-(2-chloro-3-fluorophenyl)-3-(3-methylsulphanyl-propyl)-2,4-dioxo-3,4-dihydro-2H-pyrimidin-1-yl]-methyl acetate is obtained in the form of a colourless oil.

156.3: [5-(2-chloro-3-fluorophenyl)-3-(3-methanesulphonyl-propyl)-2,4-dioxo-3,4-dihydro-2H-pyrimidin-1-yl]-methyl acetate Similarly to example 125.3, starting from 750 mg (1.9 mmol) of [5-(2-chloro-3-fluorophenyl)-3-(3-methylsulphanyl-propyl)-2,4-dioxo-3,4-dihydro-2H-pyrimidin-1-yl]-methyl acetate, 810 mg (100%) of [5-(2-chloro-3-fluorophenyl)-3-(3-methanesulphonyl-propyl)-2,4-dioxo-3,4-dihydro-2H-pyrimidin-1-yl]-methyl acetate is obtained in the form of a beige meringue.

156.4: [5-(2-chloro-3-fluorophenyl)-3-(3-methanesulphonyl-propyl)-2,4-dioxo-3,4-dihydro-2H-pyrimidin-1-yl]-acetic acid Similarly to example 115.9, starting from 810 mg (1.9 mmol) of [5-(2-chloro-3-fluorophenyl)-3-(3-methanesulphonyl-propyl)-2,4-dioxo-3,4-dihydro-2H-pyrimidin-1-yl]-methyl acetate, 750 mg (96%) of [5-(2-chloro-3-fluorophenyl)-3-(3-methanesulphonyl-propyl)-2,4-dioxo-3,4-dihydro-2H-pyrimidin-1-yl]-acetic acid is obtained in the form of a beige meringue.

156.5: 5-(2-chloro-3-fluorophenyl)-3-(3-methanesulphonyl-propyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione (Compound 156)

Similarly to example 115.10, starting from 226 mg (0.9 mmol) of 7-methoxy-3-piperidin-4-yl-1,3,4,5-tetrahydro-benzo[d][1,3]diazepin-2-one (prepared as in example 115.6) and 343 mg (0.8 mmol) of [5-(2-chloro-3-fluorophenyl)-3-(3-methanesulphonyl-propyl)-2,4-dioxo-3,4-dihydro-2H-pyrimidin-1-yl]-acetic acid, 400 mg (72%) of 5-(2-chloro-3-fluorophenyl)-3-(3-methanesulphonyl-propyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione is obtained in the form of a white solid with a melting point of 189° C.

$^1$H NMR (δ, DMSO): 1.53-1.70 (m, 4H); 1.96-2.04 (m, 2H); 2.68 (t, J=12.4 Hz, 1H); 2.88 (m, 2H); 2.98 (s, 3H); 3.15-3.19 (m, 3H); 3.35-3.37 (m, 2H); 3.67 (s, 3H); 3.94 (d, J=13.7 Hz, 1H); 4.01 (t, J=7.1 Hz, 2H); 4.28 (m, 1H); 4.43 (d, J=12.9 Hz, 1H); 4.79 (s, 2H); 6.63 (d, J=2.9 Hz, 1H); 6.67 (dd, J=8.8, 3.0 Hz, 1H); 6.98 (d, J=8.8 Hz, 1H); 7.23-7.25 (m, 1H); 7.44-7.47 (m, 2H); 7.86 (s, 1H); 8.33 (s, 1H).

EXAMPLE 157: 5-(2-CHLORO-3-FLUOROPHENYL)-1-[2-[4-(7-METHOXY-2-OXO-4,5-DIHYDRO-1H-1,3-BENZODIAZEPIN-3-YL)-1-PIPERIDYL]-2-OXO-ETHYL]-3-[2-(METHYLSULPHONIMIDOYL)ETHYL]PYRIMIDINE-2,4-DIONE (REACTION SCHEME NO. 3, COMPOUND 157)

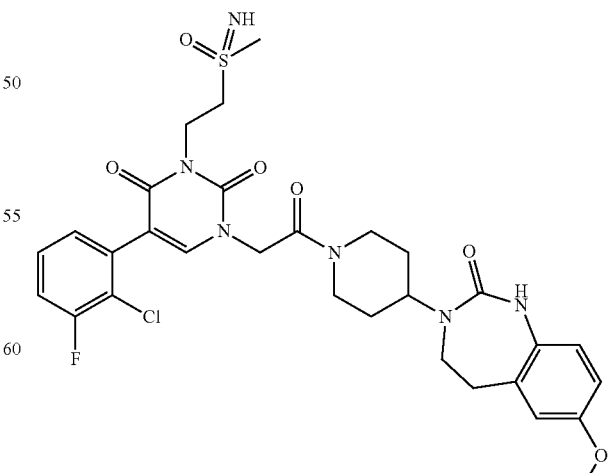

157.1: [5-(2-chloro-3-fluorophenyl)-3-(2-methylsulphanyl-ethyl)-2,4-dioxo-3,4-dihydro-2H-pyrimidin-1-yl]-methyl acetate Similarly to example 115.8, starting from 1.9 g (11.1 mmol) of 2-chloro-3-fluorophenylboronic acid and 2.5 g (7.4 mmol) of [5-bromo-3-(2-methylsulphanyl-ethyl)-2,4-dioxo-3,4-dihydro-2H-pyrimidin-1-yl]-methyl acetate (prepared as in example 112.1), 2.2 g (77%) of [5-(2-chloro-3-fluorophenyl)-3-(2-methylsulphanyl-ethyl)-2,4-dioxo-3,4-dihydro-2H-pyrimidin-1-yl]-methyl acetate is obtained in the form of an off-white solid.

157.2: [5-(2-chloro-3-fluorophenyl)-3-(2-methanesulphinyl-ethyl)-2,4-dioxo-3,4-dihydro-2H-pyrimidin-1-yl]-methyl acetate 0.9 g (4.1 mmol) of 3-chloroperoxybenzoic acid is added to a solution cooled to 0° C. containing 1.5 g (3.9 mmol) of [5-(2-chloro-3-fluorophenyl)-3-(2-methylsulphanyl-ethyl)-2,4-dioxo-3,4-dihydro-2H-pyrimidin-1-yl]-methyl acetate in 30 ml of dichloromethane. The mixture is then left to return slowly to room temperature. 20 ml of 1N aqueous solution of sodium hydroxide is added dropwise at 10° C. to 20 ml of water and then the reaction mixture is decanted. The aqueous phase is extracted twice with dichloromethane. The organic phase is washed with an aqueous solution of sodium thiosulphate, dried over magnesium sulphate, filtered and evaporated. The oil obtained is precipitated with dichloromethane and heptane. The solid is filtered, rinsed with heptane and dried. 1.4 g (90%) of [5-(2-chloro-3-fluorophenyl)-3-(2-methanesulphinyl-ethyl)-2,4-dioxo-3,4-dihydro-2H-pyrimidin-1-yl]-methyl acetate is obtained in the form of a white solid.

157.3: 2-[5-(2-chloro-3-fluorophenyl)-3-[2-(methylsulphonimidoyl)ethyl]-2,4-dioxo-pyrimidin-1-yl] methyl acetate 1.7 g (5.2 mmol) of iodobenzene diacetate is added to a solution containing 1.4 g (3.5 mmol) of [5-(2-chloro-3-fluorophenyl)-3-(2-methanesulphinyl-ethyl)-2,4-dioxo-3,4-dihydro-2H-pyrimidin-1-yl]-methyl acetate, 786 mg (7 mmol) of 2,2,2-trifluoroacetamide, 560 mg (13.9 mmol) of magnesium oxide and 184 mg (0.4 mmol) of dirhodium tetraacetate in 42 ml of dichloromethane. The mixture is stirred at room temperature for 4 hours, then filtered and evaporated. The residue is taken up in 42 ml of methanol, and then 2.4 g (17.4 mmol) of potassium carbonate is added. The mixture is stirred at room temperature for 30 minutes, then the methanol is evaporated and the residue is taken up in ethyl acetate and then water. The aqueous phase is extracted twice with ethyl acetate. The organic phase is washed with water, dried over magnesium sulphate, filtered and evaporated. After purification by silica gel chromatography eluted with ethyl acetate and then with 10% methanol, 460 mg (32%) of 2-[5-(2-chloro-3-fluorophenyl)-3-[2-(methylsulphonimidoyl)ethyl]-2,4-dioxo-pyrimidin-1-yl] methyl acetate is obtained in the form of a pale yellow solid.

157.4: 2-[5-(2-chloro-3-fluorophenyl)-3-[2-(methylsulphonimidoyl)ethyl]-2,4-dioxo-pyrimidin-1-yl] acetic acid Similarly to example 115.9, starting from 180 mg (0.4 mmol) of 2-[5-(2-chloro-3-fluorophenyl)-3-[2-(methylsulphonimidoyl)ethyl]-2,4-dioxo-pyrimidin-1-yl]methyl acetate, a certain amount of 2-[5-(2-chloro-3-fluorophenyl)-3-[2-(methylsulphonimidoyl)ethyl]-2,4-dioxo-pyrimidin-1-yl]acetic acid is obtained in the form of a pale yellow solid.

157.5: 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-[2-(methylsulphonimidoyl)ethyl]pyrimidine-2,4-dione (Compound 157)

Similarly to example 115.10, starting from 113 mg (0.4 mmol) of 7-methoxy-3-piperidin-4-yl-1,3,4,5-tetrahydro-benzo[d][1,3]diazepin-2-one (prepared as in example 115.6) and 150 mg (0.4 mmol) of 2-[5-(2-chloro-3-fluorophenyl)-3-[2-(methylsulphonimidoyl)ethyl]-2,4-dioxo-pyrimidin-1-yl]acetic acid, and after purification by chromatography on eluted silica gel, 23 mg (9%) of 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-[2-(methylsulphonimidoyl)ethyl]pyrimidine-2,4-dione is obtained in the form of a pale pink solid with a melting point of 197° C.

$^1$H NMR (δ, DMSO): 1.55 (m, 1H), 1.61-1.83 (m, 3H), 2.65 (m, 1H), 2.88 (m, 2H), 2.98 (s, 3H), 3.07-3.22 (m, 1H), 3.67 (s, 3H), 3.84 (s, 1H), 3.95 (d, J=13.7 Hz, 1H), 4.28 (m, 3H), 4.43 (d, J=13.0 Hz, 1H), 4.79 (m, 2H), 6.62 (d, J=2.9 Hz, 1H), 6.67 (dd, J=8.6, 3.0 Hz, 1H), 6.98 (d, J=8.9 Hz, 1H), 7.22 (m, 1H), 7.37-7.56 (m, 2H), 7.87 (s, 1H), 8.32 (s, 1H). The 4 missing protons are beneath the peak of water and/or of DMSO.

EXAMPLE 158: N—[(S)-2-(5-(2-CHLORO-3-FLUOROPHENYL)-3-{2-[4-(7-METHOXY-2-OXO-1,2,4,5-TETRAHYDRO-BENZO[D][1,3]DIAZEPIN-3-YL)-PIPERIDIN-1-YL]-2-OXO-ETHYL}-2,6-DIOXO-3,6-DIHYDRO-2H-PYRIMIDIN-1-YL)-PROPYL]-PROPIONAMIDE (REACTION SCHEME NO. 3, COMPOUND 158)

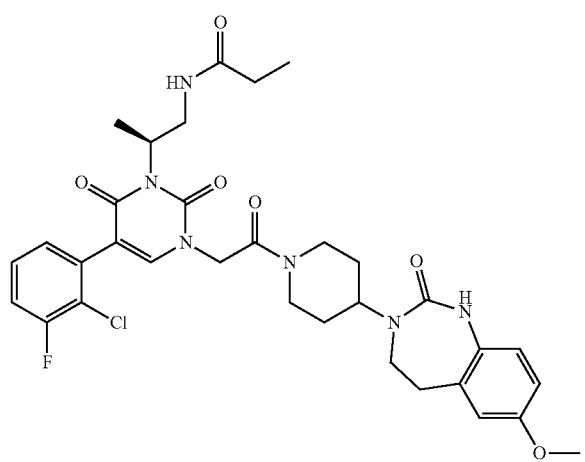 [SMILES: CCC(=O)NC[C@H](C)n1c(=O)c(-c2cccc(F)c2Cl)cn(CC(=O)N2CCC(N3CCc4cc(OC)ccc4NC3=O)CC2)c1=O]

156 μL (1.8 mmol) of propanoyl chloride is added to a solution of 1 g (1.6 mmol) of 3-((S)-2-amino-1-methyl-ethyl)-5-(2-chloro-3-fluorophenyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione prepared as described in example 119 and 0.25 mL (1.8 mmol) of triethylamine in 20 mL of dichloromethane. The reaction mixture is stirred at room temperature for 1 h, hydrolysed and extracted with dichloromethane. The organic phases are combined, washed once with water and then dried over magnesium sulphate, filtered and concentrated under vacuum. The crude product obtained is purified by silica gel chromatography eluted with a dichloromethane/methanol mixture 96/4. 0.7 g (64%) of N—[(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-propionamide is obtained in the form of a white solid.

$^1$H NMR (δ, DMSO): 0.96 (td, J=7.6, 1.7 Hz, 3H), 1.24-1.41 (d, J=8.0 Hz, 3H), 1.55 (m, 1H), 1.60-1.84 (m, 3H), 2.03 (qd, J=9.0, 8.3, 2.6 Hz, 2H), 2.60-2.76 (m, 1H), 2.80-2.96 (m, 2H), 3.15 (m, 1H), 3.36 (m, 2H), 3.52 (m, 2H), 3.67 (s, 3H), 3.95 (d, J=13.4 Hz, 1H), 4.29 (m, 1H), 4.44 (d, J=12.8 Hz, 1H), 4.57-4.88 (m, 2H), 5.00 (m, 1H), 6.60-6.70 (m, 2H), 6.98 (d, J=8.8 Hz, 1H), 7.20 (m, 1H), 7.36-7.54 (m, 2H), 7.79 (s, 1H), 7.85 (m, 1H), 8.34 (s, 1H).

EXAMPLE 159: 5-(2-CHLORO-3-FLUOROPHE-NYL)-1-{2-[4-(7-FLUORO-2-OXO-1,2,4,5-TETRAHYDRO-BENZO[D][1,3]DIAZEPIN-3-YL)-PIPERIDIN-1-YL]-2-OXO-ETHYL}-3-((S)-2-METHOXY-1-METHYLETHYL)-1H-PYRIMIDINE-2,4-DIONE (REACTION SCHEME NO. 3, COMPOUND 159)

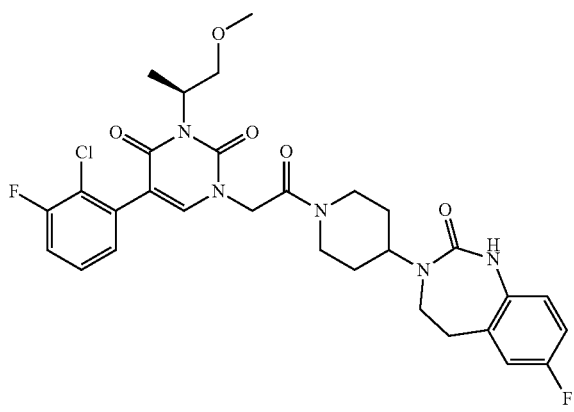 [SMILES: COC[C@H](C)n1c(=O)c(-c2cccc(F)c2Cl)cn(CC(=O)N2CCC(N3CCc4cc(F)ccc4NC3=O)CC2)c1=O]

159.1: 7-fluoro-3-piperidin-4-yl-1,3,4,5-tetrahydro-benzo[d][1,3]diazepin-2-one

Similarly to the sequence described in example 115 (115.1 to 115.9), starting from 1 g (5.5 mmol) of 2-(5-fluoro-2-nitrophenyl)acetonitrile, 315 mg of 7-fluoro-3-piperidin-4-yl-1,3,4,5-tetrahydro-benzo[d][1,3]diazepin-2-one is obtained.

159.2: N—[(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-propionamide Similarly to example 115.10, starting from 150 mg (0.6 mmol) of 7-fluoro-3-piperidin-4-yl-1,3,4,5-tetrahydro-benzo[d][1,3]diazepin-2-one and 176 mg (0.5 mmol) of [5-(2-chloro-3-fluorophenyl)-3-((S)-2-methoxy-1-methyl-ethyl)-2,4-dioxo-3,4-dihydro-2H-pyrimidin-1-yl]-acetic acid (prepared as described in example 106.3), 60 mg (21%)

of N—[(S)-2-(5-(2-chloro-3-fluorophenyl)-3-{2-[4-(7-methoxy-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]-propionamide [is obtained].

The following compounds were synthesized according to a similar procedure, using the appropriate reagents, commercially available or previously prepared:

Compound 160: 5-(2-chloro-3-fluorophenyl)-1-{2-[4-(7-fluoro-2-oxo-1,2,4,5-tetrahydro-benzo[d][1,3]diazepin-3-yl)-piperidin-1-yl]-2-oxo-ethyl}-3-(2-methanesulphonyl-ethyl)-1H-pyrimidine-2,4-dione

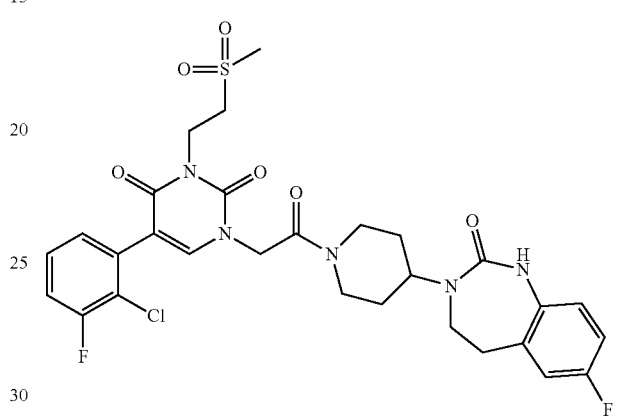

$^1$H NMR (δ, DMSO): 1.56 (m, 1H), 1.68 (m, 3H), 2.69 (m, 1H), 2.84-2.94 (m, 2H), 3.08 (s, 3H), 3.15 (m, 1H), 3.35-3.47 (m, 4H), 3.96 (d, J=13.3 Hz, 1H), 4.31 (m, 3H), 4.43 (d, J=13.1 Hz, 1H), 4.80 (m, 2H), 6.92 (m, 2H), 7.03-7.13 (m, 1H), 7.16-7.29 (m, 1H), 7.37-7.55 (m, 2H), 7.87 (s, 1H), 8.56 (s, 1H).

Compound 161: N—[(S)-2-(5-(2-chloro-3-fluorophenyl)-3-{2-[4-(7-fluoro-2-oxo-1,2,4,5-tetrahydro-benzo[d][1,3]diazepin-3-yl)-piperidin-1-yl]-2-oxo-ethyl}-2,6-dioxo-3,6-dihydro-2H-pyrimidin-1-yl)-propyl]acetamide

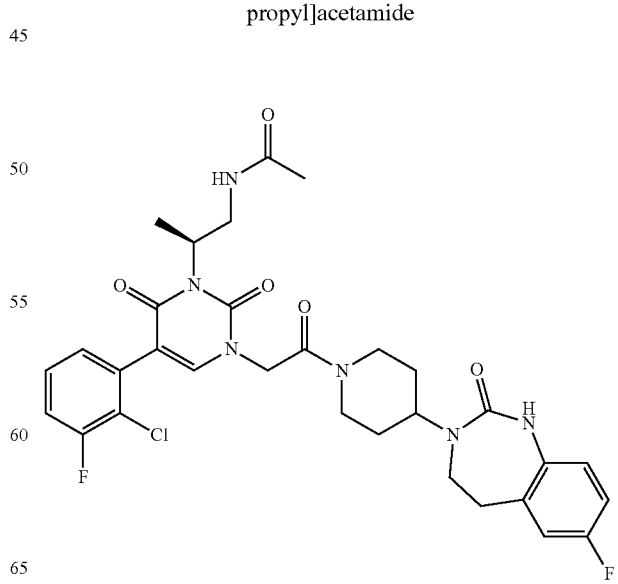

¹H NMR (δ, DMSO): 1.34 (d, J=6.8 Hz, 3H), 1.56 (m, 1H), 1.68 (m, 3H), 1.77 (s, 3H), 2.68 (m, 1H), 2.84-2.94 (m, 2H), 3.15 (m, 1H), 3.38 (m, 2H), 3.41-3.63 (m, 2H), 3.95 (d, J=13.6 Hz, 1H), 4.29 (m, 1H), 4.44 (d, J=13.0 Hz, 1H), 4.58-4.87 (m, 2H), 4.91-5.12 (m, 1H), 6.81-6.99 (m, 2H), 7.07 (m, 1H), 7.21 (m, 1H), 7.34-7.51 (m, 2H), 7.78 (s, 1H), 7.93 (t, J=5.9 Hz, 1H), 8.55 (s, 1H).

Compound 162: N—[(S)-2-(5-(2,3-dichlorophenyl)-3-{2-[4-(7-fluoro-2-oxo-1,2,4,5-tetrahydrobenzo[d][1,3]diazepin-3-yl)-piperidin-1-yl]-2-oxo-ethyl}-2,6-dioxo-3,6-dihydro-2H-pyrimidin-1-yl)-propyl] acetamide

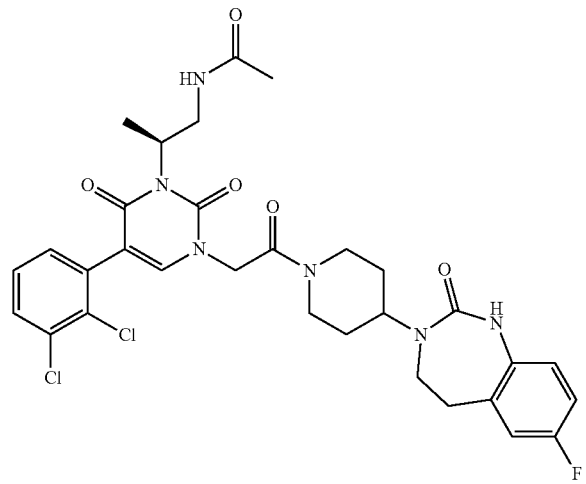 [SMILES: CC(=O)NC[C@H](C)n1c(=O)c(-c2cccc(Cl)c2Cl)cn(CC(=O)N2CCC(N3CCc4cc(F)ccc4NC3=O)CC2)c1=O]

¹H NMR (δ, DMSO): 1.34 (d, J=6.9 Hz, 3H), 1.55 (m, 1H), 1.71 (m, 3H), 1.77 (s, 3H), 2.68 (m, 1H), 2.82-2.97 (m, 2H), 3.14 (m, 1H), 3.37 (m, 2H), 3.51 (m, 2H), 3.95 (d, J=13.6 Hz, 1H), 4.29 (m, 1H), 4.44 (d, J=13.0 Hz, 1H), 4.61-4.86 (m, 2H), 5.06-4.89 (m, 1H), 6.81-7.00 (m, 2H), 7.07 (m, 1H), 7.33 (m, 1H), 7.42 (t, J=7.8 Hz, 1H), 7.68 (dd, J=8.0, 1.6 Hz, 1H), 7.77 (s, 1H), 7.92 (t, J=5.9 Hz, 1H), 8.55 (s, 1H).

Compound 163: 5-(2-chloro-3-fluorophenyl)-1-{2-[4-(9-fluoro-2-oxo-1,2,4,5-tetrahydro-benzo[d][1,3]diazepin-3-yl)-piperidin-1-yl]-2-oxo-ethyl}-3-isopropyl-1H-pyrimidine-2,4-dione

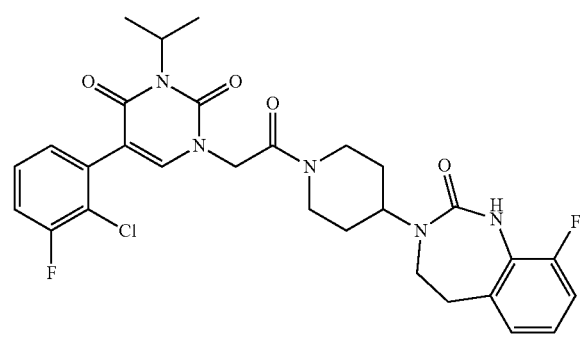 [SMILES: CC(C)n1c(=O)c(-c2cccc(F)c2Cl)cn(CC(=O)N2CCC(N3CCc4cccc(F)c4NC3=O)CC2)c1=O]

¹H NMR (δ, DMSO): 1.41 (d, J=6.8 Hz, 6H), 1.59 (m, 1H), 1.73 (m, 3H), 2.62-2.77 (m, 1H), 2.87-3.04 (m, 2H), 3.15 (m, 1H), 3.37-3.52 (m, 2H), 3.94 (d, J=13.8 Hz, 1H), 4.28 (m, 1H), 4.44 (d, J=13.4 Hz, 1H), 4.74 (m, 2H), 5.11 (hept, J=6.7 Hz, 1H), 6.87 (m, 1H), 6.94 (d, J=7.4 Hz, 1H), 7.00-7.12 (m, 1H), 7.15-7.27 (m, 1H), 7.35-7.50 (m, 3H), 7.77 (s, 1H).

EXAMPLE 164: 5-(2,3-DIFLUOROPHENYL)-3-METHYL-1-[2-OXO-2-[4-(2-OXO-3H-IMIDAZO[4,5-B]PYRIDIN-1-YL)-1-PIPERIDYL]ETHYL] PYRIMIDINE-2,4-DIONE (REACTION SCHEME NO. 4, COMPOUND 164)

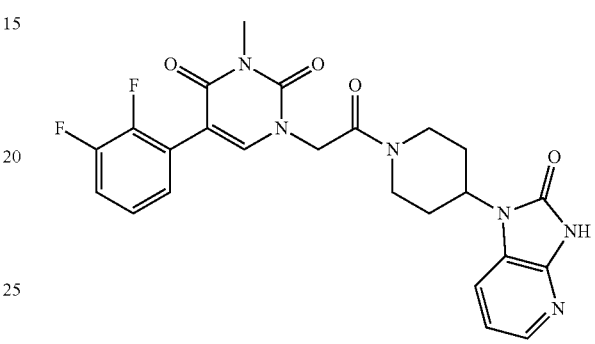

164.1: 4-(2-chloro-pyridin-3-ylamino)-piperidine-1-carboxylic acid ethyl ester 23 mL (311 mmol) of trifluoroacetic acid is added after 5 minutes to a solution of 20 g (156 mmol) of 3-amino-2-chloropyridine and 26 mL (171 mmol) of 4-oxo-1-piperidine ethyl carboxylate in 250 mL of isopropyl acetate. The reaction mixture is stirred for 30 minutes at room temperature and then 40 g (19 mmol) of sodium triacetoxyborohydride is added. The reaction mixture is stirred for 2 hours at room temperature and then 23 mL of a 10% solution of sodium hydroxide is added to pH8-9 and the mixture is heated to 50° C. After cooling, the reaction mixture is decanted and then extracted with ethyl acetate. The organic phases are combined, and dried over sodium sulphate. The solvents are evaporated and the residue is purified by silica gel chromatography eluted with a heptane/ethyl acetate 60/40 mixture. 43.2 g (98%) of 4-(2-chloro-pyridin-3-ylamino)-piperidine-1-ethyl carboxylate is obtained in the form of a colourless oil.

164.2: 4-[1-(2-chloro-pyridin-3-yl)-ureido]-piperidine-1-ethyl carboxylate 43.3 g (42.3 mmol) of 4-(2-chloro-pyridin-3-ylamino)-piperidine-1-ethyl carboxylate in solution in 200 mL of a tetrahydrofuran/isopropyl acetate 1/1 mixture is added to a solution of 15.8 mL (51 mmol) of chlorosulphonyl isocyanate in 100 mL of tetrahydrofuran. The reaction mixture is stirred for 1 hour at room temperature and then hydrolysed with 15 mL of water. After stirring for 18 h at room temperature, the reaction is stopped by adding 10% solution of sodium hydroxide up to pH 8-9 and then extracted with ethyl acetate. The organic phases are combined, washed with a saturated solution of sodium chloride and dried over sodium sulphate. The solvents are evaporated and then the residue is taken up in ether and drained. 32 g (74%) of 4-[1-(2-chloro-pyridin-3-yl)-ureido]-piperidine-1-ethyl carboxylate is obtained in the form of a white powder.

164.3: 4-(2-oxo-2,3-dihydro-imidazo[4,5-b]pyridin-1-yl)-piperidine-1-ethyl carboxylate 13.7 mg (0.06 mmol) of palladium diacetate and 52 mg (0.12 mmol) of diphenylphosphinobutane are added to a solution, previously degassed with nitrogen for 1 hour, of 1 g (3.1 mmol) of 4-[1-(2-chloro-pyridin-3-yl)-ureido]-piperidine-1-ethyl carboxylate and 1.3 g (9.2 mmol) of potassium carbonate in 10 mL of isopropanol. The reaction mixture is stirred for 3 hours at 83° C., the isopropanol is concentrated, 20 mL of water is added and the mixture is extracted with ethyl acetate. The organic phases are combined, washed with a saturated solution of sodium chloride and dried over sodium sulphate. The solvents are evaporated and then the residue is taken up in isopropyl acetate and then drained. 797 mg (90%) of 4-(2-oxo-2,3-dihydro-imidazo[4,5-b]pyridin-1-yl)-piperidine-1-ethyl carboxylate is obtained in the form of a white powder.

164.4: 1-piperidin-4-yl-1,3-dihydro-imidazo[4,5-b]pyridin-2-one dichloride 1.8 mL (34.5 mmol) of a 50% solution of sodium hydroxide and 1.7 mL of water are added to a solution of 667 mg (2.3 mmol) of 4-(2-oxo-2,3-dihydro-imidazo[4,5-b]pyridin-1-yl)-piperidine-1-ethyl carboxylate in 1.4 mL of ethanol. The reaction mixture is stirred for 18 h at 80° C. The reaction is stopped by adding 10 mL of water, then left at room temperature and washed with ethyl acetate. The aqueous phase is concentrated to dryness by azeotropic evaporation with isopropanol. The crude residue is taken up in 5 mL of isopropanol and then filtered to remove the salts. A 6N solution of hydrochloric acid in isopropanol is added; the product precipitates. After heating at 50° C. for 10 minutes and then returning to room temperature, the precipitate is drained and rinsed with isopropanol. 502 mg (75%) of 1-piperidin-4-yl-1,3-dihydro-imidazo[4,5-b]pyridin-2-one dichloride is obtained in the form of a white powder.

164.5: 5-(2,3-difluorophenyl)-3-methyl-1-[2-oxo-2-[4-(2-oxo-3H-imidazo[4,5-b]pyridin-1-yl)-1-piperidyl]ethyl]pyrimidine-2,4-dione (Compound 164)

Similarly to the examples described above, starting from 100 mg (0.34 mmol) of 2-[5-(2,3-difluorophenyl)-3-methyl-2,4-dioxo-pyrimidin-1-yl]acetic acid and 197 mg (0.7 mmol) of 1-piperidin-4-yl-1,3-dihydro-imidazo[4,5-b]pyridin-2-one dichloride, 100 mg (59%) of 5-(2,3-difluorophenyl)-3-methyl-1-[2-oxo-2-[4-(2-oxo-3H-imidazo[4,5-b]pyridin-1-yl)-1-piperidyl]ethyl]pyrimidine-2,4-dione [is obtained].

$^1$H NMR (δ, DMSO): 1.69-1.91 (m, 2H), 2.09 (m, 1H), 2.34 (m, 1H), 2.70-2.87 (m, 1H), 3.27 (m, 4H), 3.35 (d, 1H), 4.50 (m, 2H), 4.87 (m, 2H), 7.00 (dd, J=7.8, 5.2 Hz, 1H), 7.14-7.36 (m, 2H), 7.46 (dtd, J=10.1, 8.1, 1.8 Hz, 1H), 7.59 (dd, J=8.0, 1.4 Hz, 1H), 7.91 (dd, J=5.2, 1.3 Hz, 1H), 8.00 (s, 1H), 11.60 (s, 1H).

EXAMPLE 165: 5-(2-CHLORO-3-FLUOROPHENYL)-3-((S)-2-METHOXY-1-METHYLETHYL)-2,4-DIOXO-3,4-DIHYDRO-2H-PYRIMIDIN-1-YL]-1-[(2R)-2'-OXOSPIRO[1,3-DIHYDROINDENE-2,3'-1H-PYRROLO[2,3-B]PYRIDIN]-5-YL] ACETAMIDE (REACTION SCHEME 4, COMPOUND 165)

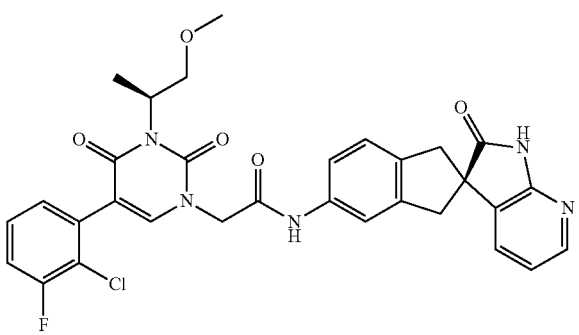 [SMILES: COC[C@H](C)n1c(=O)c(-c2cccc(F)c2Cl)cn(CC(=O)Nc2ccc3c(c2)C[C@@]2(C3)C(=O)Nc3ncccc32)c1=O]

165.1: 5-bromo-2,4-dioxo-3,4-dihydro-2H-pyrimidin-1-yl-methyl acetate 21.3 g (150 mmol) of potassium carbonate and 14.5 mL (150 mmol) of methyl bromoacetate are added to a solution of 30 g (150 mmol) of 5-bromouracil in 294 mL of N,N-dimethylformamide. The reaction mixture is stirred at room temperature for 50 min and then hydrolysed (250 mL of water and 50 mL of 1N NaOHaq) and extracted with dichloromethane (300 mL). The aqueous phases are combined and washed once with 100 mL of dichloromethane. The aqueous phase contains the expected product. The pH of the aqueous phase is adjusted to pH=6-7 with 300 mL of an aqueous solution of hydrochloric acid C=1N and 8 mL of concentrated hydrochloric acid (to avoid having an excessive volume of water). The product precipitates. The suspension is stirred for 2 h and then filtered. The solid obtained is rinsed with water and diethyl ether and then dried under vacuum at 50° C. for 24 h to give 22 g (54%) of (5-bromo-2,4-dioxo-3,4-dihydro-2H-pyrimidin-1-yl)-methyl acetate in the form of a white solid.

165.2: [5-bromo-3-((S)-2-methoxy-1-methylethyl)-2,4-dioxo-3,4-dihydro-2H-pyrimidin-1-yl]-methyl acetate 2.7 mL (11.4 mmol) of diethylazodicarboxylate is added dropwise to a solution cooled to 0° C. of 1 g (3.8 mmol) of 5-bromo-2,4-dioxo-3,4-dihydro-2H-pyrimidin-1-yl)-methyl acetate, 0.8 mL (8 mmol) of (R)-1-methoxy-propan-2-ol and 2 g (7.6 mmol) of triphenylphosphine in 20 mL of tetrahydrofuran. The reaction mixture (white suspension) is stirred at room temperature for 48 hours. The tetrahydrofuran is removed under vacuum and then the residue is taken up in ethyl acetate. The organic phase is washed once with a saturated aqueous solution of sodium hydrogen carbonate, once with water and then with a saturated aqueous solution of sodium chloride, dried over magnesium sulphate, filtered and concentrated under vacuum. The crude product is purified by silica gel chromatography eluted with a heptane/ethyl acetate 60/40 mixture. 1.2 g (78%) of [5-bromo-3-

((S)-2-methoxy-1-methylethyl)-2,4-dioxo-3,4-dihydro-2H-pyrimidin-1-yl]-methyl acetate is obtained in the form of a colourless oil.

165.3: 5-(2-chloro-3-fluorophenyl)-3-((S)-2-methoxy-1-methylethyl)-2,4-dioxo-3,4-dihydro-2H-pyrimidin-1-yl]-acetic acid 54 mg (70 μmol) of 1,1'-bis(diphenylphosphino)ferrocene palladium(II) dichloride complexed with dichloromethane is added to a solution of 400 mg (1.3 mmol) of [5-bromo-3-((S)-2-methoxy-1-methylethyl)-2,4-dioxo-3,4-dihydro-2H-pyrimidin-1-yl]-methyl acetate, 417 mg (4 mmol) of sodium carbonate and 571 mg (3.3 mmol) of 2-chloro-3-fluorophenyl boronic acid in 44 mL of 1,4-dioxane and 4 mL of water, previously degassed for 5 min. The reaction mixture is then heated at 100° C. for 2 h. 2 mL of a 1M aqueous solution of lithium hydroxide monohydrate and 2.2 mL of water are then added and the reaction mixture is stirred for 1 h. The reaction mixture is hydrolysed and then diluted with ethyl acetate. The first organic phase is discarded (impurities) and the aqueous phase is adjusted to acid pH with an aqueous solution of hydrochloric acid of concentration 1N. The product is extracted with ethyl acetate. The organic phases are combined, washed once with water and once with a saturated aqueous solution of sodium chloride, then dried over magnesium sulphate, filtered and concentrated under vacuum. The crude product is purified by silica gel chromatography eluted with a dichloromethane/methanol 95/5 mixture+0.1% of acetic acid. 240 mg (49%) of [5-(2-chloro-3-fluorophenyl)-3-((S)-2-methoxy-1-methylethyl)-2,4-dioxo-3,4-dihydro-2H-pyrimidin-1-yl]-acetic acid is obtained in the form of a yellow oil.

165.4: 5-(2-chloro-3-fluorophenyl)-3-((S)-2-methoxy-1-methylethyl)-2,4-dioxo-3,4-dihydro-2H-pyrimidin-1-yl]-1-[(2R)-2'-oxospiro[1,3-dihydroindene-2,3'-1H-pyrrolo[2,3-b]pyridin]-5-yl]acetamide (Compound 165)

162 mg (0.65 mmol) of (R)-5-amino-1,3-dihydrospiro[indene-2,3'-pyrrolo[2,3-b)pyridin]-2'(1'H)-one prepared as described in patent WO2011/005731 is added to a solution stirred beforehand for 5 min, of 240 mg (0.65 mmol) of [5-(2-chloro-3-fluorophenyl)-3-((S)-2-methoxy-1-methylethyl)-2,4-dioxo-3,4-dihydro-2H-pyrimidin-1-yl]-acetic acid, 114 mg (0.8 mmol) of 1-hydroxybenzotriazole and 161 mg (0.8 mmol) of 1-ethyl-3-(3-dimethylaminopropyl)-carbodiimide hydrochloride in 5 mL of N,N-dimethylformamide. The reaction mixture is stirred at room temperature for 18 h and then diluted with ethyl acetate. The organic phase is washed once with a saturated aqueous solution of sodium hydrogen carbonate, once with water and once with a saturated aqueous solution of sodium chloride, dried over magnesium sulphate and then filtered and concentrated under vacuum. The crude product is purified by silica gel chromatography (HP15) eluted with a dichloromethane/methanol mixture 96/4. 155 mg (39%) of 5-(2-chloro-3-fluorophenyl)-3-((S)-2-methoxy-1-methylethyl)-2,4-dioxo-3,4-dihydro-2H-pyrimidin-1-yl]-1-[(2R)-2'-oxospiro[1,3-dihydroindene-2,3'-1H-pyrrolo[2,3-b]pyridin]-5-yl] acetamide is obtained in the form of a white solid.

$^1$H NMR (δ, DMSO): 1.34 (d, J=6.9 Hz, 3H); 3.04-3.11 (m, 2H); 3.23 (s, 3H); 3.33-3.37 (m, 2H); 3.54 (dd, J=9.9, 5.9 Hz, 1H); 3.92 (dd, J=9.9, 8.2 Hz, 1H); 4.65 (s, 2H); 5.13-5.15 (m, 1H); 6.87 (dd, J=7.3, 5.3 Hz, 1H); 7.18 (dd, J=7.3, 1.6 Hz, 1H); 7.21-7.24 (m, 2H); 7.38 (d, J=8.3 Hz, 1H); 7.43-7.46 (m, 2H); 7.62 (s, 1H); 7.93 (s, 1H); 8.07 (dd, J=5.3, 1.6 Hz, 1H); 10.35 (s, 1H); 11.09 (s, 1H).

The following compounds were synthesized according to a similar procedure starting from appropriate reagents, commercially available or previously prepared:

Compound 166: 5-(2-chloro-3-fluorophenyl)-3-isopropyl-pyrimidine-2,4-dione-1-[(2R)-2'-oxospiro[1,3-dihydroindene-2,3'-1H-pyrrolo[2,3-b]pyridin]-5-yl]acetamide

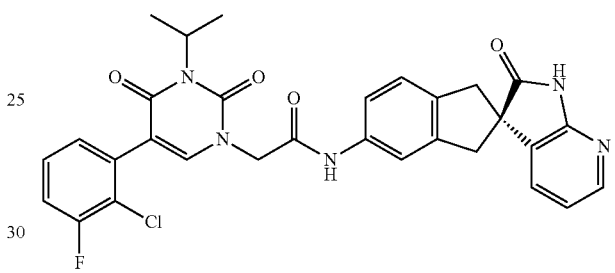

$^1$H NMR (δ, DMSO): 1.41 (d, J=6.9 Hz, 6H); 3.08 (m, 2H); 3.33 (m, 2H); 4.65 (m, 2H); 5.10-5.11 (m, 1H); 6.87 (dd, J=7.3, 5.3 Hz, 1H); 7.18 (m, 1H), 7.23 (m, 2H); 7.38 (m, 1H), 7.45 (m, 2H); 7.63 (m, 1H); 7.91 (s, 1H); 8.07 (dd, J=5.3, 1.6 Hz, 1H); 10.35 (s, 1H); 11.09 (s, 1H).

Compound 167: 5-(2,3-difluorophenyl)-3-[(1S)-2-methoxy-1-methylethyl]-pyrimidine-2,4-dione-1-[(2R)-2'-oxospiro[1,3-dihydroindene-2,3'-1H-pyrrolo[2,3-b]pyridin]-5-yl]acetamide

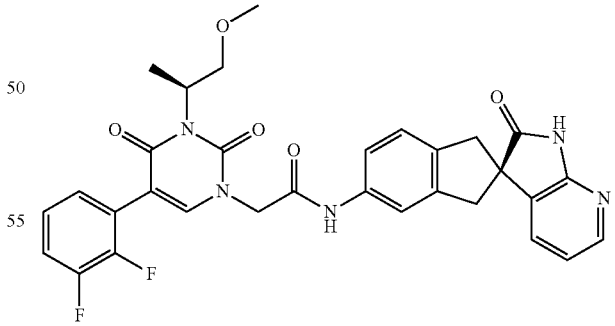

$^1$H NMR (δ, DMSO): 1.34 (d, J=6.9 Hz, 3H), 3.08 (m, 2H), 3.23 (s, 3H), 3.34 (m, 2H), 3.54 (m, 1H), 3.93 (m, 1H), 4.66 (m, 2H), 5.16 (q, J=7.1 Hz, 1H), 6.87 (dd, J=7.3, 5.3 Hz, 1H), 7.18 (dd, J=7.3, 1.7 Hz, 1H), 7.20-7.31 (m, 3H), 7.39 (m, 1H), 7.46 (m, 1H), 7.61 (m, 1H), 8.02 (s, 1H), 8.07 (dd, J=5.3, 1.7 Hz, 1H), 10.35 (s, 1H), 11.09 (s, 1H).

Compound 168: 2-[5-(2-chloro-3-fluorophenyl)-2,4-dioxo-1H-pyrimidin-3-yl]acetic acid-1-[(2R)-2'-oxospiro[1,3 dihydroindene-2,3'-1H-pyrrolo[2,3-b]pyridin]-5-yl]acetamide

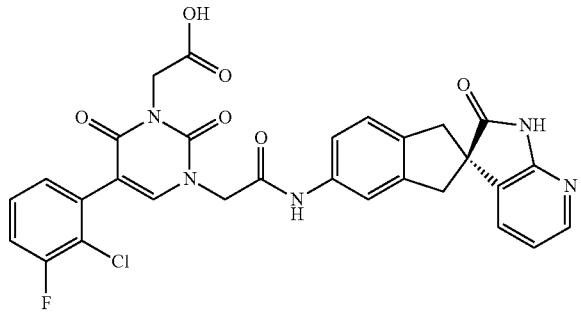 [SMILES: O=C(O)Cn1c(=O)c(-c2cccc(F)c2Cl)cn(CC(=O)Nc2ccc3c(c2)C[C@@]2(C3)C(=O)Nc3ncccc32)c1=O]

¹H NMR (δ, DMSO): 3.08 (dd, J=16.1, 12.1 Hz, 2H), 3.36 (m, 2H), 4.53 (s, 2H), 4.71 (s, 2H), 6.87 (dd, J=7.3, 5.3 Hz, 1H), 7.18 (dd, J=7.4, 1.7 Hz, 1H), 7.24 (m, 2H), 7.38 (dd, J=8.2, 2.0 Hz, 1H), 7.42-7.53 (m, 2H), 7.61 (m, 1H), 8.03 (s, 1H), 8.07 (dd, J=5.3, 1.7 Hz, 1H), 10.37 (s, 1H), 11.09 (s, 1H), 13.02 (br-s, 1H).

Compound 169: 5-(2-chloro-3-methoxyphenyl)-3-(2-methylsulphonylethyl)-pyrimidine-2,4-dione-1-[(2R)-2'-oxospiro[1,3-dihydroindene-2,3'-1H-pyrrolo[2,3-b]pyridin]-5-yl]acetamide

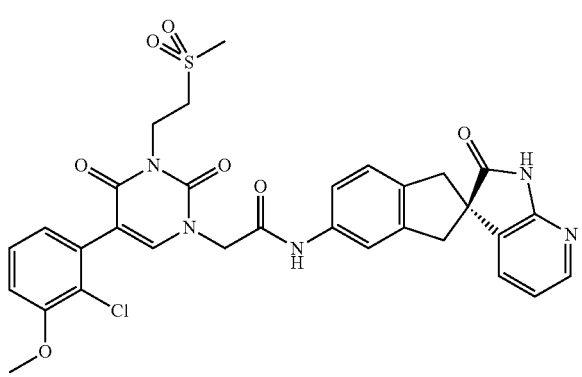 [SMILES: COc1cccc(-c2cn(CC(=O)Nc3ccc4c(c3)C[C@@]3(C4)C(=O)Nc4ncccc43)c(=O)n(CCS(C)(=O)=O)c2=O)c1Cl]

¹H NMR (δ, DMSO): 3.08-3.12 (m, 5H); 3.33-3.42 (m, 4H); 3.90 (s, 3H); 4.30 (t, J=7.2 Hz, 2H); 4.69 (m, 2H); 6.87 (dd, J=7.3, 5.3 Hz, 1H); 6.93 (dd, J=7.6, 1.4 Hz, 1H); 7.16-7.24 (m, 3H); 7.34-7.39 (m, 2H); 7.61 (m, 1H); 7.90 (s, 1H); 8.07 (dd, J=5.3, 1.6 Hz, 1H); 10.35 (s, 1H); 11.08 (s, 1H).

Compound 170: 5-(2,3-dichlorophenyl)-3-(2-methylsulphonylethyl)-pyrimidine-2,4-dione-1-[(2R)-2'-oxospiro[1,3-dihydroindene-2,3'-1H-pyrrolo[2,3-b]pyridin]-5-yl]acetamide

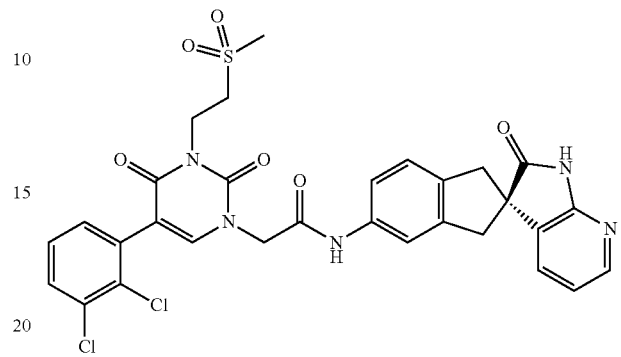

¹H NMR (δ, DMSO): 3.03-3.15 (m, 5H), 3.33-3.46 (m, 4H), 4.31 (dd, J=8.4, 6.1 Hz, 2H), 4.69 (s, 2H), 6.87 (dd, J=7.3, 5.3 Hz, 1H), 7.18 (dd, J=7.3, 1.6 Hz, 1H), 7.24 (d, J=8.1 Hz, 1H), 7.35 (dd, J=7.7, 1.6 Hz, 1H), 7.38 (dd, J=8.1, 2.0 Hz, 1H), 7.44 (t, J=7.9 Hz, 1H), 7.61 (d, J=2.0 Hz, 1H), 7.70 (dd, J=8.0, 1.6 Hz, 1H), 8.00 (s, 1H), 8.07 (dd, J=5.2, 1.6 Hz, 1H), 10.36 (s, 1H), 11.08 (br-s, 1H).

Compound 171: 5-(2,3-dimethoxyphenyl)-3-[(1R)-2-methoxy-1-methylethyl]-pyrimidine-2,4-dione-1-[(2R)-2'-oxospiro[1,3-dihydroindene-2,3'-1H-pyrrolo[2,3-b]pyridin]-5-yl]acetamide

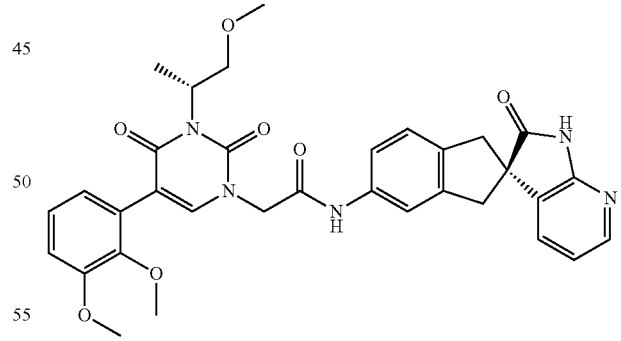

¹H NMR (δ, DMSO): 1.34 (d, J=6.8 Hz, 3H), 3.08 (m, 2H), 3.24 (s, 3H), 3.36 (m, 2H), 3.54 (m, 1H), 3.70 (s, 3H), 3.83 (s, 3H), 3.93 (m, 1H), 4.63 (s, 2H), 5.15 (m, 1H), 6.80 (m, 1H), 6.87 (m, 1H), 7.07 (d, J=4.5 Hz, 2H), 7.18 (d, J=7.4 Hz, 1H), 7.23 (d, J=8.2 Hz, 1H), 7.39 (d, J=8.1 Hz, 1H), 7.61 (s, 1H), 7.70 (s, 1H), 8.06 (dd, J=5.3, 1.5 Hz, 1H), 10.32 (s, 1H), 11.08 (s, 1H).

Compound 172: 5-(2-chloro-3-fluorophenyl)-3-(2-methylsulphonylethyl)-pyrimidine-2,4-dione-1-[(2R)-2'-oxospiro[1,3-dihydroindene-2,3'-1H-pyrrolo[2,3-b]pyridin]-5-yl]acetamide

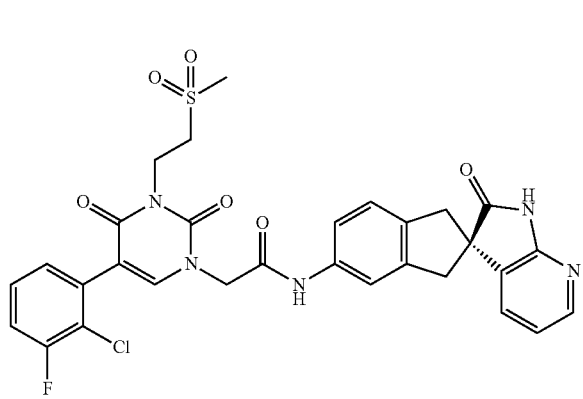 [SMILES: CS(=O)(=O)CCn1c(=O)c(-c2cccc(F)c2Cl)cn(CC(=O)Nc2ccc3c(c2)C[C@@]2(C3)C(=O)Nc3ncccc32)c1=O]

¹H NMR (δ, DMSO): 3.09 (m, 5H), 3.28-3.39 (m, 2H), 3.42 (t, J=7.3 Hz, 2H), 4.31 (t, J=7.2 Hz, 2H), 4.70 (s, 2H), 6.87 (m, 1H), 7.18 (m, 1H), 7.23 (m, 2H), 7.38 (d, J=8.1 Hz, 1H), 7.42-7.52 (m, 2H), 7.61 (s, 1H), 8.01 (s, 1H), 8.07 (d, J=5.2 Hz, 1H), 10.36 (s, 1H), 11.08 (s, 1H).

Compound 173: 5-(2-chloro-3-fluorophenyl)-3-(3-methylsulphonylpropyl)-pyrimidine-2,4-dione-1-[(2R)-2'-oxospiro[1,3-dihydroindene-2,3'-1H-pyrrolo[2,3-b]pyridin]-5-yl]acetamide

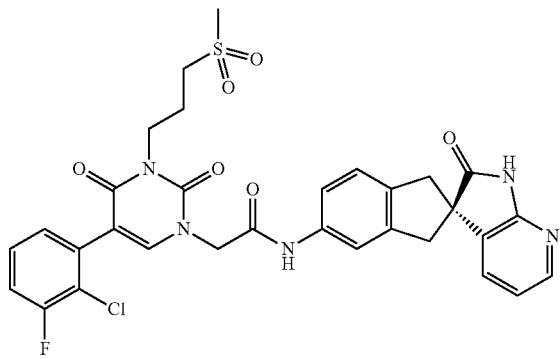 [SMILES: CS(=O)(=O)CCCn1c(=O)c(-c2cccc(F)c2Cl)cn(CC(=O)Nc2ccc3c(c2)C[C@@]2(C3)C(=O)Nc3ncccc32)c1=O]

¹H NMR (δ, DMSO): 1.96-2.04 (m, 2H); 2.98 (s, 3H); 3.09 (m, 2H); 3.18 m, 2H); 3.33-3.37 (m, 2H); 4.01 (t, J=7.0 Hz, 2H); 4.69 (s, 2H); 6.87 (dd, J=7.3, 5.3 Hz, 1H); 7.18 (dd, J=7.3, 1.6 Hz, 1H); 7.22-7.25 (m, 2H); 7.39 (m, 1H); 7.44-7.47 (m, 2H); 7.61 (m, 1H); 7.99 (s, 1H); 8.07 (dd, J=5.3, 1.6 Hz, 1H); 10.36 (s, 1H); 11.08 (s, 1H).

Compound 174: 5-(2,3-dichlorophenyl)-3-methyl-pyrimidine-2,4-dione-1-[(2R)-2'-oxospiro[1,3-dihydroindene-2,3'-1H-pyrrolo[2,3-b]pyridin]-5-yl]acetamide

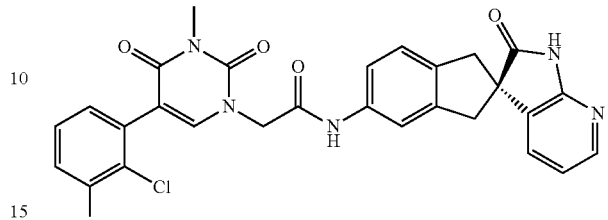

¹H NMR (δ, DMSO): 3.09 (dd, J=16.1, 11.9 Hz, 2H), 3.26 (s, 3H), 3.28-3.40 (m, 2H), 4.68 (s, 2H), 6.87 (dd, J=7.3, 5.3 Hz, 1H), 7.18 (dd, J=7.3, 1.6 Hz, 1H), 7.24 (d, J=8.1 Hz, 1H), 7.34 (dd, J=7.7, 1.7 Hz, 1H), 7.39 (dd, J=8.1, 2.0 Hz, 1H), 7.43 (t, J=7.8 Hz, 1H), 7.61 (d, J=2.0 Hz, 1H), 7.70 (dd, J=8.0, 1.6 Hz, 1H), 7.96 (s, 1H), 8.07 (dd, J=5.2, 1.7 Hz, 1H), 10.35 (s, 1H), 11.09 (s, 1H).

Compound 175: 5-(2-chloro-3-fluorophenyl)-3-[(1S)-1-methyl-2-methylsulphonyl-ethyl]-pyrimidine-2,4-dione-1-[(2R)-2'-oxospiro[1,3-dihydroindene-2,3'-1H-pyrrolo[2,3-b]pyridin]-5-yl]acetamide

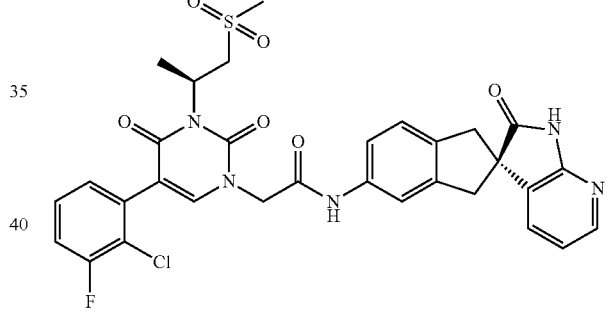

¹H NMR (δ, DMSO): 1.24 (d, J=7.0 Hz, 3H), 3.05 (s, 6H), 3.33-3.40 (min, 1H), 3.54 (m, 1H), 4.16-4.36 (m, 2H), 4.70 (s, 2H), 6.87 (m, 1H), 7.19 (dd, J=7.5, 1.7 Hz, 1H), 7.21-7.28 (m, 2H), 7.37 (dd, J=8.3, 2.0 Hz, 1H), 7.42-7.52 (m, 2H), 7.61 (m, 1H), 8.03 (s, 1H), 8.07 (dd, J=5.1, 1.9 Hz, 1H), 10.35 (s, 1H), 11.08 (s, 1H).

Compound 176: 5-(2-chloro-3-methoxyphenyl)-3-[2-methoxy-1-(methoxymethyl)ethyl]-pyrimidine-2,4-dione-1-[(2R)-2'-oxospiro[1,3-dihydroindene-2,3'-1H-pyrrolo[2,3-b]pyridin]-5-yl]acetamide

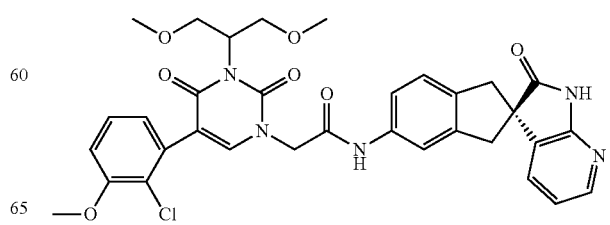

¹H NMR (δ, DMSO): 3.04-3.11 (m, 2H); 3.23 (s, 6H); 3.33-3.37 (m, 2H); 3.60 (m, 2H); 3.84 (m, 2H); 3.89 (s, 3H); 4.65 (s, 2H); 5.26 (br s, 1H); 6.87 (m, 1H); 6.93 (dd, J=7.6, 1.4 Hz, 1H); 7.16-7.19 (m, 2H); 7.24 (d, J=8.2 Hz, 1H); 7.33-7.39 (m, 2H); 7.62 (m, 1H); 7.84 (s, 1H); 8.07 (dd, J=5.3, 1.6 Hz, 1H); 10.34 (s, 1H); 11.08 (s, 1H).

Compound 177: 5-(2,3-dichlorophenyl)-3-[(1R)-2-methoxy-1-methylethyl]-pyrimidine-2,4-dione-1-[(2R)-2'-oxospiro[1,3-dihydroindene-2,3'-1H-pyrrolo[2,3-b]pyridin]-5-yl]acetamide

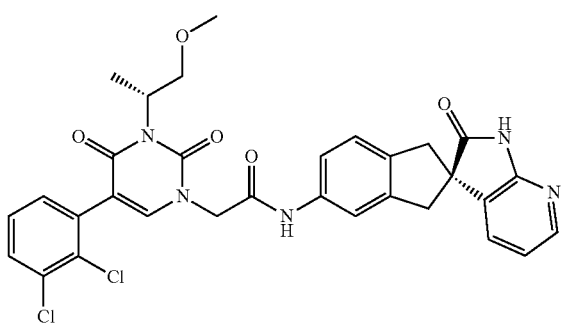

¹H NMR (δ, DMSO): 1.33 (d, J=6.9 Hz, 3H), 3.08 (m, 2H), 3.23 (s, 3H), 3.33-3.40 (m, 2H), 3.54 (m, 1H), 3.92 (m, 1H), 4.65 (s, 2H), 5.14 (m, 1H), 6.87 (m, 1H), 7.18 (dd, J=7.3, 1.7 Hz, 1H), 7.24 (d, J=8.2 Hz, 1H), 7.35 (dd, J=7.7, 1.6 Hz, 1H), 7.38 (dd, J=8.1, 2.0 Hz, 1H), 7.43 (t, J=7.9 Hz, 1H), 7.62 (m, 1H), 7.69 (dd, J=8.0, 1.5 Hz, 1H), 7.92 (s, 1H), 8.07 (dd, J=5.3, 1.7 Hz, 1H), 10.35 (s, 1H), 11.08 (s, 1H).

Compound 178: 5-(2,3-dichlorophenyl)-3-[(1S)-2-methoxy-1-methylethyl]-pyrimidine-2,4-dione-1-[(2R)-2'-oxospiro[1,3-dihydroindene-2,3'-1H-pyrrolo[2,3-b]pyridin]-5-yl]acetamide

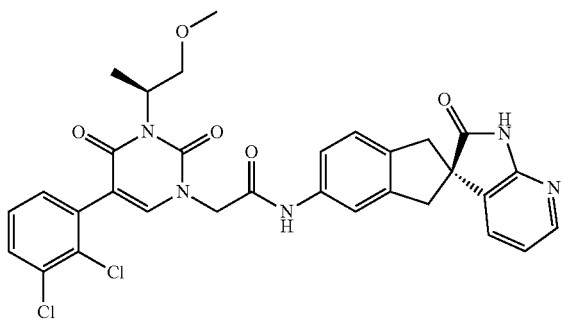 [SMILES: COC[C@H](C)n1c(=O)c(-c2cccc(Cl)c2Cl)cn(CC(=O)Nc2ccc3c(c2)C[C@@]2(C3)C(=O)Nc3ncccc32)c1=O]

¹H NMR (δ, DMSO): 1.33 (d, J=6.9 Hz, 3H), 3.01-3.14 (m, 2H), 3.23 (s, 3H), 3.40 (m, 2H), 3.54 (m, 1H), 3.92 (m, 1H), 4.64 (s, 2H), 5.14 (m, 1H), 6.87 m, 1H), 7.18 (dd, J=1.7, 7.3 Hz, 1H), 7.24 (d, J=8.2 Hz, 1H), 7.30-7.47 (m, 3H), 7.62 (m, 1H), 7.69 (dd, J=1.6, 8 Hz, 1H), 7.92 (s, 1H), 8.07 (dd, J=1.6, 5.3 Hz, 1H), 10.34 (s, 1H), 11.08 (s, 1H).

Compound 179: 5-(2-chloro-3-fluorophenyl)-3-[2-methoxy-1-(methoxymethyl)ethyl]-pyrimidine-2,4-dione-1-[(2R)-2'-oxospiro[1,3-dihydroindene-2,3'-1H-pyrrolo[2,3-b]pyridin]-5-yl]acetamide

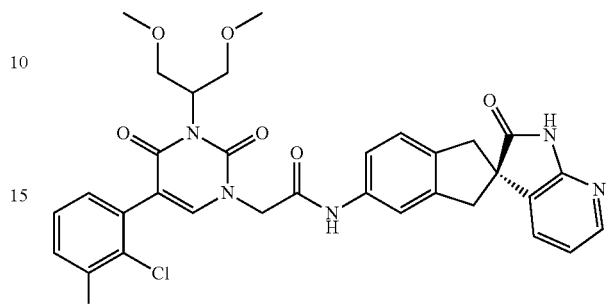

¹H NMR (δ, DMSO): 3.02-3.14 (m, 2H), 3.24 (s, 6H), 3.33-3.39 (m, 2H), 3.60 (m, 2H), 3.85 (m, 2H), 4.66 (s, 2H), 5.27 (br-s, 1H), 6.87 (m, 1H), 7.15-7.21 (m, 1H), 7.23 (m, 2H), 7.32-7.43 (m, 1H), 7.42-7.53 (m, 2H), 7.62 (s, 1H), 7.95 (s, 1H), 8.07 (dd, J=1.7, 5.4 Hz, 1H), 10.34 (s, 1H), 11.08 (s, 1H).

Compound 180: N-[2-[5-(2-chloro-3-fluorophenyl)-2,4-dioxo-pyrimidin-3-yl]ethyl]acetamide-1-[(2R)-2'-oxospiro[1,3-dihydroindene-2,3'-1H-pyrrolo[2,3-b]pyridin]-5-yl]acetamide

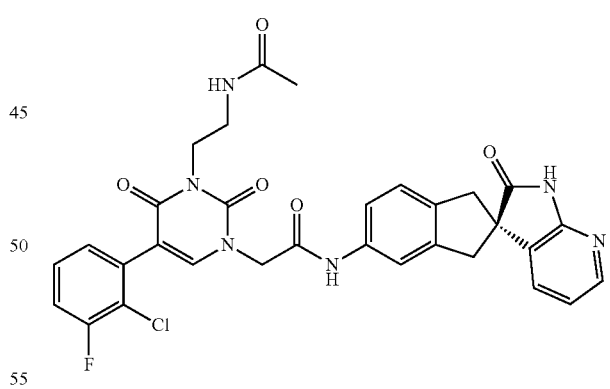

¹H NMR (δ, DMSO): 1.75 (s, 3H), 2.98-3.15 (m, 2H), 3.27-3.40 (m, 4H), 3.95 (t, J=6.3 Hz, 2H), 4.68 (s, 2H), 6.87 (m, 1H), 7.18 (dd, J=7.2, 1.6 Hz, 1H), 7.20-7.28 (m, 2H), 7.39 (dd, J=8.1, 2.0 Hz, 1H), 7.42-7.51 (m, 2H), 7.61 (m, 1H), 7.93 (t, J=6.0 Hz, 1H), 7.95 (s, 1H), 8.07 (dd, J=5.3, 1.7 Hz, 1H), 10.32 (s, 1H), 11.08 (s, 1H).

225

Compound 181: 5-(2-chloro-3-fluorophenyl)-3-[(1R)-2-methoxy-1-methylethyl]-pyrimidine-2,4-dione-1-[(2R)-2'-oxospiro[1,3-dihydroindene-2,3'-1H-pyrrolo[2,3-b]pyridin]-5-yl]acetamide

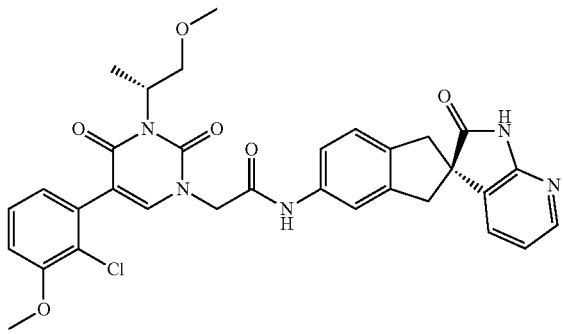 [SMILES: COC[C@@H](C)n1c(=O)c(-c2cccc(OC)c2Cl)cn(CC(=O)Nc2ccc3c(c2)C[C@@]2(C3)C(=O)Nc3ncccc32)c1=O]

¹H NMR (δ, DMSO): 1.33 (d, J=6.9 Hz, 3H); 3.08 (m, 2H); 3.23 (s, 3H); 3.36 (m, 2H); 3.54 (m, 1H); 3.89-3.91 (m, 4H); 4.64 (s, 2H); 5.13 (m, 1H); 6.87 (m, 1H); 6.93 (d, J=7.6 Hz, 1H); 7.18 (m, 2H); 7.24 (d, J=7.7 Hz, 1H); 7.33-7.39 (m, 2H); 7.63 (s, 1H); 7.82 (s, 1H); 8.07 (d, J=5.2 Hz, 1H); 10.33 (s, 1H); 11.08 (s, 1H).

Compound 182: 5-(2,3-dichlorophenyl)-3-[2-methoxy-1-(methoxymethyl)ethyl]-pyrimidine-2,4-dione-1-[(2R)-2'-oxospiro[1,3-dihydroindene-2,3'-1H-pyrrolo[2,3-b]pyridin]-5-yl]acetamide

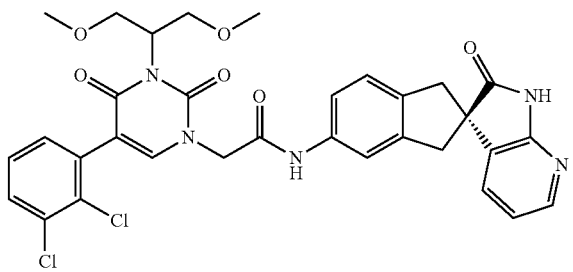 [SMILES: COCC(COC)n1c(=O)c(-c2cccc(Cl)c2Cl)cn(CC(=O)Nc2ccc3c(c2)C[C@@]2(C3)C(=O)Nc3ncccc32)c1=O]

¹H NMR (δ, DMSO): 3.04-3.11 (m, 2H); 3.24 (s, 6H); 3.33-3.34 (m, 2H); 3.60 (m, 2H); 3.85 (m, 2H); 4.66 (s, 2H); 5.22-5.29 (br-s, 1H); 6.87 (dd, J=7.3, 5.3 Hz, 1H); 7.18 (dd, J=7.3, 1.6 Hz, 1H); 7.24 (d, J=8.2 Hz, 1H); 7.33-7.44 (m, 3H); 7.62 (m, 1H); 7.69 (dd, J=8.0, 1.6 Hz, 1H); 7.94 (s, 1H); 8.07 (dd, J=5.3, 1.6 Hz, 1H); 10.35 (s, 1H); 11.08 (s, 1H).

226

Compound 183: 5-(2-chloro-3-fluorophenyl)-3-[(1R)-2-methoxy-1-methylethyl]-pyrimidine-2,4-dione-1-[(2R)-2'-oxospiro[1,3-dihydroindene-2,3'-1H-pyrrolo[2,3-b]pyridin]-5-yl]acetamide

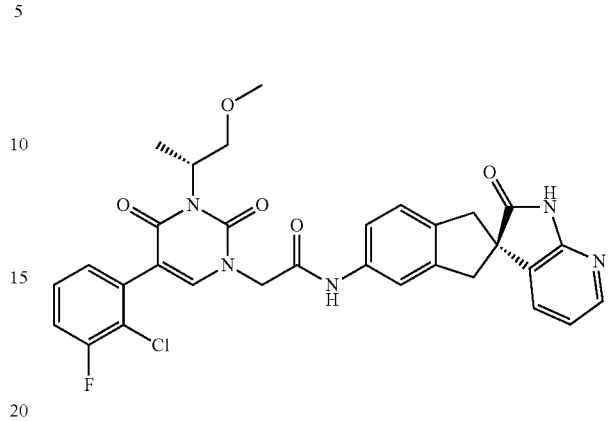

¹H NMR (δ, DMSO): 1.34 (d, J=7.0 Hz, 3H), 3.08 (m, 2H), 3.23 (s, 3H), 3.36 (m, 2H), 3.54 (m, 1H), 3.92 (m, 1H), 4.65 (s, 2H), 5.14 (q, J=7.2 Hz, 1H), 6.87 (m, 1H), 7.18 (dd, J=7.2, 1.7 Hz, 1H), 7.21-7.28 (m, 2H), 7.38 (dd, J=8.1, 1.9 Hz, 1H), 7.41-7.50 (m, 2H), 7.63 (m, 1H), 7.93 (s, 1H), 8.07 (dd, J=5.3, 1.6 Hz, 1H), 10.34 (s, 1H), 11.08 (s, 1H).

EXAMPLE 184: 5-(2-CHLORO-3-FLUOROPHENYL)-3-(2-METHANESULPHONYL-ETHYL)-1-{2-[4-(7-METHANESULPHONYL-2-OXO-1,2,4,5-TETRAHYDRO-BENZO[D][1,3]DIAZEPIN-3-YL)-PIPERIDIN-1-YL]-2-OXO-ETHYL}-1H-PYRIMIDINE-2,4-DIONE (REACTION SCHEME NO. 4, COMPOUND 184)

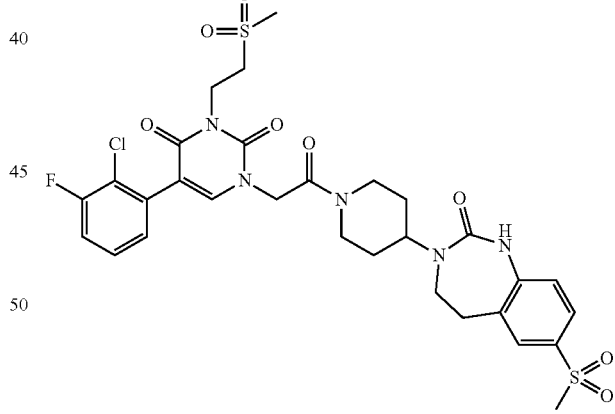

184.1: 2-(5-methylsulphanyl-2-nitrophenyl)acetonitrile

A solution of 6 g (47 mmol) of (4-chlorophenoxy)-acetonitrile and 6 g (40 mmol) of 1-methylsulphanyl-4-nitrobenzene in 60 mL of N,N-dimethylformamide is added dropwise to a solution previously cooled to −10° C. of 10.6 g (94 mmol) of potassium tert-butoxide in 120 mL of N,N-dimethylformamide. The reaction is stirred at −10° C. for 45 min before being hydrolysed with an iced solution of concentrated hydrochloric acid and then extracted with ethyl acetate. The organic phase is washed with water and then with a saturated solution of sodium chloride, dried over magnesium sulphate, filtered and then concentrated under vacuum. The crude reaction product is taken up in 1:1 Heptane:EtOAc solution and after trituration for 1 hour, the mixture is filtered and the solid is washed with a 1:1 Hept EtOAc solution, obtaining 2.9 g of 2-(5-methylsulphanyl-2-nitrophenyl)acetonitrile (58%) in the form of a solid.

184.2: 2-(5-methylsulphanyl-2-nitrophenyl)ethanamine 28 mL of a 1M solution of borane complexed with tetrahydrofuran in tetrahydrofuran is added dropwise at room temperature to a solution of 2.9 g (14 mmol) of 2-(5-methylsulphanyl-2-nitrophenyl)acetonitrile in 18 mL of tetrahydrofuran. The mixture is then heated under reflux for 3 h. The mixture is then cooled to room temperature and 6 mL of methanol is added slowly. After 10 min of stirring and of methanolysis of the borane, the mixture is concentrated under vacuum. The residue is taken up in 2-methyl-tetrahydrofuran and the organic phase is washed with 1N aqueous solution of sodium hydroxide. The aqueous phase is extracted three times with 2-methyl-tetrahydrofuran and the organic phases are combined and concentrated partially. 1 mL of acetic acid is added gently and the mixture is left to return to room temperature while stirring slowly. The mixture is then concentrated under vacuum. 3 g (79%) of 2-(5-methylsulphanyl-2-nitrophenyl)ethanamine is obtained in the form of an oil.

184.3: 4-[2-(5-methylsulphanyl-2-nitrophenyl)-ethylamino]-piperidine-1-tert-butyl carboxylate 3 g (14 mmol) of 2-(5-methylsulphanyl-2-nitrophenyl) ethanamine and 3.1 g (15.4 mmol) of 1-Boc-4-piperidone are added to 40 mL of 2-methyltetrahydrofuran. The reaction mixture is of low solubility but 4.5 g (21 mmol) of sodium triacetoxyborohydride is added slowly in portions. The mixture is stirred at room temperature for 12 h and then hydrolysed with 15 mL of an aqueous solution of sodium hydroxide of concentration 2N and extracted with 2-methyl-tetrahydrofuran. The organic phase is washed with water again until pH=6, dried over magnesium sulphate and then concentrated. 6.2 g (100%) of 4-[2-(5-methylsulphanyl-2-nitrophenyl)-ethylamino]-piperidine-1-tert-butyl carboxylate is obtained in the form of an orange-coloured oil.

184.4: 4-[2-(2-amino-5-methylsulphanyl-phenyl)-ethylamino]-piperidine-1-tert-butyl carboxylate 3.1 g (56 mmol) of iron and 0.4 g (7 mmol) of ammonium chloride are added to a solution of 5.5 g (14 mmol) of 4-[2-(5-methylsulphanyl-2-nitrophenyl)-ethylamino]-piperidine-1-tert-butyl carboxylate in 14 mL of methanol, 14 mL of 2-methyl-tetrahydrofuran (14.00 ml) and 14 mL of water. The inhomogeneous reaction mixture is heated under reflux for 3 h. Once the reaction has ended, the mixture is filtered on Celite and the precipitate is rinsed with methanol. The filtrate is concentrated until the methanol has been removed completely and is then taken up in 2-methyl-tetrahydrofuran and hydrolysed with 10 mL of a 10% solution of EDTA. The organic phase obtained is washed with water, dried over magnesium sulphate, filtered and evaporated. 6.1 g (100%) of crude residue of 4-[2-(2-amino-5-methylsulphanyl-phenyl)-ethylamino]-piperidine-1-tert-butyl carboxylate is obtained in the form of an orange-coloured solid.

184.5: 4-(7-methylsulphanyl-2-oxo-1,2,4,5-tetrahydro-benzo[d][1,3]diazepin-3-yl)-piperidine-1-tert-butyl carboxylate 2.5 g (20 mmol) of N,N'-carbonyldiimidazole is added in portions to a solution of 5.1 g (14 mmol) of 4-[2-(2-amino-5-methylsulphanyl-phenyl)-ethylamino]-piperidine-1-tert-butyl carboxylate in 77 mL of acetonitrile. The reaction mixture is stirred at room temperature for 18 hours and then diluted with ethyl acetate and hydrolysed with a saturated aqueous solution of ammonium chloride. The product is extracted with ethyl acetate. The organic phases are combined, washed once with water and once with a saturated aqueous solution of sodium chloride, then dried over magnesium sulphate, filtered and concentrated under vacuum. The crude residue is purified by silica gel chromatography eluted with a heptane/ethyl acetate mixture in increasing polarity from 7/3 to 5/5. 2.4 g (44%) of 4-[2-(2-amino-5-methylsulphanyl-phenyl)-ethylamino]-piperidine-1-tert-butyl carboxylate is obtained.

184.5: 7-methylsulphanyl-3-piperidin-4-yl-1,3,4,5-tetrahydro-benzo[d][1,3]diazepin-2-one 0.8 mL (8 mmol) of trifluoroacetic acid is added to a solution of 1.2 g (3 mmol) of 4-(7-methylsulphanyl-2-oxo-1,2,4,5-tetrahydro-benzo[d][1,3]diazepin-3-yl)-piperidine-1-tert-butyl carboxylate in 7 mL of dichloromethane. The mixture is stirred for 12 hours at room temperature and then concentrated under vacuum. The crude reaction product is taken up in toluene and co-evaporated several times. 0.8 g (90%) of 7-methylsulphanyl-3-piperidin-4-yl-1,3,4,5-tetrahydro-benzo[d][1,3]diazepin-2-one is obtained and is used in step 184.9 without additional purification.

184.6: [5-bromo-3-(2-methylsulphanyl-ethyl)-2,4-dioxo-3,4-dihydro-2H-pyrimidin-1-yl]-methyl acetate 11.8 g (85.5 mmol) of potassium carbonate and then 10.7 mL (109 mmol) of 2-chloroethylmethyl sulphide are added to a solution of 15 g (57 mmol) of 2-(5-bromo-2,4-dioxo-3,4-dihydro-2H-pyrimidin-1-yl)-methyl acetate in 250 mL of N,N-dimethylformamide. The reaction mixture is heated at 60° C. for 9 h and then hydrolysed and diluted with ethyl acetate. The product is extracted with ethyl acetate. The organic phases are combined, washed twice with water and once with a saturated aqueous solution of sodium chloride, dried over magnesium sulphate, filtered and concentrated under vacuum. The crude product is purified by silica gel chromatography eluted with a heptane/ethyl acetate 60/40 mixture. 13.3 g (69%) of [5-bromo-3-(2-methylsulphanyl-ethyl)-2,4-dioxo-3,4-dihydro-2H-pyrimidin-1-yl]-methyl acetate is obtained in the form of a white solid.

184.7: [5-(2-chloro-3-fluorophenyl)-3-(2-methylsulphanyl-ethyl)-2,4-dioxo-3,4-dihydro-2H-pyrimidin-1-yl]-methyl acetate 267 mg (0.3 mmol) of 1,1'-bis(diphenylphosphino) ferrocenepalladium(II) dichloride complexed with dichloromethane is added to a solution of 2.2 g (6.5 mmol) of [5-bromo-3-(2-methylsulphanyl-ethyl)-2,4-dioxo-3,4-dihydro-2H- pyrimidin-1-yl]-methyl acetate, 2.1 g (19.6 mmol) of sodium carbonate and 2.5 g (8.5 mmol) of 2-chloro-3-fluorophenylboronic acid in 220 mL of 1,4-dioxane and 22 mL of water, previously degassed under vacuum/nitrogen for 5 min. The reaction mixture is then heated at 100° C. for 1.5 h and then hydrolysed and diluted with ethyl acetate. The product is extracted with ethyl acetate. The organic phases are combined, washed once with water and once with a saturated aqueous solution of sodium chloride, then dried over magnesium sulphate, filtered and concentrated under vacuum.

The crude product is purified by silica gel chromatography HP 15 eluted with a heptane/ethyl acetate mixture 70/30. 1.4 g (55%) of [5-(2-chloro-3-fluorophenyl)-3-(2-methylsulphanyl-ethyl)-2,4-dioxo-3,4-dihydro-2H-pyrimidin-1-yl]-methyl acetate is obtained in the form of a cream-coloured solid.

184.8: [5-(2-chloro-3-fluorophenyl)-3-(2-methylsulphanyl-ethyl)-2,4-dioxo-3,4-dihydro-2H-pyrimidin-1-yl]-acetic acid 5.4 mL (5.4 mmol) of lithium hydroxide monohydrate and 2.8 mL of water are added to a solution of 1.4 g (3.6 mmol) of [5-(2-chloro-3-fluorophenyl)-3-(2-methylsulphanyl-ethyl)-2,4-dioxo-3,4-dihydro-2H-pyrimidin-1-yl]-methyl acetate in 28 mL of tetrahydrofuran. The reaction mixture is stirred at room temperature for 2 h and then hydrolysed and diluted with ethyl acetate. The pH of the aqueous phase is adjusted to acid pH with an aqueous solution of hydrochloric acid of concentration 1N. The product is extracted with ethyl acetate, the organic phases are combined, washed once with water and once with a saturated aqueous solution of sodium chloride, dried over magnesium sulphate, filtered and then concentrated under vacuum. 1.3 g (98%) of [5-(2-chloro-3-fluorophenyl)-3-(2-methylsulphanyl-ethyl)-2,4-dioxo-3,4-dihydro-2H-pyrimidin-1-yl]-acetic acid is obtained in the form of a cream-coloured solid.

184.9: 5-(2-chloro-3-fluorophenyl)-3-(2-methylsulphanyl-ethyl)-1-{2-[4-(7-methylsulphanyl-2-oxo-1,2,4,5-tetrahydro-benzo[d][1,3]diazepin-3-yl)-piperidin-1-yl]-2-oxo-ethyl}-1H-pyrimidine-2,4-dione 185 mg (1 mmol) of 1-ethyl-3-(3-dimethylaminopropyl) carbodiimide hydrochloride and 107 mg (1 mmol) of 1-oxy-pyridin-2-ol are added to 0.3 g (0.8 mmol) of [5-(2-chloro-3-fluorophenyl)-3-(2-methylsulphanyl-ethyl)-2,4-dioxo-3,4-dihydro-2H-pyrimidin-1-yl]-acetic acid in 2 mL of N,N-dimethylformamide. The reaction mixture is stirred for 5 min and then 281 mg (1 mmol) of 7-methylsulphanyl-3-piperidin-4-yl-1,3,4,5-tetrahydro-benzo[d][1,3]diazepin-2-one (prepared as described in 184.4) and 0.15 mL (1 mmol) of triethylamine are added. The reaction mixture is stirred at room temperature for 12 hours and then diluted with dichloromethane and water. The aqueous phase is extracted three times with dichloromethane, the organic phases are combined and washed with a saturated aqueous solution of sodium hydrogen carbonate and then with a saturated aqueous solution of sodium chloride. After drying over magnesium sulphate, the solution is filtered and then concentrated under vacuum. The crude residue obtained is purified by silica gel chromatography eluted with a heptane/ethyl acetate mixture 7/3. 520 mg (100%) of 5-(2-chloro-3-fluorophenyl)-3-(2-methylsulphanyl-ethyl)-1-{2-[4-(7-methylsulphanyl-2-oxo-1,2,4,5-tetrahydro-benzo[d][1,3]diazepin-3-yl)-piperidin-1-yl]-2-oxo-ethyl}-1H-pyrimidine-2,4-dione is obtained in the form of a white solid.

184.10: 5-(2-chloro-3-fluorophenyl)-3-(2-methanesulphonyl-ethyl)-1-{2-[4-(7-methanesulphonyl-2-oxo-1,2,4,5-tetrahydro-benzo[d][1,3]diazepin-3-yl)-piperidin-1-yl]-2-oxo-ethyl}-1H-pyrimidine-2,4-dione (Compound 184)

50 mg (0.04 mmol) of ammonium molybdate tetrahydrate and 146 μL (24 mmol) of a 30% aqueous solution of hydrogen peroxide are added to 517 mg (0.8 mmol) of 5-(2-chloro-3-fluorophenyl)-3-(2-methylsulphanyl-ethyl)-1-{2-[4-(7-methylsulphanyl-2-oxo-1,2,4,5-tetrahydro-benzo[d][1,3]diazepin-3-yl)-piperidin-1-yl]-2-oxo-ethyl}-1H-pyrimidine-2,4-dione in 3 mL of ethanol previously cooled to 0° C. The reaction is stirred at room temperature for 2 hours and then hydrolysed with water (30 mL) and extracted with dichloromethane (3×30 mL). The organic phases are combined, washed with a saturated aqueous solution of sodium thiosulphate (30 mL×4), water (20 mL×2), and a saturated aqueous solution of sodium chloride (20 mL×2), then dried over magnesium sulphate, filtered and concentrated under vacuum. After trituration of the crude residue in ethyl acetate for 12 hours and filtration, 210 mg (35%) of 5-(2-chloro-3-fluorophenyl)-3-(2-methanesulphonyl-ethyl)-1-{2-[4-(7-methanesulphonyl-2-oxo-1,2,4,5-tetrahydro-benzo[d][1,3]diazepin-3-yl)-piperidin-1-yl]-2-oxo-ethyl}-1H-pyrimidine-2,4-dione is obtained.

$^1$H NMR (400 MHz, DMSO): δ (ppm) 1.52-1.75 (m, 4H); 2.68 (t, J=11.7 Hz, 1H); 2.98 (br t, 2H); 3.06 (s, 3H); 3.10 (s, 3H); 3.14-3.18 (br m, 1H); 3.40 (br m, 4H); 3.95 (d, J=13.5 Hz, 1H); 4.27-4.43 (m, 4H); 4.79 (s, 2H); 7.18-7.23 (m, 2H); 7.42-7.45 (m, 2H); 7.54-7.58 (m, 2H); 7.86 (s, 1H); 9.13 (s, 1H).

Another compound synthesized according to a similar procedure using the appropriate reagents, or previously prepared:

Compound 185: 5-(2-chloro-3-fluorophenyl)-3-isopropyl-1-{2-[4-(7-methanesulphonyl-2-oxo-1,2,4,5-tetrahydro-benzo[d][1,3]diazepin-3-yl)-piperidin-1-yl]-2-oxo-ethyl}-1H-pyrimidine-2,4-dione

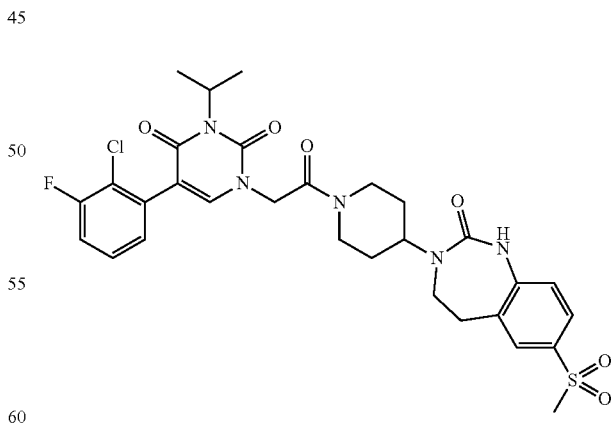

$^1$H NMR (δ, DMSO): 1.41 (d, J=6.9 Hz, 6H), 1.57 (m, 1H), 1.70 (m, 3H), 2.64-2.77 (m, 1H), 2.93-3.05 (m, 2H), 3.12 (s, 3H), 3.17 (m, 1H), 3.37-3.48 (m, 2H), 3.95 (m, 1H), 4.28-4.50 (m, 2H), 4.64-4.84 (m, 2H), 5.10 (h, J=6.8 Hz, 1H), 7.18-7.27 (m, 2H), 7.40-7.49 (m, 2H), 7.54-7.62 (m, 2H), 7.77 (s, 1H), 9.15 (s, 1H).

EXAMPLE 186: 5-(2-CHLORO-3-FLUOROPHE-NYL)-3-(2-METHANESULPHONYL-ETHYL)-1-{2-[4-(7-METHYLSULPHANYL-2-OXO-1,2,4,5-TETRAHYDRO-BENZO[D][1,3]DIAZEPIN-3-YL)-PIPERIDIN-1-YL]-2-OXO-ETHYL}-1H-PYRIMIDINE-2,4-DIONE (REACTION SCHEME NO. 4, COMPOUND 186)

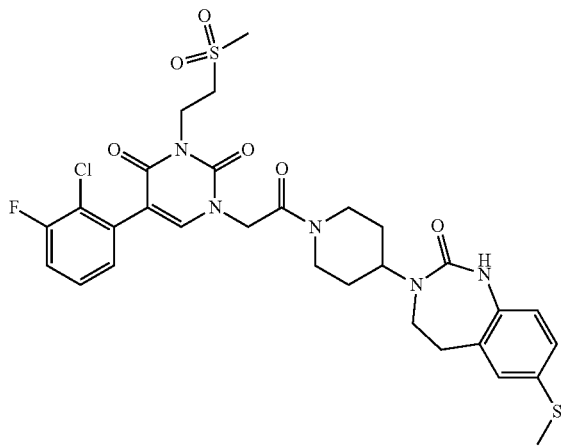 [SMILES: CSc1ccc2c(c1)CCN(C1CCN(C(=O)Cn3cc(-c4cccc(F)c4Cl)c(=O)n(CCS(C)(=O)=O)c3=O)CC1)C(=O)N2]

186.1: [5-(2-chloro-3-fluorophenyl)-3-(2-methane-sulphonyl-ethyl)-2,4-dioxo-3,4-dihydro-2H-pyrimidin-1-yl]-acetic acid A solution of 50 mg (0.04 mmol) of ammonium molybdate tetrahydrate and 146 µL (24 mmol) of a 30% aqueous solution of hydrogen peroxide are added to a solution of [5-(2-chloro-3-fluorophenyl)-3-(2-methylsulphanyl-ethyl)-2,4-dioxo-3,4-dihydro-2H-pyrimidin-1-yl]-acetic acid (prepared as described in 184.8). The reaction is stirred at room temperature for 2 hours, hydrolysed with water (30 mL) and extracted with ethyl acetate (3×30 mL). The organic phases are combined, washed with a saturated aqueous solution of sodium thiosulphate, with water and then a saturated aqueous solution of sodium chloride. After drying over sodium sulphate and vacuum filtration, 320 mg (98%) of [5-(2-chloro-3-fluorophenyl)-3-(2-methanesulphonyl-ethyl)-2,4-dioxo-3,4-dihydro-2H-pyrimidin-1-yl]-acetic acid is obtained and is used in the next step without purification.

186.2: 5-(2-chloro-3-fluorophenyl)-3-(2-methanesulphonyl-ethyl)-1-{2-[4-(7-methylsulphanyl-2-oxo-1,2,4,5-tetrahydro-benzo[d][1,3]diazepin-3-yl)-piperidin-1-yl]-2-oxo-ethyl}-1H-pyrimidine-2,4-dione (Compound 186)

182 mg (1 mmol) of 1-ethyl-3-(3-dimethylaminopropyl) carbodiimide hydrochloride and 105 mg (1 mmol) of 1-oxy-pyridin-2-ol are added to a solution of 320 mg (0.8 mmol) of [5-(2-chloro-3-fluorophenyl)-3-(2-methanesulphonyl-ethyl)-2,4-dioxo-3,4-dihydro-2H-pyrimidin-1-yl]-acetic acid in 2 mL N,N-dimethylformamide. The reaction mixture is stirred for 5 min and then 253 mg (0.9 mmol) of 7-methylsulphanyl-3-piperidin-4-yl-1,3,4,5-tetrahydro-benzo[d][1,3]diazepin-2-one and 0.15 mL (1 mmol) of triethylamine are added. The reaction mixture is stirred at room temperature for 12 hours, then diluted with dichloromethane and water. The aqueous phase is extracted three times with dichloromethane, the organic phases are combined and washed with a saturated solution of sodium hydrogen carbonate, with water and then with a saturated aqueous solution of sodium chloride. After drying over magnesium sulphate, the solution is filtered and then concentrated under vacuum.

After trituration of the crude residue in ethyl acetate for 12 hours and filtration, 210 mg (36%) of 5-(2-chloro-3-fluorophenyl)-3-(2-methanesulphonyl-ethyl)-1-{2-[4-(7-methylsulphanyl-2-oxo-1,2,4,5-tetrahydro-benzo[d][1,3]diazepin-3-yl)-piperidin-1-yl]-2-oxo-ethyl}-1H-pyrimidine-2,4-dione is obtained.

$^1$H NMR (400 MHz, DMSO): δ (ppm) 1.50-1.73 (m, 4H); 2.38 (s, 3H); 2.67 (t, J=12.4 Hz, 1H); 2.86 (d, J=6.8 Hz, 2H); 3.06 (s, 3H); 3.13 (t, J=12.4 Hz, 1H); 3.33-3.41 (m. 4H); 3.94 (d, J=13.6 Hz, 1H); 4.29 (t, J=7.4 Hz, 3H); 4.41 (d, J=12.9 Hz, 1H); 4.78 (s, 2H); 6.99 (d, J=10.8 Hz, 3H); 7.19-7.21 (m, 1H); 7.43-7.46 (m, 2H); 7.86 (s, 1H); 8.55 (s, 1H).

The following compounds were synthesized according to a similar procedure, using the appropriate reagents, commercially available or previously prepared:

Compound 187: 5-(2-chloro-3-fluorophenyl)-3-((R)-2-methoxy-1-methylethyl)-1-{2-[4-(7-methylsulphanyl-2-oxo-1,2,4,5-tetrahydro-benzo[d][1,3]diazepin-3-yl)-piperidin-1-yl]-2-oxo-ethyl}-1H-pyrimidine-2,4-dione

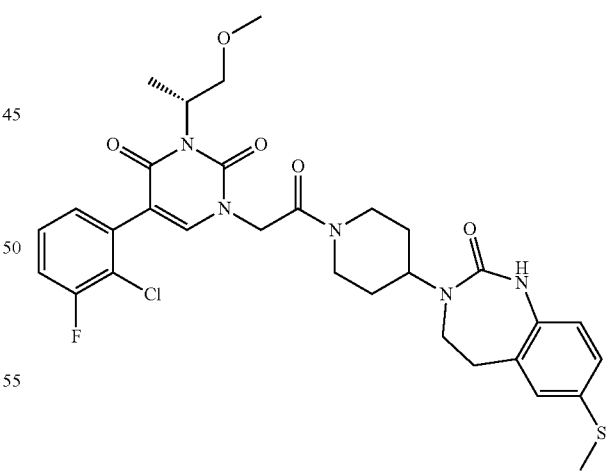

$^1$H NMR (δ, DMSO): 1.33 (d, J=7.0 Hz, 3H), 1.56 (m, 1H), 1.67 (m, 3H), 2.40 (s, 3H), 2.68 (m, 1H), 2.88 (m, 2H), 3.14 (m, 1H), 3.23 (s, 3H), 3.34-3.42 (m, 2H), 3.54 (m, 1H), 3.83-4.04 (m, 2H), 4.33 (m, 1H), 4.43 (d, J=12.8 Hz, 1H), 4.75 (m, 2H), 5.15 (m, 1H), 7.01 (m, 3H), 7.21 (m, 1H), 7.45 (m, 2H), 7.79 (s, 1H), 8.57 (s, 1H).

Compound 188: 5-(2-chloro-3-fluorophenyl)-3-(2-methoxyethyl)-1-{2-[4-(7-methylsulphanyl-2-oxo-1,2,4,5-tetrahydro-benzo[d][1,3]diazepin-3-yl)-piperidin-1-yl]-2-oxo-ethyl}-1H-pyrimidine-2,4-dione

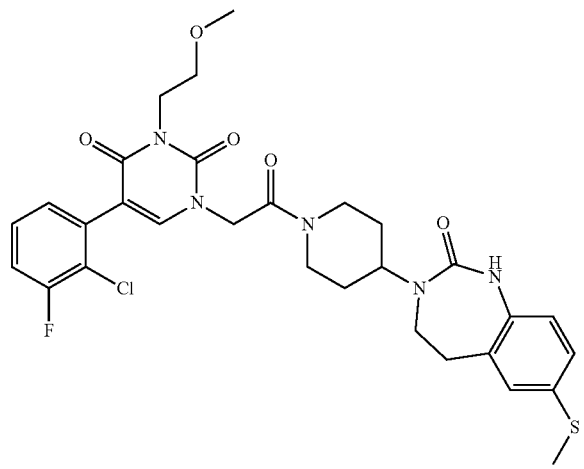 [SMILES: COCCn1c(=O)c(-c2cccc(F)c2Cl)cn(CC(=O)N2CCC(N3CCc4cc(SC)ccc4NC3=O)CC2)c1=O]

¹H NMR (δ, DMSO): 1.45-1.61 (m, 1H), 1.70 (m, 3H), 2.40 (s, 3H), 2.61-2.75 (m, 1H), 2.82-2.93 (m, 2H), 3.09-3.21 (m, 1H), 3.26 (s, 3H), 3.34-3.42 (m, 2H), 3.52 (t, J=6.1 Hz, 2H), 3.94 (d, J=13.5 Hz, 1H), 4.07 (m, 2H), 4.32 (m, 1H), 4.43 (d, J=13.0 Hz, 1H), 4.78 (m, 2H), 6.91-7.09 (m, 3H), 7.17-7.29 (m, 1H), 7.36-7.54 (m, 2H), 7.83 (s, 1H), 8.57 (s, 1H).

Compound 189: 5-(2-chloro-3-fluorophenyl)-3-isopropyl-1-{2-[4-(7-methylsulphanyl-2-oxo-1,2,4,5-tetrahydro-benzo[d][1,3]diazepin-3-yl)-piperidin-1-yl]-2-oxo-ethyl}-1H-pyrimidine-2,4-dione

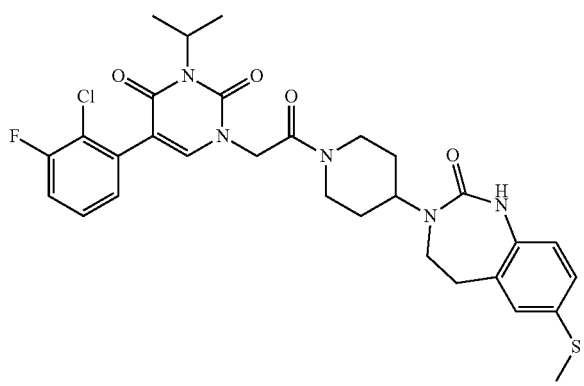 [SMILES: CSc1ccc2c(c1)CCN(C1CCN(C(=O)Cn3cc(-c4cccc(F)c4Cl)c(=O)n(C(C)C)c3=O)CC1)C(=O)N2]

¹H NMR (δ, DMSO): 1.41 (d, J=7.0 Hz, 6H), 1.56 (m, 1H), 1.63-1.86 (m, 3H), 2.40 (s, 3H), 2.68 (m, 1H), 2.78-2.95 (m, 2H), 3.15 (m, 1H), 3.33-3.45 (m, 2H), 3.94 (d, J=13.6 Hz, 1H), 4.31 (m, 1H), 4.43 (d, J=12.9 Hz, 1H), 4.74 (m, 2H), 5.11 (p, J=6.9 Hz, 1H), 7.01 (m, 3H), 7.15-7.27 (m, 1H), 7.35-7.52 (m, 2H), 7.77 (s, 1H), 8.56 (s, 1H).

EXAMPLE 190: 3-(1-{2-[5-(2,3-DIFLUOROPHENYL)-3-METHYL-2-OXO-3,4-DIHYDRO-2H-PYRIMIDIN-1-YL]-ACETYL}-PIPERIDIN-4-YL)-1,3,4,5-TETRAHYDRO-BENZO[D][1,3]DIAZEPIN-2-ONE (REACTION SCHEME NO. 3, COMPOUND 190)

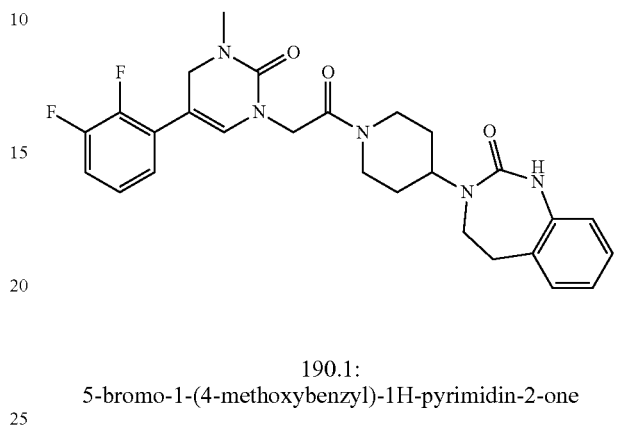

190.1: 5-bromo-1-(4-methoxybenzyl)-1H-pyrimidin-2-one 4 mL (30 mmol) of triethylamine and then 4.3 mL of 4-methoxybenzyl chloride are added to a solution of 5 g (30 mmol) of 5-bromo-2-hydroxypyrimidine in 150 mL of dichloromethane. The reaction mixture is stirred at room temperature for 48 h and then hydrolysed and diluted with dichloromethane. The product is extracted with dichloromethane and then with ethyl acetate. The organic phases are combined and concentrated under vacuum. The crude product obtained is taken up in 60 mL of ethyl acetate and then filtered. The solid obtained is dried with nitrogen for 2 h to give 4.9 g (46%) of 5-bromo-1-(4-methoxybenzyl)-1H-pyrimidin-2-one in the form of an off-white solid.

190.2: 5-bromo-1-(4-methoxybenzyl)-3,4-dihydro-1H-pyrimidin-2-one 2.5 mL (5.5 mmol) of a solution of zirconium isopropoxide in heptane of concentration 2M is added to 4.9 g (16.6 mmol) of 5-bromo-1-(4-methoxybenzyl)-1H-pyrimidin-2-one in 392 mL of isopropanol. The reaction mixture (white suspension initially) is heated at 90° C. for 48 hours. The solvents are concentrated under vacuum. The residue is taken up in dichloromethane and water. The product is extracted with dichloromethane. The organic phases are combined, washed three times with water and then filtered to remove the insolubles (zirconium salts). The filtrate is concentrated under vacuum. The crude product is purified by silica gel chromatography eluted with a heptane/ethyl acetate 50/50 mixture to give 3.45 g (70%) of 5-bromo-1-(4-methoxybenzyl)-3,4-dihydro-1H-pyrimidin-2-one in the form of a white solid.

190.3: 5-bromo-1-(4-methoxybenzyl)-3-methyl-3,4-dihydro-1H-pyrimidin-2-one 242 mg (6.1 mmol) of sodium hydride is added in portions to a solution of 1.5 g (5.1 mmol) of 5-bromo-1-(4-methoxybenzyl)-3,4-dihydro-1H-pyrimidin-2-one in 23 mL of tetrahydrofuran. The reaction mixture is stirred at room temperature for 10 min before adding 0.5 mL (7.6 mmol) of iodomethane. The reaction mixture is stirred at room temperature for 1.5 h and then hydrolysed and diluted with ethyl acetate. The product is extracted with ethyl acetate. The organic phases are combined, washed once with water and once with a saturated aqueous solution of sodium chloride, then dried over magnesium sulphate, filtered and concentrated under vacuum to give 1.6 g (100%) of 5-bromo-1-(4-methoxybenzyl)-3-methyl-3,4-dihydro-1H-pyrimidin-2-one in the form of a yellow oil. The product is used in the next step without purification.

190.4: 5-(2,3-difluorophenyl)-1-(4-methoxybenzyl)-3-methyl-3,4-dihydro-1H-pyrimidin-2-one 297 mg (0.3 mmol) of tetrakis(triphenylphosphine)palladium(0) and then 4 g (25.7 mmol) of 2,3-difluorophenylboronic acid are added to a solution of 1.6 g (5.1 mmol) of 5-bromo-1-(4-methoxybenzyl)-3-methyl-3,4-dihydro-1H-pyrimidin-2-one and 12.9 mL (25.7 mmol) of an aqueous solution of potassium carbonate of concentration 2M in 48 mL of N,N-dimethylformamide and 16 mL of water, previously degassed. The reaction mixture is heated at 90° C. for 1.5 h. After cooling, the reaction mixture is hydrolysed and then diluted with ethyl acetate. The product is extracted with ethyl acetate. The organic phases are combined, washed once with water and once with a saturated aqueous solution of sodium chloride, then dried over magnesium sulphate, filtered and concentrated under vacuum. The crude product is purified by silica gel chromatography eluted with a heptane/ethyl acetate mixture 80/20 to give 0.7 g (41%) of 5-(2,3-difluorophenyl)-1-(4-methoxybenzyl)-3-methyl-3,4-dihydro-1H-pyrimidin-2-one in the form of a yellow oil.

190.5: 5-(2,3-difluorophenyl)-3-methyl-3,4-dihydro-1H-pyrimidin-2-one 640 mg (1.9 mmol) of 5-(2,3-difluorophenyl)-1-(4-methoxybenzyl)-3-methyl-3,4-dihydro-1H-pyrimidin-2-one is dissolved in 5 mL of trifluoroacetic acid. The reaction mixture is stirred at room temperature for 30 min and then concentrated to dryness under vacuum, diluted with dichloromethane, and finally hydrolysed with a saturated aqueous solution of sodium hydrogen carbonate. The product is extracted with dichloromethane. The organic phases are combined, washed once with water and then dried over magnesium sulphate, filtered and concentrated under vacuum. The crude product obtained is purified by silica gel chromatography eluted with a dichloromethane/ethyl acetate mixture 80/20. 85 mg (20%) of 5-(2,3-difluorophenyl)-3-methyl-3,4-dihydro-1H-pyrimidin-2-one is obtained.

190.6: [5-(2,3-difluorophenyl)-3-methyl-2-oxo-3,4-dihydro-2H-pyrimidin-1-yl]-methyl acetate 18.2 mg (0.45 mmol) of sodium hydride is added in portions to 85 mg (0.4 mmol) of 5-(2,3-difluorophenyl)-3-methyl-3,4-dihydro-1H-pyrimidin-2-one in solution in 4.5 mL of N,N-dimethylformamide. After stirring for 2 min at room temperature, 40 µL (0.45 mmol) of methylchloroacetate is added. The reaction mixture is stirred at room temperature for 40 min and then hydrolysed and diluted with ethyl acetate. The product is extracted with ethyl acetate. The organic phases are combined, washed once with water and once with a saturated aqueous solution of sodium chloride, then dried over magnesium sulphate, filtered and concentrated under vacuum. 100 mg (89%) of [5-(2,3-difluorophenyl)-3-methyl-2-oxo-3,4-dihydro-2H-pyrimidin-1-yl]-methyl acetate is obtained in the form of a white solid.

190.7: 5-(2,3-difluorophenyl)-3-methyl-2-oxo-3,4-dihydro-2H-pyrimidin-1-yl]-acetic acid 100 mg (0.3 mmol) of [5-(2,3-difluorophenyl)-3-methyl-2-oxo-3,4-dihydro-2H-pyrimidin-1-yl]-methyl acetate is dissolved in 5 mL of tetrahydrofuran and 0.5 mL of water and then 0.5 mL of a 1M aqueous solution of lithium hydroxide monohydrate is added. The reaction mixture is stirred at room temperature for 1.5 h, hydrolysed and then diluted with ethyl acetate. This first ethyl acetate phase is discarded. The aqueous phase is acidified to pH=5-6 with an aqueous solution of acetic acid of concentration C=1M. The product is extracted with ethyl acetate. The organic phases are combined, washed once with water and once with a saturated aqueous solution of sodium chloride, then dried over magnesium sulphate, filtered and concentrated under vacuum. 80 mg (84%) of [5-(2,3-difluorophenyl)-3-methyl-2-oxo-3,4-dihydro-2H-pyrimidin-1-yl]-acetic acid is obtained in the form of a white solid.

190.8: 3-(1-{2-[5-(2,3-difluorophenyl)-3-methyl-2-oxo-3,4-dihydro-2H-pyrimidin-1-yl]-acetyl}-piperidin-4-yl)-1,3,4,5-tetrahydro-benzo[d][1,3]diazepin-2-one (Compound 190)

Similarly to example 51.4, starting from 80 mg (0.3 mmol) of [5-(2,3-difluorophenyl)-3-methyl-2-oxo-3,4-dihydro-2H-pyrimidin-1-yl]-acetic acid and 70 mg (0.3 mmol) of 3-piperidin-4-yl-1,3,4,5-tetrahydro-benzo[d][1,3]diazepin-2-one (prepared as described in example 16.4), 80 mg (55%) of 3-(1-{2-[5-(2,3-difluorophenyl)-3-methyl-2-oxo-3,4-dihydro-2H-pyrimidin-1-yl]-acetyl}-piperidin-4-yl)-1,3,4,5-tetrahydro-benzo[d][1,3]diazepin-2-one is obtained.

$^1$H NMR (400 MHz, DMSO): δ (ppm): 1.59-1.40 (m, 1H), 1.65 (m, 3H), 2.70-2.56 (m, 1H), 2.88 (m, 5H), 3.07 (m, 1H), 3.42-3.35 (m, 2H), 3.90 (d, J=13.6 Hz, 1H), 4.34-4.17 (m, 3H), 4.39 (s, 2H), 4.44 (d, 1H), 6.86-6.69 (m, 2H), 7.13-6.91 (m, 4H), 7.36-7.15 (m, 2H), 8.54 (s, 1H).

The following compounds were synthesized according to a similar procedure, using the appropriate reagents, commercially available or previously prepared:

Compound 191: 3-(1-{2-[5-(2,3-dichlorophenyl)-3-methyl-2-oxo-3,4-dihydro-2H-pyrimidin-1-yl]-acetyl}-piperidin-4-yl)-1,3,4,5-tetrahydro-benzo[d][1,3]diazepin-2-one

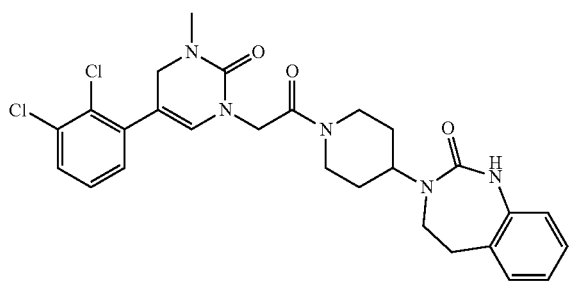 [SMILES: CN1CC(c2cccc(Cl)c2Cl)=CN(CC(=O)N2CCC(N3CCc4ccccc4NC3=O)CC2)C1=O]

$^1$H NMR (δ, DMSO): 1.45-1.60 (m, 1H), 1.61-1.75 (m, 3H), 2.60 (m, 1H), 2.84 (s, 3H), 2.88 (m, 2H), 3.07 (m, 1H), 3.36 (m, 2H), 3.90 (m, 1H), 4.21 (d, J=2.5 Hz, 2H), 4.25-4.35 (m, 3H), 4.43 (m, 1H), 6.41 (s, 1H), 6.78-6.82 (m, 1H), 7.01-7.04 (m, 3H), 7.30 (dd, J=1.7-7.7 Hz, 1H), 7.36 (t, J=7.8 Hz, 1H), 7.57 (dd, J=1.7-7.9 Hz, 1H), 8.52 (s, 1H).

Compound 192: 3-(1-{2-[5-(2-chloro-3-fluorophenyl)-3-(2-methoxyethyl)-2-oxo-3,4-dihydro-2H-pyrimidin-1-yl]-acetyl}-piperidin-4-yl)-1,3,4,5-tetrahydro-benzo[d][1,3]diazepin-2-one

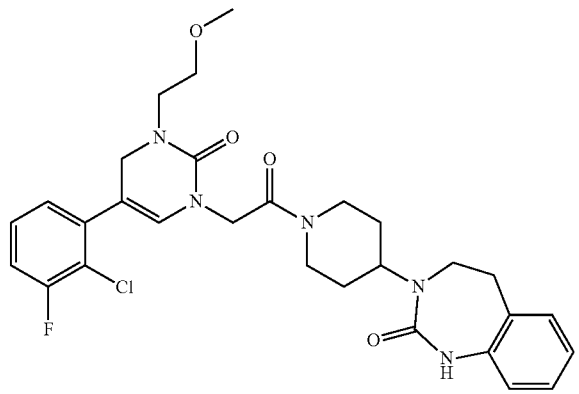 [SMILES: COCCN1CC(c2cccc(F)c2Cl)=CN(CC(=O)N2CCC(N3CCc4ccccc4NC3=O)CC2)C1=O]

¹H NMR (δ, DMSO): 1.53 (m, 1H); 1.67 (m, 3H); 2.59-2.64 (m, 1H); 2.89 (m, 2H); 3.08 (m, 1H); 3.27 (s, 3H); 3.35-3.38 (m, 2H); 3.46-3.50 (m, 4H); 3.91 (d, J=13.5 Hz, 1H); 4.35 (m, 5H); 4.44 (d, J=13.0 Hz, 1H); 6.46 (s, 1H); 6.80-6.82 (m, 1H); 7.04-7.06 (m, 3H); 7.18 (m, 1H); 7.35-7.36 (m, 2H); 8.52 (s, 1H).

Compound 193: 3-(1-{2-[5-(2-chloro-3-methoxyphenyl)-3-isopropyl-2-oxo-3,4-dihydro-2H-pyrimidin-1-yl]-acetyl}-piperidin-4-yl)-1,3,4,5-tetrahydro-benzo[d][1,3]diazepin-2-one

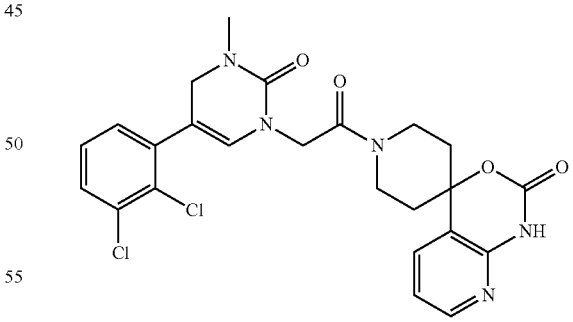

¹H NMR (δ, DMSO): 1.21 (d, J=6.9 Hz, 6H), 1.65-2.00 (m, 4H), 2.67-2.82 (m, 1H), 2.94-3.07 (m, 2H), 3.20 (m, 1H), 3.35 (m, 1H), 3.52 (m, 2H), 3.91 (s, 3H), 4.04 (d, 1H), 4.18 (m, 2H), 4.34 (d, J=16.6 Hz, 1H), 4.43 (m, 1H), 4.55 (d, J=16.6 Hz, 1H), 4.60-4.73 (m, 2H), 6.25 (s, 1H), 6.86-6.99 (m, 3H), 7.04 (dd, J=8.6, 1.3 Hz, 1H), 7.06-7.13 (m, 2H), 7.26 (t, J=8.0 Hz, 1H).

Compound 194: 3-(1-{2-[5-(2,3-dichlorophenyl)-2-oxo-3-(2,2,2-trifluoroethyl)-3,4-dihydro-2H-pyrimidin-1-yl]-acetyl}-piperidin-4-yl)-1,3,4,5-tetrahydro-benzo[d][1,3]diazepin-2-one

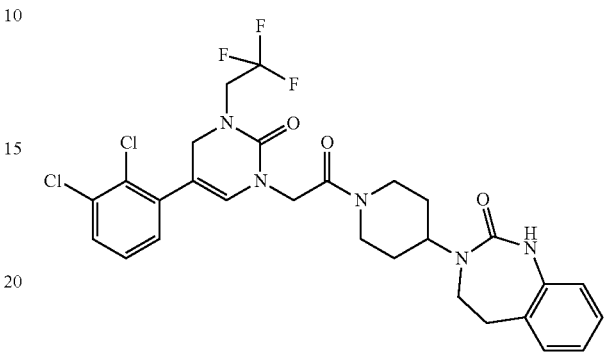

¹H NMR (δ, DMSO): 1.53 (m, 1H), 1.65 (m, 3H), 2.62 (m, 1H), 2.79-2.97 (m, 2H), 3.08 (m, 1H), 3.34-3.43 (m, 2H), 3.90 (d, J=13.4 Hz, 1H), 4.17 (m, 2H), 4.24-4.52 (m, 6H), 6.45 (s, 1H), 6.80 (m, 1H), 7.03 (m, 3H), 7.25-7.51 (m, 2H), 7.56-7.72 (m, 1H), 8.53 (s, 1H).

Compound 195: 1'-[2-[5-(2,3-dichlorophenyl)-3-methyl-2-oxo-4H-pyrimidin-1-yl]acetyl]spiro[1H-pyrido[2,3-d][1,3]oxazine-4,4'-piperidin]-2-one ¹H NMR (δ, DMSO): 2.00 (m, 4H), 2.85 (s, 3H), 2.93 (m, 1H), 3.39 (m, 1H), 3.85 (d, J=13.7 Hz, 1H), 4.22 (m, 2H), 4.37 (m, 3H), 6.41 (s, 1H), 7.09 (m, 1H), 7.22-7.45 (m, 2H), 7.58 (dd, J=7.8, 1.8 Hz, 1H), 7.71 (d, J=7.6 Hz, 1H), 8.21 (d, J=4.9 Hz, 1H), 10.86 (s, 1H).

Compound 196: 5-(2,3-dichlorophenyl)-3-methyl-1-{2-oxo-2-[4-(2-oxo-4-phenyl-2,3-dihydro-imidazol-1-yl)-piperidin-1-yl]-ethyl}-3,4-dihydro-1H-pyrimidin-2-one

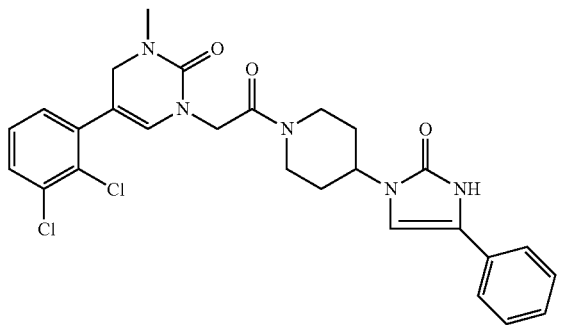 [SMILES: CN1CC(c2cccc(Cl)c2Cl)=CN(CC(=O)N2CCC(n3cc(-c4ccccc4)[nH]c3=O)CC2)C1=O]

¹H NMR (δ, DMSO): 1.54-1.93 (m, 4H), 2.70 (m, 1H), 2.85 (s, 3H), 3.15 (m, 1H), 3.95 (d, J=13.4 Hz, 1H), 4.11 (m, 1H), 4.22 (m, 2H), 4.37 (s, 2H), 4.48 (d, J=13.2 Hz, 1H), 6.40 (s, 1H), 7.10-7.22 (m, 2H), 7.35 (m, 4H), 7.50 (d, J=7.3 Hz, 2H), 7.54-7.61 (m, 1H), 10.71 (br-s, 1H).

Compound 197: 3-(1-{2-[5-(2-chloro-3-fluorophenyl)-3-methyl-2-oxo-3,4-dihydro-2H-pyrimidin-1-yl]-acetyl}-piperidin-4-yl)-1,3,4,5-tetrahydro-benzo[d][1,3]diazepin-2-one

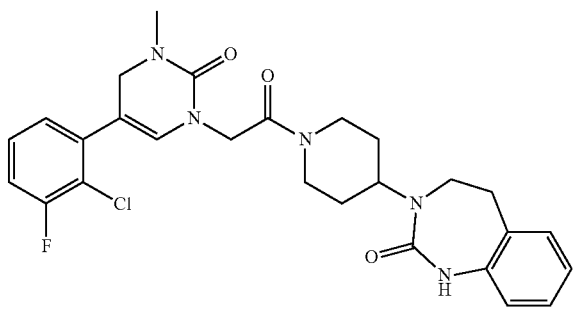 [SMILES: CN1CC(c2cccc(F)c2Cl)=CN(CC(=O)N2CCC(N3CCc4ccccc4NC3=O)CC2)C1=O]

¹H NMR (δ, DMSO): 1.52 (m, 1H), 1.65 (m, 3H), 2.61 (m, 1H), 2.85 (s, 3H), 2.88 (m, 2H), 3.08 (m, 1H), 3.37 (m, 2H), 3.90 (d, J=13.7 Hz, 1H), 4.11-4.55 (m, 6H), 6.48 (s, 1H), 6.71-6.88 (m, 1H), 7.03 (m, 3H), 7.19 (dt, J=7.3, 1.5 Hz, 1H), 7.35 (m, 2H), 8.52 (s, 1H).

Compound 198: 3-(1-{2-[5-(2-chloro-3-fluorophenyl)-3-ethyl-2-oxo-3,4-dihydro-2H-pyrimidin-1-yl]-acetyl}-piperidin-4-yl)-1,3,4,5-tetrahydro-benzo[d][1,3]diazepin-2-one

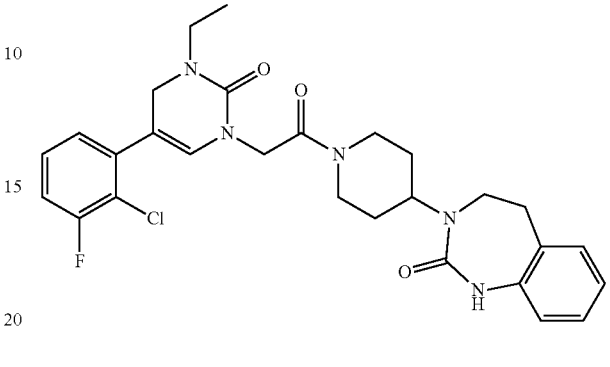

¹H NMR (δ, DMSO): 1.08 (t, J=7.1 Hz, 3H), 1.41-1.59 (m, 1H), 1.66 (m, 3H), 2.60 (m, 2H), 2.80-2.93 (m, 2H), 3.08 (m, 1H), 3.34-3.45 (m, 3H), 3.90 (d, J=13.5 Hz, 1H), 4.16-4.38 (m, 5H), 4.42 (d, J=13.5 Hz, 1H), 6.46 (s, 1H), 6.73-6.88 (m, 1H), 7.03 (m, 3H), 7.13-7.23 (m, 1H), 7.27-7.47 (m, 2H), 8.53 (s, 1H).

Compound 199: 3-(1-{2-[5-(2,3-dichlorophenyl)-3-ethyl-2-oxo-3,4-dihydro-2H-pyrimidin-1-yl]-acetyl}-piperidin-4-yl)-1,3,4,5-tetrahydro-benzo[d][1,3]diazepin-2-one

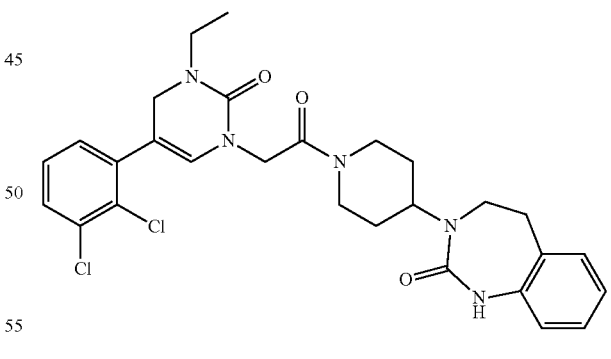

¹H NMR (δ, DMSO): 1.08 (t, J=7.1 Hz, 3H), 1.52 (m, 1H), 1.64 (m, 3H), 2.61 (m, 1H), 2.88 (m, 2H), 3.08 (m, 1H), 3.36 (m, 4H), 3.90 (d, J=13.4 Hz, 1H), 4.12-4.56 (m, 6H), 6.40 (s, 1H), 6.80 (m, 1H), 7.03 (m, 3H), 7.22-7.45 (m, 2H), 7.58 (dd, J=7.7, 1.8 Hz, 1H), 8.52 (s, 1H).

Compound 200: 3-(1-{2-[5-(2-chloro-3-fluorophenyl)-3-isopropyl-2-oxo-3,4-dihydro-2H-pyrimidin-1-yl]-acetyl}-piperidin-4-yl)-1,3,4,5-tetrahydro-benzo[d][1,3]diazepin-2-one

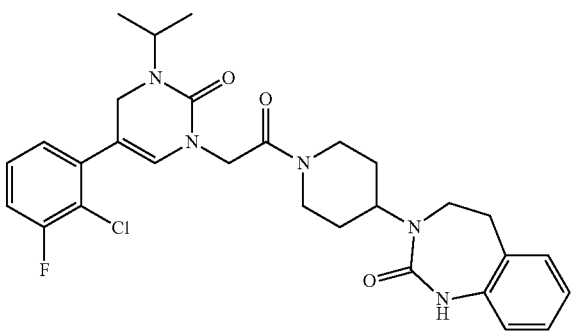

¹H NMR (δ, DMSO): 1.11 (d, J=6.8 Hz, 6H), 1.40-1.57 (m, 1H), 1.67 (m, 3H), 2.53-2.71 (m, 1H), 2.79-2.96 (m, 2H), 2.98-3.16 (m, 1H), 3.34-3.41 (m, 2H), 3.91 (d, J=13.8 Hz, 1H), 4.09 (m, 2H), 4.21-4.60 (m, 5H), 6.46 (s, 1H), 6.70-6.88 (m, 1H), 6.93-7.10 (m, 3H), 7.15-7.23 (m, 1H), 7.27-7.44 (m, 2H), 8.53 (s, 1H).

Compound 201: 3-(1-{2-[5-(2,3-dichlorophenyl)-3-isopropyl-2-oxo-3,4-dihydro-2H-pyrimidin-1-yl]-acetyl}-piperidin-4-yl)-1,3,4,5-tetrahydro-benzo[d][1,3]diazepin-2-one

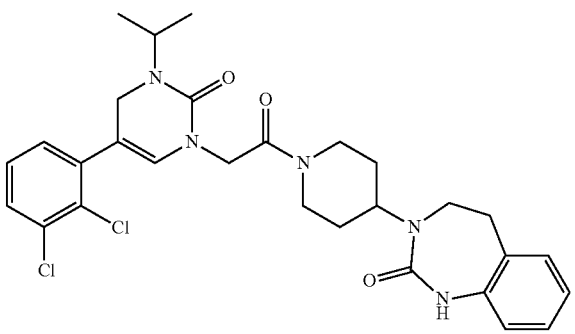 [SMILES: CC(C)N1CC(c2cccc(F)c2Cl)=CN(CC(=O)N2CCC(N3CCc4ccccc4NC3=O)CC2)C1=O]

¹H NMR (δ, DMSO): 1.17 (d, J=6.8 Hz, 6H), 1.58 (m, 1H), 1.71 (m, 3H), 2.56-2.73 (m, 1H), 2.94 (m, 2H), 3.14 (m, 1H), 3.41-3.51 (m, 2H), 3.97 (d, J=13.9 Hz, 1H), 4.12 (m, 2H), 4.33-4.44 (m, 3H), 4.46-4.62 (m, 2H), 6.46 (s, 1H), 6.86 (m, 1H), 7.09 (m, 3H), 7.33-7.47 (m, 2H), 7.64 (dd, J=8.0, 1.8 Hz, 1H), 8.58 (s, 1H).

The compounds described below are also prepared according to procedures similar to those described above throughout the experimental section using the appropriate reagents, commercially available or previously prepared according to conventional methods in organic synthesis:

Compound 208: 5-(2,3-dichlorophenyl)-3-methyl-1-[2-oxo-2-[4-(2-oxo-5-phenyl-1H-imidazol-3-yl)-1-piperidyl]ethyl]pyrimidine-2,4-dione

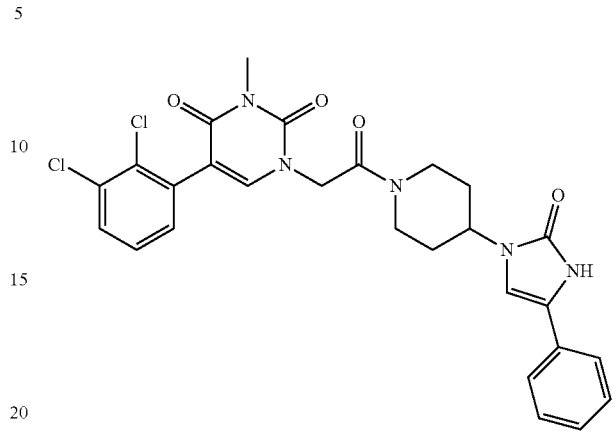

¹H NMR (δ, DMSO): 1.54-1.94 (m, 4H), 2.69-2.84 (m, 1H), 3.21 (m, 1H), 3.25 (s, 3H), 4.01 (d, J=13.0 Hz, 1H), 4.09-4.26 (m, 1H), 4.46 (d, J=12.7 Hz, 1H), 4.66-4.95 (m, 2H), 7.11-7.22 (m, 2H), 7.33 (m, 3H), 7.43 (t, J=7.8 Hz, 1H), 7.47-7.54 (m, 2H), 7.69 (dd, J=8.0, 1.6 Hz, 1H), 7.84 (s, 1H), 10.74 (m, 1H).

Compound 209: 2-[5-(2,3-dichlorophenyl)-3-methyl-2,4-dioxo-pyrimidin-1-yl]-N-[4-(2-oxo-4,5-dihydro-1H-1,3-benzodiazepin-3-yl)-1-piperidyl]acetamide

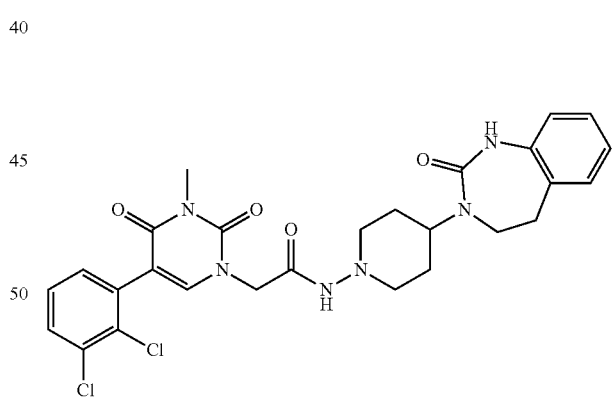

¹H NMR (δ, DMSO): 1.48-1.74 (m, 2H), 1.75-1.96 (m, 2H), 2.62 (m, 2H), 2.90 (m, 2H), 2.99 (d, J=10.6 Hz, 1H), 3.07 (m, 1H), 8.97 (br-s, 1H), 3.24 (m, 3H), 3.40 (m, 2H), 4.03 (m, 1H), 4.76 (s, 2H), 6.68-6.90 (m, 1H), 7.04 (d, J=4.7 Hz, 3H), 7.32 (m, 1H), 7.43 (t, J=7.8 Hz, 1H), 7.69 (dd, J=8.0, 1.6 Hz, 1H), 7.89 (m, 1H), 8.50 (m, 1H).

Compound 210: 5-(2,3-dichlorophenyl)-3-isopropyl-1-[2-oxo-2-[4-(2-oxo-4,5-dihydro-1H-1,3-benzodiazepin-3-yl)-1-piperidyl]ethyl]pyrimidine-2,4-dione

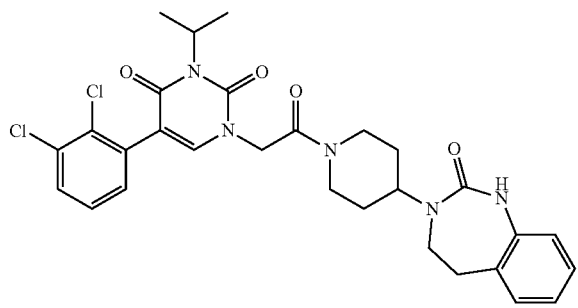 [SMILES: CC(C)n1c(=O)c(-c2cccc(Cl)c2Cl)cn(CC(=O)N2CCC(N3CCc4ccccc4NC3=O)CC2)c1=O]

$^1$H NMR (δ, DMSO): 1.40 (d, J=6.9 Hz, 6H), 1.48-1.60 (m, 1H), 1.64-1.80 (m, 3H), 2.68 (m, 1H), 2.89 (m, 2H), 3.14 (m, 1H), 3.37 (m, 2H), 3.91 (d, J=12.8 Hz, 1H), 4.25-4.38 (m, 1H), 4.43 (d, J=12.8 Hz, 1H), 4.73 (m, 2H), 5.10 (m, 1H), 6.78-6.82 (m, 1H), 7.01-7.04 (m, 3H), 7.32 (dd, J=1.6-7.7 Hz, 1H), 7.41 (t, J=7.8 Hz, 1H), 7.68 (dd, J=1.6-8.0 Hz, 1H), 7.76 (s, 1H), 8.54 (s, 1H).

Compound 211: 5-(2,3-dichlorophenyl)-3-methyl-1-[2-oxo-2-(2-oxospiro[1H-pyrido[2,3-d][1,3]oxazine-4,4'-piperidin]-1'-yl)ethyl]pyrimidine-2,4-dione

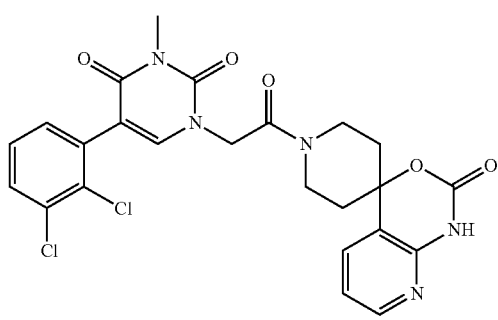 [SMILES: Cn1c(=O)c(-c2cccc(Cl)c2Cl)cn(CC(=O)N2CCC3(CC2)OC(=O)Nc2ncccc23)c1=O]

$^1$H NMR (δ, DMSO): 1.90-2.15 (m, 4H), 2.99 (m, 1H), 3.25 (s, 3H), 3.43 (m, 1H), 3.90 (d, J=12 Hz, 1H), 4.35 (d, J=12 Hz, 1H), 4.82 (m, 2H), 7.08-7.11 (m, 1H), 7.32 (dd, J=1.6-7.6 Hz, 1H), 7.43 (t, J=7.8 Hz, 1H), 7.68-7.71 (m, 2H), 7.81 (s, 1H), 8.21 (dd, J=1.6-4.9 Hz, 1H), 10.88 (br-s, 1H).

Compound 213: 5-(2,3-dichlorophenyl)-3-methyl-1-[2-oxo-2-[4-(2-oxo-4,5-dihydro-1H-pyrido[2,3-d][1,3]diazepin-3-yl)-1-piperidyl]ethyl]pyrimidine-2,4-dione

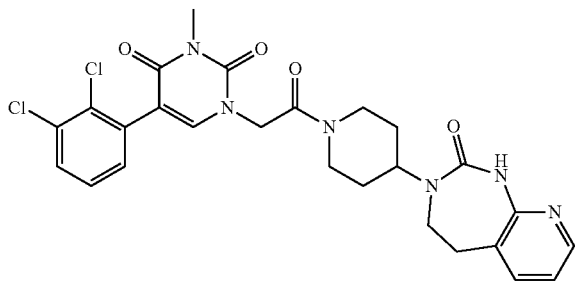 [SMILES: Cn1c(=O)c(-c2cccc(Cl)c2Cl)cn(CC(=O)N2CCC(N3CCc4cccnc4NC3=O)CC2)c1=O]

$^1$H NMR (δ, DMSO): 1.56 (m, 1H), 1.71 (m, 3H), 2.69 (m, 1H), 2.84-2.93 (m, 2H), 3.16 (m, 1H), 3.25 (s, 3H), 3.39-3.46 (m, 2H), 3.95 (d, J=14.2 Hz, 1H), 4.33 (m, 1H), 4.43 (d, J=12.4 Hz, 1H), 4.78 (s, 2H), 7.06 (m, 1H), 7.32 (dd, J=7.6, 1.6 Hz, 1H), 7.43 (t, J=7.9 Hz, 1H), 7.50 (dd, J=7.6, 1.7 Hz, 1H), 7.68 (m, 1H), 7.82 (s, 1H), 8.18 (dd, J=5.2, 1.7 Hz, 1H), 8.91 (s, 1H).

Compound 214: 5-(2,3-dimethylphenyl)-3-methyl-1-[2-oxo-2-[4-(2-oxo-5-phenyl-1H-imidazol-3-yl)-1-piperidyl]ethyl]pyrimidine-2,4-dione

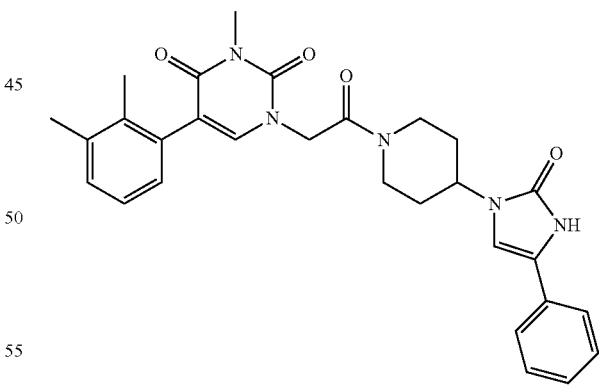

$^1$H NMR (δ, DMSO): 1.54-1.95 (m, 4H), 2.05 (s, 3H), 2.28 (s, 3H), 2.77 (m, 1H), 3.25 (m, 4H), 3.86-4.06 (d, J=13.1 Hz, 1H), 4.15 (m, 1H), 4.47 (d, J=13.1 Hz, 1H), 4.79 (m, 2H), 6.96 (d, J=7.3 Hz, 1H), 7.14 (m, 4H), 7.33 (t, J=7.6 Hz, 2H), 7.50 (d, J=7.8 Hz, 2H), 7.59 (s, 1H), 10.72 (s, 1H).

Compound 215: 5-(2,3-dichlorophenyl)-3-methyl-1-[2-oxo-2-[4-(2-oxo-1H-quinolin-3-yl)-1-piperidyl]ethyl]pyrimidine-2,4-dione

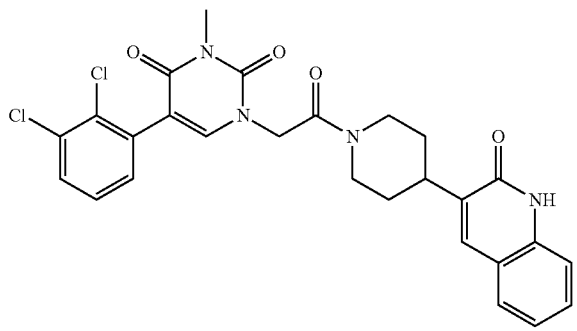 [SMILES: Cn1c(=O)c(-c2cccc(Cl)c2Cl)cn(CC(=O)N2CCC(c3cc4ccccc4[nH]c3=O)CC2)c1=O]

¹H NMR (δ, DMSO): 1.36-1.66 (m, 2H), 1.91 (m, 2H), 2.66-2.82 (m, 1H), 3.06 (m, 1H), 3.15-3.22 (m, 1H), 3.24 (s, 3H), 4.00 (d, J=13.1 Hz, 1H), 4.49 (d, J=13.0 Hz, 1H), 4.79 (s, 2H), 7.10-7.19 (m, 1H), 7.28 (d, J=8.1 Hz, 1H), 7.32 (dd, J=7.7, 1.6 Hz, 1H), 7.41 (d, J=7.9 Hz, 1H), 7.43-7.48 (m, 1H), 7.63 (dd, J=8.0, 1.4 Hz, 1H), 7.66-7.73 (m, 2H), 7.86 (s, 1H), 11.80 (s, 1H).

Compound 216: 5-(2,3-dimethylphenyl)-3-isopropyl-1-[2-oxo-2-[4-(2-oxo-4,5-dihydro-1H-pyrido[4,3-d][1,3]diazepin-3-yl)-1-piperidyl]ethyl]pyrimidine-2,4-dione

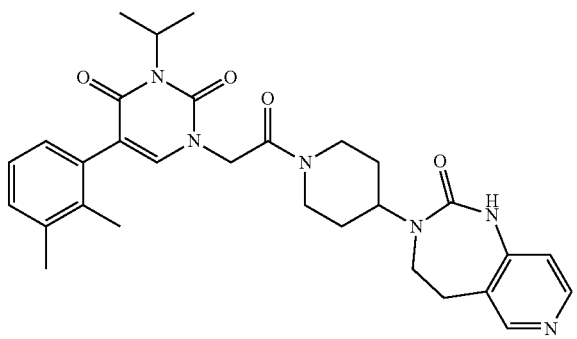 [SMILES: Cc1cccc(-c2cn(CC(=O)N3CCC(N4CCc5cnccc5NC4=O)CC3)c(=O)n(C(C)C)c2=O)c1C]

¹H NMR (δ, DMSO): 1.40 (d, J=6.8 Hz, 6H), 1.50-1.62 (m, 1H), 1.63-1.80 (m, 3H), 2.04 (s, 3H), 2.27 (s, 3H), 2.68 (m, 1H), 2.90 (m, 2H), 3.15 (m, 1H), 3.40 (m, 2H), 3.95 (m, 1H), 4.30-4.40 (m, 1H), 4.45 (d, J=13 Hz, 1H), 4.75 (m, 2H), 5.15 (m, 1H), 6.93-6.98 (m, 2H), 7.10 (t, 1H), 7.18 (d, 1H), 7.54 (s, 1H), 8.09 (d, J=5.6 Hz, 1H), 8.14 (s, 1H), 9.11 (s, 1H).

Compound 217: 5-(2,3-dimethylphenyl)-3-isopropyl-1-[2-oxo-2-[4-(2-oxo-4,5-dihydro-1H-pyrido[3,2-d][1,3]diazepin-3-yl)-1-piperidyl]ethyl]pyrimidine-2,4-dione

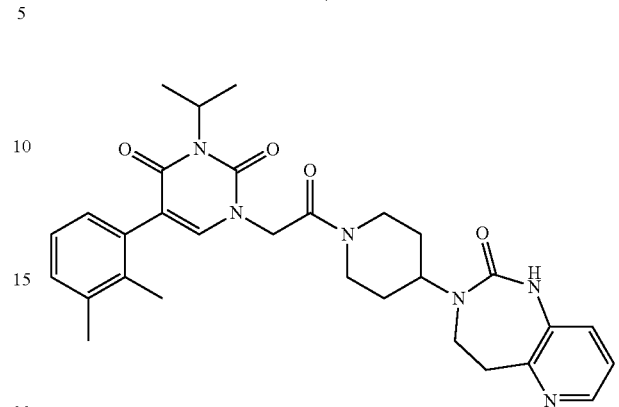

¹H NMR (δ, DMSO): 1.40 (d, J=6.8 Hz, 6H), 1.5-1.62 (m, 1H), 1.65-1.85 (m, 3H), 2.04 (s, 3H), 2.27 (s, 3H), 2.68 (m, 1H), 3.03 (m, 2H), 3.14 (m, 1H), 3.45 (m, 2H), 3.93 (d, J=12.6 Hz, 1H), 4.25-4.48 (m, 1H), 4.43 (d, J=13.2 Hz, 1H), 4.72 (m, 2H), 5.11 (m, 1H), 6.96 (d, J=7 Hz, 1H), 7.08-7.13 (m, 2H), 7.16 (d, J=7.2 Hz, 1H), 7.42 (dd, J=1.3-8.2 Hz, 1H), 7.55 (s, 1H), 8.03 (m, 1H), 8.67 (s, 1H).

Compound 218: 5-(2,3-dimethylphenyl)-3-isopropyl-1-[2-oxo-2-[4-(2-oxo-4,5-dihydro-1H-pyrido[2,3-d][1,3]diazepin-3-yl)-1-piperidyl]ethyl]pyrimidine-2,4-dione

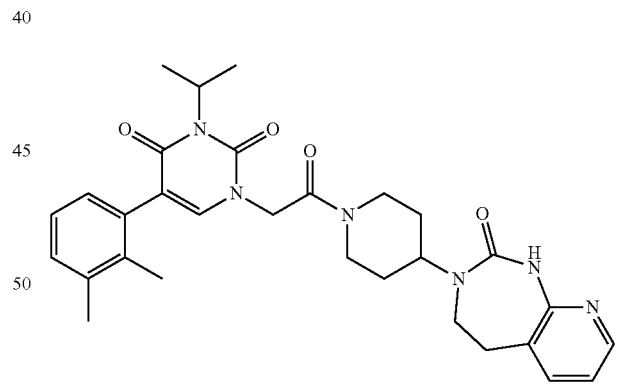

¹H NMR (δ, DMSO): 1.40 (d, 6H), 1.5-1.62 (m, 1H), 1.63-1.80 (m, 3H), 2.04 (s, 3H), 2.27 (s, 3H), 2.68 (m, 1H), 2.89 (m, 2H), 3.15 (m, 1H), 3.42 (m, 2H), 3.95 (d, J=13 Hz, 1H), 4.28-4.38 (m, 1H), 4.45 (d, J=13 Hz, 1H), 4.72 (m, 2H), 5.11 (m, 1H), 6.89-6.92 (m, 1H), 6.95 (d, J=7.2 Hz, 1H), 7.09 (t, J=7.5 Hz, 1H), 7.16 (d, J=7.2 Hz, 1H), 7.49-7.51 (m, 1H), 7.54 (s, 1H), 8.08 (m, 1H), 8.31 (s, 1H).

Compound 219: 5-(2,3-dichlorophenyl)-3-methyl-1-{2-oxo-2-[4-(2-oxo-[1,3]diazepan-1-yl)-piperidin-1-yl]-ethyl}-1H-pyrimidine-2,4-dione

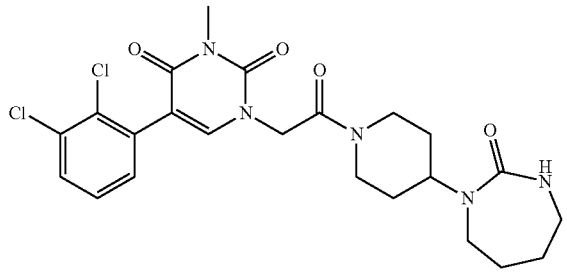 [SMILES: Cn1c(=O)c(-c2cccc(Cl)c2Cl)cn(CC(=O)N2CCC(N3CCCCNC3=O)CC2)c1=O]

¹H NMR (δ, DMSO): 1.33-1.57 (m, 5H), 1.57-1.75 (m, 3H), 2.63 (m, 1H), 2.91 (m, 2H), 3.02 (m, 2H), 3.10 (m, 1H), 3.24 (s, 3H), 3.82-4.06 (m, 2H), 4.39 (d, J=13.0 Hz, 1H), 4.65-4.87 (m, 2H), 5.93 (t, J=4.2 Hz, 1H), 7.32 (dd, J=7.5, 1.5 Hz, 1H), 7.42 (t, J=7.9 Hz, 1H), 7.69 (dd, J=8.0, 1.5 Hz, 1H), 7.82 (s, 1H).

Compound 220: 5-(3,4-dichlorophenyl)-3-methyl-1-[2-oxo-2-[4-(2-oxo-4,5-dihydro-1H-1,3-benzodiazepin-3-yl)-1-piperidyl]ethyl]pyrimidine-2,4-dione

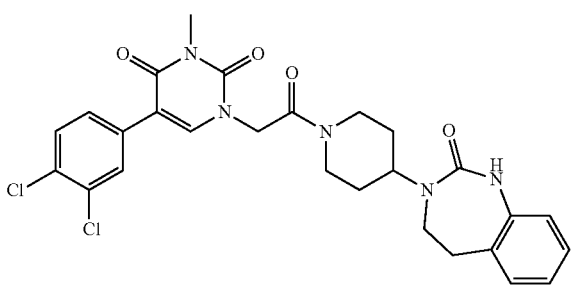 [SMILES: Cn1c(=O)c(-c2ccc(Cl)c(Cl)c2)cn(CC(=O)N2CCC(N3CCc4ccccc4NC3=O)CC2)c1=O]

¹H NMR (δ, DMSO): 1.39-1.56 (m, 1H), 1.56-1.75 (m, 3H), 2.62 (m, 1H), 2.79-2.88 (m, 2H), 3.03-3.16 (m, 1H), 3.19 (s, 3H), 3.31 (m, 2H), 3.90 (m, 1H), 4.17-4.32 (m, 1H), 4.35 (d, J=13.6 Hz, 1H), 4.74 (m, 2H), 6.67-6.83 (m, 1H), 6.90-7.06 (m, 3H), 7.54 (dd, J=8.5, 2.0 Hz, 1H), 7.62 (d, J=8.8 Hz, 1H), 7.81 (d, J=2.0 Hz, 1H), 8.05 (s, 1H), 8.46 (s, 1H).

Compound 221: 1-[2-[4-(7-bromo-2-oxo-4,5-dihydro-1H-1,3-benzodiazepin-3-yl)-1-piperidyl]-2-oxo-ethyl]-5-(2-chloro-3-fluorophenyl)-3-isopropyl-pyrimidine-2,4-dione

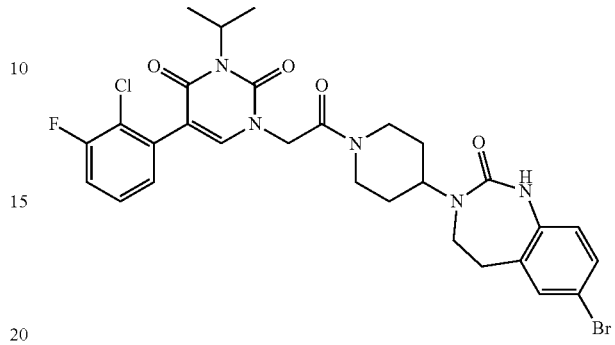

¹H NMR (δ, DMSO): 1.41 (d, J=6.8 Hz, 6H), 1.55 (m, 1H), 1.61-1.82 (m, 3H), 2.65 (m, 1H), 2.84-2.94 (m, 2H), 3.15 (m, 1H), 3.34-3.42 (m, 2H), 3.84-4.03 (m, 1H), 4.32 (m, 1H), 4.38-4.51 (m, 1H), 4.64-4.84 (m, 2H), 5.11 (hept, J=7.0 Hz, 1H), 7.01 (d, J=8.7 Hz, 1H), 7.16-7.30 (m, 3H), 7.35-7.52 (m, 2H), 7.77 (s, 1H), 8.71 (s, 1H).

Compound 222: 5-(2-chloro-3-fluorophenyl)-3-isopropyl-1-[2-[4-methyl-4-(2-oxo-4,5-dihydro-1H-1,3-benzodiazepin-3-yl)-1-piperidyl]-2-oxo-ethyl]pyrimidine-2,4-dione

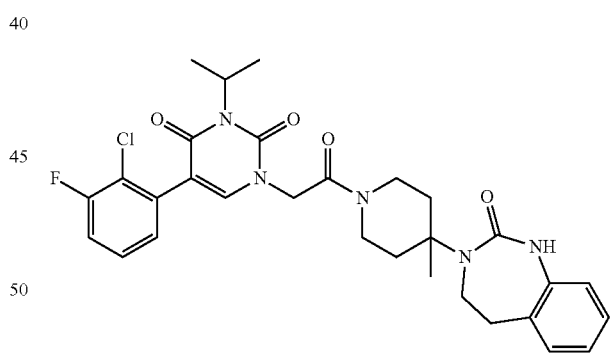

¹H NMR (δ, DMSO): 1.47-1.50 (m, 9H); 1.91-1.93 (m, 1H); 2.05-2.09 (m, 1H); 2.22-2.29 (m, 1H); 2.41-2.46 (m, 1H); 3.09 (m, 2H); 3.34 (m, 1H); 3.45-3.52 (m, 2H); 3.53-3.60 (m, 2H); 3.63-3.69 (m, 2H); 4.68 (d, J=16.5 Hz, 1H); 4.79 (d, J=16.4 Hz, 1H); 5.16-5.23 (m, 1H); 6.99-6.88 (m, 2H), 7.12-7.06 (m, 1H), 7.14 (dd, J=7.7, 1.4 Hz, 1H), 7.18 (dt, J=7.7, 1.3 Hz, 1H), 7.29-7.23 (m, 1H), 7.35 (m, 1H); 7.54 (s, 1H).

Compound 223: 5-(2-chloro-3-fluorophenyl)-3-isopropyl-1-[2-[(2S)-2-methyl-4-(2-oxo-4,5-dihydro-1H-1,3-benzodiazepin-3-yl)-1-piperidyl]-2-oxo-ethyl]pyrimidine-2,4-dione

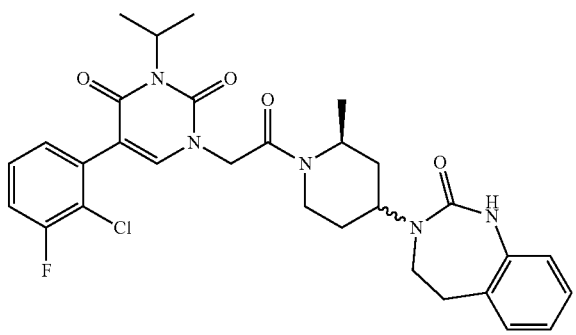 [SMILES: CC(C)n1c(=O)c(-c2cccc(F)c2Cl)cn(CC(=O)N2CCC(N3CCc4ccccc4NC3=O)C[C@@H]2C)c1=O]

¹H NMR (δ, DMSO): 1.19 (d, J=6.0 Hz, 3H), 1.41 (d, J=6.7 Hz, 6H), 1.61 (m, 1H), 1.72-1.92 (m, 2H), 2.01 (m, 1H), 2.53 (m, 1H), 2.88-2.97 (m, 2H), 3.41-3.50 (m, 2H), 3.77 (br-s, 1H), 4.06 (m, 1H), 4.54-4.86 (m, 2H), 5.10 (hept, J=6.9 Hz, 1H), 6.82 (m, 1H), 6.95-7.10 (m, 3H), 7.16-7.29 (m, 1H), 7.35-7.52 (m, 2H), 7.84 (s, 1H), 8.52 (s, 1H).

Compound 224: 2-[5-(2-chloro-3-fluorophenyl)-2,6-dioxo-3-[2-oxo-2-[4-(2-oxo-4,5-dihydro-1H-1,3-benzodiazepin-3-yl)-1-piperidyl]ethyl]pyrimidin-1-yl]propanoic acid

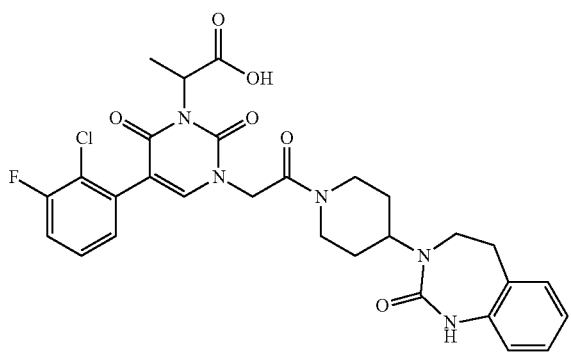 [SMILES: CC(C(=O)O)n1c(=O)c(-c2cccc(F)c2Cl)cn(CC(=O)N2CCC(N3CCc4ccccc4NC3=O)CC2)c1=O]

Mass=598.

Compound 225: 5-(2-chloro-3-fluorophenyl)-3-isopropyl-1-[2-[4-(7-methylsulphinyl-2-oxo-4,5-dihydro-1H-1,3-benzodiazepin-3-yl)-1-piperidyl]-2-oxo-ethyl]pyrimidine-2,4-dione

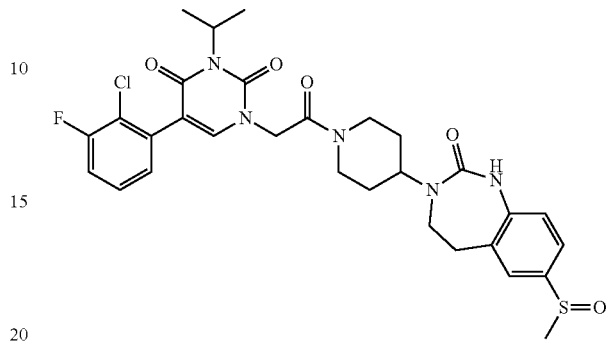

¹H NMR (δ, DMSO): 1.41 (d, J=6.9 Hz, 6H), 1.48-1.63 (m, 1H), 1.63-1.86 (m, 3H), 2.67 (m, 4H), 2.97 (m, 2H), 3.15 (m, 1H), 3.36-3.49 (m, 2H), 3.94 (d, J=13.5 Hz, 1H), 4.35 (m, 1H), 4.44 (d, J=13.5 Hz, 1H), 4.75 (m, 2H), 5.11 (hept, J=6.8 Hz, 1H), 7.18-7.26 (m, 2H), 7.36 (m, 2H), 7.40-7.49 (m, 2H), 7.77 (s, 1H), 8.90 (s, 1H).

Compound 226: 2-[5-(2-chloro-3-fluorophenyl)-2,6-dioxo-3-[2-oxo-2-[4-(2-oxo-4,5-dihydro-1H-1,3-benzodiazepin-3-yl)-1-piperidyl]ethyl]pyrimidin-1-yl]acetamide

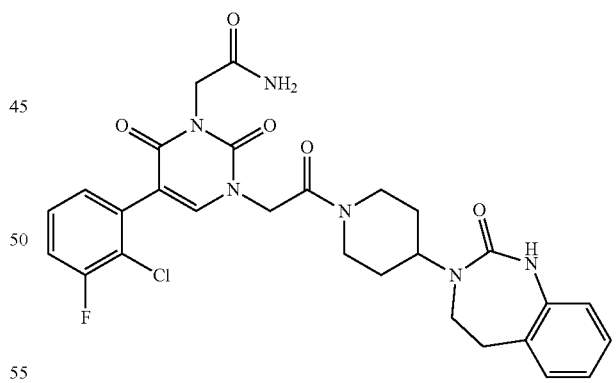

¹H NMR (δ, DMSO): 1.55 (m, 1H), 1.71 (m, 3H), 2.69 (m, 1H), 2.83-2.95 (m, 2H), 3.08-3.23 (m, 1H), 3.34-3.44 (m, 2H), 3.96 (d, J=13.7 Hz, 1H), 4.33 (m, 1H), 4.44 (m, 3H), 4.79 (s, 2H), 6.72-6.91 (m, 1H), 6.99-7.07 (m, 3H), 7.11 (br-s, 1H), 7.19-7.29 (m, 1H), 7.40-7.52 (m, 2H), 7.56 (br-s, 1H), 7.87 (s, 1H), 8.52 (s, 1H).

Compound 227: 5-(2-chloro-3-fluorophenyl)-3-(2-methylsulphinylethyl)-1-[2-oxo-2-[4-(2-oxo-4,5-dihydro-1H-1,3-benzodiazepin-3-yl)-1-piperidyl]ethyl]pyrimidine-2,4-dione

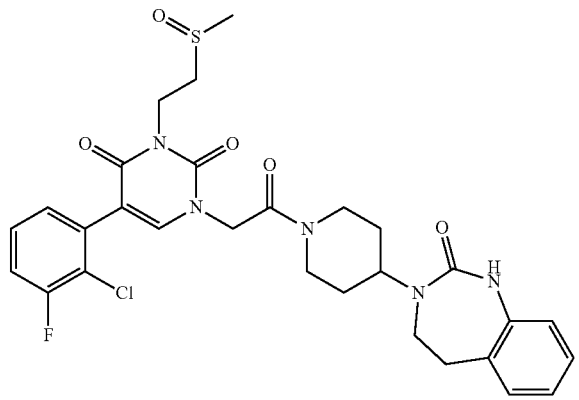 [SMILES: CS(=O)CCn1c(=O)c(-c2cccc(F)c2Cl)cn(CC(=O)N2CCC(N3CCc4ccccc4NC3=O)CC2)c1=O]

¹H NMR (δ, DMSO): 1.47-1.62 (m, 1H), 1.69 (m, 3H), 2.61 (s, 3H), 2.69 (m, 1H), 2.86-2.93 (m, 2H), 2.95 (m, 1H), 3.06 (m, 1H), 3.16 (m, 1H), 3.34-3.47 (m, 2H), 3.95 (d, J=13.6 Hz, 1H), 4.23 (m, 3H), 4.43 (d, J=12.7 Hz, 1H), 4.80 (s, 2H), 6.73-6.89 (m, 1H), 6.96-7.10 (m, 3H), 7.16-7.29 (m, 1H), 7.38-7.54 (m, 2H), 7.87 (s, 1H), 8.53 (s, 1H).

Compound 228: 5-(2-chloro-3-fluorophenyl)-3-(2-methylsulphonylethyl)-1-[2-oxo-2-[4-(2-oxo-4,5-dihydro-1H-1,3-benzodiazepin-3-yl)-1-piperidyl]ethyl]pyrimidine-2,4-dione

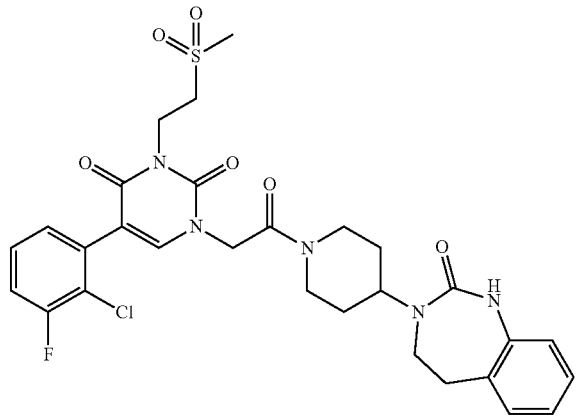 [SMILES: CS(=O)(=O)CCn1c(=O)c(-c2cccc(F)c2Cl)cn(CC(=O)N2CCC(N3CCc4ccccc4NC3=O)CC2)c1=O]

¹H NMR (δ, DMSO): 1.55 (m, 1H), 1.71 (m, 3H); 2.69 (m, 1H); 2.90 (in, 2H); 3.09 (s, 3H); 3.16 (m, 1H); 3.36-3.43 (m, 4H); 3.96 (d, J=13.6 Hz, 1H); 4.29-4.33 (m, 3H); 4.43 (d, J=12.9 Hz, 1H); 4.80 (s, 2H); 6.79-6.83 (m, 1H); 7.02-7.05 (m, 3H); 7.21-7.23 (m, 1H); 7.45-7.49 (m, 2H); 7.88 (s, 1H); 8.55 (s, 1H).

Compound 229: 5-(2-chloro-3-fluorophenyl)-3-((S)-2-methoxy-1-methylethyl)-1-{2-[4-(7-methoxy-2-oxo-1,2,4,5-tetrahydro-benzo[d][1,3]diazepin-3-yl)-piperidin-1-yl]-2-oxo-ethyl}-1H-pyrimidine-2,4-dione

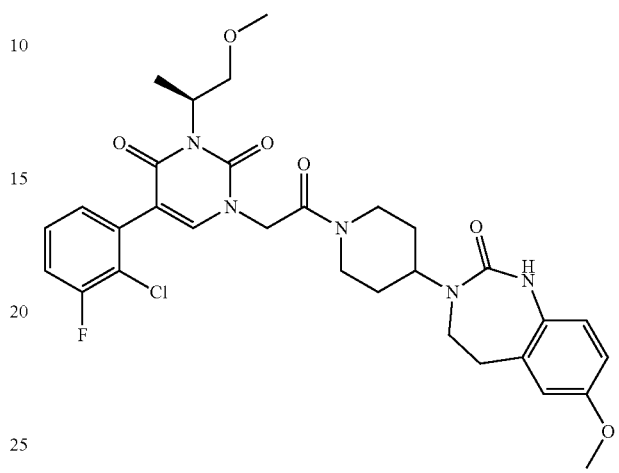

¹H NMR (δ, DMSO): 1.33 (dd, J=7.0, 1.8 Hz, 3H); 1.55 (m, 1H), 1.70 (m, 3H); 2.68 (m, 1H); 2.88 (m, 2H); 3.14 (m, 1H); 3.24 (s, 3H); 3.35-3.37 (m, 2H); 3.52-3.56 (m, 1H); 3.67 (s, 3H); 3.92 (m, 2H); 4.28 (m, 1H); 4.43 (d, J=12.8 Hz, 1H); 4.75 (m, 2H); 5.15 (m, 1H); 6.62 (d, J=2.9 Hz, 1H), 6.67 (dd, J=8.8, 3.0 Hz, 1H), 6.98 (d, J=8.8 Hz, 1H); 7.20-7.22 (m, 1H); 7.43-7.47 (m, 2H); 7.80 (s, 1H); 8.33 (s, 1H).

Compound 230: 5-(2-chloro-3-fluorophenyl)-3-isopropyl-1-[2-[4-(7-methoxy-5,5-dimethyl-2-oxo-1,4-dihydro-1,3-benzodiazepin-3-yl)-1-piperidyl]-2-oxo-ethyl]pyrimidine-2,4-dione

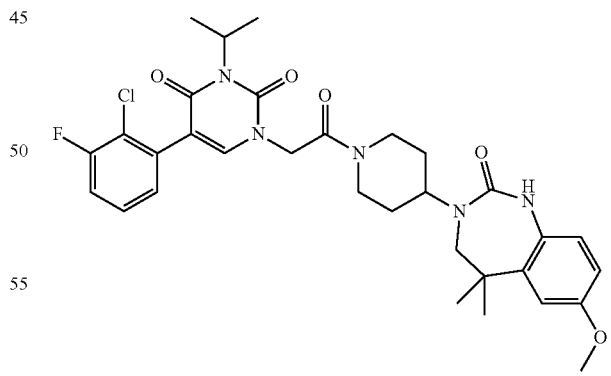

¹H NMR (δ, DMSO): 1.27 (d, 6H), 1.41 (d, J=6.8 Hz, 6H), 1.72 (m, 3H), 1.87 (m, 1H), 2.64 (m, 1H), 3.11 (m, 1H), 3.23 (s, 2H), 3.69 (s, 3H), 3.94 (d, J=13.4 Hz, 1H), 4.01 (m, 1H), 4.44 (d, J=12.7 Hz, 1H), 4.74 (m, 2H), 5.11 (p, J=6.8 Hz, 1H), 6.67 (dd, J=9.0, 3.0 Hz, 1H), 6.84 (d, J=3.0 Hz, 1H), 6.96 (d, J=8.9 Hz, 1H), 7.15-7.28 (m, 1H), 7.37-7.52 (m, 2H), 7.78 (s, 1H), 8.23 (s, 1H).

Compound 231: 5-(2,3-difluorophenyl)-3-[2-methoxy-1-(methoxymethyl)ethyl]-1-[2-[4-(7-methoxy-2-oxo-4,5-dihydro-1H-1,3-benzodiazepin-3-yl)-1-piperidyl]-2-oxo-ethyl]pyrimidine-2,4-dione

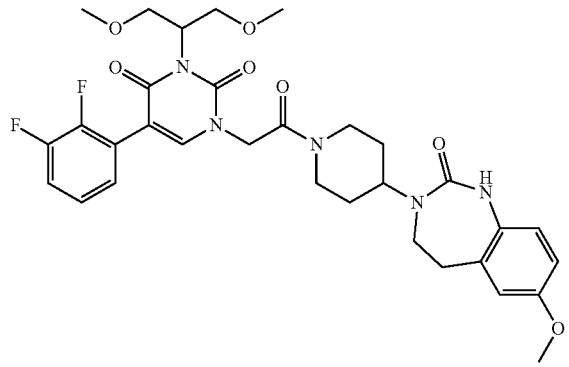 [SMILES: COCC(COC)n1c(=O)c(-c2cccc(F)c2F)cn(CC(=O)N2CCC(N3CCc4cc(OC)ccc4NC3=O)CC2)c1=O]

¹H NMR (δ, DMSO): 1.44-1.61 (m, 1H), 1.70 (m, 3H), 2.68 (m, 1H), 2.87 (m, 2H), 3.14 (m, 1H), 3.24 (s, 6H), 3.35-3.44 (m, 2H), 3.60 (m, 2H), 3.67 (s, 3H), 3.77-3.90 (m, 2H), 3.94 (d, J=13.8 Hz, 1H), 4.28 (m, 1H), 4.43 (d, J=13.2 Hz, 1H), 4.78 (m, 2H), 5.29 (br-s, 1H), 6.63 (d, J=3.0 Hz, 1H), 6.67 (dd, J=8.8, 3.0 Hz, 1H), 6.98 (d, J=8.8 Hz, 1H), 7.12-7.34 (m, 2H), 7.39-7.54 (m, 1H), 7.90 (s, 1H), 8.33 (s, 1H).

Compound 232: 5-(2-chloro-3-fluorophenyl)-3-[2-methoxy-1-(methoxymethyl)ethyl]-1-[2-[4-(7-methoxy-2-oxo-4,5-dihydro-1H-1,3-benzodiazepin-3-yl)-1-piperidyl]-2-oxo-ethyl]pyrimidine-2,4-dione

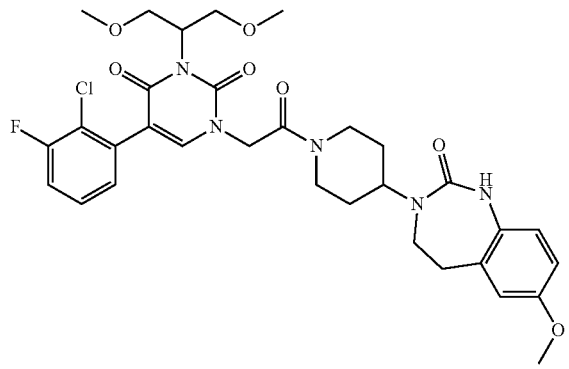 [SMILES: COCC(COC)n1c(=O)c(-c2cccc(F)c2Cl)cn(CC(=O)N2CCC(N3CCc4cc(OC)ccc4NC3=O)CC2)c1=O]

¹H NMR (δ, DMSO): 1.55 (m, 1H); 1.68 (m, 3H); 2.68 (m, 1H); 2.88 (m, 2H); 3.14 (m, 1H); 3.24 (s, 6H), 3.37 (m, 2H); 3.60 (m, 2H); 3.67 (s, 3H); 3.86 (m, 2H); 3.94 (d, J=13.5 Hz, 1H); 4.28 (m, 1H); 4.43 (d, J=12.9 Hz, 1H); 4.78 (m, 2H); 5.30 (br-s, 1H); 6.62 (d, J=3.0 Hz, 1H); 6.67 (dd, J=8.8, 3.0 Hz, 1H); 6.98 (d, J=8.8 Hz, 1H); 7.21-7.23 (m, 1H); 7.43-7.46 (m, 2H); 7.82 (s, 1H); 8.33 (s, 1H).

Compound 233: 5-(2-chloro-3-fluorophenyl)-3-[(1S)-2-methoxy-1-methylethyl]-1-[2-[4-(7-methylsulphanyl-2-oxo-4,5-dihydro-1H-1,3-benzodiazepin-3-yl)-1-piperidyl]-2-oxo-ethyl]pyrimidine-2,4-dione

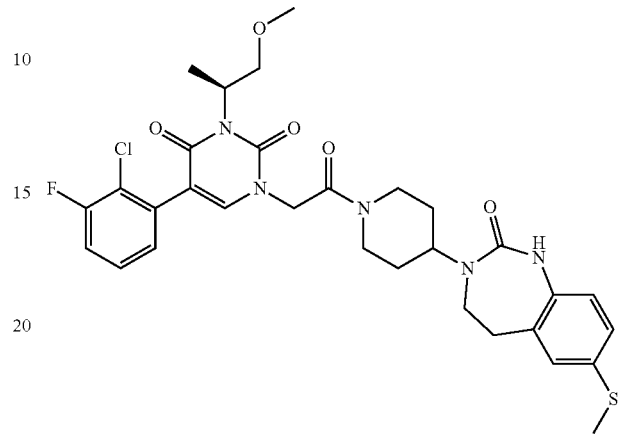

¹H NMR (δ, DMSO): 1.33 (m, 3H), 1.55 (m, 1H), 1.70 (m, 3H), 2.40 (s, 3H), 2.68 (m, 1H), 2.82-2.93 (m, 2H), 3.14 (m, 1H), 3.23 (s, 3H), 3.34-3.42 (m, 2H), 3.54 (m, 1H), 3.82-3.99 (m, 2H), 4.31 (m, 1H), 4.43 (d, J=12.7 Hz, 1H), 4.75 (m, 2H), 5.14 (m, 1H), 7.01 (m, 3H), 7.21 (m, 1H), 7.36-7.55 (m, 2H), 7.79 (s, 1H), 8.57 (s, 1H).

Compound 234: 5-(2-chloro-3-fluorophenyl)-3-(2-hydroxy-2-methylpropyl)-1-[2-oxo-2-[4-(2-oxo-4,5-dihydro-1H-1,3-benzodiazepin-3-yl)-1-piperidyl]ethyl]pyrimidine-2,4-dione

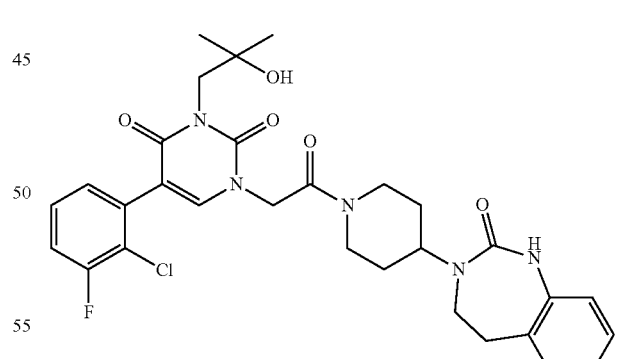

¹H NMR (δ, DMSO): 1.10 (s, 6H), 1.55 (m, 1H), 1.68 (m, 3H), 2.69 (m, 1H), 2.83-2.96 (m, 2H), 3.15 (m, 1H), 3.35-3.42 (m, 2H), 3.96 (m, 3H), 4.33 (m, 1H), 4.44 (m, 2H), 4.78 (m, 2H), 6.69-6.89 (m, 1H), 6.96-7.10 (m, 3H), 7.15-7.26 (m, 1H), 7.38-7.54 (m, 2H), 7.83 (s, 1H), 8.53 (s, 1H).

Compound 235: 5-(2-chloro-3-fluorophenyl)-1-[2-oxo-2-[4-(2-oxo-4,5-dihydro-1H-1,3-benzodiazepin-3-yl)-1-piperidyl]ethyl]-3-(2H-tetrazol-5-ylmethyl)pyrimidine-2,4-dione

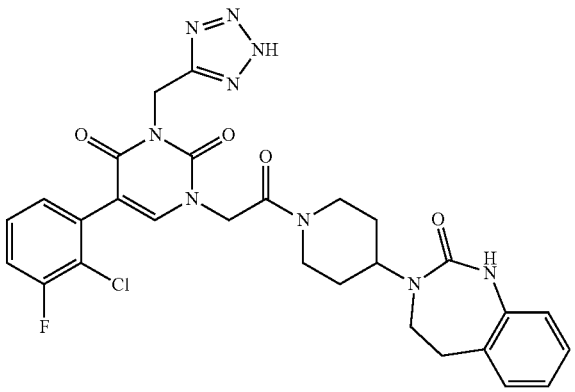 [SMILES: O=C(Cn1cc(-c2cccc(F)c2Cl)c(=O)n(Cc2nn[nH]n2)c1=O)N1CCC(N2CCc3ccccc3NC2=O)CC1]

¹H NMR (δ, DMSO): 1.55 (m, 1H), 1.68 (m, 3H), 2.70 (m, 1H), 2.89 (m, 2H), 3.18 (m, 2H), 3.37 (m, 2H), 3.95 (d, J=13.9 Hz, 1H), 4.33 (m, 1H), 4.43 (d, J=13.1 Hz, 1H), 4.81 (s, 2H), 5.36 (m, 2H), 6.81 (m, 1H), 7.04 (m, 3H), 7.17-7.31 (m, 1H), 7.37-7.56 (m, 2H), 7.94 (s, 1H), 8.53 (s, 1H).

Compound 236: 5-(2,3-difluorophenyl)-3-(2-methylsulphonylethyl)-1-[2-oxo-2-[4-(2-oxo-4,5-dihydro-1H-1,3-benzodiazepin-3-yl)-1-piperidyl]ethyl]pyrimidine-2,4-dione

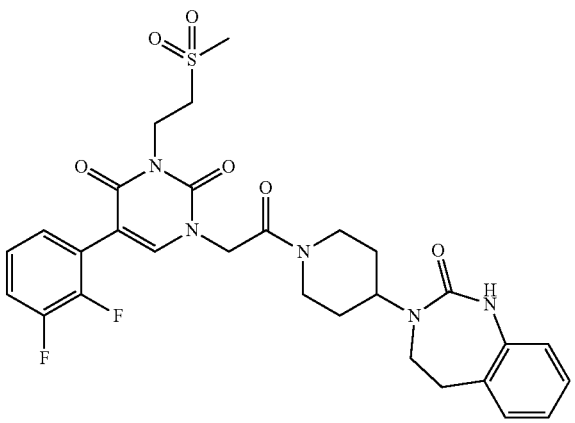 [SMILES: CS(=O)(=O)CCn1c(=O)c(-c2cccc(F)c2F)cn(CC(=O)N2CCC(N3CCc4ccccc4NC3=O)CC2)c1=O]

¹H NMR (δ, DMSO): 1.55 (m, 1H), 1.71 (m, 3H); 2.70 (m, 1H); 2.90 (m, 2H); 3.08 (s, 3H); 3.16 (m, 1H); 3.36-3.43 (m, 4H); 3.97 (d, J=13.5 Hz, 1H); 4.32 (m, 3H); 4.43 (d, J=12.9 Hz, 1H); 4.82 (s, 2H); 6.79-6.83 (m, 1H); 7.02-7.05 (m, 3H); 7.21-7.30 (m, 2H); 7.44-7.51 (m, 1H); 7.97 (s, 1H); 8.54 (s, 1H).

Compound 237: 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-[(1S)-1-methylpropyl]pyrimidine-2,4-dione

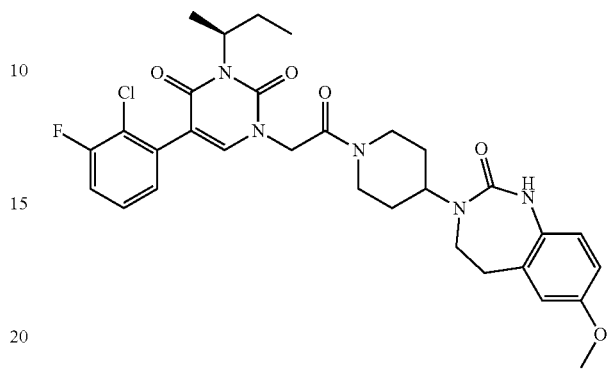

¹H NMR (δ, DMSO): 0.80 (t, J=7.4 Hz, 3H), 1.38 (d, J=6.8 Hz, 3H), 1.54 (m, 1H), 1.70 (m, 3H), 2.00-2.14 (m, 1H), 2.53 (m, 1H), 2.67 (m, 1H), 2.88 (m, 2H), 3.14 (m, 1H), 3.36 (m, 2H), 3.67 (s, 3H), 3.93 (d, J=13.4 Hz, 1H), 4.28 (m, 1H), 4.43 (d, J=13.0 Hz, 1H), 4.65-4.84 (m, 2H), 4.89 (m, 1H), 6.62 (d, J=3.0 Hz, 1H), 6.67 (dd, J=8.8, 3.0 Hz, 1H), 6.98 (d, J=8.8 Hz, 1H), 7.14-7.28 (m, 1H), 7.36-7.52 (m, 2H), 7.79 (s, 1H), 8.34 (s, 1H).

Compound 238: 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-[(1R)-1-methylpropyl]pyrimidine-2,4-dione

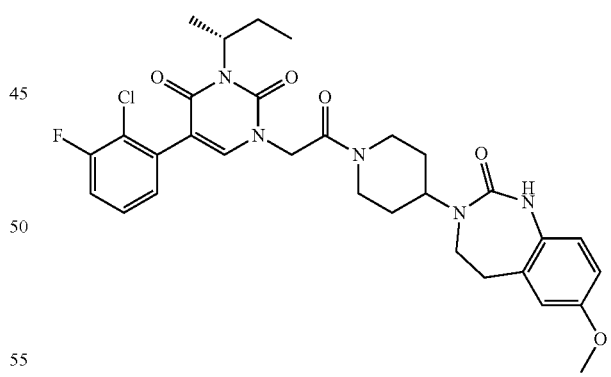

¹H NMR (δ, DMSO): 0.80 (t, J=7.4 Hz, 3H), 1.39 (d, J=6.8 Hz, 3H), 1.54 (m, 1H), 1.67 (m, 3H), 2.05 (m, 1H), 2.67 (m, 1H), 2.88 (m, 2H), 3.14 (m, 1H), 3.36 (m, 3H), 3.67 (s, 3H), 3.93 (d, J=13.6 Hz, 1H), 4.28 (m, 1H), 4.43 (d, J=12.9 Hz, 1H), 4.65-4.83 (m, 2H), 4.88 (m, 1H), 6.62 (d, J=3.0 Hz, 1H), 6.67 (dd, J=8.7, 3.0 Hz, 1H), 6.98 (d, J=8.8 Hz, 1H), 7.21 (m, 1H), 7.37-7.55 (m, 2H), 7.79 (s, 1H), 8.33 (s, 1H).

Compound 239: 5-(2-chloro-3-fluorophenyl)-3-[1-(methoxymethyl)propyl]-1-[2-[4-(7-methoxy-2-oxo-4,5-dihydro-1H-1,3-benzodiazepin-3-yl)-1-piperidyl]-2-oxo-ethyl]pyrimidine-2,4-dione

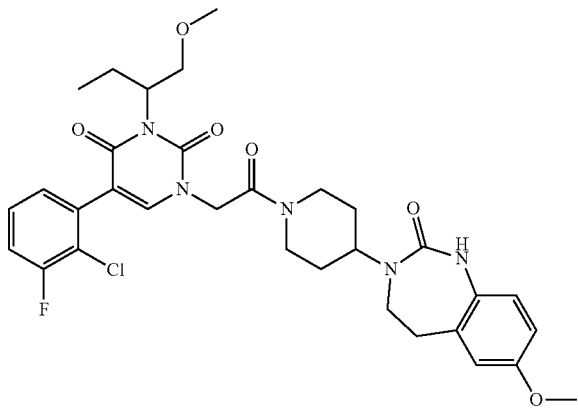 [SMILES: CCC(COC)n1c(=O)c(-c2cccc(F)c2Cl)cn(CC(=O)N2CCC(N3CCc4cc(OC)ccc4NC3=O)CC2)c1=O]

¹H NMR (δ, DMSO): 0.82 (t, J=7.4 Hz, 3H); 1.55 (m, 1H); 1.65-1.75 (m, 3H); 1.97 (m, 1H); 2.53 (m, 2H); 2.67 (m, 1H); 2.88 (m, 2H); 3.14 (m, 1H); 3.23 (s, 3H); 3.36-3.36 (m, 2H); 3.56 (m, 1H); 3.67 (s, 3H); 3.92 (m, 2H); 4.28 (m, 1H); 4.43 (d, J=12.8 Hz, 1H); 4.76 (br s, 1H); 5.02 (br s, 1H); 6.62 (d, J=2.9 Hz, 1H); 6.67 (dd, J=8.8, 3.0 Hz, 1H); 6.98 (d, J=8.8 Hz, 1H); 7.21-7.23 (m, 1H); 7.43-7.46 (m, 2H); 7.81 (s, 1H); 8.33 (s, 1H).

Compound 240: 5-(2-chloro-3-fluorophenyl)-3-(2-methoxy-2-methylpropyl)-1-[2-[4-(7-methoxy-2-oxo-4,5-dihydro-1H-1,3-benzodiazepin-3-yl)-1-piperidyl]-2-oxo-ethyl]pyrimidine-2,4-dione

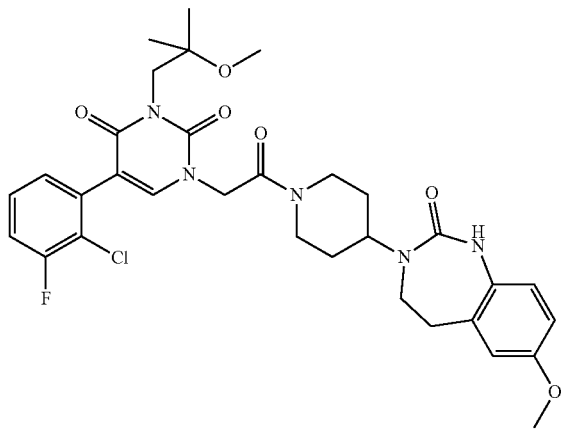 [SMILES: COc1ccc2c(c1)CCN(C1CCN(C(=O)Cn3cc(-c4cccc(F)c4Cl)c(=O)n(CC(C)(C)OC)c3=O)CC1)C(=O)N2]

¹H NMR (δ, DMSO): 1.12 (s, 6H); 1.55 (m, 1H); 1.68 (m, 3H); 2.68 (m, 1H); 2.88 (m, 2H); 3.16 (m, 4H); 3.36 (m, 2H); 3.67 (s, 3H); 3.94 (d, J=13.9 Hz, 1H); 4.01 (m, 2H); 4.28 (m, 1H); 4.43 (d, J=12.8 Hz, 1H); 4.77 (m, 2H); 6.62 (d, J=2.9 Hz, 1H); 6.67 (dd, J=8.8, 2.9 Hz, 1H); 6.98 (d, J=8.8 Hz, 1H); 7.19-7.21 (m, 1H); 7.44-7.47 (m, 2H); 7.82 (s, 1H); 8.33 (s, 1H).

Compound 241: 5-(2-chloro-3-methoxyphenyl)-3-[2-methoxy-1-(methoxymethyl)ethyl]-1-[2-[4-(7-methoxy-2-oxo-4,5-dihydro-1H-1,3-benzodiazepin-3-yl)-1-piperidyl]-2-oxo-ethyl]pyrimidine-2,4-dione

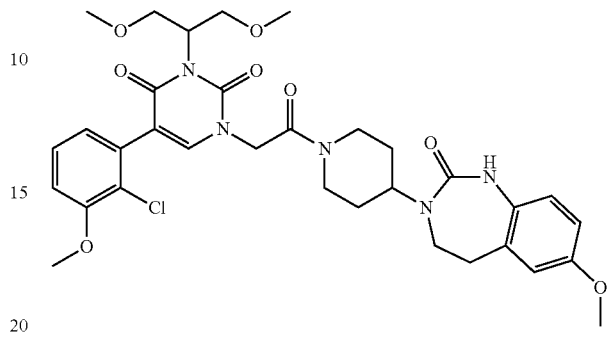

¹H NMR (δ, DMSO): 1.44-1.62 (m, 1H), 1.67 (m, 3H), 2.66 (m, 1H), 2.83-2.92 (m, 2H), 3.13 (m, 1H), 3.24 (s, 6H), 3.36 (m, 2H), 3.60 (m, 2H), 3.67 (s, 3H), 3.83 (m, 2H), 3.89 (s, 3H), 3.93 (d, J=13.4 Hz, 1H), 4.28 (m, 1H), 4.43 (d, J=12.8 Hz, 1H), 4.74 (m, 2H), 5.26 (br-s, 1H), 6.62 (d, J=3.0 Hz, 1H), 6.67 (dd, J=8.9, 3.0 Hz, 1H), 6.91 (dd, J=7.5, 1.5 Hz, 1H), 6.98 (d, J=8.7 Hz, 1H), 7.19 (dd, J=8.5, 1.5 Hz, 1H), 7.31-7.38 (m, 1H), 7.70 (s, 1H), 8.32 (s, 1H).

Compound 242: 5-(2,3-dichlorophenyl)-3-(2-methylsulphonylethyl)-1-[2-oxo-2-[4-(2-oxo-4,5-dihydro-1H-1,3-benzodiazepin-3-yl)-1-piperidyl]ethyl]pyrimidine-2,4-dione

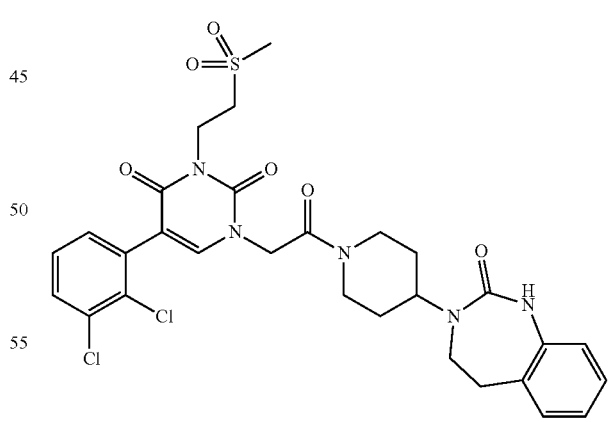

¹H NMR (δ, DMSO): 1.55 (m, 1H), 1.72 (m, 3H); 2.69 (m, 1H); 2.90 (m, 2H); 3.08 (s, 3H); 3.20 (m, 1H); 3.43-3.39 (m, 4H); 3.95 (d, J=11.9 Hz, 1H) 4.31 (m, 3H); 4.44 (d, J=11.9 Hz, 1H); 4.79 (s, 2H); 6.83-6.79 (m, 1H); 7.04 (m, 3H); 7.33 (dd, J=7.7, 1.6 Hz, 1H); 7.44 (t, J=7.9 Hz, 1H); 7.70 (dd, J=8.1, 1.6 Hz, 1H); 7.87 (s, 1H); 8.53 (s, 1H).

Compound 243: 5-(2-chloro-3-methoxyphenyl)-3-(2-methylsulphonylethyl)-1-[2-oxo-2-[4-(2-oxo-4,5-dihydro-1H-1,3-benzodiazepin-3-yl)-1-piperidyl]ethyl]pyrimidine-2,4-dione

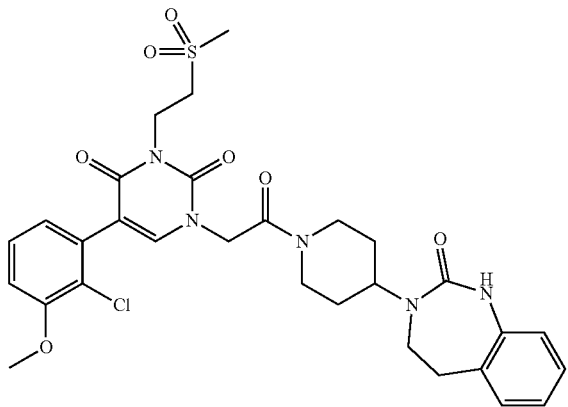 [SMILES: COc1cccc(-c2cn(CC(=O)N3CCC(N4CCc5ccccc5NC4=O)CC3)c(=O)n(CCS(C)(=O)=O)c2=O)c1Cl]

¹H NMR (δ, DMSO): 1.55 (m, 1H), 1.71 (m, 3H); 2.53 (m, 2H), 2.68 (m, 1H); 2.90 (m, 2H); 3.08 (s, 3H); 3.15 (m, 1H); 3.38 (m, 2H), 3.90 (s, 3H); 3.95 (d, J=13.6 Hz, 1H); 4.28-4.32 (m, 3H); 4.43 (d, J=13.0 Hz, 1H); 4.79 (s, 2H); 6.79-6.83 (m, 1H); 6.92 (dd, J=7.6, 1.4 Hz, 1H); 7.02-7.05 (m, 3H); 7.19-7.21 (m, 1H); 7.36 (t, J=8.0 Hz, 1H); 7.78 (s, 1H); 8.53 (s, 1H).

Compound 244: 5-(2-chloro-3-fluorophenyl)-3-[(1S)-1-methyl-2-methylsulphonyl-ethyl]-1-[2-oxo-2-[4-(2-oxo-4,5-dihydro-1H-1,3-benzodiazepin-3-yl)-1-piperidyl]ethyl]pyrimidine-2,4-dione

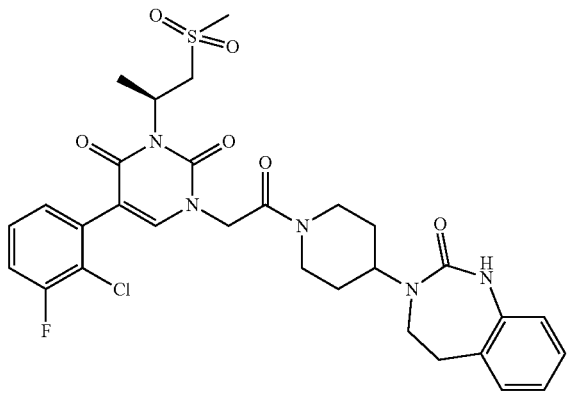 [SMILES: C[C@@H](CS(C)(=O)=O)n1c(=O)c(-c2cccc(F)c2Cl)cn(CC(=O)N2CCC(N3CCc4ccccc4NC3=O)CC2)c1=O]

¹H NMR (δ, DMSO): 1.24 (d, J=7.0 Hz, 3H), 1.57 (m, 1H), 1.69 (m, 3H), 2.70 (s, 1H), 2.84-2.95 (m, 2H), 3.06 (s, 3H), 3.16 (m, 1H), 3.35-3.43 (m, 2H), 3.53 (m, 1H), 3.95 (d, J=13.6 Hz, 1H), 4.11-4.39 (m, 3H), 4.43 (d, J=12.4 Hz, 1H), 4.80 (s, 2H), 6.81 (m, 1H), 7.04 (m, 3H), 7.23 (m, 1H), 7.38-7.54 (m, 2H), 7.90 (s, 1H), 8.52 (s, 1H).

Compound 245: 5-(2,3-dichlorophenyl)-3-[2-methoxy-1-(methoxymethyl)ethyl]-1-[2-[4-(7-methoxy-2-oxo-4,5-dihydro-1H-1,3-benzodiazepin-3-yl)-1-piperidyl]-2-oxo-ethyl]pyrimidine-2,4-dione

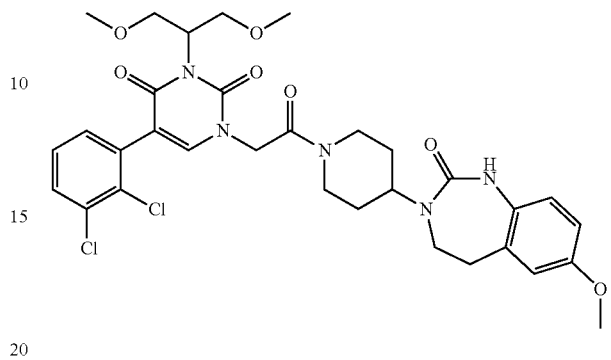

¹H NMR (δ, DMSO): 1.50-1.58 (m, 1H); 1.65-1.77 (m, 3H); 2.64-2.70 (m, 1H); 2.85-2.87 (m, 2H); 3.10-3.16 (m, 1H); 3.23 (s, 6H); 3.34-3.36 (m, 2H); 3.59 (m, 2H); 3.66 (s, 3H); 3.80-3.85 (m, 2H); 3.91-3.94 (m, 1H); 4.24-4.30 (m, 1H); 4.40-4.43 (m, 1H); 4.74 (m, 2H); 5.26 (br s, 1H); 6.61 (d, J=2.9 Hz, 1H); 6.66 (dd, J=8.8, 2.9 Hz, 1H); 6.97 (d, J=8.8 Hz, 1H); 7.33 (dd, J=7.7, 1.6 Hz, 1H); 7.42 (t, J=7.9 Hz, 1H); 7.68 (dd, J=8.1, 1.6 Hz, 1H); 7.79 (s, 1H); 8.31 (s, 1H).

Compound 246: 3-[5-(2-chloro-3-fluorophenyl)-3-[2-[4-(7-methoxy-2-oxo-4,5-dihydro-1H-1,3-benzodiazepin-3-yl)-1-piperidyl]-2-oxo-ethyl]-2,6-dioxo-pyrimidin-1-yl]propanoic acid

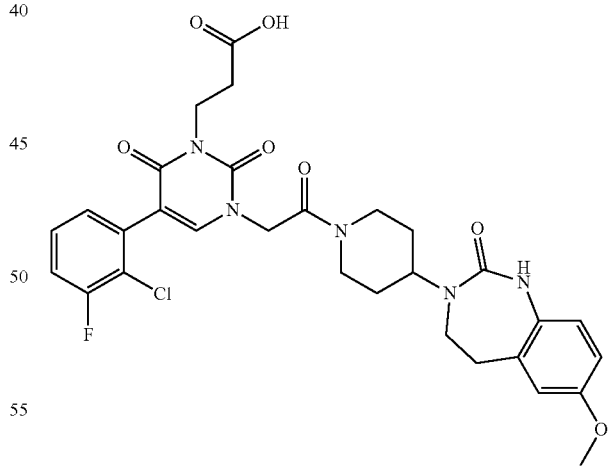

¹H NMR (δ, DMSO): 1.55 (m, 1H), 1.70 (m, 3H), 2.50 (m, 4H), 2.68 (m, 1H), 2.80-2.95 (m, 2H), 3.15 (m, 1H), 3.67 (s, 3H), 3.94 (d, J=13.6 Hz, 1H), 4.02-4.17 (m, 2H), 4.28 (m, 1H), 4.43 (d, J=12.8 Hz, 1H), 4.78 (s, 2H), 6.62 (d, J=3.0 Hz, 1H), 6.67 (dd, J=8.8, 3.0 Hz, 1H), 6.98 (d, J=8.8 Hz, 1H), 7.10-7.30 (m, 1H), 7.37-7.54 (m, 2H), 7.84 (s, 1H), 8.32 (s, 1H), 12.45 (br-s, 1H).

Compound 247: 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-[2-(1,3,4-oxadiazol-2-yl)ethyl]pyrimidine-2,4-dione

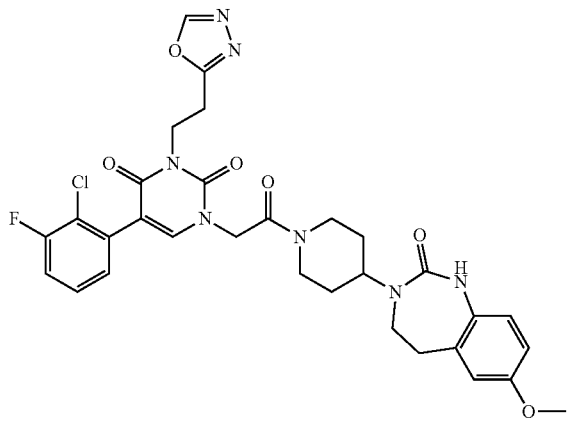 [SMILES: COc1ccc2c(c1)CCN(C1CCN(C(=O)Cn3cc(-c4cccc(F)c4Cl)c(=O)n(CCc4nnco4)c3=O)CC1)C(=O)N2]

¹H NMR (δ, DMSO): 1.54 (m, 1H); 1.68 (m, 3H); 2.68 (m, 1H); 2.88 (m, 2H); 3.19 (m, 3H); 3.36 (m, 2H); 3.67 (s, 3H); 3.94 (d, J=13.5 Hz, 1H); 4.25 (m, 3H); 4.43 (d, J=12.8 Hz, 1H); 4.77 (s, 2H); 6.63 (d, J=2.9 Hz, 1H); 6.67 (dd, J=8.8, 2.9 Hz, 1H); 6.98 (d, J=8.8 Hz, 1H); 7.18 (m, 1H); 7.46 (m, 2H); 7.86 (s, 1H); 8.33 (s, 1H); 9.13 (s, 1H).

Compound 248: 2-[5-(2-chloro-3-fluorophenyl)-3-[2-[4-(7-methoxy-2-oxo-4,5-dihydro-1H-1,3-benzodiazepin-3-yl)-1-piperidyl]-2-oxo-ethyl]-2,6-dioxo-pyrimidin-1-yl]acetic acid

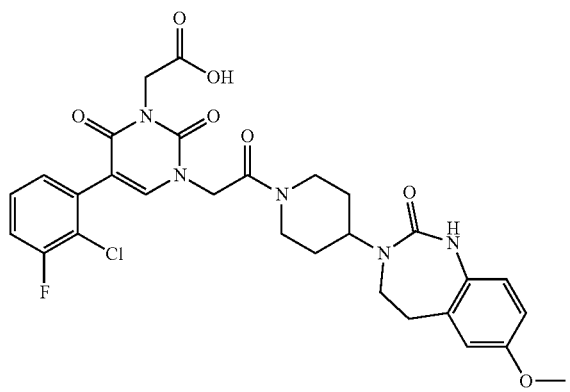 [SMILES: COc1ccc2c(c1)CCN(C1CCN(C(=O)Cn3cc(-c4cccc(F)c4Cl)c(=O)n(CC(=O)O)c3=O)CC1)C(=O)N2]

¹H NMR (δ, DMSO): 1.49-1.58 (m, 1H); 1.61-1.74 (m, 3H); 2.68 (m, 1H); 2.87-2.89 (m, 2H); 3.12-3.18 (m, 1H); 3.36 (m, 2H), 3.67 (s, 3H); 3.95 (d, J=13.6 Hz, 1H); 4.25-4.31 (m, 1H); 4.43 (d, J=12.9 Hz, 1H); 4.52 (m, 2H); 4.81 (s, 2H); 6.62 (d, J=2.9 Hz, 1H); 6.67 (dd, J=8.8, 2.9 Hz, 1H); 6.98 (d, J=8.8 Hz, 1H); 7.22-7.24 (m, 1H); 7.44-7.48 (m, 2H); 7.90 (s, 1H); 8.32 (s, 1H); 13.05 (br-s, 1H).

Compound 249: 5-(2-chloro-3-fluorophenyl)-3-[(1R)-1-methyl-2-methylsulphonyl-ethyl]-1-[2-oxo-2-[4-(2-oxo-4,5-dihydro-1H-1,3-benzodiazepin-3-yl)-1-piperidyl]ethyl]pyrimidine-2,4-dione

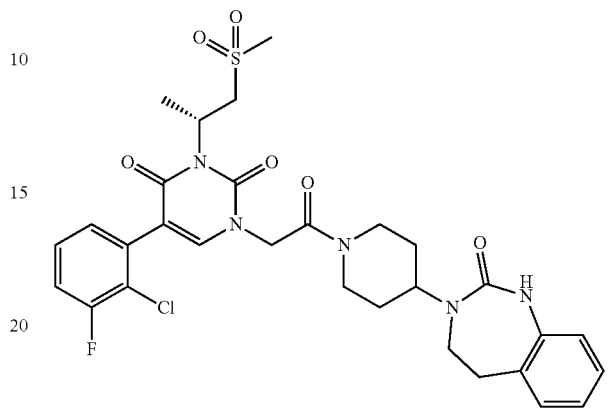

¹H NMR (δ, DMSO): 1.24 (d; J=7.03 Hz; 3H); 1.53-1.56 (m; 1H); 1.66-1.72 (m; 3H); 2.69 (m; 1H); 2.89-2.91 (m; 2H); 3.06 (s; 3H); 3.16 (m; 1H); 3.38 (m; 2H); 3.53 (m; 1H); 3.95 (d; J=13.62 Hz; 1H); 4.17-4.24 (m; 1H); 4.27-4.32 (m; 2H); 4.43 (d; J=12.93 Hz; 1H); 4.81 (m; 2H); 6.81 (m; 1H); 7.04 (m; 3H); 7.22-7.24 (m; 1H); 7.45-7.49 (m; 2H); 7.90 (s; 1H); 8.53 (s; 1H).

Compound 250: 5-(2-chloro-3-fluorophenyl)-3-(2-methylsulphonylethyl)-1-[2-oxo-2-[2-(2-oxo-4,5-dihydro-1H-1,3-benzodiazepin-3-yl)-6-azaspiro[3.3]heptan-6-yl]ethyl]pyrimidine-2,4-dione

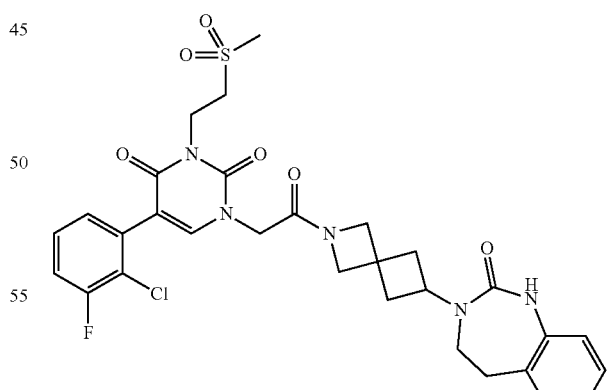

¹H NMR (δ, DMSO): 2.32-2.38 (m, 4H); 2.91-2.93 (m, 2H); 3.07 (s, 3H); 3.40-3.43 (m, 4H); 3.88 (s, 1H); 4.01 (s, 1H); 4.18 (s, 1H); 4.29-4.31 (m, 3H); 4.46-4.51 (m, 3H); 6.81-6.85 (m, 1H); 7.04-7.08 (m, 3H); 7.19-7.21 (m, 1H); 7.44-7.47 (m, 2H); 7.88 (m, 1H); 8.53 (m, 1H).

Compound 251: 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-[2-(1,2,4-triazol-4-yl)ethyl]pyrimidine-2,4-dione

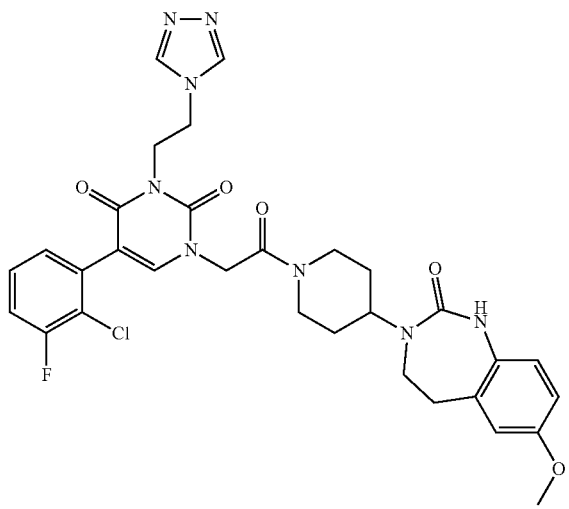 [SMILES: COc1ccc2c(c1)CCN(C1CCN(C(=O)Cn3cc(-c4cccc(F)c4Cl)c(=O)n(CCn4cnnc4)c3=O)CC1)C(=O)N2]

Mass=651

Compound 252: 5-(2-chloro-3-fluorophenyl)-1-[2-[4-(7-fluoro-2-oxo-4,5-dihydro-1H-1,3-benzodiazepin-3-yl)-1-piperidyl]-2-oxo-ethyl]-3-[(1R)-1-methyl-2-methylsulphonyl-ethyl]pyrimidine-2,4-dione

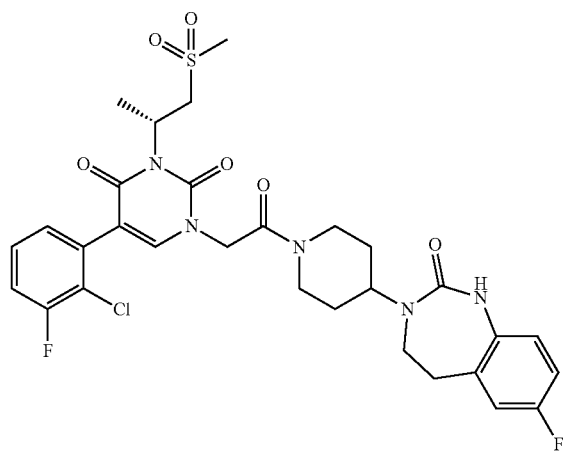 [SMILES: C[C@H](CS(C)(=O)=O)n1c(=O)c(-c2cccc(F)c2Cl)cn(CC(=O)N2CCC(N3CCc4cc(F)ccc4NC3=O)CC2)c1=O]

¹H NMR (δ, DMSO): 1.14-1.36 (m, 5H), 1.55 (m, 1H), 1.71 (m, 3H), 2.69 (m, 1H), 2.86-2.93 (m, 2H), 3.06 (s, 3H), 3.15 (m, 1H), 3.34-3.41 (m, 2H), 3.53 (m, 1H), 3.94 (d, J=13.6 Hz, 1H), 4.15-4.33 (m, 3H), 4.43 (d, J=13.0 Hz, 1H), 4.80 (m, 2H), 6.87-6.96 (m, 2H), 7.02-7.11 (m, 1H), 7.19-7.27 (m, 1H), 7.43-7.51 (m, 2H), 7.89 (s, 1H), 8.55 (s, 1H).

Compound 253: 3-[1-[2-[5-(2-chloro-3-fluorophenyl)-3-(2-methylsulphonylethyl)-2,4-dioxo-pyrimidin-1-yl]acetyl]-4-piperidyl]-2-oxo-4,5-dihydro-1H-1,3-benzodiazepine-7-carboxylic acid

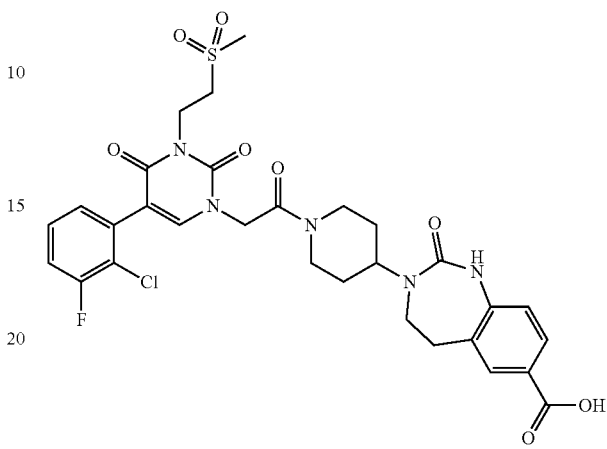

¹H NMR (δ, DMSO): 1.56 (m, 1H), 1.69 (m, 3H), 2.71 (m, 1H), 2.95 (m, 2H), 3.08 (s, 3H), 3.16 (m, 1H), 3.36-3.48 (m, 4H), 3.96 (d, J=13.4 Hz, 1H), 4.31 (m, 2H), 4.35-4.51 (m, 2H), 4.80 (m, 2H), 7.11 (d, J=8.5 Hz, 1H), 7.17-7.27 (m, 1H), 7.40-7.54 (m, 2H), 7.61 (dd, J=8.5, 2.0 Hz, 1H), 7.64 (d, J=2.0 Hz, 1H), 7.89 (s, 1H), 9.01 (s, 1H), 12.35 (br-s, 1H).

Compound 254: S-[2-[5-(2-chloro-3-fluorophenyl)-3-[2-[4-(7-methoxy-2-oxo-4,5-dihydro-1H-1,3-benzodiazepin-3-yl)-1-piperidyl]-2-oxo-ethyl]-2,6-dioxo-pyrimidin-1-yl]ethyl]ethanethioate

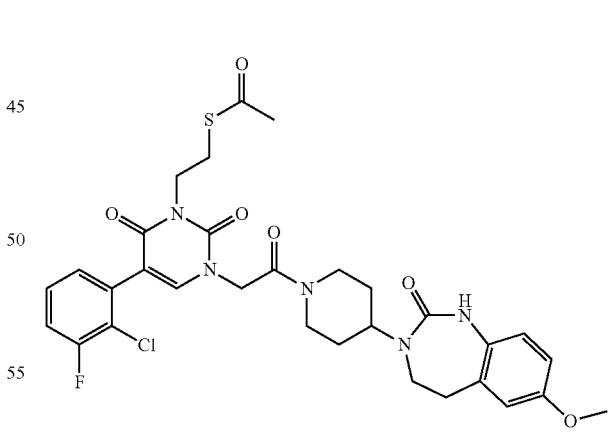

¹H NMR (δ, DMSO): 1.56 (m, 1H), 1.68 (m, 3H), 2.33 (m, 4H), 2.81-2.94 (m, 2H), 3.12 (m, 3H), 3.34-3.40 (m, 2H), 3.67 (s, 3H), 3.95 (d, J=14.0 Hz, 1H), 4.07 (m, 2H), 4.28 (m, 1H), 4.43 (d, J=12.7 Hz, 1H), 4.78 (s, 2H), 6.63 (d, J=2.9 Hz, 1H), 6.67 (dd, J=8.9, 2.9 Hz, 1H), 6.98 (d, J=8.7 Hz, 1H), 7.17-7.29 (m, 1H), 7.37-7.55 (m, 2H), 7.84 (s, 1H), 8.33 (s, 1H).

Compound 255: N-[(2S)-2-[5-(2,3-dichlorophenyl)-2,6-dioxo-3-[2-oxo-2-[4-(2-oxo-4,5-dihydro-1H-1,3-benzodiazepin-3-yl)-1-piperidyl]ethyl]pyrimidin-1-yl]propyl]acetamide

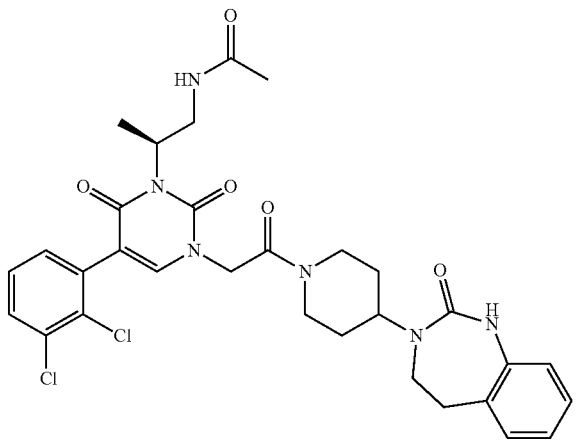 [SMILES: CC(=O)NC[C@H](C)n1c(=O)c(-c2cccc(Cl)c2Cl)cn(CC(=O)N2CCC(N3CCc4ccccc4NC3=O)CC2)c1=O]

¹H NMR (δ, DMSO): 1.34 (3H, d, J=6.91 Hz), 1.57 (1H, m), 1.69 (3H, m), 1.77 (3H, s), 2.68-2.72 (1H, m), 2.90 (2H, m), 3.15 (1H, m), 3.38 (2H, m), 3.44-3.57 (2H, m), 3.95 (1H, d, J=13.54 Hz), 4.33 (1H, m), 4.44 (1H, d, J=12.82 Hz), 4.67-4.81 (2H, m), 4.99 (1H, m), 6.81 (1H, m), 7.04 (3H, m), 7.33 (1H, m), 7.43 (1H, t, J=7.87 Hz), 7.68 (1H, dd, J=8.04, 1.58 Hz), 7.78 (1H, s), 7.93 (1H, m), 8.52 (1H, s).

Compound 256: N-[(2S)-2-[5-(2-chloro-3-fluorophenyl)-2,6-dioxo-3-[2-oxo-2-[4-(2-oxo-4,5-dihydro-1H-1,3-benzodiazepin-3-yl)-1-piperidyl]ethyl]pyrimidin-1-yl]propyl]acetamide

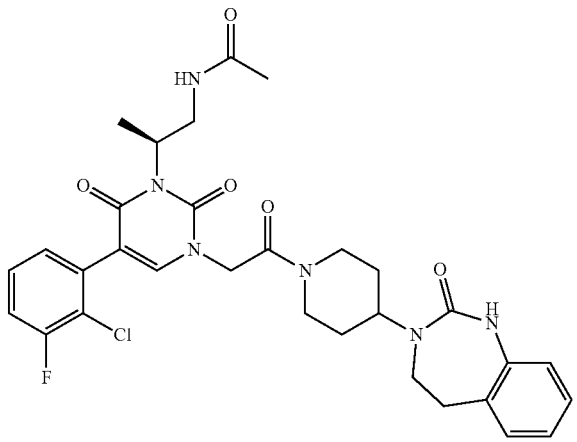 [SMILES: CC(=O)NC[C@H](C)n1c(=O)c(-c2cccc(F)c2Cl)cn(CC(=O)N2CCC(N3CCc4ccccc4NC3=O)CC2)c1=O]

¹H NMR (δ, DMSO): 1.35 (d; J=6.85 Hz; 3H); 1.57 (m; 1H); 1.70 (m; 3H); 1.77 (s; 3H); 2.69-2.72 (m; 1H); 2.90 (m; 2H); 3.16 (m; 1H); 3.39 (m; 2H); 3.49-3.57 (m; 2H); 3.96 (d; J=13.24 Hz; 1H); 4.33 (m; 1H); 4.45 (d; J=12.80 Hz; 1H); 4.75 (m; 2H); 4.99 (m; 1H); 6.82 (m; 1H); 7.03-7.05 (m; 3H); 7.22 (m; 1H); 7.45 (m; 2H); 7.79 (s; 1H); 7.93 (m; 1H); 8.53 (s; 1H).

Compound 257: 2-[5-(2-chloro-3-fluorophenyl)-3-[2-[4-(7-methoxy-2-oxo-4,5-dihydro-1H-1,3-benzodiazepin-3-yl)-1-piperidyl]-2-oxo-ethyl]-2,6-dioxo-pyrimidin-1-yl]ethanesulphonic acid

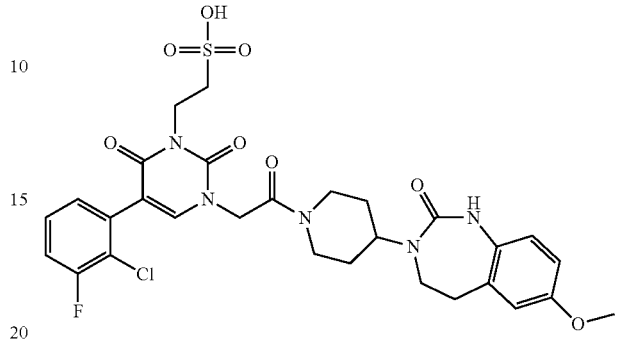

¹H NMR (δ, DMSO): 1.56 (m, 1H), 1.62-1.84 (m, 3H), 2.59-2.74 (m, 3H), 2.83-2.95 (m, 2H), 3.06-3.16 (m, 1H), 3.18 (s, 2H), 3.28-3.43 (m, 2H), 3.67 (s, 3H), 3.95 (d, J=13.5 Hz, 1H), 4.06-4.19 (m, 2H), 4.21-4.35 (m, 1H), 4.43 (d, J=12.8 Hz, 1H), 4.77 (m, 2H), 6.63 (d, J=3.0 Hz, 1H), 6.66 (dd, J=8.6, 2.9 Hz, 1H), 6.97 (d, J=8.8 Hz, 1H), 7.22 (m, 1H), 7.39-7.50 (m, 2H), 7.80 (s, 1H), 8.31 (s, 1H).

Compound 258: 5-(2-chloro-3-fluorophenyl)-3-[(1S)-1-(methoxymethyl)-2-methylsulphonyl-ethyl]-1-[2-[4-(7-methoxy-2-oxo-4,5-dihydro-1H-1,3-benzodiazepin-3-yl)-1-piperidyl]-2-oxo-ethyl]pyrimidine-2,4-dione

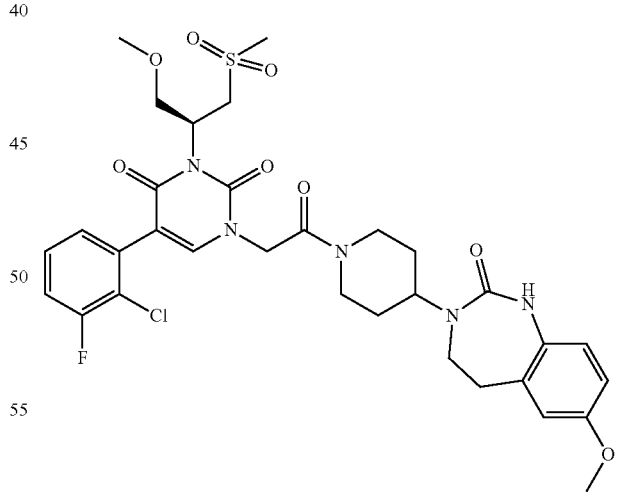

¹H NMR (δ, DMSO): 1.54 (m, 1H), 1.71 (m, 3H), 2.65 (m, 2H), 2.87 (m, 2H), 3.07 (s, 3H), 3.15 (m, 1H), 3.26 (s, 3H), 3.36 (m, 2H), 3.55-3.76 (m, 5H), 3.95 (m, 1H), 4.36 (m, 8.2 Hz, 4H), 4.80 (s, 2H), 6.62 (d, J=3.0 Hz, 1H), 6.67 (dd, J=8.6, 3.0 Hz, 1H), 6.98 (d, J=8.8 Hz, 1H), 7.15-7.28 (m, 1H), 7.38-7.53 (m, 2H), 7.89 (s, 1H), 8.32 (s, 1H).

Compound 259: 5-(2-chloro-3-fluorophenyl)-1-[2-[4-(7-methoxy-2-oxo-4,5-dihydro-1H-1,3-benzodiazepin-3-yl)-1-piperidyl]-2-oxo-ethyl]-3-(2-methyl-2-methylsulphonyl-propyl)pyrimidine-2,4-dione

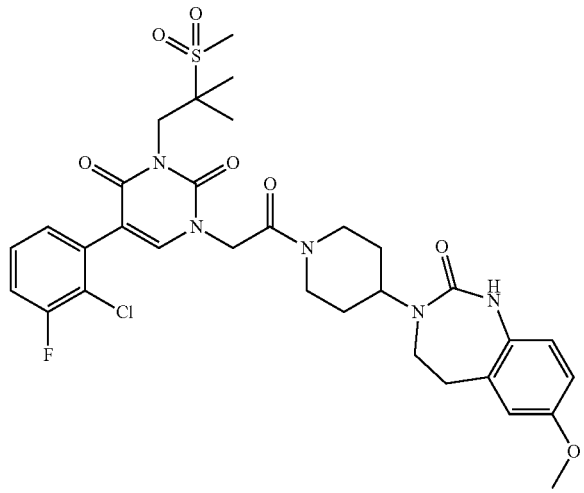 [SMILES: COc1ccc2c(c1)CCN(C1CCN(C(=O)Cn3cc(-c4cccc(F)c4Cl)c(=O)n(CC(C)(C)S(C)(=O)=O)c3=O)CC1)C(=O)N2]

$^1$H NMR (δ, DMSO): 1.30 (s, 6H); 1.52-1.58 (m, 1H); 1.64-1.77 (m, 3H); 2.68 (t, J=12.5 Hz, 1H); 2.88 (m, 2H); 3.06 (s, 3H); 3.15 (t, J=13.0 Hz, 1H); 3.36 (m, 2H); 3.67 (s, 3H); 3.94 (d, J=13.5 Hz, 1H); 4.25-4.35 (m, 3H); 4.43 (d, J=13.7 Hz, 1H); 4.80 (s, 2H); 6.62 (d, J=3.0 Hz, 1H); 6.67 (dd, J=8.9, 3.0 Hz, 1H), 6.98 (d, J=8.8 Hz, 1H); 7.22-7.24 (m, 1H); 7.45-7.48 (m, 2H); 7.89 (s, 1H); 8.33 (s, 1H).

Moreover, for purposes of illustration, the examples given below describe non-exhaustively the procedures followed for obtaining groups R1 of the compounds according to the invention.

1-Piperidin-4-yl-1,3-dihydro-imidazo[4,5-b]pyridin-2-one dihydrochloride

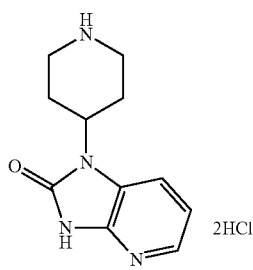 [SMILES: O=c1[nH]c2ncccc2n1C1CCNCC1]

4-(2-chloro-pyridin-3-ylamino)-piperidine-1-ethyl carboxylate

Trifluoroacetic acid is added slowly to a solution of 2-chloro-pyridin-3-ylamine and 4-oxo-piperidine-1-ethyl carboxylate in isopropyl acetate. The reaction mixture is stirred at room temperature for one hour and then sodium triacetoxyborohydride is added in portions. After stirring for two hours at room temperature, 10% aqueous solution of soda is added and the mixture is extracted with isopropyl acetate. The organic phase is dried over magnesium sulphate, filtered under vacuum and then concentrated to dryness. 4-(2-Chloro-pyridin-3-ylamino)-piperidine-1-ethyl carboxylate is obtained in the form of an orange-coloured oil.

4-[1-(2-chloro-pyridin-3-yl)-ureido]-piperidine-1-ethyl carboxylate

A solution containing 4-(2-chloro-pyridin-3-ylamino)-piperidine-1-ethyl carboxylate dissolved in tetrahydrofuran is added to a solution of chlorosulphonylisocyanate in tetrahydrofuran, cooled to −10° C. under a nitrogen stream. Isopropyl acetate is added and the mixture is stirred for one hour at −10° C. Water is added, followed by 10% aqueous solution of soda. The organic phase is recovered and then concentrated. A beige solid precipitates; it is filtered, washed with isopropyl acetate and then dried under vacuum at 60° C. 4-[1-(2-Chloro-pyridin-3-yl)-ureido]-piperidine-1-ethyl carboxylate is obtained in the form of a white solid.

4-(2-oxo-2,3-dihydro-imidazo[4,5-b]pyridin-1-yl)-piperidine-1-ethyl carboxylate

Potassium carbonate, palladium acetate trimer and 1,4-bis(diphenylphosphino)-butane are added to a suspension of 4-[1-(2-chloro-pyridin-3-yl)-ureido]-piperidine-1-ethyl carboxylate in isopropanol degassed under nitrogen. The mixture is stirred under reflux for 21 hours. Water and ethyl acetate are added. The organic phase is dried over magnesium sulphate, filtered under vacuum and then concentrated to dryness. The crude product is purified by silica gel flash chromatography eluted with a dichloromethane/methanol mixture, 95/5. 4-(2-Oxo-2,3-dihydro-imidazo[4,5-b]pyridin-1-yl)-piperidine-1-ethyl carboxylate is obtained in the form of a pale yellow solid.

1-Piperidin-4-yl-1,3-dihydro-imidazo[4,5-b]pyridin-2-one dihydrochloride

An aqueous solution of soda is added to a solution of 4-(2-oxo-2,3-dihydro-imidazo[4,5-b]pyridin-1-yl)-piperidine-1-ethyl carboxylate in ethanol and water. The reaction mixture is stirred under reflux for 12 hours, then concentrated and taken up in isopropanol. A 5N aqueous solution of hydrochloric acid is added; the product precipitates, it is filtered, rinsed with isopropanol and then dried under vacuum at 60° C. 1-Piperidin-4-yl-1,3-dihydro-imidazo[4,5-b]pyridin-2-one dihydrochloride is obtained in the form of a beige solid.

1-(4-piperidyl)-3H-imidazo[4,5-b]pyridin-2-one

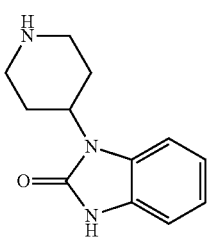 [SMILES: O=c1[nH]c2ccccc2n1C1CCNCC1]

Similarly to the synthesis of 1-piperidin-4-yl-1,3-dihydro-imidazo[4,5-b]pyridin-2-one described above, starting from 2-chloro-phenylamine, 1-(4-piperidyl)-3H-imidazo[4,5-b]pyridin-2-one is obtained in the form of a white solid.

3-piperidin-4-yl-3,4-dihydro-1H-quinazolin-2-one

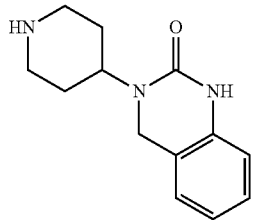 [SMILES: O=C1Nc2ccccc2CN1C1CCNCC1]

[2-(1-benzyl-piperidin-4-ylcarbamoyl)-phenyl]-tert-butyl carbamate 8.9 g (46.3 mmol) of 1-ethyl-3-(3-dimethylaminopropyl) carbodiimide hydrochloride is added to a solution of 10 g (42.1 mmol) of 2-tert-butoxycarbonylaminobenzoic acid, 10.3 ml (50.6 mmol) of 1-benzyl-piperidin-4-ylamine, 6.3 g (46.3 mmol) of 1-hydroxybenzotriazole and 17.6 ml (126.3 mmol) of triethylamine, in 120 ml of dimethylformamide. The reaction mixture is then stirred before adding [ . . . ]. The reaction mixture is heated at 70° C. for 5 hours and then hydrolysed with an aqueous solution of sodium hydrogen carbonate and diluted with ethyl acetate. The product is extracted with ethyl acetate. The organic phase is washed twice with a saturated aqueous solution of sodium hydrogen carbonate and then with a saturated aqueous solution of sodium chloride and with water, dried over magnesium sulphate and filtered. The solvents are concentrated under vacuum. 17 g (100%) of [2-(1-benzyl-piperidin-4-ylcarbamoyl)-phenyl]-tert-butyl carbamate is obtained in the form of a beige solid.

2-amino-N-(1-benzyl-piperidin-4-yl)-benzamide 30 mL (415 mmol) of trifluoroacetic acid is added dropwise to a solution of 17 g (41.5 mmol) of 2-(1-benzyl-piperidin-4-ylcarbamoyl)-phenyl]-tert-butyl carbamate in 170 ml of dichloromethane previously cooled to 0° C. The reaction mixture is stirred from 0° C. to room temperature for 20 hours. After concentration under vacuum, the residue is hydrolysed with an aqueous solution of sodium hydrogen carbonate and then diluted with ethyl acetate. The product is extracted twice with ethyl acetate. The organic phase is washed once with water and then once with a saturated aqueous solution of sodium chloride, dried over magnesium sulphate, filtered and concentrated under vacuum. 14 g (100%) of 2-amino-N-(1-benzyl-piperidin-4-yl)-benzamide is obtained in the form of a beige solid.

(2-aminobenzyl)-(1-benzyl-piperidin-4-yl)-amine 12 g (38.8 mmol) of 2-amino-N-(1-benzyl-piperidin-4-yl)-benzamide diluted in 72 ml of dioxane is added very slowly to a solution of 5.2 g (135.7 mmol) of lithium aluminium hydride in 260 ml of dioxane, previously heated under reflux. The reaction mixture (grey suspension) is then stirred and heated under reflux for 3 hours. The mixture is cooled to 0° C. and then hydrolysed slowly with 5.2 ml of 15M aqueous soda and 15.5 ml of water. The reaction mixture is then diluted with 240 ml of diethyl ether and stirred at room temperature for 55 minutes. After filtration of the salts, the filtrate is concentrated under vacuum to give 10.7 g (93%) of (2-aminobenzyl)-(1-benzyl-piperidin-4-yl)-amine in the form of a clear oil.

3-(1-benzyl-piperidin-4-yl)-3,4-dihydro-1H-quinazolin-2-one 0.9 g (5.7 mmol) of carbonyl diimidazole is added to a solution of 1.6 g (5.2 mmol) of (2-aminobenzyl)-(1-benzyl-piperidin-4-yl)-amine in 25 ml of tetrahydrofuran. The reaction mixture is stirred at room temperature for 5 hours. The solvent is removed under vacuum and then the reaction mixture is hydrolysed and diluted with ethyl acetate. After extraction with ethyl acetate, the organic phases are washed twice with water and then with a saturated aqueous solution of sodium chloride, dried over magnesium sulphate, filtered and concentrated under vacuum. The crude solid obtained is triturated in 15 ml of diethyl ether, then filtered and dried under vacuum to give 1.2 g (72%) of 3-(1-benzyl-piperidin-4-yl)-3,4-dihydro-1H-quinazolin-2-one in the form of a white solid.

3-piperidin-4-yl-3,4-dihydro-1H-quinazolin-2-one 120 mg of palladium on charcoal (10 wt %) is added to a solution of 1.2 g (3.7 mmol) of 3-(1-benzyl-piperidin-4-yl)-3,4-dihydro-1H-quinazolin-2-one in 30 ml of methanol, previously degassed with nitrogen. The mixture is then placed under a dihydrogen atmosphere for 48 hours and then filtered on Celite. The filtrate is concentrated under vacuum to give 0.9 g (100%) of 3-piperidin-4-yl-3,4-dihydro-1H-quinazolin-2-one in the form of a white solid.

3-piperidin-4-yl-1,3,4,5-tetrahydro-benzo[d][1,3]diazepin-2-one

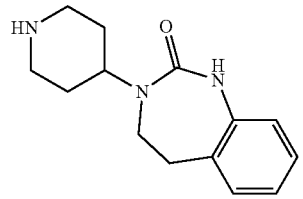 [SMILES: O=C1Nc2ccccc2CCN1C1CCNCC1]

(1-benzyl-piperidin-4-yl)-[2-(2-nitrophenyl)-ethyl]-amine 8 ml (40 mmol) of 1-benzyl-piperidin-4-ylamine is added to 4 g (17.4 mmol) of 1-(2-bromoethyl)-2-nitrobenzene and the mixture is heated at 100° C. for 18 hours. After cooling, diethyl ether is added, the mixture is filtered and the filtrate is concentrated. The crude residue is purified by silica gel chromatography eluted with an ethyl acetate/heptane mixture, 60/40, and then dichloromethane/methanol/ammonia, 95/3/2. 4.9 g (82%) of (1-benzyl-piperidin-4-yl)-[2-(2-nitrophenyl)-ethyl]-amine is obtained in the form of an orange-coloured oil.

[2-(2-aminophenyl)-ethyl]-(1-benzyl-piperidin-4-yl)-amine

Similarly to example 1.5, starting from 4.8 g (14 mmol) of (1-benzyl-piperidin-4-yl)-[2-(2-nitrophenyl)-ethyl]- amine, 140 mg of platinum oxide (10 mol %) and after purification of the residue by silica gel chromatography eluted with a dichloromethane/methanol/ammonia mixture 90/8/2, 4.6 g (100%) of [2-(2-aminophenyl)-ethyl]-(1-benzyl-piperidin-4-yl)-amine is obtained in the form of a brown oil.

3-(1-benzyl-piperidin-4-yl)-1,3,4,5-tetrahydro-benzo[d][1,3]diazepin-2-one

Similarly to example 1.4, starting from 1 g (6.5 mmol) of [2-(2-aminophenyl)-ethyl]-(1-benzyl-piperidin-4-yl)-amine, 3.9 g (78%) of 3-(1-benzyl-piperidin-4-yl)-1,3,4,5-tetrahydro-benzo[d][1,3]diazepin-2-one is obtained in the form of a white powder.

3-piperidin-4-yl-1,3,4,5-tetrahydro-benzo[d][1,3]diazepin-2-one

Similarly to example 1.5, starting from 3.7 g (11 mmol) of 3-(1-benzyl-piperidin-4-yl)-1,3,4,5-tetrahydro-benzo[d][1,3]diazepin-2-one, the reaction mixture being placed under 5 bar of dihydrogen, 2.6 g (96%) of 3-piperidin-4-yl-1,3,4,5-tetrahydro-benzo[d][1,3]diazepin-2-one is obtained in the form of a white powder.

7-bromo-3-(4-piperidyl)-4,5-dihydro-1H-1,3-benzo-diazepin-2-one

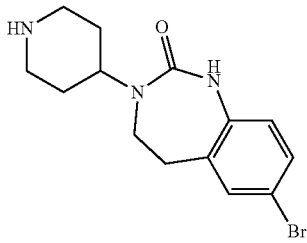 [SMILES: O=C1Nc2ccc(Br)cc2CCN1C1CCNCC1]

N-Bromosuccinimide is added to a solution of 3-piperidin-4-yl-1,3,4,5-tetrahydro-benzo[d][1,3]diazepin-2-one (prepared as described in example 16.4) in dimethylformamide. The mixture is stirred for one hour at room temperature and then water and ethyl acetate are added. After extraction with ethyl acetate, the organic phases are combined, washed with water and then with a saturated solution of sodium hydrochloride. After drying over magnesium sulphate, filtration and evaporation, the crude product is purified by phase inversion. 7-Bromo-3-(4-piperidyl)-4,5-dihydro-1H-1,3-benzodiazepin-2-one is obtained in the form of a beige solid.

7-methoxy-3-piperidin-4-yl-1,3,4,5-tetrahydro-benzo[d][1,3]diazepin-2-one

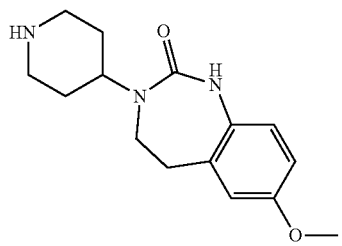 [SMILES: COc1ccc2c(c1)CCN(C1CCNCC1)C(=O)N2]

(5-methoxy-2-nitrophenyl)-acetonitrile

A solution containing 30.5 g (199 mmol) of 4-nitroanisole and 40 g (239 mmol) of (4-chlorophenoxy)-acetonitrile in 305 ml of N,N-dimethylformamide is added at −20° C. under nitrogen to a solution containing 53.6 g (478 mmol) of potassium tert-butylate in 610 ml of N,N-dimethylformamide. The reaction mixture is left to return to 0° C. and is maintained at this temperature. After 1 hour, the reaction mixture is cooled to −50° C. and hydrolysed slowly with 1000 ml of an iced 6N aqueous solution of hydrochloric acid, then 1000 ml of ethyl acetate and 500 ml of water are added. The aqueous phase is extracted with ethyl acetate. The organic phase is washed with a saturated aqueous solution of ammonium chloride and then with water, and then dried over anhydrous sodium sulphate, filtered and concentrated. The residue obtained is taken up in toluene and evaporated. The oil thus obtained is taken up, with stirring, in 250 ml of an ethyl acetate/heptane mixture (50/50) overnight and then the mixture is cooled in an ice bath and filtered. After rinsing with heptane, 26.7 g (68%) of (5-methoxy-2-nitrophenyl)-acetonitrile is obtained in the form of an orange-coloured solid.

2-(5-methoxy-2-nitrophenyl)-ethylamine 200 ml (200 mmol) of a complexed solution of borane-tetrahydrofuran is added to a solution containing 26 g (136 mmol) of (5-methoxy-2-nitrophenyl)-acetonitrile in 130 ml of 2-methyltetrahydrofuran at 60° C. After 3 hours, heating is stopped and 35 ml (863 mmol) of methanol is added slowly as well as 200 ml of a 1N aqueous solution of sodium hydroxide. The aqueous phase is then extracted with 250 ml of methyl-tetrahydrofuran. The organic phase is washed with water, dried over anhydrous sodium sulphate, filtered and concentrated partially. 400 ml of tert-butyl ether and 10 ml (175 mmol) of acetic acid are added. The mixture is cooled, stirred overnight and then concentrated and coevaporated with toluene. 40.6 g (100%) of 2-(5-methoxy-2-nitrophenyl)-ethylamine acetate is obtained in the form of a brown oil.

4-[2-(5-methoxy-2-nitrophenyl)-ethylamino]-piperidine-1-methyl carboxylate 44.5 g (210 mmol) of sodium triacetoxyhydroborate is added to a solution under nitrogen containing 40.6 g (136 mmol) of 2-(5-methoxy-2-nitrophenyl)-ethylamine acetic acid, 35.9 g (180 mmol) of N-(tert-butoxycarbonyl)-4-piperidone in 360 ml of 2-methyltetrahydrofuran. After 2 hours, the reaction mixture is hydrolysed with a 2N aqueous solution of sodium hydroxide. The aqueous phase is extracted with methyltetrahydrofuran. The organic phase is washed with water for adjustment to pH=6, dried over sodium sulphate, filtered and evaporated. 69.2 g (100%) of 4-[2-(5-methoxy-2-nitrophenyl)-ethylamino]-piperidine-1-methyl carboxylate is obtained in the form of a dark oil.

4-[2-(2-amino-5-methoxyphenyl)-ethylamino]-piperidine-1-tert-butyl carboxylate 3.7 g (70 mmol) of ammonium chloride and 31.3 g (560 mmol) of iron are added to a solution containing 69.2 g (137 mmol) of 4-[2-(5-methoxy-2-nitrophenyl)-ethylamino]-piperidine-1-methyl carboxylate in 130 ml of 2-methyltetrahydrofuran, 130 ml of methanol and 130 ml of water. The reaction mixture is heated under reflux for 4 hours and then left to return to room temperature. After 16 hours, the reaction mixture is filtered on Celite and the filtrate is concentrated until the methanol has evaporated. Methyltetrahydrofuran is added as well as a 10% solution of ethylenediaminetetraacetic acid. The organic phase is washed with water and then dried over anhydrous sodium sulphate, filtered and concentrated. 53.2 g (100%) of 4-[2-(2-amino-5-methoxyphenyl)-ethylamino]-piperidine-1-tert-butyl carboxylate is obtained in the form of an orange-coloured oil.

4-(7-methoxy-2-oxo-1,2,4,5-tetrahydro-benzo[d][1,3]diazepin-3-yl)-piperidine-1-tert-butyl carboxylate 27.2 g (168 mmol) of N,N'-carbonyldiimidazole is added in portions to a solution containing 53.2 g (137 mmol) of 4-[2-(2-amino-5-methoxyphenyl)-ethylamino]-piperidine-1-tert-butyl carboxylate at 90% in 1000 ml of toluene. After 1 hour, the precipitate formed is filtered and the filtrate is concentrated partially. The residue is washed twice with an aqueous solution of ammonium chloride. The organic phase is dried over anhydrous sodium sulphate, filtered and concentrated. 58 g of an orange-coloured oil is obtained. After purification by silica gel chromatography eluted with a mixture of ethyl acetate in heptane, following a polarity gradient (from 20% to 70% of ethyl acetate in heptane), 35 g of a yellow solid is obtained and is taken up in 200 ml of isopropyl ether under reflux, 100 ml of isopropyl ether, 100 ml of tetrahydrofuran, 80 ml of ethanol and 300 ml of methanol. The mixture is filtered and then concentrated. After purification by silica gel chromatography eluted with a mixture of ethyl acetate in heptane, following a polarity gradient (from 20% to 100% of ethyl acetate in heptane), 21.1 g (34%) of 4-(7-methoxy-2-oxo-1,2,4,5-tetrahydro-benzo[d][1,3]diazepin-3-yl)-piperidine-1-tert-butyl carboxylate is obtained in the form of a beige solid.

7-methoxy-3-piperidin-4-yl-1,3,4,5-tetrahydro-benzo[d][1,3]diazepin-2-one 35 ml (380 mmol) of trifluoroacetic acid is added at 0° C. to a solution containing 83% of 4-(7-methoxy-2-oxo-1,2,4,5-tetrahydro-benzo[d][1,3]diazepin-3-yl)-piperidine-1-tert-butyl carboxylate in 300 ml of dichloromethane. After 15 hours, the reaction mixture is concentrated slowly in a rotary evaporator. The residue is coevaporated with toluene, taken up in 250 ml of dichloromethane and then the mixture is adjusted to pH=10 with 1N aqueous solution of sodium hydroxide. The aqueous phase is extracted with dichloromethane, the organic phase is dried over anhydrous sodium sulphate, filtered and concentrated. 12.7 g (96%) of 7-methoxy-3-piperidin-4-yl-1,3,4,5-tetrahydro-benzo[d][1,3]diazepin-2-one is obtained in the form of a beige solid.

3-(4-methyl-piperidin-4-yl)-1,3,4,5-tetrahydro-benzo[d][1,3]diazepin-2-one

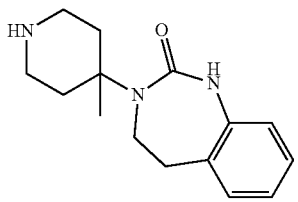 [SMILES: CC1(N2CCc3ccccc3NC2=O)CCNCC1]

4-methyl-4-[2-(2-nitrophenyl)-acetylamino]-piperidine-1-tert-butyl carboxylate

Similarly to example 1.6, starting from 2-nitrophenylacetic acid and 4-amino-4-methyl-piperidine-1-tert-butyl carboxylate, 4-methyl-4-[2-(2-nitrophenyl)-acetylamino]-piperidine-1-tert-butyl carboxylate is obtained in the form of a white solid.

4-methyl-4-[2-(2-nitrophenyl)-ethylamino]-piperidine-1-tert-butyl carboxylate

Similarly to example 115.2, starting from 4-methyl-4-[2-(2-nitrophenyl)-acetylamino]-piperidine-1-tert-butyl carboxylate and borane methyl sulphide complex, 4-methyl-4-[2-(2-nitrophenyl)-ethylamino]-piperidine-1-tert-butyl carboxylate is obtained in the form of a white paste.

4-[2-(2-aminophenyl)-ethylamino]-4-methyl-piperidine-1-tert-butyl-carboxylate

Similarly to example 115.4, starting from 4-methyl-4-[2-(2-nitrophenyl)-ethylamino]-piperidine-1-tert-butyl carboxylate, 4-[2-(2-aminophenyl)-ethylamino]-4-methyl-piperidine-1-tert-butyl-carboxylate is obtained in the form of a colourless oil.

4-methyl-4-(2-oxo-1,2,4,5-tetrahydro-benzo[d][1,3]diazepin-3-yl)-piperidine-1-tert-butyl-carboxylate Similarly to example 1.4, starting from 4-[2-(2-aminophenyl)-ethylamino]-4-methyl-piperidine-1-tert-butyl-carboxylate, 4-methyl-4-(2-oxo-1,2,4,5-tetrahydro-benzo[d][1,3]diazepin-3-yl)-piperidine-1-tert-butyl-carboxylate is obtained in the form of a white solid.

3-(4-methyl-piperidin-4-yl)-1,3,4,5-tetrahydro-benzo[d][1,3]diazepin-2-one

Similarly to example 115.11, starting from 4-methyl-4-(2-oxo-1,2,4,5-tetrahydro-benzo[d][1,3]diazepin-3-yl)-piperidine-1-tert-butyl-carboxylate, 3-(4-methyl-piperidin-4-yl)-1,3,4,5-tetrahydro-benzo[d][1,3]diazepin-2-one is obtained in the form of a colourless oil.

9-fluoro-3-piperidin-4-yl-1,3,4,5-tetrahydro-benzo[d][1,3]diazepin-2-one

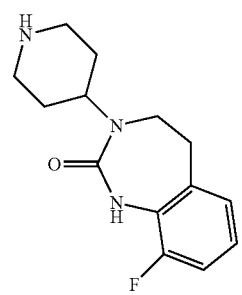 [SMILES: O=C1Nc2c(F)cccc2CCN1C1CCNCC1]

N-(1-benzyl-piperidin-4-yl)-2-(3-fluoro-2-nitrophenyl)-acetamide

Similarly to example 1.6, starting from 4-amino-1-benzylpiperidine and 2-(3-fluoro-2-nitrophenyl) acetic acid, N-(1-benzyl-piperidin-4-yl)-2-(3-fluoro-2-nitrophenyl)-acetamide is obtained in the form of a yellow solid.

[2-(2-amino-3-fluorophenyl)-ethyl]-(1-benzyl-piperidin-4-yl)-amine

Similarly to example 1.3, starting from N-(1-benzyl-piperidin-4-yl)-2-(3-fluoro-2-nitrophenyl)-acetamide, [2-(2-amino-3-fluorophenyl)-ethyl]-(1-benzyl-piperidin-4-yl)-amine is obtained in the form of a brown oil.

3-(1-benzyl-piperidin-4-yl)-9-fluoro-1,3,4,5-tetrahydro-benzo[d][1,3]diazepin-2-one Similarly to example 1.4, starting from [2-(2-amino-3-fluorophenyl)-ethyl]-(1-benzyl-piperidin-4-yl)-amine, 3-(1-benzyl-piperidin-4-yl)-9-fluoro-1,3,4,5-tetrahydro-benzo[d][1,3]diazepin-2-one is obtained in the form of a yellow oil.

9-fluoro-3-piperidin-4-yl-1,3,4,5-tetrahydro-benzo[d][1,3]diazepin-2-one

Similarly to example 1.5, starting from 3-(1-benzyl-piperidin-4-yl)-9-fluoro-1,3,4,5-tetrahydro-benzo[d][1,3]diazepin-2-one, 9-fluoro-3-piperidin-4-yl-1,3,4,5-tetrahydro-benzo[d][1,3]diazepin-2-one is obtained in the form of a yellow oil.

7-fluoro-3-piperidin-4-yl-1,3,4,5-tetrahydro-benzo[d][1,3]diazepin-2-one

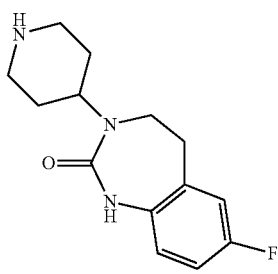 [SMILES: O=C1Nc2ccc(F)cc2CCN1C1CCNCC1]

Similarly to the synthesis of 9-fluoro-3-piperidin-4-yl-1,3,4,5-tetrahydro-benzo[d][1,3]diazepin-2-one, starting from 2-(5-fluoro-2-nitrophenyl)-ethylamine and 1-Boc-4-piperidone, 7-fluoro-3-piperidin-4-yl-1,3,4,5-tetrahydro-benzo[d][1,3]diazepin-2-one is obtained in the form of a yellow solid.

7-piperidin-4-yl-5,6,7,9-tetrahydro-1,7,9-triaza-benzocyclohepten-8-one

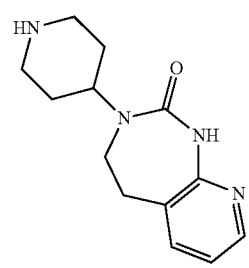 [SMILES: O=C1Nc2ncccc2CCN1C1CCNCC1]

Similarly to the synthesis of 9-fluoro-3-piperidin-4-yl-1,3,4,5-tetrahydro-benzo[d][1,3]diazepin-2-one, starting from (2-amino-pyridin-3-yl)-acetic acid and 4-amino-1-benzylpiperidine, 7-piperidin-4-yl-5,6,7,9-tetrahydro-1,7,9-triaza-benzocyclohepten-8-one is obtained in the form of a white solid.

7-piperidin-4-yl-5,6,7,9-tetrahydro-2,7,9-triaza-benzocyclohepten-8-one

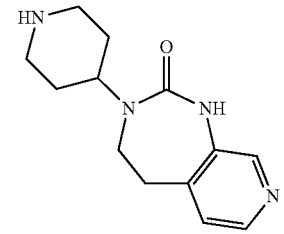 [SMILES: O=C1Nc2cnccc2CCN1C1CCNCC1]

Similarly to the synthesis of 7-piperidin-4-yl-5,6,7,9-tetrahydro-1,7,9-triaza-benzocyclohepten-8-one, starting from (3-amino-pyridin-4-yl)-acetic acid and 4-amino-1-benzylpiperidine, 7-piperidin-4-yl-5,6,7,9-tetrahydro-2,7,9-triaza-benzocyclohepten-8-one is obtained in the form of a white solid.

7-piperidin-4-yl-5,7,8,9-tetrahydro-2,5,7-triaza-benzocyclohepten-6-one

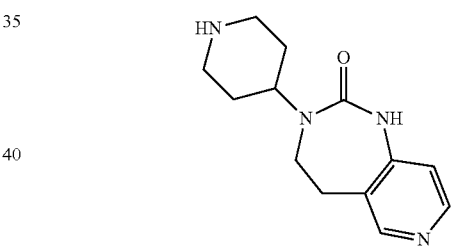

Similarly to the synthesis of 7-piperidin-4-yl-5,6,7,9-tetrahydro-1,7,9-triaza-benzocyclohepten-8-one, starting from (4-amino-pyridin-3-yl)-acetic acid and 4-amino-1-benzylpiperidine, 7-piperidin-4-yl-5,7,8,9-tetrahydro-2,5,7-triaza-benzocyclohepten-6-one is obtained in the form of a white solid.

7-piperidin-4-yl-5,7,8,9-tetrahydro-1,5,7-triaza-benzocyclohepten-6-one

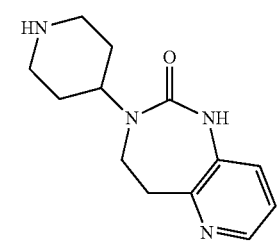 [SMILES: O=C1Nc2cccnc2CCN1C1CCNCC1]

Similarly to the synthesis of 7-piperidin-4-yl-5,6,7,9-tetrahydro-1,7,9-triaza-benzocyclohepten-8-one, starting from (5-amino-pyridin-3-yl)-acetic acid and 4-amino-1-benzylpiperidine, 7-piperidin-4-yl-5,7,8,9-tetrahydro-1,5,7-triaza-benzocyclohepten-6-one is obtained in the form of a white solid.

3-piperidin-4-yl-3,4-dihydro-1H-pyrido[2,3-d]pyrimidin-2-one

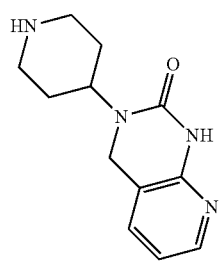 [SMILES: O=C1Nc2ncccc2CN1C1CCNCC1]

Similarly to the synthesis of 3-piperidin-4-yl-3,4-dihydro-1H-quinazolin-2-one (described in example 1.5), and starting from 2-tert-butoxycarbonylamino-nicotinic acid, 3-piperidin-4-yl-3,4-dihydro-1H-pyrido[2,3-d]pyrimidin-2-one is obtained in the form of a beige solid.

7-methylsulphanyl-3-piperidin-4-yl-1,3,4,5-tetrahydro-benzo[d][1,3]diazepin-2-one

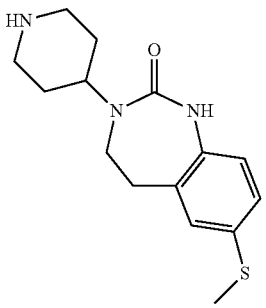 [SMILES: CSc1ccc2c(c1)CCN(C1CCNCC1)C(=O)N2]

Similarly to the synthesis of 7-methoxy-3-piperidin-4-yl-1,3,4,5-tetrahydro-benzo[d][1,3]diazepin-2-one (described in example 115.6), and starting from 1-Boc-4-piperidone and 2-(5-methylsulphanyl-2-nitrophenyl)-ethylamine, 7-methylsulphanyl-3-piperidin-4-yl-1,3,4,5-tetrahydro-benzo[d][1,3]diazepin-2-one is obtained in the form of a white solid.

7-methylsulphinyl-3-(4-piperidyl)-4,5-dihydro-1H-1,3-benzodiazepin-2-one

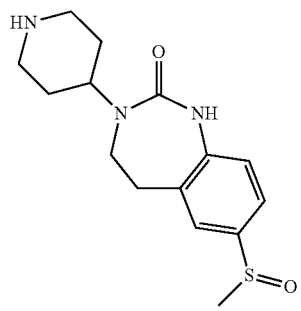 [SMILES: CS(=O)c1ccc2c(c1)CCN(C1CCNCC1)C(=O)N2]

Similarly to the synthesis of 7-methylsulphanyl-3-piperidin-4-yl-1,3,4,5-tetrahydro-benzo[d][1,3]diazepin-2-one, and after oxidation by 3-chloroperoxybenzoic acid, 7-methylsulphinyl-3-(4-piperidyl)-4,5-dihydro-1H-1,3-benzodiazepin-2-one is obtained in the form of a white solid.

7-methylsulphonyl-3-(4-piperidyl)-4,5-dihydro-1H-1,3-benzodiazepin-2-one

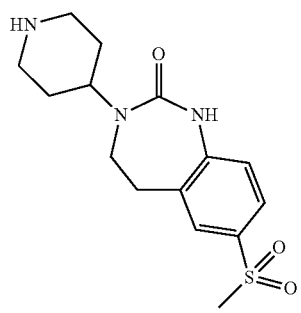 [SMILES: CS(=O)(=O)c1ccc2c(c1)CCN(C1CCNCC1)C(=O)N2]

Similarly to the synthesis of 7-methylsulphanyl-3-piperidin-4-yl-1,3,4,5-tetrahydro-benzo[d][1,3]diazepin-2-one, and after oxidation by hydrogen peroxide in the presence of ammonium molybdate tetrahydrate, 3-chloroperoxybenzoic acid, 7-methylsulphonyl-3-(4-piperidyl)-4,5-dihydro-1H-1,3-benzodiazepin-2-one is obtained in the form of a white solid.

3-piperidin-4-yl)-2-oxo-2,3,4,5-tetrahydro-1H-benzo[d][1,3]diazepine-7-carboxylic acid

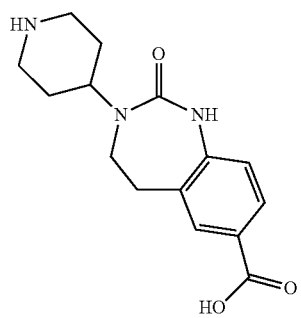 [SMILES: O=C(O)c1ccc2c(c1)CCN(C1CCNCC1)C(=O)N2]

Starting from 7-bromo-3-(4-piperidyl)-4,5-dihydro-1H-1,3-benzodiazepin-2-one, and after carboxylation with sodium hydride, n-butyllithium and carbon dioxide, 3-piperidin-4-yl)-2-oxo-2,3,4,5-tetrahydro-1H-benzo[d][1,3]diazepine-7-carboxylic acid is obtained in the form of a white solid.

5,5-dimethyl-3-(4-piperidyl)-1,4-dihydro-1,3-benzodiazepin-2-one

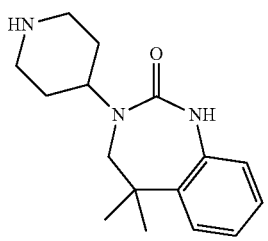 [SMILES: CC1(C)CN(C2CCNCC2)C(=O)Nc2ccccc21]

Similarly to the synthesis of 7-methoxy-3-piperidin-4-yl-1,3,4,5-tetrahydro-benzo[d][1,3]diazepin-2-one (described in example 115.6), and starting from 1-Boc-4-piperidone and 2-(5-methoxy-2-nitrophenyl)-2-methyl-propylamine, 5,5-dimethyl-3-(4-piperidyl)-1,4-dihydro-1,3-benzodiazepin-2-one is obtained in the form of a beige solid.

5-methyl-3-(4-piperidyl)-4,5-dihydro-1H-1,3-benzodiazepin-2-one

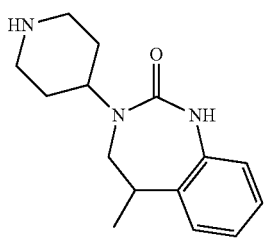 [SMILES: CC1CN(C2CCNCC2)C(=O)Nc2ccccc21]

Similarly to the synthesis of 7-methoxy-3-piperidin-4-yl-1,3,4,5-tetrahydro-benzo[d][1,3]diazepin-2-one (described in example 115.6), and starting from 1-Boc-4-piperidone and 2-(5-methoxy-2-nitrophenyl)-propylamine, 5-methyl-3-(4-piperidyl)-4,5-dihydro-1H-1,3-benzodiazepin-2-one is obtained in the form of a white solid.

4-methyl-3-(4-piperidyl)-4,5-dihydro-1H-1,3-benzodiazepin-2-one

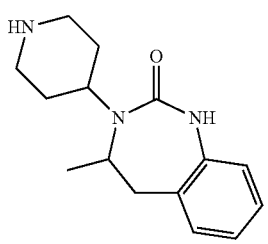 [SMILES: CC1Cc2ccccc2NC(=O)N1C1CCNCC1]

Similarly to the synthesis of 7-methoxy-3-piperidin-4-yl-1,3,4,5-tetrahydro-benzo[d][1,3]diazepin-2-one (described in example 115.6), and starting from 1-Boc-4-piperidone and 2-(5-methoxy-2-nitrophenyl)-1-methyl-ethylamine, 4-methyl-3-(4-piperidyl)-4,5-dihydro-1H-1,3-benzodiazepin-2-one is obtained in the form of a white solid.

3-(6-azaspiro[3.3]heptan-2-yl)-4,5-dihydro-1H-1,3-benzodiazepin-2-one

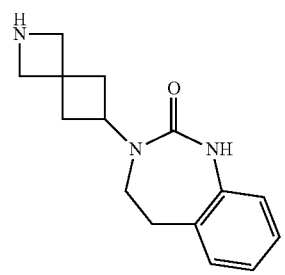 [SMILES: O=C1Nc2ccccc2CCN1C1CC2(CNC2)C1]

Similarly to the synthesis of 7-methoxy-3-piperidin-4-yl-1,3,4,5-tetrahydro-benzo[d][1,3]diazepin-2-one (described in example 115.6), and starting from 1-(2-bromoethyl)-2-nitrobenzene and 6-amino-2-aza-spiro[3.3]heptane-2-tert-butyl carboxylate, 3-(6-azaspiro[3.3]heptan-2-yl)-4,5-dihydro-1H-1,3-benzodiazepin-2-one is obtained in the form of a white solid.

4-phenyl-1-piperidin-4-yl-1,3-dihydro-imidazol-2-one

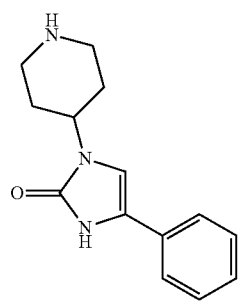 [SMILES: O=c1[nH]c(-c2ccccc2)cn1C1CCNCC1]

4-(2-oxo-4-phenyl-2,3-dihydro-imidazol-1-yl)-piperidine-1-tert-butyl-carboxylate N-Boc-4-amino-piperidine and N,N-diisopropylethylamine in solution in dichloromethane are added to a solution of 2-bromoacetophenone in dichloromethane. The reaction mixture is stirred at room temperature for sixteen hours, then sodium cyanate is added, as well as glacial acetic acid. After extraction with water and dichloromethane, the organic phase is dried, then filtered and concentrated to dryness. 4-(2-Oxo-4-phenyl-2,3-dihydro-imidazol-1-yl)-piperidine-1-tert-butyl-carboxylate is obtained in the form of a cream-coloured solid.

4-phenyl-1-piperidin-4-yl-1,3-dihydro-imidazol-2-one

Similarly to example 1.2, starting from 4-(2-oxo-4-phenyl-2,3-dihydro-imidazol-1-yl)-piperidine-1-tert-butyl-carboxylate, 4-phenyl-1-piperidin-4-yl-1,3-dihydro-imidazol-2-one is obtained in the form of an orange-coloured solid.

spiro[1H-pyrido[2,3-d][1,3]oxazine-4,4'-piperidin]-2-one

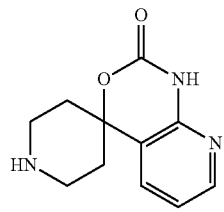 [SMILES: O=C1Nc2ncccc2C2(CCNCC2)O1]

(6-chloro-pyridin-2-yl)-tert-butyl carbamate 2-amino-6-chloropyridine and sodium bis(trimethylsilyl) amide are dissolved in tetrahydrofuran. A solution of di-tert-butyl dicarbonate in tetrahydrofuran is added dropwise. The reaction mixture is stirred at room temperature for twenty hours. Water and ethyl acetate are added, and the product is extracted with ethyl acetate. The organic phases are combined, washed once with water and once with a saturated aqueous solution of sodium chloride, then dried over magnesium sulphate, filtered and concentrated under vacuum. (6-Chloro-pyridin-2-yl)-tert-butyl carbamate is obtained in the form of a brown solid.

7'-chloro-2'-oxo-1',2'-dihydro-1H-spiro[piperidine-4,4'-pyrido[2,3-d][1,3]oxazine]-1-benzyl carboxylate n-Butyllithium is added dropwise to a solution at −20° C. of N,N,N',N'-tetramethylethylenediamine in tetrahydrofuran. After stirring for thirty minutes, the mixture is cooled to −78° C. and a solution of (6-chloro-pyridin-2-yl)-tert-butyl carbamate in tetrahydrofuran is added. The reaction is maintained at −50° C. for two hours and then a solution of 4-oxo-piperidine-1-benzyl carboxylate in tetrahydrofuran is added dropwise. The reaction mixture is brought back to room temperature slowly and then heated at 40° C. for 18 hours. The reaction mixture is hydrolysed with a saturated aqueous solution of sodium hydrogen carbonate and then diluted with dichloromethane. The product is extracted with dichloromethane, the organic phases are combined, washed once with water and then dried over magnesium sulphate, filtered and concentrated under vacuum. The crude product is chromatographed on silica gel eluted with a heptane/ethyl acetate mixture, 70/30 and then 50/50. 7'-chloro-2'-oxo-1',2'-dihydro-1H-spiro[piperidine-4,4'-pyrido[2,3-d][1,3]oxazine]-1-benzyl carboxylate is obtained in the form of a yellow solid.

spiro[1H-pyrido[2,3-d][1,3]oxazine-4,4'-piperidin]-2-one

Similarly to example 98.4, starting from 7'-chloro-2'-oxo-1',2'-dihydro-1H-spiro[piperidine-4,4'-pyrido[2,3-d][1,3]oxazine]-1-benzyl carboxylate, spiro[1H-pyrido[2,3-d][1,3]oxazine-4,4'-piperidin]-2-one is obtained in the form of a yellow solid.

The invention further relates to the compounds according to the invention for use thereof as a medicinal product.

Preferably, the compounds according to the invention are used in the prevention and/or treatment of inflammatory diseases with a neurogenic component.

The term "prevention of" or "prevent" inflammatory diseases with a neurogenic component signifies reducing and/or avoiding the appearance of the symptoms of these diseases.

The term "treatment of" or "treat" inflammatory diseases with a neurogenic component signifies reducing and/or inhibiting the development of these diseases and/or of their symptoms.

"Inflammatory diseases with a neurogenic component" preferably means inflammatory diseases of the skin with a neurogenic component selected from rosacea of type I (erythematous) and type II (papulopustular), atopic dermatitis, chronic eczema of the hands, psoriasis in its various forms (psoriasis vulgaris, of the scalp, arthritic, pustular, guttate), facial erythema, erythema pudicitiae, urticaria (acute, senile pruritus, prurigo nodularis) and acne, or headaches with neurogenic inflammation such as migraines.

The inflammatory diseases of the skin with a neurogenic component are preferably selected from type I (erythematous) rosacea, atopic dermatitis, psoriasis vulgaris and psoriasis of the scalp, and urticaria of the senile pruritus and prurigo nodularis type, even more preferably type I (erythematous) rosacea.

The compounds according to the invention may also be used in the prevention and/or treatment of inflammatory diseases with a vascular component such as infantile haemangiomata or purpura senilis.

The interest in the novel CGRP receptor antagonist heterocyclic compounds according to the invention in the treatment of inflammatory diseases with a neurogenic component is based on clinical elements emphasizing the parallel between notably rosacea and migraine:
   the facial localization of the lesions in patients with rosacea is similar to the zones of innervation by the trigeminal nerve, which is also implicated in migraine;
   the prevalence of migraine sufferers among patients with rosacea is demonstrated by epidemiological studies (≥27% vs 13% in the general population).
It is also based on experimental data:
   the vasodilator effect of CGRP on the cutaneous vessels has been demonstrated clinically: injection of low doses of CGRP subcutaneously induces erythema that lasts for several hours;
   topical application of capsaicin induces release of neuropeptides, including CGRP, which is reflected in cutaneous vasodilatation;
   injection of αCGRP intravenously in the mouse causes the appearance of a flush that is predominantly measurable at the level of the face of the animal. In mRamp1 gene knockout mice, no vasodilator response to this flush with CGRP is observed. Moreover, in these mice, no oedema appears in a model of local neurogenic inflammation induced by the topical application of a TRPV1 agonist. These results seem to confirm a major role of CGRP release in neurogenic inflammation and in flushing.

For this purpose, in general, the compounds according to the invention display good affinity for the CGRP receptor and thus good antagonist activity to the CGRP receptor.

This activity is more particularly illustrated by the GPCR GeneBLAzer® cellular dosage assay, which supplies a uniform method for monitoring the cellular response to candidate medicinal products.

In the GeneBLAzer® GPCR Cell-based Assay model supplied by Invitrogen (Lifetechnologies), activation of the CALCLR:RAMP1 receptor leads to expression of a reporter gene (beta-lactamase). The activity of beta-lactamase is quantified by FRET (fluorescence resonance energy transfer) in the presence of a fluorescent substrate and is directly proportional to the activation of the receptor.

The GeneBLAzer® CALCRL:RAMP CRE-bla HEK293F lines are HEK293F cells that stably overexpress the CALCRL and RAMP1 receptors as well as the reporter gene of beta-lactamase under the control of the cAMP response element (CRE).

The substrate of beta-lactamase contains two fluorophores (fluorescein and coumarin) joined together by a beta-lactam nucleus. In the absence of beta-lactamase and when it is excited at $\lambda=409$ nm, the substrate remains intact and the wavelength of emission of fluorescence from coumarin ($\lambda=460$ nm) excites the fluorescein, which emits in its turn ($\lambda=530$ nm). However, when beta-lactamase is expressed, the substrate is cleaved, separating the two fluorophores and interrupting FRET. The emission from the coumarin will then be proportional to the activation of the receptor.

The cells are seeded in 384-well microplates at a rate of 10 000 cells per well and incubated for 18 hours at 37° C. Vertical serial dilutions of agonist ($\alpha$-Calcitonin Gene Related Peptide for RAMP1) are added in competition with horizontal serial dilutions of antagonists to be tested. After incubation for 3 hours at 37° C., the substrate of the beta-lactamase is added to each well and the microplate is incubated for 2 hours at room temperature. The fluorescence is then measured using a microplate reader ($\lambda_{excitation}=409$ nm, $\lambda_{emission\ 1}=460$ nm, $\lambda_{emission\ 2}=530$ nm).

The following table details the different conditions applied to the different lines used:

| Line | Invitrogen Ref. | Species | Receptor | Agonist | Agonist range (nM) | Antagonist range (nM) |
|---|---|---|---|---|---|---|
| HEK hRAMP1 | K1437 | Human | CALCRL: RAMP1 | αCGRP (NEOMPS, #SC113) | 0.002-10 | 0.04-10000 |

The fluorescence data are normalized using negative controls (cells not stimulated) and positive controls (agonist at saturating concentration).

The dissociation constants for each state of the receptor ["*Mechanistic analysis of the function of agonists and allosteric modulators: reconciling two-state and operational models*" David Roche, *British Journal of Pharmacology* (2013) 169 1189-1202] (KdR=affinity for the rest state and KdA=affinity for the activated state) are calculated and the KdR/KdA ratio represents the intrinsic efficacy of the ligand tested: if KdR=KdA, the ligand tested is a neutral antagonist. The different EC50s of the agonist obtained at each concentration of antagonist tested are linearized (Schild regression ["*Quantitation in receptor pharmacology*" Terry P. Kenakin, *Receptors and Channels* (2001) 7 371-385]) in order to determine the apparent affinity (Kdapp) of the antagonist. This value is called apparent because it may fluctuate as a function of the constitutive activation and expression of the receptor and is comparable to Kb in the case of a neutral antagonist.

The affinity results thus obtained for each of the compounds according to the invention tested are presented in Table I below, in which:

Kdapp represents the affinity of the compound for the CGRP receptor;
A represents a Kdapp<10 nM;
B represents a Kdapp between 10 and 100 nM;
C represents a Kdapp between 101 and 500 nM; and
D represents a Kdapp between 501 nM and 5000 nM.

TABLE I

| Kdapp hCGRP (nM) | Compound No. |
|---|---|
| A (<10 nM) | 14; 16-19; 22-24; 28-31; 47; 51-54; 72-73; 83; 89-90; 93; 95-98; 100-101; 103-106; 108; 110; 112-124; 126-128; 130-132; 134-140; 142-146; 148; 152; 155-162; 165-166; 170; 178; 184-189; 192; 199; 202-203; 205-208; 210; 213; 215; 220-221; 225-229; 231-249; 251-259 |
| B (10-100 nM) | 1; 4; 8-9; 11-13; 20-21; 25-27; 33; 35; 37-38; 40; 46; 48; 55-57; 59-63; 66-69; 76; 81; 85-88; 91-92; 94; 99; 102; 109; 111; 129; 133; 147; 149-150; 153; 164; 167; 169; 171-177; 179-183; 190; 193-198; 200-201; 204; 211; 214; 250 |
| C (101-500 nM) | 2-3; 6; 10; 34; 41-42; 45; 49; 64-65; 70-71; 78; 84; 141; 154; 168; 216-217; 224; 230 |
| D (501-5000 nM) | 5; 7; 15; 32; 36; 39; 43-44; 50; 58; 74-75; 77; 79-80; 82; 107; 151; 163; 191; 209; 218-219; 222-223 |

Taking into account the results listed in the above table, the compounds according to the invention displaying a Kdapp classified A have very strong affinity for the CGRP receptor. Moreover, these compounds have a KdR/KdA ratio=1 and therefore an antagonist activity of the CGRP receptor.

To the extent that neurogenic inflammation plays an important role in the physiopathology notably of rosacea and migraine, the antagonists to the CGRP receptor according to the invention should thus make it possible to reduce or completely eliminate this inflammation, resulting in an effect that persists after the treatment stops.

Besides their potential as regards biological activity as a powerful and selective antagonist of human CGRP-R, these compounds, advantageously the uracil derivatives, display metabolic instability at the hepatic level and should thus present a limited risk of hepatotoxicity.

This is illustrated more particularly by the test of metabolic stability in the presence of human hepatic microsomes presented below.

Human hepatic microsomes (Becton Dickinson) are incubated at a protein concentration of 0.5 mg/mL in the reaction mixture.

The reaction mixture of the microsomes consists of phosphate buffer pH: 7.4 at 100 mM, $MgCl_2$ at 100 mM (50/50), a system for generating ATP consisting of a mixture of nicotinamide adenine diphosphate (NADP), glucose-6-phosphate (G6P) at 1 mg/mL and glucose-6-phosphate dehydrogenase (G6PDH) at 4 U/mL. The compounds are tested at 1 µM (DMSO 0.1%).

The samples are taken from the incubation medium after adding the microsomes, at time 15 minutes. The metabolic reaction is stopped by adding methanol (1 volume incubation medium/3 volumes of methanol). The percentage of the parent product remaining after 15 minutes is measured by LC/MS/MS analysis.

The results obtained are listed in Table 2 below.

TABLE 2

| Compound No. | % of product remaining at 15 min (human hepatic microsomes) |
|---|---|
| Olcegepant | 100 |
| Telcagepant | 100 |
| MK-3207 | 100 |
| 25 | 8 |
| 30 | 16 |
| 63 | 45 |
| 110 | 1 |
| 112 | 0 |
| 114 | 41 |
| 115 | 0 |
| 120 | 1 |
| 142 | 65 |
| 143 | 42 |
| 149 | 26 |
| 150 | 0 |
| 158 | 0 |
| 165 | 0 |
| 193 | 18 |
| 206 | 1 |
| 232 | 1 |
| 237 | 3 |
| 240 | 0 |
| 251 | 4 |

According to the results obtained, the compounds of formula (I) according to the invention display metabolic instability at the hepatic level relative to the compounds known from the prior art tested and should thus present a limited risk of hepatotoxicity.

The compounds according to the invention may also be formulated in pharmaceutical compositions for human use. Said compositions comprise at least one compound of general formula (I) according to the invention in a pharmaceutically acceptable vehicle.

"Pharmaceutically acceptable vehicle" means a vehicle suitable for use in contact with human cells, compatible with the skin, the mucosae and the appendages, without toxicity, irritation, undue allergic response, and proportioned at a reasonable benefit/risk ratio.

Preferably, the compound of general formula (I) according to the invention is present in a pharmaceutical composition for topical application, which reduces considerably any side-effect at the hepatic level.

The invention claimed is:

1. A heterocyclic compound of formula (I), or an enantiomer thereof, or a pharmaceutically acceptable salt thereof,

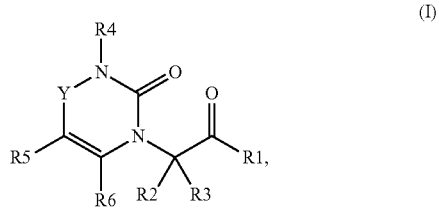

(I)

wherein,

Y is —CH$_2$, —C(O), —C(CH$_3$)$_2$, or a spirocyclopropyl;

R1 is

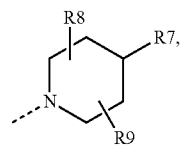

(1-1)

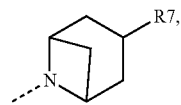

(1-2)

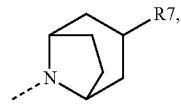

(1-3)

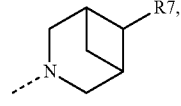

(1-4)

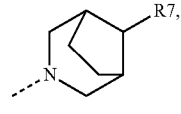

(1-5)

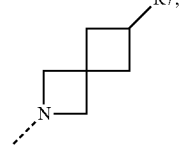

(1-6)

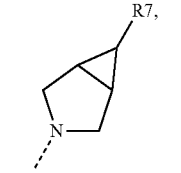

(1-7)

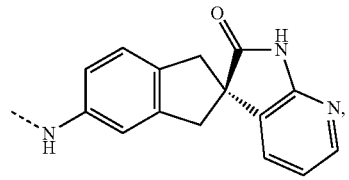

(1-8)

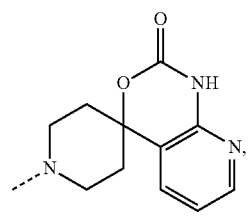

(1-9)

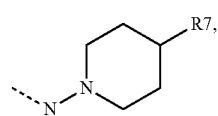

(1-10)

-continued
(1-11) 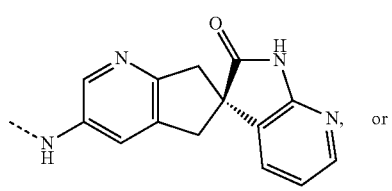
or
(1-12) 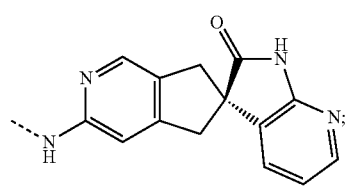
R2, R3, and R6, which may be identical or different, are a hydrogen atom, F, or —CH$_3$;
R4 is a hydrogen atom, an alkyl, an alkene, an alkyne, a cycloalkyl, a cycloalkene, an aralkyl, a heteroaralkyl, or one of the following:
(4-1) 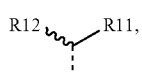
(4-2) 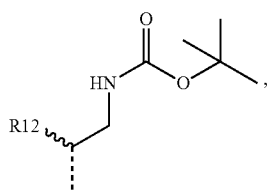
(4-3) 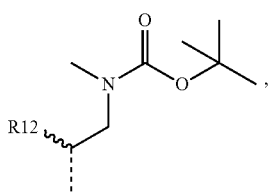
(4-4) 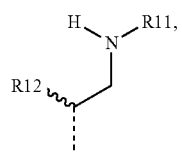
(4-5) 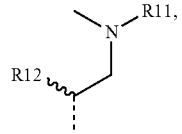
(4-6) 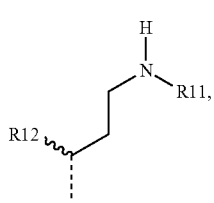
-continued
(4-7) 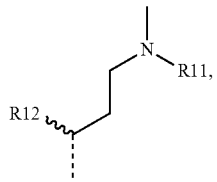
(4-8) 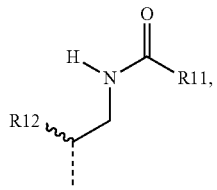
(4-9) 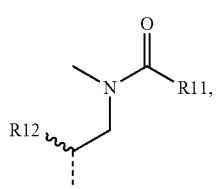
(4-10) 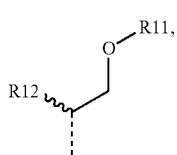
(4-11) 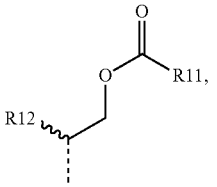
(4-12) 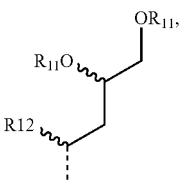
(4-13) 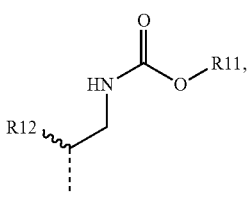
(4-14) 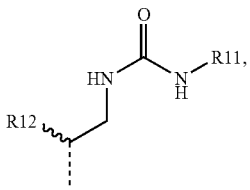

(4-15) 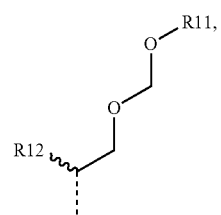
(4-16) 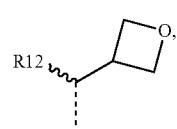
(4-17) 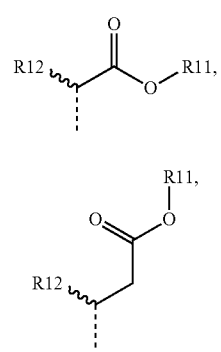
(4-18)
(4-19) 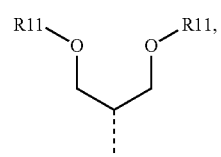
(4-20) 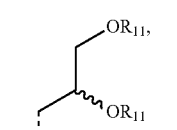
(4-21) 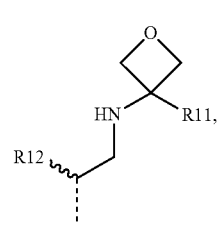
(4-22) 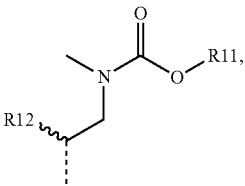
(4-23) 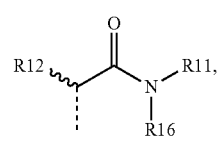
(4-24) 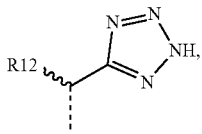
(4-25) 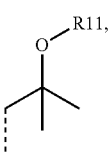
(4-26) 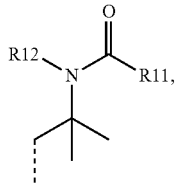
(4-27) 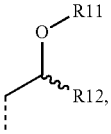
(4-28) 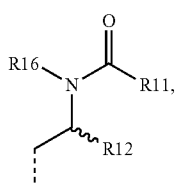
(4-29) 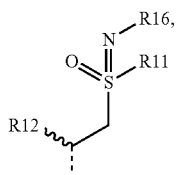
(4-30) 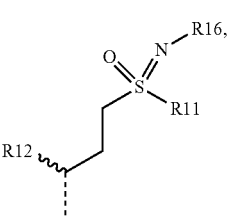
(4-31) 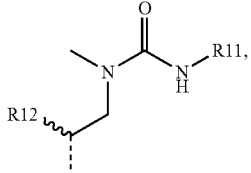
(4-32) 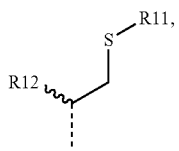

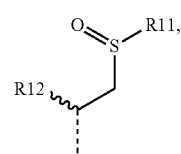 (4-33)
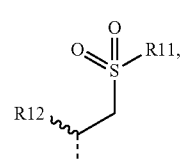 (4-34)
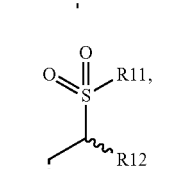 (4-35)
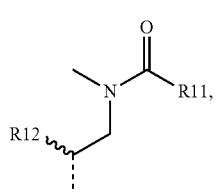 (4-36)
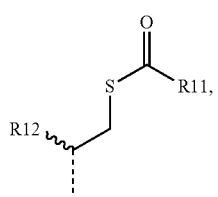 (4-37)
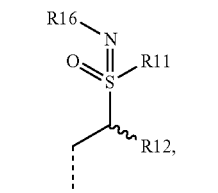 (4-38)
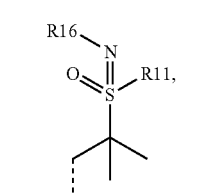 (4-39)
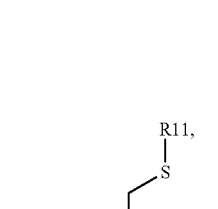 (4-40)
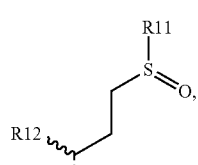 (4-41)
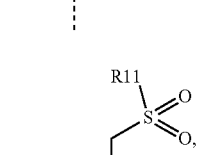 (4-42)
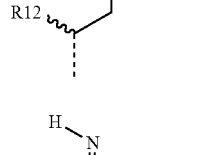 (4-43)
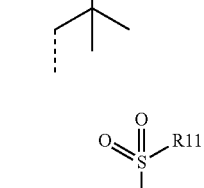 (4-44)
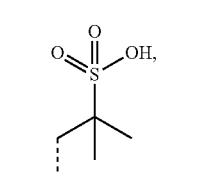 (4-45)
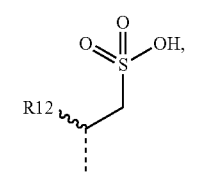 (4-46)
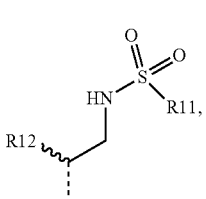 (4-47)
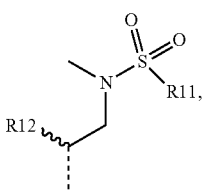 (4-48)

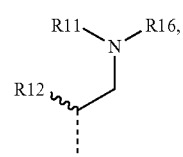 (4-49)
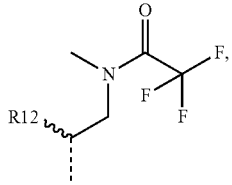 (4-50)
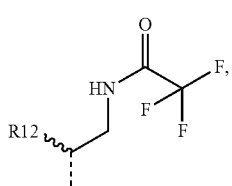 (4-51)
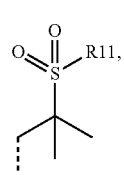 (4-52)
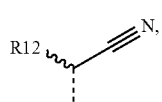 (4-53)
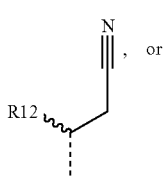 (4-54)
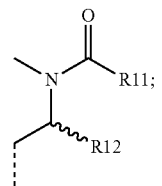 (4-55)
R5 is a halogen; an alkyl; a cycloalkyl optionally substituted with R13, R14, and/or R15; an alkene; a cycloalkene; an alkyne; an ether; or one of the following:
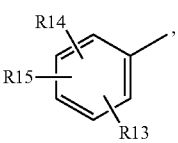 (5-1)
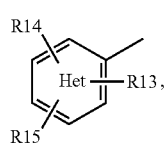 (5-2)
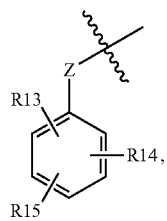 (5-3)
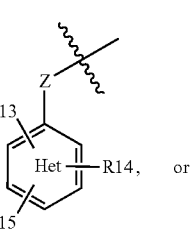 (5-4)
(5-5)
with Het representing 1 to 3 nitrogen atoms among the 6 atoms of the aromatic ring, and these nitrogen atoms may, independently of one another, be substituted with an oxygen atom to form an N-oxide group;
R7 is
(7-1)
(7-2)
(7-3)
(7-4)

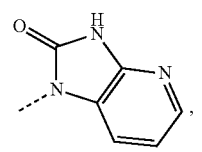
(7-5)
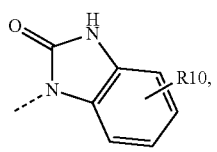
(7-6)
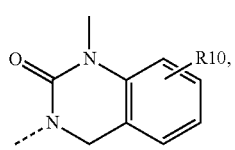
(7-7)
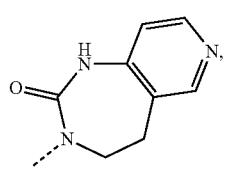
(7-8)
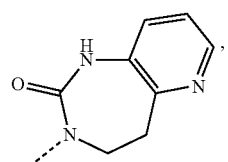
(7-9)
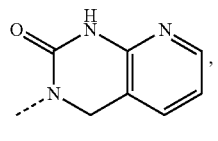
(7-10)
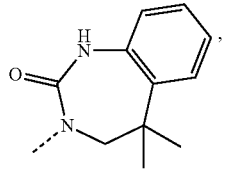
(7-11)
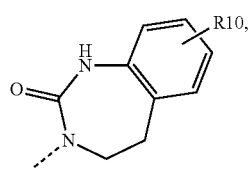
(7-12)
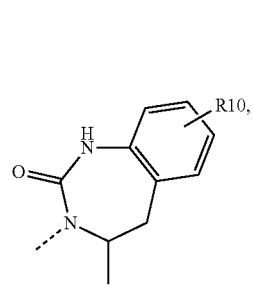
(7-13)
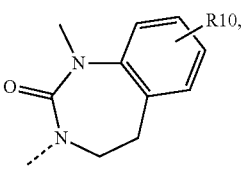
(7-14)
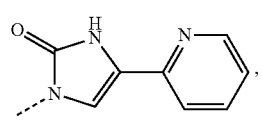
(7-15)
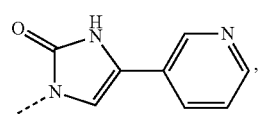
(7-16)
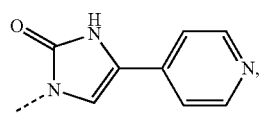
(7-17)
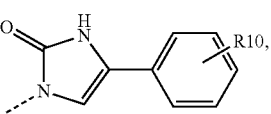
(7-18)
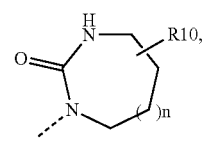
(7-19)
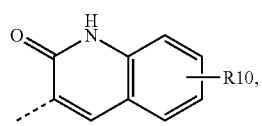
(7-20)
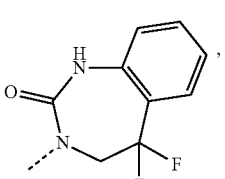
(7-21)
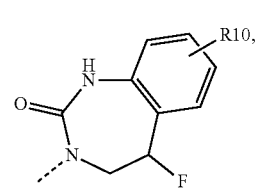
(7-22)
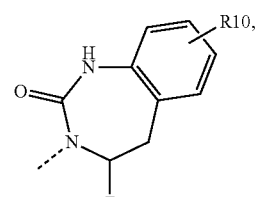
(7-23)

-continued (7-24) 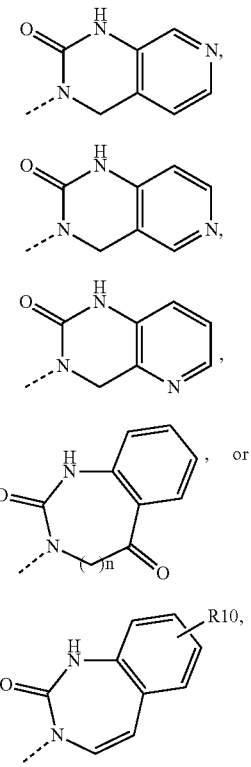

(7-25)

(7-26)

(7-27)

(7-28)

with n=0 or 1;
R8 and R9, which may be identical or different, are a hydrogen atom, F, or —CH$_3$;
R10 is hydrogen atom, —OR11, —SR11, —NR11R12, —S(O)R11, —SO$_2$R11, —OC(O)R11, —CO$_2$R11, a halogen, —NO$_2$, —CN, —C(O)NR11R12, —CF$_3$, or —OCF$_3$;
R11 and R12, which may be identical or different, are a hydrogen atom, a C1-C6 alkyl, CF$_3$, or an ether;
R13, R14, and R15, which may be identical or different, are a hydrogen atom, a C1-C6 alkyl, a cycloalkyl, —OR16, —NR16R17, a halogen, —OCF$_3$, —CF$_3$, —CN, —CO$_2$R16, —CONR16R17, —NO$_2$, —OCH$_2$OR16, —SR16, —S(O)R16, —SO$_2$R16, or an ether;
A, B, and D, which may be identical or different, are a C, N, O, or S atom;
R16 and R17, which may be identical or different, are a hydrogen atom, a C1-C6 alkyl, or —C(O)R18;
Z is —CH$_2$, O, or —NR18; and
R18 is a hydrogen atom or a C1-C3 alkyl.

2. The compound of formula (I) according to claim 1, or an enantiomer thereof, or a pharmaceutically acceptable salt thereof, wherein:
Y is —CH$_2$ or —C(O);
R1 is (1-1) 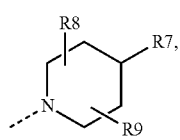

-continued (1-6) 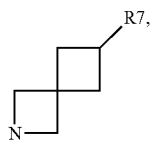

(1-8) 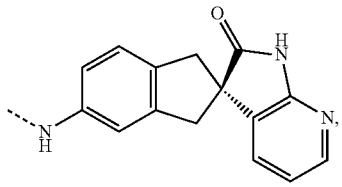

(1-9) 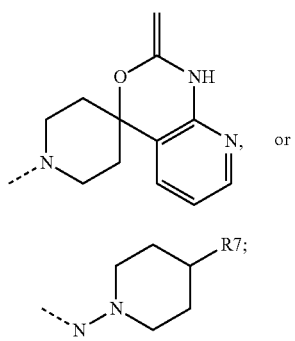

(1-10) 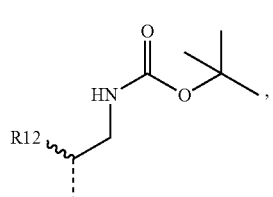

R2, R3, and R6, which may be identical or different, are a hydrogen atom, F, or —CH$_3$;
R4 is a C1-C4 alkyl, an aralkyl, a heteroaralkyl, or one of the following:

(4-2) 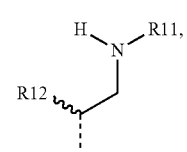

(4-4) 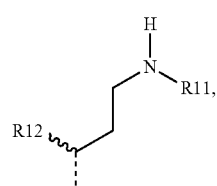

(4-6) 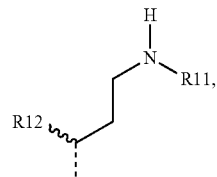

(4-7)

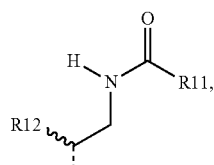 (4-8)
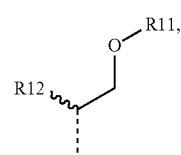 (4-10)
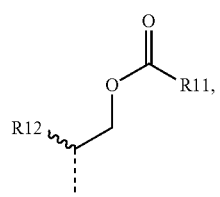 (4-11)
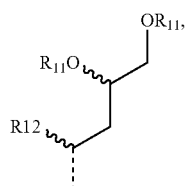 (4-12)
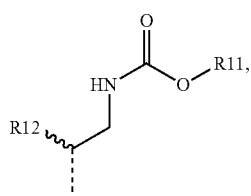 (4-13)
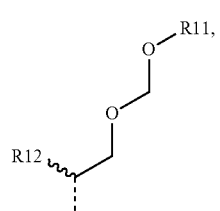 (4-15)
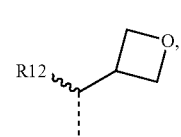 (4-16)
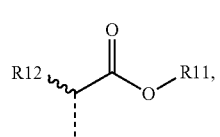 (4-17)
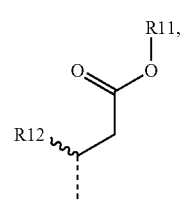 (4-18)
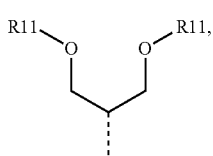 (4-19)
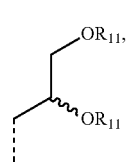 (4-20)
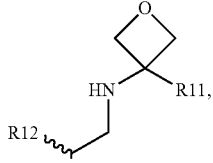 (4-21)
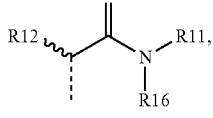 (4-23)
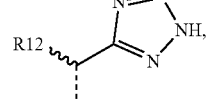 (4-24)
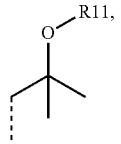 (4-25)
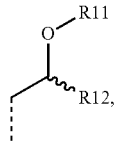 (4-27)
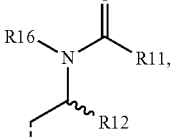 (4-28)
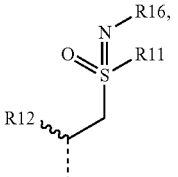 (4-29)

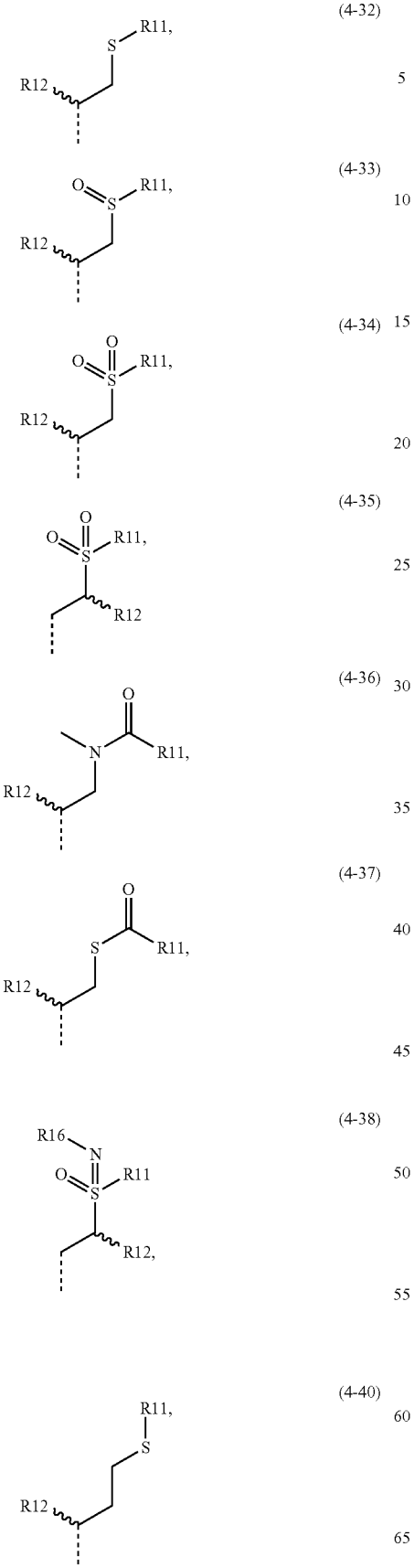
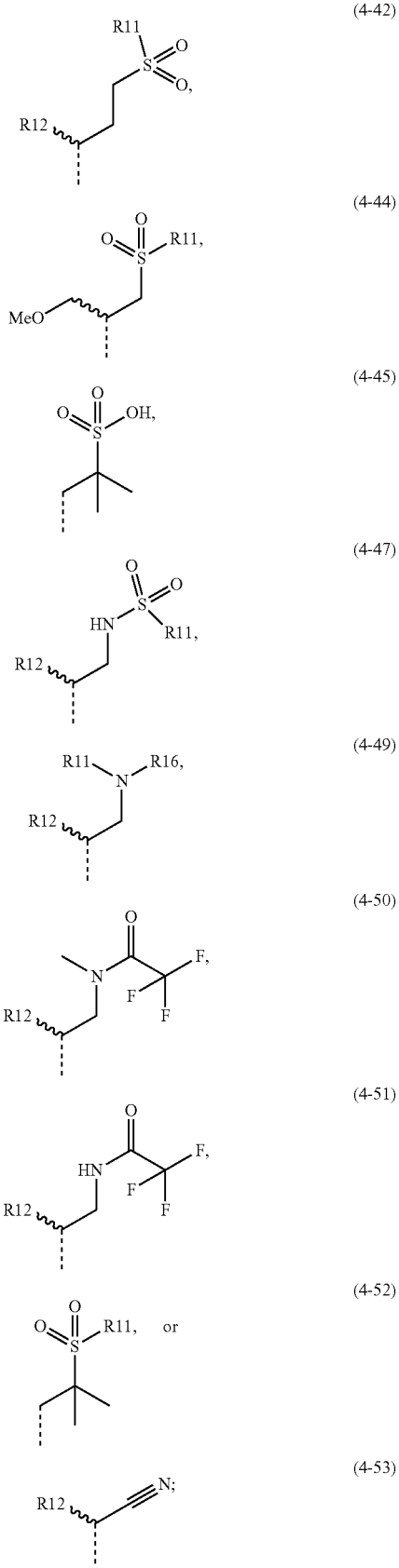

R5 is Br, —CH₃, a cyclohexene, or one of the following:
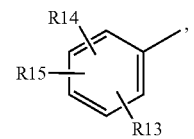
(5-1)
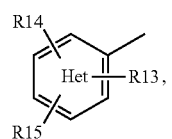
(5-2)
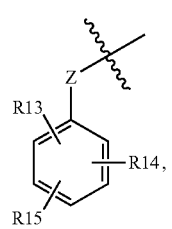
(5-3)
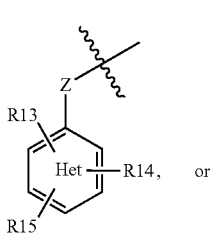
(5-4)
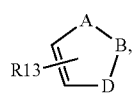
(5-5)
with Het representing 1 to 2 nitrogen atoms among the 6 atoms of the aromatic ring, and these nitrogen atoms may, independently of one another, be substituted with an oxygen atom to form an N-oxide group;
R7 is
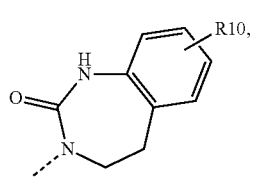
(7-1)
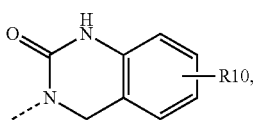
(7-2)
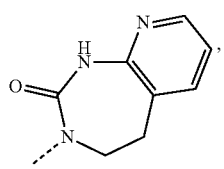
(7-3)
-continued
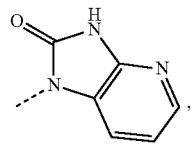
(7-5)
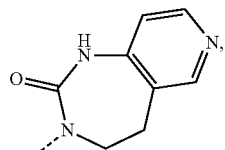
(7-8)
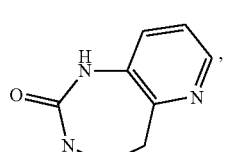
(7-9)
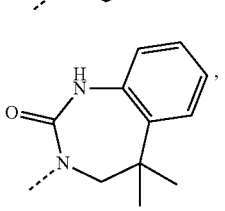
(7-11)
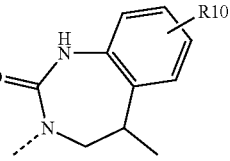
(7-12)
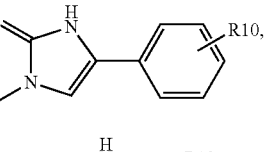
(7-18)
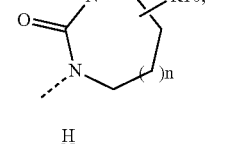
(7-19)
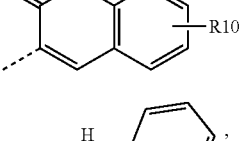
(7-20)
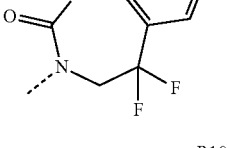
(7-21)
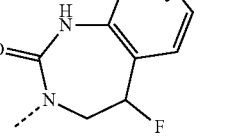
(7-22)

-continued

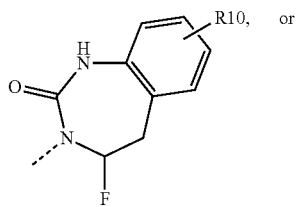 (7-23)

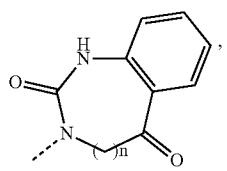 (7-27)

with n=1;
R8 and R9, which may be identical or different, are a hydrogen atom, F, or —CH₃;
R10 is a hydrogen atom, —OR11, —SR11, —S(O)R11, —SO₂R11, —CO₂H, Br, or F;
R11 and R12, which may be identical or different, are a hydrogen atom or a C1-C3 alkyl;
R13, R14, and R15, which may be identical or different, are a hydrogen atom, —CH₃, —OR16, a halogen, —OCF₃, —CN, —CO₂R16, —SR16, —S(O)R16, or —SO₂R16;
A, B, and D, which are identical or different, are a C, N, or S atom;
R16 is a hydrogen atom or a C1-C6 alkyl; and
Z is —CH₂ or O.

3. The compound of general formula (I) according to claim 1, or an enantiomer thereof, or a pharmaceutically acceptable salt thereof, wherein:
Y is —CH₂ or —C(O);
R1 is

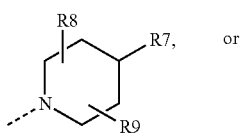 (1-1)

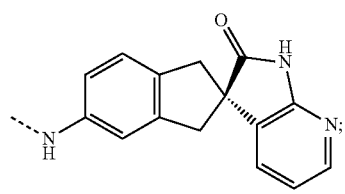 (1-8)

R2, R3, and R6 are a hydrogen atom;
R4 is a C1-C4 alkyl; a heteroaralkyl of formula

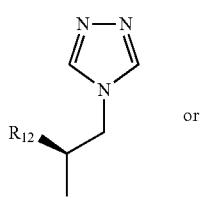 (4-56)

or

-continued

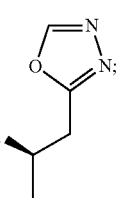 (4-57)

or one of the following:

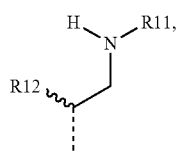 (4-4)

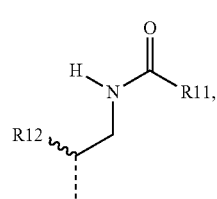 (4-8)

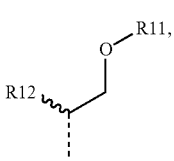 (4-10)

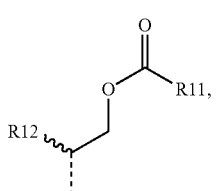 (4-11)

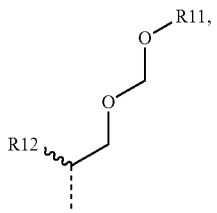 (4-15)

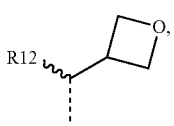 (4-16)

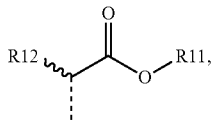 (4-17)

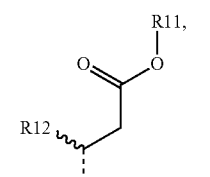 (4-18)
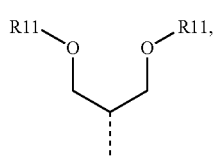 (4-19)
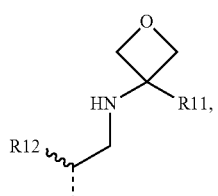 (4-21)
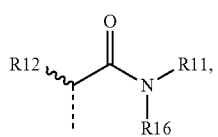 (4-23)
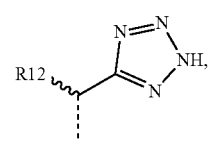 (4-24)
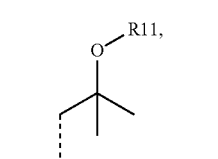 (4-25)
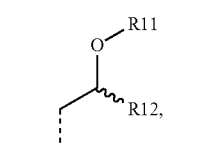 (4-27)
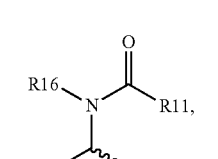 (4-28)
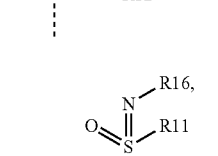 (4-29)
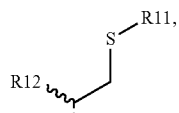 (4-32)
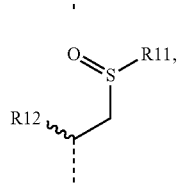 (4-33)
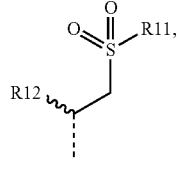 (4-34)
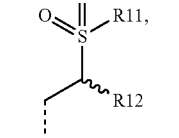 (4-35)
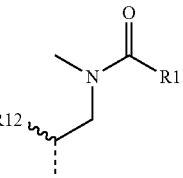 (4-36)
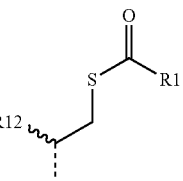 (4-37)
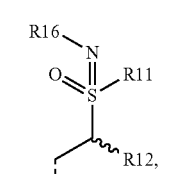 (4-38)
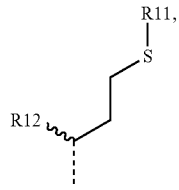 (4-40)

309
-continued (4-42)
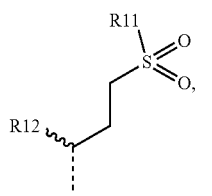

(4-44)
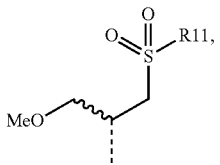

(4-45)
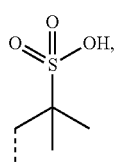

(4-47)
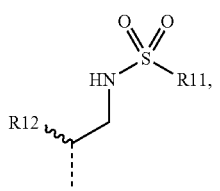

(4-49)
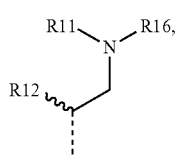

(4-52)
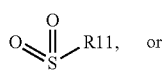

(4-53)
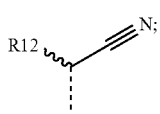

R5 is (5-1)
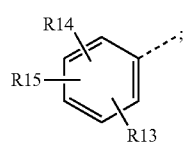

310

R7 is (7-1)
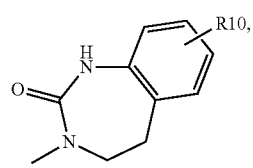

(7-2)
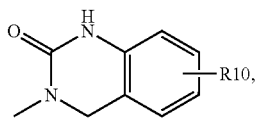

(7-3)
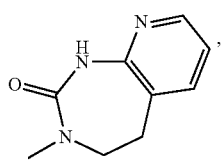

(7-12)
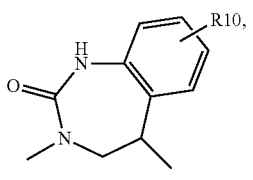

(7-18)
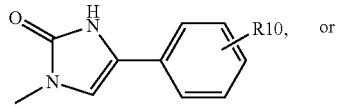

(7-20)
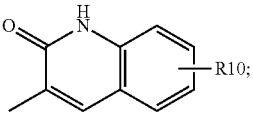

R8 and R9 are a hydrogen atom;

R10 is a hydrogen atom, —OR11, —SR11, —S(O)R11, —SO$_2$R11, —CO$_2$H, Br, or F;

R11 and R12, which may be identical or different, are a hydrogen atom or a C1-C2 alkyl;

R13, R14, and R15, which may be identical or different, are a hydrogen atom, —CH$_3$, —OR16, a halogen, or —OCF$_3$; and R16 is a hydrogen atom or a C1-C6 alkyl.

4. The compound of formula (I) according to claim 1, or an enantiomer thereof, or a pharmaceutically acceptable salt thereof, wherein:

Y is —C(O);

R1 is (1-1)
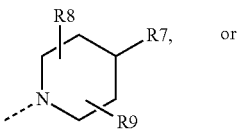

-continued

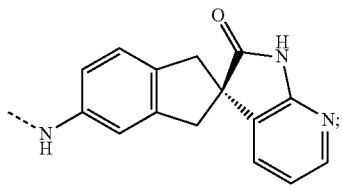

R2, R3, and R6 are a hydrogen atom;
R4 is (4-4)
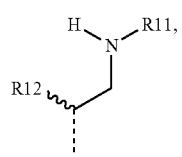

(4-8)
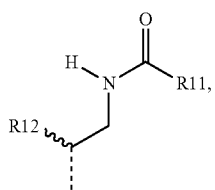

(4-10)
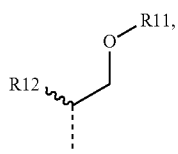

(4-34)
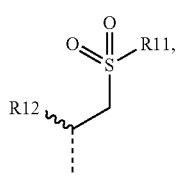

(4-35) or
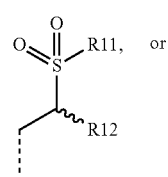

(4-47)
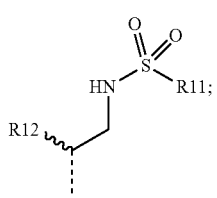

R5 is (5-1)
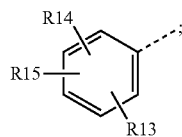

R7 is (7-1)
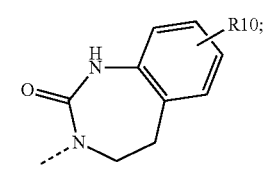

R8 and R9 are a hydrogen atom;
R10 is a hydrogen atom, —OR11, —SR11, or Br;
R11 and R12, which may be identical or different, are a hydrogen atom or a C1-C2 alkyl;
R13, R14, and R15, which may be identical or different, are a hydrogen atom, —OR16, F, or Cl; and
R16 is a C1-C3 alkyl.

5. A compound of formula (I) according to claim 1, or an enantiomer thereof, or a pharmaceutically acceptable salt thereof, wherein:
Y is —C(O);
R1 is (1-1)
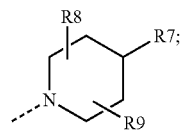

R2, R3, are R6 are a hydrogen atom;
R4 is (4-8)
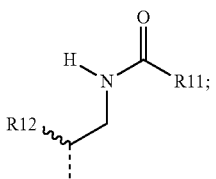

R5 is (5-1)
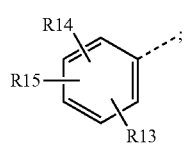

R7 is

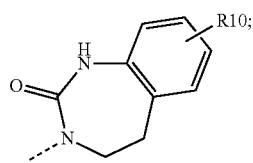
(7-1)

R8 and R9 are a hydrogen atom;
R10 is —OR11;
R11 and R12, which may be identical or different, are —CH$_3$ or —CH$_2$CH$_3$;
R13, R14, R15, which may be identical or different, are a hydrogen atom, —OR16, F, or Cl; and
R16 is a C1-C3 alkyl.

6. A pharmaceutical composition comprising the compound of formula (I) according to claim 1, or an enantiomer thereof, or a pharmaceutically acceptable salt thereof and a pharmaceutically acceptable vehicle.

7. A cosmetic composition comprising the compound of formula (I) according to claim 1, or an enantiomer thereof, or a pharmaceutically acceptable salt thereof.

8. A topical composition comprising the compound of formula (I) according to claim 1, or an enantiomer thereof, or a pharmaceutically accept salt thereof, and a pharmaceutically acceptable vehicle.

9. A method of preventing or treating inflammatory skin disease with a neurogenic component, the method comprising administering the pharmaceutical composition according to claim 6, to a patient suffering from inflammatory skin disease.

10. The method according to claim 9, wherein the inflammatory skin disease is rosacea, atopic dermatitis, psoriasis erythema, acne, eczema, or urticaria.

11. The method according to claim 10, wherein the psoriasis is psoriasis vulgaris, psoriasis of the scalp, arthritic psoriasis, pustular psoriasis, or guttate psoriasis.

12. The method of claim 10, wherein the erythema is facial erythema or erythema pudicitiae.

13. The method of claim 10, wherein the urticaria is acute urticaria, senile pruritic urticaria, or prurigo nodularis urticaria.

14. The method according to claim 10, wherein the rosacea is type I (erythematous) rosacea or type II (papulopustular) rosacea.

15. The method according to claim 10, wherein the inflammatory skin disease is type I (erythematous) rosacea.

16. The method according to claim 9, wherein the pharmaceutical composition is administered topically.

17. A method of treating migraine, the method comprising administering the pharmaceutical composition according to claim 6 to a patient suffering from migraine.

18. The method according to claim 10, wherein the eczema is chronic eczema of the hands.

* * * * *